US008404926B2

(12) United States Patent
Meyer et al.

(10) Patent No.: US 8,404,926 B2
(45) Date of Patent: Mar. 26, 2013

(54) USE OF A SEED SPECIFIC PROMOTER TO DRIVE ODP1 EXPRESSION IN CRUCIFEROUS OILSEED PLANTS TO INCREASE OIL CONTENT WHILE MAINTAINING NORMAL GERMINATION

(75) Inventors: Knut Meyer, Wilmington, DE (US); Howard Glenn Damude, Hockessin, DE (US); John D. Everard, Wilmington, DE (US); Kevin G. Ripp, Wilmington, DE (US); Kevin L. Stecca, Bear, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 217 days.

(21) Appl. No.: 12/752,175

(22) Filed: Apr. 1, 2010

(65) Prior Publication Data

US 2010/0257635 A1    Oct. 7, 2010

Related U.S. Application Data

(60) Provisional application No. 61/165,548, filed on Apr. 1, 2009.

(51) Int. Cl.
*C12N 15/82* (2006.01)
*C12N 15/29* (2006.01)
*A01H 5/00* (2006.01)
*A01H 5/10* (2006.01)

(52) U.S. Cl. ........ 800/281; 800/298; 800/278; 800/287; 800/306; 435/320.1

(58) Field of Classification Search ........................ None
See application file for complete search history.

(56) References Cited

U.S. PATENT DOCUMENTS

| | | | |
|---|---|---|---|
| 5,107,065 A | 4/1992 | Shewmaker et al. | |
| 5,968,809 A | 10/1999 | Knutzon et al. | |
| 6,072,050 A | 6/2000 | Bowen et al. | |
| 6,512,165 B1 | 1/2003 | Ross et al. | |
| 6,555,673 B1 | 4/2003 | Bowen et al. | |
| 7,157,621 B2 * | 1/2007 | Allen et al. | 800/298 |
| 2003/0135889 A1 | 7/2003 | Ross et al. | |
| 2003/0226166 A1 | 12/2003 | Falco et al. | |

FOREIGN PATENT DOCUMENTS

| | | |
|---|---|---|
| WO | 9967405 A2 | 12/1999 |
| WO | 0028058 A2 | 5/2000 |
| WO | 0200904 A2 | 1/2002 |
| WO | 0208269 A2 | 1/2002 |
| WO | 03001902 A2 | 1/2003 |
| WO | 2004071467 A2 | 8/2004 |
| WO | 2005075655 A2 | 8/2005 |
| WO | 2006000732 A1 | 1/2006 |
| WO | 2007061845 A2 | 5/2007 |

OTHER PUBLICATIONS

Bowie et al, Science 247:1306-1310, 1990.*
McConnell et al, Nature 411 (6838):709-713, 2001.*
Marsch-Martinez et al (2006, Plant Mol. Biol. 62:825-843).*
Boutilier et al (2002, The Plant Cell 14:1737-1749).*
Kagaya et al (1995, Mol. Gen. Genet. 248 :668-674).*
Sebastien Baud et al., "A Spatiotemporal Analysis of Enzymatic Activities Associated With Carbon Metabolism in Wild-Type and Mutant Embryos of *Arabidopsis* Using in Situ Histochemistry", The Plant Journal, Vol. 46:155-169, 2006.
Sebastien Baud et al., "Structure and Expression Profile of the Sucrose Synthase Multigene Family in *Arabidopsis*", Journal of Experimental Botany, Vol. 55(396):397-409, 2004.
R.N. Beachy et al., "Accumulation and Assembly of Soybean B-Conglycinin in Seeds of Transformed Petunia Plants",The EMBO Journal, Vol. 4(12):3047-3053, 1985.
Daniel M. Becker et al., "A CDNA Encoding a Human CCAAT-Binding Protein Cloned by Functional Complementation in Yeast", Proc. Natl. Acad. Sci. USA, Vol. 88:1968-1972, 1991.
Alex Cernac et al., "WRINKLED1 Encodes an AP2/EREB Domain Protein Involved in the Control of Storage Compound Biosynthesis in *Arabidopsis*", The Plant Journal, 40:575-585, 2004.
Gary N. Drews et al., "Negative Regulation of the *Arabidopsis* Homeotic Gene Agamous by the APETALA2 Product", Cell, Vol. 65(6):991-1002, 1991.
David Edwards et al., "Multiple Genes Encoding the Conserved CCAAT-Box Transcription Factor Complex Are Expressed in *Arabidopsis*", Plant Physiol., vol. 117:1015-1022, 1998.
Johan Ericsson et al., "Synergistic Binding of Sterol Regulatory Element-Binding Protein and NF-Y to the Farnesyl Diphosphate Synthase Promoter Is Critical for Sterol-Regulated Expression of the Gene", The Journal of Biological Chemistry, vol. 271(40):24359-24364, 1996.
Robert B. Goldberg et al., "Regulation of Gene Expression During Plant Embryogenesis", Cell, vol. 56(2):149-160, 1989.
National Center for Biotechnology Information General Identifier No. 32364685, Accession No. AAP80382, Aug. 23, 2004, A.Cernac et al., "WRINKLED1 [*Arabidopsis thaliana*]", Biochemistry and Molecular Biology, MSU, East Lansing, Michigan, USA.
Vivian F. Irish et al., "Function of the APETALA-1 Gene During *Arabidopsis* Floral Development", The Plant Cell, Vol. 2:741-753, 1990.
Simon M. Jackson et al., "NF-Y Has a Novel Role in Sterol-Dependent Transcription of Two Cholesterogenic Genes", The Journal of Biological Chemistry, vol. 270(37):21445-21448, 1995.
K. Diane Jofuku et al., "Control of *Arabidopsis* Flower and Seed Development by the Homeotic Gene APETALA2", The Plant Cell, vol. 6:1211-1225, 1994.
Xiao-Yan Li et al., "Evolutionary Variation of the CCAAT-Binding Transcription Factor NF-Y", Nucleic Acids Research, vol. 20(5):1087-1091, 1991.
Yonghua Li et al., "Oil Content of Arabidopsis Seeds: The Influence of Seed Anatomy, Light and Plant-To-Plant Variation", Elsevier Phytochemistry, vol. 67:904-915, 2006.
Jose M. Lopez et al., "Sterol Regulation of Acetyl Coenzyme a Carboxylase: A Mechanism for Coordinate Control of Cellular Lipid", Proc. Natl. Acad. Sci. USA, vol. 93:1049-1053, 1996.

(Continued)

*Primary Examiner* — Stuart F Baum
(74) *Attorney, Agent, or Firm* — Alston & Bird LLP

(57) ABSTRACT

A recombinant DNA construct comprising a polynucleotide encoding an ODP1 polypeptide operably linked to a sucrose synthase 2 promoter where this construct can be used to increase oil content in the seeds of a cruciferous oilseed plant while maintaining normal germination is disclosed. A method for increasing oil content in the seeds of a cruciferous oilseed plant while maintaining normal germination using this construct is also disclosed.

23 Claims, 4 Drawing Sheets

OTHER PUBLICATIONS

Figure 2:
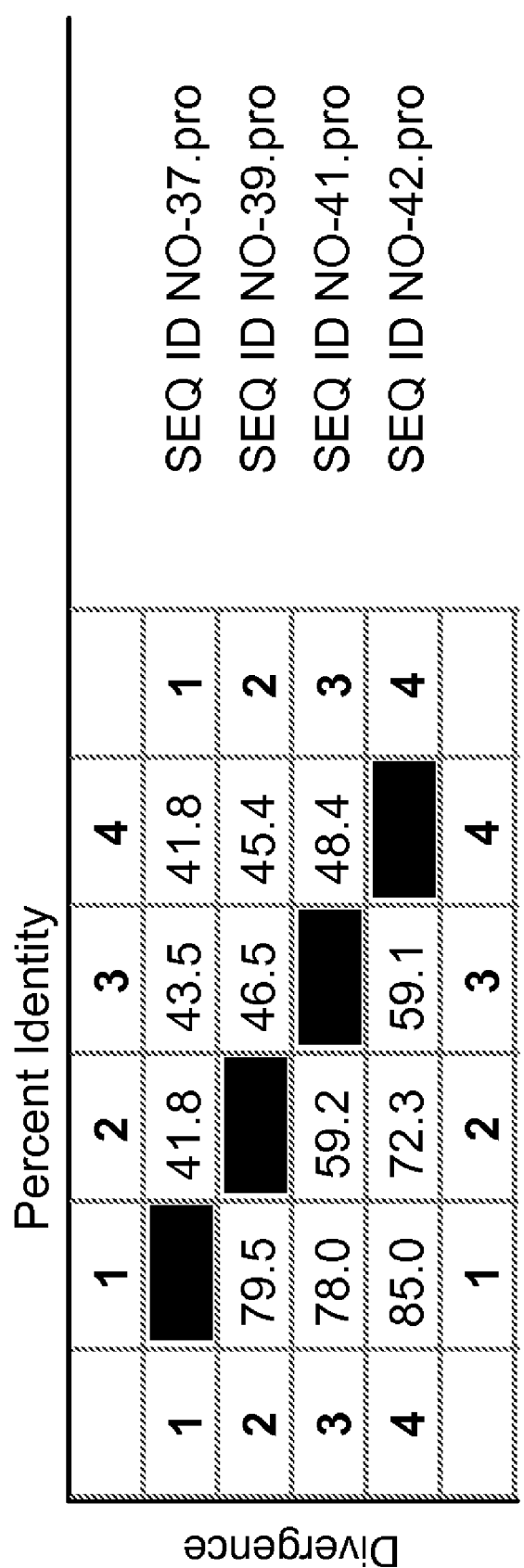

Tamar Lotan et al., "*Arabidopsis* Leafy COTYLEDON1 Is Sufficient to Induce Embryo Development in Vegetative Cells", Cell, vol. 93:1195-1205, 1998.

S.L. Mcknight et al, "Is CCAAT/Enhancer-Binding Protein a Central Regulator of Energy Metabolism?", Genes Dev. vol. 3:2021-2024, 1989.

Jack K. Okamuro et al., "The AP2 Domain of APETALA2 Defines a Large New Family of DNA Binding Proteins in Arabidopsis", Proc. Natl. Acad. Sci. USA, vol. 94:7076-7081, 1997.

Karim Roder et al., "NF-Y Binds to the Inverted CCAAT Box, An Essential Element for C AMP-Dependent Regulation of the Rat Fatty Acid Synthase (FAS) Gene", Gene, vol. 184:21-26, 1997.

Sari A. Ruuska et al., "Contrapuntal Networks of Gene Expression During *Arabidopsis* Seed Filling", The Plant Cell, Vol. 14:1191-1206, 2002.

Satrajit Sinha et al., "Recombinant Rat CBF-C, The Third Subunit of CBF/NFY, Allows Formation of a Protein-DNA Complex With CBF-A and CBF-B and With Yeast HAP2 and HAP3", Proc. Natl. Acad. Sci. USA, vol. 92:1624-1628, 1995.

Masaru Ohme-Takagi et al., "Ethylene-Inducible DNA Binding Proteins That Interact With an Ethylene-Responsive Element", The Plant Cell, Vol. 7:173-182, 1995.

U.S. Appl. No. 61/578,903, filed Dec. 22, 2011, Damude.

* cited by examiner

FIG. 1A

```
M........S........S...........R........R...... Consensus #1
          10        20        30        40        50        60

1  MERSQRQSPPPPSPSSS-SSSVSADTVLVPPGKRRRAATAKAGAEPNKRIR------    SEQ ID NO-37.pro
 1  MKRSPASSCSSSTSSV---------GFEAPIEKRRP--------KHPRNNLKSQKC---   SEQ ID NO-39.pro
 1  MRRSPSVSTSSSSSSCVGGGGFDSNNINLAAPPRRPQSEKTGAKRRKRNQ-DDAKCEIE   SEQ ID NO-41.pro
 1  MKKRLTTSTCSSSPSSSVSSSTTTSSPIQSEAP--RP--------KRAKRAK-KSS---   SEQ ID NO-42.pro ............RSS.YRGVTRHRWTGRFEAHLWDK..........KK.G.QVYLG Consensus #1
          70        80        90       100       110       120

51  ----KDPAAAAAGKRSSVYRGVTRHRWTGRFEAHLWDKHCLAALHNKKGRQVYLG----   SEQ ID NO-37.pro
41  ----KQNQTTTGGRRSSIYRGVTRHRWTGRFEAHLWDKSSWNNIQSKK-GRQVYLG---   SEQ ID NO-39.pro
60  NRNGNNNNSSNNNASSGRRSSIYRGVTRHRWTGRFEAHLWDKSSWNSIQNKK-GRQVYLG  SEQ ID NO-41.pro
46  -PSGDKSHNPTS-PASTRRSSIYRGVTRHRWTGRFEAHLWDKSSWNSIQNKK-GKQVYLG  SEQ ID NO-42.pro AYD.EE.AA..YDLAALKYWG....LNFP.E.Y..E..EM..V..EEYLASLRR.SSGFS Consensus #1
         130       140       150       160       170       180

103 AYDSEEAAARAYDLAALKYWGPETLLNFPVEDYSSEMPEMEAVSREEYLASLRRSSGFS   SEQ ID NO-37.pro
 92 AYDTEESAARTYDLAALKYWGKDATLNFPIETYTKELEEMDKVSREEYLASLRRSSGFS   SEQ ID NO-39.pro
119 AYDNEEAAARTYDLAALKYWGPGTTLNFPVESYRNEIEEMRKVTKEEYLASLRRSSGFS   SEQ ID NO-41.pro
103 AYDSEEAAAHTYDLAALKYWGPDTILNFPAFTYTKELEEMQRVTKEEYLASLRRQSSGFS  SEQ ID NO-42.pro
```

FIG. 1B

```
         RG.SKYRGVARHHHNGRWEARIGRV.G.KYLYLGT..TQEEAA.AYD.AAIEYRG.NAVT  Consensus #1
              190       200       210       220       230       240
              ....|....|....|....|....|....|....|....|....|....|....|
    163  RGVSKYRGVARHHHNGRWEARIGRVFGNKYLYLYLGTFDTQEEAAKAYDLAAIEYRGVNAVT  SEQ ID NO-37.pro
    152  RGLSKYRGVARHHHNGRWEARIGRVCGNKYLYLYLGTYKTQEEAAVAYDMAAIEYRGVNAVT  SEQ ID NO-39.pro
    179  RGVSKYRGVARHHHNGRWEARIGRVFGSKYLYLYLGTYNTQEEAAAAYDMAAIEYRGVNAVT  SEQ ID NO-41.pro
    163  RGVSKYRGVARHHHNGRWEARIGRVFGNKYLYLYLGTYNTQEEAAAAYDMAAIEYRGANAVT  SEQ ID NO-42.pro NFDIS.Y...................................E................  Consensus #1
              250       260       270       280       290       300
              ....|....|....|....|....|....|....|....|....|....|....|
    223  NFDISCYLDH-------PLFLAQLQQEPQVVPALNQ--------EPQPDQSETGTTEQE--  SEQ ID NO-37.pro
    212  NFDISNYMDKIKKKN------DQTQQQQTE--AQTETVPNSSDSEEVEVEQQTTITTP---  SEQ ID NO-39.pro
    239  NFDISNYIGRLENKSSVFP---------------------AAEQP--LQPNC----S----  SEQ ID NO-41.pro
    223  NFDISNYIDRL-KKKGVFPFPVNQANHQEGILVEAKQEVETREAKEPREEVKQQYVEEP--  SEQ ID NO-42.pro P...............................................L.W........  Consensus #1
              310       320       330       340       350       360
              ....|....|....|....|....|....|....|....|....|....|....|
    267  PESSSEAKTPDGSAEPDENAVP---------DDTAEPLTTVDDSIEEGL-WSPCMDY----  SEQ ID NO-37.pro
    263  PPS----ENLHMPPQQHQVQYT--PHVSPREEESSLIIMDHVLEQDLPWSF--MYTG----  SEQ ID NO-39.pro
    269  PASSSEEGEVVQQQQQQTTMAFSGSPLQFPSMENSPTTME--EDHDLHWSF--LDTG----  SEQ ID NO-41.pro
    282  PQEEEEKEEEEKAEQQEAEIVGYSEEAAVVNCCIDSSTIMEMDRCGDNNELAWNFCMMDTG  SEQ ID NO-42.pro
```

FIG. 1C

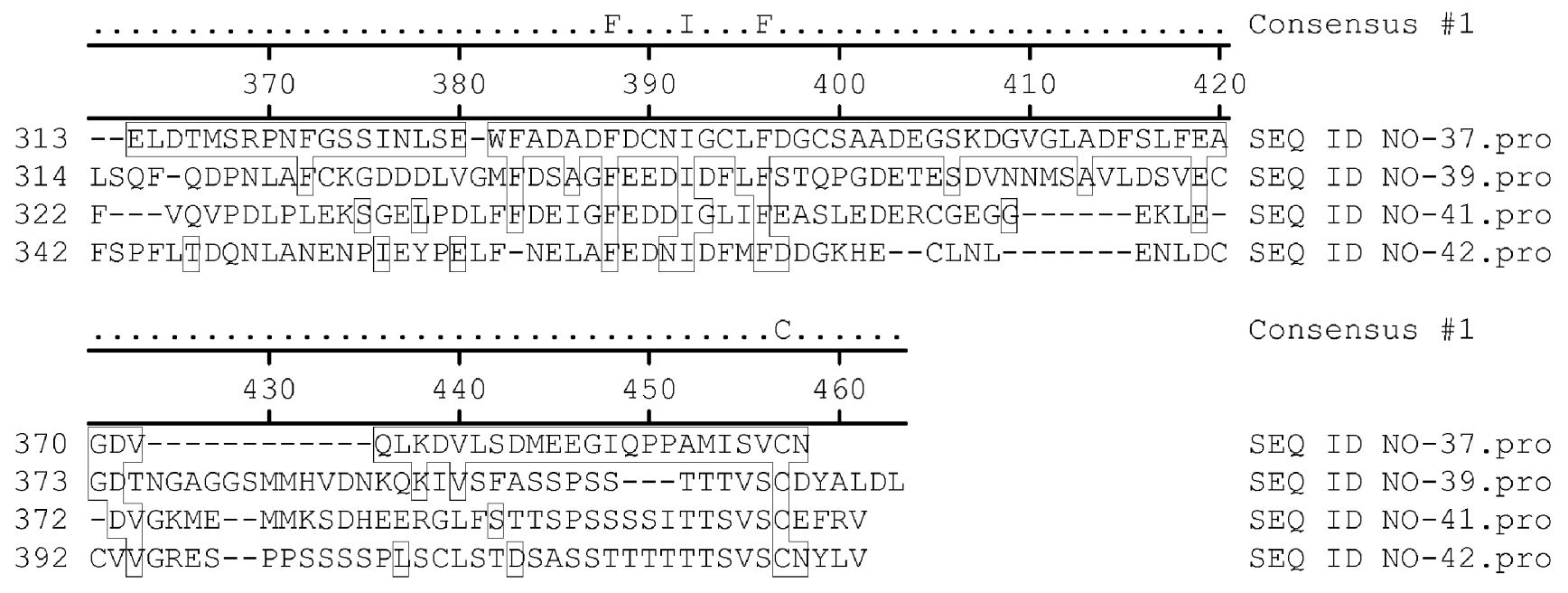

```
                                              F..I...F................                    Consensus #1
          370       380       390       400       410       420
    ....|....|....|....|....|....|....|....|....|....|....|....|
313 --ELDTMSRPNFGSSINLSE-WFADADFDCNIGCLFDGCSAADEGSKDGVGLADFSLFEA   SEQ ID NO-37.pro
314 LSQF-QDPNLAFCKGDDDLVGMFDSAGFEEDIDFLFSTQPGDETESDVNNMSAVLDSVEC   SEQ ID NO-39.pro
322 F---VQVPDLPLEKSGELPDLFEDEIGFEDDIGLIFEASLEDERCGEG----EKLE---   SEQ ID NO-41.pro
342 FSPFLTDQNLANENPIEYPELF-NELAFEDNIDFMFDDGKHE---CLNL------ENLDC   SEQ ID NO-42.pro C.....                                       Consensus #1
          430       440       450       460
    ....|....|....|....|....|....|....|....|
370 GDV-------QLKDVLSDMEEGIQPPAMISVCN                              SEQ ID NO-37.pro
373 GDTNGAGGSMMHVDNKQKIMSFASSPSS---TTTVSCDYALDL                    SEQ ID NO-39.pro
372 -DVGKME--MMKSDHEERGLFSTTSPSSSSITTSVSCEFRV                      SEQ ID NO-41.pro
392 CVVGRES--PPSSSSPLSCLSTDSASSTTTTTTSVSCNYLV                      SEQ ID NO-42.pro
```

USE OF A SEED SPECIFIC PROMOTER TO DRIVE ODP1 EXPRESSION IN CRUCIFEROUS OILSEED PLANTS TO INCREASE OIL CONTENT WHILE MAINTAINING NORMAL GERMINATION

CROSS REFERENCE TO RELATED APPLICATIONS

This application claims the benefit of U.S. Provisional Application No. 61/165,548, filed Apr. 1, 2009, the entire content of which is herein incorporated by reference.

FIELD OF THE INVENTION

This invention is in the field of biotechnology, in particular, this pertains to increasing oil content while maintaining normal germination in a cruciferous oilseed plant using a seed specific promoter to drive expression of ODP1.

BACKGROUND OF THE INVENTION

Plant lipids have a variety of industrial and nutritional uses and are central to plant membrane function and climatic adaptation. These lipids represent a vast array of chemical structures, and these structures determine the physiological and industrial properties of the lipid. Many of these structures result either directly or indirectly from metabolic processes that alter the degree of unsaturation of the lipid. Different metabolic regimes in different plants produce these altered lipids, and either domestication of exotic plant species or modification of agronomically adapted species is usually required to produce economically large amounts of the desired lipid.

There are serious limitations to using mutagenesis to alter fatty acid composition and content. Screens will rarely uncover mutations that a) result in a dominant ("gain-of-function") phenotype, b) are in genes that are essential for plant growth, and c) are in an enzyme that is not rate-limiting and that is encoded by more than one gene. In cases where desired phenotypes are available in mutant corn lines, their introgression into elite lines by traditional breeding techniques is slow and expensive, since the desired oil compositions are likely the result of several recessive genes.

Recent molecular and cellular biology techniques offer the potential for overcoming some of the limitations of the mutagenesis approach, including the need for extensive breeding. Some of the particularly useful technologies are seed-specific expression of foreign genes in transgenic plants (see Goldberg et al (1989) *Cell* 56:149-160), and the use of antisense RNA to inhibit plant target genes in a dominant and tissue-specific manner (see van der Krol et al (1988) *Gene* 72:45-50). Other advances include the transfer of foreign genes into elite commercial varieties of commercial oilcrops, such as soybean (Chee et al (1989) *Plant Physiol.* 91:1212-1218; Christou et al (1989) *Proc. Natl. Acad. Sci. U.S.A.* 86:7500-7504; Hinchee et al (1988) *Bio/Technology* 6:915-922; EPO publication 0 301 749 A2), rapeseed (De Block et al (1989) *Plant Physiol.* 91:694-701), and sunflower (Everett et al (1987) *Bio/Technology* 5:1201-1204), and the use of genes as restriction fragment length polymorphism (RFLP) markers in a breeding program, which makes introgression of recessive traits into elite lines rapid and less expensive (Tanksley et al (1989) *Bio/Technology* 7:257-264). However, application of each of these technologies requires identification and isolation of commercially-important genes.

Transcription factors generally bind DNA in a sequence-specific manner and either activate or repress transcription initiation. The specific mechanisms of these interactions remain to be fully elucidated. At least three types of separate domains have been identified within transcription factors. One is necessary for sequence-specific DNA recognition, one for the activation/repression of transcriptional initiation, and one for the formation of protein-protein interactions (such as dimerization). Studies indicate that many plant transcription factors can be grouped into distinct classes based on their conserved DNA binding domains (Katagiri F and Chua N H, 1992, *Trends Genet.* 8:22-27; Menkens A E, Schindler U and Cashmore A R, 1995, *Trends in Biochem Sci.* 13:506-510; Martin C and Paz-Ares J, 1997, *Trends Genet.* 13:67-73). Each member of these families interacts and binds with distinct DNA sequence motifs that are often found in multiple gene promoters controlled by different regulatory signals.

Several transcription factor families have been identified in plants. For example, nucleotide sequences encoding the following transcription factors families have been identified: Alfin-like, AP2 (APETALA2) and EREBPs (ethylene-responsive element binding proteins), ARF, AUX/IAA, bHLH, bZIP, C2C2 (Zn), C2C2 (Co-like), C2C2 (D of), C2C2 (GATA), C2C2 (YABBY), C2H2 (Zn), C3H-type, CCAAT, CCAAT HAP3, CCAAT HAP5, CPP (Zn), DRAP1, E2F/DP, GARP, GRAS, HMG-BOX, HOMED BOX, HSF, Jumanji, LFY, LIM, MADS Box, MYB, NAC, NIN-like, Polycomb-like, RAV-like, SBP, TCP, TFIID, Transfactor, Trihelix, TUBBY, and WRKY.

WO 2005/075655 published on Aug. 18, 2005 describes an AP2 domain transcription factor ODP2 (ovule development protein 2) and methods of U.S. Pat. No. 7,157,621 which issued on Jan. 2, 2007, describes the alteration of oil traits in plants through controlled expression of selected genes in plants.

The AP2/ERF family of proteins is a plant-specific class of putative transcription factors that have been shown to regulate a wide-variety of developmental processes and are characterized by the presence of an AP2/ERF DNA binding domain. The AP2/ERF proteins have been subdivided into two distinct subfamilies based on whether they contain one (ERF subfamily) or two (AP2 subfamily) DNA binding domains.

Specifically, AP2 (APETALA2) and EREBPs (ethylene-responsive element binding proteins) are the prototypic members of a family of transcription factors unique to plants, whose distinguishing characteristic is that they contain the so-called AP2 DNA-binding domain. AP2/EREBP genes form a large multigene family, and they play a variety of roles throughout the plant life cycle. AP2/EREBP genes are key regulators of several developmental processes, including floral organ identity determination and leaf epidermal cell identity. In *Arabidopsis thaliana*, the homeotic gene APETALA2 (AP2) has been shown to control three salient processes during development: (1) the specification of flower organ identity throughout floral organogenesis (Jofuku et al., *Plant Cell* 6:1211-1225, 1994); (2) establishment of flower meristem identity (Irish and Sussex, *Plant Cell* 2:8:741-753, 1990); and (3) the temporal and spatial regulation of flower homeotic gene activity (Drews et al., *Cell* 65:6:991-1002, 1991). DNA sequence analysis suggests that AP2 encodes a theoretical polypeptide of 432 aa, with a distinct 68 aa repeated motif termed the AP2 domain. This domain has been shown to be essential for AP2 functions and contains within the 68 aa, an eighteen amino acid core region that is predicted to form an amphipathic α-helix (Jofuku et al., *Plant Cell* 6:1211-1225, 1994). AP2-like domain-containing transcription factors have been also been identified in both *Arabidopsis thaliana*

(Okamuro et al., *Proc. Natl. Acad. Sci. USA* 94:7076-7081, 1997) and in tobacco with the identification of the ethylene responsive element binding proteins (EREBPs) (Ohme-Takagi and Shinshi, *Plant Cell* 7:2:173-182, 1995). In *Arabidopsis*, these RAP2 (related to AP2) genes encode two distinct subfamilies of AP2 domain-containing proteins designated AP2-like and EREBP-like (Okamuro et al., *Proc. Natl. Acad. Sci. USA* 94:7076-7081, 1997). In vitro DNA binding has not been shown to date using the RAP2 proteins. Based upon the presence of two highly conserved motifs YRG and RAYD within the AP2 domain, it has been proposed that binding DNA binding occurs in a manner similar to that of AP2 proteins.

As was noted above, regulation of transcription of most eukaryotic genes is coordinated through sequence-specific binding of proteins to the promoter region located upstream of the gene. Many of these protein-binding sequences have been conserved during evolution and are found in a wide variety of organisms. One such feature is the "CCAAT" sequence element (Edwards et al, 1998, *Plant Physiol.* 117: 1015-1022). CCAAT boxes are a feature of gene promoters in many eukaryotes including several plant gene promoters.

HAP proteins constitute a large family of transcription factors first identified in yeast. They combine to from a heteromeric protein complex that activates transcription by binding to CCAAT boxes in eukaryotic promoters. The orthologous HAP proteins display a high degree of evolutionary conservation in their functional domains in all species studied to date (Li et al., 1991, *Nucleic Acids Res.* 20:1087-1091).

WO 00/28058 published on May 18, 2000 describes HAP3-type CCAAT-box binding transcriptional activator polynucleotides and polypeptides, especially, the leafy cotyledon 1 transcriptional activator (LEC1) polynucleotides and polypeptides.

WO 99/67405 describes leafy cotyledon1 genes and their uses.

The human, murine and plant homologues of CCAAT-binding proteins have been isolated and characterized based on their sequence similarity with their yeast counterparts (Li et al., 1991, *Nucleic Acids Res.* 20:1087-1091). This high degree of sequence homology translates remarkably into functional interchangeability among orthologue proteins of different species (Sinha et al, 1995, *Proc. Natl. Acad. Sci. USA* 92:1624-1628). Unlike yeast, multiple forms of each HAP homolog have been identified in plants (Edwards et al, 1998, *Plant Physiol.* 117:1015-1022).

Molecular and genetic analysis revealed HAP members to be involved in the control of diverse and critical biological processes ranging from development and cell cycle regulation to metabolic control and homeostasis (Lotan et al, 1998, *Cell* 93:1195-1205; Lopez et al, 1996, *Proc. Natl. Acad. Sci. USA* 93:1049-1053). In yeast, HAPs are involved in the transcriptional control of metabolic processes such as the regulation of catabolic derepression of cyc1 and other genes involved in respiration (Becker et al., 1991, *Proc. Natl. Acad. Sci. USA* 88:1968-1972).

In mammalian systems, several reports describe HAPs as direct or indirect regulators of several important genes involved in lipid biosynthesis such as fatty acid synthase (Roder et al, 1997, *Gene* 184:21-26), farnesyl diphosphate (FPP) synthase (Jackson et al, 1995, *J. Biol. Chem.* 270: 21445-21448; Ericsson et al, 1996, *J. Biol. Chem.* 217:24359-24364), glycerol-3-phosphate acyltransferase (GPA, Jackson et al, 1997), acetyl-CoA carboxylase (ACC, Lopez et al, 1996, *Proc. Natl. Acad. Sci. USA* 93:1049-1053) and 3-hydroxy-3-methylglutaryl-coenzyme A (HMG-CoA) synthase (Jackson et al, 1995, *J. Biol. Chem.* 270:21445-21448), among others.

In addition, other CCAAT-binding transcription factors have also been reported to be involved in different aspects of the control of lipid biosynthesis and adipocyte growth and differentiation in mammalian systems (see McKnight et al, 1989).

It appears that the currently available evidence to date points to a family of proteins of the CCAAT-binding transcription factors as important modulators of metabolism and lipid biosynthesis in mammalian systems. Such a determination has not been made for plant systems.

Other polypeptides that influence ovule and embryo development and stimulate cell growth, such as, Lec1, Kn1, WUSCHEL, Zwille and Aintegumeta (ANT) allow for increased transformation efficiencies when expressed in plants. See, for example, U.S. Application No. 2003/0135889, herein incorporated by reference. In fact, a maize Lec1 homologue of the *Arabidopsis* embryogenesis controlling gene AtLEC1, has been shown to increase oil content and transformation efficiencies in plants. See, for example, WO 03001902 and U.S. Pat. No. 6,512,165.

The putative AP2/EREBP transcription factor WRINKLED1 (WR11) is involved in the regulation of seed storage metabolism in *Arabidopsis* (Cermac and Benning, 2004, Plant J. 40:575-585). Expression of the WR11 cDNA under the control of the CaMV 35S promoter led to increased seed oil content. Oil-accumulating seedlings, however, showed aberrant development consistent with a prolonged embryonic state. Nucleic acid molecules encoding WRINKLED1-LIKE polypeptides and methods of use are also described in International Publication No. WO 2006/00732 A2.

Because transcription factors regulate transcription and orchestrate gene expression in plants and other organisms, control of transcription factor gene expression provides a powerful means for altering plant phenotype. The transformation of plants with transcription factors, however, can result in aberrant development based on the overexpression and/or ectopic expression of the transcription factor. In the current invention, it has been found that use of a seed specific promoter, such as SUS2 from *Arabidopsis*, can drive expression of an ODP1 gene thereby increasing oil content in the seeds of a cruciferous oilseed plant without negatively affecting germination and seedling establishment.

SUMMARY OF THE INVENTION

In a first embodiment, the present invention concerns a recombinant DNA construct comprising a polynucleotide encoding an ODP1 polypeptide operably linked to a sucrose synthase 2 promoter wherein said construct increases oil content in the seeds of a cruciferous oilseed plant while maintaining normal germination and further wherein the amino acid sequence of said ODP1 polypeptide has at least 80%, at least 90%, at least 95% or 100% sequence identity to a sequence selected from the group consisting of SEQ ID NO:37, SEQ ID NO:39, and SEQ ID NO:41.

In another embodiment, the present invention concerns a recombinant construct comprising a sucrose synthase 2 promoter which comprises: (a) the nucleotide sequence of SEQ ID NO:43, SEQ ID NO:72 or SEQ ID NO:73, or (b) a nucleotide sequence comprising a functional fragment of the nucleotide sequence of SEQ ID NO:43, SEQ ID NO:72 or SEQ ID NO:73.

In another embodiment, the present invention concerns a transgenic cruciferous oilseed plant comprising in its genome the recombinant DNA construct of the invention. Also included are transgenic seeds obtained from such transgenic cruciferous oilseed plants, wherein the transgenic seed comprises in its genome the recombinant DNA construct of the invention.

In another embodiment, the present invention concerns a method for producing a transgenic cruciferous oilseed plant comprising transforming a cruciferous oilseed plant cell with the recombinant construct of the invention and regenerating a transgenic plant from the transformed plant cell, wherein the transgenic cruciferous oilseed plant comprises in its genome the recombinant DNA construct of the invention.

In another embodiment, the present invention concerns a method for increasing oil content in seeds of a transgenic cruciferous oilseed plant while maintaining normal germination, said method comprising:
(a) transforming a cruciferous oilseed plant cell with a recombinant DNA construct comprising a polynucleotide encoding an ODP1 polypeptide, wherein the amino acid sequence of said ODP1 polypeptide has at least 80%, at least 90% or at least 95% sequence identity with a sequence selected from the group consisting of SEQ ID NO:37, SEQ ID NO:39, and SEQ ID NO:41, said sequence being operably linked to a seed specific promoter;
(b) regenerating a transgenic cruciferous oilseed plant from the transformed cell of step (a), wherein said plant comprises the recombinant DNA construct;
(c) (c) obtaining a transgenic progeny plant derived from the transgenic cruciferous oilseed plant of step (b), wherein the transgenic progeny plant comprises in its genome the recombinant DNA construct;
(d) assaying the transgenic progeny plant obtained from step (c) for oil level and germination; and
(e) selecting those transgenic progeny plants having seeds with an increased level of oil and normal germination when compared to seeds obtained from a control cruciferous oilseed plant, wherein said control plant does not comprise the recombinant DNA construct.

In another embodiment, the present invention concerns a method of the invention wherein the ODP1 polypeptide is a maize ODP1 polypeptide and, more specifically, the amino acid sequence of the ODP1 polypeptide comprises the sequence of SEQ ID NO:37. In addition, the seed specific promoter can be a sucrose synthase 2 promoter and, more specifically, the nucleotide sequence of sucrose synthase 2 promoter comprises (a) the nucleotide sequence of SEQ ID NO:43, SEQ ID NO:72 or SEQ ID NO:73; or (b) a nucleotide sequence comprising a functional fragment of the nucleotide sequence of SEQ ID NO:43, SEQ ID NO:72 or SEQ ID NO:73.

In another embodiment, the present invention concerns oil or by-products obtained from transgenic seed of the invention.

In another embodiment, the cruciferous oilseed plant or seed of any of the compositions or methods of the present invention can be canola or *Arabidopsis* or other plant species including but not limited to the following: *Barbarea vulgaris, Brassica campestris, Brassica carinata, Brassica elongate, Brassica fruticulosa, Brassica hirta, Brassica juncea, Brassica napus, Brassica narinosa, Brassica nigra, Brassica oleracea, Brassica perviridis, Brassica rapa, Brassica rupestris, Brassica septiceps, Brassica tournefortii, Brassica verna, Camelina sativa, Crambe abyssinica, Lepidium campestre, Raphanus sativus, Sinapis alba.*

BRIEF DESCRIPTION OF THE DRAWINGS AND SEQUENCE LISTING

The invention can be more fully understood from the following detailed description and the accompanying drawings and Sequence Listing which form a part of this application.

FIG. 1A-1C show a multiple alignment of the ODP1 polypeptides of *Zea mays* (SEQ ID NO:37), *Glycine max* (SEQ ID NO:39), *Momordica charantia* (SEQ ID NO:41), and the WRINKLED1 gene from *Arabidopsis thaliana* (SEQ ID NO:42; NCBI GI NO. 32364685). The multiple alignment was assembled using the Clustal V method of alignment with the default parameters. Residues that match SEQ ID NO:37 exactly are enclosed in a box. Above the alignment is shown a consensus sequence. A residue is shown in the consensus sequence when all residues at that position are identical.

FIG. 2 shows the percent sequence identity and divergence for each pair of polypeptides from the multiple alignment of FIG. 1A-1C. The consensus sequence is set forth as SEQ ID NO: 74.

SEQ ID NO:1 is the nucleotide sequence of vector pKS121/BS.
SEQ ID NO:2 is the nucleotide sequence of vector pDsRedxKS121/BS.
SEQ ID NO:3 is the nucleotide sequence of vector pKS332,
SEQ ID NO:4 is the nucleotide sequence of PCR primer MWG345.
SEQ ID NO:5 is the nucleotide sequence of PCR primer MWG346.
SEQ ID NO:6 is the nucleotide sequence of vector pKS336,
SEQ ID NO:7 is the nucleotide sequence of the T-DNA of the plant transformation vector pZBL120xKS336.
SEQ ID NO:8 is the nucleotide sequence of PCR primer MWG339.
SEQ ID NO:9 is the nucleotide sequence of PCR primer MWG340.
SEQ ID NO:10 is the nucleotide sequence of vector pKS333.
SEQ ID NO:11 is the nucleotide sequence of the T-DNA of the plant transformation vector pZBL120xKS333.
SEQ ID NO:12 is the nucleotide sequence of PCR primer MWG341.
SEQ ID NO:13 is the nucleotide sequence of PCR primer MWG342.
SEQ ID NO:14 is the nucleotide sequence of vector pKS334.
SEQ ID NO:15 is the nucleotide sequence of the T-DNA of the plant transformation vector pZBL120xKS334.
SEQ ID NO:16 is the nucleotide sequence of vector pKR132.
SEQ ID NO:17 is the nucleotide sequence of vector pKR627.
SEQ ID NO:18 is the nucleotide sequence of vector KS294.
SEQ ID NO:19 is the nucleotide sequence of vector pKR1142.
SEQ ID NO:20 is the nucleotide sequence of vector pKR1141.
SEQ ID NO:21 is the nucleotide sequence of PCR primer SuSy-5.
SEQ ID NO:22 is the nucleotide sequence of PCR primer SuSy-3.
SEQ ID NO:23 is the nucleotide sequence of vector pLF122.

SEQ ID NO:24 is the nucleotide sequence of vector pKR1155.

SEQ ID NO:25 is the nucleotide sequence of vector pKR1158.

SEQ ID NO:26 is the nucleotide sequence of vector pKR1167.

SEQ ID NO:27 is the nucleotide sequence of vector pKR92.

SEQ ID NO:28 is the nucleotide sequence of vector pKR1223.

SEQ ID NO:29 is the nucleotide sequence of vector pKR268.

SEQ ID NO:30 is the nucleotide sequence of vector pKR1143.

SEQ ID NO:31 is the nucleotide sequence of vector pKR1147.

SEQ ID NO:32 is the nucleotide sequence of vector pKR1220.

SEQ ID NO:33 is the nucleotide sequence of vector pKR1144.

SEQ ID NO:34 is the nucleotide sequence of vector pKR1149.

SEQ ID NO:35 is the nucleotide sequence of vector pKR1221.

SEQ ID NO:36 is the nucleotide sequence of the maize ODP1 coding region from cDNA clone cde1c.pk003.o22.

SEQ ID NO:37 is the amino acid sequence of the maize ODP1 encoded by

SEQ ID NO:36. SEQ ID NO:37 is identical to SEQ ID NO:320 in U.S. Pat. No. 7,157,621.

SEQ ID NO:38 is the nucleotide sequence of the soybean ODP1 coding region from cDNA clone se3.pk0003.f5.

SEQ ID NO:39 is the amino acid sequence of the soybean ODP1 encoded by SEQ ID NO:38. SEQ ID NO:39 is identical to SEQ ID NO:481 in U.S. Pat. No. 7,157,621.

SEQ ID NO:40 is the nucleotide sequence of the *Momordica charantia* ODP1 coding region from cDNA clone fds1n.pk015.115.

SEQ ID NO:41 is the amino acid sequence of the *Momordica charantia* ODP1 encoded by SEQ ID NO:40. SEQ ID NO:41 is identical to SEQ ID NO:477 in U.S. Pat. No. 7,157,621.

SEQ ID NO:42 is the amino acid sequence of WRINKLED1 (WR11) from *Arabidopsis thaliana* and corresponds to NCBI GI NO. 32364685.

SEQ ID NO:43 is the nucleotide sequence of the sucrose synthase 2 (SUS2) promoter from *Arabidopsis thaliana* that is present in vector pKR1223.

SEQ ID NO:44 is the nucleotide sequence of the canola SUS2 homolog.

SEQ ID NO:45 is the amino acid sequence of the canola SUS2 homolog encoded by SEQ ID NO:44.

SEQ ID NO:46 is the nucleotide sequence of primer a.

SEQ ID NO:47 is the nucleotide sequence of primer b.

SEQ ID NO:48 is the nucleotide sequence of primer c.

SEQ ID NO:49 is the nucleotide sequence of primer d.

SEQ ID NO:50 is the nucleotide sequence of "PvuII rapa cons", a genomic sequence of canola variety NS1822BC that was generated with primers a and b.

SEQ ID NO:51 is the nucleotide sequence of "1,6 DraI gene cons", a genomic sequence of canola variety NS1822BC that was generated with primers c and d.

SEQ ID NO:52 is the nucleotide sequence of primer SA188.

SEQ ID NO:53 is the nucleotide sequence of primer SA189.

SEQ ID NO:54 is the nucleotide sequence of primer SA190.

SEQ ID NO:55 is the nucleotide sequence of primer SA191.

SEQ ID NO:56 is the nucleotide sequence of "BN SUS2 prom1/PCR blunt", which is derived from 1,6 DraI gene cons (SEQ ID NO:51).

SEQ ID NO:57 is the nucleotide sequence of "BN SUS2 prom2/PCR blunt", which is derived from PvuII rapa cons (SEQ ID NO:50).

SEQ ID NO:58 is the nucleotide sequence of vector KS427.

SEQ ID NO:59 is the nucleotide sequence of vector KS130.

SEQ ID NO:60 is the nucleotide sequence of vector KS432.

SEQ ID NO:61 is the nucleotide sequence of vector ARALO80,

SEQ ID NO:62 is the nucleotide sequence of primer D6 fwd.

SEQ ID NO:63 is the nucleotide sequence of primer D6 rev,

SEQ ID NO:64 is the nucleotide sequence of vector KS119.

SEQ ID NO:65 is the nucleotide sequence of vector KS430.

SEQ ID NO:66 is the nucleotide sequence of vector ARALO78.

SEQ ID NO:67 is the nucleotide sequence of vector KS428.

SEQ ID NO:68 is the nucleotide sequence of vector KS429.

SEQ ID NO:69 is the nucleotide sequence of vector ARALO77.

SEQ ID NO:70 is the nucleotide sequence of vector KS431.

SEQ ID NO:71 is the nucleotide sequence of vector ARALO79.

SEQ ID NO:72 is the nucleotide sequence of the sucrose synthase 2-1 (BnSUS2-1) promoter from *Brassica napus* that is present in BN SUS2 prom1/PCR blunt.

SEQ ID NO:73 is the nucleotide sequence of the sucrose synthase 2-2 (BnSUS2-2) promoter from *Brassica napus* that is present in BN SUS2 prom2/PCR blunt.

The sequence descriptions and Sequence Listing attached hereto comply with the rules governing nucleotide and/or amino acid sequence disclosures in patent applications as set forth in 37 C.F.R. §1.821-1.825.

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. §1.822.

DETAILED DESCRIPTION OF THE INVENTION

All patents, patent applications, and publications cited herein are incorporated by reference in their entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

Units, prefixes, and symbols may be denoted in their SI accepted form. Unless otherwise indicated, nucleic acids are written left to right in 5' to 3' orientation; amino acid sequences are written left to right in amino to carboxyl orientation, respectively. Numeric ranges recited within the specification are inclusive of the numbers defining the range and include each integer within the defined range. Amino acids may be referred to herein by either commonly known three letter symbols or by the one-letter symbols recommended by the IUPAC-IUB Biochemical Nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms ($5^{th}$ edition, 1993). The terms defined below are more fully defined by reference to the specification as a whole.

In the context of this disclosure, a number of terms and abbreviations are used. The following definitions are provided.

The term "ODP1" refers to an ovule development protein 1 that is involved with increasing oil content.

The term "sucrose synthase" (SUS) refers to an enzyme used in carbohydrate metabolism that catalyzes the reversible conversion of sucrose and uridine diphosphate (UDP) to UDP-glucose and fructose in vitro. The terms "*Arabidopsis* sucrose synthase 2", "AtSuSy" and "AtSUS2") are used interchangeably herein. The *Arabidopsis* sucrose synthase 2 gene is from genomic locus At5g49190, The term "germination" refers to the initial stages in the growth of a seed to form a seedling.

The term "recombinant" refers to an artificial combination of two otherwise separated segments of sequence, e.g., by chemical synthesis or by the manipulation of isolated segments of nucleic acids by genetic engineering techniques.

The terms "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., *EMBO J.* 4:2411-2418 (1985); De Almeida et al., *Mol. Gen. Genetics* 218:78-86 (1989)), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others.

This construct may comprise any combination of deoxyribonucleotides, ribonucleotides, and/or modified nucleotides. The construct may be transcribed to form an RNA, wherein the RNA may be capable of forming a double-stranded RNA and/or hairpin structure. This construct may be expressed in the cell, or isolated or synthetically produced. The construct may further comprise a promoter, or other sequences which facilitate manipulation or expression of the construct.

As used herein, "encodes" or "encoding" refers to a DNA sequence which can be processed to generate an RNA and/or polypeptide.

As used herein, "expression" or "expressing" refers to production of a functional product, such as, the generation of an RNA transcript from an introduced construct, an endogenous DNA sequence, or a stably incorporated heterologous DNA sequence. The term may also refer to a polypeptide produced from an mRNA generated from any of the above DNA precursors. Thus, expression of a nucleic acid fragment may refer to transcription of the nucleic acid fragment (e.g., transcription resulting in mRNA or other functional RNA) and/or translation of RNA into a precursor or mature protein (polypeptide).

As used herein, "heterologous" with respect to a sequence means a sequence that originates from a foreign species, or, if from the same species, is substantially modified from its native form in composition and/or genomic locus by deliberate human intervention. For example, with respect to a nucleic acid, it can be a nucleic acid that originates from a foreign species, or is synthetically designed, or, if from the same species, is substantially modified from its native form in composition and/or genomic locus by deliberate human intervention. A heterologous protein may originate from a foreign species or, if from the same species, is substantially modified from its original form by deliberate human intervention.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

The term "plant parts" includes differentiated and undifferentiated tissues including, but not limited to the following: roots, stems, shoots, leaves, pollen, seeds, tumor tissue and various forms of cells and culture (e.g., single cells, protoplasts, embryos and callus tissue). The plant tissue may be in plant or in a plant organ, tissue or cell culture.

The term "plant organ" refers to plant tissue or group of tissues that constitute a morphologically and functionally distinct part of a plant.

"Progeny" comprises any subsequent generation of a plant. Progeny will inherit, and stably segregate, genes and transgenes from its parent plant(s).

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into ac ell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

The term "genome" as it applies to a plant cells encompasses not only chromosomal DNA found within the nucleus, but organelle DNA found within subcellular components (e.g., mitochondrial, plastid) of the cell.

The term "isolated" refers to material, such as a nucleic acid or a protein, which is: (1) substantially or essentially free from components which normally accompany or interact with the material as found in its naturally occurring environment or (2) if the material is in its natural environment, the material has been altered by deliberate human intervention to a composition and/or placed at a locus in the cell other than the locus native to the material.

As used herein, "nucleic acid" means a polynucleotide and includes single or double-stranded polymer of deoxyribonucleotide or ribonucleotide bases. Nucleic acids may also include fragments and modified nucleotides. Thus, the terms "polynucleotide", "nucleic acid sequence", "nucleotide sequence" or "nucleic acid fragment" are used interchangeably and is a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deosycytidylate, "G" for guanylate or deoxyguanylate, "U" for uridlate, "T" for deosythymidylate, "R" for purines (A or G), "Y" for pyrimidines (C or T), "K" for G or T, "H" for A or C or T, "I" for inosine, and "N" for any nucleotide.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric genes to produce the desired phenotype in a transformed plant. Chimeric genes can be designed for use in suppression by linking a nucleic acid fragment or subfragment thereof, whether or not it encodes an active enzyme, in the sense or antisense orientation relative to a plant promoter sequence.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

The terms "homology", "homologous", "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

"Sequence identity" or "identity" in the context of nucleic acid or polypeptide sequences refers to the nucleic acid bases or amino acid residues in two sequences that are the same when aligned for maximum correspondence over a specified comparison window.

Thus, "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90%, or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The "Clustal V method of alignment" corresponds to the alignment method labeled Clustal V (described by Higgins and Sharp, CABIOS. 5:151-153 (1989); Higgins, D. G. et al. (1992) Comput. Appl. Biosci. 8:189-191) and found in the MEGALIGN™ program of the LASERGENE bioinformatics computing suite (DNASTAR Inc., Madison, Wis.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

"BLASTN method of alignment" is an algorithm provided by the National Center for Biotechnology Information (NCBI) to compare nucleotide sequences using default parameters.

It is well understood by one skilled in the art that many levels of sequence identity are useful in identifying polypeptides, from other species, wherein such polypeptides have the same or similar function or activity. Useful examples of percent identities include, but are not limited to, 50%, 55%, 60%, 65%, 70%, 75%, 80%, 85%, 90%, or 95%, or any integer percentage from 50% to 100%. Indeed, any integer amino acid identity from 50% to 100% may be useful in describing the present invention, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Also, of interest is any full-length or partial complement of this isolated nucleotide fragment.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

The term "genome" as it applies to a plant cells encompasses not only chromosomal DNA found within the nucleus, but organelle DNA found within subcellular components (e.g., mitochondrial, plastid) of the cell.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to: promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters". New promoters of various types useful in plant cells are constantly being discovered; numerous examples may be found in the compilation by Okamuro, J. K., and Goldberg, R. B. *Biochemistry of Plants* 15:1-82 (1989).

"Functional variants" of the regulatory sequences (e.g., promoters) are also encompassed by the compositions of the present invention. Functional variants include, for example, the native regulatory sequences of the invention having one or more nucleotide substitutions, deletions or insertions. Functional variants of the invention may be created by site-directed nutagenesis, induced mutation, or may occur as allelic variants (polymorphisms).

As used herein, a "functional fragment" of a regulatory sequence (e.g. a promoter) is a functional variant formed by one or more deletions from a larger regulatory element. For example, the 5' portion of a sequence with promoter activity may be deleted without abolishing promoter activity, as described by Zhu et al., *Plant Cell* 7:1681-1689 (1995). Such variants should retain promoter activity, particularly the ability to drive expression in seed or seed tissues. Activity can be measured by Northern blot analysis, reporter activity measurements when using transcriptional fusions, and the like. See, for example, Sambrook et al. (1989) Molecular Cloning: A Laboratory Manual ($2^{nd}$ ed., Cold Spring Harbor Laboratory, Cold Spring Harbor, N.Y.).

"Translation leader sequence" refers to a polynucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D., *Mol. Biotechnol.* 3:225-236 (1995)).

"3' non-coding sequences", "transcription terminator" or "termination sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al. *Plant Cell* 1:671-680 (1989).

"RNA transcript" refers to the product resulting from RNA polymerase-catalyzed transcription of a DNA sequence. When the RNA transcript is a perfect complementary copy of the DNA sequence, it is referred to as the primary transcript. A RNA transcript is referred to as the mature RNA when it is a RNA sequence derived from post-transcriptional processing of the primary transcript. "Messenger RNA" or "mRNA" refers to the RNA that is without introns and that can be translated into protein by the cell. "cDNA" refers to a DNA that is complementary to, and synthesized from, a mRNA template using the enzyme reverse transcriptase. The cDNA can be single-stranded or converted into double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory: Cold Spring Harbor, N.Y. (1989). Transformation methods are well known to those skilled in the art and are described infra.

"PCR" or "polymerase chain reaction" is a technique for the synthesis of large quantities of specific DNA segments and consists of a series of repetitive cycles (Perkin Elmer Cetus Instruments, Norwalk, Conn.). Typically, the double-stranded DNA is heat denatured, the two primers complementary to the 3' boundaries of the target segment are annealed at low temperature and then extended at an intermediate temperature. One set of these three consecutive steps is referred to as a "cycle".

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host (i.e., to a discrete nucleic acid fragment into which a nucleic acid sequence or fragment can be moved.)

The term "expression", as used herein, refers to the production of a functional end-product (e.g., a mRNA or a protein [either precursor or mature]).

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms.

As used herein, "transgenic" refers to a plant or a cell which comprises within its genome a heterologous polynucleotide. Preferably, the heterologous polynucleotide is stably integrated within the genome such that the polynucleotide is passed on to successive generations. The heterologous polynucleotide may be integrated into the genome alone or as part of an expression construct. Transgenic is used herein to include any cell, cell line, callus, tissue, plant part or plant, the genotype of which has been altered by the presence of heterologous nucleic acid including those transgenics-initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

The present invention concerns a recombinant DNA construct comprising a polynucleotide encoding an ODP1 polypeptide operably linked to a sucrose synthase 2 promoter wherein said construct increases oil content in the seeds of a cruciferous oilseed plant while maintaining normal germination and further wherein the amino acid sequence of said ODP1 polypeptide has at least 80% sequence identity to a sequence selected from the group consisting of SEQ ID NO:37, SEQ ID NO:39, and SEQ ID NO:41.

In another embodiment, the sequence identity can be at least 90% or 95%.

In another embodiment the ODP1 polypeptide comprises a sequence selected from the group consisting of SEQ ID NO:37, SEQ ID NO:39, and SEQ ID NO:41.

In another, embodiment, the sucrose synthase 2 promoter comprises: (a) the nucleotide sequence of SEQ ID NO:43, SEQ ID NO:72 or SEQ ID NO:73; or (b) a nucleotide sequence comprising a functional fragment of the nucleotide sequence of SEQ ID NO:43, SEQ ID NO:72 or SEQ ID NO:73.

ODP1 is a member of the APETALA2 (AP2) family of proteins that play a role in a variety of biological events including, but not limited to, oil content. The AP2/ERF, family of proteins is a plant-specific class of putative transcription factors that have been shown to regulate a wide-variety of developmental processes and are characterized by the presence of an AP2/ERF DNA binding domain. The AP2/ERF proteins have been subdivided into two distinct subfamilies based on whether they contain one (ERF subfamily) or two (AP2 subfamily) DNA binding domains.

Specifically, AP2 (APETALA2) and EREBPs (ethylene-responsive element binding proteins) are the prototypic members of a family of transcription factors unique to plants, whose distinguishing characteristic is that they contain the so-called AP2 DNA-binding domain. AP2/EREBP genes form a large multigene family, and they playa variety of roles throughout the plant life cycle. AP2/EREBP genes are key regulators of several developmental processes, including floral organ identity determination and leaf epidermal cell identity. In *Arabidopsis thaliana*, the homeotic gene APETALA2 (AP2) has been shown to control three salient processes during development: (1) the specification of flower organ identity throughout floral organogenesis (Jofuku et al., Plant Cell 6:1211-1225, 1994); (2) establishment of flower meristem identity (Irish and Sussex, Plant Cell 2:8:741-753, 1990); and (3) the temporal and spatial regulation of flower homeotic gene activity (Drews et al., Cell 65:6:991-1002, 1991). DNA sequence analysis suggests that AP2 encodes a theoretical polypeptide of 432 aa, with a distinct 68 aa repeated motif termed the AP2 domain. This domain has been shown to be essential for AP2 functions and contains within the 68 aa, an eighteen amino acid core region that is predicted to form an amphipathic α-helix (Jofuku et al., Plant Cell 6:1211-1225, 1994). Ap2-like domain-containing transcription factors have been also been identified in both *Arabidopsis thaliana* (Okamuro et al., Proc. Natl. Acad. Sci. USA 94:7076-7081, 1997) and in tobacco with the identification of the ethylene responsive element binding proteins (EREBPs) (Ohme-Takagi and Shinshi, Plant Cell 7:2:173-182, 1995). In *Arabidopsis*, these RAP2 (related to AP2) genes encode two distinct subfamilies of AP2 domain-containing proteins designated AP2-like and EREBP-like (Okamuro et al., Proc. Natl. Acad. Sci. USA 94:7076-7081, 1997). In vitro DNA binding has not been shown to date using the RAP2 proteins. Based upon the presence of two highly conserved motifs YRG and RAYD within the AP2 domain, it has been proposed that binding DNA binding occurs in a manner similar to that of AP2 proteins.

In another embodiment, the present invention concerns a transgenic cruciferous oilseed plant comprising in its genome the recombinant DNA construct of the invention. Also of interest is a transgenic seed obtained from a transgenic plant as described herein, wherein said seed comprises in its genome a recombinant DNA construct of the invention.

In still another aspect, the present invention concerns a method for producing a transgenic cruciferous oilseed plant comprising transforming a cruciferous oilseed plant cell with a recombinant construct of the invention and regenerating a transgenic plant from the transformed plant cell.

This invention concerns a transgenic seed obtained from a transgenic plant made by a method of the invention, wherein said seed comprises in its genome a recombinant DNA construct of the invention.

In another aspect, the present invention concerns a method for increasing oil content in seeds of a transgenic cruciferous oilseed plant while maintaining normal germination, said method comprising:

(a) transforming a cruciferous oilseed plant cell with a recombinant DNA construct comprising a polynucleotide encoding an ODP1 polypeptide, wherein the amino acid sequence of said ODP1 polypeptide has at least 80%, at least 90% or at least 95% sequence identity with a sequence selected from the group consisting of SEQ ID NO:37, SEQ ID NO:39, and SEQ ID NO:41, said sequence being operably linked to a seed specific promoter;

(b) regenerating a transgenic cruciferous oilseed plant from the transformed cell of step (a), wherein said plant comprises the recombinant DNA construct;

(c) obtaining a transgenic progeny plant derived from the transgenic cruciferous oilseed plant of step (b), wherein the transgenic progeny plant comprises in its genome the recombinant DNA construct;

(d) assaying the transgenic progeny plant obtained from step (c) for oil level and germination; and (e) selecting those transgenic progeny plants having seeds with an increased level of oil and normal germination when compared to seeds obtained from a control cruciferous oilseed plant, wherein said control plant does not comprise the recombinant DNA construct.

Preferably, the ODP1 polypeptide is a maize ODP1 polypeptide and, more preferably, the amino acid sequence of the ODP1 polypeptide comprises the sequence of SEQ ID NO:37.

With respect to the seed specific promoter, it can be a sucrose synthase 2 promoter and preferably, the nucleotide sequence of sucrose synthase 2 promoter comprises: (a) the nucleotide sequence of SEQ ID NO:43, SEQ ID NO:72 or SEQ ID NO:73; or (b) a nucleotide sequence comprising a functional fragment of the nucleotide sequence of SEQ ID NO:43, SEQ ID NO:72 or SEQ ID NO:73.

The transgenic cruciferous oil seeds described herein of the invention can be processed to yield oil and/or seed by-products.

In another embodiment, the present invention concerns a recombinant DNA construct comprising a polynucleotide encoding a heterologous polypeptide operably linked to a sucrose synthase 2 promoter, wherein the sucrose synthase 2 promoter comprises: (a) the nucleotide sequence of SEQ ID NO:43, SEQ ID NO:72 or SEQ ID NO:73; (b) a nucleotide sequence comprising a functional fragment of the nucleotide sequence of SEQ ID NO:43, SEQ ID NO:72 or SEQ ID NO:73; or (c) a nucleotide sequence with at least 80%, at least 90% or at least 95% sequence identity to the nucleotide sequence of SEQ ID NO:43, SEQ ID NO:72 or SEQ ID NO:73; wherein the nucleotide sequence of (a), (b) or (c) has seed-specific promoter activity in a plant. The invention also concerns a transgenic plant, plant cell and seed comprising the recombinant DNA construct. The transgenic plant may be a transgenic cruciferous plant.

The nucleotide and deduced amino acid sequence of the canola SUS2 homolog transcript model are set forth as SEQ ID NO:44 and SEQ ID NO:45, respectively.

NCBI GI NO. 150912532 is the nucleotide sequence of the 5'-end of a *Brassica oleracea* cDNA.

SEQ ID NO:72 is the nucleotide sequence of the sucrose synthase 2-1 (BnSUS2-1) promoter from *Brassica napus* that is present in BN SUS2 prom1/PCR blunt. Comparison of SEQ ID NO:72 with SEQ ID NO:44 and NCBI GI NO. 150912532 indicate that nucleotide 427 is at or near the beginning of the 5'-Untranslated region of the canola SUS2 gene. Consequently, a fragment comprising nucleotides 1-426 of SEQ ID NO:72 would be expected to have seed-specific promoter activity in a plant.

SEQ ID NO:73 is the nucleotide sequence of the sucrose synthase 2-2 (BnSUS2-2) promoter from *Brassica napus* that is present in BN SUS2 prom2/PCR blunt. Comparison of SEQ ID NO:73 with SEQ ID NO:44 and NCBI GI NO. 150912532 indicate that nucleotide 1766 is at or near the beginning of the 5'-Untranslated region of the canola SUS2 gene. Consequently, a fragment comprising nucleotides 1-1765 of SEQ ID NO:73 would be expected to have seed-specific promoter activity in a plant.

The cruciferous oilseed plant (or seed) of any of the compositions or methods of the present invention can be canola or *Arabidopsis* or other plant species including but not limited to the following: *Barbarea vulgaris, Brassica campestris, Brassica carinata, Brassica elongate, Brassica fruticulosa, Brassica hirta, Brassica juncea, Brassica napus, Brassica narinosa, Brassica nigra, Brassica oleracea, Brassica perviridis, Brassica rapa, Brassica rupestris, Brassica septiceps, Brassica tournefortii, Brassica verna, Camelina sativa, Crambe abyssinica, Lepidium campestre, Raphanus sativus, Sinapis alba.*

Methods of isolating seed oils are well known in the art: (Young et al., Processing of Fats and Oils, In *The Lipid Handbook*, Gunstone et al., eds., Chapter 5 pp 253-257; Chapman & Hall: London (1994)). Seed by-products include but are not limited to the following: meal, lecithin, gums, free fatty acids, pigments, soap, stearine, tocopherols, sterols and volatiles.

The production of edible vegetable oils including canola oil involves two overall processes, mechanical pressing and extraction, and further processing to remove impurities. The techniques used are similar for most vegetable oils produced from the seeds of plants. The crushing and extraction processes utilized by the canola industry today produce very little change to the fatty acid profile of the oil and the nutritional qualities of the meal.

For example, canola seeds are crushed into two component parts, oil and meal, which are then further manufactured into a wide variety of products. Further manufacturing, called refining, improves the color, flavor and shelf life of canola oil.

Canola oil is extracted in several stages. The first stage in processing canola is to roll or flake the seed. This ruptures cells and makes the oil easier to extract. Next the flaked or rolled seeds are cooked and subjected to a mild pressing process which removes some of the oil and compresses the seeds into large chunks called "cake fragments." The cake fragments undergo further processing to remove most of the remaining oil. The oil extracted during each step is combined. The oil is then subjected to processing according to the end product requirements. Different treatments are used to process salad oils, margarines, and shortenings.

Specifically, canola seed is cleaned by a number of different methods including air aspiration, indent cylinder cleaning, sieve screening, or a combination of these. Cleaning ensures that the seed is free of extraneous plant and other foreign material which is referred to in the industry as "dockage". Seed generally contains less than 2.5% dockage following the cleaning process. Seed that has been cleaned is ready for subsequent crushing into canola oil and meal.

Seed which will be processed for oil and meal is preconditioned using mild heat treatment, and moisture is then adjusted to improve subsequent oil extraction. Following preconditioning, canola seed is next crushed and flaked and then heated slightly. These processes help to maximize oil recovery. The canola flakes are then "prepressed" in screw presses or expellers to reduce the oil content from about 42% in the seed (on an 8% moisture basis) to between 16-20%. Screw pressing also compresses the flakes into more dense cakes (called "press cake") which facilitates oil extraction.

Press cake which results from seed processing is next subjected to one of two types of oil extraction to remove much of the remaining oil. Oil may be extracted using either hexane ("solvent") extraction or by "cold-pressing" (also referred to as "expeller pressing"). The end-market into which the oil is sold generally dictates which form of extraction will be used. Hexane is the extraction medium used for the bulk of canola oil which is sold into the commodity grocery chain market as well as to the food industry. Cold-pressed canola oil represents a much smaller volume sold to consumers and is generally marketed in specialty food stores. Both extraction processes result in an oil essentially bland in taste, light yellow in color, and with excellent nutritional and stability properties.

Hexane extraction reduces the oil content of the press cake to very low levels. Oil recovery from canola seed is approximately 96% when this form of extraction is used. This is accomplished by maximizing contact of the hexane with the press cake through a series of soakings or washings. Residual hexane in the extracted press cake and oil is easily removed by evaporation at low temperature. Solvent residues in oils and meals, when produced in accordance with good manufacturing practice, can be said to be truly insignificant.

The oil which is produced during the extraction process is referred to as "crude oil" because it contains various compounds which must be removed to ensure a product with good stability and shelf-life. These impurities include phospholipids, mucilaginous gums, free fatty acids, color pigments and fine meal particles. Different methods are used to remove these by-products including water precipitation or organic acids in combination with water. Once removed, these, by-products are added to the canola meal fraction in order to increase its feeding value (energy) and make it an even more nutritious product.

Following water precipitation and/or organic acid processing, the oil will still contain color compounds which, if not removed would make it unattractive to the consumer and also reduce its stability. These compounds are extracted through a process called bleaching. In contrast to what may be implied by the term, bleaching does not involve the use of harsh chemicals. Instead, during the bleaching process, the oil is moved through a natural, diatomaceous clay to remove color compounds and other by-products.

Deodorization is the final step in the refining of all vegetable oils, including canola. Deodorization involves the use of steam distillation with the objective being the removal of any residual compounds which, if retained, could impart an adverse odor and taste to the oil. The oil produced is referred to as "refined oil".

In still another embodiment, this invention concerns a transgenic progeny plant obtained from the plant of claim 7 or 12, wherein said transgenic progeny plant comprises the recombinant DNA construct.

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants is well known in the art (Weissbach and Weissbach, In: Methods for Plant Molecular Biology, (Eds.), Academic: San Diego, Calif. (1988)). This regeneration and growth process typically includes the steps of selection of transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

Normal germination of transgenic plant seed is defined as germination frequency that is very similar to the germination frequency of seed of the untransformed variety under produced under identical conditions.

In addition to the above discussed procedures, practitioners are familiar with the standard resource materials which describe specific conditions and procedures for: the construction, manipulation and isolation of macromolecules (e.g., DNA molecules, plasmids, etc.); the generation of recombinant DNA fragments and recombinant expression constructs; and, the screening and isolating of clones. See, for example: Sambrook et al., Molecular Cloning: A Laboratory Manual, Cold Spring Harbor: NY (1989); Maliga et al., Methods in Plant Molecular Biology, Cold Spring Harbor: NY (1995); Birren et al., Genome Analysis: Detecting Genes, Vol. 1, Cold Spring Harbor: NY (1998); Birren et al., Genome Analysis: Analyzing DNA, Vol. 2, Cold Spring Harbor: NY (1998); Plant Molecular Biology: A Laboratory Manual, eds. Clark, Springer: NY (1997).

Examples of cruciferous oilseed plants that can be used to practice the invention include, but are not limited to, *Brassica* species, and *Arabidopsis thaliana*.

Assays for gene expression based on the transient expression of cloned nucleic acid constructs have been developed by introducing the nucleic acid molecules into plant cells by polyethylene glycol treatment, electroporation, or particle bombardment (Marcotte et al., *Nature* 335:454-457 (1988); Marcotte et al., *Plant Cell* 1:523-532 (1989); McCarty et al., *Cell* 66:895-905 (1991); Hattori et al., *Genes Dev.* 6:609-618 (1992); Goff et al., *EMBO J.* 9:2517-2522 (1990)).

Transient expression systems may be used to functionally dissect gene constructs (see generally, Maliga et al., Methods in Plant Molecular Biology, Cold Spring Harbor Press (1995)). It is understood that any of the nucleic acid molecules of the present invention can be introduced into a plant cell in a permanent or transient manner in combination with other genetic elements such as vectors, promoters, enhancers etc.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant organisms and the screening and isolating of clones, (see for example, Sambrook et al., Molecular Cloning: A Laboratory Manual, Cold Spring Harbor Press (1989); Maliga et al., Methods in Plant Molecular Biology, Cold Spring Harbor Press (1995); Birren et al., Genome Analysis: Detecting Genes, 1, Cold Spring Harbor, N.Y. (1998); Birren et al., Genome Analysis: Analyzing DNA, 2, Cold Spring Harbor, N.Y. (1998); Plant Molecular Biology: A Laboratory Manual, eds. Clark, Springer, New York (1997)).

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The meaning of abbreviations is as follows: "sec" means second(s), "min" means minute(s), "h" means hour(s), "d" means day(s), "µL" means microliter(s), "mL" means milliliter(s), "L" means liter(s), "µM" means micromolar, "mM" means millimolar, "M" means molar, "mmol" means millimole(s), "µmole" mean micromole(s), "g" means gram(s), "µg" means microgram(s), "ng" means nanogram(s), "U" means unit(s), "bp" means base pair(s) and "kB" means kilobase(s).

Example 1

Construction of Vector pZBL120xKS336 for Expression of a Zea mays ODP1 Under Control of a Beta-Conqlycinin Promoter Plasmid pKS332 was constructed via a number of different intermediate vectors. The AscI cassette containing Kti3 Promoter::NotI::Kti3 Terminator from pKS121 (PCT Application No. WO 02/00904) was blunt-end cloned into the NotI (filled-in) site on pBLUESCRIPT® II SK+ (Stratagene) to give pKS121/BS (Seq ID NO:1). The NcoI/NotI fragment from expression vector pDsRed-Express (Clontech) was blunt-end cloned into the NotI (filled-in) site of pKS121/BS to give pDsRedxKS121/BS (SEQ ID NO:2). The BamHI cassette containing Kti3 Promoter::DsRed::Kti3 Terminator in pDS-REDxKS121/BS (SEQ ID NO:1) was ligated into the BamHI site of pKS123 (PCT Application No. WO 02/08269) to give pKS332 (SEQ ID NO:3). A DNA fragment encoding the ODP1 polypeptide from maize, Zm-ODP1, described in U.S. Pat. No. 7,157,621, was synthesized by PCR with primers to introduce NotI sites at both ends. Applicants cDNA clone cde1c.pk003.o22 (SEQ ID NO:319 in U.S. Pat. No. 7,157,621) was used as template in a PCR reaction using primers MWG345 (SEQ ID NO:4) and MWG346 (SEQ ID NO:5). The resulting PCR product was digested with NotI restriction enzyme and ligated into the NotI site of pKS332 to give pKS336 (SEQ ID NO:6). Plasmid pKS336 contains the ZM-ODP1 protein-coding region of cDNA clone cde1c.pk003.o22 fused at its 5' terminus with the promoter of the soybean gene for the α'-subunit of β-conglycinin (Beachy et al. (1985) EMBO J. 4:3047-3053) and at its 3' end with the terminator sequence from the phaseolin gene of common bean, Phaseolus vulgaris (Doyle et al. (1986) J. Biol. Chem. 261:9228-9238). The β-conglycinin promoter directs strong seed-specific expression of transgenes in transformed plants.

A 5.9 kb DNA fragment containing the ZM-ODP1 and DsRed expression cassettes was excised from KS336 using the restriction enzyme AscI and the ends were filled-in with T4 DNA polymerase (Promega, Madison, USA). This fragment was ligated to linearized DNA of the Agrobacterium tumefaciens binary vector pZBL120, which had been linearized with EcoRI and BamHI and the ends filled-in, to give pZBL120xKS336. The T-DNA of the plant transformation vector pZBL120xKS336 is set forth as SEQ ID NO:7.

It is noted that the binary vector pZBL120 is identical to the pZBL1 binary vector (American Type Culture Collection Accession No. 209128) described in U.S. Pat. No. 5,968,793, except the NOS promoter was replaced with a 963 bp 35S promoter (NCBI Accession No. V00141; also known as NCBI General Indentifier No. 58821) from nucleotide 6494 to 7456 in the NOS Promoter::nptII::OCS Terminator cassette. The new 35S Promoter::nptII::OCS Terminator cassette serves as a kanamycin (Kan) resistance plant selection marker in pZBL120.

Example 2

Generation and Analysis of Oil Content of Transgenic Arabidopsis Lines Containing a Beta-Conglycinin Promoter::ZM-ODP1::Phaseolin Terminator Expression Cassette Plasmid DNA of pZBL120xKS336, containing the beta-conglycinin promoter::ZM-ODP1::phaseolin terminator expression cassette, was introduced into Agrobacterium tumefaciens NTL4 (Luo et al, Molecular Plant-Microbe Interactions (2001) 14(1):98-103) by electroporation. Briefly, 1 µg plasmid DNA was mixed with 100 µL of electrocompetent cells on ice. The cell suspension was transferred to a 100 µL electroporation cuvette (1 mm gap width) and electroporated using a BIORAD electroporator set to 1 kV, 400Ω and 25 µF. Cells were transferred to 1 mL LB medium and incubated for 2 h at 30° C. Cells were plated onto LB medium containing 50 µg/mL kanamycin. Plates were incubated at 30° C. for 60 h. Recombinant Agrobacterium cultures (500 mL LB, 50 µg/mL kanamycin) were inoculated from single colonies of transformed agrobacterium cells and grown at 30° C. for 60 h. Cells were harvested by centrifugation (5000×g, 10 min) and resuspended in 1 L of 5% (W/V) sucrose containing 0.05% (V/V) Silwet. Arabidopsis plants were grown in soil at a density of 30 plants per 100 cm$^2$ pot in METRO-MIX® 360 soil mixture for 4 weeks (22° C., 16 h light/8 h dark, 100 µE m$^{-2}$s$^{-1}$). Plants were repeatedly dipped into the *Agrobacterium* suspension harboring the binary vector pZBL120xKS336 and kept in a dark, high humidity environment for 24 h. Plants were grown for three to four weeks under standard plant growth conditions described above and plant material was harvested and dried for one week at ambient temperatures in paper bags. Seeds were harvested using a 0.425 mm mesh brass sieve.

Cleaned *Arabidopsis* seeds (2 grams, corresponding to about 100,000 seeds) were sterilized by washes in 45 mL of 80% ethanol, 0.01% TRITON® X-100, followed by 45 mL of 30% (V/V) household bleach in water, 0.01% TRITON® X-100 and finally by repeated rinsing in sterile water. Aliquots of 20,000 seeds were transferred to square plates (20× 20 cm) containing 150 mL of sterile plant growth medium comprised of 0.5×MS salts, 0.53% (W/V) sorbitol, 0.05 MES/KOH (pH 5.8), 200 µg/mL TIMENTIN®, and 50 µg/mL kanamycin solidified with 10 g/L agar. Homogeneous dispersion of the seed on the medium was facilitated by mixing the aqueous seed suspension with an equal volume of melted plant growth medium. Plates were incubated under standard growth conditions for ten days. Kanamycin-resistant seedlings were transferred to plant growth medium without selective agent and grown for one week before transfer to soil. Plants were grown to maturity and T2 seeds were harvested and plated on selective media containing kanamycin. Approximately 100 events were generated in this manner. Wild-type (WT) control plants were grown in the same flat containing pZBL120xKS336 T1 plants. T2 seed were harvested and oil content was measured by NMR as follows.

NMR Based Analysis of Seed Oil Content:

Seed oil content was determined using a Maran Ultra NMR analyzer (Resonance Instruments Ltd, Whitney, Oxfordshire, UK). Samples (e.g., batches of *Arabidopsis* seed ranging in weight between 5 and 200 mg) were placed into pre-weighed 2 mL polypropylene tubes (Corning Inc, Corning N.Y., USA; Part no. 430917) previously labeled with unique bar code identifiers. Samples were then placed into 96 place carriers and processed through the following series of steps by an ADEPT COBRA 600™ SCARA robotic system:
1. pick up tube (the robotic arm was fitted with a vacuum pickup devise);
2. read bar code;
3. expose tube to antistatic device (ensured that *Arabidopsis* seed were not adhering to the tube walls);
4. weigh tube (containing the sample), to 0.0001 g precision;
5. take NMR reading; measured as the intensity of the proton spin echo 1 msec after a 22.95 MHz signal had been applied to the sample (data was collected for 32 NMR scans per sample);
6. return tube to rack; and
7. repeat process with next tube.

Bar codes, tubes weights and NMR readings were recorded by a computer connected to the system. Sample weight was determined by subtracting the polypropylene tube weight from the weight of the tube containing the sample.

Seed oil content (on a % seed weight basis) of *Arabidopsis* seed was calculated as follows:

mg oil=(NMR signal−2.1112)/37.514;

% oil=[(mg oil)/1000]/[g of seed sample weight]×100.

Prior to establishing this formula, *Arabidopsis* seed oil was extracted as follows. Approximately 5 g of mature *Arabidopsis* seed (cv Columbia) were ground to a fine powder using a mortar and pestle. The powder was placed into a 33×94 mm paper thimble (Ahlstrom # 7100-3394; Ahlstrom, Mount Holly Springs, Pa., USA) and the oil extracted during approximately 40 extraction cycles with petroleum ether (BP 39.9-51.7° C.) in a Soxhlet apparatus. The extract was allowed to cool and the crude oil was recovered by removing the solvent under vacuum in a rotary evaporator. Calibration parameters were determined by precisely weighing 11 standard samples of partially purified *Arabidopsis* oil (samples contained 3.6, 6.3, 7.9, 9.6, 12.8, 16.3, 20.3, 28.2, 32.1, 39.9 and 60 mg of partially purified *Arabidopsis* oil) weighed to a precision of 0.0001 g) into 2 mL polypropylene tubes (Corning Inc, Corning N.Y., USA; Part no. 430917) and subjecting them to NMR analysis. A calibration curve of oil content (% seed weight basis) to NMR value was established.

Seed oil content of most transgenic lines was increased when compared to oil content of seed collected from wild-type control plants grown in the same flat. The phenotype of two representative transgenic lines, C00536 and C00576, are described below in detail. Kanamycin-resistant T2 seedlings were transferred from selective growth media to soil. For C00536, thirteen T2 plants were grown with four wild-type (WT) control plants. For C00576 ten T2 plants were grown with seven WT control plants. Plants were grown to maturity, T3 seed were harvested from individual plants and subjected to oil quantitation by NMR.

Data are summarized in Table 1. Presence of the pZBL120xKS336 transgene is associated with an increase in oil content in transgenic T3 seed when compared *Arabidopsis* plants of identical genetic background that lack the transgene.

TABLE 1

Oil Content of T3 Seed of pZBL120xKS336 Transgenics

| Exp | Event ID | Plant # | % Oil |
| --- | --- | --- | --- |
| 1 | C00536 | 1 | 45.7 |
| 1 | C00536 | 2 | 45.1 |
| 1 | C00536 | 3 | 45.0 |
| 1 | C00536 | 4 | 44.6 |
| 1 | C00536 | 5 | 44.0 |
| 1 | C00536 | 6 | 43.7 |
| 1 | C00536 | 7 | 43.5 |
| 1 | C00536 | 8 | 42.8 |
| 1 | C00536 | 9 | 42.7 |
| 1 | C00536 | 10 | 42.0 |
| 1 | C00536 | 11 | 42.0 |
| 1 | C00536 | 12 | 41.9 |
| 1 | C00536 | 13 | 39.9 |
| 1 | C00536 | AVG | 43.3 |
| 1 | WT | 1 | 39.5 |
| 1 | WT | 2 | 37.5 |
| 1 | WT | 3 | 37.0 |
| 1 | WT | 4 | 34.7 |
| 1 | WT | AVG | 37.2 |
| 2 | C00576 | 1 | 48.0 |
| 2 | C00576 | 2 | 47.9 |
| 2 | C00576 | 3 | 45.9 |
| 2 | C00576 | 4 | 45.3 |
| 2 | C00576 | 5 | 44.5 |
| 2 | C00576 | 6 | 43.7 |
| 2 | C00576 | 7 | 43.6 |
| 2 | C00576 | 8 | 42.1 |
| 2 | C00576 | 9 | 41.9 |
| 2 | C00576 | 10 | 41.0 |
| 2 | C00576 | AVG | 44.4 |
| 2 | WT | 1 | 42.2 |
| 2 | WT | 2 | 40.9 |
| 2 | WT | 3 | 40.4 |
| 2 | WT | 4 | 39.3 |
| 2 | WT | 5 | 38.7 |
| 2 | WT | 6 | 38.0 |
| 2 | WT | 7 | 37.8 |
| 2 | WT | AVG | 39.6 |

Transgenic T3 seed selections that no longer segregated for the DsRed marker gene were identified by visual inspection using a suitable light source. For both events non-segregating transgenic seed were planted in soil alongside untransformed WT plants.

T4 seed were harvested from individual T3 plants and WT controls. Oil content was measured by NMR (Table 2). Presence of the pZBL120xKS336 transgene is associated with an increase in oil content in transgenic T4 seed when compared to *Arabidopsis* plants of identical genetic background that lack the transgene.

TABLE 2

Oil Content of T4 Seed of pZBL120xKS336 Transgenics

| Exp | Event ID | Plant # | % Oil |
|---|---|---|---|
| 1 | C00536 | 1 | 46.5 |
| 1 | C00536 | 2 | 46.5 |
| 1 | C00536 | 3 | 46.4 |
| 1 | C00536 | 4 | 46.3 |
| 1 | C00536 | 5 | 46.3 |
| 1 | C00536 | 6 | 46.2 |
| 1 | C00536 | 7 | 46.2 |
| 1 | C00536 | 8 | 46.2 |
| 1 | C00536 | 9 | 46.2 |
| 1 | C00536 | 10 | 46.1 |
| 1 | C00536 | 11 | 46.0 |
| 1 | C00536 | 12 | 45.8 |
| 1 | C00536 | 13 | 45.2 |
| 1 | C00536 | 14 | 45.1 |
| 1 | C00536 | 15 | 45.1 |
| 1 | C00536 | 16 | 44.5 |
| 1 | C00536 | 17 | 43.5 |
| 1 | C00536 | 18 | 43.4 |
| 1 | C00536 | AVG | 45.6 |
| 1 | WT | 1 | 44.8 |
| 1 | WT | 2 | 44.6 |
| 1 | WT | 3 | 42.3 |
| 1 | WT | 4 | 42.1 |
| 1 | WT | 5 | 42.0 |
| 1 | WT | AVG | 43.2 |
| 2 | C00536 | 1 | 45.7 |
| 2 | C00536 | 2 | 45.6 |
| 2 | C00536 | 3 | 45.6 |
| 2 | C00536 | 4 | 45.4 |
| 2 | C00536 | 5 | 45.4 |
| 2 | C00536 | 6 | 45.4 |
| 2 | C00536 | 7 | 45.4 |
| 2 | C00536 | 8 | 45.4 |
| 2 | C00536 | 9 | 45.4 |
| 2 | C00536 | 10 | 45.1 |
| 2 | C00536 | 11 | 45.1 |
| 2 | C00536 | 12 | 45.0 |
| 2 | C00536 | 13 | 44.8 |
| 2 | C00536 | 14 | 44.7 |
| 2 | C00536 | 15 | 44.6 |
| 2 | C00536 | 16 | 44.5 |
| 2 | C00536 | 17 | 43.5 |
| 2 | C00536 | 18 | 43.1 |
| 2 | C00536 | AVG | 45.0 |
| 2 | WT | 1 | 43.8 |
| 2 | WT | 2 | 43.3 |
| 2 | WT | 3 | 42.3 |
| 2 | WT | 4 | 41.8 |
| 2 | WT | 5 | 41.5 |
| 2 | WT | 6 | 40.2 |
| 2 | WT | AVG | 42.1 |
| 3 | C00576 | 1 | 45.3 |
| 3 | C00576 | 2 | 44.8 |
| 3 | C00576 | 3 | 44.7 |
| 3 | C00576 | 4 | 44.7 |
| 3 | C00576 | 5 | 44.4 |
| 3 | C00576 | 6 | 44.2 |
| 3 | C00576 | 7 | 44.2 |
| 3 | C00576 | 8 | 44.2 |
| 3 | C00576 | 9 | 44.2 |
| 3 | C00576 | 10 | 44.0 |
| 3 | C00576 | 11 | 43.8 |
| 3 | C00576 | 12 | 43.3 |
| 3 | C00576 | 13 | 43.1 |
| 3 | C00576 | 14 | 43.0 |
| 3 | C00576 | 15 | 41.8 |
| 3 | C00576 | 16 | 41.1 |
| 3 | C00576 | AVG | 43.8 |
| 3 | WT | 1 | 43.8 |
| 3 | WT | 2 | 42.9 |
| 3 | WT | 3 | 42.4 |
| 3 | WT | 4 | 41.9 |
| 3 | WT | 5 | 41.6 |
| 3 | WT | 6 | 40.3 |
| 3 | WT | 7 | 37.5 |
| 3 | WT | 8 | 41.1 |
| 3 | WT | AVG | 41.4 |
| 4 | C00576 | 1 | 46.6 |
| 4 | C00576 | 2 | 46.4 |
| 4 | C00576 | 3 | 46.3 |
| 4 | C00576 | 4 | 46.2 |
| 4 | C00576 | 5 | 46.2 |
| 4 | C00576 | 6 | 46.2 |
| 4 | C00576 | 7 | 46.2 |
| 4 | C00576 | 8 | 45.7 |
| 4 | C00576 | 9 | 45.7 |
| 4 | C00576 | 10 | 45.6 |
| 4 | C00576 | 11 | 45.6 |
| 4 | C00576 | 12 | 45.4 |
| 4 | C00576 | 13 | 45.4 |
| 4 | C00576 | 14 | 45.1 |
| 4 | C00576 | 15 | 45.0 |
| 4 | C00576 | 16 | 44.3 |
| 4 | C00576 | 17 | 44.2 |
| 4 | C00576 | AVG | 45.7 |
| 4 | WT | 1 | 44.7 |
| 4 | WT | 2 | 44.6 |
| 4 | WT | 3 | 44.4 |
| 4 | WT | 4 | 43.7 |
| 4 | WT | 5 | 43.5 |
| 4 | WT | 6 | 42.2 |
| 4 | WT | AVG | 43.9 |

A total of five flats were planted using WT seed and homozygous T4 seed of C00536 and C00576. Twenty-four transgenic T4 plants were grown alongside twelve WT plants. Plants were grown to maturity. From each flat WT and transgenic seed were bulk-harvested. Oil content of bulk seed samples was measured by NMR (Table 3). Presence of the pZBL120xKS336 transgene is associated with an increase in oil content in transgenic T5 seed when compared to *Arabidopsis* plants of identical genetic background that lack the transgene.

Seed oil content in a given plant is a highly variable trait that responds strongly to plant growth conditions (Li Y, Beisson F, Pollard M, Ohlrogge J (2006) Oil content of *Arabidopsis* seeds: The influence of seed anatomy, light and plant-to-plant variation, Phytochemistry 67:904-915). It is therefore important that an increase in oil content associated with a particular strategy is observed in multiple environments, over several generations and under conditions that allow for maximal oil accumulation by isogenic control lines. The increase in oil content associated with presence of the pZBL120xKS336 transgene was consistently observed over three generations and in different growth chambers. The average oil increase associated with two different pZBL120xKS336 transgenic events was at least 2% points and as high as 3.6% points (i.e., an oil increase of as high as 8.5% compared to untransformed WT seed). This oil increase was observed under growth conditions in which untransformed *Arabidopsis* seed produced the expected levels of oil, indicating that oil seed storage lipid accumulation was operating at maximum levels.

TABLE 3

Oil Content of T5 Seed of pZBL120xKS336 Transgenics

| Flat ID | Event ID | Oil (%) | Δ Oil (% Points) | Δ Oil (%) |
|---|---|---|---|---|
| A | C00576 | 45.1 | 1.7 | 3.9 |
|   | WT | 43.5 |   |   |
| B | C00576 | 46.4 | 1.9 | 4.2 |
|   | WT | 44.5 |   |   |
| C | C00576 | 44.8 | 2.3 | 5.5 |
|   | WT | 42.5 |   |   |
| D | C00576 | 45.5 | 2.0 | 4.7 |
|   | WT | 43.4 |   |   |
| E | C00576 | 44.6 | 2.0 | 4.7 |
|   | WT | 42.6 |   |   |
| AVG | C00576 |   | 2.0 | 4.6 |
| A | C00536 | 45.9 | 3.3 | 7.8 |
|   | WT | 42.6 |   |   |
| B | C00536 | 45.8 | 3.4 | 8.1 |
|   | WT | 42.4 |   |   |
| C | C00536 | 46.7 | 4.7 | 11.2 |
|   | WT | 42.0 |   |   |
| D | C00536 | 44.7 | 3.9 | 9.6 |
|   | WT | 40.8 |   |   |
| E | C00536 | 46.2 | 2.6 | 6.0 |
|   | WT | 43.5 |   |   |
| AVG | C00536 |   | 3.6 | 8.5 |

Example 3

Construction of Vector pZBL120xKS333 for Expression of a *Momordica charantia* ODP1 Under Control of a Beta-Conglycinin Promoter An ODP1 protein-coding region from balsam pear (*Momordica charantia*) described in detail in U.S. Pat. No. 7,157,621 was synthesized by PCR with primers to introduce NotI sites at both ends of the gene. Applicants cDNA clone fds1n.pk015.115 was used a template in the PCR reaction using primers MWG339 (SEQ ID NO:8) and MWG340 (SEQ ID NO:9). The resulting PCR product was digested with NotI restriction enzyme and ligated into the NotI site of pKS332 to give pKS333 (SEQ ID NO:10).
A 6.1 kb DNA fragment containing the MC-ODP1 and DsRed expression cassettes was excised from KS333 using the restriction enzyme AscI, the ends were filled-in with T4 DNA polymerase (Promega, Madison, USA) and the fragment was blunt-end ligated to DNA of the *Agrobacterium tumefaciens* binary vector pZBL120, which had been linearized with EcoRI and BamHI and the ends filled-in. The resulting plant transformation vector was designated pZBL120xKS333, and the T-DNA of this vector is set forth as SEQ ID NO:11.

Example 4

Construction of Vector pZBL120xKS334 for Expression of a *Glycine max* ODP1 Under Control of a Beta-Conglycinin Promoter An ODP1 protein-coding region from soybean described in detail in U.S. Pat. No. 7,157,621 was synthesized by PCR with primers to introduce NotI sites at both ends of the gene. Applicants cDNA clone se3.pk0003.f5 was used as template in the PCR reaction using primers MWG341 (SEQ ID NO:12) and MWG342 (SEQ ID NO:13). The resulting PCR product was digested with NotI restriction enzyme and ligated into the NotI site of pKS332 to give pKS334 (SEQ ID NO:14).
A 6.1 kb DNA fragment containing the GM-ODP1 and DsRed expression cassettes was excised from KS334 using the restriction enzyme AscI, the ends were filled-in with T4 DNA polymerase (Promega, Madison, USA) and the fragment was blunt-end ligated to DNA of the *Agrobacterium tumefaciens* binary vector pZBL120, which had been linearized with EcoRI and BamHI and the ends filled-in. The resulting plant transformation vector was designated pZBL120xKS334, and the T-DNA of this vector is set forth as SEQ ID NO:15.

Example 5

Generation of *Arabidopsis* Lines Transformed with *Momordica charantia* ODP1 or *Glycine max* ODP1 and Analysis of Seed Oil Content Binary vector constructs pZBL120xKS333 (*Momordica charantia* ODP1) and pZBL120xKS334 (*Glycine max* ODP1) were used for *Arabidopsis* transformation using the floral dip method as described above. Transgenic lines were selected on plant growth media containing kanamycin. 75 and 190 lines were generated with pZBL120xKS333 and pZBL120xKS334, respectively. T1 plants of all lines were grown with 13 untransformed WT plants in the same growth Chamber. Plants were grown to maturity. Seed were harvested form individual plants and oil content was measured by NMR (TABLE 4)

TABLE 4

Oil Content of T2 seed of pZBL120xKS333 and pZBL120xKS334 Transgenics

| *Arabidopsis* Line | # of Plants | % Oil Range | Average % Oil |
|---|---|---|---|
| pZBL120xKS333 | 77 | 25.5-46.6 | 41.7 |
| pZBL120xKS334 | 180 | 16.0-48.1 | 40.7 |
| WT | 13 | 31.9-43.2 | 39.1 |

T2 seed of two representative transgenic lines, 4445 (pZBL120xKS333) and 4485 (pZBL120xKS334), had an oil content of 45.1% and 45.2% respectively. T2 seed of these two lines were germinated on selective media, seedlings were transferred to soil, T2 plants were grown to maturity and T3 seed were harvested. After one more round of germination on selective media and seed production for each event five flats were planted with 24 kanamycin-resistant 4445 or 4485 seedlings and 12 WT seedlings. Plants were grown to maturity. From each flat WT and transgenic seed were bulk-harvested. Oil content of bulk seed samples was measured by NMR (Table 5). Presence of the pZBL120xKS333 or pZBL120xKS334 transgenes is associated with an increase in oil content in transgenic T5 seed when compared to *Arabidopsis* plants of identical genetic background that lack the transgene.

TABLE 5

Oil Content of T5 seed of pZBL120xKS333 and pZBL120xKS334 Transgenics

| Flat ID | Construct | Event ID | Oil (%) | Δ Oil (% Points) | Δ Oil (%) |
|---|---|---|---|---|---|
| A | pZBL120xKS333 | 4445 | 44.9 | 0.7 | 1.5 |
|   |               | WT   | 44.2 |     |     |
| B | pZBL120xKS333 | 4445 | 45.3 | 1.8 | 4.0 |
|   |               | WT   | 43.6 |     |     |
| C | pZBL120xKS333 | 4445 | 46.0 | 2.4 | 5.4 |
|   |               | WT   | 43.7 |     |     |
| D | pZBL120xKS333 | 4445 | 44.6 | 1.4 | 3.2 |
|   |               | WT   | 43.2 |     |     |
| E | pZBL120xKS333 | 4445 | 43.2 | −0.6 | −1.4 |
|   |               | WT   | 43.8 |     |     |
| AVG | pZBL120xKS333 |    |      | 1.1 | 2.5 |
| A | pZBL120xKS334 | 4485 | 45.4 | 2.8 | 6.7 |
|   |               | WT   | 42.5 |     |     |
| B | pZBL120xKS334 | 4485 | 44.4 | 1.3 | 3.1 |
|   |               | WT   | 43.1 |     |     |
| C | pZBL120xKS334 | 4485 | 44.5 | 1.7 | 4.0 |
|   |               | WT   | 42.8 |     |     |
| D | pZBL120xKS334 | 4485 | 45.1 | 1.5 | 3.3 |
|   |               | WT   | 43.7 |     |     |
| E | pZBL120xKS334 | 4485 | 45.4 | 1.6 | 3.8 |
|   |               | WT   | 43.8 |     |     |
| AVG | pZBL120xKS334 |    |      | 1.8 | 4.2 |

The oil increase associated with presence of the *Momordica charantia* ODP1 transgene (pZBL120xKS333) is 1.1% points (i.e., an oil increase of 2.5% compared to untransformed WT seed).

The oil increase associated with presence of the *Glycine max* ODP1 transgene (pZBL120xKS334) is 1.8% points (i.e., an oil increase of 4.2% compared to untransformed WT seed).

Example 6

Compositional Analysis of *Arabidopsis* Seed Transformed with *Zea mays* ODP1, *Momordica charantia* ODP1 or *Glycine max* ODP1

T5 seed of *Arabidopsis* events C00536, 4445 and 4485 carrying pZBL120xKS336 (*Zea mays* ODP), pZBL120xKS333 (*Momordica charantia* ODP1) and pZBL120xKS334 (*Glycine max* ODP1) transgenes, respectively, and WT seed derived from plants grown alongside each of the transgenic events were subjected to compositional analysis as described below. Seed weight was measured by determining the weight of 100 seed. This analysis was performed in triplicate.

Tissue Preparation:

*Arabidopsis* seed (approximately 0.5 g in a ½×2" polycarbonate vial) was ground to a homogeneous paste in a GENO-GRINDER® (3×30 sec at 1400 strokes per minute, with a 15 sec interval between each round of agitation). After the second round of agitation the vials were removed and the *Arabidopsis* paste was scraped from the walls with a spatula prior to the last burst of agitation.

Determination of Protein Content:

Protein contents were estimated by combustion analysis on a Thermo FINNIGAN™ Flash 1112EA combustion analyzer running in the NCS mode (vanadium pentoxide was omitted) according to instructions of the manufacturer. Triplicate samples of the ground pastes, 4-8 mg, weighed to an accuracy of 0.001 mg on a METTLER-TOLEDO® MX5 micro balance, were used for analysis. Protein contents were calculated by multiplying % N, determined by the analyzer, by 6.25. Final protein contents were expressed on a % tissue weight basis.

Determination of Non-structural Carbohydrate Content:

Sub-samples (30-35 mg) of the ground paste were weighed (to an accuracy of 0.1 mg) into 13×100 mm glass tubes; the tubes had TEFLON® lined screw-cap closures. Three replicates were prepared for each sample tested.

Lipid extraction was performed by adding 2 ml aliquots of heptane to each tube. The tubes were vortex mixed and placed into an ultrasonic bath (VWR Scientific Model 750D) filled with water heated to 60° C. The samples were sonicated at full-power (~360 W) for 15 min and were then centrifuged (5 min×1700 g). The supernatants were transferred to clean 13×100 mm glass tubes and the pellets were extracted 2 more times with heptane (2 ml, second extraction; 1 ml third extraction) with the supernatants from each extraction being pooled. After lipid extraction 1 ml acetone was added to the pellets and after vortex mixing, to fully disperse the material, they were taken to dryness in a Speedvac.

Non-structural Carbohydrate Extraction and Analysis:

Two ml of 80% ethanol was added to the dried pellets from above. The samples were thoroughly vortex mixed until the plant material was fully dispersed in the solvent prior to sonication at 60° C. for 15 min. After centrifugation, 5 min× 1700 g, the supernatants were decanted into clean 13×100 mm glass tubes. Two more extractions with 80% ethanol were performed and the supernatants from each were pooled. The extracted pellets were suspended in acetone and dried (as above). An internal standard β-phenyl glucopyranoside (100 µl of a 0.5000+/−0.0010 g/100 ml stock) was added to each extract prior to drying in a Speedvac. The extracts were maintained in a desiccator until further analysis.

The acetone dried powders from above were suspended in 0.9 ml MOPS (3-N[Morpholino]propane-sulfonic acid; 50 mM, 5 mM CaCl$_2$, pH 7.0) buffer containing 100 U of heat-stable α-amylase (from *Bacillus licheniformis*; Sigma A-4551). Samples were placed in a heat block (90° C.) for 75 min and were vortex mixed every 15 min. Samples were then allowed to cool to room temperature and 0.6 ml acetate buffer (285 mM, pH 4.5) containing 5 U amyloglucosidase (Roche 110 202 367 001) was added to each. Samples were incubated for 15-18 h at 55° C. in a water bath fitted with a reciprocating shaker; standards of soluble potato starch (Sigma S-2630) were included to ensure that starch digestion went to completion.

Post-digestion the released carbohydrates were extracted prior to analysis. Absolute ethanol (6 ml) was added to each tube and after vortex mixing the samples were sonicated for 15 min at 60° C. Samples were centrifuged (5 min×1700 g) and the supernatants were decanted into clean 13×100 mm glass tubes. The pellets were extracted 2 more times with 3 ml of 80% ethanol and the resulting supernatants were pooled. Internal standard (100 ul β-phenyl glucopyranoside, as above) was added to each sample prior to drying in a Speedvac.

Sample Preparation and Analysis:

The dried samples from the soluble and starch extractions described above were solubilized in anhydrous pyridine (Sigma-Aldrich P57506) containing 30 mg/ml of hydroxylamine HCl (Sigma-Aldrich 159417). Samples were placed on an orbital shaker (300 rpm) overnight and were then heated for 1 hr (75° C.) with vigorous vortex mixing applied every 15 min. After cooling to room temperature, 1 ml hexamethyldisilazane (Sigma-Aldrich H-4875) and 100 µl trifluoroacetic acid (Sigma-Aldrich T-6508) were added. The samples were vortex mixed and the precipitates were allowed to settle prior to transferring the supernatants to GC sample vials.

Samples were analyzed on an Agilent 6890 gas chromatograph fitted with a DB-17MS capillary column (15m×0.32 mm×0.25 um film). Inlet and detector temperatures were both 275° C. After injection (2 µl, 20:1 split) the initial column temperature (150° C.) was increased to 180° C. at a rate of 3° C./min and then at 25° C./min to a final temperature of 320° C. The final temperature was maintained for 10 min. The carrier gas was $H_2$ at a linear velocity of 51 cm/sec. Detection was by flame ionization. Data analysis was performed using Agilent ChemStation software. Each sugar was quantified relative to the internal standard and detector responses were applied for each individual carbohydrate (calculated from standards run with each set of samples). Final carbohydrate concentrations were expressed on a tissue weight basis.

sistent change in protein content or seed weight that can be attributed to the pZBL120xKS333, 334 and 336 transgenes.

Example 7

Germination Assays of *Arabidopsis* Seed Transformed with *Zea mays* ODP1, *Momordica charantia* ODP1 or *Glycine max* ODP1

T5 seed of *Arabidopsis* events C00536, 4445 and 4485 carrying pZBL120xKS336 (*Zea mays* ODP1), pZBL120xKS333 (*Momordica charantia* ODP1) and pZBL120xKS334 (*Glycine max* ODP1) transgenes, respectively, were subjected to germination assays on standard *Arabidopsis* growth media (see above) containing either 10 g $L^{-1}$ sucrose or equimolar amounts of sorbitol (5.3 g $L^{-1}$). Seeds were surface-sterilized and homogeneous dispersion of the seed on the medium was facilitated by mixing the aqueous

TABLE 6

Composition Analysis of pZBL120xKS336, pZBL120xKS333 and pZBL120xKS334 Transgenic Seed and WT Control Seed

| Construct | Event ID | Oil (%, NMR) | Protein % | Seed Weight (µg) | fructose (µg $mg^{-1}$ seed) |
|---|---|---|---|---|---|
| pZBL120xKS336 | C00536 | 46.7 | 15.7 | 24 | 0.6 |
| | WT | 42 | 18.1 | 24 | 1 |
| | Δ TG/WT % | 11.2 | −13.3 | 0.0 | −40.0 |

| Construct | Event ID | glucose (µg $mg^{-1}$ seed) | sucrose (µg $mg^{-1}$ seed) | raffinose (µg $mg^{-1}$ seed) | stachyose (µg $mg^{-1}$ seed) |
|---|---|---|---|---|---|
| pZBL120xKS336 | C00536 | 8.5 | 17.2 | 0.4 | 2.1 |
| | WT | 12.1 | 29.2 | 0.8 | 3.1 |
| | ΔTG/WT % | −29.8 | −41.1 | −50.0 | −32.3 |

| Construct | Event ID | Oil (%, NMR) | Protein % | Seed Weight (µg) | fructose (µg $mg^{-1}$ seed) |
|---|---|---|---|---|---|
| pZBL120xKS333 | 4445 | 46 | 15 | 21.7 | 1 |
| | WT | 43.7 | 14.8 | 20.7 | 1.2 |
| | Δ TG/WT % | 5.3 | 1.4 | 4.8 | −16.7 |

| Construct | Event ID | glucose (µg $mg^{-1}$ seed) | sucrose (µg $mg^{-1}$ seed) | raffinose (µg $mg^{-1}$ seed) | stachyose (µg $mg^{-1}$ seed) |
|---|---|---|---|---|---|
| pZBL120xKS333 | 4445 | 7.8 | 14.6 | 0.5 | 2 |
| | WT | 10.3 | 26.6 | 0.6 | 3.6 |
| | Δ TG/WT % | −24.3 | −45.1 | −16.7 | −44.4 |

| Construct | Event ID | Oil (%, NMR) | Protein % | Seed Weight (µg) | fructose (µg $mg^{-1}$ seed) |
|---|---|---|---|---|---|
| pZBL120xKS334 | 4485 | 45.4 | 14.8 | 20.3 | 0.6 |
| | WT | 42.5 | 14.5 | 20.7 | 0.9 |
| | Δ TG/WT % | 6.8 | 2.1 | −1.9 | −33.3 |

| Construct | Event ID | glucose (µg $mg^{-1}$ seed) | sucrose (µg $mg^{-1}$ seed) | raffinose (µg $mg^{-1}$ seed) | stachyose (µg $mg^{-1}$ seed) |
|---|---|---|---|---|---|
| pZBL120xKS334 | 4485 | 6.3 | 11.7 | 0.5 | 1.6 |
| | WT | 10.4 | 30.4 | 0.7 | 3.3 |
| | Δ TG/WT % | −39.4 | −61.5 | −28.6 | −51.5 |

Table 6 shows that a reduction of soluble carbohydrates is consistently associated with presence of the pZBL120xKS333, 334 and 336 transgenes. There is no conseed suspension with an equal volume of melted plant growth medium containing the either sucrose or sorbitol. Plates were incubated under standard conditions (22° C., 16 h light/8 h dark, 100 μE m$^{-2}$s$^{-1}$) and germination rate and seedling phenotype was scored 14 days after plating (Table 7).

TABLE 7

Germination Assays for pZBL120xKS336, pZBL120xKS333 and pZBL120xKS334 Transgenic Seeds

| Line ID | Media Type | | Total Seed (#) | Altered Seedling Morphology (#) | No Germination (#) | Healthy Seedlings (#) |
|---|---|---|---|---|---|---|
| C00536 | sucrose | | 93 | 69 | 2 | 22 |
| C00536 | sucrose | | 84 | 50 | 3 | 31 |
| C00536 | sucrose | | 90 | 73 | 3 | 14 |
| C00536 | sorbitol | | 95 | 6 | 89 | 0 |
| C00536 | sorbitol | | 112 | 24 | 88 | 0 |
| C00536 | sorbitol | | 100 | 49 | 51 | 0 |
| 4445 | sucrose | | 82 | 24 | 22 | 36 |
| 4445 | sucrose | | 63 | 24 | 7 | 32 |
| 4445 | sucrose | | 94 | 36 | 12 | 46 |
| 4445 | sorbitol | | 106 | 70 | 36 | 0 |
| 4445 | sorbitol | | 119 | 77 | 42 | 0 |
| 4445 | sorbitol | | 106 | 97 | 9 | 0 |
| 4485 | sucrose | | 98 | 50 | 48 | 0 |
| 4485 | sucrose | | 109 | 37 | 70 | 2 |
| 4485 | sucrose | | 129 | 80 | 39 | 10 |
| 4485 | sorbitol | | 131 | 24 | 107 | 0 |
| 4485 | sorbitol | | 128 | 25 | 103 | 0 |
| 4485 | sorbitol | | 127 | 23 | 102 | 2 |
| Line ID | Media Type | | Altered Seedling Morphology (%) | No Germination (%) | Healthy Seedlings (%) | |
| C00536 | sucrose | | 74.2 | 2.2 | 23.7 | |
| C00536 | sucrose | | 59.5 | 3.6 | 36.9 | |
| C00536 | sucrose | | 81.1 | 3.3 | 15.6 | |
| C00536 | sucrose | AVG | 71.6 | 3.0 | 25.4 | |
| C00536 | sorbitol | | 6.3 | 93.7 | 0.0 | |
| C00536 | sorbitol | | 21.4 | 78.6 | 0.0 | |
| C00536 | sorbitol | | 49.0 | 51.0 | 0.0 | |
| C00536 | sorbitol | AVG | 25.6 | 74.4 | 0.0 | |
| 4445 | sucrose | | 29.3 | 26.8 | 43.9 | |
| 4445 | sucrose | | 38.1 | 11.1 | 50.8 | |
| 4445 | sucrose | | 38.3 | 12.8 | 48.9 | |
| 4445 | sucrose | AVG | 35.2 | 16.9 | 47.9 | |
| 4445 | sorbitol | | 66.0 | 34.0 | 0.0 | |
| 4445 | sorbitol | | 64.7 | 35.3 | 0.0 | |
| 4445 | sorbitol | | 91.5 | 8.5 | 0.0 | |
| 4445 | sorbitol | AVG | 74.1 | 25.9 | 0.0 | |
| 4485 | sucrose | | 51.0 | 49.0 | 0.0 | |

TABLE 7-continued

Germination Assays for pZBL120xKS336, pZBL120xKS333 and pZBL120xKS334 Transgenic Seeds

| | | | | | |
|---|---|---|---|---|---|
| 4485 | sucrose | | 33.9 | 64.2 | 1.8 |
| 4485 | sucrose | | 62.0 | 30.2 | 7.8 |
| 4485 | sucrose | AVG | 49.0 | 47.8 | 3.2 |
| 4485 | sorbitol | | 18.3 | 81.7 | 0.0 |
| 4485 | sorbitol | | 19.5 | 80.5 | 0.0 |
| 4485 | sorbitol | | 18.1 | 80.3 | 1.6 |
| 4485 | sorbitol | AVG | 18.7 | 80.8 | 0.5 |

It is evident that germination and/or seedling development is significantly affected in all events analyzed. Germination is improved in the presence of sucrose; however, in events carrying pZBL120xKS336 and pZBL120xKS334 the seed germinating on sucrose containing media gave rise to seedlings with altered morphology, namely the presence of leaf structures that fail to become green and which resemble non-photosynthetic cotyledon tissue.

Total fatty acid (FA) composition and content of seedling tissue of C00536, 4485 and WT seedlings were measured 14 days after plating on media containing 10 g L$^{-1}$ sucrose. Briefly, seedling tissue was frozen on dry ice or by incubation in a −80° C. freezer for two h followed by lyophilization for 48 h.

Dried seedling tissue was ground to a fine powder using a GENOGRINDER® vial (½"X2" polycarbonate) and a steel ball (SPEX Centriprep (Metuchen, N.J., U.S.A.). Grinding time was 30 sec at 1450 oscillations per min. Ten mg of tissue were weighed into Eppendorf tubes. The tissue was extracted using 100 μL heptane at room temperature under continuous shaking for 2 h. Heptane extracts were cleared by centrifugation and 25 μL of extract was derivatized to fatty acid methyl esters as follows. One mL of a 25% sodium methoxide stock solution was added to 24 mL of HPLC grade methanol. Sodium methoxide was stored under an inert gas.

Five μL of a 17:0 TAG (Nu-Chek Prep, Elysian, Minn., USA) stock solution (10 mg/mL) was combined with 25 μL of heptane tissue extract in a glass culture tube and 500 μL of 1% sodium methoxide was added. Samples were derivatized in a water bath at 50° C. for 15 min. Samples were allowed to cool to RT and 1 mL of 1M NaCl was added followed by brief mixing. FAMEs were extracted into 1 mL of heptane and 4 μL sample were quantitated by GC analysis (Table 8).

TABLE 8

Fatty Acid Composition and Total Fatty Acid Content of Seedling Tissue of WT Plants and pZBL120xKS334 and pZBL120xKS336 Transgenic Plants Grown on Sucrose-Containing Media

| | % Total FA | | | | | | | | | Total FA |
|---|---|---|---|---|---|---|---|---|---|---|
| Event ID | 16:0 | 18:0 | 18:1 | 18:2 | 18:3 | 20:0 | 20:1 | 20:2 | 22:0 | (% DW) |
| WT | 13.5 | 10.0 | 42.3 | 15.2 | 15.6 | 1.0 | 0.9 | 0.0 | 1.5 | 4.3 |
| 4485 | 11.8 | 2.7 | 13.2 | 26.6 | 26.7 | 2.5 | 13.5 | 2.2 | 0.7 | 18.6 |
| C00536 | 7.9 | 2.3 | 15.0 | 17.7 | 32.4 | 3.2 | 18.2 | 2.0 | 1.2 | 21.9 |

Table 8 demonstrates that seedling tissue of transgenic lines carrying pZBL120xKS334 and pZBL120xKS336 transgenes showed increased fatty acid content when compared to WT seedlings. Moreover, the fatty acid profile of transgenic seedling tissue is similar to that of *Arabidopsis* WT seed in that it contains significant levels (>15%) of C20 fatty acids.

In summary, use of a strong heterologous seed storage protein promoter (soybean β-conglycinin promoter) for expression in *Arabidopsis* of ODP1 genes from a diverse range of plant species belonging to the families of Leguminosae, Cucurbitaceae and Poaceae, resulted in increased seed storage lipid accumulation at the expense of soluble carbohydrates. However, seed germination and seedling establishment was negatively affected in transgenic lines expressing ODP1 genes under control of a strong heterologous seed storage protein promoter.

Example 8

Construction of *Arabidopsis* Expression Vector pKR1223 for Expression of *Zea mays* ODP Under Control of the Seed-Specific, Low Strength *Arabidopsis* Sucrose Synthase Promoter The present example describes the synthesis of *Arabidopsis* expression vector pKR1223 which allows for expression of the *Zea mays* ODP gene under control of the promoter of an *Arabidopsis* sucrose synthase gene (At5g49190). Additionally, vector pKR1223 provides seed-specific expression of the DsRed gene in order to visualize positive transformants as well as constitutive expression of the npt gene for selection on kanamycin.

Plasmid pKR132 (SEQ ID NO:16) which is described in PCT Publication No. WO 2004/071467 (the contents of which are incorporated by reference), was digested with BamHI/SalI and the fragment containing the soy albumin promoter was cloned into the BamHI/XhoI fragment of the pCR-Blunt® cloning vector (Invitrogen Corporation) to produce the starting vector pKR627 (SEQ ID NO:17).

Plasmid KS294 (SEQ ID NO:18) contains a NotI site flanked by the SCP1 promoter and the phaseolin transcription terminator (SCP1Pro::NotI::PhasTerm). The SCP1 promoter is a synthetic constitutive promoter comprising a portion of the CaMV 35S promoter (Odell et al. (1985) Nature 313:810-812) and the Rsyn7-Syn II Core synthetic consensus promoter (U.S. Pat. Nos. 6,072,050 and 6,555,673, the contents of which are incorporated by reference). See also, for example, US20030226166, Table 13 (the contents of which are incorporated by reference). Downstream of this element is the Tobacco Mosaic Virus (TMV) omega 5'-UTR translational enhancer element (Gallie et al. (1992) Nucleic Acid Research 20:4631-4638), followed by the NotI site and the 3' transcription termination region of the phaseolin gene (Doyle et al., (1986) J. Biol. Chem. 261:9228-9238). The XbaI fragment of KS294 (SEQ ID NO:18), containing the SCP1Pro::NotI::PhasTerm cassette, was cloned into the XbaI site of pKR627 (SEQ ID NO:17) to produce pKR1142 (SEQ ID NO:19).

The BamHI fragment of KS334 (SEQ ID NO:14; Example 1), containing the Kti3Pro:DsRed:Kti3Term cassette, was cloned into the BamHI site of pKR278 (SEQ ID NO:20), which was previously described in U.S. Patent Publication No. US20080095915 (the contents of which are incorporated by reference), to produce vector pKR1141 (SEQ ID NO:20).

Genomic DNA was isolated from 3 week-old wild-type *Arabidopsis* col-0 seedlings using the DNEASY® Plant Mini Kit (Qiagen, Valencia, Calif.) and following the manufacture's protocol. An *Arabidopsis* Sucrose Synthase ("AtSuSy"; "AtSUS2") promoter derived from gene At5g49190 was PCR-amplified from *Arabidopsis* genomic DNA using oligonucleotides SuSy-5 (SEQ ID NO:21) and SuSy-3 (SEQ ID NO:22) with the PHUSION™ High-Fidelity DNA Polymerase (Cat. No. F553S, Finnzymes Oy, Finland), following the manufacturer's protocol. The resulting DNA fragment was cloned into the pCR®-BLUNT® cloning vector using the ZERO BLUNT® PCR Cloning Kit (Invitrogen Corporation), following the manufacturer's protocol, to produce pLF122 (SEQ ID NO:23).

The BamHI/NotI fragment of pLF122 (SEQ ID NO:23), containing the AtSuSy promoter, was cloned into the BamHI/NotI fragment of pKR1142 (SEQ ID NO:19), containing the phaseolin terminator, to produce pKR1155 (SEQ ID NO:24).

The Asp718/BsiWI fragment of pKR1155 (SEQ ID NO:24), containing the AtSuSy promoter, was cloned into the BsiWI site of pKR1141 (SEQ ID NO:20), to produce pKR1158 (SEQ ID NO:25).

The NotI fragment of KS336 (SEQ ID NO:6; Example 1), containing the corn ODP, was cloned into the NotI site of pKR1158 (SEQ ID NO:25), to produce pKR1167 (SEQ ID NO:26).

The AscI fragment of pKR1167 (SEQ ID NO:26), containing the corn ODP gene, was cloned into the AscI fragment of pKR92 (SEQ ID NO:27) which was previously described in WO2007/061845 (published on May 31, 2007, the contents of which are herein incorporated by reference) to produce pKR1223 (SEQ ID NO:28).

Example 9

Construction of *Arabidopsis* Expression Vector pKR1220 for Expression of the Corn ODP Under Control of the Seed-Specific, Medium-Strength Soy Annexin Promoter The present example describes the synthesis of *Arabidopsis* expression vector pKR1220 which allows for seed-specific expression of the corn ODP gene under control of the soy annexin promoter. Additionally, vector pKR1220 provides seed-specific expression of the DsRed gene in order to visualize positive transformants and constituitive expression of the npt gene for selection on kanamycin.

The BsiWI fragment of pKR268 (SEQ ID NO:29; which is described in PCT Publication No. WO 04/071467, the contents of which are herein incorporated by reference), containing the AnnexinPro::NotI::BD30Term cassette, was cloned into the BsiWI site of pKR1141 (SEQ ID NO:20) to give pKR1143 (SEQ ID NO:30).

The NotI fragment of KS336 (SEQ ID NO:6), containing the corn ODP1 gene, was cloned into the NotI site of pKR1143 (SEQ ID NO:30), to produce pKR1147 (SEQ ID NO:31).

The AscI fragment of pKR1147 (SEQ ID NO:31), containing the corn ODP1 gene, was cloned into the AscI fragment of pKR92 (SEQ ID NO:27) to produce pKR1220 (SEQ ID NO:32).

Example 10

Construction of *Arabidopsis* Expression Vector pKR1221 for Expression of the Corn ODP Under Control of the Constitutive, Medium Strength SCP1 Promoter The present example describes the synthesis of *Arabidopsis* expression vector pKR1221 which allows for constituitive expression of the corn ODP1 gene under control of the SCP1 promoter. Additionally, vector pKR1221 provides seed-specific expression of the DSred gene in order to visualize positive transformants and constituitive expression of the npt gene for selection on kanamycin.

The Asp718/BsiWI fragment of pKR1142 (SEQ ID NO:19), containing the SCP1Pro::NotI::PhasTerm cassette, was cloned into the BsiWI site of pKR1141 (SEQ ID NO:20), to produce pKR1144 (SEQ ID NO:33).

The NotI fragment of KS336 (SEQ ID NO:6), containing the corn ODP1, was cloned into the NotI site of pKR1144 (SEQ ID NO:33), to produce pKR1149 (SEQ ID NO:34).

The AscI fragment of pKR1149 (SEQ ID NO:34), containing the corn ODP1 gene, was cloned into the AscI fragment of pKR92 (SEQ ID NO:27) to produce pKR1221 (SEQ ID NO:35).

Example 11

Generation and Analysis of T2 Seed of *Arabidopsis* Lines Transformed with Corn ODP Under Control of the SCP1, Annexin or Sucrose Synthase Promoters Plasmid DNA of pKR1220, pKR1221 and pKR1223 was introduced into *Agrobacterium tumefaciens* NTL4 (Luo et al, *Molecular Plant-Microbe Interactions* (2001) 14(1):98-103) by electroporation. Briefly, 1 µg plasmid DNA was mixed with 100 µL of electro-competent cells on ice. The cell suspension was transferred to a 100 µL electroporation cuvette (1 mm gap width) and electroporated using a BIORAD electroporator set to 1 kV, 400Ω and 25 µF. Cells were transferred to 1 mL LB medium and incubated for 2 h at 30° C. Cells were plated onto LB medium containing 50 µg/mL kanamycin. Plates were incubated at 30° C. for 60 h. Recombinant *Agrobacterium* cultures (500 mL LB, 50 µg/mL kanamycin) were inoculated from single colonies of transformed *Agrobacterium* cells and grown at 30° C. for 60 h. Cells were harvested by centrifugation (5000×g, 10 min) and resuspended in 1 L of 5% (W/V) sucrose containing 0.05% (V/V) Silwet. *Arabidopsis* plants were grown in soil at a density of 30 plants per 100 cm² pot in METRO-MIX® 360 soil mixture for 4 weeks (22° C., 16 h light/8 h dark, 100 µE m⁻²s⁻¹). Plants were repeatedly dipped into the *Agrobacterium* suspension harboring the relevant binary vector and kept in a dark, high humidity environment for 24 h. Plants were grown for three to four weeks under standard plant growth conditions described above and plant material was harvested and dried for one week at ambient temperatures in paper bags. Seeds were harvested using a 0.425 mm mesh brass sieve.

Cleaned *Arabidopsis* seeds (2 grams, corresponding to about 100,000 seeds) were sterilized by washes in 45 mL of 80% ethanol, 0.01% TRITON® X-100, followed by 45 mL of 30% (V/V) household bleach in water, 0.01% TRITON®X-100 and finally by repeated rinsing in sterile water. Aliquots of 20,000 seeds were transferred to square plates (20×20 cm) containing 150 mL of sterile plant growth medium comprised of 0.5×MS salts, 0.53% (W/V) sorbitol, 0.05 MES/KOH (pH 5.8), 200 µg/mL TIMENTIN®, and 50 µg/mL kanamycin solidified with 10 g/L agar. Homogeneous dispersion of the seed on the medium was facilitated by mixing the aqueous seed suspension with an equal volume of melted plant growth medium. Plates were incubated under standard growth conditions for ten days. Kanamycin-resistant seedlings were transferred to plant growth medium without selective agent and grown for one week before transfer to soil. Plants were grown to maturity and T2 seeds were harvested and plated on selective media containing kanamycin. Approximately 100 events were generated in this manner. Wild-type control plants were grown in the same flat containing transgenic T1 plants. T2 seeds were harvested and oil content was measured by NMR (Tables 9 and 10).

TABLE 9

Data from Germination Assays for T2 Seed of pKR1220, pKR1221 and pKR1223 Transgenics on Selective Medium Containing Kanamycin and Sorbitol

| Event ID | pKR | Total Seed (#) | Transgenic Seed (#) | ASM* (#) | Kan$^S$ (#) | No Germination (#) | Healthy SeedLings (#) | Δ Oil % points |
|---|---|---|---|---|---|---|---|---|
| 35634 | 1220 | 122 | 110 | 11 | 12 | 31 | 68 | 2.6 |
| 36062 | 1220 | 134 | 127 | 25 | 7 | 85 | 17 | 2.4 |
| 35637 | 1220 | 147 | 133 | 16 | 14 | 100 | 17 | 2.4 |
| 36066 | 1220 | 143 | 123 | 22 | 20 | 59 | 42 | 2 |
| 35636 | 1220 | 116 | 105 | 19 | 11 | 62 | 24 | 1.7 |
| 36059 | 1220 | 101 | 85 | 14 | 16 | 52 | 19 | 1.6 |
| 36104 | 1221 | 104 | 104 | 6 | 0 | 96 | 2 | 4.7 |
| 36078 | 1221 | 83 | 66 | 0 | 17 | 66 | 0 | 3 |
| 36087 | 1221 | 93 | 89 | 0 | 4 | 89 | 0 | 2 |
| 36090 | 1221 | 103 | 103 | 1 | 0 | 98 | 4 | 1.9 |
| 36101 | 1221 | 134 | 126 | 0 | 8 | 126 | 0 | 1.7 |
| 36122 | 1221 | 108 | 92 | 0 | 16 | 92 | 0 | 1.7 |
| 36162 | 1223 | 92 | 83 | 8 | 9 | 20 | 55 | 5.3 |
| 36210 | 1223 | 112 | 111 | 2 | 1 | 21 | 88 | 4.4 |
| 36151 | 1223 | 144 | 142 | 66 | 2 | 40 | 36 | 3.6 |
| 36194 | 1223 | 94 | 91 | 14 | 3 | 11 | 66 | 3.4 |
| 36157 | 1223 | 101 | 77 | 14 | 24 | 10 | 53 | 3.4 |
| 36181 | 1223 | 160 | 149 | 15 | 11 | 88 | 46 | 3.3 |
| 36199 | 1223 | 103 | 95 | 17 | 8 | 12 | 66 | 3.2 |
| 36208 | 1223 | 119 | 110 | 22 | 9 | 20 | 68 | 3.1 |
| 36161 | 1223 | 134 | 120 | 19 | 14 | 33 | 68 | 3 |
| 36200 | 1223 | 144 | 140 | 0 | 4 | 101 | 39 | 2.8 |
| 36154 | 1223 | 110 | 99 | 10 | 11 | 7 | 82 | 2.7 |
| 36209 | 1223 | 109 | 106 | 10 | 3 | 31 | 65 | 2.6 |
| 36179 | 1223 | 172 | 147 | 10 | 25 | 68 | 69 | 2.6 |
| 36180 | 1223 | 162 | 149 | 16 | 13 | 51 | 82 | 2.6 |

TABLE 9-continued

Data from Germination Assays for T2 Seed of pKR1220, pKR1221 and pKR1223 Transgenics on Selective Medium Containing Kanamycin and Sorbitol

| Event ID | pKR | Total Seed (#) | Transgenic Seed (#) | ASM* (#) | Kan$^S$ (#) | No Germination (#) | Healthy SeedLings (#) | Δ Oil % points |
|---|---|---|---|---|---|---|---|---|
| 36213 | 1223 | 146 | 127 | 22 | 19 | 57 | 48 | 2.4 |
| 36206 | 1223 | 86 | 79 | 17 | 7 | 0 | 62 | 2.2 |

*"ASM" denotes Altered Seedling Morphology

TABLE 10

Results from Germination Assays for T2 Seed of pKR1220, pKR1221 and pKR1223 Transgenics on Selective Medium Containing Kanamycin and Sorbitol

| Event ID | pKR | % ASM* | % No Germination | % Healthy Seedlings | Δ Oil % Points |
|---|---|---|---|---|---|
| 35634 | 1220 | 10.0 | 28.2 | 61.8 | 2.6 |
| 36062 | 1220 | 19.7 | 66.9 | 13.4 | 2.4 |
| 35637 | 1220 | 12.0 | 75.2 | 12.8 | 2.4 |
| 36066 | 1220 | 17.9 | 48.0 | 34.1 | 2.0 |
| 35636 | 1220 | 18.1 | 59.0 | 22.9 | 1.7 |
| 36059 | 1220 | 16.5 | 61.2 | 22.4 | 1.6 |
| AVG | | 15.7 | 56.4 | 27.9 | 2.1 |
| 36104 | 1221 | 5.8 | 92.3 | 1.9 | 4.7 |
| 36078 | 1221 | 0.0 | 100.0 | 0.0 | 3.0 |
| 36087 | 1221 | 0.0 | 100.0 | 0.0 | 2.0 |
| 36090 | 1221 | 1.0 | 95.1 | 3.9 | 1.9 |
| 36101 | 1221 | 0.0 | 100.0 | 0.0 | 1.7 |
| 36122 | 1221 | 0.0 | 100.0 | 0.0 | 1.7 |
| AVG | | 1.1 | 97.9 | 1.0 | 2.5 |
| 36162 | 1223 | 9.6 | 24.1 | 66.3 | 5.3 |
| 36210 | 1223 | 1.8 | 18.9 | 79.3 | 4.4 |
| 36151 | 1223 | 46.5 | 28.2 | 25.4 | 3.6 |
| 36194 | 1223 | 15.4 | 12.1 | 72.5 | 3.4 |
| 36157 | 1223 | 18.2 | 13.0 | 68.8 | 3.4 |
| 36181 | 1223 | 10.1 | 59.1 | 30.9 | 3.3 |
| 36199 | 1223 | 17.9 | 12.6 | 69.5 | 3.2 |
| 36208 | 1223 | 20.0 | 18.2 | 61.8 | 3.1 |
| 36161 | 1223 | 15.8 | 27.5 | 56.7 | 3.0 |
| 36200 | 1223 | 0.0 | 72.1 | 27.9 | 2.8 |
| 36154 | 1223 | 10.1 | 7.1 | 82.8 | 2.7 |
| 36209 | 1223 | 9.4 | 29.2 | 61.3 | 2.6 |
| 36179 | 1223 | 6.8 | 46.3 | 46.9 | 2.6 |
| 36180 | 1223 | 10.7 | 34.2 | 55.0 | 2.6 |
| 36213 | 1223 | 17.3 | 44.9 | 37.8 | 2.4 |
| 36206 | 1223 | 21.5 | 0.0 | 78.5 | 2.2 |
| AVG | | 14.4 | 28.0 | 57.6 | 3.2 |

*"ASM" denotes Altered Seedling Morphology

Example 12

Analysis of T3 and T4 Seed of *Arabidopsis* Plants Transformed with *Zea mays* ODP Under Control of the *Arabidopsis* Sucrose Synthase Promoter T2 seeds of pKR1223 transformation events 36162, 36180 and 36181 were germinated on selective media containing kanamycin. Twenty-four kanamycin-resistant seedlings were planted in soil along side twelve untransformed WT *Arabidopsis* plants. Plants were grown to maturity and T3 seed samples were harvested from individual T2 plants. A bulk seed sample was generated from all WT plants in a given flat. Oil content was measured by NMR (Table 11).

TABLE 11

Oil Content of T3 Seed of pKR1223 Transgenics

| Event | Plant # | % oil |
|---|---|---|
| 36162 | 1 | 44.6 |
| 36162 | 2 | 44.5 |
| 36162 | 3 | 44.4 |
| 36162 | 4 | 44.3 |
| 36162 | 5 | 44.3 |
| 36162 | 6 | 44.2 |
| 36162 | 7 | 44.2 |
| 36162 | 8 | 43.9 |
| 36162 | 9 | 43.8 |
| 36162 | 10 | 43.7 |
| 36162 | 11 | 43.7 |
| 36162 | 12 | 43.7 |
| 36162 | 13 | 43.7 |
| 36162 | 14 | 43.7 |
| 36162 | 15 | 43.6 |
| 36162 | 16 | 43.5 |
| 36162 | 17 | 43.5 |
| 36162 | 18 | 43.5 |
| 36162 | 19 | 43.4 |
| 36162 | 20 | 43.0 |
| 36162 | 21 | 42.8 |
| 36162 | 22 | 42.2 |
| 36162 | 23 | 41.8 |
| 36162 | 24 | 36.4 |
| 36162 | AVG | 43.4 |
| WT in 36162 Exp. | AVG | 41.8 |
| 36180 | 1 | 44.5 |
| 36180 | 2 | 44.3 |
| 36180 | 3 | 43.8 |
| 36180 | 4 | 43.8 |
| 36180 | 5 | 43.7 |
| 36180 | 6 | 43.6 |
| 36180 | 7 | 43.6 |
| 36180 | 8 | 43.6 |
| 36180 | 9 | 43.5 |
| 36180 | 10 | 43.4 |
| 36180 | 11 | 43.3 |
| 36180 | 12 | 43.3 |
| 36180 | 13 | 43.3 |
| 36180 | 14 | 43.3 |
| 36180 | 15 | 43.2 |
| 36180 | 16 | 43.2 |
| 36180 | 17 | 43.1 |
| 36180 | 18 | 43.1 |
| 36180 | 19 | 42.9 |
| 36180 | 20 | 42.9 |
| 36180 | 21 | 42.8 |
| 36180 | 22 | 42.8 |
| 36180 | 23 | 42.7 |
| 36180 | 24 | 42.6 |
| 36180 | AVG | 43.3 |
| WT in 36180 Exp. | AVG | 41.9 |
| 36181 | 1 | 47.2 |
| 36181 | 2 | 46.3 |
| 36181 | 3 | 46.2 |
| 36181 | 4 | 46.1 |

TABLE 11-continued

Oil Content of T3 Seed of pKR1223 Transgenics

| Event | Plant # | % oil |
|---|---|---|
| 36181 | 5 | 45.9 |
| 36181 | 6 | 45.7 |
| 36181 | 7 | 45.4 |
| 36181 | 8 | 45.0 |
| 36181 | 9 | 45.0 |
| 36181 | 10 | 45.0 |
| 36181 | 11 | 45.0 |
| 36181 | 12 | 44.9 |
| 36181 | 13 | 44.9 |
| 36181 | 14 | 44.8 |
| 36181 | 15 | 44.7 |
| 36181 | 16 | 44.6 |
| 36181 | 17 | 44.5 |
| 36181 | 18 | 44.4 |
| 36181 | 19 | 44.4 |
| 36181 | 20 | 43.8 |
| 36181 | 21 | 43.8 |
| 36181 | 22 | 43.6 |
| 36181 | 23 | 43.3 |
| 36181 | 24 | 42.6 |
| 36181 | AVG | 44.9 |
| WT in 36181 Exp. | AVG | 41.9 |

Transgenic T3 seed selections of events 36180 and 36162 that no longer segregated for the DsRed marker gene were identified by visual inspection using a suitable light source. These T3 selections that were homozygous for the pKR1223 transgene were subjected to germination assays on plant growth media containing sucrose or sorbitol as described above (Table 12).

TABLE 12

Germination Assays for T3 Seed of pKR1223 Transgenics

| Event | Media Type | Total Seed (#) | ASM* (#) | No Germination (#) | Healthy Seedlings (#) |
|---|---|---|---|---|---|
| 36180 | sucrose | 83 | 0 | 0 | 83 |
| 36180 | sucrose | 111 | 0 | 0 | 111 |
| 36180 | sucrose | 110 | 0 | 0 | 110 |
| 36180 | sorbitol | 121 | 0 | 0 | 121 |
| 36180 | sorbitol | 128 | 0 | 0 | 128 |
| 36180 | sorbitol | 118 | 0 | 0 | 118 |
| 36162 | sucrose | 88 | 0 | 0 | 88 |
| 36162 | sucrose | 111 | 1 | 1 | 109 |
| 36162 | sucrose | 90 | 0 | 0 | 90 |
| 36162 | sorbitol | 97 | 0 | 0 | 97 |
| 36162 | sorbitol | 103 | 0 | 0 | 103 |
| 36162 | sorbitol | 107 | 2 | 0 | 105 |

| Event | Media Type | | ASM* (%) | No Germination (%) | Healthy Seedlings (%) |
|---|---|---|---|---|---|
| 36180 | sucrose | | 0.0 | 0.0 | 100.0 |
| 36180 | sucrose | | 0.0 | 0.0 | 100.0 |
| 36180 | sucrose | | 0.0 | 0.0 | 100.0 |
| 36180 | sucrose | AVG | 0.0 | 0.0 | 100.0 |
| 36180 | sorbitol | | 0.0 | 0.0 | 100.0 |
| 36180 | sorbitol | | 0.0 | 0.0 | 100.0 |
| 36180 | sorbitol | AVG | 0.0 | 0.0 | 100.0 |
| 36162 | sucrose | | 0.0 | 0.0 | 100.0 |
| 36162 | sucrose | | 0.9 | 0.9 | 98.2 |
| 36162 | sucrose | | 0.0 | 0.0 | 100.0 |
| 36162 | sucrose | AVG | 0.3 | 0.3 | 99.4 |
| 36162 | sorbitol | | 0.0 | 0.0 | 100.0 |
| 36162 | sorbitol | | 0.0 | 0.0 | 100.0 |
| 36162 | sorbitol | | 1.9 | 0.0 | 98.1 |
| 36162 | sorbitol | AVG | 0.6 | 0.0 | 99.4 |

*"ASM" denotes Altered Seedling Morphology

Transgenic T3 seed selections of events 36180 and 36162 that no longer segregated for the DsRed marker gene were identified by visual inspection using a suitable light source. In case of event 36181 no T3 seed selections could be identified that did not segregate for the DS red marker in a total of 24 progeny seed samples derived from 24 kanamycin-resistant T2 plants. Moreover, when T3 seed were plated on selective agarose media, 25% of seed failed to germinate and 25% of the seedlings were sensitive to kanamycin. It is concluded that the transgene insertion in event 36181 can only be maintained in the heterozygous state. The homozygous nature of T3 seed selections of events 36180 and 36162 suggests that the seed phenotype of event 36181 is related to the transgene insertion site and not the transgene itself. It is believed that a gene that is important for development of viable seed was disrupted by the transgene insertion.

T3 seed selections of events 36180 and 36162 that were homozygous for the transgene insertion and T3 seed selections of event 36181 that were heterozygous for the transgene insertion were germinated on selective media containing kanamycin. Three flats were planted for every transgenic event as follows: 24 seedlings were planted in each flat next to 12 WT seedlings at identical developmental stage. Plants were grown to maturity for approximately eight weeks and seed were harvested in bulk from all transgenic and WT plants in a given flat. Oil content of seed was measured by NMR as described in Example 1. Results are summarized in Table 13. In all three events presence of the pKR1223-derived transgene leads to an increase in oil content that ranges between 0.7 and 2.2% points (1.6-5.4%).

TABLE 13

Oil Content of T4 Seed of pKR1223 Transgenics

| Flat ID | Event ID | Oil (%) | Δ Oil (% Points) | Δ Oil (%) |
|---|---|---|---|---|
| A | 36181 | 42.8 | 2.2 | 5.4 |
| | WT | 40.6 | | |
| B | 36181 | 43.5 | 2.1 | 5.2 |
| | WT | 41.4 | | |
| C | 36181 | 40.8 | 1.5 | 4.0 |
| | WT | 39.2 | | |
| | AVG | | 2.0 | 4.9 |
| A | 36180 | 44.5 | 1.8 | 4.2 |
| | WT | 42.7 | | |
| B | 36180 | 43.6 | 1.9 | 4.6 |
| | WT | 41.7 | | |
| C | 36180 | 43.2 | 1.2 | 2.8 |
| | WT | 42.0 | | |
| | AVG | | 1.6 | 3.9 |
| A | 36162 | 43.3 | 1.4 | 3.4 |
| | WT | 41.9 | | |
| B | 36162 | 43.6 | 0.7 | 1.6 |
| | WT | 42.9 | | |
| C | 36162 | 43.8 | 1.0 | 2.4 |
| | WT | 42.7 | | |
| | AVG | | 1.0 | 2.5 |

T4 seed of events 36162 and 36180 were subjected to compositional analysis as described in Example 6.

TABLE 14

Composition of pKR1223 Transgenic T4 Seed and WT Control Seed

| Event | Oil (%, NMR) | Protein (%) | Seed Weight (µg) | Fructose (µg mg$^{-1}$ seed) |
|---|---|---|---|---|
| 36162 | 43.3 | 14.94 | 20.33 | 2.13 |
| WT | 41.9 | 15.05 | 19 | 2.39 |
| Δ TG/WT % | 3.3 | −0.7 | 7.0 | −10.9 |

| Event | Glucose (µg mg$^{-1}$ seed) | Sucrose (µg mg$^{-1}$ seed) | Raffinose (µg mg$^{-1}$ seed) | Stachyose (µg mg$^{-1}$ seed) |
|---|---|---|---|---|
| 36162 | 4.82 | 11.32 | 0.56 | 1.52 |
| WT | 5.17 | 14.28 | 0.64 | 1.58 |
| ΔTG/WT % | −6.8 | −20.7 | −12.5 | −3.8 |

| Event | Oil (%, NMR) | Protein (%) | Seed Weight (µg) | Fructose (µg mg$^{-1}$ seed) |
|---|---|---|---|---|
| 36180 | 43.6 | 15.17 | 21 | 2.07 |
| WT | 41.7 | 15.16 | 21 | 2.45 |
| Δ TG/WT % | 4.6 | 0.1 | 0.0 | −15.5 |

| Event | Glucose (µg mg$^{-1}$ seed) | Sucrose (µg mg$^{-1}$ seed) | Raffinose (µg mg$^{-1}$ seed) | Stachyose (µg mg$^{-1}$ seed) |
|---|---|---|---|---|
| 36180 | 4.49 | 11.14 | 0.5 | 1.46 |
| WT | 4.97 | 14.08 | 0.57 | 1.45 |
| Δ TG/WT % | −9.7 | −20.9 | −12.3 | 0.7 |

A reduction of soluble carbohydrates (mainly sucrose) was consistently associated with the presence of the pKR1223 transgene in events 36162 and 36180. There was no consistent change in protein content or seed weight that can be attributed to the presence of the transgene.

In summary, use of a promoter of the *Arabidopsis* sucrose synthase (SUS2) gene (At5g49190) for expression of maize ODP1 resulted in increased seed storage lipid accumulation at the expense of soluble carbohydrates. Seed germination and seedling establishment was not affected.

Example 13

Identification of Seed Specific Promoters to Drive ODP1 Expression in Cruciferous Oilseed Plants The sucrose synthase gene family and the role of specific gene family members during seed development, specifically the mobilization of sucrose for seed storage compound biosynthesis, has been described (Ruuska S A, Girke T, Benning C and Ohlrogge J B (2002) Contrapuntal networks of gene expression during *Arabidopsis* seed filling. Plant Cell 14: 1191-1206; Baud S, Vaultier M-N and Rochat C (2004) Structure and expression profile of the sucrose synthase multigene family in *Arabidopsis*. J Exp Bot 55: 397-409; and Baud S and Graham I A (2006) A spatiotemporal analysis of enzymatic activities associated with carbon metabolism in wild-type and mutant embryos of *Arabidopsis* using in situ histochemistry. Plant J 46: 155-169). The current invention describes the unexpected utility of a promoter sequence of a specific gene family member, At5g49190, to direct expression of heterologous ODP1 genes in a manner that allows for increased accumulation of oil during seed development of cruciferous oil seed without affecting germination and seedling establishment of the resulting seed. At5g49190 is expressed during seedling development in synchrony with accumulation of oil and protein (supra). Genes homologous to At5g49190 can be identified in other plant species based on sequence similarity to the At5g49190 gene product and expression pattern of the homolog during seed development. One skilled in the art will recognize that promoter sequences of these genes will have utility for expression of ODP1 genes for increased oil biosynthesis in cruciferous oil seed which is accompanied by unaltered seed germination and seedling establishment.

Example 14

Identification of Canola Promoters to Drive ODP1 Expression in Cruciferous Oilseed Plants Public EST and genomic sequence collections of Canola were searched with the deduced amino acid sequence of At5g49190 (AtSUS2). Several ESTs and genomic sequences were identified and assembled into a single contiguous sequence that represents a transcript model of the canola homolog of At5g49190. The nucleotide and deduced amino acid sequence of the canola SUS2 homolog transcript model are set forth as SEQ ID NO:44 and SEQ ID NO:45, respectively.

Primers a (SEQ ID NO:46) b (SEQ ID NO:47) c (SEQ ID NO:48) and d (SEQ ID NO:49) were used in genome walking experiments according to manufacturer instructions (Clontech, Calif., USA). Briefly genomic DNA of Pioneer Hi-Bred International, Inc., spring canola variety NS1822BC was isolated using standard protocols and digested with PvuII or DraI. After adaptor ligation PCR PvuII and DraI-digested genomic DNA was used as template in PCR reactions with Primer a (SEQ ID:46) and Primer c (SEQ ID NO:48), respectively. PCR products generated with primers a (SEQ ID NO: 46) and c (SEQ ID NO:48) were amplified with primers b (SEQ ID NO:47) and d (SEQ ID NO:49), respectively. In both rounds of PCR experiments adaptor specific primers were used with primers a-d. Use of primers a and b generated PCR products of 2.1 kb. Primers c and d generated PCR products of 0.7 kb. These PCR products were cloned using the PCR blunt cloning system (Invitrogen, CA, USA) and sequenced.

SEQ ID NO:50 (PvuII rapa cons) is genomic sequence of canola variety NS1822BC that was generated with primers a and b. It is comprised of 312 bp of a canola SUS2 homolog and 1924 bp of sequence upstream of the inferred start codon of the SUS2 gene. This 1924 bp sequence (including the 5' untranslated region) is designated the BnSUS2-2 promoter (SEQ ID NO:73).

SEQ ID NO:51 (1,6 DraI gene cons) is genomic sequence of canola variety NS1822BC that was generated with primers c and d. It is comprised of 37 bp of a canola SUS2 gene and 586 bp of sequence upstream of the inferred start codon of the SUS2 gene. This 586 bp sequence (including the 5' untranslated region) is designated the BnSUS2-1 promoter (SEQ ID NO:72).

Plasmid DNA of clone #6 containing 1,6 DraI gene cons (SEQ ID NO:51) was used in a PCR reaction with primers SA188 (SEQ ID NO:52) and SA189 (SEQ ID NO:53) using PHUSION™ DNA polymerase (New England Biolabs, Inc.). Plasmid DNA of clone #45 containing PvuII rapa cons (SEQ ID NO:50) was used in a PCR reaction with primers SA190 (SEQ ID NO:54) and SA191 (SEQ ID NO:55). PCR products from both reactions were cloned into PCR blunt (Invitrogen, CA, USA) according to manufacturer instructions and sequenced. BN SUS2 prom1/PCR blunt is derived from 1,6 DraI gene cons (SEQ ID NO:51). It's sequence is set forth as SEQ ID NO:56. BN SUS2 prom2/PCR blunt is derived from PvuII rapa cons (SEQ ID NO:50). It's sequence is set forth as SEQ ID NO:57.

BN SUS2 prom1/PCR blunt (SEQ ID NO:56) was linearized with XbaI and NotI and ligated with a NotI-XbaI fragment from KS332 (SEQ ID NO:3) containing Phas terminator and Kti promoter DS red gene and Kti terminator cassette to give KS427 (SEQ ID NO:58). KS427 (SEQ ID NO:58) was linearized with NotI. A delta-6 desaturase gene of *Mortierella alpina* was excised from KS130 (SEQ ID NO:59) using NotI and ligated to NotI linearized KS427 (SEQ ID NO:58) to give KS432 (SEQ ID NO:60). Expression cassettes for DSred and delta-6 desaturase genes were excised as a single DNA fragment by digestion with AscI and inserted into AscI linearized pKR92 (SEQ ID NO:27) to give ARALO80 (SEQ ID NO:61). The ARALO80 vector contains the following expression unit: BnSUS2-1 promoter::*M. alpina* delta-6 desaturase::phaseolin terminator.

Prior to this KS130 (SEQ ID NO:59) was constructed as follows: Plasmid DNA of CGR-5, which is described in U.S. Pat. No. 5,968,809, was used in a PCR reaction with primers D6 fwd (SEQ ID NO:62) and D6 rev (SEQ ID NO:63). The PCR product was digested with NotI and ligated to NotI-linearized and de-phosphorylated KS119 vector (SEQ ID NO:64) to give KS130 (SEQ ID NO:59). Vector KS119 (SEQ ID NO:64) is described in International Publication No. WO2004071467.

The maize ODP1 gene was excised from KS336 (SEQ ID NO:6) using NotI and ligated to NotI linearized KS427 (SEQ ID NO:58) to give KS430 (SEQ ID NO:65). Expression cassettes for DSred and maize ODP1 genes were excised as a single fragment by digestion with AscI and inserted into AscI linearized pKR92 (SEQ ID NO:27) to give ARALO78 (SEQ ID NO:66). The ARALO78 vector contains the following expression unit: BnSUS2-1 promoter::ZM-ODP1::phaseolin terminator.

BN SUS2 pro2/PCR blunt (SEQ ID NO:57) was linearized with XbaI and NotI and ligated with a NotI-XbaI fragment from KS332 (SEQ ID NO:3) containing Phas terminator and Kti promoter DS red gene and Kti terminator cassette to give KS428 (SEQ ID NO:67). KS428 (SEQ ID NO:67) was linearized with NotI. The delta-6 desaturase gene was exised from KS130 (SEQ ID NO:59) using NotI and ligated to NotI-linearized KS428 (SEQ ID NO:67) to give KS429 (SEQ ID NO:68). Expression cassettes for DSred and delta-6 desaturase genes were excised as a single DNA fragment by digestion with AscI and inserted into AscI linearized pKR92 (SEQ ID NO:27) to give ARALO77 (SEQ ID NO:69). The ARALO77 vector contains the following expression unit: BnSUS2-2 promoter::*M. alpina* delta-6 desaturase::phaseolin terminator.

The maize ODP1 gene was excised from KS336 (SEQ ID NO:6) using NotI and ligated to NotI-linearized KS428 (SEQ ID NO:67) to give KS431 (SEQ ID NO:70). Expression cassettes for DSred and maize ODP1 genes were excised by digestion with AscI and inserted into AscI linearized pKR92 (SEQ ID NO:27 to give ARALO79 (SEQ ID NO:71). The ARALO79 vector contains the following expression unit: BnSUS2-2 promoter::ZM-ODP1::phaseolin terminator.

Plasmid DNA of ARALO77, ARALO78, ARALO79 and ARALO80 were used for *Agrobacterium*-mediated transformation of *Arabidopsis* plants as described in Example 2.

Example 15

Analysis of Progeny Seed of *Arabidopsis* Plants Transformed with *Zea mays* ODP Under Control of Canola Sucrose Synthase Promoters Oil content of progeny seed (e.g., T2 seed) of transgenic lines generated with ARALO78 and ARALO79 can be measured by NMR as described in Example 2. Progeny seed (e.g., T2 seed) of transgenic events generated with ARALO78 and ARALO79 are expected to show increased oil content when compared to seed of untransformed control plants grown alongside the transgenic events.

What is claimed is:

1. A recombinant DNA construct comprising a polynucleotide encoding an ODP1 polypeptide operably linked to a sucrose synthase 2 promoter (SUS2) wherein the SUS2 promoter comprises a nucleotide sequence having at least 95% sequence identity to SEQ ID NO:43, wherein said nucleotide sequence has seed specific promoter activity and wherein the amino acid sequence of said ODP1 polypeptide has at least 90% sequence identity to SEQ ID NO:37 and comprises two APETALA2 (AP2) domains and wherein expression of said ODP1 polypeptide increases oil content in the seeds of a cruciferous oilseed plant while maintaining normal germination.

2. The recombinant DNA construct of claim 1 wherein the amino acid sequence of said ODP1 polypeptide has at least 95% sequence identity to SEQ ID NO:37.

3. The recombinant DNA construct of claim 1 wherein the amino acid sequence of said ODP1 polypeptide comprises SEQ ID NO:37.

4. The recombinant DNA construct of claim 1 wherein the sucrose synthase 2 promoter comprises the nucleotide sequence of SEQ ID NO:43.

5. The recombinant DNA construct of claim 1 wherein the oilseed plant is canola or *Arabidopsis*.

6. A transgenic cruciferous oilseed plant comprising in its genome the recombinant DNA construct of claim 1.

7. The transgenic cruciferous oilseed plant of claim 6 wherein the cruciferous oilseed plant is selected from the group consisting of canola and *Arabidopsis*.

8. A transgenic seed obtained from the plant of claim 6, wherein said seed comprises in its genome said recombinant DNA construct.

9. A method for producing a transgenic cruciferous oilseed plant comprising transforming a cruciferous oilseed plant cell with the recombinant DNA construct of claim 1 and regenerating a transgenic cruciferous oilseed plant from the transformed cruciferous oilseed plant cell, wherein the transgenic cruciferous oilseed plant comprises in its genome said recombinant DNA construct.

10. The method of claim 9 wherein the cruciferous oilseed plant is selected from the group consisting of canola and *Arabidopsis*.

11. A method for increasing oil content in seeds of a transgenic cruciferous oilseed plant while maintaining normal germination, said method comprising:
  (a) transforming a cruciferous oilseed plant cell with a recombinant DNA construct comprising a polynucleotide encoding an ODP1 polypeptide, wherein the amino acid sequence of said ODP1 polypeptide has at least 90% sequence identity to SEQ ID NO:37 and comprises two APETALA2 (AP2) domains, said polynucleotide being operably linked to a promoter having a nucleotide sequence at least 95% identical to SEQ ID NO:43, wherein said nucleotide sequence has seed specific promoter activity;
  (b) regenerating a transgenic cruciferous oilseed plant from the transformed cell of step (a), wherein said plant comprises the recombinant DNA construct;
  (c) obtaining a transgenic progeny plant derived from the transgenic cruciferous oilseed plant of step (b), wherein the transgenic progeny plant comprises in its genome the recombinant DNA construct;
  (d) assaying the transgenic progeny plant obtained from step (c) for oil level and germination; and
  (e) selecting those transgenic progeny plants having seeds comprising said recombinant DNA construct and having an increased level of oil and normal germination when compared to seeds obtained from a control cruciferous oilseed plant, wherein said control plant does not comprise the recombinant DNA construct.

12. The method of claim 11 wherein the amino acid sequence of the ODP1 polypeptide comprises the sequence of SEQ ID NO:37.

13. The method of claim 11 wherein the promoter comprises SEQ ID NO:43.

14. The method of claim 13 wherein the ODP1 polypeptide comprises at least 95% sequence identity to SEQ ID NO: 37.

15. The method of claim 11 wherein the cruciferous oilseed plant is canola or *Arabidopsis*.

16. The recombinant DNA construct of claim 2, wherein the sucrose synthase 2 promoter comprises the nucleotide sequence of SEQ ID NO:43.

17. The recombinant DNA construct of claim 3, wherein the sucrose synthase 2 promoter comprises the nucleotide sequence of SEQ ID NO:43

18. The transgenic cruciferous oilseed plant of claim 6, wherein the amino acid sequence of said ODP1 polypeptide comprises SEQ ID NO:37.

19. The transgenic cruciferous oilseed plant of claim 6, wherein the sucrose synthase 2 promoter comprises the nucleotide sequence of SEQ ID NO:43 and wherein the amino acid sequence of said ODP1 polypeptide has at least 95% sequence identity to SEQ ID NO:37.

20. The transgenic cruciferous oilseed plant of claim 6, wherein the sucrose synthase 2 promoter comprises the nucleotide sequence of SEQ ID NO:43 and wherein the amino acid sequence of said ODP1 polypeptide comprises SEQ ID NO:37.

21. A transgenic seed obtained from the plant of claim 6, wherein said seed comprises in its genome said recombinant DNA construct and wherein the amino acid sequence of said ODP1 polypeptide comprises SEQ ID NO:37.

22. A transgenic seed obtained from the plant of claim 6, wherein said seed comprises in its genome said recombinant DNA construct and wherein the sucrose synthase 2 promoter comprises the nucleotide sequence of SEQ ID NO:43 and wherein the amino acid sequence of said ODP1 polypeptide has at least 95% sequence identity to SEQ ID NO:37.

23. A transgenic seed obtained from the plant of claim 6, wherein said seed comprises in its genome said recombinant DNA construct and wherein the sucrose synthase 2 promoter comprises the nucleotide sequence of SEQ ID NO:43 and wherein the amino acid sequence of said ODP1 polypeptide comprises SEQ ID NO:37.

* * * * *

UNITED STATES PATENT AND TRADEMARK OFFICE
CERTIFICATE OF CORRECTION

PATENT NO.        : 8,404,926 B2
APPLICATION NO.   : 12/752175
DATED             : March 26, 2013
INVENTOR(S)       : Meyer et al.

It is certified that error appears in the above-identified patent and that said Letters Patent is hereby corrected as shown below:

IN THE SPECIFICATION

Column 2, line 23, delete "(D of)" and insert --(Dof)-- therefor

Column 4, line 16, delete "Led" and insert --Lec1-- therefor

Column 4, line 20, delete "Led" and insert --Lec1-- therefor

Column 4, line 26, delete "WR11" and insert --WRI1-- therefor

Column 4, line 28, delete "WR11" and insert --WRI1-- therefor

Column 15, line 67, delete the "-" between "transgenics" and "initially"

Column 16, line 44, delete "playa" and insert --play a-- therefor

Column 21, line 55, delete "Beta-Conqlycinin" and insert --Beta-Conglycinin-- therefor Signed and Sealed this
Eighteenth Day of June, 2013

Teresa Stanek Rea
*Acting Director of the United States Patent and Trademark Office*

SEQUENCE LISTING

```
<160> NUMBER OF SEQ ID NOS: 74

<210> SEQ ID NO 1
<211> LENGTH: 5280
<212> TYPE: DNA
<213> ORGANISM: Artificial Sequence
<220> FEATURE:
<223> OTHER INFORMATION: vector pKS121/BS
<220> FEATURE:
<221> NAME/KEY: misc_feature
<222> LOCATION: (4090)..(4090)
<223> OTHER INFORMATION: n is a, c, g, or t

<400> SEQUENCE: 1
ggccgccacc gcggtggagc tccagctttt gttcccttta gtgagggtta attgcgcgct      60
tggcgtaatc atggtcatag ctgtttcctg tgtgaaattg ttatccgctc acaattccac     120
acaacatacg agccggaagc ataaagtgta aagcctgggg tgcctaatga gtgagctaac     180
tcacattaat tgcgttgcgc tcactgcccg ctttccagtc gggaaacctg tcgtgccagc     240
tgcattaatg aatcggccaa cgcgcgggga gaggcggttt gcgtattggg cgctcttccg     300
cttcctcgct cactgactcg ctgcgctcgg tcgttcggct gcggcgagcg gtatcagctc     360
actcaaaggc ggtaatacgg ttatccacag aatcagggga taacgcagga agaacatgt     420 gagcaaaagg ccagcaaaag gccaggaacc gtaaaaaggc cgcgttgctg gcgttttcc     480 ataggctccg cccccctgac gagcatcaca aaaatcgacg ctcaagtcag aggtggcgaa    540
```

```
acccgacagg actataaaga taccaggcgt ttccccctgg aagctccctc gtgcgctctc     600
ctgttccgac cctgccgctt accggatacc tgtccgcctt ctcccttcg ggaagcgtgg      660 cgctttctca tagctcacgc tgtaggtatc tcagttcggt gtaggtcgtt cgctccaagc    720
tgggctgtgt gcacgaaccc cccgttcagc ccgaccgctg cgccttatcc ggtaactatc    780
gtcttgagtc caacccggta agacacgact tatcgccact ggcagcagcc actggtaaca    840
ggattagcag agcgaggtat gtaggcggtg ctacagagtt cttgaagtgg tggcctaact    900
acggctacac tagaaggaca gtatttggta tctgcgctct gctgaagcca gttaccttcg    960
gaaaaagagt tggtagctct tgatccggca aacaaaccac cgctggtagc ggtggttttt   1020
ttgtttgcaa gcagcagatt acgcgcagaa aaaaggatc tcaagaagat cctttgatct   1080
tttctacggg gtctgacgct cagtggaacg aaaactcacg ttaagggatt ttggtcatga   1140
gattatcaaa aaggatcttc acctagatcc ttttaaatta aaatgaagt tttaaatcaa    1200 tctaaagtat atatgagtaa acttggtctg acagttacca atgcttaatc agtgaggcac   1260
ctatctcagc gatctgtcta tttcgttcat ccatagttgc ctgactcccc gtcgtgtaga   1320
taactacgat acgggagggc ttaccatctg gccccagtgc tgcaatgata ccgcgagacc   1380
cacgctcacc ggctccagat ttatcagcaa taaaccagcc agccggaagg gccgagcgca   1440
gaagtggtcc tgcaacttta tccgcctcca tccagtctat taattgttgc cgggaagcta   1500
gagtaagtag ttcgccagtt aatagtttgc gcaacgttgt tgccattgct acaggcatcg   1560
tggtgtcacg ctcgtcgttt ggtatggctt cattcagctc cggttcccaa cgatcaaggc   1620
gagttacatg atcccccatg ttgtgcaaaa aagcggttag ctccttcggt cctccgatcg   1680
ttgtcagaag taagttggcc gcagtgttat cactcatggt tatggcagca ctgcataatt   1740
ctcttactgt catgccatcc gtaagatgct tttctgtgac tggtgagtac tcaaccaagt   1800
cattctgaga atagtgtatg cggcgaccga gttgctcttg cccggcgtca atacgggata   1860
ataccgcgcc acatagcaga actttaaaag tgctcatcat tggaaaacgt tcttcggggc   1920
gaaaactctc aaggatctta ccgctgttga tccagttc gatgtaaccc actcgtgcac    1980
ccaactgatc ttcagcatct tttactttca ccagcgtttc tgggtgagca aaaacaggaa   2040
ggcaaaatgc cgcaaaaaag gaataagggc gacacggaa atgttgaata ctcatactct    2100
tcctttttca atattattga agcatttatc agggttattg tctcatgagc ggatacatat   2160
ttgaatgtat ttagaaaaat aaacaaatag gggttccgcg cacatttccc cgaaaagtgc   2220
cacctgacgc gccctgtagc ggcgcattaa gcgcggcggg tgtggtggtt acgcgcagcg   2280
tgaccgctac acttgccagc gccctagcgc ccgctccttt cgctttcttc ccttcctttc   2340
tcgccacgtt cgccggcttt ccccgtcaag ctctaaatcg ggggctccct ttagggttcc   2400
gatttagtgc tttacggcac ctcgacccca aaaaacttga ttagggtgat ggttcacgta   2460
gtgggccatc gccctgatag acggtttttc gccctttgac gttggagtcc acgttcttta   2520
atagtggact cttgttccaa actggaacaa cactcaaccc tatctcggtc tattcttttg   2580
atttataagg gattttgccg atttcggcct attggttaaa aaatgagctg atttaacaaa   2640
aatttaacgc gaattttaac aaaatattaa cgcttacaat ttccattcgc cattcaggct   2700
gcgcaactgt tgggaagggc gatcggtgcg ggcctcttcg ctattacgcc agctggcgaa   2760
agggggatgt gctgcaaggc gattaagttg ggtaacgcca gggttttccc agtcacgacg   2820
ttgtaaaacg acggccagtg agcgcgcgta atacgactca ctatagggcg aattgggtac   2880
cgggcccccc ctcgaggtcg acggtatcga taagcttgat atcgaattcc tgcagcccgg   2940
```

```
gggatccact agttctagag cggcgcgccg tcgacggata taatgagccg taaacaaaga    3000
tgattaagta gtaattaata cgtactagta aaagtggcaa aagataacga gaaagaacca    3060
atttctttgc attcggcctt agcggaaggc atatataagc tttgattatt ttatttagtg    3120
taatgatttc gtacaaccaa agcatttatt tagtactctc acacttgtgt cgcggccgct    3180
tgggggcta tggaagactt tcttagttag ttgtgtgaat aagcaatgtt gggagaatcg     3240
ggactactta taggatagga ataaaacaga aaagtattaa gtgctaatga aatatttaga    3300
ctgataatta aaatcttcac gtatgtccac ttgatataaa aacgtcagga ataaaggaag    3360
tacagtagaa tttaaaggta ctcttttat atatacccgt gttctctttt tggctagcta     3420
gttgcataaa aaataatcta tattttatc attattttaa atatcttatg agatggtaaa     3480
tatttatcat aattttttt actattattt attatttgtg tgtgtaatac atatagaagt     3540
taattacaaa ttttatttac tttttcatta ttttgatatg attcaccatt aatttagtgt    3600
tattatttat aatagttcat tttaatcttt ttgtatatat tatgcgtgca gtactttttt    3660
cctacatata actactatta cattttattt atataatatt tttattaatg aattttcgtg    3720
ataatatgta atattgttca ttattattc agatttttta aaaatatttg tgttattatt    3780
tatgaaatat gtaattttt tagtatttga ttttatgatg ataaagtgtt ctaaattcaa     3840
aagaaggggg aaagcgtaaa cattaaaaaa cgtcatcaaa caaaaacaaa atcttgttaa    3900
taaagataaa actgtttgtt ttgatcactg ttatttcgta atataaaaac attatttata    3960
tttatattgt tgacaaccaa atttgcctat caaatctaac caatataatg catgcgtggc    4020
aggtaatgta ctaccatgaa cttaagtcat gacataataa accgtgaatc tgaccaatgc    4080
atgtacctan ctaaattgta tttgtgacac gaagcaaatg attcaattca caatggagat    4140
gggaaacaaa taatgaagaa cccagaacta agaaagcttt tctgaaaaat aaaataaagg    4200
caatgtcaaa agtatactgc atcatcagtc cagaaagcac atgatatttt tttatcagta    4260
tcaatgcagc tagttttatt ttacaatatc gatatagcta gtttaaatat attgcagcta    4320
gatttataaa tatttgtgtt attatttatc atttgtgtaa tcctgttttt agtattttag    4380
tttatatatg atgataatgt attccaaatt taaagaagg gaaataaatt taaacaagaa     4440
aaaaagtcat caaacaaaaa acaaatgaaa gggtggaaag atgttaccat gtaatgtgaa    4500
tgttacagta tttcttttat tatagagtta acaaattaac taatatgatt ttgttaataa    4560
tgataaaata ttttttttat tattatttca taatataaaa atagtttact taatatataaa   4620
aaaattctat cgttcacaac aaagttggcc acctaattta accatgcatg tacccatgga    4680
ccatattagg taaccatcaa acctgatgaa gagataaaga gatgaagact taagtcataa    4740
cacaaaacca taaaaaacaa aaatacaatc aaccgtcaat ctgaccaatg catgaaaaag    4800
ctgcaatagt gagtggcgac acaaagcaca tgattttctt acaacggaga taaaaccaaa    4860
aaaatatttc atgaacaacc tagaacaaat aaagctttta tataataaat atataaataa    4920
ataaaggcta tggaataata tacttcaata tatttggatt aaataaattg ttggcggggt    4980
tgatatattt atacacacct aaagtcactt caatctcatt ttcacttaac ttttattttt    5040
tttttctttt tatttatcat aaagagaata ttgataatat actttttaac atatttttat    5100
gacatttttt attggtgaaa acttattaaa aatcataaat tttgtaagtt agatttattt    5160
aaagagttcc tcttcttatt ttaaattttt taataaattt ttaaataact aaaatttgtg    5220
ttaaaaatgt taaaaagtg tgttattaac ccttctcttc gaggatccaa gcttggcgcg    5280
```

-continued

```
<210> SEQ ID NO 2
<211> LENGTH: 5968
<212> TYPE: DNA
<213> ORGANISM: Artificial Sequence
<220> FEATURE:
<223> OTHER INFORMATION: vector pDsRedxKS121/BS;DNA
<220> FEATURE:
<221> NAME/KEY: misc_feature
<222> LOCATION: (5052)..(5052)
<223> OTHER INFORMATION: n is a, c, g, or t

<400> SEQUENCE: 2
catggcctcc tccgaggacg tcatcaagga gttcatgcgc ttcaaggtgc gcatggaggg      60
ctccgtgaac ggccacgagt tcgagatcga gggcgagggc gagggccgcc cctacgaggg     120
cacccagacc gccaagctga aggtgaccaa gggcggcccc ctgcccttcg cctgggacat     180
cctgtccccc cagttccagt acggctccaa ggtgtacgtg aagcaccccg ccgacatccc     240
cgactacaag aagctgtcct tccccgaggg cttcaagtgg gagcgcgtga tgaacttcga     300
ggacggcggc gtggtgaccg tgacccagga ctcctccctg caggacggct ccttcatcta     360
caaggtgaag ttcatcggcg tgaacttccc ctccgacggc cccgtaatgc agaagaagac     420
tatgggctgg gaggcctcca ccgagcgcct gtaccccgc gacggcgtgc tgaagggcga     480
gatccacaag gccctgaagc tgaaggacgg cggccactac ctggtggagt tcaagtccat     540
ctacatggcc aagaagcccg tgcagctgcc cggctactac tacgtggact ccaagctgga     600
catcacctcc cacaacgagg actacaccat cgtggagcag tacgagcgcg ccgagggccg     660
ccaccacctg ttcctgtagc ggccggccgc gacacaagtg tgagagtact aaataaatgc     720
tttggttgta cgaaatcatt acactaaata aaataatcaa agcttatata tgccttccgc     780
taaggccgaa tgcaaagaaa ttggttcttt ctcgttatct tttgccactt ttactagtac     840
gtattaatta ctacttaatc atctttgttt acggctcatt atatccgtcg acggcgcgcc     900
gctctagaac tagtggatcc cccgggctgc aggaattcga tatcaagctt atcgataccg     960
tcgacctcga ggggggcccc ggtacccaat tcgccctata gtgagtcgta ttacgcgcgc    1020
tcactggccg tcgttttaca acgtcgtgac tgggaaaacc ctggcgttac ccaacttaat    1080
cgccttgcag cacatccccc tttcgccagc tggcgtaata gcgaagaggc ccgcaccgat    1140
cgcccttccc aacagttgcg cagcctgaat ggcgaatgga aattgtaagc gttaatattt    1200
tgttaaaatt cgcgttaaat ttttgttaaa tcagctcatt ttttaaccaa taggccgaaa    1260
tcggcaaaat cccttataaa tcaaaagaat agaccgagat agggttgagt gttgttccag    1320
tttggaacaa gagtccacta ttaaagaacg tggactccaa cgtcaaaggg cgaaaaaccg    1380
tctatcaggg cgatggccca ctacgtgaac catcaccta atcaagtttt ttggggtcga    1440
ggtgccgtaa agcactaaat cggaacccta agggagcccc cgatttaga gcttgacggg    1500 gaaagccggc gaacgtggcg agaaaggaag ggaagaaagc gaaaggagcg gcgctaggg    1560 cgctggcaag tgtagcggtc acgctgcgcg taaccaccac acccgccgcg cttaatgcgc    1620
cgctacaggg cgcgtcaggt ggcacttttc ggggaaatgt gcgcggaacc cctatttgtt    1680
tatttttcta aatacattca aatatgtatc cgctcatgag acaataaccc tgataaatgc    1740
ttcaataata ttgaaaaagg aagagtatga gtattcaaca tttccgtgtc gcccttattc    1800 cctttttgc ggcattttgc cttcctgttt ttgctcaccc agaaacgctg gtgaaagtaa    1860
aagatgctga agatcagttg ggtgcacgag tgggttacat cgaactggat ctcaacagcg    1920
gtaagatcct tgagagtttt cgccccgaag aacgttttcc aatgatgagc acttttaaag    1980
ttctgctatg tggcgcggta ttatcccgta ttgacgccgg gcaagagcaa ctcggtcgcc    2040
```

```
gcatacacta ttctcagaat gacttggttg agtactcacc agtcacagaa aagcatctta    2100
cggatggcat gacagtaaga gaattatgca gtgctgccat aaccatgagt gataacactg    2160
cggccaactt acttctgaca acgatcggag gaccgaagga gctaaccgct tttttgcaca    2220
acatggggga tcatgtaact cgccttgatc gttgggaacc ggagctgaat gaagccatac    2280
caaacgacga gcgtgacacc acgatgcctg tagcaatggc aacaacgttg cgcaaactat    2340
taactggcga actacttact ctagcttccc ggcaacaatt aatagactgg atggaggcgg    2400
ataaagttgc aggaccactt ctgcgctcgg cccttccggc tggctggttt attgctgata    2460
aatctggagc cggtgagcgt gggtctcgcg gtatcattgc agcactgggg ccagatggta    2520
agccctcccg tatcgtagtt atctacacga cggggagtca ggcaactatg gatgaacgaa    2580
atagacagat cgctgagata ggtgcctcac tgattaagca ttggtaactg tcagaccaag    2640
tttactcata tatactttag attgatttaa aacttcattt ttaatttaaa aggatctagg    2700
tgaagatcct ttttgataat ctcatgacca aaatccctta acgtgagttt cgttccact    2760 gagcgtcaga ccccgtagaa aagatcaaag gatcttcttg agatcctttt tttctgcgcg    2820
taatctgctg cttgcaaaca aaaaaaccac cgctaccagc ggtggtttgt ttgccggatc    2880
aagagctacc aactcttttt ccgaaggtaa ctggcttcag cagagcgcag ataccaaata    2940
ctgtccttct agtgtagccg tagttaggcc accacttcaa gaactctgta gcaccgccta    3000
catacctcgc tctgctaatc ctgttaccag tggctgctgc cagtggcgat aagtcgtgtc    3060
ttaccgggtt ggactcaaga cgatagttac cggataaggc gcagcggtcg ggctgaacgg    3120
ggggttcgtg cacacagccc agcttggagc gaacgaccta caccgaactg agatacctac    3180
agcgtgagct atgagaaagc gccacgcttc ccgaagggag aaaggcggac aggtatccgg    3240
taagcggcag ggtcggaaca ggagagcgca cgagggagct tccaggggga aacgcctggt    3300
atctttatag tcctgtcggg tttcgccacc tctgacttga gcgtcgattt ttgtgatgct    3360
cgtcaggggg gcggagccta tggaaaaacg ccagcaacgc ggccttttta cggttcctgg    3420
ccttttgctg gccttttgct cacatgttct ttcctgcgtt atccctgat tctgtggata    3480 accgtattac cgcctttgag tgagctgata ccgctcgccg cagccgaacg accgagcgca    3540
gcgagtcagt gagcgaggaa gcggaagagc gcccaatacg caaaccgcct ctccccgcgc    3600
gttggccgat tcattaatgc agctggcacg acaggtttcc cgactggaaa gcgggcagtg    3660
agcgcaacgc aattaatgtg agttagctca ctcattaggc accccaggct ttacactta    3720 tgcttccggc tcgtatgttg tgtggaattg tgagcggata acaatttcac acaggaaaca    3780
gctatgacca tgattacgcc aagcgcgcaa ttaaccctca ctaaagggaa caaaagctgg    3840
agctccaccg cggtggcggc ccgcgccaag cttggatcct cgaagagaag ggttaataac    3900
acactttttt aacatttttta acacaaattt tagttattta aaaatttatt aaaaaattta    3960
aaataagaag aggaactctt taaataaatc taacttacaa aatttatgat ttttaataag    4020
ttttcaccaa taaaaaatgt cataaaaata tgttaaaaag tatattatca atattctctt    4080
tatgataaat aaaagaaaa aaaaaataaa agttaagtga aatgagatt gaagtgactt    4140 taggtgtgta taaatatatc aaccccgcca acaatttatt taatccaaat atattgaagt    4200
atattattcc atagccttta tttatttata tatttattat ataaaagctt tatttgttct    4260
aggttgttca tgaaatattt ttttggtttt atctccgttg taagaaaatc atgtgctttg    4320
tgtcgccact cactattgca gctttttcat gcattggtca gattgacggt tgattgtatt    4380
tttgtttttt atggttttgt gttatgactt aagtcttcat ctctttatct cttcatcagg    4440
```

```
tttgatggtt acctaatatg gtccatgggt acatgcatgg ttaaattagg tggccaactt      4500
tgttgtgaac gatagaattt tttttatatt aagtaaacta tttttatatt atgaaataat      4560
aataaaaaaa atattttatc attattaaca aaatcatatt agttaatttg ttaactctat      4620
aataaaagaa atactgtaac attcacatta catggtaaca tctttccacc ctttcatttg      4680 tttttgttt gatgactttt tttcttgttt aaatttattt cccttctttt aaatttggaa       4740
tacattatca tcatatataa actaaaatac taaaaacagg attacacaaa tgataaataa      4800
taacacaaat atttataaat ctagctgcaa tatatttaaa ctagctatat cgatattgta      4860
aaataaaact agctgcattg atactgataa aaaaatatca tgtgctttct ggactgatga      4920
tgcagtatac ttttgacatt gcctttattt tatttttcag aaaagctttc ttagttctgg      4980
gttcttcatt atttgtttcc catctccatt gtgaattgaa tcatttgctt cgtgtcacaa      5040
atacaattta gntaggtaca tgcattggtc agattcacgg tttattatgt catgacttaa      5100
gttcatggta gtacattacc tgccacgcat gcattatatt ggttagattt gataggcaaa      5160
tttggttgtc aacaatataa atataaataa tgttttttata ttacgaaata acagtgatca      5220
aaacaaacag ttttatcttt attaacaaga ttttgttttt gttgatgac gttttttaat       5280 gtttacgctt tcccccttct tttgaattta gaacacttta tcatcataaa atcaaatact      5340
aaaaaaatta catatttcat aaataataac acaaatattt ttaaaaaatc tgaaataata      5400
atgaacaata ttacatatta tcacgaaaat tcattaataa aaatattata taaataaaat      5460
gtaatagtag ttatatgtag gaaaaaagta ctgcacgcat aatatataca aaaagattaa      5520
aatgaactat tataaataat aacactaaat taatggtgaa tcatatcaaa ataatgaaaa      5580
agtaaataaa atttgtaatt aacttctata tgtattacac acacaaataa taaataatag      5640
taaaaaaaat tatgataaat atttaccatc tcataagata tttaaaataa tgataaaaat      5700
atagattatt ttttatgcaa ctagctagcc aaaaagagaa cacgggtata tataaaaga      5760 gtacctttaa attctactgt acttccttta ttcctgacgt ttttatatca agtggacata      5820
cgtgaagatt ttaattatca gtctaaatat ttcattagca cttaatactt ttctgttta      5880 ttcctatcct ataagtagtc ccgattctcc caacattgct tattcacaca actaactaag      5940
aaagtcttcc atagccccc aagcggcc                                          5968
```

<210> SEQ ID NO 3
<211> LENGTH: 10058
<212> TYPE: DNA
<213> ORGANISM: Artificial Sequence
<220> FEATURE:
<223> OTHER INFORMATION: vector pKS332
<220> FEATURE:
<221> NAME/KEY: misc_feature
<222> LOCATION: (1178)..(1178)
<223> OTHER INFORMATION: n is a, c, g, or t

<400> SEQUENCE: 3

```
gatcctcgaa gagaagggtt aataacacac ttttttaaca ttttttaacac aaattttagt      60 tatttaaaaa tttattaaaa aatttaaaat aagaagagga actctttaaa taaatctaac      120
ttacaaaatt tatgattttt aataagtttt caccaataaa aaatgtcata aaatatgtt       180 aaaaagtata ttatcaatat tctctttatg ataaataaaa agaaaaaaaa aataaaagtt      240
aagtgaaaat gagattgaag tgactttagg tgtgtataaa tatatcaacc ccgccaacaa      300
tttatttaat ccaaatatat tgaagtatat tattccatag cctttatta tttatatatt       360 tattatataa aagctttatt tgttctaggt tgttcatgaa atatttttt ggttttatct       420
```

```
ccgttgtaag aaaatcatgt gctttgtgtc gccactcact attgcagctt tttcatgcat    480
tggtcagatt gacggttgat tgtattttg tttttatgg ttttgtgtta tgacttaagt    540
cttcatctct ttatctcttc atcaggtttg atggttacct aatatggtcc atgggtacat    600
gcatggttaa attaggtggc caactttgtt gtgaacgata gaattttttt tatattaagt    660
aaactatttt tatattatga aataataata aaaaaaatat tttatcatta ttaacaaaat    720
catattagtt aatttgttaa ctctataata aagaaatac tgtaacattc acattacatg     780
gtaacatctt tccacccttt catttgtttt tgtttgatg acttttttc ttgtttaaat      840
ttatttccct tcttttaaat ttggaataca ttatcatcat atataaacta aaatactaaa    900
aacaggatta cacaaatgat aaataataac acaaatattt ataaatctag ctgcaatata    960
tttaaactag ctatatcgat attgtaaaat aaaactagct gcattgatac tgataaaaaa   1020
atatcatgtg ctttctggac tgatgatgca gtatactttt gacattgcct ttattttatt   1080
tttcagaaaa gctttcttag ttctgggttc ttcattattt gttcccatc tccattgtga    1140
attgaatcat ttgcttcgtg tcacaaatac aatttagnta ggtacatgca ttggtcagat   1200
tcacggttta ttatgtcatg acttaagttc atggtagtac attacctgcc acgcatgcat   1260
tatattggtt agatttgata ggcaaatttg gttgtcaaca atataaatat aaataatgtt   1320
tttatattac gaaataacag tgatcaaaac aaacagtttt atctttatta acaagatttt   1380
gttttttgttt gatgacgttt tttaatgttt acgctttccc ccttcttttg aatttagaac  1440
actttatcat cataaaatca aatactaaaa aaattacata tttcataaat aataacacaa   1500
atatttttaa aaaatctgaa ataataatga acaatattac atattatcac gaaaattcat   1560
taataaaaat attatataaa taaatgtaa tagtagttat atgtaggaaa aaagtactgc    1620
acgcataata tatacaaaaa gattaaaatg aactattata aataataaca ctaaattaat   1680
ggtgaatcat atcaaaataa tgaaaaagta aataaaattt gtaattaact tctatatgta   1740
ttacacacac aaataataaa taatagtaaa aaaaattatg ataaatattt accatctcat   1800
aagatattta aaataatgat aaaaatatag attatttttt atgcaactag ctagccaaaa   1860
agagaacacg ggtatatata aaaagagtac ctttaaattc tactgtactt cctttattcc   1920
tgacgttttt atatcaagtg gacatacgtg aagattttaa ttatcagtct aaatatttca   1980
ttagcactta atacttttct gttttattcc tatcctataa gtagtcccga ttctcccaac   2040
attgcttatt cacacaacta actaagaaag tcttccatag ccccccaagc ggcccatggc   2100
ctcctccgag gacgtcatca aggagttcat gcgcttcaag gtgcgcatgg agggctccgt   2160
gaacggccac gagttcgaga tcgagggcga gggcgagggc cgcccctacg agggcaccca   2220
gaccgccaag ctgaaggtga ccaagggcgg ccccctgccc ttcgcctggg acatcctgtc   2280
cccccagttc cagtacggct ccaaggtgta cgtgaagcac cccgccgaca tccccgacta   2340
caagaagctg tccttccccg agggcttcaa gtgggagcgc gtgatgaact tcgaggacgg   2400
cggcgtggtg accgtgaccc aggactcctc cctgcaggac ggctccttca tctacaaggt   2460
gaagttcatc ggcgtgaact tccctccga cggccccgta atgcagaaga agactatggg   2520
ctggaggcc tccaccgagc gcctgtaccc ccgcgacggc gtgctgaagg gcgagatcca   2580
caaggccctg aagctgaagg acggcggcca ctacctggtg gagttcaagt ccatctacat   2640
ggccaagaag cccgtgcagc tgcccggcta ctactacgtg gactccaagc tggacatcac   2700
ctcccacaac gaggactaca ccatcgtgga gcagtacgag cgcgccgagg ccgccacca    2760
cctgttcctg tagcggccgg ccgcgacaca agtgtgagag tactaaataa atgctttggt   2820
```

```
tgtacgaaat cattacacta aataaaataa tcaaagctta tatatgcctt ccgctaaggc   2880
cgaatgcaaa gaaattggtt ctttctcgtt atcttttgcc acttttacta gtacgtatta   2940
attactactt aatcatcttt gtttacggct cattatatcc gtcgacggcg cgccgctcta   3000
gaactagtgg atccgtcgac ggcgcgcccg atcatccgga tatagttcct cctttcagca   3060
aaaaacccct caagacccgt ttagaggccc caagggggtta tgctagttat tgctcagcgg   3120
tggcagcagc caactcagct tccttcggg ctttgttagc agccggatcg atccaagctg    3180
tacctcacta ttcctttgcc ctcggacgag tgctggggcg tcggtttcca ctatcggcga   3240
gtacttctac acagccatcg gtccagacgg ccgcgcttct gcgggcgatt tgtgtacgcc   3300
cgacagtccc ggctccggat cggacgattg cgtcgcatcg accctgcgcc caagctgcat   3360
catcgaaatt gccgtcaacc aagctctgat agagttggtc aagaccaatg cggagcatat   3420
acgcccggag ccgcggcgat cctgcaagct ccggatgcct ccgctcgaag tagcgcgtct   3480
gctgctccat acaagccaac cacggcctcc agaagaagat gttggcgacc tcgtattggg   3540
aatccccgaa catcgcctcg ctccagtcaa tgaccgctgt tatgcggcca ttgtccgtca   3600
ggacattgtt ggagccgaaa tccgcgtgca cgaggtgccg gacttcgggg cagtcctcgg   3660
cccaaagcat cagctcatcg agagcctgcg cgacggacgc actgacggtg tcgtccatca   3720
cagtttgcca gtgatacaca tggggatcag caatcgcgca tatgaaatca cgccatgtag   3780
tgtattgacc gattccttgc ggtccgaatg ggccgaaccc gctcgtctgg ctaagatcgg   3840
ccgcagcgat cgcatccata gcctccgcga ccggctgcag aacagcgggc agttcggttt   3900
caggcaggtc ttgcaacgtg cacccctgtg cacggcggga gatgcaatag gtcaggctct   3960
cgctgaattc cccaatgtca agcacttccg gaatcgggag cgcggccgat gcaaagtgcc   4020
gataaacata acgatctttg tagaaaccat cggcgcagct atttacccgc aggacatatc   4080
cacgccctcc tacatcgaag ctgaaagcac gagattcttc gccctccgag agctgcatca   4140
ggtcggagac gctgtcgaac ttttcgatca gaaacttctc gacagacgtc gcggtgagtt   4200
caggcttttc catgggtata tctccttctt aaagttaaac aaaattattt ctagagggaa   4260
accgttgtgg tctccctata gtgagtcgta ttaatttcgc gggatcgaga tcgatccaat   4320
tccaatccca caaaaatctg agcttaacag cacagttgct cctctcagag cagaatcggg   4380
tattcaacac cctcatatca actactacgt tgtgtataac ggtccacatg ccggtatata   4440
cgatgactgg ggttgtacaa aggcggcaac aaacggcgtt cccggagttg cacacaagaa   4500
atttgccact attacagagg caagagcagc agctgacgcg tacacaacaa gtcagcaaac   4560
agacaggttg aacttcatcc ccaaggagag agctcaactc aagcccaaga gctttgctaa   4620
ggccctaaca agcccaccaa agcaaaaagc ccactggctc acgctaggaa ccaaaaggcc   4680
cagcagtgat ccagccccaa aagagatctc ctttgccccg gagattacaa tggacgattt   4740
cctctatctt tacgatctag gaaggaagtt cgaaggtgaa ggtgacgaca ctatgttcac   4800
cactgataat gagaaggtta gcctcttcaa tttcagaaag aatgctgacc cacagatggt   4860
tagagaggcc tacgcagcag gtctcatcaa gacgatctac ccgagtaaca atctccagga   4920
gatcaaatac cttcccaaga aggttaaaga tgcagtcaaa agattcagga ctaattgcat   4980
caagaacaca gagaaagaca tatttctcaa gatcagaagt actattccag tatggacgat   5040
tcaaggcttg cttcataaac caaggcaagt aatagagatt ggagtctcta aaaaggtagt   5100
tcctactgaa tctaaggcca tgcatggagt ctaagattca aatcgaggat ctaacagaac   5160
tcgccgtgaa gactggcgaa cagttcatac agagtctttt acgactcaat gacaagaaga   5220
```

-continued

```
aaatcttcgt caacatggtg gagcacgaca ctctggtcta ctccaaaaat gtcaaagata    5280
cagtctcaga agaccaaagg gctattgaga cttttcaaca aaggataatt tcgggaaacc    5340
tcctcggatt ccattgccca gctatctgtc acttcatcga aaggacagta gaaaaggaag    5400
gtggctccta caaatgccat cattgcgata aaggaaaggc tatcattcaa gatgcctctg    5460
ccgacagtgg tcccaaagat ggaccccac ccacgaggag catcgtggaa aaagaagacg     5520
ttccaaccac gtcttcaaag caagtggatt gatgtgacat ctccactgac gtaagggatg    5580
acgcacaatc ccactatcct tcgcaagacc cttcctctat ataaggaagt tcatttcatt    5640
tggagaggac acgctcgagc tcatttctct attacttcag ccataacaaa agaactcttt    5700
tctcttctta ttaaaccatg aaaaagcctg aactcaccgc gacgtctgtc gagaagtttc    5760
tgatcgaaaa gttcgacagc gtctccgacc tgatgcagct ctcggagggc gaagaatctc    5820
gtgctttcag cttcgatgta ggagggcgtg gatatgtcct gcgggtaaat agctgcgccg    5880
atggtttcta caaagatcgt tatgtttatc ggcactttgc atcggccgcg ctcccgattc    5940
cggaagtgct tgacattggg gaattcagcg agagcctgac ctattgcatc tcccgccgtg    6000
cacagggtgt cacgttgcaa gacctgcctg aaaccgaact gcccgctgtt ctgcagccgg    6060
tcgcggaggc catggatgcg atcgctgcgg ccgatcttag ccagacgagc gggttcggcc    6120
cattcggacc gcaaggaatc ggtcaataca ctacatggcg tgatttcata tgcgcgattg    6180
ctgatcccca tgtgtatcac tggcaaactg tgatggacga caccgtcagt gcgtccgtcg    6240
cgcaggctct cgatgagctg atgctttggg ccgaggactg ccccgaagtc cggcacctcg    6300
tgcacgcgga tttcggctcc aacaatgtcc tgacggacaa tggccgcata acagcggtca    6360
ttgactggag cgaggcgatg ttcggggatt cccaatacga ggtcgccaac atcttcttct    6420
ggaggccgtg gttggcttgt atggagcagc agacgcgcta cttcgagcgg aggcatccgg    6480
agcttgcagg atcgccgcgg ctccgggcgt atatgctccg cattggtctt gaccaactct    6540
atcagagctt ggttgacggc aatttcgatg atgcagcttg ggcgcagggt cgatgcgacg    6600
caatcgtccg atccggagcc gggactgtcg ggcgtacaca atcgcccgc agaagcgcgg    6660 ccgtctggac cgatggctgt gtagaagtac tcgccgatag tggaaaccga cgccccagca    6720
ctcgtccgag ggcaaaggaa tagtgaggta cctaaagaag gagtgcgtcg aagcagatcg    6780
ttcaaacatt tggcaataaa gtttcttaag attgaatcct gttgccggtc ttgcgatgat    6840
tatcatataa tttctgttga attacgttaa gcatgtaata attaacatgt aatgcatgac    6900
gttatttatg agatgggttt ttatgattag agtcccgcaa ttatacattt aatacgcgat    6960
agaaaacaaa atatagcgcg caaactagga taaattatcg cgcgcggtgt catctatgtt    7020
actagatcga tgtcgaatct gatcaacctg cattaatgaa tcggccaacg cgcggggaga    7080
ggcggtttgc gtattgggcg ctcttccgct tcctcgctca ctgactcgct gcgctcggtc    7140
gttcggctgc ggcgagcggt atcagctcac tcaaaggcgg taatacggtt atccacagaa    7200
tcaggggata acgcaggaaa gaacatgtga gcaaaaggcc agcaaaaggc caggaaccgt    7260
aaaaaggccg cgttgctggc gttttccat aggctccgcc cccctgacga gcatcacaaa    7320
aatcgacgct caagtcagag gtggcgaaac ccgacaggac tataaagata ccaggcgttt    7380
ccccctggaa gctccctcgt gcgctctcct gttccgaccc tgccgcttac cggatacctg    7440
tccgcctttc tcccttcggg aagcgtggcg ctttctcaat gctcacgctg taggtatctc    7500
agttcggtgt aggtcgttcg ctccaagctg ggctgtgtgc acgaaccccc cgttcagccc    7560
gaccgctgcg ccttatccgg taactatcgt cttgagtcca acccggtaag acacgactta    7620
```

```
tcgccactgg cagcagccac tggtaacagg attagcagag cgaggtatgt aggcggtgct   7680
acagagttct tgaagtggtg gcctaactac ggctacacta aaggacagt atttggtatc    7740 tgcgctctgc tgaagccagt taccttcgga aaaagagttg gtagctcttg atccggcaaa   7800
caaaccaccg ctggtagcgg tggttttttt gtttgcaagc agcagattac gcgcagaaaa   7860
aaaggatctc aagaagatcc tttgatcttt tctacggggt ctgacgctca gtggaacgaa   7920
aactcacgtt aagggatttt ggtcatgaca ttaacctata aaaataggcg tatcacgagg   7980
ccctttcgtc tcgcgcgttt cggtgatgac ggtgaaaacc tctgacacat gcagctcccg   8040
gagacggtca cagcttgtct gtaagcggat gccgggagca gacaagcccg tcagggcgcg   8100
tcagcgggtg ttggcgggtg tcggggctgg cttaactatg cggcatcaga gcagattgta   8160
ctgagagtgc accatatgga catattgtcg ttagaacgcg gctacaatta atacataacc   8220
ttatgtatca tacacatacg atttaggtga cactatagaa cggcgcgcca agcttttgat   8280
ccatgccctt catttgccgc ttattaatta atttggtaac agtccgtact aatcagttac   8340
ttatccttcc cccatcataa ttaatcttgg tagtctcgaa tgccacaaca ctgactagtc   8400
tcttggatca taagaaaaag ccaaggaaca aaagaagaca aaacacaatg agagtatcct   8460
ttgcatagca atgtctaagt tcataaaatt caaacaaaaa cgcaatcaca cacagtggac   8520
atcacttatc cactagctga tcaggatcgc cgcgtcaaga aaaaaaaact ggaccccaaa   8580
agccatgcac aacaacacgt actcacaaag gtgtcaatcg agcagcccaa acattcacc   8640 aactcaaccc atcatgagcc ctcacatttg ttgtttctaa cccaacctca aactcgtatt   8700
ctcttccgcc acctcatttt tgtttatttc aacacccgtc aaactgcatg ccaccccgtg   8760
gccaaatgtc catgcatgtt aacaagacct atgactataa atagctgcaa tctcggccca   8820
ggttttcatc atcaagaacc agttcaatat cctagtacac cgtattaaag aatttaagat   8880
atactgcggc cgcaagtatg aactaaaatg catgtaggtg taagagctca tggagagcat   8940
ggaatattgt atccgaccat gtaacagtat aataactgag ctccatctca cttcttctat   9000
gaataaacaa aggatgttat gatatattaa cactctatct atgcaccttta ttgttctatg   9060 ataaatttcc tcttattatt ataaatcatc tgaatcgtga cggcttatgg aatgcttcaa   9120
atagtacaaa aacaaatgtg tactataaga ctttctaaac aattctaacc ttagcattgt   9180
gaacgagaca taagtgttaa aagacataa caattataat ggaagaagtt tgtctccatt    9240
tatatattat atattaccca cttatgtatt atattaggat gttaaggaga cataacaatt   9300
ataaagagag aagtttgtat ccatttatat attatatact acccattat atattatact    9360 tatccactta tttaatgtct ttataaggtt tgatccatga tatttctaat attttagttg   9420
atatgtatat gaaagggtac tatttgaact ctcttactct gtataaaggt tggatcatcc   9480
ttaaagtggg tctatttaat tttattgctt cttacagata aaaaaaaaat tatgagttgg   9540
tttgataaaa tattgaagga tttaaaataa taataaata catataatat atgtatataa    9600
atttattata atataacatt tatctataaa aagtaaata ttgtcataaa tctatacaat    9660
cgtttagcct tgctggacga atctcaatta tttaaacgag agtaaacata tttgactttt   9720
tggttattta acaaattatt atttaacact atatgaaatt tttttttttta tcagcaaaga   9780 ataaaattaa attaagaagg acaatggtgt cccaatcctt atacaaccaa cttccacaag   9840
aaagtcaagt cagagacaac aaaaaaacaa gcaaggaaa ttttttaatt tgagttgtct    9900
tgtttgctgc ataattatg cagtaaaaca ctacacataa cccttttagc agtagagcaa    9960
tggttgaccg tgtgcttagc ttcttttatt ttatttttttt atcagcaaag aataaataaa  10020
```
ataaaatgag acacttcagg gatgtttcaa caagcttg             10058

```
<210> SEQ ID NO 4
<211> LENGTH: 34
<212> TYPE: DNA
<213> ORGANISM: Artificial Sequence
<220> FEATURE:
<223> OTHER INFORMATION: PCR primer MWG345

<400> SEQUENCE: 4
```
gaattcgcgg ccgcatggag agatctcaac ggca                 34

```
<210> SEQ ID NO 5
<211> LENGTH: 34
<212> TYPE: DNA
<213> ORGANISM: Artificial Sequence
<220> FEATURE:
<223> OTHER INFORMATION: PCR primer MWG346

<400> SEQUENCE: 5
```
gaattcgcgg ccgcttagtt gcacacactg atca                 34

```
<210> SEQ ID NO 6
<211> LENGTH: 11251
<212> TYPE: DNA
<213> ORGANISM: Artificial Sequence
<220> FEATURE:
<223> OTHER INFORMATION: vector pKS336
<220> FEATURE:
<221> NAME/KEY: misc_feature
<222> LOCATION: (3542)..(3542)
<223> OTHER INFORMATION: n is a, c, g, or t

<400> SEQUENCE: 6
```
ggccgcatgg agagatctca acggcagtct cctccgccac cgtcgccgtc ctcctcctcg    60
tcctccgtct ccgcggacac cgtcctcgtc cctcccggaa agaggcggag ggcggcgacg   120
gccaaggccg gcgccgagcc taataagagg atccgcaagg accccgccgc cgccgccgcg   180
gggaagagga gctccgtcta caggggagtc accaggcaca ggtggacggg caggttcgag   240
gcgcatctct gggacaagca ctgcctcgcc gcgctccaca acaagaagaa aggcaggcaa   300
gtctacctgg gggcgtatga cagcgaggag gcagctgctc gtgcctatga cctcgcagct   360
ctcaagtact ggggtcctga gactctgctc aacttccctg tggaggatta ctccagcgag   420
atgccggaga tggaggccgt gtcccggag gagtacctgg cctccctccg ccgcaggagc   480
agcggcttct ccaggggcgt ctccaagtac agaggcgtcg ccaggcatca ccacaacggg   540
aggtgggagg cacggattgg gcgagtcttt gggaacaagt acctctactt gggaacattt   600
gacactcaag aagaggcagc caaggcctat gaccttgcgg ccattgaata ccgtggcgtc   660
aatgctgtaa ccaacttcga catcagctgc tacctggacc accgctgtt cctggcacag   720 ctccaacagg agccacaggt ggtgccggca ctcaaccaag aacctcaacc tgatcagagc   780
gaaaccggaa ctacagagca agagccggag tcaagcgaag ccaagacacc ggatggcagt   840
gcagaacccg atgagaacgc ggtgcctgac gacaccgcgg agcccctcac cacagtcgac   900
gacagcatcg aagagggctt gtggagccct tgcatggatt acgagctaga caccatgtcg   960 agaccaaaact ttggcagctc aatcaatctg agcgagtggt cgctgacgc agacttcgac  1020 tgcaacatcg gatgcctgtt cgatgggtgt tctgcggctg acgaaggaag caaggatggt  1080
gtaggtctgg cagatttcag tctgtttgag gcaggtgatg tccagctgaa ggatgttctt  1140
tcggatatgg aagagggat acaacctcca gcgatgatca gtgtgtgcaa cgcggccgca  1200

```
agtatgaact aaaatgcatg taggtgtaag agctcatgga gagcatggaa tattgtatcc    1260
gaccatgtaa cagtataata actgagctcc atctcacttc ttctatgaat aaacaaagga    1320
tgttatgata tattaacact ctatctatgc accttattgt tctatgataa atttcctctt    1380
attattataa atcatctgaa tcgtgacggc ttatggaatg cttcaaatag tacaaaaaca    1440
aatgtgtact ataagacttt ctaaacaatt ctaaccttag cattgtgaac gagacataag    1500
tgttaagaag acataacaat tataatggaa gaagtttgtc tccatttata tattatatat    1560
tacccactta tgtattatat taggatgtta aggagacata acaattataa agagagaagt    1620
ttgtatccat ttatatatta tatactaccc atttatatat tatacttatc cacttattta    1680
atgtctttat aaggtttgat ccatgatatt tctaatattt tagttgatat gtatatgaaa    1740
gggtactatt tgaactctct tactctgtat aaaggttgga tcatccttaa agtgggtcta    1800
tttaatttta ttgcttctta cagataaaaa aaaaattatg agttggtttg ataaaatatt    1860
gaaggattta aaataataat aaataacata taatatatgt atataaattt attataatat    1920
aacatttatc tataaaaaag taaatattgt cataaatcta tacaatcgtt tagccttgct    1980
ggacgaatct caattattta aacgagagta aacatatttg acttttggt tatttaacaa    2040 attattattt aacactatat gaattttttt tttttatcag caaagaataa aattaaatta    2100
agaaggacaa tggtgtccca atccttatac aaccaacttc cacaagaaag tcaagtcaga    2160
gacaacaaaa aaacaagcaa aggaaatttt taatttgag ttgtcttgtt tgctgcataa    2220
tttatgcagt aaaacactac acataaccct tttagcagta gagcaatggt tgaccgtgtg    2280
cttagcttct tttattttat ttttttatca gcaaagaata aataaaataa aatgagacac    2340
ttcagggatg tttcaacaag cttggatcct cgaagagaag ggtaataac acactttttt    2400 aacatttta acacaaattt tagttattta aaaatttatt aaaaaattta aaataagaag    2460
aggaactctt taaataaatc taacttacaa aatttatgat ttttaataag ttttcaccaa    2520
taaaaaatgt cataaaaata tgttaaaaag tatattatca atattctctt tatgataaat    2580
aaaaagaaaa aaaaaataaa agttaagtga aaatgagatt gaagtgactt taggtgtgta    2640
taaatatatc aaccccgcca acaatttatt taatccaaat atattgaagt atattattcc    2700
atagccttta tttatttata tatttattat ataaaagctt tatttgttct aggttgttca    2760
tgaaatattt ttttggtttt atctccgttg taagaaaatc atgtgctttg tgtcgccact    2820
cactattgca gcttttttcat gcattggtca gattgacggt tgattgtatt tttgttttt    2880 atggttttgt gttatgactt aagtcttcat ctctttatct cttcatcagg tttgatggtt    2940
acctaatatg gtccatgggt acatgcatgg ttaaattagg tggccaactt tgttgtgaac    3000
gatagaattt ttttttatatt aagtaaacta ttttttatatt atgaaataat aataaaaaaa    3060
atattttatc attattaaca aaatcatatt agttaatttg ttaactctat aataaaagaa    3120
atactgtaac attcacatta catggtaaca tctttccacc ctttcatttg ttttttgttt    3180
gatgactttt tttcttgttt aaatttattt cccttctttt aaatttggaa tacattatca    3240
tcatatataa actaaaatac taaaaacagg attacacaaa tgataaataa taacacaaat    3300
atttataaat ctagctgcaa tatatttaaa ctagctatat cgatattgta aaataaaact    3360
agctgcattg atactgataa aaaaatatca tgtgcttttct ggactgatga tgcagtatac    3420
ttttgacatt gcctttattt tatttttcag aaaagctttc ttagttctgg gttcttcatt    3480
atttgtttcc catctccatt gtgaattgaa tcatttgctt cgtgtcacaa atacaattta    3540
gntaggtaca tgcattggtc agattcacgg tttattatgt catgacttaa gttcatggta    3600
```

```
gtacattacc tgccacgcat gcattatatt ggttagattt gataggcaaa tttggttgtc    3660
aacaatataa atataaataa tgttttata ttacgaaata acagtgatca aaacaaacag    3720
ttttatcttt attaacaaga ttttgttttt gtttgatgac gttttttaat gtttacgctt    3780
tcccccttct tttgaattta gaacactta tcatcataaa atcaaatact aaaaaaatta    3840
catatttcat aaataataac acaaatattt taaaaaatc tgaaataata atgaacaata    3900
ttacatatta tcacgaaaat tcattaataa aaatattata taaataaaat gtaatagtag    3960
ttatatgtag gaaaaaagta ctgcacgcat aatatataca aaaagattaa aatgaactat    4020
tataaataat aacactaaat taatggtgaa tcatatcaaa ataatgaaaa agtaaataaa    4080
atttgtaatt aacttctata tgtattacac acacaaataa taaataatag taaaaaaaat    4140
tatgataaat atttaccatc tcataagata tttaaaataa tgataaaaat atagattatt    4200
ttttatgcaa ctagctagcc aaaaagagaa cacgggtata tataaaaaga gtacctttaa    4260
attctactgt acttccttta ttcctgacgt ttttatatca agtggacata cgtgaagatt    4320
ttaattatca gtctaaatat ttcattagca cttaatactt ttctgtttta ttcctatcct    4380
ataagtagtc ccgattctcc caacattgct tattcacaca actaactaag aaagtcttcc    4440 atagccccc aagcggccca tggcctcctc cgaggacgtc atcaaggagt tcatgcgctt    4500
caaggtgcgc atggagggct ccgtgaacgg ccacgagttc gagatcgagg gcgagggcga    4560
gggccgcccc tacgagggca cccagaccgc caagctgaag gtgaccaagg gcggccccct    4620
gcccttcgcc tgggacatcc tgtcccccca gttccagtac ggctccaagg tgtacgtgaa    4680 gcacccgcc gacatccccg actacaagaa gctgtccttc cccgagggct tcaagtggga    4740
gcgcgtgatg aacttcgagg acggcggcgt ggtgaccgtg acccaggact cctccctgca    4800
ggacggctcc ttcatctaca aggtgaagtt catcggcgtg aacttcccct ccgacggccc    4860
cgtaatgcag aagaagacta tgggctggga ggcctccacc gagcgcctgt accccgcga    4920 cggcgtgctg aagggcgaga tccacaaggc cctgaagctg aaggacggcg ccactacct    4980 ggtggagttc aagtccatct acatggccaa gaagcccgtg cagctgcccg gctactacta    5040
cgtggactcc aagctggaca tcacctccca aacgaggac tacaccatcg tggagcagta    5100
cgagcgcgcc gagggccgcc accacctgtt cctgtagcgg ccggccgcga cacaagtgtg    5160
agagtactaa ataatgctt tggttgtacg aaatcattac actaaataaa ataatcaaag    5220
cttatatatg ccttccgcta aggccgaatg caaagaaatt ggttcttct cgttatcttt    5280 tgccactttt actagtacgt attaattact acttaatcat ctttgtttac ggctcattat    5340
atccgtcgac ggcgcgccgc tctagaacta gtggatccgt cgacggcgcg cccgatcatc    5400
cggatatagt tcctccttc agcaaaaaac ccctcaagac ccgtttagag gccccaaggg    5460
gttatgctag ttattgctca gcggtggcag cagccaactc agcttccttt cgggctttgt    5520
tagcagccgg atcgatccaa gctgtacctc actattcctt tgccctcgga cgagtgctgg    5580
ggcgtcggtt ccactatcg gcagtactt ctacacagcc atcggtccag acggccgcgc    5640
ttctgcgggc gatttgtgta cgcccgacag tcccggctcc ggatcggacg attgcgtcgc    5700
atcgaccctg cgcccaagct gcatcatcga aattgccgtc aaccaagctc tgatagagtt    5760
ggtcaagacc aatgcggagc atatacgccc ggagccgcgg cgatcctgca agctccggat    5820
gcctccgctc gaagtagcgc gtctgctgct ccatacaagc caaccacggc ctccagaaga    5880
agatgttggc gacctcgtat tgggaatccc cgaacatcgc ctcgctccag tcaatgaccg    5940
ctgttatgcg gccattgtcc gtcaggacat gttggagcc gaaatccgcg tgcacgaggt    6000
```

```
gccggacttc ggggcagtcc tcggcccaaa gcatcagctc atcgagagcc tgcgcgacgg    6060
acgcactgac ggtgtcgtcc atcacagttt gccagtgata cacatgggga tcagcaatcg    6120
cgcatatgaa atcacgccat gtagtgtatt gaccgattcc ttgcggtccg aatgggccga    6180
acccgctcgt ctggctaaga tcggccgcag cgatcgcatc catagcctcc gcgaccggct    6240
gcagaacagc gggcagttcg gtttcaggca ggtcttgcaa cgtgacaccc tgtgcacggc    6300
gggagatgca ataggtcagg ctctcgctga attccccaat gtcaagcact tccggaatcg    6360
ggagcgcggc cgatgcaaag tgccgataaa cataacgatc tttgtagaaa ccatcggcgc    6420
agctatttac ccgcaggaca tatccacgcc ctcctacatc gaagctgaaa gcacgagatt    6480
cttcgccctc cgagagctgc atcaggtcgg agacgctgtc gaacttttcg atcagaaact    6540
tctcgacaga cgtcgcggtg agttcaggct tttccatggg tatatctcct tcttaaagtt    6600
aaacaaaatt atttctagag ggaaaccgtt gtggtctccc tatagtgagt cgtattaatt    6660
tcgcgggatc gagatcgatc caattccaat cccacaaaaa tctgagctta acagcacagt    6720
tgctcctctc agagcagaat cgggtattca acaccctcat atcaactact acgttgtgta    6780
taacggtcca catgccggta tatacgatga ctggggttgt acaaaggcgg caacaaacgg    6840
cgttcccgga gttgcacaca agaaatttgc cactattaca gaggcaagag cagcagctga    6900
cgcgtacaca acaagtcagc aaacagacag gttgaacttc atccccaaag gagaagctca    6960
actcaagccc aagagctttg ctaaggccct aacaagccca ccaaagcaaa agcccactg     7020 gctcacgcta ggaaccaaaa ggcccagcag tgatccagcc ccaaaagaga tctcctttgc    7080
cccggagatt acaatggacg atttcctcta tctttacgat ctaggaagga agttcgaagg    7140
tgaaggtgac gacactatgt tcaccactga taatgagaag gttagcctct tcaatttcag    7200
aaagaatgct gacccacaga tggttagaga ggcctacgca gcaggtctca tcaagacgat    7260
ctacccgagt aacaatctcc aggagatcaa ataccttccc aagaaggtta agatgcagt     7320 caaaagattc aggactaatt gcatcaagaa cacagagaaa gacatatttc tcaagatcag    7380
aagtactatt ccagtatgga cgattcaagg cttgcttcat aaaccaaggc aagtaataga    7440
gattggagtc tctaaaaagg tagttcctac tgaatctaag gccatgcatg gagtctaaga    7500
ttcaaatcga ggatctaaca gaactcgccg tgaagactgg cgaacagttc atacagagtc    7560
ttttacgact caatgacaag aagaaaatct tcgtcaacat ggtggagcac gacactctgg    7620
tctactccaa aaatgtcaaa gatacagtct cagaagacca aagggctatt gagacttttc    7680
aacaaaggat aatttcggga aacctcctcg gattccattg cccagctatc tgtcacttca    7740 tcgaaggac agtagaaaag gaaggtggct cctacaaatg ccatcattgc gataaaggaa    7800
aggctatcat tcaagatgcc tctgccgaca gtggtcccaa agatggaccc ccacccacga    7860
ggagcatcgt ggaaaaagaa gacgttccaa ccacgtcttc aaagcaagtg gattgatgtg    7920
acatctccac tgacgtaagg gatgacgcac aatcccacta tccttcgcaa gacccttcct    7980
ctatataagg aagttcattt catttggaga ggacacgctc gagctcattt ctctattact    8040
tcagccataa caaaagaact cttttctctt cttattaaac catgaaaaag cctgaactca    8100
ccgcgacgtc tgtcgagaag tttctgatcg aaaagttcga cagcgtctcc gacctgatgc    8160
agctctcgga gggcgaagaa tctcgtgctt tcagcttcga tgtaggaggg cgtggatatg    8220
tcctgcgggt aaatagctgc gccgatggtt tctacaaaga tcgttatgtt tatcggcact    8280
ttgcatcggc cgcgctcccg attccggaag tgcttgacat tggggaattc agcgagagcc    8340
tgacctattg catctcccgc cgtgcacagg gtgtcacgtt gcaagacctg cctgaaaccg    8400
```

```
aactgcccgc tgttctgcag ccggtcgcgg aggccatgga tgcgatcgct gcggccgatc   8460
ttagccagac gagcgggttc ggcccattcg gaccgcaagg aatcggtcaa tacactacat   8520
ggcgtgattt catatgcgcg attgctgatc cccatgtgta tcactggcaa actgtgatgg   8580
acgacaccgt cagtgcgtcc gtcgcgcagg ctctcgatga gctgatgctt tgggccgagg   8640
actgccccga agtccggcac ctcgtgcacg cggatttcgg ctccaacaat gtcctgacgg   8700
acaatggccg cataacagcg gtcattgact ggagcgaggc gatgttcggg gattcccaat   8760
acgaggtcgc caacatcttc ttctggaggc cgtggttggc ttgtatggag cagcagacgc   8820
gctacttcga gcggaggcat ccggagcttg caggatcgcc gcggctccgg gcgtatatgc   8880
tccgcattgg tcttgaccaa ctctatcaga gcttggttga cggcaatttc gatgatgcag   8940
cttgggcgca gggtcgatgc gacgcaatcg tccgatccgg agccgggact gtcgggcgta   9000
cacaaatcgc ccgcagaagc gcggccgtct ggaccgatgg ctgtgtagaa gtactcgccg   9060
atagtggaaa ccgacgcccc agcactcgtc cgagggcaaa ggaatagtga ggtacctaaa   9120
gaaggagtgc gtcgaagcag atcgttcaaa catttggcaa taaagtttct taagattgaa   9180
tcctgttgcc ggtcttgcga tgattatcat ataatttctg ttgaattacg ttaagcatgt   9240
aataattaac atgtaatgca tgacgttatt tatgagatgg gtttttatga ttagagtccc   9300
gcaattatac atttaatacg cgatagaaaa caaaatatag cgcgcaaact aggataaatt   9360
atcgcgcgcg gtgtcatcta tgttactaga tcgatgtcga atctgatcaa cctgcattaa   9420
tgaatcggcc aacgcgcggg gagaggcggt ttgcgtattg ggcgctcttc cgcttcctcg   9480
ctcactgact cgctgcgctc ggtcgttcgg ctgcggcgag cggtatcagc tcactcaaag   9540
gcggtaatac ggttatccac agaatcaggg gataacgcag gaaagaacat gtgagcaaaa   9600
ggccagcaaa aggccaggaa ccgtaaaaag gccgcgttgc tggcgttttt ccataggctc   9660
cgcccccctg acgagcatca caaaaatcga cgctcaagtc agaggtggcg aaacccgaca   9720
ggactataaa gataccaggc gtttccccct ggaagctccc tcgtgcgctc tcctgttccg   9780
accctgccgc ttaccggata cctgtccgcc tttctccctt cgggaagcgt ggcgctttct   9840
caatgctcac gctgtaggta tctcagttcg gtgtaggtcg ttcgctccaa gctgggctgt   9900
gtgcacgaac cccccgttca gcccgaccgc tgcgccttat ccggtaacta tcgtcttgag   9960
tccaacccgg taagacacga cttatcgcca ctggcagcag ccactggtaa caggattagc  10020
agagcgaggt atgtaggcgg tgctacagag ttcttgaagt ggtggcctaa ctacggctac  10080
actagaagga cagtatttgg tatctgcgct ctgctgaagc cagttacctt cggaaaaaga  10140
gttggtagct cttgatccgg caaacaaacc accgctggta gcggtggttt ttttgtttgc  10200
aagcagcaga ttacgcgcag aaaaaaagga tctcaagaag atcctttgat cttttctacg  10260
gggtctgacg ctcagtggaa cgaaaactca cgttaaggga ttttggtcat gacattaacc  10320
tataaaaata ggcgtatcac gaggcccttt cgtctcgcgc gtttcggtga tgacggtgaa  10380
aacctctgac acatgcagct cccggagacg gtcacagctt gtctgtaagc ggatgccggg  10440
agcagacaag cccgtcaggg cgcgtcagcg ggtgttggcg ggtgtcgggg ctggcttaac  10500
tatgcggcat cagagcagat tgtactgaga gtgcaccata tggacatatt gtcgttagaa  10560
cgcggctaca attaatacat aaccttatgt atcatacaca tacgatttag gtgacactat  10620
agaacggcgc gccaagcttt tgatccatgc ccttcatttg ccgcttatta attaatttgg  10680
taacagtccg tactaatcag ttacttatcc ttcccccatc ataattaatc ttggtagtct  10740
cgaatgccac aacactgact agtctcttgg atcataagaa aaagccaagg aacaaaagaa  10800
```

```
gacaaaacac aatgagagta tcctttgcat agcaatgtct aagttcataa aattcaaaca    10860
aaaacgcaat cacacacagt ggacatcact tatccactag ctgatcagga tcgccgcgtc    10920
aagaaaaaaa aactggaccc caaaagccat gcacaacaac acgtactcac aaaggtgtca    10980
atcgagcagc ccaaaacatt caccaactca acccatcatg agccctcaca tttgttgttt    11040
ctaacccaac ctcaaactcg tattctcttc cgccacctca tttttgttta tttcaacacc    11100
cgtcaaactg catgccaccc cgtggccaaa tgtccatgca tgttaacaag acctatgact    11160
ataaatagct gcaatctcgg cccaggtttt catcatcaag aaccagttca atatcctagt    11220
acaccgtatt aaagaattta agatatactg c                                  11251

<210> SEQ ID NO 7
<211> LENGTH: 9060
<212> TYPE: DNA
<213> ORGANISM: Artificial Sequence
<220> FEATURE:
<223> OTHER INFORMATION: T-DNA of vector pZBL120xKS336
<220> FEATURE:
<221> NAME/KEY: misc_feature
<222> LOCATION: (1856)..(1856)
<223> OTHER INFORMATION: n is a, c, g, or t

<400> SEQUENCE: 7 aattcaacg gtatatatcc tgccgtcgac tctagaggat ccgcgccgtc gacggatata      60
atgagccgta aacaaagatg attaagtagt aattaatacg tactagtaaa agtggcaaaa    120
gataacgaga agaaccaat ttctttgcat tcggccttag cggaaggcat atataagctt     180
tgattatttt atttagtgta atgatttcgt acaaccaaag catttattta gtactctcac    240
acttgtgtcg cggccggccg ctacaggaac aggtggtggc ggccctcggc gcgctcgtac    300
tgctccacga tggtgtagtc ctcgttgtgg gaggtgatgt ccagcttgga gtccacgtag    360
tagtagccgg gcagctgcac gggcttcttg gccatgtaga tggacttgaa ctccaccagg    420
tagtggccgc cgtccttcag cttcagggcc ttgtggatct cgcccttcag cacgccgtcg    480
cgggggtaca ggcgctcggt ggaggcctcc cagcccatag tcttcttctg cattacgggg    540
ccgtcggagg ggaagttcac gccgatgaac ttcaccttgt agatgaagga gccgtcctgc    600
agggaggagt cctgggtcac ggtcaccacg ccgccgtcct cgaagttcat cacgcgctcc    660
cacttgaagc cctcggggaa ggacagcttc ttgtagtcgg ggatgtcggc ggggtgcttc    720
acgtacacct tggagccgta ctggaactgg ggggacagga tgtcccaggc gaagggcagg    780
gggccgccct tggtcacctt cagcttggcg gtctgggtgc cctcgtaggg gcggccctcg    840
cctctgccct cgatctcgaa ctcgtggccg ttcacggagc cctccatgcg caccttgaag    900
cgcatgaact ccttgatgac gtcctcggag gaggccatgg gccgcttggg gggctatgga    960
agactttctt agttagttgt gtgaataagc aatgttggga gaatcgggac tacttatagg   1020
ataggaataa aacagaaaag tattaagtgc taatgaaata tttagactga taattaaaat   1080
cttcacgtat gtccacttga tataaaaacg tcaggaataa aggaagtaca gtagaattta   1140
aaggtactct ttttatatat acccgtgttc tcttttggc tagctagttg cataaaaaat    1200
aatctatatt tttatcatta ttttaaatat cttatgagat ggtaaatatt tatcataatt   1260 tttttacta ttatttatta tttgtgtgtg taatacatat agaagttaat tacaaatttt    1320
atttactttt tcattatttt gatatgattc accattaatt tagtgttatt atttataata   1380
gttcatttta atcttttttgt atatattatg cgtgcagtac tttttttccta catataacta   1440 ctattacatt ttatttatat aatatttttta ttaatgaatt ttcgtgataa tatgtaatat   1500
```

```
tgttcattat tatttcagat ttttttaaaaa tatttgtgtt attatttatg aaatatgtaa    1560 ttttttagt atttgatttt atgatgataa agtgttctaa attcaaaaga agggggaaag      1620
cgtaaacatt aaaaaacgtc atcaaacaaa aacaaaatct tgttaataaa gataaaactg     1680
tttgttttga tcactgttat ttcgtaatat aaaaacatta tttatattta tattgttgac    1740
aaccaaattt gcctatcaaa tctaaccaat ataatgcatg cgtggcaggt aatgtactac    1800
catgaactta agtcatgaca taataaaccg tgaatctgac caatgcatgt acctanctaa    1860
attgtatttg tgacacgaag caaatgattc aattcacaat ggagatggga aacaaataat    1920
gaagaaccca gaactaagaa agcttttctg aaaaataaaa taaaggcaat gtcaaaagta    1980
tactgcatca tcagtccaga aagcacatga tattttttta tcagtatcaa tgcagctagt    2040 tttatttac aatatcgata tagctagttt aaatatattg cagctagatt tataaatatt     2100
tgtgttatta tttatcattt gtgtaatcct gttttagta ttttagttta tatgtgatga     2160
taatgtattc caaatttaaa agaagggaaa taaatttaaa caagaaaaaa agtcatcaaa    2220
caaaaaacaa atgaaagggt ggaaagatgt taccatgtaa tgtgaatgtt acagtatttc    2280
ttttattata gagttaacaa attaactaat atgatttttgt taataatgat aaaatatttt   2340
ttttattatt atttcataat ataaaaatag tttacttaat ataaaaaaaa ttctatcgtt    2400
cacaacaaag ttggccacct aatttaacca tgcatgtacc catggaccat attaggtaac    2460
catcaaacct gatgaagaga taaagagatg aagacttaag tcataacaca aaaccataaa    2520
aaacaaaaat acaatcaacc gtcaatctga ccaatgcatg aaaaagctgc aatagtgagt    2580
ggcgacacaa agcacatgat tttcttacaa cggagataaa accaaaaaaa tatttcatga    2640
acaacctaga acaaataaag cttttatata ataaatatat aaataaataa aggctatgga    2700
ataatatact tcaatatatt tggattaaat aaattgttgg cggggttgat atatttatac    2760
acacctaaag tcacttcaat ctcattttca cttaactttt attttttttt tcttttattt    2820
tatcataaag agaatattga taatatactt tttaacatat ttttatgaca tttttattg     2880 gtgaaaactt attaaaaatc ataaattttg taagttagat ttatttaaag agttcctctt    2940 cttatttaa attttttaat aaattttaa ataactaaaa tttgtgttaa aaatgttaaa      3000
aaagtgtgtt attaaccctt ctcttcgagg atccaagctt gttgaaacat ccctgaagtg    3060
tctcatttta ttttatttat tctttgctga taaaaaaata aaataaaaga agctaagcac    3120
acggtcaacc attgctctac tgctaaaagg gttatgtgta gtgttttact gcataaatta    3180
tgcagcaaac aagacaactc aaattaaaaa atttcctttg cttgttttt tgttgtctct     3240 gacttgactt tcttgtggaa gttggttgta taaggattgg gacaccattg tccttcttaa    3300
tttaatttta ttctttgctg ataaaaaaaa aaatttcata tagtgttaaa taataatttg    3360
ttaaataacc aaaaagtcaa atatgtttac tctcgtttaa ataattgaga ttcgtccagc    3420
aaggctaaac gattgtatag atttatgaca atatttactt ttttatagat aaatgttata    3480
ttataataaa tttatataca tatattatat gttatttatt attattttaa atccttcaat    3540
attttatcaa accaactcat aatttttttt ttatctgtaa gaagcaataa aattaaatag    3600
acccacttta aggatgatcc aacctttata cagagtaaga gagttcaaat agtacccttt    3660
catatacata tcaactaaaa tattagaaat atcatggatc aaaccttata aagacattaa    3720
ataagtggat aagtataata tataaatggg tagtatataa tatataaatg gatacaaact    3780 tctctctttta taattgttat gtctccttaa catcctaata taatacataa gtgggtaata   3840
tataatatat aaatggagac aaacttcttc cattataatt gttatgtctt cttaacacttt   3900
```

```
atgtctcgtt cacaatgcta aggttagaat tgtttagaaa gtcttatagt acacatttgt    3960
ttttgtacta tttgaagcat tccataagcc gtcacgattc agatgattta taataataag    4020
aggaaattta tcatagaaca ataaggtgca tagatagagt gttaatatat cataacatcc    4080
tttgtttatt catagaagaa gtgagatgga gctcagttat tatactgtta catggtcgga    4140
tacaatattc catgctctcc atgagctctt acacctacat gcattttagt tcatacttgc    4200
ggccgcgttg cacacactga tcatcgctgg aggttgtatc ccctcttcca tatccgaaag    4260
aacatccttc agctggacat cacctgcctc aaacagactg aaatctgcca gacctacacc    4320
atccttgctt ccttcgtcag ccgcagaaca cccatcgaac aggcatccga tgttgcagtc    4380
gaagtctgcg tcagcgaacc actcgctcag attgattgag ctgccaaagt ttggtctcga    4440
catggtgtct agctcgtaat ccatgcaagg gctccacaag ccctcttcga tgctgtcgtc    4500
gactgtggtg aggggctccg cggtgtcgtc aggcaccgcg ttctcatcgg gttctgcact    4560
gccatccggt gtcttggctt cgcttgactc cggctcttgc tctgtagttc cggtttcgct    4620
ctgatcaggt tgaggttctt ggttgagtgc cggcaccacc tgtggctcct gttggagctg    4680
tgccaggaac agcgggtggt ccaggtagca gctgatgtcg aagttggtta cagcattgac    4740
gccacggtat tcaatggccg caaggtcata ggccttggct gcctcttctt gagtgtcaaa    4800
tgttcccaag tagaggtact tgttcccaaa gactcgccca atccgtgcct cccacctccc    4860
gttgtggtga tgcctggcga cgcctctgta cttggagacg cccctggaga agccgctgct    4920
cctgcggcgg agggaggcca ggtactcctc ccgggacacg gcctccatct ccggcatctc    4980
gctggagtaa tcctccacag ggaagttgag cagagtctca ggaccccagt acttgagagc    5040
tgcgaggtca taggcacgag cagctgcctc ctcgctgtca tacgccccca ggtagacttg    5100
cctgcctttc ttcttgttgt ggagcgcggc gaggcagtgc ttgtcccaga tgcgcctc     5160 gaacctgccc gtccacctgt gcctggtgac tcccctgtag acggagctcc tcttccccgc    5220
ggcggcggcg gcggggtcct tgcggatcct cttattaggc tcggcgccgg ccttggccgt    5280
cgccgccctc cgcctctttc cgggagggac gaggacggtg tccgcggaga cggaggacga    5340
ggaggaggac ggcgacggtg gcggaggaga ctgccgttga tctctcca tgcggccgca    5400 gtatatctta aattctttaa tacggtgtac taggatattg aactggttct tgatgatgaa    5460
aacctgggcc gagattgcag ctatttatag tcataggtct tgttaacatg catggacatt    5520
tggccacggg gtggcatgca gtttgacggg tgttgaaata acaaaaatg aggtggcgga     5580 agagaatacg agtttgaggt tgggttagaa acaacaaatg tgagggctca tgatgggttg    5640
agttggtgaa tgttttgggc tgctcgattg acacctttgt gagtacgtgt tgttgtgcat    5700
ggcttttggg gtccagtttt ttttcttga cgcggcgatc ctgatcagct agtggataag    5760
tgatgtccac tgtgtgtgat tgcgttttg tttgaattt atgaacttag acattgctat    5820
gcaaaggata ctctcattgt gttttgtctt cttttgttcc ttggcttttt cttatgatcc    5880
aagagactag tcagtgttgt ggcattcgag actaccaaga ttaattatga tgggggaagg    5940
ataagtaact gattagtacg gactgttacc aaattaatta ataagcggca aatgaagggc    6000
atggatcaaa agcttggcgc gaattcactg gccgtcgttt tacaacgtcg tgactgggaa    6060
aaccctggcg ttacccaact taatcgcctt gcagcacatc ccccttttcgc cagctggcgt    6120 aatagcgaag aggcccgcac cgatcgccct tcccaacagt tgcgcagcct gaatggcgaa    6180
tggatcgatc cgtcgatcga ccaaagcggc catcgtgcct ccccactcct gcagttcggg    6240
ggcatggatg cgcggatagc cgctgctggt ttcctggatg ccgacggatt tgcactgccg    6300
```

```
gtagaactcc gcgaggtcgt ccagcctcag gcagcagctg aaccaactcg cgaggggatc   6360
gagcccctgc tgagcctcga catgttgtcg caaaattcgc cctggacccg cccaacgatt   6420
tgtcgtcact gtcaaggttt gacctgcact tcatttgggg cccacataca ccaaaaaaat   6480
gctgcataat tctcggggca gcaagtcggt tacccggccg ccgtgctgga ccggggttgaa   6540 tggtgcccgt aactttcggt agagcggacg gccaatactc aacttcaagg aatctcaccc   6600
atgcgcgccg gcggggaacc ggagttccct tcagtgaacg ttattagttc gccgctcggt   6660
gtgtcgtaga tactagcccc tgggccttt  tgaaatttga ataagattta tgtaatcagt   6720
cttttaggtt tgaccggttc tgccgctttt tttaaaattg gatttgtaat aataaaacgc   6780
aattgtttgt tattgtggcg ctctatcata gatgtcgcta taaacctatt cagcacaata   6840
tattgttttc attttaatat tgtacatata agtagtaggg tacaatcagt aaattgaacg   6900
gagaatatta ttcataaaaa tacgatagta acgggtgata tattcattag aatgaaccga   6960
aaccggcggt aaggatctga gctacacatg ctcaggtttt ttacaacgtg cacaacagaa   7020
ttgaaagcaa atatcatgcg atcataggcg tctcgcatat ctcattaaag caggggtgg    7080 gcgaagaact ccagcatgag atccccgcgc tggaggatca tccagccggc gtcccggaaa   7140
acgattccga agcccaacct ttcatagaag gcggcggtgg aatcgaaatc tcgtgatggc   7200
aggttgggcg tcgcttggtc ggtcatttcg aaccccagag tcccgctcag aagaactcgt   7260
caagaaggcg atagaaggcg atgcgctgcg aatcgggagc ggcgataccg taaagcacga   7320
ggaagcggtc agcccattcg ccgccaagct cttcagcaat atcacgggta gccaacgcta   7380
tgtcctgata gcggtccgcc acacccagcc ggccacagtc gatgaatcca gaaaagcggc   7440
cattttccac catgatattc ggcaagcagg catcgccatg ggtcacgacg agatcctcgc   7500
cgtcgggcat gcgcgccttg agcctggcga acagttcggc tggcgcgagc ccctgatgct   7560
cttcgtccag atcatcctga tcgacaagac cggcttccat ccgagtacgt gctcgctcga   7620
tgcgatgttt cgcttggtgg tcgaatgggc aggtagccgg atcaagcgta tgcagccgcc   7680
gcattgcatc agccatgatg gatactttct cggcaggagc aaggtgagat gacaggagat   7740
cctgccccgg cacttcgccc aatagcagcc agtcccttcc cgcttcagtg acaacgtcga   7800
gcacagctgc gcaaggaacg cccgtcgtgg ccagccacga tagccgcgct gcctcgtcct   7860
gcagttcatt cagggcaccg gacaggtcgg tcttgacaaa aagaaccggg cgcccctgcg   7920
ctgacagccg gaacacggcg gcatcagagc agccgattgt ctgttgtgcc cagtcatagc   7980
cgaatagcct ctccacccaa gcggccggag aacctgcgtg caatccatct tgttcaatca   8040
tgcgaaacga tccccgcaag cttggagact ggtgatttca gcgtgtcctc tccaaatgaa   8100
atgaacttcc ttatatagag gaagggtctt gcgaaggata gtgggattgt gcgtcatccc   8160
ttacgtcagt ggagatatca catcaatcca cttgctttga agacgtggtt ggaacgtctt   8220
ctttttccac gatgctcctc gtgggtgggg gtccatcttt gggaccactg tcggcagagg   8280
catcttcaac gatggccttt cctttatcgc aatgatggca tttgtaggag ccaccttcct   8340
tttccactat cttcacaata aagtgacaga tagctgggca atggaatccg aggaggtttc   8400
cggatattac cctttgttga aaagtctcaa ttgcccttg  gtcttctgag actgtatctt   8460
tgatattttt ggagtagaca agcgtgtcgt gctccaccat gttgacgaag attttcttct   8520
tgtcattgag tcgtaagaga ctctgtatga actgttcgcc agtctttacg gcgagttctg   8580
ttaggtcctc tatttgaatc tttgactcca tggcctttga ttcagtggga actacctttt   8640
tagagactcc aatctctatt acttgccttg gtttgtgaag caagccttga atcgtccata   8700
```

```
ctggaatagt acttctgatc ttgagaaata tatctttctc tgtgttcttg atgcagttag   8760
tcctgaatct tttgactgca tctttaacct tcttgggaag gtatttgatc tcctggagat   8820
tattgctcgg gtagatcgtc ttgatgagac ctgctgcgta agcctctcta accatctgtg   8880
ggttagcatt ctttctgaaa ttgaaaaggc taatcttctc attatcagtg gtgaacatgg   8940
tatcgtcacc ttctccgtcg aacttcctga ctagatcgta gagatagagg aagtcgtcca   9000
ttgtgatctc tggggcaaag gagatctgaa ttatcattta caattgaata tatcctgcca   9060

<210> SEQ ID NO 8
<211> LENGTH: 34
<212> TYPE: DNA
<213> ORGANISM: Artificial Sequence
<220> FEATURE:
<223> OTHER INFORMATION: PCR primer MWG339

<400> SEQUENCE: 8
gaattcgcgg ccgccatgag aaggtctccc tctg                                34

<210> SEQ ID NO 9
<211> LENGTH: 34
<212> TYPE: DNA
<213> ORGANISM: Artificial Sequence
<220> FEATURE:
<223> OTHER INFORMATION: PCR primer MWG340

<400> SEQUENCE: 9
gaattcgcgg ccgctcaaac cctaaattca cacg                                34

<210> SEQ ID NO 10
<211> LENGTH: 11299
<212> TYPE: DNA
<213> ORGANISM: Artificial Sequence
<220> FEATURE:
<223> OTHER INFORMATION: vector pKS333
<220> FEATURE:
<221> NAME/KEY: misc_feature
<222> LOCATION: (3588)..(3588)
<223> OTHER INFORMATION: n is a, c, g, or t

<400> SEQUENCE: 10
ggccgccatg agaaggtctc cctctgtttc tacttcctcc tcctcctcct cctcctgcgt     60
cggcggcggc ggcttcgaca gcaataatct caatctcgcc gcccctccgc gccggccgca    120
atcggagaag accggagcga aacgccggaa gcggaatcag gacgacgcca aatgcgagat    180
tgagaatcgt aacggtaata acaacaacag cagcaacaac aatgcctctt ccggccgccg    240
gagctccatt tacagaggag tcactaggca ccgatggacc ggccggttcg aagcgcatct    300
ctgggacaag agttcgtgga atagcattca gaacaaaaaa ggaaggcaag tttatttggg    360
agcatacgat aacgaggaag ctgccgcccg aacttatgac ctcgctgccc tcaagtactg    420
gggtcccgga accaccctca atttcccggt agagtcgtac aggaatgaaa tagaagaaat    480
gcggaaagtt acgaaggagg agtatttggc gtcgttacgg cggcggagca gcggattttc    540
gagaggcgta tcgaagtacc gcggcgtggc ccgccaccac cacaacgcc ggtgggaggc    600 gcggatcggc cgtgttttcg gaagcaaata tctttacctg gaacttaca acacacaaga    660 ggaagcagca gcagcatatg acatggctgc aattgagtac agaggggtca atgcagtgac    720
caatttcgac atcagcaatt acattgggcg gctggagaat aaatcatcag tttttccagc    780
agcagagcag cccctacagc ccaactgctc ccctgcttcc tcttctgagg aaggcgaagt    840
agtacagcag caacagcaac agacgacgat ggcgttctca ggctcgcccc tccagttccc    900
```

```
gtcgatggag aacagcccga cgacaatgga ggaggatcat gatctgcatt ggtcattcct    960
agacacgggg ttcgtgcagg tccccgacct cccctcgag aagtctggcg aattgcctga   1020
cctgttcttt gatgagatcg ggttcgagga cgacatcggg ttgatattcg aggcgagctt   1080
ggaagacgag aggtgcgggg aggggggtga gaagttagaa gatgtgggga aaatggagat   1140
gatgaagagt gatcatgagg agaggggtt gttctcgact acttcgccat cttcgtcgtc   1200
gataaccacc tcggtttcgt gtgaatttag ggtttgagcg gccgcaagta tgaactaaaa   1260
tgcatgtagg tgtaagagct catggagagc atggaatatt gtatccgacc atgtaacagt   1320
ataataactg agctccatct cacttcttct atgaataaac aaaggatgtt atgatatatt   1380
aacactctat ctatgcacct tattgttcta tgataaattt cctcttatta ttataaatca   1440
tctgaatcgt gacggcttat ggaatgcttc aaatagtaca aaaacaaatg tgtactataa   1500
gactttctaa acaattctaa ccttagcatt gtgaacgaga cataagtgtt aagaagacat   1560
aacaattata atggaagaag tttgtctcca tttatatatt atatattacc cacttatgta   1620
ttatattagg atgttaagga gacataacaa ttataaagag agaagtttgt atccatttat   1680
atattatata ctacccattt atatattata cttatccact tatttaatgt ctttataagg   1740
tttgatccat gatatttcta atattttagt tgatatgtat atgaaagggt actatttgaa   1800
ctctcttact ctgtataaag gttggatcat ccttaaagtg ggtctattta atttattgc   1860 ttcttacaga taaaaaaaaa attatgagtt ggtttgataa atattgaag gatttaaaat   1920 aataataaat aacatataat atatgtatat aaatttatta taatataaca tttatctata   1980
aaaaagtaaa tattgtcata aatctataca atcgtttagc cttgctggac gaatctcaat   2040
tatttaaacg agagtaaaca tatttgactt tttggttatt taacaaatta ttatttaaca   2100
ctatatgaaa ttttttttt tatcagcaaa gaataaaatt aaattaagaa ggacaatggt   2160
gtcccaatcc ttatacaacc aacttccaca agaaagtcaa gtcagagaca acaaaaaaac   2220
aagcaaagga aattttttaa tttgagttgt cttgtttgct gcataattta tgcagtaaaa   2280
cactacacat aacccttta gcagtagagc aatggttgac cgtgtgctta gcttcttta   2340 ttttattttt ttatcagcaa agaataaata aaataaaatg agacacttca gggatgtttc   2400
aacaagcttg gatcctcgaa gagaagggt aataacacac ttttttaaca tttttaacac   2460 aaatttagt tatttaaaaa tttattaaaa aatttaaaat aagaagagga actctttaaa   2520
taaatctaac ttacaaaatt tatgattttt aataagtttt caccaataaa aaatgtcata   2580
aaaatatgtt aaaaagtata ttatcaatat tctctttatg ataaataaaa agaaaaaaaa   2640
aataaaagtt aagtgaaaat gagattgaag tgacttaggg tgtgtataaa tatatcaacc   2700
ccgccaacaa tttatttaat ccaaatatat tgaagtatat tattccatag cctttattta   2760
tttatatatt tattatataa aagctttatt tgttctaggt tgttcatgaa atatttttt   2820 ggttttatct ccgttgtaag aaaatcatgt gctttgtgtc gccactcact attgcagctt   2880
tttcatgcat tggtcagatt gacggttgat tgtattttg ttttttatgg ttttgtgtta   2940
tgacttaagt cttcatctct ttatctcttc atcaggtttg atggttacct aatatggtcc   3000
atgggtacat gcatggttaa attaggtggc aactttgtt gtgaacgata gaatttttt   3060 tatattaagt aaactatttt tatattatga ataataata aaaaaatat tttatcatta   3120 ttaacaaaat catattagtt aatttgttaa ctctataata aaagaaatac tgtaacattc   3180
acattacatg gtaacatctt tccacccttt catttgtttt ttgtttgatg actttttttc   3240
ttgtttaaat ttattccct tcttttaaat ttggaataca ttatcatcat atataaacta   3300
```

```
aaatactaaa aacaggatta cacaaatgat aaataataac acaaatatt  ataaatctag   3360 ctgcaatata tttaaactag ctatatcgat attgtaaaat aaaactagct gcattgatac   3420
tgataaaaaa atatcatgtg ctttctggac tgatgatgca gtatacttt  gacattgcct   3480 ttattttatt tttcagaaaa gctttcttag ttctgggttc ttcattattt gtttcccatc   3540
tccattgtga attgaatcat ttgcttcgtg tcacaaatac aatttagnta ggtacatgca   3600
ttggtcagat tcacggttta ttatgtcatg acttaagttc atggtagtac attacctgcc   3660
acgcatgcat tatattggtt agatttgata ggcaaattg  gttgtcaaca atataaaatat  3720 aaataatgtt tttatattac gaaataacag tgatcaaaac aaacagttt  atctttatta   3780 acaagatttt gttttgttt  gatgacgttt tttaatgttt acgctttccc cttcttttg    3840 aatttagaac actttatcat cataaaatca aatactaaaa aaattacata tttcataaat   3900
aataacacaa atattttaa  aaaatctgaa ataataatga acaatattac atattatcac   3960
gaaaattcat taataaaaat attatataaa taaaatgtaa tagtagttat atgtaggaaa   4020
aaagtactgc acgcataata tatacaaaaa gattaaaatg aactattata aataataaca   4080
ctaaattaat ggtgaatcat atcaaaataa tgaaaaagta aataaaattt gtaattaact   4140
tctatatgta ttacacacac aaataataaa taatagtaaa aaaaattatg ataaatattt   4200
accatctcat aagatattta aaataatgat aaaaatatag attattttt  atgcaactag   4260 ctagccaaaa agagaacacg ggtatatata aaaagagtac ctttaaattc tactgtactt   4320
cctttattcc tgacgttttt atatcaagtg gacatacgtg aagattttaa ttatcagtct   4380
aaatatttca ttagcactta atacttttct gttttattcc tatcctataa gtagtcccga   4440
ttctcccaac attgcttatt cacacaacta actaagaaag tcttccatag ccccccaagc   4500
ggcccatggc ctcctccgag gacgtcatca aggagttcat gcgcttcaag gtgcgcatgg   4560
agggctccgt gaacggccac gagttcgaga tcgaggggcga gggcgagggc cgcccctacg   4620
agggcaccca gaccgccaag ctgaaggtga ccaagggcgg ccccctgccc ttcgcctggg   4680
acatcctgtc cccccagttc cagtacggct ccaaggtgta cgtgaagcac ccgccgaca    4740 tccccgacta caagaagctg ccttccccg  agggcttcaa gtgggagcgc gtgatgaact   4800
tcgaggacgg cggcgtggtg accgtgaccc aggactcctc cctgcaggac ggctccttca   4860
tctacaaggt gaagttcatc ggcgtgaact tcccctccga cggccccgta atgcagaaga   4920
agactatggg ctgggaggcc tccaccgagc gcctgtaccc ccgcgacggc gtgctgaagg   4980
gcgagatcca caaggccctg aagctgaagg acggcggcca ctacctggtg gagttcaagt   5040
ccatctacat ggccaagaag cccgtgcagc tgcccggcta ctactacgtg gactccaagc   5100
tggacatcac ctcccacaac gaggactaca ccatcgtgga gcagtacgag cgcgccgagg   5160
gccgccacca cctgttcctg tagcggccgg ccgcgacaca agtgtgagag tactaaataa   5220
atgctttggt tgtacgaaat cattcacacta aataaaataa tcaaagctta tatatgcctt   5280
ccgctaaggc cgaatgcaaa gaaattggtt cttctctcgtt atcttttgcc acttttacta   5340
gtacgtatta attactactt aatcatcttt gtttacggct cattatatcc gtcgacggcg   5400
cgggccgctc tagaactagt ggatccgtcg acggcgcgcc cgatcatccg gatatagttc   5460 ctccttttcag caaaaaaccc ctcaagaccc gtttagaggc cccaagggt tatgctagtt   5520 attgctcagc ggtggcagca gccaactcag cttcctttcg ggctttgtta gcagccggat   5580
cgatccaagc tgtacctcac tattcctttg ccctcggacg agtgctgggg cgtcggtttc   5640
cactatcggc gagtacttct acacagccat cggtccagac ggccgcgctt ctgcgggcga   5700
```

```
tttgtgtacg cccgacagtc ccggctccgg atcggacgat tgcgtcgcat cgaccctgcg    5760
cccaagctgc atcatcgaaa ttgccgtcaa ccaagctctg atagagttgg tcaagaccaa    5820
tgcggagcat atacgcccgg agccgcggcg atcctgcaag ctccggatgc ctccgctcga    5880
agtagcgcgt ctgctgctcc atacaagcca accacggcct ccagaagaag atgttggcga    5940
cctcgtattg ggaatcccg aacatcgcct cgctccagtc aatgaccgct gttatgcggc     6000
cattgtccgt caggacattg ttggagccga atccgcgtg cacgaggtgc cggacttcgg     6060
ggcagtcctc ggcccaaagc atcagctcat cgagagcctg cgcgacggac gcactgacgg    6120
tgtcgtccat cacagtttgc cagtgataca catggggatc agcaatcgcg catatgaaat    6180
cacgccatgt agtgtattga ccgattcctt gcggtccgaa tgggccgaac ccgctcgtct    6240
ggctaagatc ggccgcagcg atcgcatcca tagcctccgc gaccggctgc agaacagcgg    6300
gcagttcggt ttcaggcagg tcttgcaacg tgacacctg tgcacggcgg gagatgcaat     6360
aggtcaggct ctcgctgaat tccccaatgt caagcacttc cggaatcggg agcgcggccg    6420
atgcaaagtg ccgataaaca taacgatctt tgtagaaacc atcggcgcag ctatttaccc    6480
gcaggacata tccacgccct cctacatcga agctgaaagc acgagattct cgccctccg     6540 agagctgcat caggtcggag acgctgtcga acttttcgat cagaaacttc tcgacagacg    6600
tcgcggtgag ttcaggcttt tccatgggta tatctccttc ttaaagttaa acaaaattat    6660
ttctagaggg aaaccgttgt ggtctcccta tagtgagtcg tattaatttc gcgggatcga    6720
gatcgatcca attccaatcc cacaaaaatc tgagcttaac agcacagttg ctcctctcag    6780
agcagaatcg ggtattcaac accctcatat caactactac gttgtgtata cggtccaca    6840 tgccggtata tacgatgact ggggttgtac aaaggcggca acaaacggcg ttcccggagt    6900
tgcacacaag aaatttgcca ctattacaga ggcaagagca gcagctgacg cgtacacaac    6960
aagtcagcaa acagacaggt tgaacttcat ccccaaagga gaagctcaac tcaagcccaa    7020
gagctttgct aaggccctaa caagcccacc aaagcaaaaa gcccactggc tcacgctagg    7080
aaccaaaagg cccagcagtg atccagcccc aaaagagatc tcctttgccc cggagattac    7140
aatggacgat ttcctctatc tttacgatct aggaaggaag ttcgaaggtg aaggtgacga    7200
cactatgttc accactgata atgagaaggt tagcctcttc aatttcagaa agaatgctga    7260
cccacagatg gttagagagg cctacgcagc aggtctcatc aagacgatct acccgagtaa    7320
caatctccag gagatcaaat accttcccaa gaaggttaaa gatgcagtca aaagattcag    7380
gactaattgc atcaagaaca cagagaaaga catatttctc aagatcagaa gtactattcc    7440
agtatggacg attcaaggct tgcttcataa accaaggcaa gtaatagaga ttggagtctc    7500
taaaaaggta gttcctactg aatctaaggc catgcatgga gtctaagatt caaatcgagg    7560
atctaacaga actcgccgtg aagactggcg aacagttcat acagagtctt ttacgactca    7620
atgacaagaa gaaaatcttc gtcaacatgg tggagcacga cactctggtc tactccaaaa    7680
atgtcaaaga tacagtctca gaagaccaaa gggctattga acttttcaa caaggataa    7740 tttcgggaaa cctcctcgga ttccattgcc cagctatctg tcacttcatc gaaggacag    7800 tagaaaagga aggtggctcc tacaaatgcc atcattgcga taaggaaag gctatcattc    7860 aagatgcctc tgccgacagt ggtcccaaag atgaccccc acccacgagg agcatcgtgg    7920
aaaaagaaga cgttccaacc acgtcttcaa agcaagtgga ttgatgtgac atctccactg    7980
acgtaaggga tgacgcacaa tcccactatc cttcgcaaga cccttcctct atataaggaa    8040
gttcatttca tttggagagg acacgctcga gctcatttct ctattacttc agccataaca    8100
```

| | |
|---|---|
| aaagaactct tttctcttct tattaaacca tgaaaaagcc tgaactcacc gcgacgtctg | 8160 |
| tcgagaagtt tctgatcgaa aagttcgaca gcgtctccga cctgatgcag ctctcggagg | 8220 |
| gcgaagaatc tcgtgctttc agcttcgatg taggagggcg tggatatgtc ctgcgggtaa | 8280 |
| atagctgcgc cgatggtttc tacaaagatc gttatgttta tcggcacttt gcatcggccg | 8340 |
| cgctcccgat tccggaagtg cttgacattg gggaattcag cgagagcctg acctattgca | 8400 |
| tctcccgccg tgcacagggt gtcacgttgc aagacctgcc tgaaaccgaa ctgcccgctg | 8460 |
| ttctgcagcc ggtcgcggag gccatggatg cgatcgctgc ggccgatctt agccagacga | 8520 |
| gcgggttcgg cccattcgga ccgcaaggaa tcggtcaata cactacatgg cgtgatttca | 8580 |
| tatgcgcgat tgctgatccc catgtgtatc actggcaaac tgtgatggac gacaccgtca | 8640 |
| gtgcgtccgt cgcgcaggct ctcgatgagc tgatgctttg ggccgaggac tgccccgaag | 8700 |
| tccggcacct cgtgcacgcg gatttcggct ccaacaatgt cctgacggac aatggccgca | 8760 |
| taacagcggt cattgactgg agcgaggcga tgttcgggga ttcccaatac gaggtcgcca | 8820 |
| acatcttctt ctggaggccg tggttggctt gtatggagca gcagacgcgc tacttcgagc | 8880 |
| ggaggcatcc ggagcttgca ggatcgccgc ggctccgggc gtatatgctc cgcattggtc | 8940 |
| ttgaccaact ctatcagagc ttggttgacg gcaatttcga tgatgcagct gggcgcagg | 9000 |
| gtcgatgcga cgcaatcgtc cgatccggag ccgggactgt cgggcgtaca caatcgccc | 9060 |
| gcagaagcgc ggccgtctgg accgatggct gtgtagaagt actcgccgat agtggaaacc | 9120 |
| gacgccccag cactcgtccg agggcaaagg aatagtgagg tacctaaaga aggagtgcgt | 9180 |
| cgaagcagat cgttcaaaca tttggcaata aagtttctta agattgaatc ctgttgccgg | 9240 |
| tcttgcgatg attatcatat aatttctgtt gaattacgtt aagcatgtaa taattaacat | 9300 |
| gtaatgcatg acgttattta tgagatgggt ttttatgatt agagtcccgc aattatacat | 9360 |
| ttaatacgcg atagaaaaca aaatatagcg cgcaaactag gataaattat cgcgcgcggt | 9420 |
| gtcatctatg ttactagatc gatgtcgaat ctgatcaacc tgcattaatg aatcggccaa | 9480 |
| cgcgcgggga gaggcggttt gcgtattggg cgctcttccg cttcctcgct cactgactcg | 9540 |
| ctgcgctcgg tcgttcggct gcggcgagcg gtatcagctc actcaaaggc ggtaatacgg | 9600 |
| ttatccacag aatcagggga taacgcagga agaacatgt gagcaaaagg ccagcaaaag | 9660 |
| gccaggaacc gtaaaaaggc cgcgttgctg gcgtttttcc ataggctccg ccccctgac | 9720 |
| gagcatcaca aaaatcgacg ctcaagtcag aggtggcgaa acccgacagg actataaaga | 9780 |
| taccaggcgt ttccccctgg aagctccctc gtgcgctctc ctgttccgac cctgccgctt | 9840 |
| accggatacc tgtccgcctt tctcccttcg ggaagcgtgg cgctttctca atgctcacgc | 9900 |
| tgtaggtatc tcagttcggt gtaggtcgtt cgctccaagc tgggctgtgt gcacgaaccc | 9960 |
| cccgttcagc ccgaccgctg cgccttatcc ggtaactatc gtcttgagtc aacccggta | 10020 |
| agacacgact tatcgccact ggcagcagcc actggtaaca ggattagcag agcgaggtat | 10080 |
| gtaggcggtg ctacagagtt cttgaagtgg tggcctaact acggctacac tagaaggaca | 10140 |
| gtatttggta tctgcgctct gctgaagcca gttaccttcg gaaaaagagt tggtagctct | 10200 |
| tgatccggca acaaaccac cgctggtagc ggtggttttt tgtttgcaa gcagcagatt | 10260 |
| acgcgcagaa aaaaggatc tcaagaagat cctttgatct tttctacggg gtctgacgct | 10320 |
| cagtggaacg aaaactcacg ttaagggatt ttggtcatga cattaaccta taaaaatagg | 10380 |
| cgtatcacga ggcccttcg tctcgcgcgt ttcggtgatg acggtgaaaa cctctgacac | 10440 |
| atgcagctcc cggagacggt cacagcttgt ctgtaagcgg atgccgggag cagacaagcc | 10500 |

```
cgtcagggcg cgtcagcggg tgttggcggg tgtcggggct ggcttaacta tgcggcatca    10560
gagcagattg tactgagagt gcaccatatg gacatattgt cgttagaacg cggctacaat    10620
taatacataa ccttatgtat catacacata cgatttaggt gacactatag aacggcgcgc    10680
caagcttttg atccatgccc ttcatttgcc gcttattaat taatttggta acagtccgta    10740
ctaatcagtt acttatcctt cccccatcat aattaatctt ggtagtctcg aatgccacaa    10800
cactgactag tctcttggat cataagaaaa agccaaggaa caaagaaga caaaacacaa     10860 tgagagtatc ctttgcatag caatgtctaa gttcataaaa ttcaaacaaa aacgcaatca    10920
cacacagtgg acatcactta tccactagct gatcaggatc gccgcgtcaa gaaaaaaaaa    10980
ctggacccca aaagccatgc acaacaacac gtactcacaa aggtgtcaat cgagcagccc    11040
aaaacattca ccaactcaac ccatcatgag ccctcacatt tgttgtttct aacccaacct    11100
caaactcgta ttctcttccg ccacctcatt tttgtttatt tcaacacccg tcaaactgca    11160
tgccaccccg tggccaaatg tccatgcatg ttaacaagac ctatgactat aaatagctgc    11220
aatctcggcc caggttttca tcatcaagaa ccagttcaat atcctagtac accgtattaa    11280
agaatttaag atatactgc                                                 11299

<210> SEQ ID NO 11
<211> LENGTH: 9142
<212> TYPE: DNA
<213> ORGANISM: Artificial Sequence
<220> FEATURE:
<223> OTHER INFORMATION: T-DNA of vector pZBL120xKS333
<220> FEATURE:
<221> NAME/KEY: misc_feature
<222> LOCATION: (1892)..(1892)
<223> OTHER INFORMATION: n is a, c, g, or t

<400> SEQUENCE: 11
aattacaacg gtatatatcc tgccgtcgac tctagaggat ccgcgccgtc gacggatcca      60
ctagttctag agcggccgc gccgtcgacg gatataatga gccgtaaaca aagatgatta     120
agtagtaatt aatacgtact agtaaaagtg gcaaaagata acgagaaaga accaatttct    180
ttgcattcgg ccttagcgga aggcatatat aagctttgat tattttattt agtgtaatga    240
tttcgtacaa ccaaagcatt tatttagtac tctcacactt gtgtcgcggc cggccgctac    300
aggaacaggt ggtggcggcc ctcggcgcgc tcgtactgct ccacgatggt gtagtcctcg    360
ttgtgggagg tgatgtccag cttggagtcc acgtagtagt agccgggcag ctgcacgggc    420
ttcttggcca tgtagatgga cttgaactcc accaggtagt ggccgccgtc cttcagcttc    480
agggccttgt ggatctcgcc cttcagcacg ccgtcgcggg ggtacaggcg ctcggtggag    540
gcctcccagc ccatagtctt cttctgcatt acggggccgt cggaggggaa gttcacgccg    600
atgaacttca ccttgtagat gaaggagccg tcctgcaggg aggagtcctg ggtcacggtc    660
accacgccgc cgtcctcgaa gttcatcacg cgctcccact gaagccctc ggggaaggac     720 agcttcttgt agtcgggat gtcggcgggg tgcttcacgt acaccttgga gccgtactgg      780
aactgggggg acaggatgtc ccaggcgaag ggcaggggc cgcccttggt caccttcagc     840
ttggcggtct gggtgccctc gtaggggcgg ccctcgccct cgccctcgat ctcgaactcg    900
tggccgttca cggagccctc catgcgcacc ttgaagcgca tgaactcctt gatgacgtcc    960
tcggaggagg ccatgggccg cttgggggc tatggaagac tttcttagtt agttgtgtga    1020
ataagcaatg ttgggagaat cgggactact tataggatag gaataaaaca gaaaagtatt    1080
aagtgctaat gaaatatttta gactgataat taaaatcttc acgtatgtcc acttgatata    1140
```

```
aaaacgtcag gaataaagga agtacagtag aatttaaagg tactcttttt atatataccc    1200
gtgttctctt tttggctagc tagttgcata aaaataatc tatattttta tcattatttt     1260
aaatatctta tgagatggta aatatttatc ataattttt ttactattat ttattatttg     1320
tgtgtgtaat acatatagaa gttaattaca aattttattt acttttcat tattttgata    1380 tgattcacca ttaatttagt gttattattt ataatagttc attttaatct ttttgtatat    1440
attatgcgtg cagtactttt ttcctacata taactactat tacattttat ttatataata    1500
tttttattaa tgaattttcg tgataatatg taatattgtt cattattatt tcagattttt    1560
taaaaatatt tgtgttatta tttatgaaat atgtaatttt tttagtattt gatttatga    1620 tgataaagtg ttctaaattc aaagaaggg ggaaagcgta aacattaaaa aacgtcatca    1680
aacaaaaaca aaatcttgtt aataaagata aaactgtttg ttttgatcac tgttatttcg    1740
taatataaaa acattattta tatttatatt gttgacaacc aaatttgcct atcaaatcta    1800
accaatataa tgcatgcgtg gcaggtaatg tactaccatg aacttaagtc atgacataat    1860
aaaccgtgaa tctgaccaat gcatgtacct anctaaattg tatttgtgac acgaagcaaa    1920
tgattcaatt cacaatggag atgggaaaca aataatgaag aacccagaac taagaaagct    1980
tttctgaaaa ataaaataaa ggcaatgtca aaagtatact gcatcatcag tccagaaagc    2040
acatgatatt tttttatcag tatcaatgca gctagtttta ttttacaata tcgatatagc    2100
tagtttaaat atattgcagc tagatttata aatatttgtg ttattattta tcatttgtgt    2160
aatcctgttt ttagtatttt agtttatata tgatgataat gtattccaaa tttaaagaa     2220 gggaaataaa tttaaacaag aaaaaaagtc atcaaacaaa aaacaaatga aagggtggaa    2280
agatgttacc atgtaatgtg aatgttacag tatttctttt attatagagt taacaaatta    2340
actaatatga ttttgttaat aatgataaaa tatttttttt attattattt cataatataa    2400
aaatagttta cttaatataa aaaaaattct atcgttcaca acaaagttgg ccacctaatt    2460
taaccatgca tgtacccatg gaccatatta ggtaaccatc aaacctgatg aagagataaa    2520
gagatgaaga cttaagtcat aacacaaaac cataaaaaac aaaaatacaa tcaaccgtca    2580
atctgaccaa tgcatgaaaa agctgcaata gtgagtggcg acacaaagca catgattttc    2640
ttacaacgga gataaaacca aaaaaatatt tcatgaacaa cctagaacaa ataaagcttt    2700
tatataataa atatataaat aaataaaggc tatggaataa tatacttcaa tatatttgga    2760
ttaaataaat tgttggcggg gttgatatat ttatacacac ctaaagtcac ttcaatctca    2820
ttttcactta acttttattt tttttttctt tttatttatc ataaagagaa tattgataat    2880
atacttttta acatattttt atgacatttt ttattggtga aaacttatta aaaatcataa    2940
attttgtaag ttagatttat ttaaagagtt cctcttctta ttttaaattt tttaataaat    3000
ttttaaataa ctaaaatttg tgttaaaaat gttaaaaaag tgtgttatta acccttctct    3060
tcgaggatcc aagcttgttg aaacatccct gaagtgtctc atttattt atttattctt    3120 tgctgataaa aaaataaaat aaagaagct aagcacacgg tcaaccattg ctctactgct    3180
aaaagggtta tgtgtagtgt tttactgcat aaattatgca gcaaacaaga caactcaaat    3240
taaaaaattt cctttgcttg tttttttgtt gtctctgact tgactttctt gtggaagttg    3300
gttgtataag gattgggaca ccattgtcct tcttaattta attttattct ttgctgataa    3360
aaaaaaaaat ttcatatagt gttaaataat aatttgttaa ataaccaaaa agtcaaatat    3420
gtttactctc gtttaaataa ttgagattcg tccagcaagg ctaaacgatt gtatagattt    3480
atgacaatat ttacttttt atagataaat gttatattat aataaattta tatacatata    3540
```

```
ttatatgtta tttattatta ttttaaatcc ttcaatattt tatcaaacca actcataatt    3600
ttttttttat ctgtaagaag caataaaatt aaatagaccc actttaagga tgatccaacc    3660
tttatacaga gtaagagagt tcaaatagta ccctttcata tacatatcaa ctaaaatatt    3720
agaaatatca tggatcaaac cttataaaga cattaaataa gtggataagt ataatatata    3780
aatgggtagt atataatata taaatggata caaacttctc tctttataat tgttatgtct    3840
ccttaacatc ctaatataat acataagtgg gtaatatata atatataaat ggagacaaac    3900
ttcttccatt ataattgtta tgtcttctta acacttatgt ctcgttcaca atgctaaggt    3960
tagaattgtt tagaaagtct tatagtacac atttgttttt gtactatttg aagcattcca    4020
taagccgtca cgattcagat gatttataat aataagagga aatttatcat agaacaataa    4080
ggtgcataga tagagtgtta atatatcata acatcctttg tttattcata gaagaagtga    4140
gatggagctc agttattata ctgttacatg gtcggataca atattccatg ctctccatga    4200
gctcttacac ctacatgcat tttagttcat acttgcggcc gctcaaaccc taaattcaca    4260
cgaaaccgag gtggttatcg acgacgaaga tggcgaagta gtcgagaaca accccctctc    4320
ctcatgatca ctcttcatca tctccatttt ccccacatct tctaacttct cacccccctc    4380
cccgcacctc tcgtcttcca agctcgcctc gaatatcaac ccgatgtcgt cctcgaaccc    4440
gatctcatca aagaacaggt caggcaattc gccagacttc tcgaggggga ggtcggggac    4500
ctgcacgaac cccgtgtcta ggaatgacca atgcagatca tgatcctcct ccattgtcgt    4560
cgggctgttc tccatcgacg ggaactggag gggcagcct gagaacgcca tcgtcgtctg    4620
ttgctgttgc tgctgtacta cttcgccttc ctcagaagag gaagcagggg agcagttggg    4680
ctgtaggggc tgctctgctg ctggaaaaac tgatgattta ttctccagcc gcccaatgta    4740
attgctgatg tcgaaattgg tcactgcatt gaccctctg tactcaattg cagccatgtc    4800
atatgctgct gctgcttcct cttgtgtgtt gtaagttccc aggtaaagat atttgcttcc    4860
gaaaacacgg ccgatccgcg cctcccaccg gccgttgtgg tggtggcggg ccacgccgcg    4920
gtacttcgat acgcctctcg aaaatccgct gctccgccgc cgtaacgacg ccaaatactc    4980
ctccttcgta actttccgca tttcttctat ttcattcctg tacgactcta ccgggaaatt    5040
gagggtggtt ccgggacccc agtacttgag ggcagcgagg tcataagttc gggcggcagc    5100
ttcctcgtta tcgtatgctc ccaaataaac ttgccttcct ttttttgttct gaatgctatt    5160 ccacgaactc ttgtcccaga gatgcgcttc gaaccggccg gtccatcggt gcctagtgac    5220
tcctctgtaa atggagctcc ggcggccgga agaggcattg ttgttgctgc tgttgttgtt    5280
attaccgtta cgattctcaa tctcgcattt ggcgtcgtcc tgattccgct tccggcgttt    5340
cgctccggtc ttctccgatt gcggccggcg cggaggggcg gcgagattga gattattgct    5400
gtcgaagccg ccgccgccga cgcaggagga ggaggaggag gaggaagtag aaacagaggg    5460
agaccttctc atggcggccg cagtatatct taaattcttt aatacggtgt actaggatat    5520
tgaactggtt cttgatgatg aaaacctggg ccgagattgc agctatttat agtcataggt    5580
cttgttaaca tgcatggaca tttggccacg gggtggcatg cagtttgacg ggtgttgaaa    5640
taaacaaaaa tgaggtggcg gaagagaata cgagtttgag gttgggttag aaacaacaaa    5700
tgtgagggct catgatgggt tgagttggtg aatgttttgg gctgctcgat tgacacctttt    5760 gtgagtacgt gttgttgtgc atggcttttg gggtccagtt ttttttttctt gacgcggcga    5820 tcctgatcag ctagtggata agtgatgtcc actgtgtgtg attgcgtttt tgtttgaatt    5880
ttatgaactt agacattgct atgcaaagga tactctcatt gtgtttttgtc ttcttttgtt    5940
```

```
ccttggcttt tccttatgat ccaagagact agtcagtgtt gtggcattcg agactaccaa    6000
gattaattat gatgggggaa ggataagtaa ctgattagta cggactgtta ccaaattaat    6060
taataagcgg caaatgaagg gcatggatca aaagcttggc gcgaattcac tggccgtcgt    6120
tttacaacgt cgtgactggg aaaaccctgg cgttacccaa cttaatcgcc ttgcagcaca    6180
tccccctttc gccagctggc gtaatagcga agaggcccgc accgatcgcc cttcccaaca    6240
gttgcgcagc ctgaatggcg aatggatcga tccgtcgatc gaccaaagcg gccatcgtgc    6300
ctccccactc ctgcagttcg ggggcatgga tgcgcggata gccgctgctg gtttcctgga    6360
tgccgacgga tttgcactgc cggtagaact ccgcgaggtc gtccagcctc aggcagcagc    6420
tgaaccaact cgcgagggga tcgagcccct gctgagcctc gacatgttgt cgcaaaattc    6480
gccctggacc cgcccaacga tttgtcgtca ctgtcaaggt tgacctgca  cttcatttgg    6540 ggcccacata caccaaaaaa atgctgcata attctcgggg cagcaagtcg gttacccggc    6600
cgccgtgctg gaccgggttg aatggtgccc gtaactttcg gtagagcgga cggccaatac    6660
tcaacttcaa ggaatctcac ccatgcgcgc cggcggggaa ccggagttcc cttcagtgaa    6720
cgttattagt tcgccgctcg gtgtgtcgta gatactagcc cctggggcct tttgaaattt    6780
gaataagatt tatgtaatca gtcttttagg tttgaccggt tctgccgctt ttttaaaat    6840 tggatttgta ataataaaac gcaattgttt gttattgtgg cgctctatca tagatgtcgc    6900
tataacccta ttcagcacaa tatattgttt tcattttaat attgtacata aagtagtag    6960 ggtacaatca gtaaattgaa cggagaatat tattcataaa aatacgatag taacgggtga    7020
tatattcatt agaatgaacc gaaaccggcg gtaaggatct gagctacaca tgctcaggtt    7080
ttttacaacg tgcacaacag aattgaaagc aaatatcatg cgatcatagg cgtctcgcat    7140
atctcattaa agcaggggt gggcgaagaa ctccagcatg agatccccgc gctggaggat    7200
catccagccg cgtcccgga aaacgattcc gaagcccaac cttcataga aggcggcggt    7260 ggaatcgaaa tctcgtgatg gcaggttggg cgtcgcttgg tcggtcattt cgaaccccag    7320
agtcccgctc agaagaactc gtcaagaagg cgatagaagg cgatgcgctg cgaatcggga    7380
gcggcgatac cgtaaagcac gaggaagcgg tcagcccatt cgccgccaag ctcttcagca    7440
atatcacggg tagccaacgc tatgtcctga tagcggtccg ccacacccag ccggccacag    7500
tcgatgaatc cagaaaagcg gccattttcc accatgatat tcggcaagca ggcatcgcca    7560
tgggtcacga cgagatcctc gccgtcgggc atgcgcgcct tgagcctggc gaacagttcg    7620
gctggcgcga gcccctgatg ctcttcgtcc agatcatcct gatcgacaag accggcttcc    7680
atccgagtac gtgctcgctc gatgcgatgt ttcgcttggt ggtcgaatgg gcaggtagcc    7740
ggatcaagcg tatgcagccg ccgcattgca tcagccatga tggatacttt ctcggcagga    7800
gcaaggtgag atgacaggag atcctgcccc ggcacttcgc ccaatagcag ccagtccctt    7860
cccgcttcag tgacaacgtc gagcacagct gcgcaaggaa cgcccgtcgt ggccagccac    7920
gatagccgcg ctgcctcgtc ctgcagttca ttcagggcac cggacaggtc ggtcttgaca    7980
aaaagaaccg ggcgcccctg cgctgacagc cggaacacgg cggcatcaga gcagccgatt    8040
gtctgttgtg cccagtcata gccgaatagc ctctccaccc aagcggccgg agaacctgcg    8100
tgcaatccat cttgttcaat catgcgaaac gatcccgca agcttggaga ctggtgattt    8160
cagcgtgtcc tctccaaatg aaatgaactt ccttatatag aggaagggtc ttgcgaagga    8220
tagtgggatt gtgcgtcatc ccttacgtca gtggagatat cacatcaatc cacttgcttt    8280
gaagacgtgg ttggaacgtc ttcttttcc acgatgctcc tcgtgggtgg gggtccatct    8340
```

-continued

| | |
|---|---|
| ttgggaccac tgtcggcaga ggcatcttca acgatggcct ttcctttatc gcaatgatgg | 8400 |
| catttgtagg agccaccttc cttttccact atcttcacaa taaagtgaca gatagctggg | 8460 |
| caatggaatc cgaggaggtt tccggatatt acccttttgtt gaaaagtctc aattgccctt | 8520 |
| tggtcttctg agactgtatc tttgatattt ttggagtaga caagcgtgtc gtgctccacc | 8580 |
| atgttgacga agattttctt cttgtcattg agtcgtaaga gactctgtat gaactgttcg | 8640 |
| ccagtctttta cggcgagttc tgttaggtcc tctatttgaa tctttgactc catggccttt | 8700 |
| gattcagtgg gaactacctt tttagagact ccaatctcta ttacttgcct tggttttgtga | 8760 |
| agcaagcctt gaatcgtcca tactggaata gtacttctga tcttgagaaa tatatctttc | 8820 |
| tctgtgttct tgatgcagtt agtcctgaat cttttgactg catctttaac cttcttggga | 8880 |
| aggtatttga tctcctggag attattgctc gggtagatcg tcttgatgag acctgctgcg | 8940 |
| taagcctctc taaccatctg tgggttagca ttctttctga aattgaaaag gctaatcttc | 9000 |
| tcattatcag tggtgaacat ggtatcgtca ccttctccgt cgaacttcct gactagatcg | 9060 |
| tagagataga ggaagtcgtc cattgtgatc tctggggcaa aggagatctg aattatcatt | 9120 |
| tacaattgaa tatatcctgc ca | 9142 |

<210> SEQ ID NO 12
<211> LENGTH: 34
<212> TYPE: DNA
<213> ORGANISM: Artificial Sequence
<220> FEATURE:
<223> OTHER INFORMATION: PCR primer MWG341

<400> SEQUENCE: 12

| | |
|---|---|
| gaattcgcgg ccgcatgaag aggtctccag catc | 34 |

<210> SEQ ID NO 13
<211> LENGTH: 34
<212> TYPE: DNA
<213> ORGANISM: Artificial Sequence
<220> FEATURE:
<223> OTHER INFORMATION: PCR primer MWG342

<400> SEQUENCE: 13

| | |
|---|---|
| gaattcgcgg ccgctcatag atctagagca tagt | 34 |

<210> SEQ ID NO 14
<211> LENGTH: 11304
<212> TYPE: DNA
<213> ORGANISM: Artificial Sequence
<220> FEATURE:
<223> OTHER INFORMATION: vector pKS334
<220> FEATURE:
<221> NAME/KEY: misc_feature
<222> LOCATION: (3593)..(3593)
<223> OTHER INFORMATION: n is a, c, g, or t

<400> SEQUENCE: 14

| | |
|---|---|
| ggccgcatga agaggtctcc agcatcttct tgttcatcat ctacttcctc tgttgggttt | 60 |
| gaagctccca ttgaaaaaag aaggcctaag catccaagga ggaataattt gaagtcacaa | 120 |
| aaatgcaagc agaaccaaac caccactggt ggcagaagaa gctctatcta tagaggagtt | 180 |
| acaaggcata ggtggacagg gaggtttgaa gctcacctat gggataagag ctcttggaac | 240 |
| aacattcaga gcaagaaggg tcgacaagtt tatttggggg catatgatac tgaagaatct | 300 |
| gcagcccgta cctatgacct tgcagccctt aaatactggg gaaaagatgc aaccctgaat | 360 |
| ttcccgatag aaacttatac caaggagctc gaggaaatgg acaaggtttc aagagaagaa | 420 |

```
tatttggctt ctttgcggcg ccaaagcagt ggcttttcta gaggcctgtc taagtaccgt    480 gggggttgcta ggcatcatca taatggtcgc tgggaagcac gaattggaag agtatgcgga    540
aacaagtacc tctacttggg gacatataaa actcaagagg aggcagcagt ggcatatgac    600
atggcagcaa tagagtaccg tggagtcaat gcagtgacca attttgacat aagcaactac    660
atggacaaaa taagaagaa aaatgaccaa acccaacaac aacaaacaga agcacaaacg    720
gaaacagttc ctaactcctc tgactctgaa gaagtagaag tagaacaaca gacaacaaca    780
ataaccacac caccccatc tgaaaatctg cacatgccac cacagcagca ccaagttcaa    840
tacacccccc atgtctctcc aagggaagaa gaatcatcat cactgatcac aattatggac    900
catgtgcttg agcaggatct gccatggagc ttcatgtaca ctggcttgtc tcagtttcaa    960
gatccaaact ggctttctg caaaggtgat gatgacttgg tgggcatgtt tgatagtgca   1020
gggtttgagg aagacattga ttttctgttc agcactcaac ctggtgatga gactgagagt   1080
gatgtcaaca atatgagcgc agttttggat agtgttgagt gtggagacac aaatgggggct   1140 ggtggaagca tgatgcatgt ggataacaag cagaagatag tatcatttgc ttcttcacca   1200
tcatctacaa ctacagtttc ttgtgactat gctctagatc tagcggccgc aagtatgaac   1260
taaaatgcat gtaggtgtaa gagctcatgg agagcatgga atattgtatc cgaccatgta   1320
acagtataat aactgagctc catctcactt cttctatgaa taaacaaagg atgttatgat   1380
atattaacac tctatctatg caccttattg ttctatgata aatttcctct tattattata   1440
aatcatctga atcgtgacgg cttatggaat gcttcaaata gtacaaaac aaatgtgtac   1500 tataagactt tctaaacaat tctaaccta gcattgtgaa cgagacataa gtgttaagaa   1560
gacataacaa ttataatgga agaagtttgt ctccatttat atattatata ttacccactt   1620
atgtattata ttaggatgtt aaggagacat aacaattata aagagagaag tttgtatcca   1680
tttatatatt atatactacc catttatata ttatacttat ccacttattt aatgtctta   1740 taaggtttga tccatgatat ttctaatatt ttagttgata tgtatatgaa agggtactat   1800
ttgaactctc ttactctgta taaaggttgg atcatcctta aagtgggtct atttaatttt   1860
attgcttctt acagataaaa aaaaaattat gagttggttt gataaaatat tgaaggattt   1920
aaaataataa taaataacat ataatatatg tatataaatt tattataata taacattttat   1980 ctataaaaaa gtaaatattg tcataaatct atacaatcgt ttagccttgc tggacgaatc   2040
tcaattattt aaacgagagt aaacatattt gacttttttgg ttatttaaca aattattatt   2100
taacactata tgaaattttt ttttttatca gcaaagaata aaattaaatt aagaaggaca   2160
atggtgtccc aatccttata caaccaactt ccacaagaaa gtcaagtcag agacaacaaa   2220
aaaacaagca aggaaatttt tttaatttga gttgtcttgt ttgctgcata atttatgcag   2280
taaaacacta cacataaccc ttttagcagt agagcaatgg ttgaccgtgt gcttagcttc   2340 ttttattttta tttttttatc agcaaagaat aaataaata aatgagaca cttcagggat   2400 gtttcaacaa gcttggatcc tcgaagagaa gggttaataa cacacttttt taacattttt   2460
aacacaaatt ttagttattt aaaaatttat taaaaatttt aaaataagaa gaggaactct   2520
ttaaataaat ctaacttaca aaatttgta ttttaataa gttttcacca ataaaaaatg   2580
tcataaaaat atgttaaaaa gtatattatc aatattctct ttatgataaa taaaagaaa   2640 aaaaaaataa aagttaagtg aaatgagat tgaagtgact ttaggtgtgt ataaatatat   2700
caaccccgcc aacaatttat ttaatccaaa tatattgaag tatattattc catagccttt   2760
atttatttat atatttatta tataaaagct ttatttgttc taggttgttc atgaaatatt   2820
```

```
tttttggttt tatctccgtt gtaagaaaat catgtgcttt gtgtcgccac tcactattgc    2880 agcttttttca tgcattggtc agattgacgg ttgattgtat ttttgttttt tatggttttg   2940
tgttatgact taagtcttca tctctttatc tcttcatcag gtttgatggt tacctaatat    3000
ggtccatggg tacatgcatg gttaaattag gtggccaact ttgttgtgaa cgatagaatt    3060 tttttatat taagtaaact atttttatat tatgaaataa taataaaaaa aatattttat     3120
cattattaac aaaatcatat tagttaattt gttaactcta taataaaaga aatactgtaa   3180
cattcacatt acatggtaac atcttttccac cctttcattt gttttttgtt tgatgacttt   3240
ttttcttgtt taaatttatt tcccttcttt taaatttgga atacattatc atcatatata    3300
aactaaaata ctaaaaacag gattacacaa atgataaaata ataacacaaa tatttataaa   3360
tctagctgca atatatttaa actagctata tcgatattgt aaaataaaac tagctgcatt   3420
gatactgata aaaaatatc atgtgctttc tggactgatg atgcagtata cttttgacat    3480
tgcctttatt ttattttttca gaaaagcttt cttagttctg ggttcttcat tatttgtttc   3540
ccatctccat tgtgaattga atcatttgct tcgtgtcaca aatacaattt agntaggtac    3600
atgcattggt cagattcacg gtttattatg tcatgactta agttcatggt agtacattac   3660
ctgccacgca tgcattatat tggttagatt tgataggcaa atttggttgt caacaatata   3720
aatataaata atgtttttat attacgaaat aacagtgatc aaaacaaaca gttttatctt   3780
tattaacaag attttgtttt tgtttgatga cgttttttaa tgtttacgct ttccccccttc   3840 ttttgaattt agaacacttt atcatcataa aatcaaatac taaaaaaatt acatatttca    3900
taaataataa cacaaatatt tttaaaaaat ctgaaataat aatgaacaat attacatatt   3960
atcacgaaaa ttcattaata aaaatattat ataaataaaa tgtaatagta gttatatgta   4020
ggaaaaaagt actgcacgca taatatatac aaaaagatta aaatgaacta ttataaataa   4080
taacactaaa ttaatggtga atcatatcaa aataatgaaa aagtaaataa aatttgtaat   4140
taacttctat atgtattaca cacacaaata ataaataata gtaaaaaaaa ttatgataaa   4200
tatttaccat ctcataagat atttaaaata atgataaaaa tatagattat tttttatgca   4260
actagctagc caaaaagaga acacgggtat atataaaaag agtacccttta aattctactg   4320 tacttccttt attcctgacg ttttatatc aagtggacat acgtgaagat tttaattatc    4380
agtctaaata tttcattagc acttaatact tttctgtttt attcctatcc tataagtagt   4440
cccgattctc ccaacattgc ttattcacac aactaactaa gaaagtcttc catagccccc   4500
caagcggccc atggcctcct ccgaggacgt catcaaggag ttcatgcgct tcaaggtgcg   4560
catggagggc tccgtgaacg gccacgagtt cgagatcgag ggcgagggcg agggccgccc   4620
ctacgagggc acccagaccg ccaagctgaa ggtgaccaag ggcggccccc tgcccttcgc   4680
ctgggacatc ctgtccccccc agttccagta cggctccaag gtgtacgtga agcaccccgc   4740
cgacatcccc gactacaaga agctgtcctt ccccgagggc ttcaagtggg agcgcgtgat   4800
gaacttcgag gacggcggcg tggtgaccgt gacccaggac tcctccctgc aggacggctc   4860
cttcatctac aaggtgaagt tcatcggcgt gaacttcccc tccgacggcc ccgtaatgca   4920
gaagaagact atgggctggg aggcctccac cgagcgcctg tacccccgcg acggcgtgct   4980
gaagggcgag atccacaagg ccctgaagct gaaggacggc ggccactacc tggtggagtt   5040
caagtccatc tacatggcca agaagcccgt gcagctgccc ggctactact acgtggactc   5100
caagctggac atcacctccc acaacgagga ctacaccatc gtggagcagt acgagcgcgc   5160
cgagggccgc caccacctgt tcctgtagcg gccggccgcg acacaagtgt gagagtacta   5220
```

```
aataaatgct tggttgtac gaaatcatta cactaaataa aataatcaaa gcttatatat   5280
gccttccgct aaggccgaat gcaaagaaat tggttctttc tcgttatctt ttgccacttt   5340
tactagtacg tattaattac tacttaatca tctttgttta cggctcatta tatccgtcga   5400
cggcgcgggc cgctctagaa ctagtggatc cgtcgacggc gcgcccgatc atccggatat   5460
agttcctcct ttcagcaaaa aacccctcaa gacccgttta gaggcccaa ggggttatgc   5520 tagttattgc tcagcggtgg cagcagccaa ctcagcttcc tttcgggctt tgttagcagc   5580
cggatcgatc caagctgtac ctcactattc ctttgccctc ggacgagtgc tggggcgtcg   5640
gtttccacta tcggcgagta cttctacaca gccatcggtc cagacggccg cgcttctgcg   5700
ggcgatttgt gtacgcccga cagtcccggc tccggatcgg acgattgcgt cgcatcgacc   5760
ctgcgcccaa gctgcatcat cgaaattgcc gtcaaccaag ctctgataga gttggtcaag   5820
accaatgcgg agcatatacg cccggagccg cggcgatcct gcaagctccg gatgcctccg   5880
ctcgaagtag cgcgtctgct gctccataca agccaaccac ggcctccaga agaagatgtt   5940
ggcgacctcg tattgggaat ccccgaacat cgcctcgctc cagtcaatga ccgctgttat   6000
gcggccattg tccgtcagga cattgttgga gccgaaatcc gcgtgcacga ggtgccggac   6060
ttcggggcag tcctcggccc aaagcatcag ctcatcgaga gcctgcgcga cggacgcact   6120
gacggtgtcg tccatcacag tttgccagtg atacacatgg ggatcagcaa tcgcgcatat   6180
gaaatcacgc catgtagtgt attgaccgat tccttgcggt ccgaatgggc cgaacccgct   6240
cgtctggcta agatcggccg cagcgatcgc atccatagcc tccgcgaccg gctgcagaac   6300
agcgggcagt tcggtttcag gcaggtcttg caacgtgaca ccctgtgcac ggcgggagat   6360
gcaataggtc aggctctcgc tgaattcccc aatgtcaagc acttccggaa tcgggagcgc   6420
ggccgatgca aagtgccgat aaacataacg atctttgtag aaaccatcgg cgcagctatt   6480
tacccgcagg acatatccac gccctcctac atcgaagctg aaagcacgag attcttcgcc   6540
ctccgagagc tgcatcaggt cggagacgct gtcgaacttt tcgatcagaa acttctcgac   6600
agacgtcgcg gtgagttcag gcttttccat gggtatatct ccttcttaaa gttaaacaaa   6660
attatttcta gagggaaacc gttgtggtct ccctatagtg agtcgtatta atttcgcggg   6720
atcgagatcg atccaattcc aatcccacaa aaatctgagc ttaacagcac agttgctcct   6780
ctcagagcag aatcgggtat tcaacaccct catatcaact actacgttgt gtataacggt   6840
ccacatgccg gtatatacga tgactggggt tgtacaaagg cggcaacaaa cggcgttccc   6900
ggagttgcac acaagaaatt tgccactatt acagaggcaa gagcagcagc tgacgcgtac   6960
acaacaagtc agcaaacaga caggttgaac ttcatcccca aaggagaagc tcaactcaag   7020
cccaagagct ttgctaaggc cctaacaagc ccaccaaagc aaaaagccca ctggctcacg   7080
ctaggaacca aaaggcccag cagtgatcca gccccaaaag agatctcctt tgccccggag   7140
attacaatgg acgatttcct ctatctttac gatctaggaa ggaagttcga aggtgaaggt   7200
gacgacacta tgttcaccac tgataatgag aaggttagcc tcttcaattt cagaaagaat   7260
gctgacccac agatggttag agaggcctac gcagcaggtc tcatcaagac gatctacccg   7320
agtaacaatc tccaggagat caaataccct tcccaagaagg ttaaagatgc agtcaaaaga   7380
ttcaggacta attgcatcaa gaacacagag aaagacatat ttctcaagat cagaagtact   7440
attccagtat ggacgattca aggcttgctt cataaaccaa ggcaagtaat agagattgga   7500
gtctctaaaa aggtagttcc tactgaatct aaggccatgc atggagtcta agattcaaat   7560
cgaggatcta acagaactcg ccgtgaagac tggcgaacag ttcatacaga gtcttttacg   7620
```

```
actcaatgac aagaagaaaa tcttcgtcaa catggtggag cacgacactc tggtctactc    7680
caaaaatgtc aaagatacag tctcagaaga ccaaagggct attgagactt ttcaacaaag    7740
gataatttcg ggaaacctcc tcggattcca ttgcccagct atctgtcact tcatcgaaag    7800
gacagtagaa aaggaaggtg gctcctacaa atgccatcat tgcgataaag gaaaggctat    7860
cattcaagat gcctctgccg acagtggtcc caaagatgga ccccacccca cgaggagcat    7920
cgtggaaaaa gaagacgttc caaccacgtc ttcaaagcaa gtggattgat gtgacatctc    7980
cactgacgta agggatgacg cacaatccca ctatccttcg caagacccct cctctatata    8040
aggaagttca tttcatttgg agaggacacg ctcgagctca tttctctatt acttcagcca    8100
taacaaaaga actcttttct cttcttatta aaccatgaaa aagcctgaac tcaccgcgac    8160
gtctgtcgag aagtttctga tcgaaaagtt cgacagcgtc tccgacctga tgcagctctc    8220
ggagggcgaa gaatctcgtg ctttcagctt cgatgtagga gggcgtggat atgtcctgcg    8280
ggtaaatagc tgcgccgatg gtttctacaa agatcgttat gtttatcggc actttgcatc    8340
ggccgcgctc ccgattccgg aagtgcttga cattggggaa ttcagcgaga gcctgaccta    8400
ttgcatctcc cgccgtgcac agggtgtcac gttgcaagac ctgcctgaaa ccgaactgcc    8460
cgctgttctg cagccggtcg cggaggccat ggatgcgatc gctgcggccg atcttagcca    8520
gacgagcggg ttcggcccat tcggaccgca aggaatcggt caatacacta catggcgtga    8580
tttcatatgc gcgattgctg atccccatgt gtatcactgg caaactgtga tggacgacac    8640
cgtcagtgcg tccgtcgcgc aggctctcga tgagctgatg ctttgggccg aggactgccc    8700
cgaagtccgg cacctcgtgc acgcggattt cggctccaac aatgtcctga cggacaatgg    8760
ccgcataaca gcggtcattg actggagcga ggcgatgttc ggggattccc aatacgaggt    8820
cgccaacatc ttcttctgga ggccgtggtt ggcttgtatg gagcagcaga cgcgctactt    8880
cgagcggagg catccggagc ttgcaggatc gccgcggctc cgggcgtata tgctccgcat    8940
tggtcttgac caactctatc agagcttggt tgacggcaat ttcgatgatg cagcttgggc    9000
gcagggtcga tgcgacgcaa tcgtccgatc cggagccggg actgtcgggc gtacacaaat    9060
cgcccgcaga agcgcggccg tctggaccga tggctgtgta aagtactcg ccgatagtgg    9120
aaaccgacgc cccagcactc gtccgagggc aaaggaatag tgaggtacct aaagaaggag    9180
tgcgtcgaag cagatcgttc aaacatttgg caataaagtt tcttaagatt gaatcctgtt    9240
gccggtcttg cgatgattat catataattt ctgttgaatt acgttaagca tgtaataatt    9300
aacatgtaat gcatgacgtt atttatgaga tgggttttta tgattagagt cccgcaatta    9360
tacatttaat acgcgataga aaacaaaata tagcgcgcaa actaggataa attatcgcgc    9420
gcggtgtcat ctatgttact agatcgatgt cgaatctgat caacctgcat taatgaatcg    9480
gccaacgcgc ggggagaggc ggtttgcgta ttgggcgctc ttccgcttcc tcgctcactg    9540
actcgctgcg ctcggtcgtt cggctgcggc gagcggtatc agctcactca aaggcggtaa    9600
tacggttatc cacagaatca ggggataacg caggaaagaa catgtgagca aaaggccagc    9660
aaaaggccag gaaccgtaaa aaggccgcgt tgctggcgtt tttccatagg ctccgccccc    9720
ctgacgagca tcacaaaaat cgacgctcaa gtcagaggtg gcgaaacccg acaggactat    9780
aaagatacca ggcgtttccc cctggaagct ccctcgtgcg ctctcctgtt ccgaccctgc    9840
cgcttaccgg atacctgtcc gcctttctcc cttcgggaag cgtggcgctt tctcaatgct    9900
cacgctgtag gtatctcagt tcggtgtagg tcgttcgctc caagctgggc tgtgtgcacg    9960
aaccccccgt tcagcccgac cgctgcgcct tatccggtaa ctatcgtctt gagtccaacc   10020
```

| | | | | |
|---|---|---|---|---|
| cggtaagaca | cgacttatcg | ccactggcag | cagccactgg | taacaggatt agcagagcga | 10080 |
| ggtatgtagg | cggtgctaca | gagttcttga | agtggtggcc | taactacggc tacactagaa | 10140 |
| ggacagtatt | tggtatctgc | gctctgctga | agccagttac | cttcggaaaa agagttggta | 10200 |
| gctcttgatc | cggcaaacaa | accaccgctg | gtagcggtgg | ttttttttgtt tgcaagcagc | 10260 |
| agattacgcg | cagaaaaaaa | ggatctcaag | aagatccttt | gatcttttct acggggtctg | 10320 |
| acgctcagtg | gaacgaaaac | tcacgttaag | ggattttggt | catgacatta acctataaaa | 10380 |
| ataggcgtat | cacgaggccc | tttcgtctcg | cgcgtttcgg | tgatgacggt gaaaacctct | 10440 |
| gacacatgca | gctcccggag | acggtcacag | cttgtctgta | agcggatgcc gggagcagac | 10500 |
| aagcccgtca | gggcgcgtca | gcgggtgttg | gcgggtgtcg | gggctggctt aactatgcgg | 10560 |
| catcagagca | gattgtactg | agagtgcacc | atatggacat | attgtcgtta gaacgcggct | 10620 |
| acaattaata | cataaccta | tgtatctac | atacgatt | taggtgacac tatagaacgg | 10680 |
| cgcgccaagc | ttttgatcca | tgcccttcat | ttgccgctta | ttaattaatt tggtaacagt | 10740 |
| ccgtactaat | cagttactta | tccttccccc | atcataatta | atcttggtag tctcgaatgc | 10800 |
| cacaacactg | actagtctct | tggatcataa | gaaaaagcca | aggaacaaaa gaagacaaaa | 10860 |
| cacaatgaga | gtatcctttg | catagcaatg | tctaagttca | taaaattcaa acaaaaacgc | 10920 |
| aatcacacac | agtggacatc | acttatccac | tagctgatca | ggatcgccgc gtcaagaaaa | 10980 |
| aaaaactgga | ccccaaaagc | catgcacaac | aacacgtact | cacaaaggtg tcaatcgagc | 11040 |
| agcccaaaac | attcaccaac | tcacccatc | atgagccctc | acatttgttg tttctaaccc | 11100 |
| aacctcaaac | tcgtattctc | ttccgccacc | tcattttgt | ttatttcaac acccgtcaaa | 11160 |
| ctgcatgcca | ccccgtggcc | aaatgtccat | gcatgttaac | aagacctatg actataaata | 11220 |
| gctgcaatct | cggcccaggt | tttcatcatc | aagaaccagt | tcaatatcct agtacaccgt | 11280 |
| attaaagaat | ttaagatata | ctgc | | | 11304 |

<210> SEQ ID NO 15
<211> LENGTH: 9147
<212> TYPE: DNA
<213> ORGANISM: Artificial Sequence
<220> FEATURE:
<223> OTHER INFORMATION: T-DNA of vector pZBL120xKS334
<220> FEATURE:
<221> NAME/KEY: misc_feature
<222> LOCATION: (1892)..(1892)
<223> OTHER INFORMATION: n is a, c, g, or t

<400> SEQUENCE: 15

| | | | | |
|---|---|---|---|---|
| aattacaacg | gtatatatcc | tgccgtcgac | tctagaggat | ccgcgccgtc gacggatcca | 60 |
| ctagttctag | agcggccgc | gccgtcgacg | gatataatga | gccgtaaaca aagatgatta | 120 |
| agtagtaatt | aatacgtact | agtaaaagtg | gcaaaagata | acgagaaaga accaatttct | 180 |
| ttgcattcgg | ccttagcgga | aggcatatat | aagctttgat | tattttattt agtgtaatga | 240 |
| tttcgtacaa | ccaaagcatt | tatttagtac | tctcacactt | gtgtcgcggc cggccgctac | 300 |
| aggaacaggt | ggtggcggcc | ctcggcgcgc | tcgtactgct | ccacgatggt gtagtcctcg | 360 |
| ttgtgggagg | tgatgtccag | cttggagtcc | acgtagtagt | agccgggcag ctgcacgggc | 420 |
| ttcttggcca | tgtagatgga | cttgaactcc | accaggtagt | ggccgccgtc cttcagcttc | 480 |
| agggccttgt | ggatctcgcc | cttcagcacg | ccgtcgcggg | ggtacaggcg ctcggtggag | 540 |
| gcctcccagc | ccatagtctt | cttctgcatt | acggggccgt | cggaggggaa gttcacgccg | 600 |
| atgaacttca | ccttgtagat | gaaggagccg | tcctgcaggg | aggagtcctg ggtcacggtc | 660 |

| | |
|---|---|
| accacgccgc cgtcctcgaa gttcatcacg cgctcccact tgaagccctc ggggaaggac | 720 |
| agcttcttgt agtcggggat gtcggcgggg tgcttcacgt acaccttgga gccgtactgg | 780 |
| aactgggggg acaggatgtc ccaggcgaag ggcagggggc cgcccttggt caccttcagc | 840 |
| ttggcggtct gggtgccctc gtaggggcgg ccctcgccct cgcctcgat ctcgaactcg | 900 |
| tggccgttca cggagccctc catgcgcacc ttgaagcgca tgaactcctt gatgacgtcc | 960 |
| tcggaggagg ccatgggccg cttgggggc tatggaagac tttcttagtt agttgtgtga | 1020 |
| ataagcaatg ttgggagaat cgggactact tataggatag gaataaaaca gaaaagtatt | 1080 |
| aagtgctaat gaaatattta gactgataat taaaatcttc acgtatgtcc acttgatata | 1140 |
| aaaacgtcag gaataaagga agtacagtag aatttaaagg tactctttt atatataccc | 1200 |
| gtgttctctt tttggctagc tagttgcata aaaaataatc tatatttta tcattatttt | 1260 |
| aaatatctta tgagatggta atatttatc ataattttt ttactattat ttattatttg | 1320 |
| tgtgtgtaat acatatagaa gttaattaca aattttattt acttttcat tattttgata | 1380 |
| tgattcacca ttaatttagt gttattattt ataatagttc attttaatct ttttgtatat | 1440 |
| attatgcgtg cagtactttt ttcctacata taactactat tacattttat ttatataata | 1500 |
| ttttattaa tgaattttcg tgataatatg taatattgtt cattattatt tcagatttt | 1560 |
| taaaatatt tgtgttatta tttatgaaat atgtaatttt tttagtattt gattttatga | 1620 |
| tgataaagtg ttctaaattc aaaagaaggg ggaaagcgta acattaaaa aacgtcatca | 1680 |
| aacaaaaaca aaatcttgtt aataaagata aaactgtttg ttttgatcac tgttatttcg | 1740 |
| taatataaaa acattattta tatttatatt gttgacaacc aaatttgcct atcaaatcta | 1800 |
| accaatataa tgcatgcgtg gcaggtaatg tactaccatg aacttaagtc atgacataat | 1860 |
| aaaccgtgaa tctgaccaat gcatgtacct anctaaattg tatttgtgac acgaagcaaa | 1920 |
| tgattcaatt cacaatggag atgggaaaca aataatgaag aacccagaac taagaaagct | 1980 |
| tttctgaaaa ataaaataaa ggcaatgtca aaagtatact gcatcatcag tccagaaagc | 2040 |
| acatgatatt tttttatcag tatcaatgca gctagtttta ttttacaata tcgatatagc | 2100 |
| tagtttaaat atattgcagc tagatttata aatatttgtg ttattattta tcatttgtgt | 2160 |
| aatcctgttt ttagtatttt agtttatata tgatgataat gtattccaaa tttaaaagaa | 2220 |
| gggaaataaa tttaaacaag aaaaaagtc atcaaacaaa aaacaaatga aagggtggaa | 2280 |
| agatgttacc atgtaatgtg aatgttacag tatttctttt attatagagt taacaaatta | 2340 |
| actaatatga ttttgttaat aatgataaaa tatttttttt attattattt cataatataa | 2400 |
| aaatagttta cttaatataa aaaaaattct atcgttcaca acaaagttgg ccacctaatt | 2460 |
| taaccatgca tgtacccatg gaccatatta ggtaaccatc aaacctgatg aagagataaa | 2520 |
| gagatgaaga cttaagtcat aacacaaaac cataaaaaac aaaatacaa tcaaccgtca | 2580 |
| atctgaccaa tgcatgaaaa agctgcaata gtgagtggcg acacaaagca catgattttc | 2640 |
| ttacaacgga gataaaacca aaaaatatt tcatgaacaa cctagaacaa ataaagcttt | 2700 |
| tatataataa atatataaat aaataaaggc tatggaataa tatacttcaa tatatttgga | 2760 |
| ttaaataaat tgttggcggg gttgatatat ttatacacac ctaaagtcac ttcaatctca | 2820 |
| ttttcactta acttttattt ttttttcttt ttatttatc ataaagagaa tattgataat | 2880 |
| atacttttta acatatttt atgacatttt ttattggtga aaacttatta aaaatcataa | 2940 |
| attttgtaag ttagatttat ttaaagagtt cctcttctta ttttaaattt tttaataaat | 3000 |
| ttttaaataa ctaaaatttg tgttaaaaat gttaaaaaag tgtgttatta accttctct | 3060 |

```
tcgaggatcc aagcttgttg aaacatccct gaagtgtctc attttatttt atttattctt    3120
tgctgataaa aaaataaaat aaaagaagct aagcacacgg tcaaccattg ctctactgct    3180
aaaagggtta tgtgtagtgt tttactgcat aaattatgca gcaaacaaga caactcaaat    3240
taaaaaattt cctttgcttg tttttttgtt gtctctgact tgactttctt gtggaagttg    3300
gttgtataag gattgggaca ccattgtcct tcttaattta attttattct ttgctgataa    3360
aaaaaaaaat ttcatatagt gttaaataat aatttgttaa ataaccaaaa agtcaaatat    3420
gtttactctc gtttaaataa ttgagattcg tccagcaagg ctaaacgatt gtatagattt    3480
atgacaatat ttacttttt atagataaat gttatattat aataaattta tatacatata     3540
ttatatgtta tttattatta ttttaaatcc ttcaatattt tatcaaacca actcataatt    3600
tttttttat ctgtaagaag caataaaatt aaatagaccc actttaagga tgatccaacc     3660
tttatacaga gtaagagagt tcaaatagta cccttttcata tacatatcaa ctaaatatt    3720
agaaatatca tggatcaaac cttataaaga cattaaataa gtggataagt ataatatata    3780
aatgggtagt atataatata taaatggata caaacttctc tctttataat tgttatgtct    3840
ccttaacatc ctaatataat acataagtgg gtaatatata atatataaat ggagacaaac    3900
ttcttccatt ataattgtta tgtcttctta acacttatgt ctcgttcaca atgctaaggt    3960
tagaattgtt tagaaagtct tatagtacac atttgttttt gtactatttg aagcattcca    4020
taagccgtca cgattcagat gatttataat aataagagga aatttatcat agaacaataa    4080
ggtgcataga tagagtgtta atatatcata acatcctttg tttattcata gaagaagtga    4140
gatggagctc agttattata ctgttacatg gtcggataca atattccatg ctctccatga    4200
gctcttacac ctacatgcat tttagttcat acttgcggcc gctagatcta gagcatagtc    4260
acaagaaact gtagttgtag atgatggtga agaagcaaat gatactatct tctgcttgtt    4320
atccacatgc atcatgcttc caccagcccc atttgtgtct ccacactcaa cactatccaa    4380
aactgcgctc atattgttga catcactctc agtctcatca ccaggttgag tgctgaacag    4440
aaaatcaatg tcttcctcaa accctgcact atcaaacatg cccaccaagt catcatcacc    4500
tttgcagaaa gccaagtttg gatcttgaaa ctgagacaag ccagtgtaca tgaagctcca    4560
tggcagatcc tgctcaagca catggtccat aattgtgatc agtgatgatg attcttcttc    4620
ccttggagag acatgggggg tgtattgaac ttggtgctgc tgtggtggca tgtgcagatt    4680
ttcagatggg ggtggtgtgg ttattgttgt tgtctgttgt tctacttcta cttcttcaga    4740
gtcagaggag ttaggaactg tttccgtttg tgcttctgtt tgttgttgtt gggtttggtc    4800
atttttcttc tttattttgt ccatgtagtt gcttatgtca aaattggtca ctgcattgac    4860
tccacggtac tctattgctg ccatgtcata tgccactgct gcctcctctt gagttttata    4920
tgtccccaag tagaggtact tgtttccgca tactcttcca attcgtgctt cccagcgacc    4980
attatgatga tgcctagcaa ccccacggta cttagacagg cctctagaaa agccactgct    5040
ttggcgccgc aaagaagcca atattcttc tcttgaaacc ttgtccattt cctcgagctc     5100
cttggtataa gtttctatcg ggaaattcag ggttgcatct tttccccagt atttaagggc    5160
tgcaaggtca taggtacggg ctgcagattc ttcagtatca tatgccccca aataaacttg    5220
tcgacccttc ttgctctgaa tgttgttcca agagctctta tcccataggt gagcttcaaa    5280
cctccctgtc cacctatgcc ttgtaactcc tctatagata gagcttcttc tgccaccagt    5340
ggtggtttgg ttctgcttgc attttgtga cttcaaatta ttcctcctg gatgcttagg      5400
ccttcttttt tcaatgggag cttcaaaccc aacagaggaa gtagatgatg aacaagaaga    5460
```

```
tgctggagac ctcttcatgc ggccgcagta tatcttaaat tctttaatac ggtgtactag   5520
gatattgaac tggttcttga tgatgaaaac ctgggccgag attgcagcta tttatagtca   5580
taggtcttgt taacatgcat ggacatttgg ccacggggtg gcatgcagtt tgacgggtgt   5640
tgaaataaac aaaaatgagg tggcggaaga gaatacgagt ttgaggttgg gttagaaaca   5700
acaaatgtga gggctcatga tgggttgagt tggtgaatgt tttgggctgc tcgattgaca   5760
cctttgtgag tacgtgttgt tgtgcatggc ttttggggtc cagttttttt ttcttgacgc   5820
ggcgatcctg atcagctagt ggataagtga tgtccactgt gtgtgattgc gttttttgttt  5880
gaattttatg aacttagaca ttgctatgca aaggatactc tcattgtgtt ttgtcttctt   5940
ttgttccttg gcttttttctt atgatccaag agactagtca gtgttgtggc attcgagact  6000
accaagatta attatgatgg gggaaggata agtaactgat tagtacggac tgttaccaaa   6060
ttaattaata agcggcaaat gaagggcatg gatcaaaagc ttggcgcgaa ttcactggcc   6120
gtcgttttac aacgtcgtga ctgggaaaac cctggcgtta cccaacttaa tcgccttgca   6180
gcacatcccc ctttcgccag ctggcgtaat agcgaagagg cccgcaccga tcgcccttcc   6240
caacagttgc gcagcctgaa tggcgaatgg atcgatccgt cgatcgacca aagcggccat   6300
cgtgcctccc cactcctgca gttcgggggc atggatgcgc ggatagccgc tgctggtttc   6360
ctggatgccg acggatttgc actgccggta gaactccgcg aggtcgtcca gcctcaggca   6420
gcagctgaac caactcgcga ggggatcgag ccctgctga gcctcgacat gttgtcgcaa   6480
aattcgccct ggaccgccc aacgatttgt cgtcactgtc aaggtttgac ctgcacttca    6540
tttggggccc acatacacca aaaaatgct gcataattct cggggcagca agtcggttac    6600
ccggccgcc tgctggaccg ggttaatgg tgcccgtaac tttcggtaga gcggacggcc     6660
aatactcaac ttcaaggaat ctcacccatg cgcgccggcg gggaaccgga gttccccttca  6720
gtgaacgtta ttagttcgcc gctcggtgtg tcgtagatac tagcccctgg ggccttttga   6780
aatttgaata agatttatgt aatcagtctt ttaggtttga ccggttctgc cgctttttt    6840
aaaattggat ttgtaataat aaaacgcaat tgtttgttat tgtggcgctc tatcatagat   6900
gtcgctataa acctattcag cacaatatat tgttttcatt ttaatattgt acatataagt   6960
agtagggtac aatcagtaaa ttgaacggag aatattattc ataaaaatac gatagtaacg   7020
ggtgatatat tcattagaat gaaccgaaac cggcggtaag gatctgagct acacatgctc   7080
aggttttta caacgtgcac aacagaattg aaagcaaata tcatgcgatc ataggcgtct   7140
cgcatatctc attaaagcag ggggtgggcg aagaactcca gcatgagatc cccgcgctgg   7200
aggatcatcc agccggcgtc ccggaaaacg attccgaagc caaccttttc atagaaggcg   7260
gcggtggaat cgaaatctcg tgatggcagg ttgggcgtcg cttggtcggt catttcgaac   7320
cccagagtcc cgctcagaag aactcgtcaa gaaggcgata gaaggcgatg cgctgcgaat   7380
cgggagcggc gataccgtaa agcacgagga agcggtcagc ccattcgccg ccaagctctt   7440
cagcaatatc acgggtagcc aacgctatgt cctgatagcg gtccgccaca cccagccggc   7500
cacagtcgat gaatccagaa aagcggccat tttccaccat gatattcggc aagcaggcat   7560
cgccatggt cacgacgaga tcctcgccgt cgggcatgcg cgccttgagc ctggcgaaca    7620
gttcggctgg cgcgagcccc tgatgctctt cgtccagatc atcctgatcg acaagaccgg   7680
cttccatccg agtacgtgct cgctcgatgc gatgtttcgc ttggtggtcg aatgggcagg   7740
tagccggatc aagcgtatgc agccgccgca ttgcatcagc catgatggat actttctcgg   7800
caggagcaag gtgagatgac aggagatcct gccccggcac ttcgcccaat agcagccagt   7860
```

```
ccct tcccgc ttcagtgaca acgtcgagca cagctgcgca aggaacgccc gtcgtggcca    7920
gccacgatag ccgcgctgcc tcgtcctgca gttcattcag ggcaccggac aggtcggtct    7980
tgacaaaaag aaccgggcgc ccctgcgctg acagccggaa cacggcggca tcagagcagc    8040
cgattgtctg ttgtgcccag tcatagccga atagcctctc acccaagcg  gccggagaac    8100
ctgcgtgcaa tccatcttgt tcaatcatgc gaaacgatcc ccgcaagctt ggagactggt    8160
gatttcagcg tgtcctctcc aaatgaaatg aacttcctta tatagaggaa gggtcttgcg    8220
aaggatagtg ggattgtgcg tcatccctta cgtcagtgga gatatcacat caatccactt    8280
gctttgaaga cgtggttgga acgtcttctt tttccacgat gctcctcgtg ggtggggtc     8340
catctttggg accactgtcg gcagaggcat cttcaacgat ggcctttcct ttatcgcaat    8400
gatggcattt gtaggagcca ccttcctttt ccactatctt cacaataaag tgacagatag    8460
ctgggcaatg gaatccgagg aggtttccgg atattaccct ttgttgaaaa gtctcaattg    8520
cccctttggtc ttctgagact gtatctttga tatttttgga gtagacaagc gtgtcgtgct    8580
ccaccatgtt gacgaagatt ttcttcttgt cattgagtcg taagagactc tgtatgaact    8640
gttcgccagt ctttacggcg agttctgtta ggtcctctat ttgaatcttt gactccatgg    8700
cctttgattc agtgggaact accttttttag agactccaat ctctattact tgccttggtt    8760
tgtgaagcaa gccttgaatc gtccatactg gaatagtact tctgatcttg agaaatatat    8820
ctttctctgt gttcttgatg cagttagtcc tgaatctttt gactgcatct ttaaccttct    8880
tgggaaggta tttgatctcc tggagattat tgctcgggta gatcgtcttg atgagacctg    8940
ctgcgtaagc ctctctaacc atctgtgggt tagcattctt tctgaaattg aaaaggctaa    9000
tcttctcatt atcagtggtg aacatggtat cgtcaccttc tccgtcgaac ttcctgacta    9060
gatcgtagag atagaggaag tcgtccattg tgatctctgg ggcaaggag  atctgaatta    9120
tcatttacaa ttgaatatat cctgcca                                        9147

<210> SEQ ID NO 16
<211> LENGTH: 3983
<212> TYPE: DNA
<213> ORGANISM: Artificial Sequence
<220> FEATURE:
<223> OTHER INFORMATION: vector pKR132

<400> SEQUENCE: 16
ctagagtcga cctgcaggca tgcaagcttg gcgtaatcat ggtcatagct gtttcctgtg      60
tgaaattgtt atccgctcac aattccacac aacatacgag ccggaagcat aaagtgtaaa    120
gcctggggtg cctaatgagt gagctaactc acattaattg cgttgcgctc actgcccgct    180
ttccagtcgg gaaacctgtc gtgccagctg cattaatgaa tcggccaacg cgcggggaga    240
ggcggtttgc gtattgggcg ctcttccgct tcctcgctca ctgactcgct gcgctcggtc    300
gttcggctgc ggcgagcggt atcagctcac tcaaaggcgg taatacggtt atccacagaa    360
tcagggggata acgcaggaaa gaacatgtga gcaaaaggcc agcaaaaggc caggaaccgt    420
aaaaaggccg cgttgctggc gttttttccat aggctccgcc cccctgacga gcatcacaaa    480
aatcgacgct caagtcagag gtggcgaaac ccgacaggac tataaagata ccaggcgttt    540
ccccctggaa gctccctcgt gcgctctcct gttccgaccc tgccgcttac cggatacctg    600
tccgcctttc tcccttcggg aagcgtggcg ctttctcata gctcacgctg taggtatctc    660
agttcggtgt aggtcgttcg ctccaagctg ggctgtgtgc acgaaccccc cgttcagccc    720
gaccgctgcg ccttatccgg taactatcgt cttgagtcca acccggtaag acacgactta    780
```

```
tcgccactgg cagcagccac tggtaacagg attagcagag cgaggtatgt aggcggtgct    840
acagagttct tgaagtggtg gcctaactac ggctacacta aaggacagta tttggtatc     900 tgcgctctgc tgaagccagt taccttcgga aaaagagttg gtagctcttg atccggcaaa    960
caaaccaccg ctggtagcgg tggttttttt gtttgcaagc agcagattac gcgcagaaaa   1020
aaaggatctc aagaagatcc tttgatcttt tctacggggt ctgacgctca gtggaacgaa   1080
aactcacgtt aagggatttt ggtcatgaga ttatcaaaaa ggatcttcac ctagatcctt   1140
ttaaattaaa aatgaagttt taaatcaatc taaagtatat atgagtaaac ttggtctgac   1200
agttaccaat gcttaatcag tgaggcacct atctcagcga tctgtctatt tcgttcatcc   1260
atagttgcct gactccccgt cgtgtagata actacgatac gggagggctt accatctggc   1320
cccagtgctg caatgatacc gcgagaccca cgctcaccgg ctccagattt atcagcaata   1380
aaccagccag ccggaagggc cgagcgcaga agtggtcctg caactttatc cgcctccatc   1440
cagtctatta attgttgccg ggaagctaga gtaagtagtt cgccagttaa tagttttgcgc   1500 aacgttgttg ccattgctac aggcatcgtg gtgtcacgct cgtcgtttgg tatggcttca   1560
ttcagctccg gttcccaacg atcaaggcga gttacatgat cccccatgtt gtgcaaaaaa   1620
gcggttagct ccttcggtcc tccgatcgtt gtcagaagta agttggccgc agtgttatca   1680
ctcatggtta tggcagcact gcataattct cttactgtca tgccatccgt aagatgcttt   1740
tctgtgactg gtgagtactc aaccaagtca ttctgagaat agtgtatgcg gcgaccgagt   1800
tgctcttgcc cggcgtcaat acgggataat accgcgccac atagcagaac tttaaaagtg   1860
ctcatcattg gaaaacgttc ttcggggcga aaactctcaa ggatcttacc gctgttgaga   1920
tccagttcga tgtaacccac tcgtgcaccc aactgatctt cagcatcttt tactttcacc   1980
agcgtttctg ggtgagcaaa aacaggaagg caaaatgccg caaaaaaggg aataagggcg   2040
acacggaaat gttgaatact catactcttc ctttttcaat attattgaag catttatcag   2100
ggttattgtc tcatgagcgg atacatattt gaatgtattt agaaaaataa acaaatagg    2160 gttccgcgca catttccccg aaaagtgcca cctgacgtct aagaaaccat tattatcatg   2220
acattaacct ataaaaatag gcgtatcacg aggccctttc gtctcgcgcg tttcggtgat   2280
gacggtgaaa acctctgaca catgcagctc ccggagacgg tcacagcttg tctgtaagcg   2340
gatgccggga gcagacaagc ccgtcagggc gcgtcagcgg gtgttggcgg gtgtcggggc   2400
tggcttaact atgcggcatc agagcagatt gtactgagag tgcaccatat gcggtgtgaa   2460
ataccgcaca gatgcgtaag gagaaaatac cgcatcaggc gccattcgcc attcaggctg   2520
cgcaactgtt gggaagggcg atcggtgcgg gcctcttcgc tattacgcca gctggcgaaa   2580
gggggatgtg ctgcaaggcg attaagttgg gtaacgccag ggttttccca gtcacgacgt   2640
tgtaaaacga cggccagtga attcgagctc ggtacccggg gatcctctag acctgcaggc   2700
caactgcgtt tggggctcca gattaaacga cgccgtttcg ttcctttcgc ttcacggctt   2760
aacgatgtcg tttctgtctg tgcccaaaaa ataaaggcat tgttatttg caccagatat   2820 ttactaagtg caccctagtt tgacaagtag gcgataatta caaatagatg cggtgcaaat   2880
aataaatttt gaaggaaata attacaaaag aacagaactt atatttactt tattttaaaa   2940
aactaaaatg aaagaacaaa aaaagtaaaa aatacaaaaa atgtgcttta accactttca   3000
ttatttgtta cagaaagtat gattctactc aaattgatct gttgtatctg gtgctgcctt   3060
gtcacactgg cgatttcaat cccctaaaga tatggtgcaa actgcgaagt gatcaatatc   3120
tgctcggtta atttagatta attaataata ttcaacgtga tgtaccaaaa aaagacaatt   3180
```

```
ttttgctcca ttgacaaatt aaacctcatc aaggtaattt ccaaacctat aagcaaaaaa      3240
atttcacatt aattggcccg caatcctatt agtcttatta tactagagta ggaaaaaaaa      3300
caattacaca acttgtctta ttattctcta tgctaatgaa tattttttcc ttttgttaga      3360
aatcagtgtt tcctaattta ttgagtatta attccactca ccgcatatat ttaccgttga      3420
ataagaaaat tttacacata attctttttt agataaataa ttttttttata ctagatctta      3480 tatgattacg tgaagccaag tgggttatac taatgatata taatgtttga tagtaatcag      3540
tttataaacc aaatgcatgg aaatgttacg tggaagcacg taaattaaca agcattgaag      3600
caaatgcagc caccgcacca aaaccacccc acttcacttc cacgtaccat attccatgca      3660
actacaacac cctaaaactt caataaatgc cccacccttc acttcacttc acccatcaat      3720
agcaagcggc cgcgaagtta aaagcaatgt tgtcacttgt cgtactaaca catgatgtga      3780
tagtttatgc tagctagcta aacataagc tgtctctgag tgtgttgtat attaataaag       3840
atcatcactg gtgaatggtg atcgtgtacg taccctactt agtaggcaat ggaagcactt      3900
agagtgtgct ttgtgcatgg ccttgcctct gttttgagac ttttgtaatg ttttcgagtt      3960
taaatctttg cctttgcgta cgt                                              3983

<210> SEQ ID NO 17
<211> LENGTH: 4746
<212> TYPE: DNA
<213> ORGANISM: Artificial Sequence
<220> FEATURE:
<223> OTHER INFORMATION: vector pKR627

<400> SEQUENCE: 17
gatcctctag acctgcaggc caactgcgtt tggggctcca gattaaacga cgccgtttcg        60
ttcctttcgc ttcacggctt aacgatgtcg tttctgtctg tgcccaaaaa ataaaggcat       120
ttgttatttg caccagatat ttactaagtg caccctagtt tgacaagtag gcgataatta       180
caaatagatg cggtgcaaat aataaatttt gaaggaaata attacaaaag aacagaactt       240
atatttactt tattttaaaa aactaaaatg aaagaacaaa aaaagtaaaa aatacaaaaa       300
atgtgcttta accactttca ttatttgtta cagaaagtat gattctactc aaattgatct       360
gttgtatctg gtgctgcctt gtcacactgg cgatttcaat cccctaaaga tatggtgcaa       420
actgcgaagt gatcaatatc tgctcggtta atttagatta attaataata ttcaacgtga       480
tgtaccaaaa aaagacaatt ttttgctcca ttgacaaatt aaacctcatc aaggtaattt       540
ccaaacctat aagcaaaaaa atttcacatt aattggcccg caatcctatt agtcttatta       600
tactagagta ggaaaaaaaa caattacaca acttgtctta ttattctcta tgctaatgaa       660
tattttttcc ttttgttaga aatcagtgtt tcctaattta ttgagtatta attccactca       720
ccgcatatat ttaccgttga ataagaaaat tttacacata attctttttta agataaataa      780 ttttttttata ctagatctta tatgattacg tgaagccaag tgggttatac taatgatata      840
taatgtttga tagtaatcag tttataaacc aaatgcatgg aaatgttacg tggaagcacg       900
taaattaaca agcattgaag caaatgcagc caccgcacca aaaccacccc acttcacttc       960
cacgtaccat attccatgca actacaacac cctaaaactt caataaatgc cccacccttc      1020
acttcacttc acccatcaat agcaagcggc cgcgaagtta aaagcaatgt tgtcacttgt      1080
cgtactaaca catgatgtga tagtttatgc tagctagcta aacataagc tgtctctgag       1140 tgtgttgtat attaataaag atcatcactg gtgaatggtg atcgtgtacg taccctactt      1200
agtaggcaat ggaagcactt agagtgtgct ttgtgcatgg ccttgcctct gttttgagac      1260
```

```
ttttgtaatg ttttcgagtt taaatctttg cctttgcgta cgtctagagt cgagcatgca    1320
tctagagggc ccaattcgcc ctatagtgag tcgtattaca attcactggc cgtcgtttta    1380
caacgtcgtg actgggaaaa ccctggcgtt acccaactta atcgccttgc agcacatccc    1440
cctttcgcca gctggcgtaa tagcgaagag gcccgcaccg atcgcccttc ccaacagttg    1500
cgcagcctat acgtacggca gtttaaggtt tacacctata aaagagagag ccgttatcgt    1560
ctgtttgtgg atgtacagag tgatattatt gacacgccgg ggcgacggat ggtgatcccc    1620
ctggccagtg cacgtctgct gtcagataaa gtctcccgtg aactttaccc ggtggtgcat    1680
atcggggatg aaagctggcg catgatgacc accgatatgg ccagtgtgcc ggtctccgtt    1740
atcggggaag aagtggctga tctcagccac cgcgaaaatg acatcaaaaa cgccattaac    1800
ctgatgttct gggaatata  aatgtcaggc atgagattat caaaaaggat cttcacctag    1860
atccttttca cgtagaaagc cagtccgcag aaacggtgct gaccccggat gaatgtcagc    1920
tactgggcta tctggacaag ggaaaacgca agcgcaaaga aaagcaggt  agcttgcagt    1980 gggcttacat ggcgatagct agactgggcg gttttatgga cagcaagcga accggaattg    2040
ccagctgggg cgccctctgg taaggttggg aagccctgca aagtaaactg gatggctttc    2100
tcgccgccaa ggatctgatg gcgcagggga tcaagctctg atcaagagac aggatgagga    2160
tcgtttcgca tgattgaaca agatggattg cacgcaggtt ctccggccgc ttgggtggag    2220
aggctattcg gctatgactg ggcacaacag acaatcggct gctctgatgc cgccgtgttc    2280
cggctgtcag cgcaggggcg cccggttctt tttgtcaaga ccgacctgtc cggtgccctg    2340
aatgaactgc aagacgaggc agcgcggcta tcgtggctgg ccacgacggg cgttccttgc    2400
gcagctgtgc tcgacgttgt cactgaagcg ggaagggact ggctgctatt gggcgaagtg    2460
ccggggcagg atctcctgtc atctcacctt gctcctgccg agaaagtatc catcatggct    2520
gatgcaatgc ggcggctgca tacgcttgat ccggctacct gcccattcga ccaccaagcg    2580
aaacatcgca tcgagcgagc acgtactcgg atggaagccg tcttgtcga  tcaggatgat    2640 ctggacgaag agcatcaggg gctcgcgcca gccgaactgt tcgccaggct caaggcgagc    2700
atgcccgacg gcgaggatct cgtcgtgacc catggcgatg cctgcttgcc gaatatcatg    2760
gtggaaaatg gccgcttttc tggattcatc gactgtggcc ggctgggtgt ggcggaccgc    2820
tatcaggaca tagcgttggc tacccgtgat attgctgaag agcttggcgg cgaatgggct    2880
gaccgcttcc tcgtgcttta cggtatcgcc gctcccgatt cgcagcgcat cgccttctat    2940
cgccttcttg acgagttctt ctgaattatt aacgcttaca atttcctgat gcggtatttt    3000
ctccttacgc atctgtgcgg tatttcacac cgcatacagg tggcactttt cggggaaatg    3060
tgcgcggaac ccctatttgt ttatttttct aaatacattc aaatatgtat ccgctcatga    3120
gacaataacc ctgataaatg cttcaataat agcacgtgag gagggccacc atggccaagt    3180
tgaccagtgc cgttccggtg ctcaccgcgc gcgacgtcgc cggagcggtc gagttctgga    3240
ccgaccggct cgggttctcc cgggacttcg tggaggacga cttcgccggt gtggtccggg    3300
acgacgtgac cctgttcatc agcgcggtcc aggaccaggt ggtgccggac aacaccctgg    3360
cctgggtgtg gtgcgcggc  ctggacgagc tgtacgccga gtggtcggag gtcgtgtcca    3420
cgaacttccg ggacgcctcc gggccggcca tgaccgagat cggcgagcag ccgtgggggc    3480
gggagttcgc cctgcgcgac ccggccggca actgcgtgca cttcgtggcc gaggagcagg    3540
actgacacgt gctaaaactt catttttaat ttaaaaggat ctaggtgaag atcctttttg    3600
ataatctcat gaccaaaatc ccttaacgtg agttttcgtt ccactgagcg tcagacccccg    3660
```

```
tagaaaagat caaaggatct tcttgagatc cttttttct gcgcgtaatc tgctgcttgc   3720
aaacaaaaaa accaccgcta ccagcggtgg tttgtttgcc ggatcaagag ctaccaactc   3780
tttttccgaa ggtaactggc ttcagcagag cgcagatacc aaatactgtc cttctagtgt   3840
agccgtagtt aggccaccac ttcaagaact ctgtagcacc gcctacatac ctcgctctgc   3900
taatcctgtt accagtggct gctgccagtg gcgataagtc gtgtcttacc gggttggact   3960
caagacgata gttaccggat aaggcgcagc ggtcgggctg aacggggggt tcgtgcacac   4020
agcccagctt ggagcgaacg acctacaccg aactgagata cctacagcgt gagctatgag   4080
aaagcgccac gcttcccgaa gggagaaagg cggacaggta tccggtaagc ggcagggtcg   4140
gaacaggaga gcgcacgagg gagcttccag ggggaaacgc ctggtatctt tatagtcctg   4200
tcgggtttcg ccacctctga cttgagcgtc gatttttgtg atgctcgtca ggggggcgga   4260
gcctatggaa aaacgccagc aacgcggcct ttttacggtt cctgggcttt tgctggcctt   4320
ttgctcacat gttctttcct gcgttatccc ctgattctgt ggataaccgt attaccgcct   4380
ttgagtgagc tgataccgct cgccgcagcc gaacgaccga gcgcagcgag tcagtgagcg   4440
aggaagcgga agagcgccca atacgcaaac cgcctctccc cgcgcgttgg ccgattcatt   4500
aatgcagctg gcacgacagg tttcccgact ggaaagcggg cagtgagcgc aacgcaatta   4560
atgtgagtta gctcactcat taggcacccc aggctttaca ctttatgctt ccggctcgta   4620
tgttgtgtgg aattgtgagc ggataacaat ttcacacagg aaacagctat gaccatgatt   4680
acgccaagct atttaggtga cgcgttagaa tactcaagct atgcatcaag cttggtaccg   4740
agctcg                                                               4746

<210> SEQ ID NO 18
<211> LENGTH: 4330
<212> TYPE: DNA
<213> ORGANISM: Artificial Sequence
<220> FEATURE:
<223> OTHER INFORMATION: vector KS294

<400> SEQUENCE: 18
agcttggaat tcgggatctg agtctagaaa tccgtcaaca tggtggagca cgacactctc     60
gtctactcca agaatatcaa agatacagtc tcagaagacc aaagggctat tgagactttt    120
caacaaaggg taatatcggg aaacctcctc ggattccatt gcccagctat ctgtcacttc    180
atcaaaagga cagtagaaaa ggaaggtggc acctacaaat gccatcattg cgataaagga    240
aaggctatcg ttcaagatgc ctctgccgac agtggtccca agatggaccc ccacccacg     300
aggagcatcg tggaaaaaga agacgttcca accacgtctt caaagcaagt ggattgatgt    360
gatgatccta tgcgtatggt atgacgtgtg ttcaagatga tgacttcaaa cctacctatg    420
acgtatggta tgaacgtgtg tcgactgatg acttagatcc actcgagcgg ctataaatac    480
gtacctacgc accctgcgct accatcccta gagctgcagc ttattttac aacaattacc    540
aacaacaaca aacaacaaac aacattacaa ttactattta caattacagt cgacccggga    600
tcgtacctct agggtggcgg ccgcaagtat gaactaaaat gcatgtaggt gtaagagctc    660
atggagagca tggaatattg tatccgacca tgtaacagta taataactga gctccatctc    720
acttcttcta tgaataaaca aaggatgtta tgatatatta acactctatc tatgcacctt    780
attgttctat gataaatttc ctcttattat tataaatcat ctgaatcgtg acggcttatg    840
gaatgcttca aatagtacaa aaacaaatgt gtactataag actttctaaa caattctaac    900
cttagcattg tgaacgagac ataagtgtta agaagacata acaattataa tggaagaagt    960
```

```
ttgtctccat ttatatatta tatattaccc acttatgtat tatattagga tgttaaggag    1020
acataacaat tataaagaga gaagtttgta tccatttata tattatatac tacccattta    1080
tatattatac ttatccactt atttaatgtc tttataaggt ttgatccatg atatttctaa    1140
tattttagtt gatatgtata tgaaagggta ctatttgaac tctcttactc tgtataaagg    1200
ttggatcatc cttaaagtgg gtctatttaa ttttattgct tcttacagat aaaaaaaaaa    1260
ttatgagttg gtttgataaa atattgaagg atttaaaata ataataaata acatataata    1320
tatgtatata aatttattat aatataacat ttatctataa aaaagtaaat attgtcataa    1380
atctatacaa tcgtttagcc ttgctggacg aatctcaatt atttaaacga gagtaaacat    1440
atttgacttt ttggttattt aacaaattat tatttaacac tatatgaaat ttttttttt     1500 atcagcaaag aataaaatta aattaagaag gacaatggtg tcccaatcct tatacaacca    1560
acttccacaa gaaagtcaag tcagagacaa caaaaaaaca agcaaaggaa attttttaat    1620
ttgagttgtc ttgtttgctg cataatttat gcagtaaaac actacacata acccttttag    1680
cagtagagca atggttgacc gtgtgcttag cttcttttat tttattttt tatcagcaaa      1740 gaataaataa aataaaatga gacacttcag ggatgtttca acaagctcta gactggaatt    1800
cgtcgacggc gcgcccgatc atccggatat agttcctcct ttcagcaaaa aacccctcaa    1860
gacccgttta gaggccccaa ggggttatgc tagttattgc tcagcggtgg cagcagccaa    1920
ctcagcttcc tttcgggctt tgttagcagc cggatcgatc caagctgtac ctcactattc    1980 cttttgccctc ggacgagtgc tggggcgtcg gtttccacta tcggcgagta cttctacaca   2040
gccatcggtc cagacggccg cgcttctgcg ggcgatttgt gtacgcccga cagtcccggc    2100
tccggatcgg acgattgcgt cgcatcgacc ctgcgcccaa gctgcatcat cgaaattgcc    2160
gtcaaccaag ctctgataga gttggtcaag accaatgcgg agcatatacg cccggagccg    2220
cggcgatcct gcaagctccg gatgcctccg ctcgaagtag cgcgtctgct gctccataca    2280
agccaaccac ggcctccaga agaagatgtt ggcgacctcg tattgggaat ccccgaacat    2340
cgcctcgctc cagtcaatga ccgctgttat gcggccattg tccgtcagga cattgttgga    2400
gccgaaatcc gcgtgcacga ggtgccggac ttcggggcag tcctcggccc aaagcatcag    2460
ctcatcgaga gcctgcgcga cggacgcact gacggtgtcg tccatcacag tttgccagtg    2520
atacacatgg ggatcagcaa tcgcgcatat gaaatcacgc catgtagtgt attgaccgat    2580
tccttgcggt ccgaatgggc cgaacccgct cgtctggcta agatcggccg cagcgatcgc    2640
atccatagcc tccgcgaccg gctgcagaac agcgggcagt tcggtttcag gcaggtcttg    2700
caacgtgaca ccctgtgcac ggcgggagat gcaataggtc aggctctcgc tgaattcccc    2760
aatgtcaagc acttccggaa tcgggagcgc ggccgatgca aagtgccgat aaacataacg    2820
atctttgtag aaaccatcgg cgcagctatt tacccgcagg acatatccac gccctcctac    2880
atcgaagctg aaagcacgag attcttcgcc ctccgagagc tgcatcaggt cggagacgct    2940
gtcgaacttt tcgatcagaa acttctcgac agacgtcgcg gtgagttcag gcttttccat    3000
gggtatatct ccttcttaaa gttaaacaaa attatttcta gagggaaacc gttgtggtct    3060
ccctatagtg agtcgtatta atttcgcggg atcgagatct gatcaacctg cattaatgaa    3120
tcggccaacg cgcggggaga ggcggtttgc gtattgggcg ctcttccgct tcctcgctca    3180
ctgactcgct gcgctcggtc gttcggctgc ggcgagcggt atcagctcac tcaaaggcgg    3240
taatacggtt atccacagaa tcaggggata acgcaggaaa gaacatgtga gcaaaaggcc    3300
agcaaaaggc caggaaccgt aaaaaggccg cgttgctggc gtttttccat aggctccgcc    3360
```

| | |
|---|---|
| cccctgacga gcatcacaaa aatcgacgct caagtcagag gtggcgaaac ccgacaggac | 3420 |
| tataaagata ccaggcgttt ccccctggaa gctccctcgt gcgctctcct gttccgaccc | 3480 |
| tgccgcttac cggatacctg tccgcctttc tcccttcggg aagcgtggcg ctttctcaat | 3540 |
| gctcacgctg taggtatctc agttcggtgt aggtcgttcg ctccaagctg ggctgtgtgc | 3600 |
| acgaaccccc cgttcagccc gaccgctgcg ccttatccgg taactatcgt cttgagtcca | 3660 |
| acccggtaag acacgactta tcgccactgg cagcagccac tggtaacagg attagcagag | 3720 |
| cgaggtatgt aggcggtgct acagagttct tgaagtggtg gcctaactac ggctacacta | 3780 |
| gaaggacagt atttggtatc tgcgctctgc tgaagccagt taccttcgga aaaagagttg | 3840 |
| gtagctcttg atccggcaaa caaccaccg ctggtagcgg tggttttttt gtttgcaagc | 3900 |
| agcagattac gcgcagaaaa aaaggatctc aagaagatcc tttgatcttt tctacggggt | 3960 |
| ctgacgctca gtggaacgaa aactcacgtt aagggatttt ggtcatgaca ttaacctata | 4020 |
| aaaataggcg tatcacgagg ccctttcgtc tcgcgcgttt cggtgatgac ggtgaaaacc | 4080 |
| tctgacacat gcagctcccg gagacggtca cagcttgtct gtaagcggat gccgggagca | 4140 |
| gacaagcccg tcagggcgcg tcagcgggtg ttggcgggtg tcggggctgg cttaactatg | 4200 |
| cggcatcaga gcagattgta ctgagagtgc accatatgga catattgtcg ttagaacgcg | 4260 |
| gctacaatta atacataacc ttatgtatca tacacatacg atttaggtga cactatagaa | 4320 |
| cggcgcgcca | 4330 |

<210> SEQ ID NO 19
<211> LENGTH: 5195
<212> TYPE: DNA
<213> ORGANISM: Artificial Sequence
<220> FEATURE:
<223> OTHER INFORMATION: vector pKR1142

<400> SEQUENCE: 19

| | |
|---|---|
| ctagagggcc caattcgccc tatagtgagt cgtattacaa ttcactggcc gtcgttttac | 60 |
| aacgtcgtga ctgggaaaac cctggcgtta cccaacttaa tcgccttgca gcacatcccc | 120 |
| ctttcgccag ctggcgtaat agcgaagagg cccgcaccga tcgcccttcc caacagttgc | 180 |
| gcagcctata cgtacggcag tttaaggttt acacctataa aagagagagc cgttatcgtc | 240 |
| tgtttgtgga tgtacagagt gatattattg acacgccggg cgacggatg gtgatccccc | 300 |
| tggccagtgc acgtctgctg tcagataaag tctcccgtga actttacccg gtggtgcata | 360 |
| tcggggatga aagctggcgc atgatgacca ccgatatggc cagtgtgccg gtctccgtta | 420 |
| tcggggaaga agtggctgat ctcagccacc gcgaaaatga catcaaaaac gccattaacc | 480 |
| tgatgttctg gggaatataa atgtcaggca tgagattatc aaaaaggatc ttcacctaga | 540 |
| tccttttcac gtagaaagcc agtccgcaga aacggtgctg accccggatg aatgtcagct | 600 |
| actgggctat ctggacaagg gaaaacgcaa gcgcaaagag aaagcaggta gcttgcagtg | 660 |
| ggcttacatg gcgatagcta actgggcgg ttttatggac agcaagcgaa ccggaattgc | 720 |
| cagctggggc gccctctggt aaggttggga agccctgcaa agtaaactgg atggcttttct | 780 |
| cgccgccaag gatctgatgg cgcaggggat caagctctga tcaagagaca ggatgaggat | 840 |
| cgtttcgcat gattgaacaa gatggattgc acgcaggttc tccggccgct tgggtggaga | 900 |
| ggctattcgg ctatgactgg gcacaacaga caatcggctg ctctgatgcc gccgtgttcc | 960 |
| ggctgtcagc gcagggcgc ccggttcttt ttgtcaagac cgacctgtcc ggtgccctga | 1020 |
| atgaactgca agacgaggca gcgcggctat cgtggctggc cacgacgggc gttccttgcg | 1080 |

```
cagctgtgct cgacgttgtc actgaagcgg gaagggactg gctgctattg ggcgaagtgc   1140
cggggcagga tctcctgtca tctcaccttg ctcctgccga gaaagtatcc atcatggctg   1200
atgcaatgcg gcggctgcat acgcttgatc cggctacctg cccattcgac caccaagcga   1260
aacatcgcat cgagcgagca cgtactcgga tggaagccgg tcttgtcgat caggatgatc   1320
tggacgaaga gcatcagggg ctcgcgccag ccgaactgtt cgccaggctc aaggcgagca   1380
tgcccgacgg cgaggatctc gtcgtgaccc atggcgatgc ctgcttgccg aatatcatgg   1440
tggaaaatgg ccgcttttct ggattcatcg actgtggccg gctgggtgtg gcggaccgct   1500
atcaggacat agcgttggct acccgtgata ttgctgaaga gcttggcggc gaatgggctg   1560
accgcttcct cgtgctttac ggtatcgccg ctcccgattc gcagcgcatc gccttctatc   1620
gccttcttga cgagttcttc tgaattatta acgcttacaa tttcctgatg cggtattttc   1680
tccttacgca tctgtgcggt atttcacacc gcatacaggt ggcacttttc ggggaaatgt   1740
gcgcggaacc cctatttgtt tatttttcta aatacattca aatatgtatc cgctcatgag   1800
acaataaccc tgataaatgc ttcaataata gcacgtgagg agggccacca tggccaagtt   1860
gaccagtgcc gttccggtgc tcaccgcgcg cgacgtcgcc ggagcggtcg agttctggac   1920
cgaccggctc gggttctccc gggacttcgt ggaggacgac ttcgccggtg tggtccggga   1980
cgacgtgacc ctgttcatca gcgcggtcca ggaccaggtg gtgccggaca caccctggc    2040 ctgggtgtgg gtgcgcggcc tggacgagct gtacgccgag tggtcggagg tcgtgtccac   2100
gaacttccgg gacgcctccg gccggccat gaccgagatc ggcgagcagc cgtgggggcg    2160
ggagttcgcc ctgcgcgacc cggccggcaa ctgcgtgcac ttcgtggccg aggagcagga   2220
ctgacacgtg ctaaaacttc atttttaatt taaaaggatc taggtgaaga tccttttga    2280 taatctcatg accaaaatcc cttaacgtga gttttcgttc cactgagcgt cagaccccgt   2340
agaaaagatc aaaggatctt cttgagatcc ttttttttctg cgcgtaatct gctgcttgca   2400
aacaaaaaaa ccaccgctac cagcggtggt ttgtttgccg gatcaagagc taccaactct   2460
ttttccgaag gtaactggct tcagcagagc gcagatacca aatactgtcc ttctagtgta   2520
gccgtagtta ggccaccact tcaagaactc tgtagcaccg cctacatacc tcgctctgct   2580
aatcctgtta ccagtggctg ctgccagtgg cgataagtcg tgtcttaccg ggttggactc   2640
aagacgatag ttaccggata aggcgcagcg gtcgggctga acggggggtt cgtgcacaca   2700
gcccagcttg gagcgaacga cctacaccga actgagatac ctacagcgtg agctatgaga   2760
aagcgccacg cttcccgaag ggagaaaggc ggacaggtat ccggtaagcg gcagggtcgg   2820
aacaggagag cgcacgaggg agcttccagg gggaaacgcc tggtatcttt atagtcctgt   2880
cgggtttcgc cacctctgac ttgagcgtcg atttttgtga tgctcgtcag ggggggcggag   2940 cctatggaaa aacgccagca acgcggcctt tttacggttc ctgggctttt gctggccttt   3000
tgctcacatg ttctttcctg cgttatcccc tgattctgtg gataaccgta ttaccgcctt   3060
tgagtgagct gataccgctc gccgcagccg aacgaccgag cgcagcgagt cagtgagcga   3120
ggaagcggaa gagcgcccaa tacgcaaacc gcctctcccc gcgcgttggc cgattcatta   3180
atgcagctgg cacgacaggt ttcccgactg gaaagcgggc agtgagcgca acgcaattaa   3240
tgtgagttag ctcactcatt aggcacccca ggctttacac tttatgcttc cggctcgtat   3300
gttgtgtgga attgtgagcg gataacaatt tcacacagga aacagctatg accatgatta   3360
cgccaagcta tttaggtgac gcgttagaat actcaagcta tgcatcaagc ttggtaccga   3420
gctcggatcc tctagaaatc cgtcaacatg gtggagcacg acactctcgt ctactccaag   3480
```

```
aatatcaaag atacagtctc agaagaccaa agggctattg agacttttca acaaagggta    3540
atatcgggaa acctcctcgg attccattgc ccagctatct gtcacttcat caaaaggaca    3600
gtagaaaagg aaggtggcac ctacaaatgc catcattgcg ataaaggaaa ggctatcgtt    3660
caagatgcct ctgccgacag tggtcccaaa gatggacccc cacccacgag gagcatcgtg    3720
gaaaaagaag acgttccaac cacgtcttca agcaagtgg attgatgtga tgatcctatg    3780
cgtatggtat gacgtgtgtt caagatgatg acttcaaacc tacctatgac gtatggtatg    3840
aacgtgtgtc gactgatgac ttagatccac tcgagcggct ataaatacgt acctacgcac    3900
cctgcgctac catccctaga gctgcagctt attttacaa caattaccaa caacaacaaa      3960
caacaaacaa cattacaatt actatttaca attacagtcg acccgggatc gtacctctag    4020
ggtggcggcc gcaagtatga actaaaatgc atgtaggtgt aagagctcat ggagagcatg    4080
gaatattgta tccgaccatg taacagtata taactgagc tccatctcac ttcttctatg       4140
aataaacaaa ggatgttatg atatattaac actctatcta tgcaccttat tgttctatga    4200
taaatttcct cttattatta taaatcatct gaatcgtgac ggcttatgga atgcttcaaa    4260
tagtacaaaa acaaatgtgt actataagac tttctaaaca attctaacct tagcattgtg    4320
aacgagacat aagtgttaag aagacataac aattataatg gaagaagttt gtctccattt    4380
atatattata tattcccac ttatgtatta tattaggatg ttaaggagac ataacaatta      4440
taaagagaga agtttgtatc catttatata ttatatacta cccatttata tattatactt    4500
atccacttat ttaatgtctt tataaggttt gatccatgat atttctaata ttttagttga    4560
tatgtatatg aaagggtact atttgaactc tcttactctg tataaaggtt ggatcatcct    4620
taaagtgggt ctatttaatt ttattgcttc ttacagataa aaaaaaaatt atgagttggt    4680
ttgataaaat attgaaggat ttaaaataat aataaataac atataatata tgtatataaa    4740
tttattataa tataacatttt atctataaaa agtaaatat tgtcataaat ctatacaatc      4800
gtttagcctt gctggacgaa tctcaattat ttaaacgaga gtaaacatat ttgactttt      4860 ggttatttaa caaattatta tttaacacta tatgaaattt ttttttttat cagcaaagaa    4920
taaaattaaa ttaagaagga caatggtgtc ccaatcctta tacaaccaac ttccacaaga    4980
aagtcaagtc agagacaaca aaaaaacaag caaaggaaat ttttaatt gagttgtctt       5040 gtttgctgca taatttatgc agtaaaacac tacacataac ccttttagca gtagagcaat    5100
ggttgaccgt gtgcttagct tcttttattt tattttttta tcagcaaaga ataaataaaa    5160
taaaatgaga cacttcaggg atgtttcaac aagct                              5195
```

<210> SEQ ID NO 20
<211> LENGTH: 8314
<212> TYPE: DNA
<213> ORGANISM: Artificial Sequence
<220> FEATURE:
<223> OTHER INFORMATION: vector pKR1141
<220> FEATURE:
<221> NAME/KEY: misc_feature
<222> LOCATION: (6481)..(6481)
<223> OTHER INFORMATION: n is a, c, g, or t

<400> SEQUENCE: 20

```
gatccgtcga cggcgcgccc gatcatccgg atatagttcc tcctttcagc aaaaaacccc      60
tcaagacccg tttagaggcc ccaaggggtt atgctagtta ttgctcagcg gtggcagcag    120
ccaactcagc ttcctttcgg gctttgttag cagccggatc gatccaagct gtacctcact    180
attcctttgc cctcggacga gtgctggggc gtcggtttcc actatcggcg agtacttcta    240
```

```
cacagccatc ggtccagacg gccgcgcttc tgcgggcgat ttgtgtacgc ccgacagtcc    300
cggctccgga tcggacgatt gcgtcgcatc gaccctgcgc ccaagctgca tcatcgaaat    360
tgccgtcaac caagctctga tagagttggt caagaccaat gcggagcata tacgcccgga    420
gccgcggcga tcctgcaagc tccggatgcc tccgctcgaa gtagcgcgtc tgctgctcca    480
tacaagccaa ccacggcctc cagaagaaga tgttggcgac ctcgtattgg gaatccccga    540
acatcgcctc gctccagtca atgaccgctg ttatgcggcc attgtccgtc aggacattgt    600
tggagccgaa atccgcgtgc acgaggtgcc ggacttcggg gcagtcctcg gcccaaagca    660
tcagctcatc gagagcctgc gcgacggacg cactgacggt gtcgtccatc acagtttgcc    720
agtgatacac atggggatca gcaatcgcgc atatgaaatc acgccatgta gtgtattgac    780
cgattccttg cggtccgaat gggccgaacc cgctcgtctg gctaagatcg gccgcagcga    840
tcgcatccat agcctccgcg accggctgca gaacagcggg cagttcggtt tcaggcaggt    900
cttgcaacgt gacaccctgt gcacggcggg agatgcaata ggtcaggctc tcgctgaatt    960
ccccaatgtc aagcacttcc ggaatcggga gcgcggccga tgcaaagtgc cgataaacat   1020
aacgatcttt gtagaaacca tcggcgcagc tatttacccg caggacatat ccacgccctc   1080
ctacatcgaa gctgaaagca cgagattctt cgccctccga gagctgcatc aggtcggaga   1140
cgctgtcgaa cttttcgatc agaaacttct cgacagacgt cgcggtgagt tcaggctttt   1200
ccatgggtat atctccttct taaagttaaa caaaattatt tctagaggga aaccgttgtg   1260
gtctccctat agtgagtcgt attaatttcg cgggatcgag atcgatccaa ttccaatccc   1320
acaaaaatct gagcttaaca gcacagttgc tcctctcaga gcagaatcgg gtattcaaca   1380
ccctcatatc aactactacg ttgtgtataa cggtccacat gccggtatat acgatgactg   1440
gggttgtaca aaggcggcaa caaacggcgt tcccggagtt gcacacaaga aatttgccac   1500
tattacagag gcaagagcag cagctgacgc gtacacaaca agtcagcaaa cagacaggtt   1560
gaacttcatc cccaaaggag aagctcaact caagcccaag agctttgcta aggccctaac   1620
aagcccacca aagcaaaaag cccactggct cacgctagga accaaaaggc ccagcagtga   1680
tccagcccca aaagagatct cctttgcccc ggagattaca atggacgatt tcctctatct   1740
ttacgatcta ggaaggaagt tcgaaggtga aggtgacgac actatgttca ccactgataa   1800
tgagaaggtt agcctcttca atttcagaaa gaatgctgac ccacagatgg ttagagaggc   1860
ctacgcagca ggtctcatca agacgatcta cccgagtaac aatctccagg agatcaaata   1920
ccttcccaag aaggttaaag atgcagtcaa aagattcagg actaattgca tcaagaacac   1980
agagaaagac atatttctca agatcagaag tactattcca gtatggacga ttcaaggctt   2040
gcttcataaa ccaaggcaag taatagagat tggagtctct aaaaaggtag ttcctactga   2100
atctaaggcc atgcatggag tctaagattc aaatcgagga tctaacagaa ctcgccgtga   2160
agactggcga acagttcata cagagtcttt tacgactcaa tgacaagaag aaaatcttcg   2220
tcaacatggt ggagcacgac actctggtct actccaaaaa tgtcaaagat acagtctcag   2280
aagaccaaag ggctattgag acttttcaac aaaggataat ttcgggaaac ctcctcggat   2340
tccattgccc agctatctgt cacttcatcg aaaggacagt agaaaaggaa ggtggctcct   2400
acaaatgcca tcattgcgat aaaggaaagg ctatcattca agatgcctct gccgacagtg   2460
gtcccaaaga tggaccccca cccacgagga gcatcgtgga aaagaagac gttccaacca   2520 cgtcttcaaa gcaagtggat tgatgtgaca tctccactga cgtaagggat gacgcacaat   2580
cccactatcc ttcgcaagac ccttcctcta tataaggaag ttcatttcat ttggagagga   2640
```

```
cacgctcgag ctcatttctc tattacttca gccataacaa aagaactctt ttctcttctt    2700
attaaaccat gaaaaagcct gaactcaccg cgacgtctgt cgagaagttt ctgatcgaaa    2760
agttcgacag cgtctccgac ctgatgcagc tctcggaggg cgaagaatct cgtgctttca    2820
gcttcgatgt aggagggcgt ggatatgtcc tgcgggtaaa tagctgcgcc gatggtttct    2880
acaaagatcg ttatgtttat cggcactttg catcggccgc gctcccgatt ccggaagtgc    2940
ttgacattgg ggaattcagc gagagcctga cctattgcat ctcccgccgt gcacagggtg    3000
tcacgttgca agacctgcct gaaaccgaac tgcccgctgt tctgcagccg gtcgcggagg    3060
ccatggatgc gatcgctgcg gccgatctta gccagacgag cgggttcggc ccattcggac    3120
cgcaaggaat cggtcaatac actacatggc gtgatttcat atgcgcgatt gctgatcccc    3180
atgtgtatca ctggcaaact gtgatggacg acaccgtcag tgcgtccgtc gcgcaggctc    3240
tcgatgagct gatgctttgg gccgaggact gccccgaagt ccggcacctc gtgcacgcgg    3300
atttcggctc caacaatgtc ctgacggaca atggccgcat aacagcggtc attgactgga    3360
gcgaggcgat gttcggggat tcccaatacg aggtcgccaa catcttcttc tggaggccgt    3420
ggttggcttg tatggagcag cagacgcgct acttcgagcg gaggcatccg gagcttgcag    3480
gatcgccgcg gctccgggcg tatatgctcc gcattggtct tgaccaactc tatcagagct    3540
tggttgacgg caatttcgat gatgcagctt gggcgcaggg tcgatgcgac gcaatcgtcc    3600
gatccggagc cgggactgtc gggcgtacac aaatcgcccg cagaagcgcg gccgtctgga    3660
ccgatggctg tgtagaagta ctcgccgata gtggaaaccg acgccccagc actcgtccga    3720
gggcaaagga atagtgaggt acctaaagaa ggagtgcgtc gaagcagatc gttcaaacat    3780
ttggcaataa agtttcttaa gattgaatcc tgttgccggt cttgcgatga ttatcatata    3840
atttctgttg aattacgtta agcatgtaat aattaacatg taatgcatga cgttatttat    3900
gagatgggtt tttatgatta gagtcccgca attatacatt taatacgcga tagaaaacaa    3960
aatatagcgc gcaaactagg ataaattatc gcgcgcggtg tcatctatgt tactagatcg    4020
atgtcgaatc gatcaacctg cattaatgaa tcggccaacg cgcggggaga ggcggtttgc    4080
gtattgggcg ctcttccgct tcctcgctca ctgactcgct gcgctcggtc gttcggctgc    4140
ggcgagcggt atcagctcac tcaaaggcgg taatacggtt atccacagaa tcaggggata    4200
acgcaggaaa gaacatgtga gcaaaaggcc agcaaaaggc caggaaccgt aaaaaggccg    4260
cgttgctggc gtttttccat aggctccgcc cccctgacga gcatcacaaa aatcgacgct    4320
caagtcagag gtggcgaaac ccgacaggac tataaagata ccaggcgttt ccccctggaa    4380
gctccctcgt gcgctctcct gttccgaccc tgccgcttac cggatacctg tccgcctttc    4440
tcccttcggg aagcgtggcg ctttctcaat gctcacgctg taggtatctc agttcggtgt    4500
aggtcgttcg ctccaagctg ggctgtgtgc acgaaccccc cgttcagccc gaccgctgcg    4560
ccttatccgg taactatcgt cttgagtcca acccggtaag acacgactta tcgccactgg    4620
cagcagccac tggtaacagg attagcagag cgaggtatgt aggcggtgct acagagttct    4680
tgaagtggtg gcctaactac ggctacacta gaaggacagt atttggtatc tgcgctctgc    4740
tgaagccagt taccttcgga aaaagagttg gtagctcttg atccggcaaa caaaccaccg    4800
ctggtagcgg tggttttttt gtttgcaagc agcagattac gcgcagaaaa aaaggatctc    4860
aagaagatcc tttgatcttt tctacggggt ctgacgctca gtggaacgaa aactcacgtt    4920
aagggatttt ggtcatgaca ttaacctata aaaataggcg tatcacgagg ccctttcgtc    4980
tcgcgcgttt cggtgatgac ggtgaaaacc tctgacacat gcagctcccg gagacggtca    5040
```

```
cagcttgtct gtaagcggat gccgggagca gacaagcccg tcagggcgcg tcagcgggtg   5100
ttggcgggtg tcggggctgg cttaactatg cggcatcaga gcagattgta ctgagagtgc   5160
accatatgga catattgtcg ttagaacgcg gctacaatta atacataacc ttatgtatca   5220
tacacatacg atttaggtga cactatagaa cggcgcgcca agcttggatc tcctgcagga   5280
tctggccggc cggatctcgt acggatcctc gaagagaagg gttaataaca cactttttta   5340 acattttaa cacaaatttt agttatttaa aaatttatta aaaaatttaa aataagaaga    5400
ggaactcttt aaataaatct aacttacaaa atttatgatt tttaataagt tttcaccaat   5460
aaaaaatgtc ataaaaatat gttaaaaagt atattatcaa tattctcttt atgataaata   5520
aaaagaaaaa aaaaataaaa gttaagtgaa aatgagattg aagtgacttt aggtgtgtat   5580
aaatatatca accccgccaa caatttattt aatccaaata tattgaagta tattattcca   5640
tagcctttat ttatttatat atttattata taaaagcttt atttgttcta ggttgttcat   5700
gaaatatttt tttggtttta tctccgttgt aagaaaatca tgtgctttgt gtcgccactc   5760
actattgcag cttttttcatg cattggtcag attgacggtt gattgtattt ttgtttttta   5820
tggttttgtg ttatgactta agtcttcatc tctttatctc ttcatcaggt ttgatggtta   5880
cctaatatgg tccatgggta catgcatggt taaattaggt ggccaacttt gttgtgaacg   5940 atagaattt ttttatatta agtaaactat tttatatta tgaaataata ataaaaaaaa    6000
tattttatca ttattaacaa aatcatatta gttaatttgt taactctata ataaagaaa    6060 tactgtaaca ttcacattac atggtaacat cttttccaccc tttcatttgt tttttgtttg  6120 atgactttt ttcttgttta aatttatttc ccttctttta aatttggaat acattatcat    6180
catatataaa ctaaaatact aaaaacagga ttacacaaat gataaataat aacacaaata   6240
tttataaatc tagctgcaat atatttaaac tagctatatc gatattgtaa aataaaacta   6300
gctgcattga tactgataaa aaaatatcat gtgctttctg gactgatgat gcagtatact   6360
tttgacattg cctttatttt attttttcaga aaagctttct tagttctggg ttcttcatta   6420
tttgtttccc atctccattg tgaattgaat catttgcttc gtgtcacaaa tacaatttag   6480
ntaggtacat gcattggtca gattcacggt ttattatgtc atgacttaag ttcatggtag   6540
tacattacct gccacgcatg cattatattg gttagatttg ataggcaaat ttggttgtca   6600
acaatataaa tataaataat gttttatat tacgaaataa cagtgatcaa aacaaacagt    6660
tttatcttta ttaacaagat tttgtttttg tttgatgacg tttttaatg tttacgcttt     6720 cccccttctt ttgaatttag aacactttat catcataaaa tcaaatacta aaaaaattac   6780
atatttcata aataataaca caaatatttt taaaaaatct gaaataataa tgaacaatat   6840
tacatattat cacgaaaatt cattaataaa aatattatat aaataaaatg taatagtagt   6900
tatatgtagg aaaaaagtac tgcacgcata atatatacaa aaagattaaa atgaactatt   6960
ataaataata acactaaatt aatggtgaat catatcaaaa taatgaaaaa gtaaataaaa   7020
tttgtaatta acttctatat gtattacaca cacaaataat aaataatagt aaaaaaaatt   7080
atgataaata tttaccatct cataagatat ttaaaataat gataaaaata tagattattt   7140
tttatgcaac tagctagcca aaaagagaac acgggtatat ataaaagag tacctttaaa    7200 ttctactgta cttcctttat tcctgacgtt tttatatcaa gtggacatac gtgaagattt   7260
taattatcag tctaaatatt tcattagcac ttaatacttt tctgttttat tcctatccta   7320
taagtagtcc cgattctccc aacattgctt attcacacaa ctaactaaga aagtcttcca   7380 tagccccca agcggcccat ggcctcctcc gaggacgtca tcaaggagtt catgcgcttc    7440
```

```
aaggtgcgca tggagggctc cgtgaacggc cacgagttcg agatcgaggg cgagggcgag    7500
ggccgcccct acgagggcac ccagaccgcc aagctgaagg tgaccaaggg cggcccctg    7560 cccttcgcct gggacatcct gtcccccag ttccagtacg gctccaaggt gtacgtgaag    7620
caccccgccg acatcccga ctacaagaag ctgtccttcc ccgagggctt caagtgggag    7680
cgcgtgatga acttcgagga cggcggcgtg gtgaccgtga cccaggactc ctccctgcag    7740
gacggctcct tcatctacaa ggtgaagttc atcggcgtga acttccctc cgacggccc    7800 gtaatgcaga agaagactat gggctgggag gcctccaccg agcgcctgta ccccgcgac    7860 ggcgtgctga agggcgagat ccacaaggcc ctgaagctga aggacggcgg ccactacctg    7920
gtggagttca gtccatcta catggccaag aagcccgtgc agctgcccgg ctactactac    7980
gtggactcca agctggacat cacctcccac aacgaggact acaccatcgt ggagcagtac    8040
gagcgcgccg agggccgcca ccacctgttc ctgtagcggc cggccgcgac acaagtgtga    8100
gagtactaaa taaatgcttt ggttgtacga aatcattaca ctaaataaaa taatcaaagc    8160
ttatatatgc cttccgctaa ggccgaatgc aaagaaattg gttctttctc gttatctttt    8220
gccactttta ctagtacgta ttaattacta cttaatcatc tttgtttacg gctcattata    8280
tccgtcgacg gcgcgggccg ctctagaact agtg                                 8314

<210> SEQ ID NO 21
<211> LENGTH: 35
<212> TYPE: DNA
<213> ORGANISM: Artificial Sequence
<220> FEATURE:
<223> OTHER INFORMATION: PCR primer SuSy-5

<400> SEQUENCE: 21
tcctgcaggt ctactcttta catgttcttt actcc                              35

<210> SEQ ID NO 22
<211> LENGTH: 34
<212> TYPE: DNA
<213> ORGANISM: Artificial Sequence
<220> FEATURE:
<223> OTHER INFORMATION: PCR primer SuSy-3

<400> SEQUENCE: 22
agcggccgcg attttttctc agaggcaaaa acac                                34

<210> SEQ ID NO 23
<211> LENGTH: 5531
<212> TYPE: DNA
<213> ORGANISM: Artificial Sequence
<220> FEATURE:
<223> OTHER INFORMATION: vector pLF122

<400> SEQUENCE: 23
cctgaattct gcagatatcc atcacactgg cggccgctcg agcatgcatc tagagggccc    60
aattcgccct atagtgagtc gtattacaat tcactggccg tcgttttaca acgtcgtgac    120
tgggaaaacc ctggcgttac ccaacttaat cgccttgcag cacatccccc tttcgccagc    180
tggcgtaata gcgaagaggc ccgcaccgat cgcccttccc aacagttgcg cagcctatac    240
gtacggcagt ttaaggttta cacctataaa agagagagcc gttatcgtct gtttgtggat    300
gtacagagtg atattattga cacgccgggg cgacggatgg tgatccccct ggccagtgca    360
cgtctgctgt cagataaagt ctcccgtgaa ctttacccgg tggtgcatat cggggatgaa    420
agctggcgca tgatgaccac cgatatggcc agtgtgccgg tctccgttat cggggaagaa    480
```

```
gtggctgatc tcagccaccg cgaaaatgac atcaaaaacg ccattaacct gatgttctgg    540
ggaatataaa tgtcaggcat gagattatca aaaaggatct tcacctagat ccttttcacg    600
tagaaagcca gtccgcagaa acggtgctga ccccggatga atgtcagcta ctgggctatc    660
tggacaaggg aaaacgcaag cgcaaagaga aagcaggtag cttgcagtgg gcttacatgg    720
cgatagctag actgggcggt tttatggaca gcaagcgaac cggaattgcc agctggggcg    780
ccctctggta aggttgggaa gccctgcaaa gtaaactgga tggctttctc gccgccaagg    840
atctgatggc gcaggggatc aagctctgat caagagacag gatgaggatc gtttcgcatg    900
attgaacaag atggattgca cgcaggttct ccggccgctt gggtggagag gctattcggc    960
tatgactggg cacaacagac aatcggctgc tctgatgccg ccgtgttccg gctgtcagcg   1020
caggggcgcc cggttctttt tgtcaagacc gacctgtccg gtgccctgaa tgaactgcaa   1080
gacgaggcag cgcggctatc gtggctggcc acgacgggcg ttccttgcgc agctgtgctc   1140
gacgttgtca ctgaagcggg aagggactgg ctgctattgg gcgaagtgcc ggggcaggat   1200
ctcctgtcat ctcaccttgc tcctgccgag aaagtatcca tcatggctga tgcaatgcgg   1260
cggctgcata cgcttgatcc ggctacctgc ccattcgacc accaagcgaa acatcgcatc   1320
gagcgagcac gtactcggat ggaagccggt cttgtcgatc aggatgatct ggacgaagag   1380 catcagggge tcgcgccagc cgaactgttc gccaggctca aggcgagcat gcccgacggc   1440
gaggatctcg tcgtgaccca tggcgatgcc tgcttgccga atatcatggt ggaaaatggc   1500
cgcttttctg gattcatcga ctgtggccgg ctgggtgtgg cggaccgcta tcaggacata   1560
gcgttggcta cccgtgatat tgctgaagag cttggcggcg aatgggctga ccgcttcctc   1620
gtgctttacg gtatcgccgc tcccgattcg cagcgcatcg ccttctatcg ccttcttgac   1680
gagttcttct gaattattaa cgcttacaat ttcctgatgc ggtattttct ccttacgcat   1740
ctgtgcggta tttcacaccg catacaggtg cacttttcg gggaaatgtg cgcggaaccc   1800
ctatttgttt attttctaa atacattcaa atatgtatcc gctcatgaga caataaccct   1860
gataaatgct tcaataatag cacgtgagga gggccaccat ggccaagttg accagtgccg   1920
ttccggtgct caccgcgcgc gacgtcgccg gagcggtcga gttctggacc gaccggctcg   1980
ggttctcccg ggacttcgtg gaggacgact tcgccggtgt ggtccgggac gacgtgaccc   2040
tgttcatcag cgcggtccag gaccaggtgg tgccggacaa caccctggcc tgggtgtggg   2100
tgcgcggcct ggacgagctg tacgccgagt ggtcggaggt cgtgtccacg aacttccggg   2160
acgcctccgg gccggccatg accgagatcg gcgagcagcc gtggggccgg gagttcgccc   2220
tgcgcgaccc ggccggcaac tgcgtgcact tcgtggccga ggagcaggac tgacacgtgc   2280
taaaacttca tttttaattt aaaaggatct aggtgaagat cctttttgat aatctcatga   2340
ccaaaatccc ttaacgtgag ttttcgttcc actgagcgtc agaccccgta gaaaagatca   2400
aaggatcttc ttgagatcct ttttttctgc gcgtaatctg ctgcttgcaa acaaaaaaac   2460
caccgctacc agcggtggtt tgtttgccgg atcaagagct accaactctt tttccgaagg   2520
taactggctt cagcagagcg cagataccaa atactgtcct tctagtgtag ccgtagttag   2580
gccaccactt caagaactct gtagcaccgc ctacatacct cgctctgcta atcctgttac   2640
cagtggctgc tgccagtggc gataagtcgt gtcttaccgg gttggactca agacgatagt   2700
taccggataa ggcgcagcgg tcgggctgaa cggggggttc gtgcacacag cccagcttgg   2760
agcgaacgac ctacaccgaa ctgagatacc tacagcgtga gctatgagaa agcgccacgc   2820
ttcccgaagg gagaaaggcg gacaggtatc cggtaagcgg cagggtcgga acaggagagc   2880
```

```
gcacgaggga gcttccaggg ggaaacgcct ggtatcttta tagtcctgtc gggtttcgcc   2940
acctctgact tgagcgtcga tttttgtgat gctcgtcagg ggggcggagc ctatggaaaa   3000
acgccagcaa cgcggccttt ttacggttcc tgggcttttg ctggcctttt gctcacatgt   3060
tctttcctgc gttatcccct gattctgtgg ataaccgtat taccgccttt gagtgagctg   3120
ataccgctcg ccgcagccga acgaccgagc gcagcgagtc agtgagcgag gaagcggaag   3180
agcgcccaat acgcaaaccg cctctccccg cgcgttggcc gattcattaa tgcagctggc   3240
acgacaggtt tcccgactgg aaagcgggca gtgagcgcaa cgcaattaat gtgagttagc   3300
tcactcatta ggcaccccag gctttacact ttatgcttcc ggctcgtatg ttgtgtggaa   3360
ttgtgagcgg ataacaattt cacacaggaa acagctatga ccatgattac gccaagctat   3420
ttaggtgacg cgttagaata ctcaagctat gcatcaagct tggtaccgag ctcggatcca   3480
ctagtaacgg ccgccagtgt gctggaattc aggtcctgca ggtctactct ttacatgttc   3540
tttactccgt ctcaaaattt cctttttttg ttggctctct ccgaacgagt tggagaaatc   3600
gttaacccta atcgaagatc tagattcctc tacatacgtt tgatctctct ctcagtatgg   3660
attacaaagc gccaaggaga tactactcac acggagttgt tgcgagacag caagatttcg   3720
caacagatat agttacgaga agaagacctt atgtccctta cgaccgtcca aataagtttt   3780
caaggagtct ggtttggacg tcaaaagagt acaaatcacc cgagggcaat aatatgccaa   3840
ggaccaatga tgtgtcaccg aaaccaccag ttttaggttt ggcgaggaag aatgctgctt   3900
gtgggccaat gagatcttct agtctcagaa aatgggtatg taagtattgg aaagatggaa   3960
agtgcaagag gggtgagcag tgccagttct acactcttg gtcttgtttc cctggattgg   4020
ccatggtagc ttctcttgaa gggcacaata aggaactaaa ggggatcgct ctccctgagg   4080
gttcagataa actcttttca gtcagtattg atggtacatt gcgagtttgg gactgcaatt   4140
ctggtcagtg tgtacattcc atcaaccttg acgcagaagc agggtctcta atcagtgaag   4200
gcccttgggt tttccttggc ttgccaaacg ctataaaggc ttttaacgtt caaaccagtc   4260
aagatttgca tcttcaagca gcaggggtgg ttggtcaggt gaatgcaatg actattgcaa   4320
acggaatgct ttttgctgga acaagttctg gtagtatctt agtctggaaa gctactacag   4380
actctgagtc tgatccattc aaatacttga catctcttga gggacatagt ggtgaagtca   4440
cttgttttgc tgttggaggt caaatgctat actctggttc tgtcgataaa caatcaaga   4500 tgtgggatct caacaccctg caatgtataa tgaccctgaa gcaacatacc ggcactgtca   4560
cttcactctt atgttgggat aaatgtttga tatcgtcttc cttggatggg accataaaag   4620
tttgggctta ttctgaaaac ggaatcttga aagttgttca aactcgcaga caagaacaga   4680
gtagtgttca tgctctttct ggtatgcatg atgcagaagc caaaccgata atattctgct   4740
cttaccaaaa cggaaccgtt ggcattttcg acctaccatc tttttcaagaa agaggaagga   4800 tgttctctac gcacacgatc gccacactca caattggtcc tcaaggattg ttattcagtg   4860
gagacgagag tggtaacttg cgtgtatgga ccttagctgc tggcaacaaa gtttagtctt   4920
ttcgactaaa gaattctgat ttaattttgt ggtttatatg ttgagttaac tgttaagaga   4980
gttttatttt gtaataggtg tatcagtcaa taaacaatct ttgtatcaac caaatgtaat   5040
ttttctcgtt aattcgattt cagagttttt actttaagat aaacaaactc tttcacacat   5100
catttaatga aagtggagaa gcttaaaaaa caaacaaaga aactgatcca ttttttggcgg   5160 gtcttcttct actcttattc atatgtgtta acgaactata gcgtaaaatt cagagcaagc   5220
gatctccgat ttgaacgtgg ctatcaccgg aggcccacca ctacgggcga tacgctctaa   5280
```

```
gtgaggatta aagtgctctg gtggtgacgt tgaagaaact cgcccatggt ttttgttatc    5340
tctgcagcca agtgtcgttc tttcttcgcc acttctcatc aagctacagt gaatttaaaa    5400
atggcgtctt tctttgatct cgtatacata agctggattg gtttcttaaa caaattcctc    5460
tccttttggg tcttctgggt ttgccttgta agtgtttgtg ttttttgcctc tgagaaaaaa    5520 tcgcggccgc t                                                         5531
```

<210> SEQ ID NO 24
<211> LENGTH: 6644
<212> TYPE: DNA
<213> ORGANISM: Artificial Sequence
<220> FEATURE:
<223> OTHER INFORMATION: vector pKR1155

<400> SEQUENCE: 24

```
ggccgcaagt atgaactaaa atgcatgtag gtgtaagagc tcatggagag catggaatat      60
tgtatccgac catgtaacag tataataact gagctccatc tcacttcttc tatgaataaa     120
caaaggatgt tatgatatat taacactcta tctatgcacc ttattgttct atgataaatt     180
tcctcttatt attataaatc atctgaatcg tgacggctta tggaatgctt caaatagtac     240
aaaaacaaat gtgtactata agactttcta aacaattcta accttagcat tgtgaacgag     300
acataagtgt taagaagaca taacaattat aatggaagaa gtttgtctcc atttatatat     360
tatatattac ccacttatgt attatattag gatgttaagg agacataaca attataaaga     420
gagaagtttg tatccattta tatattatat actaccatt tatatattat acttatccac      480
ttatttaatg tctttataag gtttgatcca tgatatttct aatattttag ttgatatgta     540
tatgaaaggg tactatttga actctcttac tctgtataaa ggttggatca tccttaaagt     600
gggtctattt aattttattg cttcttacag ataaaaaaaa aattatgagt tggtttgata     660
aaatattgaa ggatttaaaa taataataaa taacatataa tatatgtata taaatttatt     720
ataatataac atttatctat aaaaaagtaa atattgtcat aaatctatac aatcgtttag     780
ccttgctgga cgaatctcaa ttatttaaac gagagtaaac atatttgact ttttggttat     840
ttaacaaatt attatttaac actatatgaa attttttttt ttatcagcaa agaataaaat     900
taaattaaga aggacaatgg tgtcccaatc cttatacaac caacttccac aagaaagtca     960
agtcagagac aacaaaaaaa caagcaaagg aaatttttta atttgagttg tcttgtttgc    1020
tgcataattt atgcagtaaa acactacaca taacccttt agcagtagag caatggttga     1080
ccgtgtgctt agcttctttt atttttattttt tttatcagca aagaataaat aaaataaaat    1140
gagacacttc agggatgttt caacaagctc tagagggccc aattcgccct atagtgagtc    1200
gtattacaat tcactggccg tcgttttaca acgtcgtgac tgggaaaacc ctggcgttac    1260
ccaacttaat cgccttgcag cacatccccc tttcgccagc tggcgtaata gcgaagaggc    1320
ccgcaccgat cgcccttccc aacagttgcg cagcctatac gtacggcagt ttaaggttta    1380
cacctataaa agagagagcc gttatcgtct gtttgtggat gtacagagtg atattattga    1440
cacgccgggg cgacggatgg tgatccccct ggccagtgca cgtctgctgt cagataaagt    1500
ctcccgtgaa ctttacccgg tggtgcatat cggggatgaa agctggcgca tgatgaccac    1560
cgatatggcc agtgtgccgg tctccgttat cggggaagaa gtggctgatc tcagccaccg    1620
cgaaaatgac atcaaaaacg ccattaacct gatgttctgg ggaatataaa tgtcaggcat    1680
gagattatca aaaaggatct tcacctagat ccttttcacg tagaaagcca gtccgcagaa    1740
acggtgctga ccccggatga atgtcagcta ctgggctatc tggacaaggg aaaacgcaag    1800
```

```
cgcaaagaga aagcaggtag cttgcagtgg gcttacatgg cgatagctag actgggcggt   1860
tttatggaca gcaagcgaac cggaattgcc agctggggcg ccctctggta aggttgggaa   1920
gccctgcaaa gtaaactgga tggcttttctc gccgccaagg atctgatggc gcagggatc    1980 aagctctgat caagagacag gatgaggatc gtttcgcatg attgaacaag atggattgca   2040
cgcaggttct ccggccgctt gggtggagag gctattcggc tatgactggg cacaacagac   2100
aatcggctgc tctgatgccg ccgtgttccg gctgtcagcg caggggcgcc cggttctttt   2160
tgtcaagacc gacctgtccg gtgccctgaa tgaactgcaa gacgaggcag cgcggctatc   2220
gtggctggcc acgacgggcg ttccttgcgc agctgtgctc gacgttgtca ctgaagcggg   2280
aagggactgg ctgctattgg gcgaagtgcc ggggcaggat ctcctgtcat ctcaccttgc   2340
tcctgccgag aaagtatcca tcatggctga tgcaatgcgg cggctgcata cgcttgatcc   2400
ggctacctgc ccattcgacc accaagcgaa acatcgcatc gagcgagcac gtactcggat   2460
ggaagccggt cttgtcgatc aggatgatct ggacgaagag catcagggc tcgcgccagc    2520 cgaactgttc gccaggctca aggcgagcat gcccgacggc gaggatctcg tcgtgaccca   2580
tggcgatgcc tgcttgccga atatcatggt ggaaaatggc cgcttttctg gattcatcga   2640
ctgtggccgg ctgggtgtgg cggaccgcta tcaggacata gcgttggcta cccgtgatat   2700
tgctgaagag cttggcggcg aatgggctga ccgcttcctc gtgctttacg gtatcgccgc   2760
tcccgattcg cagcgcatcg ccttctatcg ccttcttgac gagttcttct gaattattaa   2820
cgcttacaat ttcctgatgc ggtatttct ccttacgcat ctgtgcggta tttcacaccg    2880
catacaggtg cacttttcg gggaaatgtg cgcggaaccc ctatttgttt attttctaa     2940 atacattcaa atatgtatcc gctcatgaga caataaccct gataaatgct tcaataatag   3000
cacgtgagga gggccaccat ggccaagttg accagtgccg ttccggtgct caccgcgcgc   3060
gacgtcgccg gagcggtcga gttctggacc gaccggctcg ggttctcccg ggacttcgtg   3120
gaggacgact tcgccggtgt ggtccgggac gacgtgaccc tgttcatcag cgcggtccag   3180
gaccaggtgg tgccggacaa cacctggcc tgggtgtggg tgcgcggcct ggacgagctg    3240
tacgccgagt ggtcggaggt cgtgtccacg aacttccggg acgcctccgg ccggccatg    3300 accgagatcg cgagcagcc gtgggggcgg gagttcgccc tgcgcgaccc ggccggcaac    3360
tgcgtgcact tcgtggccga ggagcaggac tgacacgtgc taaaacttca ttttttaattt   3420 aaaaggatct aggtgaagat ccttttttgat aatctcatga ccaaaatccc ttaacgtgag   3480
ttttcgttcc actgagcgtc agacccgta gaaaagatca aggatcttc ttgagatcct      3540 tttttctgc gcgtaatctg ctgcttgcaa acaaaaaaac caccgctacc agcggtggtt    3600
tgtttgccgg atcaagagct accaactctt tttccgaagg taactggctt cagcagagcg   3660
cagataccaa atactgtcct tctagtgtag ccgtagttag gccaccactt caagaactct   3720
gtagcaccgc ctacatacct cgctctgcta atcctgttac cagtggctgc tgccagtggc   3780
gataagtcgt gtcttaccgg gttggactca agacgatagt taccggataa ggcgcagcgg   3840
tcgggctgaa cggggggttc gtgcacacag cccagcttgg agcgaacgac ctacaccgaa   3900
ctgagatacc tacagcgtga gctatgagaa agcgccacgc ttcccgaagg gagaaaggcg   3960
gacaggtatc cggtaagcgg cagggtcgga acaggagagc gcacgaggga gcttccaggg   4020
ggaaacgcct ggtatcttta tagtcctgtc gggtttcgcc acctctgact tgagcgtcga   4080
tttttgtgat gctcgtcagg ggggcggagc ctatggaaaa acgccagcaa gcggcctttt   4140
ttacggttcc tggccttttg ctggcctttt gctcacatgt tctttcctgc gttatcccct   4200
```

```
gattctgtgg ataaccgtat taccgccttt gagtgagctg ataccgctcg ccgcagccga   4260
acgaccgagc gcagcgagtc agtgagcgag gaagcggaag agcgcccaat acgcaaaccg   4320
cctctccccg cgcgttggcc gattcattaa tgcagctggc acgacaggtt tcccgactgg   4380
aaagcgggca gtgagcgcaa cgcaattaat gtgagttagc tcactcatta ggcaccccag   4440
gctttacact ttatgcttcc ggctcgtatg ttgtgtggaa ttgtgagcgg ataacaattt   4500
cacacaggaa acagctatga ccatgattac gccaagctat ttaggtgacg cgttagaata   4560
ctcaagctat gcatcaagct tggtaccgag ctcggatcca ctagtaacgg ccgccagtgt   4620
gctggaattc aggtcctgca ggtctactct ttacatgttc tttactccgt ctcaaaattt   4680 ccttttttg ttggctctct ccgaacgagt tggagaaatc gttaaccctaa tcgaagatc    4740 tagattcctc tacatacgtt tgatctctct ctcagtatgg attacaaagc gccaaggaga   4800
tactactcac acgagttgt tgcgagacag caagatttcg caacagatat agttacgaga    4860 agaagaccctt atgtcccctta cgaccgtcca aataagtttt caaggagtct ggtttggacg  4920 tcaaagagt acaaatcacc cgagggcaat aatatgccaa ggaccaatga tgtgtcaccg    4980
aaaccaccag ttttaggttt ggcgaggaag aatgctgctt gtgggccaat gagatcttct   5040
agtctcagaa aatgggtatg taagtattgg aaagatggaa agtgcaagag gggtgagcag   5100
tgccagttct tacactcttg gtcttgtttc cctggattgg ccatggtagc ttctcttgaa   5160
gggcacaata aggaactaaa ggggatcgct ctccctgagg gttcagataa actcttttca   5220
gtcagtattg atggtacatt gcgagtttgg gactgcaatt ctggtcagtg tgtacattcc   5280
atcaaccttg acgcagaagc agggtctcta atcagtgaag gcccttgggt tttccttggc   5340
ttgccaaacg ctataaaggc ttttaacgtt caaaccagtc aagatttgca tcttcaagca   5400
gcaggggtgg ttggtcaggt gaatgcaatg actattgcaa acggaatgct ttttgctgga   5460
acaagttctg gtagtatctt agtctggaaa gctactacag actctgagtc tgatccattc   5520
aaatacttga catctcttga gggacatagt ggtgaagtca cttgttttgc tgttggaggt   5580
caaatgctat actctggttc tgtcgataaa acaatcaaga tgtgggatct caacaccctg   5640
caatgtataa tgaccctgaa gcaacatacc ggcactgtca cttcactctt atgttgggat   5700
aaatgtttga tatcgtcttc cttggatggg accataaaag tttgggctta ttctgaaaac   5760
ggaatcttga agttgttca aactcgcaga caagaacaga gtagtgttca tgctctttct    5820
ggtatgcatg atgcagaagc caaaccgata atattctgct cttaccaaaa cggaaccgtt   5880
ggcattttcg acctaccatc tttttcaagaa agaggaagga tgttctctac gcacacgatc   5940
gccacactca caattggtcc tcaaggattg ttattcagtg gagacgagag tggtaacttg   6000
cgtgtatgga ccttagctgc tggcaacaaa gtttagtctt ttcgactaaa gaattctgat    6060
ttaattttgt ggtttatatg ttgagttaac tgttaagaga gttttatttt gtaataggtg   6120
tatcagtcaa taaacaatct ttgtatcaac caaatgtaat ttttctcgtt aattcgattt   6180
cagagttttt actttaagat aaacaaactc tttcacacat catttaatga agtggagaa    6240 gcttaaaaaa caaacaaaga aactgatcca tttttggcgg gtcttcttct actcttattc   6300
atatgtgtta cgaactata gcgtaaaatt cagagcaagc gatctccgat ttgaacgtgg    6360
ctatcaccgg aggcccacca ctacgggcga tacgctctaa gtgaggatta aagtgctctg   6420
gtggtgacgt tgaagaaact cgcccatggt ttttgttatc tctgcagcca agtgtcgttc   6480
tttcttcgcc acttctcatc aagctacagt gaatttaaaa atggcgtctt ctttgatct    6540 cgtatacata agctggattg gtttcttaaa caaattcctc tccttttggg tcttctgggt   6600
```

```
ttgccttgta agtgtttgtg tttttgcctc tgagaaaaaa tcgc            6644
```

<210> SEQ ID NO 25
<211> LENGTH: 11736
<212> TYPE: DNA
<213> ORGANISM: Artificial Sequence
<220> FEATURE:
<223> OTHER INFORMATION: vector pKR1158
<220> FEATURE:
<221> NAME/KEY: misc_feature
<222> LOCATION: (7136)..(7136)
<223> OTHER INFORMATION: n is a, c, g, or t

<400> SEQUENCE: 25

```
gtacgagatc cggccggcca gatcctgcag gagatccaag cttggcgcgc cgttctatag     60
tgtcacctaa atcgtatgtg tatgatacat aaggttatgt attaattgta gccgcgttct    120
aacgacaata tgtccatatg gtgcactctc agtacaatct gctctgatgc cgcatagtta    180
agccagcccc gacacccgcc aacacccgct gacgcgccct gacgggcttg tctgctcccg    240
gcatccgctt acagacaagc tgtgaccgtc tccgggagct gcatgtgtca gaggttttca    300
ccgtcatcac cgaaacgcgc gagacgaaag ggcctcgtga tacgcctatt tttataggtt    360
aatgtcatga ccaaaatccc ttaacgtgag ttttcgttcc actgagcgtc agaccccgta    420
gaaaagatca aaggatcttc ttgagatcct ttttttctgc gcgtaatctg ctgcttgcaa    480
acaaaaaaac caccgctacc agcggtggtt tgtttgccgg atcaagagct accaactctt    540
tttccgaagg taactggctt cagcagagcg cagataccaa atactgtcct tctagtgtag    600
ccgtagttag gccaccactt caagaactct gtagcaccgc ctacatacct cgctctgcta    660
atcctgttac cagtggctgc tgccagtggc gataagtcgt gtcttaccgg gttggactca    720
agacgatagt taccggataa ggcgcagcgg tcgggctgaa cggggggttc gtgcacacag    780
cccagcttgg agcgaacgac ctacaccgaa ctgagatacc tacagcgtga gcattgagaa    840
agcgccacgc ttcccgaagg gagaaaggcg gacaggtatc cggtaagcgg cagggtcgga    900
acaggagagc gcacgaggga gcttccaggg ggaaacgcct ggtatcttta tagtcctgtc    960
gggtttcgcc acctctgact tgagcgtcga ttttttgtgat gctcgtcagg ggggcggagc   1020
ctatggaaaa acgccagcaa cgcggccttt ttacggttcc tggccttttg ctggcctttt   1080
gctcacatgt tctttcctgc gttatcccct gattctgtgg ataaccgtat taccgccttt   1140
gagtgagctg ataccgctcg ccgcagccga acgaccgagc gcagcgagtc agtgagcgag   1200
gaagcggaag agcgcccaat acgcaaaccg cctctccccg cgcgttggcc gattcattaa   1260
tgcaggttga tcgattcgac atcgatctag taacatagat gacaccgcgc gcgataattt   1320
atcctagttt gcgcgctata ttttgttttc tatcgcgtat aaatgtata attgcgggac   1380
tctaatcata aaaacccatc tcataaataa cgtcatgcat tacatgttaa ttattacatg   1440
cttaacgtaa ttcaacagaa attatatgat aatcatcgca agaccggcaa caggattcaa   1500
tcttaagaaa ctttattgcc aaatgtttga acgatctgct tcgacgcact ccttctttag   1560
gtacctcact attcctttgc cctcggacga gtgctggggc gtcggtttcc actatcggcg   1620
agtacttcta cacagccatc ggtccagacg gccgcgcttc tgcgggcgat ttgtgtacgc   1680
ccgacagtcc cggctccgga tcggacgatt gcgtcgcatc gaccctgcgc ccaagctgca   1740
tcatcgaaat tgccgtcaac caagctctga tagagttggt caagaccaat gcggagcata   1800
tacgcccgga gccgcggcga tcctgcaagc tccggatgcc tccgctcgaa gtagcgcgtc   1860
tgctgctcca tacaagccaa ccacggcctc cagaagaaga tgttggcgac ctcgtattgg   1920
```

```
gaatccccga acatcgcctc gctccagtca atgaccgctg ttatgcggcc attgtccgtc    1980
aggacattgt tggagccgaa atccgcgtgc acgaggtgcc ggacttcggg gcagtcctcg    2040
gcccaaagca tcagctcatc gagagcctgc gcgacgacg cactgacggt gtcgtccatc     2100
acagtttgcc agtgatacac atggggatca gcaatcgcgc atatgaaatc acgccatgta    2160
gtgtattgac cgattccttg cggtccgaat gggccgaacc cgctcgtctg gctaagatcg    2220
gccgcagcga tcgcatccat ggcctccgcg accggctgca gaacagcggg cagttcggtt    2280
tcaggcaggt cttgcaacgt gacaccctgt gcacggcggg agatgcaata ggtcaggctc    2340
tcgctgaatt ccccaatgtc aagcacttcc ggaatcggga gcgcggccga tgcaaagtgc    2400
cgataaacat aacgatcttt gtagaaacca tcggcgcagc tatttacccg caggacatat    2460
ccacgccctc ctacatcgaa gctgaaagca cgagattctt cgccctccga gagctgcatc    2520
aggtcggaga cgctgtcgaa cttttcgatc agaaacttct cgacagacgt cgcggtgagt    2580
tcaggctttt tcatggttta ataagaagag aaaagagttc ttttgttatg gctgaagtaa    2640
tagagaaatg agctcgagcg tgtcctctcc aaatgaaatg aacttcctta tatagaggaa    2700
gggtcttgcg aaggatagtg ggattgtgcg tcatccctta cgtcagtgga gatgtcacat    2760
caatccactt gctttgaaga cgtggttgga acgtcttctt tttccacgat gctcctcgtg    2820 ggtggggtc catctttggg accactgtcg gcagaggcat cttgaatgat agcctttcct     2880
ttatcgcaat gatggcattt gtaggagcca ccttcctttt ctactgtcct ttcgatgaag    2940
tgacagatag ctgggcaatg gaatccgagg aggtttcccg aaattatcct ttgttgaaaa    3000
gtctcaatag ccctttggtc ttctgagact gtatctttga cattttttgga gtagaccaga   3060 gtgtcgtgct ccaccatgtt gacgaagatt ttcttcttgt cattgagtcg taaaagactc    3120
tgtatgaact gttcgccagt cttcacggcg agttctgtta gatcctcgat ttgaatctta    3180
gactccatgc atggccttag attcagtagg aactaccttt ttagagactc caatctctat    3240
tacttgcctt ggtttatgaa gcaagccttg aatcgtccat actggaatag tacttctgat    3300
cttgagaaat atgtctttct ctgtgttctt gatgcaatta gtcctgaatc ttttgactgc    3360
atctttaacc ttcttgggaa ggtatttgat ctcctggaga ttgttactcg ggtagatcgt    3420
cttgatgaga cctgctgcgt aggcctctct aaccatctgt gggtcagcat tctttctgaa    3480
attgaagagg ctaaccttct cattatcagt ggtgaacata gtgtcgtcac cttcaccttc    3540
gaacttcctt cctagatcgt aaagatagag gaaatcgtcc attgtaatct ccggggcaaa    3600
ggagatctct tttgggctg gatcactgct gggccttttg gttcctagcg tgagccagtg     3660 ggcttttgc tttggtgggc ttgttagggc cttagcaaag ctcttgggct tgagttgagc     3720
ttctcctttg gggatgaagt tcaacctgtc tgtttgctga cttgttgtgt acgcgtcagc    3780
tgctgctctt gcctctgtaa tagtggcaaa tttcttgtgt gcaactccgg gaacgccgtt    3840
tgttgccgcc tttgtacaac cccagtcatc gtatataccg gcatgtggac cgttatacac    3900
aacgtagtag ttgatatgag ggtgttgaat acccgattct gctctgagag gagcaactgt    3960
gctgttaagc tcagattttt gtgggattgg aattggatcg atctcgatcc cgcgaaatta    4020
atacgactca ctatagggag accacaacgg tttccctcta gaaataattt tgtttaactt    4080
taagaaggag atatacccat ggaaaagcct gaactcaccg cgacgtctgt cgagaagttt    4140
ctgatcgaaa agttcgacag cgtctccgac ctgatgcagc tctcggaggg cgaagaatct    4200
cgtgctttca gcttcgatgt aggagggcgt ggatatgtcc tgcgggtaaa tagctgcgcc    4260
gatggtttct acaaagatcg ttatgtttat cggcactttg catcggccgc gctcccgatt    4320
```

```
ccggaagtgc ttgacattgg ggaattcagc gagagcctga cctattgcat ctcccgccgt   4380
gcacagggtg tcacgttgca agacctgcct gaaaccgaac tgcccgctgt tctgcagccg   4440
gtcgcggagg ctatggatgc gatcgctgcg gccgatctta gccagacgag cgggttcggc   4500
ccattcggac cgcaaggaat cggtcaatac actacatggc gtgatttcat atgcgcgatt   4560
gctgatcccc atgtgtatca ctggcaaact gtgatggacg acaccgtcag tgcgtccgtc   4620
gcgcaggctc tcgatgagct gatgctttgg gccgaggact gccccgaagt ccggcacctc   4680
gtgcacgcgg atttcggctc caacaatgtc ctgacggaca atggccgcat aacagcggtc   4740
attgactgga gcgaggcgat gttcggggat tcccaatacg aggtcgccaa catcttcttc   4800
tggaggccgt ggttggcttg tatgcagcag cagacgcgct acttcgagcg gaggcatccg   4860
gagcttgcag gatcgccgcg gctccgggcg tatatgctcc gcattggtct tgaccaactc   4920
tatcagagct tggttgacgg caatttcgat gatgcagctt gggcgcaggg tcgatgcgac   4980
gcaatcgtcc gatccggagc cgggactgtc gggcgtacac aaatcgcccg cagaagcgcg   5040
gccgtctgga ccgatggctg tgtagaagta ctcgccgata gtggaaaccg acgccccagc   5100
actcgtccga gggcaaagga atagtgaggt acagcttgga tcgatccggc tgctaacaaa   5160
gcccgaaagg aagctgagtt ggctgctgcc accgctgagc aataactagc ataacccctt   5220
ggggcctcta aacgggtctt gaggggtttt ttgctgaaag gaggaactat atccggatga   5280
tcgggcgcgc cgtcgacgga tccactagtt ctagagcggc ccgcgccgtc gacggatata   5340
atgagccgta aacaaagatg attaagtagt aattaatacg tactagtaaa agtggcaaaa   5400
gataacgaga aagaaccaat ttctttgcat tcggccttag cggaaggcat atataagctt   5460
tgattatttt atttagtgta atgatttcgt acaaccaaag catttattta gtactctcac   5520
acttgtgtcg cggccggccg ctacaggaac aggtggtggc ggcctcggc gcgctcgtac   5580 tgctccacga tggtgtagtc ctcgttgtgg gaggtgatgt ccagcttgga gtccacgtag   5640
tagtagccgg gcagctgcac gggcttcttg gccatgtaga tggacttgaa ctccaccagg   5700
tagtggccgc cgtccttcag cttcagggcc ttgtggatct cgcccttcag cacgccgtcg   5760
cgggggtaca ggcgctcggt ggaggcctcc cagcccatag tcttcttctg cattacgggg   5820
ccgtcggagg ggaagttcac gccgatgaac ttcaccttgt agatgaagga gccgtcctgc   5880
agggaggagt cctgggtcac ggtcaccacg ccgccgtcct cgaagttcat cacgcgctcc   5940
cacttgaagc cctcggggaa ggacagcttc ttgtagtcgg ggatgtcggc ggggtgcttc   6000
acgtacacct tggagccgta ctggaactgg ggggacagga tgtcccaggc gaagggcagg   6060
gggccgccct tggtcacctt cagcttggcg gtctgggtgc cctcgtaggg gcggccctcg   6120
ccctcgccct cgatctcgaa ctcgtggccg ttcacggagc cctccatgcg caccttgaag   6180
cgcatgaact ccttgatgac gtcctcggag gaggccatgg gccgcttggg gggctatgga   6240
agactttctt agttagttgt gtgaataagc aatgttggga gaatcgggac tacttatagg   6300
ataggaataa aacagaaaag tattaagtgc taatgaaata tttagactga taattaaaat   6360
cttcacgtat gtccacttga tataaaaacg tcaggaataa aggaagtaca gtagaattta   6420
aaggtactct ttttatatat acccgtgttc tcttttggc tagctagttg cataaaaaat   6480
aatctatatt tttatcatta ttttaaatat cttatgagat ggtaaatatt tatcataatt   6540
ttttttacta ttatttatta tttgtgtgtg taatacatat agaagttaat tacaaatttt   6600
atttactttt tcattatttt gatatgattc accattaatt tagtgttatt atttataata   6660
gttcatttta atcttttttgt atatattatg cgtgcagtac ttttttccta catataacta   6720
```

```
ctattacatt ttatttatat aatattttta ttaatgaatt ttcgtgataa tatgtaatat    6780
tgttcattat tatttcagat tttttaaaaa tatttgtgtt attatttatg aaatatgtaa    6840 ttttttagt atttgatttt atgatgataa agtgttctaa attcaaaaga aggggaaag     6900 cgtaaacatt aaaaaacgtc atcaaacaaa aacaaaatct tgttaataaa gataaaactg    6960
tttgttttga tcactgttat ttcgtaatat aaaaacatta tttatattta tattgttgac    7020
aaccaaattt gcctatcaaa tctaaccaat ataatgcatg cgtggcaggt aatgtactac    7080
catgaactta agtcatgaca taataaaccg tgaatctgac caatgcatgt acctanctaa    7140
attgtatttg tgacacgaag caaatgattc aattcacaat ggagatggga aacaaataat    7200
gaagaaccca gaactaagaa agcttttctg aaaaataaaa taaaggcaat gtcaaaagta    7260
tactgcatca tcagtccaga aagcacatga tatttttta tcagtatcaa tgcagctagt    7320 tttatttac aatatcgata tagctagttt aaatatattg cagctagatt tataaatatt    7380
tgtgttatta tttatcattt gtgtaatcct gtttttagta tttagttta tatatgatga    7440 taatgtattc caaatttaaa agaagggaaa taaatttaaa caagaaaaaa agtcatcaaa    7500 caaaaacaa atgaaagggt ggaaagatgt taccatgtaa tgtgaatgtt acagtatttc    7560
ttttattata gagttaacaa attaactaat atgattttgt taataatgat aaaatatttt    7620
ttttattatt atttcataat ataaaaatag tttacttaat ataaaaaaaa ttctatcgtt    7680
cacaacaaag ttggccacct aatttaacca tgcatgtacc catggaccat attaggtaac    7740
catcaaacct gatgaagaga taagagatg aagacttaag tcataacaca aaaccataaa    7800
aaacaaaaat acaatcaacc gtcaatctga ccaatgcatg aaaaagctgc aatagtgagt    7860
ggcgacacaa agcacatgat tttcttacaa cggagataaa accaaaaaaa tatttcatga    7920
acaacctaga acaaataaag cttttatata ataaatatat aaataaataa aggctatgga    7980
ataatatact tcaatatatt tggattaaat aaattgttgg cggggttgat atatttatac    8040
acacctaaag tcacttcaat ctcatttca cttaactttt attttttttt tcttttattt    8100
tatcataaag agaatattga taatatactt tttaacatat ttttatgaca ttttttattg    8160
gtgaaaactt attaaaaatc ataaattttg taagttagat ttatttaaag agttcctctt    8220
cttattttaa attttttaat aaattttaa ataactaaaa tttgtgttaa aaatgttaaa    8280
aaagtgtgtt attaaccctt ctcttcgagg atccgtaccg agctcggatc cactagtaac    8340
ggccgccagt gtgctggaat tcaggtcctg caggtctact cttttacatgt tctttactcc    8400 gtctcaaaat ttccttttt tgttggctct ctccgaacga gttggagaaa tcgttaaccc    8460
taatcgaaga tctagattcc tctacatacg tttgatctct ctctcagtat ggattacaaa    8520
gcgccaagga gatactactc acacggagtt gttgcgagac agcaagattt cgcaacagat    8580
atagttacga gaagaagacc ttatgtccct tacgaccgtc caaataagtt ttcaaggagt    8640
ctggtttgga cgtcaaaaga gtacaaatca cccgagggca ataatatgcc aaggaccaat    8700
gatgtgtcac cgaaaccacc agttttaggt ttggcgagga agaatgctgc ttgtgggcca    8760
atgagatctt ctagtctcag aaaatgggta tgtaagtatt ggaaagatgg aaagtgcaag    8820 agggtgagc agtgccagtt cttacactct tggtcttgtt tccctggatt ggccatggta    8880
gcttctcttg aagggcacaa taaggaacta aaggggatcg ctctccctga gggttcagat    8940
aaactctttt cagtcagtat tgatggtaca ttgcgagttt gggactgcaa ttctggtcag    9000
tgtgtacatt ccatcaacct tgacgcagaa gcagggtctc taatcagtga aggcccttgg    9060
gttttccttg gcttgccaaa cgctataaag gcttttaacg ttcaaaccag tcaagatttg    9120
```

```
catcttcaag cagcaggggt ggttggtcag gtgaatgcaa tgactattgc aaacggaatg    9180 cttttttgctg gaacaagttc tggtagtatc ttagtctgga aagctactac agactctgag   9240
tctgatccat tcaaatactt gacatctctt gagggacata gtggtgaagt cacttgtttt   9300
gctgttggag gtcaaatgct atactctggt tctgtcgata aaacaatcaa gatgtgggat   9360
ctcaacaccc tgcaatgtat aatgaccctg aagcaacata ccggcactgt cacttcactc   9420
ttatgttggg ataaatgttt gatatcgtct tccttggatg ggaccataaa agtttgggct   9480
tattctgaaa acggaatctt gaaagttgtt caaactcgca gacaagaaca gagtagtgtt   9540
catgctcttt ctggtatgca tgatgcagaa gccaaaccga taatattctg ctcttaccaa   9600
aacggaaccg ttggcatttt cgacctacca tcttttcaag aaagaggaag gatgttctct   9660
acgcacacga tcgccacact cacaattggt cctcaaggat tgttattcag tggagacgag   9720
agtggtaact tgcgtgtatg gaccttagct gctggcaaca aagtttagtc ttttcgacta   9780
aagaattctg atttaatttt gtggtttata tgttgagtta actgttaaga gagttttatt   9840
ttgtaatagg tgtatcagtc aataaacaat ctttgtatca accaaatgta attttttctcg  9900 ttaattcgat ttcagagttt ttactttaag ataaacaaac tctttcacac atcatttaat   9960
gaaagtggag aagcttaaaa aacaaacaaa gaaactgatc cattttttggc gggtcttctt  10020 ctactcttat tcatatgtgt taacgaacta tagcgtaaaa ttcagagcaa gcgatctccg  10080
atttgaacgt ggctatcacc ggaggcccac cactacgggc gatacgctct aagtgaggat  10140
taaagtgctc tggtggtgac gttgaagaaa ctcgcccatg gttttttgtta tctctgcagc 10200 caagtgtcgt tctttcttcg ccacttctca tcaagctaca gtgaatttaa aaatggcgtc  10260
tttctttgat ctcgtataca taagctggat tggtttctta aacaaattcc tctccttttg  10320
ggtcttctgg gtttgccttg taagtgtttg tgttttttgcc tctgagaaaa aatcgcggcc 10380
gcaagtatga actaaaatgc atgtaggtgt aagagctcat ggagagcatg gaatattgta  10440
tccgaccatg taacagtata ataactgagc tccatctcac ttcttctatg aataaacaaa  10500
ggatgttatg atatattaac actctatcta tgcaccttat tgttctatga taaatttcct  10560
cttattatta taaatcatct gaatcgtgac ggcttatgga atgcttcaaa tagtacaaaa  10620
acaaatgtgt actataagac tttctaaaca attctaacct tagcattgtg aacgagacat  10680
aagtgttaag aagacataac aattataatg gaagaagttt gtctccattt atatattata  10740
tattacccac ttatgtatta tattaggatg ttaaggagac ataacaatta taaagagaga  10800
agtttgtatc catttatata ttatatacta cccatttata tattatactt atccacttat  10860
ttaatgtctt tataaggttt gatccatgat atttctaata ttttagttga tatgtatatg  10920
aaagggtact atttgaactc tcttactctg tataaaggtt ggatcatcct taaagtgggt  10980
ctatttaatt ttattgcttc ttacagataa aaaaaaaatt atgagttggt ttgataaaat  11040
attgaaggat ttaaaataat aataaataac atataatata tgtatataaa tttattataa  11100 tataacatttt atctataaaa aagtaaatat tgtcataaat ctatacaatc gtttagcctt  11160
gctggacgaa tctcaattat ttaaacgaga gtaaacatat ttgactttttt ggttatttaa  11220 caaattatta tttaacacta tatgaaattt tttttttttat cagcaaagaa taaaattaaa  11280
ttaagaagga caatggtgtc ccaatcctta tacaaccaac ttccacaaga aagtcaagtc   11340
agagacaaca aaaaaacaag caaaggaaat tttttaattt gagttgtctt gtttgctgca   11400
taatttatgc agtaaaacac tacacataac ccttttagca gtagagcaat ggttgaccgt   11460
gtgcttagct tcttttattt tattttttta tcagcaaaga ataaataaaa taaaatgaga   11520
```

```
cacttcaggg atgtttcaac aagctctaga gggcccaatt cgccctatag tgagtcgtat    11580
tacaattcac tggccgtcgt tttacaacgt cgtgactggg aaaaccctgg cgttacccaa    11640
cttaatcgcc ttgcagcaca tccccctttc gccagctggc gtaatagcga agaggcccgc    11700
accgatcgcc cttcccaaca gttgcgcagc ctatac                              11736
```

<210> SEQ ID NO 26
<211> LENGTH: 12929
<212> TYPE: DNA
<213> ORGANISM: Artificial Sequence
<220> FEATURE:
<223> OTHER INFORMATION: vector pKR1167
<220> FEATURE:
<221> NAME/KEY: misc_feature
<222> LOCATION: (8496)..(8496)
<223> OTHER INFORMATION: n is a, c, g, or t

<400> SEQUENCE: 26

```
ggccgcaagt atgaactaaa atgcatgtag gtgtaagagc tcatggagag catggaatat      60
tgtatccgac catgtaacag tataataact gagctccatc tcacttcttc tatgaataaa     120
caaaggatgt tatgatatat taacactcta tctatgcacc ttattgttct atgataaatt     180
tcctcttatt attataaatc atctgaatcg tgacggctta tggaatgctt caaatagtac     240
aaaaacaaat gtgtactata agactttcta acaattcta accttagcat gtgaacgag      300 acataagtgt taagaagaca taacaattat aatggaagaa gtttgtctcc atttatatat     360
tatatattac ccacttatgt attatattag gatgttaagg agacataaca attataaga      420 gagaagtttg tatccattta tatattatat actacccatt tatatattat acttatccac     480
ttatttaatg tctttataag gtttgatcca tgatatttct aatattttag ttgatatgta     540
tatgaaaggg tactatttga actctcttac tctgtataaa ggttggatca tccttaaagt     600
gggtctattt aattttattg cttcttacag ataaaaaaaa aattatgagt tggtttgata     660
aaatattgaa ggatttaaaa taataataaa taacatataa tatatgtata taaatttatt     720 ataaatataac atttatctat aaaaaagtaa atattgtcat aaatctatac aatcgtttag    780
ccttgctgga cgaatctcaa ttatttaaac gagagtaaac atatttgact ttttggttat     840
ttaacaaatt attatttaac actatatgaa atttttttt ttatcagcaa agaataaaat      900
taaattaaga aggacaatgg tgtcccaatc cttatacaac caacttccac aagaaagtca     960
agtcagagac aacaaaaaa caagcaaagg aaattttta atttgagttg tcttgtttgc      1020
tgcataattt atgcagtaaa acactacaca taacccttt agcagtagag caatggttga    1080
ccgtgtgctt agcttctttt attttatttt tttatcagca aagaataaat aaaataaaat    1140
gagacacttc agggatgttt caacaagctc tagagggccc aattcgccct atagtgagtc    1200
gtattacaat tcactggccg tcgttttaca acgtcgtgac tgggaaaacc ctggcgttac    1260
ccaacttaat cgccttgcag cacatccccc tttcgccagc tggcgtaata gcgaagaggc    1320
ccgcaccgat cgcccttccc aacagttgcg cagcctatac gtacgagatc cggccggcca   1380
gatcctgcag gagatccaag cttggcgcgc cgttctatag tgtcacctaa atcgtatgtg    1440
tatgatacat aaggttatgt attaattgta gccgcgttct aacgacaata tgtccatatg    1500
gtgcactctc agtacaatct gctctgatgc cgcatagtta agccagcccc gacacccgcc    1560
aacacccgct gacgcgccct gacgggcttg tctgctcccg gcatccgctt acagacaagc    1620
tgtgaccgtc tccgggagct gcatgtgtca gaggttttca ccgtcatcac cgaaacgcgc    1680
gagacgaaag ggcctcgtga tacgcctatt tttataggtt aatgtcatga ccaaaatccc    1740
```

```
ttaacgtgag ttttcgttcc actgagcgtc agacccgta gaaaagatca aaggatcttc    1800
ttgagatcct ttttttctgc gcgtaatctg ctgcttgcaa acaaaaaaac caccgctacc    1860
agcggtggtt tgtttgccgg atcaagagct accaactctt tttccgaagg taactggctt    1920
cagcagagcg cagataccaa atactgtcct tctagtgtag ccgtagttag gccaccactt    1980
caagaactct gtagcaccgc ctacatacct cgctctgcta atcctgttac cagtggctgc    2040
tgccagtggc gataagtcgt gtcttaccgg gttggactca agacgatagt taccggataa    2100
ggcgcagcgg tcgggctgaa cggggggttc gtgcacacag cccagcttgg agcgaacgac    2160
ctacaccgaa ctgagatacc tacagcgtga gcattgagaa agcgccacgc ttcccgaagg    2220
gagaaaggcg gacaggtatc cggtaagcgg cagggtcgga acaggagagc gcacgaggga    2280
gcttccaggg ggaaacgcct ggtatcttta tagtcctgtc gggtttcgcc acctctgact    2340
tgagcgtcga ttttgtgat gctcgtcagg ggggcggagc ctatggaaaa acgccagcaa    2400
cgcggccttt ttacggttcc tggccttttg ctggcctttt gctcacatgt tctttcctgc    2460
gttatcccct gattctgtgg ataaccgtat taccgccttt gagtgagctg ataccgctcg    2520
ccgcagccga acgaccgagc gcagcgagtc agtgagcgag gaagcggaag agcgcccaat    2580
acgcaaaccg cctctccccg cgcgttggcc gattcattaa tgcaggttga tcgattcgac    2640
atcgatctag taacatagat gacaccgcgc gcgataattt atcctagttt gcgcgctata    2700
ttttgttttc tatcgcgtat taaatgtata attgcgggac tctaatcata aaaacccatc    2760
tcataaataa cgtcatgcat tacatgttaa ttattacatg cttaacgtaa ttcaacagaa    2820
attatatgat aatcatcgca agaccggcaa caggattcaa tcttaagaaa ctttattgcc    2880
aaatgtttga acgatctgct tcgacgcact ccttctttag gtacctcact attccttgc    2940 cctcggacga gtgctggggc gtcggtttcc actatcggcg agtacttcta cacagccatc    3000
ggtccagacg gccgcgcttc tgcggcgat tgtgtacgc ccgacagtcc cggctccgga    3060
tcggacgatt gcgtcgcatc gaccctgcgc ccaagctgca tcatcgaaat tgccgtcaac    3120
caagctctga tagagttggt caagaccaat gcggagcata tacgcccgga gccgcggcga    3180
tcctgcaagc tccggatgcc tccgctcgaa gtagcgcgtc tgctgctcca tacaagccaa    3240
ccacggcctc cagaagaaga tgttggcgac ctcgtattgg gaatccccga acatcgcctc    3300
gctccagtca atgaccgctg ttatgcggcc attgtccgtc aggacattgt tggagccgaa    3360
atccgcgtgc acgaggtgcc ggacttcggg gcagtcctcg gcccaaagca tcagctcatc    3420
gagagcctgc gcgacggacg cactgacggt gtcgtccatc acagtttgcc agtgatacac    3480
atggggatca gcaatcgcgc atatgaaatc acgccatgta gtgtattgac cgattccttg    3540
cggtccgaat gggccgaacc cgctcgtctg gctaagatcg gccgcagcga tcgcatccat    3600
ggcctccgcg accggctgca gaacagcggg cagttcggtt tcaggcaggt cttgcaacgt    3660
gacaccctgt gcacggcggg agatgcaata ggtcaggctc tcgctgaatt ccccaatgtc    3720
aagcacttcc ggaatcggga gcgcggccga tgcaaagtgc cgataaacat aacgatcttt    3780
gtagaaacca tcggcgcagc tatttacccg caggacatat ccacgccctc ctacatcgaa    3840
gctgaaagca cgagattctt cgccctccga gagctgcatc aggtcggaga cgctgtcgaa    3900
cttttcgatc agaaacttct cgacagacgt cgcggtgagt tcaggctttt tcatggttta    3960
ataagaagag aaaagagttc ttttgttatg gctgaagtaa tagagaaatg agctcgagcg    4020
tgtcctctcc aaatgaaatg aacttcctta tatagaggaa gggtcttgcg aaggatagtg    4080
ggattgtgcg tcatccctta cgtcagtgga gatgtcacat caatccactt gctttgaaga    4140
```

```
cgtggttgga acgtcttctt tttccacgat gctcctcgtg ggtggggggtc catctttggg    4200 accactgtcg gcagaggcat cttgaatgat agcctttcct ttatcgcaat gatggcattt    4260
gtaggagcca ccttccttt ctactgtcct ttcgatgaag tgacagatag ctgggcaatg    4320
gaatccgagg aggtttcccg aaattatcct ttgttgaaaa gtctcaatag cccttttggtc   4380 ttctgagact gtatctttga cattttttgga gtagaccaga gtgtcgtgct ccaccatgtt   4440
gacgaagatt ttcttcttgt cattgagtcg taaaagactc tgtatgaact gttcgccagt   4500
cttcacggcg agttctgtta gatcctcgat ttgaatctta gactccatgc atggccttag   4560
attcagtagg aactaccttt ttagagactc caatctctat tacttgcctt ggtttatgaa    4620
gcaagccttg aatcgtccat actgaatag tacttctgat cttgagaaat atgtctttct    4680
ctgtgttctt gatgcaatta gtcctgaatc ttttgactgc atctttaacc ttcttgggaa    4740
ggtatttgat ctcctggaga ttgttactcg ggtagatcgt cttgatgaga cctgctgcgt    4800
aggcctctct aaccatctgt gggtcagcat tcttttctgaa attgaagagg ctaaccttct   4860
cattatcagt ggtgaacata gtgtcgtcac cttcaccttc gaacttcctt cctagatcgt    4920
aaagatagag gaaatcgtcc attgtaatct ccggggcaaa ggagatctct tttggggctg    4980
gatcactgct gggccttttg gttcctagcg tgagccagtg ggcttttttgc tttggtgggc    5040 ttgttagggc cttagcaaag ctctgggct tgagttgagc ttctcctttg gggatgaagt     5100
tcaacctgtc tgtttgctga cttgttgtgt acgcgtcagc tgctgctctt gcctctgtaa    5160
tagtggcaaa tttcttgtgt gcaactccgg gaacgccgtt tgttgccgcc tttgtacaac    5220
cccagtcatc gtatataccg gcatgtggac cgttatacac aacgtagtag ttgatatgag    5280
ggtgttgaat acccgattct gctctgagag gagcaactgt gctgttaagc tcagattttt    5340
gtgggattgg aattggatcg atctcgatcc cgcgaaatta atacgactca ctatagggag    5400
accacaacgg tttccctcta gaaataattt tgtttaactt taagaaggag atatacccat    5460
ggaaaagcct gaactcaccg cgacgtctgt cgagaagttt ctgatcgaaa agttcgacag    5520
cgtctccgac ctgatgcagc tctcggaggg cgaagaatct cgtgctttca gcttcgatgt    5580
aggagggcgt ggatatgtcc tgcgggtaaa tagctgcgcc gatggtttct acaaagatcg    5640
ttatgtttat cggcactttg catcggccgc gctcccgatt ccggaagtgc ttgacattgg    5700
ggaattcagc gagagcctga cctattgcat ctcccgccgt gcacagggtg tcacgttgca    5760
agacctgcct gaaaccgaac tgcccgctgt tctgcagccg gtcgcggagg ctatggatgc    5820
gatcgctgcg gccgatctta ccagacgag cgggttcggc ccattcggac cgcaaggaat    5880
cggtcaatac actacatggc gtgatttcat atgcgcgatt gctgatcccc atgtgtatca    5940
ctggcaaact gtgatggacg acaccgtcag tgcgtccgtc gcgcaggctc tcgatgagct    6000
gatgctttgg gccgaggact gccccgaagt ccggcacctc gtgcacgcgg atttcggctc    6060
caacaatgtc ctgacggaca atggccgcat aacagcggtc attgactgga gcgaggcgat    6120
gttcggggat tcccaatacg aggtcgccaa catcttcttc tggaggccgt ggttggcttg    6180 tatgagcag cagacgcgct acttcgagcg gaggcatccg gagcttgcag atcgccgcg    6240 gctccgggcg tatatgctcc gcattggtct tgaccaactc tatcagagct tggttgacgg    6300
caatttcgat gatgcagctt gggcgcaggg tcgatgcgac gcaatcgtcc gatccggagc    6360
cgggactgtc gggcgtacac aaatcgcccg cagaagcgcg gccgtctgga ccgatggctg    6420
tgtagaagta ctcgccgata gtggaaaccg acgccccagc actcgtccga gggcaaagga    6480
atagtgaggt acagcttgga tcgatccggc tgctaacaaa gcccgaaagg aagctgagtt    6540
```

```
ggctgctgcc accgctgagc aataactagc ataacccctt ggggcctcta acgggtctt    6600 gaggggtttt ttgctgaaag gaggaactat atccggatga tcgggcgcgc cgtcgacgga    6660
tccactagtt ctagagcggc ccgcgccgtc gacggatata atgagccgta aacaaagatg    6720
attaagtagt aattaatacg tactagtaaa agtggcaaaa gataacgaga aagaaccaat    6780
ttctttgcat tcggccttag cggaaggcat atataagctt tgattatttt atttagtgta    6840
atgatttcgt acaaccaaag catttattta gtactctcac acttgtgtcg cggccggccg    6900
ctacaggaac aggtggtggc ggccctcggc gcgctcgtac tgctccacga tggtgtagtc    6960
ctcgttgtgg gaggtgatgt ccagcttgga gtccacgtag tagtagccgg gcagctgcac    7020
gggcttcttg gccatgtaga tggacttgaa ctccaccagg tagtggccgc cgtccttcag    7080
cttcagggcc ttgtggatct cgcccttcag cacgccgtcg cggggtaca ggcgctcggt      7140 ggaggcctcc cagcccatag tcttcttctg cattacgggg ccgtcggagg gaagttcac     7200 gccgatgaac ttcaccttgt agatgaagga gccgtcctgc agggaggagt cctgggtcac    7260
ggtcaccacg ccgccgtcct cgaagttcat cacgcgctcc cacttgaagc cctcggggaa    7320
ggacagcttc ttgtagtcgg ggatgtcggc ggggtgcttc acgtacacct tggagccgta    7380
ctggaactgg ggggacagga tgtcccaggc gaagggcagg gggccgccct tggtcaccct    7440
cagcttggcg gtctgggtgc cctcgtaggg gcggccctcg ccctcgccct cgatctcgaa    7500
ctcgtggccg ttcacggagc cctccatgcg caccttgaag cgcatgaact ccttgatgac    7560
gtcctcggag gaggccatgg gccgcttggg gggctatgga agactttctt agttagttgt    7620
gtgaataagc aatgttggga gaatcgggac tacttatagg ataggaataa aacagaaaag    7680
tattaagtgc taatgaaata tttagactga taattaaaat cttcacgtat gtccacttga    7740
tataaaaacg tcaggaataa aggaagtaca gtagaattta aaggtactct ttttatatat    7800
acccgtgttc tcttttttggc tagctagttg cataaaaaat aatctatatt tttatcatta    7860
ttttaaatat cttatgagat ggtaaatatt tatcataatt ttttttacta ttatttatta    7920
tttgtgtgtg taatacatat agaagttaat tacaaatttt atttactttt tcattatttt    7980
gatatgattc accattaatt tagtgttatt atttataata gttcatttta atcttttttgt   8040 atatattatg cgtgcagtac tttttttccta catataacta ctattacatt ttatttatat   8100 aatatttta ttaatgaatt ttcgtgataa tatgtaatat tgttcattat tatttcagat    8160
tttttaaaaa tatttgtgtt attatttatg aaatatgtaa ttttttttagt atttgattttt  8220 atgatgataa agtgttctaa attcaaaaga agggggaaag cgtaaacatt aaaaaacgtc    8280
atcaaacaaa aacaaaatct tgttaataaa gataaaactg tttgttttga tcactgttat    8340
ttcgtaatat aaaaacatta tttatattta tattgttgac aaccaaattt gcctatcaaa    8400
tctaaccaat ataatgcatg cgtggcaggt aatgtactac catgaactta agtcatgaca    8460
taataaaccg tgaatctgac caatgcatgt acctanctaa attgtatttg tgacacgaag    8520
caaatgattc aattcacaat ggagatggga acaaataat gaagaaccca gaactaagaa    8580
agcttttctg aaaaataaaa taaaggcaat gtcaaaagta tactgcatca tcagtccaga    8640
aagcacatga tattttttta tcagtatcaa tgcagctagt tttattttac aatatcgata    8700
tagctagttt aaatatattg cagctagatt tataaatatt tgtgttatta tttatcattt    8760
gtgtaatcct gttttttagta ttttagttta tatatgatga taatgtattc caaatttaaa   8820
agaagggaaa taaatttaaa caagaaaaaa agtcatcaaa caaaaaacaa atgaaagggt    8880
ggaaagatgt taccatgtaa tgtgaatgtt acagtatttc ttttattata gagttaacaa    8940
```

```
attaactaat atgattttgt taataatgat aaaatatttt ttttattatt atttcataat   9000
ataaaaatag tttacttaat ataaaaaaaa ttctatcgtt cacaacaaag ttggccacct   9060
aatttaacca tgcatgtacc catggaccat attaggtaac catcaaacct gatgaagaga   9120
taaagagatg aagacttaag tcataacaca aaaccataaa aaacaaaaat acaatcaacc   9180
gtcaatctga ccaatgcatg aaaaagctgc aatagtgagt ggcgacacaa agcacatgat   9240
tttcttacaa cggagataaa accaaaaaaa tatttcatga acaacctaga acaaataaag   9300
ctttttatata ataaatatat aaataaataa aggctatgga ataatatact tcaatatatt   9360
tggattaaat aaattgttgg cggggttgat atatttatac acacctaaag tcacttcaat   9420
ctcattttca cttaactttt attttttttt tcttttttatt tatcataaag agaatattga   9480
taatatactt tttaacatat ttttatgaca tttttttattg gtgaaaactt attaaaaatc   9540
ataaattttg taagttagat ttatttaaag agttcctctt cttattttaa attttttaat   9600
aaattttttaa ataactaaaa tttgtgttaa aaatgttaaa aaagtgtgtt attaacccctt   9660
ctcttcgagg atccgtaccg agctcggatc cactagtaac ggccgccagt gtgctggaat   9720
tcaggtcctg caggtctact ctttacatgt tctttactcc gtctcaaaat ttccttttt   9780
tgttggctct ctccgaacga gttggagaaa tcgttaaccc taatcgaaga tctagattcc   9840
tctacatacg tttgatctct ctctcagtat ggattacaaa gcgccaagga gatactactc   9900
acacggagtt gttgcgagac agcaagattt cgcaacagat atagttacga gaagaagacc   9960
ttatgtccct tacgaccgtc caaataagtt ttcaaggagt ctggtttgga cgtcaaaaga  10020
gtacaaatca cccgagggca ataatatgcc aaggaccaat gatgtgtcac cgaaaccacc  10080
agttttaggt ttggcgagga agaatgctgc ttgtgggcca atgagatctt ctagtctcag  10140
aaaatgggta tgtaagtatt ggaagatgg aaagtgcaag aggggtgagc agtgccagtt  10200
cttacactct tggtcttgtt tccctggatt ggccatggta gcttctcttg aagggcacaa  10260
taaggaacta aaggggatcg ctctccctga gggttcagat aaactctttt cagtcagtat  10320
tgatggtaca ttgcgagttt gggactgcaa ttctggtcag tgtgtacatt ccatcaacct  10380
tgacgcagaa gcagggtctc taatcagtga aggcccttgg gttttccttg gcttgccaaa  10440
cgctataaag gcttttaacg ttcaaaccag tcaagatttg catcttcaag cagcaggggt  10500
ggttggtcag gtgaatgcaa tgactattgc aaacggaatg cttttttgctg gaacaagttc  10560
tggtagtatc ttagtctgga aagctactac agactctgag tctgatccat tcaaatactt  10620
gacatctctt gagggacata gtggtgaagt cacttgtttt gctgttggag gtcaaatgct  10680
atactctggt tctgtcgata aaacaatcaa gatgtgggat ctcaacaccc tgcaatgtat  10740
aatgaccctg aagcaacata ccggcactgt cacttcactc ttatgttggg ataaatgttt  10800
gatatcgtct tccttggatg ggaccataaa agtttgggct tattctgaaa acggaatctt  10860
gaaagttgtt caaactcgca gacaagaaca gagtagtgtt catgctcttt ctggtatgca  10920
tgatgcagaa gccaaaccga taatattctg ctcttaccaa aacggaaccg ttggcatttt  10980
cgacctacca tcttttcaag aaagaggaag gatgttctct acgcacacga tcgccacact  11040
cacaattggt cctcaaggat tgttattcag tggagacgag agtggtaact tgcgtgtatg  11100
gacccttagct gctggcaaca agtttagtc ttttcgacta agaattctg atttaatttt  11160
gtggttata tgttgagtta actgttaaga gagttttatt ttgtaatagg tgtatcagtc  11220
aataaacaat ctttgtatca accaaatgta atttttctcg ttaattcgat ttcagagttt  11280
ttactttaag ataaacaaac tctttcacac atcatttaat gaaagtggag aagcttaaaa  11340
```

```
aacaaacaaa gaaactgatc cattttttggc gggtcttctt ctactcttat tcatatgtgt    11400
taacgaacta tagcgtaaaa ttcagagcaa gcgatctccg atttgaacgt ggctatcacc    11460
ggaggcccac cactacgggc gatacgctct aagtgaggat taaagtgctc tggtggtgac    11520
gttgaagaaa ctcgcccatg gttttttgtta tctctgcagc caagtgtcgt tctttcttcg    11580
ccacttctca tcaagctaca gtgaatttaa aaatggcgtc tttctttgat ctcgtataca    11640
taagctggat tggtttctta aacaaattcc tctccttttg ggtcttctgg gtttgccttg    11700
taagtgtttg tgttttttgcc tctgagaaaa aatcgcggcc gcatggagag atctcaacgg    11760
cagtctcctc cgccaccgtc gccgtcctcc tcctcgtcct ccgtctccgc ggacaccgtc    11820
ctcgtccctc ccggaaagag gcggagggcg gcgacggcca aggccggcgc cgagcctaat    11880
aagaggatcc gcaaggaccc cgccgccgcc gccgcgggga agaggagctc cgtctacagg    11940
ggagtcacca gcacaggtg gacgggcagg ttcgaggcgc atctctggga caagcactgc    12000
ctcgccgcgc tccacaacaa gaagaaaggc aggcaagtct acctggggc gtatgacagc    12060 gaggaggcag ctgctcgtgc ctatgacctc gcagctctca gtactggggg tcctgagact    12120
ctgctcaact tccctgtgga ggattactcc agcgagatgc cggagatgga ggccgtgtcc    12180
cgggaggagt acctggcctc cctccgccgc aggagcagcg gcttctccag gggcgtctcc    12240
aagtacagag gcgtcgccag gcatcaccac aacgggaggt gggaggcacg gattgggcga    12300
gtctttggga caagtacct ctacttggga acatttgaca ctcaagaaga ggcagccaag    12360
gcctatgacc ttgcggccat tgaataccgt ggcgtcaatg ctgtaaccaa cttcgacatc    12420
agctgctacc tggaccaccc gctgttcctg gcacagctcc aacaggagcc acaggtggtg    12480
ccggcactca accaagaacc tcaacctgat cagagcgaaa ccggaactac agagcaagag    12540
ccggagtcaa gcgaagccaa gacaccggat ggcagtgcag aacccgatga gaacgcggtg    12600
cctgacgaca ccgcggagcc cctcaccaca gtcgacgaca gcatcgaaga gggcttgtgg    12660
agcccttgca tggattacga gctagacacc atgtcgagac caaactttgg cagctcaatc    12720
aatctgagcg agtggttcgc tgacgcagac ttcgactgca acatcggatg cctgttcgat    12780
gggtgttctg cggctgacga aggaagcaag gatggtgtag gtctggcaga tttcagtctg    12840
tttgaggcag gtgatgtcca gctgaaggat gttctttcgg atatggaaga ggggatacaa    12900
cctccagcga tgatcagtgt gtgcaacgc                                      12929
```

<210> SEQ ID NO 27
<211> LENGTH: 13268
<212> TYPE: DNA
<213> ORGANISM: Artificial Sequence
<220> FEATURE:
<223> OTHER INFORMATION: vector pKR92

<400> SEQUENCE: 27

```
cgcgcctcga gtgggcggat ccccccgggct gcaggaattc actggccgtc gttttacaac     60
gtcgtgactg ggaaaaccct ggcgttaccc aacttaatcg ccttgcagca catcccccttt    120 tcgccagctg gcgtaatagc gaagaggccc gcaccgatcc cccttcccaa cagttgcgca    180
gcctgaatgg cgaatggatc gatccatcgc gatgtacctt tgttagtca gcctctcgat    240 tgctcatcgt cattacacag taccgaagtt tgatcgatct agtaacatag atgacaccgc    300
gcgcgataat ttatcctagt ttgcgcgcta tattttgttt tctatcgcgt attaaatgta    360
taattgcggg actctaatca taaaaaccca tctcataaat aacgtcatgc attacatgtt    420
aattattaca tgcttaacgt aattcaacag aaattatatg ataatcatcg caagaccggc    480
```

```
aacaggattc aatcttaaga aactttattg ccaaatgttt gaacgatctg cttcgacgca    540
ctccttcttt actccaccat ctcgtcctta ttgaaaacgt gggtagcacc aaaacgaatc    600
aagtcgctgg aactgaagtt accaatcacg ctggatgatt tgccagttgg attaatcttg    660
cctttccccg catgaataat attgatgaat gcatgcgtga ggggtagttc gatgttggca    720
atagctgcaa ttgccgcgac atcctccaac gagcataatt cttcagaaaa atagcgatgt    780
tccatgttgt cagggcatgc atgatgcacg ttatgaggtg acggtgctag gcagtattcc    840
ctcaaagttt catagtcagt atcatattca tcattgcatt cctgcaagag agaattgaga    900
cgcaatccac acgctgcggc aaccttccgg cgttcgtggt ctatttgctc ttggacgttg    960
caaacgtaag tgttggatcg atccggggtg ggcgaagaac tccagcatga gatccccgcg   1020
ctggaggatc atccagccgg cgtcccggaa aacgattccg aagcccaacc tttcatagaa   1080
ggcggcggtg gaatcgaaat ctcgtgatgg caggttgggc gtcgcttggt cggtcatttc   1140
gaaccccaga gtcccgctca gaagaactcg tcaagaaggc gatagaaggc gatgcgctgc   1200
gaatcgggag cggcgatacc gtaaagcacg aggaagcggt cagcccattc gccgccaagc   1260
tcttcagcaa tatcacgggt agccaacgct atgtcctgat agcggtccgc cacacccagc   1320
cggccacagt cgatgaatcc agaaaagcgg ccattttcca ccatgatatt cggcaagcag   1380
gcatcgccat gggtcacgac gagatcctcg ccgtcgggca tgcgcgcctt gagcctggcg   1440
aacagttcgg ctggcgcgag cccctgatgc tcttcgtcca gatcatcctg atcgacaaga   1500
ccggcttcca tccgagtacg tgctcgctcg atgcgatgtt tcgcttggtg gtcgaatggg   1560
caggtagccg gatcaagcgt atgcagccgc cgcattgcat cagccatgat ggatactttc   1620
tcggcaggag caaggtgaga tgacaggaga tcctgccccg gcacttcgcc caatagcagc   1680
cagtcccttc ccgcttcagt gacaacgtcg agcacagctg cgcaaggaac gcccgtcgtg   1740
gccagccacg atagccgcgc tgcctcgtcc tgcagttcat tcagggcacc ggacaggtcg   1800
gtcttgacaa aaagaaccgg gcgcccctgc gctgacagcc ggaacacggc ggcatcagag   1860
cagccgattg tctgttgtgc ccagtcatag ccgaatagcc tctccaccca gcggccgga    1920
gaacctgcgt gcaatccatc ttgttcaatc atgcgaaacg atccccgcaa gcttggagac   1980
tggtgatttc agcgtgtcct ctccaaatga aatgaacttc cttatataga ggaagggtct   2040
tgcgaaggat agtgggattg tgcgtcatcc cttacgtcag tggagatatc acatcaatcc   2100
acttgctttg aagacgtggt tggaacgtct tcttttttcca cgatgctcct cgtgggtggg   2160
ggtccatctt tgggaccact gtcggcagag gcatcttcaa cgatggcctt tcctttatcg   2220
caatgatggc atttgtagga gccaccttcc ttttccacta tcttcacaat aaagtgacag   2280
atagctgggc aatggaatcc gaggaggttt ccggatatta cccttgttg aaaagtctca    2340
attgccctt ggtcttctga gactgtatct ttgatatttt tggagtagac aagcgtgtcg    2400
tgctccacca tgttgacgaa gattttcttc ttgtcattga gtcgtaagag actctgtatg   2460
aactgttcgc cagtctttac ggcgagttct gttaggtcct ctatttgaat ctttgactcc   2520
atggcctttg attcagtggg aactaccttt ttagagactc caatctctat tacttgcctt   2580
ggtttgtgaa gcaagccttg aatcgtccat actggaatag tacttctgat cttgagaaat   2640
atatcttttct ctgtgttctt gatgcagtta gtcctgaatc ttttgactgc atctttaacc   2700
ttcttgggaa ggtatttgat ctcctggaga ttattgctcg ggtagatcgt cttgatgaga   2760
cctgctgcgt aagcctctct aaccatctgt gggttagcat tctttctgaa attgaaaagg   2820
ctaatcttct cattatcagt ggtgaacatg gtatcgtcac cttctccgtc gaacttcctg   2880
```

```
actagatcgt agagatagag gaagtcgtcc attgtgatct ctggggcaaa ggagtctgaa    2940
ttaattcgat atggtggatt tatcacaaat gggacccgcc gccgacagag gtgtgatgtt    3000
aggccaggac tttgaaaatt tgcgcaacta tcgtatagtg gccgacaaat tgacgccgag    3060
ttgacagact gcctagcatt tgagtgaatt atgtgaggta atgggctaca ctgaattggt    3120
agctcaaact gtcagtattt atgtatatga gtgtatattt tcgcataatc tcagaccaat    3180
ctgaagatga aatgggtatc tgggaatggc gaaatcaagg catcgatcgt gaagtttctc    3240
atctaagccc ccatttggac gtgaatgtag acacgtcgaa ataaagattt ccgaattaga    3300
ataatttgtt tattgctttc gcctataaat acgacggatc gtaatttgtc gttttatcaa    3360
aatgtacttt catttataa taacgctgcg gacatctaca tttttgaatt gaaaaaaat     3420 tggtaattac tctttctttt tctccatatt gaccatcata ctcattgctg atccatgtag    3480
atttcccgga catgaagcca tttacaattg aatatatcct gccgccgctg ccgctttgca    3540
cccggtggag cttgcatgtt ggtttctacg cagaactgag ccggttaggc agataaattc    3600
cattgagaac tgagccatgt gcaccttccc cccaacacgg tgagcgacgg ggcaacggag    3660
tgatccacat gggacttta acatcatcc gtcggatggc gttgcgagag aagcagtcga      3720
tccgtgagat cagccgacgc accgggcagg cgcgcaacac gatcgcaaag tatttgaacg    3780
caggtacaat cgagccgacg ttcacgcgga acgaccaagc aagctagctt taatgcggta    3840
gtttatcaca gttaaattgc taacgcagtc aggcaccgtg tatgaaatct aacaatgcgc    3900
tcatcgtcat cctcggcacc gtcaccctgg atgctgtagg cataggcttg gttatgccgg    3960
tactgccggg cctcttgcgg gatatcgtcc attccgacag catcgccagt cactatggcg    4020
tgctgctagc gctatatgcg ttgatgcaat ttctatgcgc acccgttctc ggagcactgt    4080
ccgaccgctt tggccgccgc ccagtcctgc tcgcttcgct acttggagcc actatcgact    4140
acgcgatcat ggcgaccaca cccgtcctgt ggtccaaccc ctccgctgct atagtgcagt    4200
cggcttctga cgttcagtgc agccgtcttc tgaaaacgac atgtcgcaca agtcctaagt    4260
tacgcgacag gctgccgccc tgcccttttc ctggcgtttt cttgtcgcgt gttttagtcg    4320
cataaagtag aatacttgcg actagaaccg gagacattac gccatgaaca agagcgccgc    4380
cgctggcctg ctgggctatg cccgcgtcag caccgacgac caggacttga ccaaccaacg    4440
ggccgaactg cacgcggccg gctgcaccaa gctgttttcc gagaagatca ccggcaccag    4500
gcgcgaccgc ccggagctgg ccaggatgct tgaccaccta cgccctggcg acgttgtgac    4560
agtgaccagg ctagaccgcc tggcccgcag cacccgcgac ctactggaca ttgccgagcg    4620
catccaggag gccggcgcgg gcctgcgtag cctggcagag ccgtgggccg acaccaccac    4680
gccggccggc cgcatggtgt tgaccgtgtt cgccggcatt gccgagttcg agcgttccct    4740
aatcatcgac cgcacccgga gcgggcgcga ggccgccaag gcccgaggcg tgaagtttgg    4800
cccccgccct accctcaccc cggcacagat cgcgcacgcc cgcgagctga tcgaccagga    4860
aggccgcacc gtgaaagagg cggctgcact gcttggcgtg catcgctcga ccctgtaccg    4920
cgcacttgag cgcagcgagg aagtgacgcc caccgaggcc aggcggcgcg gtgccttccg    4980
tgaggacgca ttgaccgagg ccgacgccct ggcggccgcc gagaatgaac gccaagagga    5040
acaagcatga aaccgcacca ggacggccag gacgaaccgt ttttcattac cgaagagatc    5100
gaggcggaga tgatcgcggc cgggtacgtg ttcgagccgc ccgcgcacgt ctcaaccgtg    5160
cggctgcatg aaatcctggc cggtttgtct gatgccaagc tggcggcctg gccggccagc    5220
ttggccgctg aagaaaccga gcgccgccgt ctaaaaaggt gatgtgtatt tgagtaaaac    5280
```

```
agcttgcgtc atgcggtcgc tgcgtatatg atgcgatgag taaataaaca aatacgcaag    5340
ggaacgcatg aagttatcgc tgtacttaac cagaaaggcg ggtcaggcaa gacgaccatc    5400
gcaacccatc tagcccgcgc cctgcaactc gccggggccg atgttctgtt agtcgattcc    5460
gatccccagg gcagtgcccg cgattgggcg gccgtgcggg aagatcaacc gctaaccgtt    5520
gtcggcatcg accgcccgac gattgaccgc gacgtgaagg ccatcggccg gcgcgacttc    5580
gtagtgatcg acggagcgcc ccaggcggcg gacttggctg tgtccgcgat caaggcagcc    5640
gacttcgtgc tgattccggt gcagccaagc ccttacgaca tatggccac cgccgacctg    5700 gtggagctgg ttaagcagcg cattgaggtc acggatggaa ggctacaagc ggcctttgtc    5760
gtgtcgcggg cgatcaaagg cacgcgcatc ggcggtgagg ttgccgaggc gctggccggg    5820
tacgagctgc ccattcttga gtcccgtatc acgcagcgcg tgagctaccc aggcactgcc    5880
gccgccggca caaccgttct tgaatcagaa cccgagggcg acgctgcccg cgaggtccag    5940
gcgctggccg ctgaaattaa atcaaaactc atttgagtta atgaggtaaa gagaaaatga    6000
gcaaaagcac aaaacacgcta agtgccggcc gtccgagcgc acgcagcagc aaggctgcaa    6060
cgttggccag cctggcagac acgccagcca tgaagcgggt caactttcag ttgccggcgg    6120
aggatcacac caagctgaag atgtacgcgg tacgccaagg caagaccatt accgagctgc    6180
tatctgaata catcgcgcag ctaccagagt aaatgagcaa atgaataaat gagtagatga    6240
attttagcgg ctaaaggagg cggcatggaa aatcaagaac aaccaggcac cgacgccgtg    6300 gaatgccca tgtgtggagg aacgggcggt tggccaggcg taagcggctg ggttgtctgc    6360
cggccctgca atggcactgg aacccccaag cccgaggaat cggcgtgagc ggtcgcaaac    6420
catccggccc ggtacaaatc ggcgcggcgc tgggtgatga cctggtggag aagttgaagg    6480
ccgcgcaggc cgcccagcgg caacgcatcg aggcagaagc acgcccggt gaatcgtggc    6540 aagcggccgc tgatcgaatc cgcaaagaat cccggcaacc gccggcagcc ggtgcgccgt    6600
cgattaggaa gccgcccaag ggcgacgagc aaccagattt tttcgttccg atgctctatg    6660
acgtgggcac ccgcgatagt cgcagcatca tggacgtggc cgttttccgt ctgtcgaagc    6720
gtgaccgacg agctggcgag gtgatccgct acgagcttcc agacgggcac gtagaggttt    6780
ccgcagggcc ggccggcatg gccagtgtgt gggattacga cctggtactg atggcggttt    6840
cccatctaac cgaatccatg aaccgatacc gggaagggaa gggagacaag cccggccgcg    6900
tgttccgtcc acacgttgcg gacgtactca agttctgccg gcgagccgat ggcggaaagc    6960
agaaagacga cctggtagaa acctgcattc ggttaaacac cacgcacgtt gccatgcagc    7020
gtacgaagaa ggccaagaac ggccgcctgg tgacggtatc cgagggtgaa gccttgatta    7080
gccgctacaa gatcgtaaag agcgaaaccg ggcggccgga gtacatcgag atcgagctag    7140
ctgattggat gtaccgcgag atcacagaag gcaagaaccc ggacgtgctg acggttcacc    7200
ccgattactt tttgatcgat cccggcatcg gccgttttct ctaccgcctg cacgccgcg    7260 ccgcaggcaa ggcagaagcc agatggttgt tcaagacgat ctacgaacgc agtggcagcg    7320
ccggagagtt caagaagttc tgtttcaccg tgcgcaagct gatcgggtca aatgacctgc    7380
cggagtacga tttgaaggag gaggcggggc aggctggccc gatcctagtc atgcgctacc    7440
gcaacctgat cgagggcgaa gcatccgccg gttcctaatg tacggagcag atgctagggc    7500
aaattgccct agcaggggaa aaaggtcgaa aaggtctctt tcctgtggat agcacgtaca    7560
ttgggaaccc aaagccgtac attgggaacc ggaacccgta cattgggaac ccaaagccgt    7620
acattgggaa ccggtcacac atgtaagtga ctgatataaa agagaaaaaa ggcgattttt    7680
```

```
ccgcctaaaa ctctttaaaa cttattaaaa ctcttaaaac ccgcctggcc tgtgcataac   7740
tgtctggcca gcgcacagcc gaagagctgc aaaaagcgcc tacccttcgg tcgctgcgct   7800
ccctacgccc cgccgcttcg cgtcggccta tcgcggccgc tggccgctca aaaatggctg   7860
gcctacggcc aggcaatcta ccagggcgcg gacaagccgc gccgtcgcca ctcgaccgcc   7920
ggcgcccaca tcaaggcacc ctgcctcgcg cgtttcggtg atgacggtga aaacctctga   7980
cacatgcagc tcccggagac ggtcacagct tgtctgtaag cggatgccgg gagcagacaa   8040
gcccgtcagg gcgcgtcagc gggtgttggc ggtgtcggg gcgcagccat gacccagtca    8100
cgtagcgata gcggagtgta tactggctta actatgcggc atcagagcag attgtactga   8160
gagtgcacca tatgcggtgt gaaataccgc acagatgcgt aaggagaaaa taccgcatca   8220
ggcgctcttc cgcttcctcg ctcactgact cgctgcgctc ggtcgttcgg ctgcggcgag   8280
cggtatcagc tcactcaaag gcggtaatac ggttatccac agaatcaggg gataacgcag   8340
gaaagaacat gtgagcaaaa ggccagcaaa aggccaggaa ccgtaaaaag gccgcgttgc   8400
tggcgttttt ccataggctc cgcccccctg acgagcatca caaaaatcga cgctcaagtc   8460
agaggtggcg aaacccgaca ggactataaa gataccaggc gtttccccct ggaagctccc   8520
tcgtgcgctc tcctgttccg accctgccgc ttaccggata cctgtccgcc tttctccctt   8580
cgggaagcgt ggcgctttct catagctcac gctgtaggta tctcagttcg gtgtaggtcg   8640
ttcgctccaa gctgggctgt gtgcacgaac cccccgttca gcccgaccgc tgcgccttat   8700
ccggtaacta tcgtcttgag tccaacccgg taagacacga cttatcgcca ctggcagcag   8760
ccactggtaa caggattagc agagcgaggt atgtaggcgg tgctacagag ttcttgaagt   8820
ggtggcctaa ctacggctac actagaagga cagtatttgg tatctgcgct ctgctgaagc   8880
cagttacctt cggaaaaaga gttggtagct cttgatccgg caaacaaacc accgctggta   8940
gcggtggttt ttttgtttgc aagcagcaga ttacgcgcag aaaaaaagga tctcaagaag   9000
atcctttgat cttttctacg gggtctgacg ctcagtggaa cgaaaactca cgttaaggga   9060
ttttggtcat gagattatca aaaaggatct cacctagatc ccttttaaat taaaaatgaa   9120
gttttaaatc aatctaaagt atatatgagt aaacttggtc tgacagttac caatgcttaa   9180
tcagtgaggc acctatctca gcgatctgtc tatttcgttc atccatagtt gcctgactcc   9240
ccgtcgtgta gataactacg atacgggagg gcttaccatc tggccccagt gctgcaatga   9300
taccgcgaga cccacgctca ccggctccag atttatcagc aataaaccag ccagccggaa   9360
gggccgagcg cagaagtggt cctgcaactt tatccgcctc catccagtct attaattgtt   9420
gccgggaagc tagagtaagt agttcgccag ttaatagttt cgcaacgtt gttgccattg    9480 ctacaggcat cgtggtgtca cgctcgtcgt ttggtatggc ttcattcagc tccggttccc   9540
aacgatcaag gcgagttaca tgatccccca tgttgtgcaa aaaagcggtt agctccttcg   9600
gtcctccgat cgttgtcaga agtaagttgg ccgcagtgtt atcactcatg gttatggcag   9660
cactgcataa ttctcttact gtcatgccat ccgtaagatg cttttctgtg actggtgagt   9720
actcaaccaa gtcattctga gaatagtgta tgcggcgacc gagttgctct tgcccggcgt   9780
caacacggga taataccgcg ccacatagca gaactttaaa agtgctcatc attggaaaag   9840
acctgcaggg ggggggggc gctgaggtct gcctcgtgaa gaaggtgttg ctgactcata    9900
ccaggcctga atcgccccat catccagcca gaaagtgagg gagccacggt tgatgagagc   9960
tttgttgtag gtggaccagt tggtgatttt gaacttttgc tttgccacgg aacggtctgc  10020
gttgtcggga agatgcgtga tctgatcctt caactcagca aaagttcgat ttattcaaca  10080
```

```
aagccgccgt cccgtcaagt cagcgtaatg ctctgccagt gttacaacca attaaccaat   10140
tctgattaga aaaactcatc gagcatcaaa tgaaactgca atttattcat atcaggatta   10200
tcaataccat attttttgaaa aagccgtttc tgtaatgaag gagaaaactc accgaggcag   10260
ttccatagga tggcaagatc ctggtatcgg tctgcgattc cgactcgtcc aacatcaata   10320
caacctatta atttcccctc gtcaaaaata aggttatcaa gtgagaaatc accatgagtg   10380
acgactgaat ccggtgagaa tggcaaaagc ttatgcattt ctttccagac ttgttcaaca   10440
ggccagccat tacgctcgtc atcaaaatca ctcgcatcaa ccaaaccgtt attcattcgt   10500
gattgcgcct gagcgagacg aaatacgcga tcgctgttaa aaggacaatt acaaacagga   10560
atcgaatgca accggcgcag gaacactgcc agcgcatcaa caatattttc acctgaatca   10620
ggatattctt ctaatacctg gaatgctgtt ttcccgggga tcgcagtggt gagtaaccat   10680
gcatcatcag gagtacggat aaaatgcttg atggtcggaa gaggcataaa ttccgtcagc   10740
cagtttagtc tgaccatctc atctgtaaca tcattggcaa cgctacctt gccatgtttc    10800 agaaacaact ctggcgcatc gggcttccca tacaatcgat agattgtcgc acctgattgc   10860
ccgacattat cgcgagccca tttataccca tataaatcag catccatgtt ggaatttaat   10920
cgcggcctcg agcaagacgt ttcccgttga atatggctca taacacccct tgtattactg   10980
tttatgtaag cagacagttt tattgttcat gatgatatat ttttatcttg tgcaatgtaa   11040
catcagagat tttgagacac aacgtggctt tcccccccccc ccctgcaggt caattcggtc   11100
gatatggcta ttacgaagaa ggctcgtgcg cggagtcccg tgaactttcc cacgcaacaa   11160
gtgaaccgca ccgggtttgc cggaggccat ttcgttaaaa tgcgcagcca tggctgcttc   11220
gtccagcatg gcgtaatact gatcctcgtc ttcggctggc ggtatattgc cgatgggctt   11280
caaaagccgc cgtggttgaa ccagtctatc cattccaagg tagcgaactc gaccgcttcg   11340
aagctcctcc atggtccacg ccgatgaatg acctcggcct tgtaaagacc gttgatcgct   11400
tctgcgaggg cgttgtcgtg ctgtcgccga cgcttccgat agatggctcg atacctgctt   11460
ctgccaaccg ctcggaatag cgaaaggaca cgtattgaac accgcgatcc gagtgatgca   11520
ctaggccgcc atgagcggga cgccgatcat gatgagcctc ctcgagggca tcgaggacaa   11580
agcctgcatg tgctgtccgg ctcgcccgcc atccgacaat gcgacgggcg aagacgtcga   11640
tcacgaaggc cacgtagacg aagccctccc aagtggcgac ataagtacgg acatgcgcaa   11700
aggctttccc ggtttgtcgc tgatggtgca agagacgctg aagcgcgatc cgatgcgcag   11760
gcatctgttc gtcttccgcg gtcgtggcgg tggcctgatc aaggtcactc gccgaagagc   11820
tgcatgattg gctcgaaacc gagcggggga aattgtcgcg cagttctccc gtcgccgagg   11880
cgataaatta catgctcaag cgatgggatg gcattacgtc attcctcgat gacggcccga   11940
tttgcctgac gaacaatgct gccgaacgaa cgctcagagg ctatgtactc ggcaggaagt   12000
catggctgtt tgccggatcg gatcgttgtg ctgaacgtgc ggcgttcatg gcgacactga   12060
tcatgagcgc caagctcaat aacatcgatc cgcaggcctg gcttgccgac gtccgcgccg   12120
accttgcgga cgctccgatc agcaggcttg agcaacagct gccgtggaac tggacatcca   12180
agacactgag tgctcaggcg gcctgacctg cggccttcac cggatactta ccccattatc   12240
gcagattgcg atgaagcatc agcgtcattc agcaatcttg ccaaagtatg caggctcgcg   12300
agaatcgacg tgcgaaaccg gctggttgcg ccaaagatcc gcttgcggag cggtcgaaca   12360
ttcatgctgg gacttcaaga ggtcgagtag aggaagaacc ggaaaggttg caccggaaaa   12420
tatgcgttcc tttggagagc gcctcatgga cgtgaacaaa tcgcccggac caaggatgcc   12480
```

```
acggatacaa aagctcgcga agctcggtcc cgtgggtgtt ctgtcgtctc gttgtacaac    12540
gaaatccatt cccattccgc gctcaagatg gcttcccctc ggcagttcat cagggctaaa    12600
tcaatctagc cgacttgtcc ggtgaaatgg gctgcactcc aacagaaaca atcaaacaaa    12660
catacacagc gacttattca cacgagctca aattacaacg gtatatatcc tgccagtcag    12720
catcatcaca ccaaaagtta ggcccgaata gtttgaaatt agaaagctcg caattgaggt    12780
ctacaggcca aattcgctct tagccgtaca atattactca ccggtgcgat gcccccatc    12840 gtaggtgaag gtggaaatta atgatccatc ttgagaccac aggcccacaa cagctaccag    12900
tttcctcaag ggtccaccaa aaacgtaagc gcttacgtac atggtcgata agaaaaggca    12960
atttgtagat gttaacatcc aacgtcgctt tcagggatcg atccaatacg caaaccgcct    13020
ctccccgcgc gttggccgat tcattaatgc agctggcacg acaggtttcc cgactggaaa    13080
gcgggcagtg agcgcaacgc aattaatgtg agttagctca ctcattaggc acccaggct    13140 ttacactttta tgcttccggc tcgtatgttg tgtggaattg tgagcggata caatttcac    13200 acaggaaaca gctatgacca tgattacgcc aagcttgcat gcctgcaggt cgactctaga    13260
ggatctgg                                                            13268

<210> SEQ ID NO 28
<211> LENGTH: 20921
<212> TYPE: DNA
<213> ORGANISM: Artificial Sequence
<220> FEATURE:
<223> OTHER INFORMATION: vector pKR1223
<220> FEATURE:
<221> NAME/KEY: misc_feature
<222> LOCATION: (15083)..(15083)
<223> OTHER INFORMATION: n is a, c, g, or t

<400> SEQUENCE: 28
cgcgccagat cctctagagt cgacctgcag gcatgcaagc ttggcgtaat catggtcata      60
gctgtttcct gtgtgaaatt gttatccgct cacaattcca cacaacatac gagccggaag    120
cataaagtgt aaagcctggg gtgcctaatg agtgagctaa ctcacattaa ttgcgttgcg    180
ctcactgccc gctttccagt cgggaaacct gtcgtgccag ctgcattaat gaatcggcca    240
acgcgcgggg agaggcggtt tgcgtattgg atcgatccct gaaagcgacg ttggatgtta    300
acatctacaa attgcctttt cttatcgacc atgtacgtaa gcgcttacgt ttttggtgga    360
cccttgagga aactggtagc tgttgtgggc ctgtggtctc aagatggatc attaatttcc    420
accttcacct acgatggggg gcatcgcacc ggtgagtaat attgtacggc taagagcgaa    480
tttggcctgt agacctcaat tgcgagcttt ctaatttcaa actattcggg cctaactttt    540
ggtgtgatga tgctgactgg caggatatat accgttgtaa tttgagctcg tgtgaataag    600
tcgctgtgta tgtttgtttg attgtttctg ttggagtgca gcccatttca ccggacaagt    660
cggctagatt gatttagccc tgatgaactg ccagggggaa gccatcttga gcgcggaatg    720
ggaatggatt tcgttgtaca acgagacgac agaacaccca cgggaccgag cttcgcgagc    780
ttttgtatcc gtggcatcct tggtccggc gatttgttca cgtccatgag gcgctctcca    840
aaggaacgca tattttccgg tgcaaccttt ccggttcttc ctctactcga cctcttgaag    900
tcccagcatg aatgttcgac cgctccgcaa gcggatcttt ggcgcaacca gccggtttcg    960
cacgtcgatt ctcgcgagcc tgcatacttt ggcaagattg ctgaatgacg ctgatgcttc   1020
atcgcaatct gcgataatgg ggtaagtatc cggtgaaggc cgcaggtcag gccgcctgag   1080
cactcagtgt cttggatgtc cagttccacg gcagctgttg ctcaagcctg ctgatcggag   1140
```

```
cgtccgcaag gtcggcgcgg acgtcggcaa gccaggcctg cggatcgatg ttattgagct    1200
tggcgctcat gatcagtgtc gccatgaacg ccgcacgttc agcacaacga tccgatccgg    1260
caaacagcca tgacttcctg ccagtacat  agcctctgag cgttcgttcg gcagcattgt    1320
tcgtcaggca aatcgggccg tcatcgagga atgacgtaat gccatcccat cgcttgagca    1380
tgtaatttat cgcctcggcg acgggagaac tgcgcgacaa tttccccgc  tcggtttcga    1440
gccaatcatg cagctcttcg gcgagtgacc ttgatcaggc caccgccacg accgcggaag    1500
acgaacagat gcctgcgcat cggatcgcgc ttcagcgtct cttgcaccat cagcgacaaa    1560
ccgggaaagc ctttgcgcat gtccgtactt atgtcgccac ttgggagggc ttcgtctacg    1620
tggccttcgt gatcgacgtc ttcgcccgtc gcattgtcgg atggcgggcg agccggacag    1680
cacatgcagg ctttgtcctc gatgccctcg aggaggctca tcatgatcgg cgtcccgctc    1740
atggcggcct agtgcatcac tcggatcgcg gtgttcaata cgtgtccttt cgctattccg    1800
agcggttggc agaagcaggt atcgagccat ctatcggaag cgtcggcgac agcacgacaa    1860
cgccctcgca gaagcgatca acggtctta  caaggccgag gtcattcatc ggcgtggacc    1920
atggaggagc ttcgaagcgg tcgagttcgc taccttggaa tggatagact ggttcaacca    1980
cggcggcttt tgaagcccat cggcaatata ccgccagccg aagacgagga tcagtattac    2040
gccatgctgg acgaagcagc catggctgcg cattttaacg aaatggcctc cggcaaaccc    2100
ggtgcggttc acttgttgcg tgggaaagtt cacgggactc cgcgcacgag ccttcttcgt    2160
aatagccata tcgaccgaat tgacctgcag gggggggggg gaaagccacg ttgtgtctca    2220
aaatctctga tgttacattg cacaagataa aaatatatca tcatgaacaa taaaactgtc    2280
tgcttacata aacagtaata caaggggtgt tatgagccat attcaacggg aaacgtcttg    2340
ctcgaggccg cgattaaatt ccaacatgga tgctgattta tatgggtata aatgggctcg    2400
cgataatgtc gggcaatcag gtgcgacaat ctatcgattg tatgggaagc ccgatgcgcc    2460
agagttgttt ctgaaacatg gcaaaggtag cgttgccaat gatgttacag atgagatggt    2520
cagactaaac tggctgacgg aatttatgcc tcttccgacc atcaagcatt ttatccgtac    2580
tcctgatgat gcatggttac tcaccactgc gatccccggg aaaacagcat ccaggtatt     2640
agaagaatat cctgattcag gtgaaaatat tgttgatgcg ctggcagtgt tcctgcgccg    2700
gttgcattcg attcctgttt gtaattgtcc ttttaacagc gatcgcgtat ttcgtctcgc    2760
tcaggcgcaa tcacgaatga ataacggttt ggttgatgcg agtgattttg atgacgagcg    2820
taatggctgg cctgttgaac aagtctggaa agaaatgcat aagcttttgc cattctcacc    2880
ggattcagtc gtcactcatg gtgatttctc acttgataac cttattttg  acgaggggaa    2940
attaataggt tgtattgatg ttggacgagt cggaatcgca gaccgatacc aggatcttgc    3000
catcctatgg aactgcctcg gtgagttttc tccttcatta cagaaacggc ttttcaaaa     3060
atatggtatt gataatcctg atatgaataa attgcagttt catttgatgc tcgatgagtt    3120
tttctaatca gaattggtta attggttgta acactggcag agcattacgc tgacttgacg    3180
ggacggcggc tttgttgaat aaatcgaact tttgctgagt tgaaggatca gatcacgcat    3240
cttcccgaca acgcagaccg ttccgtggca aagcaaaagt tcaaaatcac caactggtcc    3300
acctacaaca aagctctcat caaccgtggc tccctcactt tctggctgga tgatgggcg     3360
attcaggcct ggtatgagtc agcaacacct tcttcacgag gcagacctca gcgcccccc     3420
ccccctgcag gtcttttcca atgatgagca cttttaaagt tctgctatgt ggcgcggtat    3480
tatcccgtgt tgacgccggg caagagcaac tcggtcgccg catacactat tctcagaatg    3540
```

```
acttggttga gtactcacca gtcacagaaa agcatcttac ggatggcatg acagtaagag    3600
aattatgcag tgctgccata accatgagtg ataacactgc ggccaactta cttctgacaa    3660
cgatcggagg accgaaggag ctaaccgctt ttttgcacaa catgggggat catgtaactc    3720
gccttgatcg ttgggaaccg gagctgaatg aagccatacc aaacgacgag cgtgacacca    3780
cgatgcctgt agcaatggca acaacgttgc gcaaactatt aactggcgaa ctacttactc    3840
tagcttcccg gcaacaatta atagactgga tggaggcgga taaagttgca ggaccacttc    3900
tgcgctcggc ccttccggct ggctggttta ttgctgataa atctggagcc ggtgagcgtg    3960
ggtctcgcgg tatcattgca gcactggggc cagatggtaa gccctcccgt atcgtagtta    4020
tctacacgac ggggagtcag gcaactatgg atgaacgaaa tagacagatc gctgagatag    4080
gtgcctcact gattaagcat tggtaactgt cagaccaagt ttactcatat atactttaga    4140
ttgatttaaa acttcatttt taatttaaaa ggatctaggt gaagatcctt tttgataatc    4200
tcatgaccaa aatcccttaa cgtgagtttt cgttccactg agcgtcagac cccgtagaaa    4260
agatcaaagg atcttcttga gatccttttt ttctgcgcgt aatctgctgc ttgcaaacaa    4320
aaaaaccacc gctaccagcg gtggtttgtt tgccggatca agagctacca actcttttc    4380 cgaaggtaac tggcttcagc agagcgcaga taccaaatac tgtccttcta gtgtagccgt    4440
agttaggcca ccacttcaag aactctgtag caccgcctac atacctcgct ctgctaatcc    4500
tgttaccagt ggctgctgcc agtggcgata agtcgtgtct taccgggttg gactcaagac    4560
gatagttacc ggataaggcg cagcggtcgg gctgaacggg gggttcgtgc acacagccca    4620
gcttggagcg aacgacctac accgaactga gatacctaca gcgtgagcta tgagaaagcg    4680
ccacgcttcc cgaagggaga aaggcggaca ggtatccggt aagcggcagg gtcggaacag    4740
gagagcgcac gagggagctt ccaggggggaa acgcctggta tctttatagt cctgtcgggt    4800
ttcgccacct ctgacttgag cgtcgatttt tgtgatgctc gtcagggggg cggagcctat    4860
ggaaaaacgc cagcaacgcg gcctttttac ggttcctggc cttttgctgg ccttttgctc    4920
acatgttctt tcctgcgtta tcccctgatt ctgtggataa ccgtattacc gcctttgagt    4980
gagctgatac cgctcgccgc agccgaacga ccgagcgcag cgagtcagtg agcgaggaag    5040
cggaagagcg cctgatgcgg tattttctcc ttacgcatct gtgcggtatt tcacaccgca    5100
tatggtgcac tctcagtaca atctgctctg atgccgcata gttaagccag tatacactcc    5160
gctatcgcta cgtgactggg tcatggctgc gccccgacac ccgccaacac ccgctgacgc    5220
gccctgacgg gcttgtctgc tcccggcatc cgcttacaga caagctgtga ccgtctccgg    5280
gagctgcatg tgtcagaggt tttcaccgtc atcaccgaaa cgcgcgaggc agggtgcctt    5340
gatgtgggcg ccggcggtcg agtggcgacg gcgcggcttg tccgcgccct ggtagattgc    5400
ctggccgtag gccagccatt tttgagcggc agcggccgc gataggccga cgcgaagcgg    5460
cggggcgtag ggagcgcagc gaccgaaggg taggcgcttt ttgcagctct tcggctgtgc    5520
gctggccaga cagttatgca caggccaggc gggttttaag agttttaata agttttaaag    5580
agttttaggc ggaaaaatcg cctttttttct cttttatatc agtcacttac atgtgtgacc    5640
ggttcccaat gtacggcttt gggttcccaa tgtacgggtt ccggttccca atgtacggct    5700
ttgggttccc aatgtacgtg ctatccacag gaaagagacc ttttcgacct tttccctg    5760 ctagggcaat tgccctagc atctgctccg tacattagga accggcggat gcttcgccct    5820
cgatcaggtt gcggtagcgc atgactagga tcggccagc ctgccccgcc tcctccttca    5880
aatcgtactc cggcaggtca tttgacccga tcagcttgcg cacggtgaaa cagaacttct    5940
```

```
tgaactctcc ggcgctgcca ctgcgttcgt agatcgtctt gaacaaccat ctggcttctg    6000
ccttgcctgc ggcgcggcgt gccaggcggt agagaaaacg gccgatgccg ggatcgatca    6060
aaaagtaatc ggggtgaacc gtcagcacgt ccgggttctt gccttctgtg atctcgcggt    6120
acatccaatc agctagctcg atctcgatgt actccggccg cccggtttcg ctctttacga    6180
tcttgtagcg gctaatcaag gcttcaccct cggataccgt caccaggcgg ccgttcttgg    6240
ccttcttcgt acgctgcatg gcaacgtgcg tggtgtttaa ccgaatgcag gtttctacca    6300
ggtcgtcttt ctgctttccg ccatcggctc gccggcagaa cttgagtacg tccgcaacgt    6360
gtggacggaa cacgcggccg ggcttgtctc ccttcccttc ccggtatcgg ttcatggatt    6420
cggttagatg ggaaaccgcc atcagtacca ggtcgtaatc ccacacactg gccatgccgg    6480
ccggccctgc ggaaacctct acgtgcccgt ctggaagctc gtagcggatc acctcgccag    6540
ctcgtcggtc acgcttcgac agacggaaaa cggccacgtc catgatgctg cgactatcgc    6600
gggtgcccac gtcatagagc atcggaacga aaaaatctgg ttgctcgtcg cccttgggcg    6660
gcttcctaat cgacggcgca ccggctgccg gcggttgccg ggattctttg cggattcgat    6720
cagcggccgc ttgccacgat tcaccggggc gtgcttctgc ctcgatgcgt tgccgctggg    6780
cggcctgcgc ggccttcaac ttctccacca ggtcatcacc cagcgccgcg ccgatttgta    6840
ccgggccgga tggtttgcga ccgctcacgc cgattcctcg gcttgggggg ttccagtgcc    6900
attgcagggc cggcagacaa cccagccgct tacgcctggc caaccgcccg ttcctccaca    6960 catgggcat tccacggcgt cggtgcctgg ttgttcttga ttttccatgc cgcctccttt    7020
agccgctaaa attcatctac tcatttattc atttgctcat ttactctggt agctgcgcga    7080
tgtattcaga tagcagctcg gtaatggtct tgccttggcg taccgcgtac atcttcagct    7140
tggtgtgatc ctccgccggc aactgaaagt tgacccgctt catggctggc gtgtctgcca    7200
ggctggccaa cgttgcagcc ttgctgctgc gtgcgctcgg acggccggca cttagcgtgt    7260
ttgtgctttt gctcattttc tctttacctc attaactcaa atgagttttg atttaatttc    7320
agcggccagc gcctggacct cgcgggcagc gtcgccctcg ggttctgatt caagaacggt    7380
tgtgccggcg gcggcagtgc ctgggtagct cacgcgctgc gtgatacggg actcaagaat    7440
gggcagctcg tacccggcca gcgcctcggc aacctcaccg ccgatgcgcg tgcctttgat    7500
cgcccgcgac acgacaaagg ccgcttgtag ccttccatcc gtgacctcaa tgcgctgctt    7560
aaccagctcc accaggtcgg cggtggccca tatgtcgtaa gggcttggct gcaccggaat    7620
cagcacgaag tcggctgcct tgatcgcgga cacagccaag tccgccgcct ggggcgctcc    7680
gtcgatcact acgaagtcgc gccggccgat ggccttcacg tcgcggtcaa tcgtcgggcg    7740
gtcgatgccg acaacggtta gcggttgatc ttcccgcacg gccgcccaat cgcgggcact    7800
gccctgggga tcggaatcga ctaacagaac atcggcccg gcgagttgca gggcgcgggc    7860
tagatgggtt gcgatggtcg tcttgcctga cccgcctttc tggttaagta cagcgataac    7920
ttcatgcgtt cccttgcgta tttgtttatt tactcatcgc atcatatacg cagcgaccgc    7980
atgacgcaag ctgttttact caaatacaca tcaccttttt agacggcggc gctcggtttc    8040
ttcagcggcc aagctggccg gccaggccgc cagcttggca tcagacaaac cggccaggat    8100
ttcatgcagc cgcacggttg agacgtgcgc gggcggctcg aacacgtacc cggccgcgat    8160
catctccgcc tcgatctctt cggtaatgaa aaacggttcg tcctggccgt cctggtgcgg    8220
tttcatgctt gttcctcttg gcgttcattc tcggcggccg ccaggcgtc ggcctcggtc    8280 aatgcgtcct cacggaaggc accgcgccgc ctggcctcgg tgggcgtcac ttcctcgctg    8340
```

```
cgctcaagtg cgcggtacag ggtcgagcga tgcacgccaa gcagtgcagc cgcctctttc   8400
acggtgcggc cttcctggtc gatcagctcg cgggcgtgcg cgatctgtgc cggggtgagg   8460
gtagggcggg ggccaaactt cacgcctcgg gccttggcgg cctcgcgccc gctccgggtg   8520
cggtcgatga ttagggaacg ctcgaactcg gcaatgccgg cgaacacggt caacaccatg   8580
cggccggccg gcgtggtggt gtcggcccac ggctctgcca ggctacgcag gcccgcgccg   8640
gcctcctgga tgcgctcggc aatgtccagt aggtcgcggg tgctgcgggc caggcggtct   8700
agcctggtca ctgtcacaac gtcgccaggg cgtaggtggt caagcatcct ggccagctcc   8760
gggcggtcgc gcctggtgcc ggtgatcttc tcggaaaaca gcttggtgca gccggccgcg   8820
tgcagttcgg cccgttggtt ggtcaagtcc tggtcgtcgg tgctgacgcg gcatagccc    8880
agcaggccag cggcggcgct cttgttcatg gcgtaatgtc tccggttcta gtcgcaagta   8940
ttctacttta tgcgactaaa acacgcgaca agaaaacgcc aggaaaaggg cagggcggca   9000
gcctgtcgcg taacttagga cttgtgcgac atgtcgtttt cagaagacgg ctgcactgaa   9060
cgtcagaagc cgactgcact atagcagcgg aggggttgga ccacaggacg ggtgtggtcg   9120
ccatgatcgc gtagtcgata gtggctccaa gtagcgaagc gagcaggact gggcggcggc   9180
caaagcggtc ggacagtgct ccgagaacgg gtgcgcatag aaattgcatc aacgcatata   9240
gcgctagcag cacgccatag tgactggcga tgctgtcgga atggacgata tcccgcaaga   9300
ggcccggcag taccggcata accaagccta tgcctacagc atccagggtg acggtgccga   9360
ggatgacgat gagcgcattg ttagatttca tacacggtgc ctgactgcgt tagcaattta   9420
actgtgataa actaccgcat taaagctagc ttgcttggtc gttccgcgtg aacgtcggct   9480
cgattgtacc tgcgttcaaa tactttgcga tcgtgttgcg cgcctgcccg gtgcgtcggc   9540
tgatctcacg gatcgactgc ttctctcgca acgccatccg acggatgatg tttaaaagtc   9600
ccatgtggat cactccgttg ccccgtcgct caccgtgttg gggggaaggt gcacatggct   9660
cagttctcaa tggaaattat ctgcctaacc ggctcagttc tgcgtagaaa ccaacatgca   9720
agctccaccg ggtgcaaagc ggcagcggcg gcaggatata ttcaattgta aatggcttca   9780
tgtccgggaa atctacatgg atcagcaatg agtatgatgg tcaatatgga gaaaagaaa    9840
gagtaattac caattttttt tcaattcaaa aatgtagatg tccgcagcgt tattataaaa   9900
tgaaagtaca ttttgataaa acgacaaatt acgatccgtc gtatttatag gcgaaagcaa   9960
taaacaaatt attctaattc ggaaatcttt atttcgacgt gtctacattc acgtccaaat  10020
gggggcttag atgagaaact tcacgatcga tgccttgatt tcgccattcc cagatcccaa  10080
tttcatcttc agattggtct gagattatgc gaaaatatac actcatatac ataaatactg  10140
acagtttgag ctaccaattc agtgtagccc attacctcac ataattcact caaatgctag  10200
gcagtctgtc aactcggcgt caatttgtcg gccactatac gatagttgcg caaatttttca  10260
aagtcctggc ctaacatcac acctctgtcg gcggcgggtc ccatttgtga taaatccacc  10320
atatcgaatt aattcagact cctttgcccc agagatcaca atggacgact tcctctatct  10380
ctacgatcta gtcaggaagt tcgacggaga aggtgacgat accatgttca ccactgataa  10440
tgagaagatt agccttttca atttcagaaa gaatgctaac ccacagatgg ttagagaggc  10500
ttacgcagca ggtctcatca agacgatcta cccgagcaat aatctccagg agatcaaata  10560
ccttcccaag aaggttaaag atgcagtcaa aagattcagg actaactgca tcaagaacac  10620
agagaaagat atatttctca agatcagaag tactattcca gtatggacga ttcaaggctt  10680
gcttcacaaa ccaaggcaag taatagagat tggagtctct aaaaaggtag ttcccactga  10740
```

```
atcaaaggcc atggagtcaa agattcaaat agaggaccta acagaactcg ccgtaaagac    10800
tggcgaacag ttcatacaga gtctcttacg actcaatgac aagaagaaaa tcttcgtcaa    10860
catggtggag cacgcacagc ttgtctactc caaaaatatc aaagatacag tctcagaaga    10920
ccaaagggca attgagactt tcaacaaag ggtaatatcc ggaaacctcc tcggattcca    10980
ttgcccagct atctgtcact ttattgtgaa gatagtggaa aaggaaggtg gctcctacaa    11040
atgccatcat tgcgataaag gaaaggccat cgttgaagat gcctctgccg acagtggtcc    11100
caaagatgga cccccaccca cgaggagcat cgtggaaaaa gaagacgttc caaccacgtc    11160
ttcaaagcaa gtggattgat gtgatatctc cactgacgta agggatgacg cacaatccca    11220
ctatccttcg caagaccctt cctctatata aggaagttca tttcatttgg agaggacacg    11280
ctgaaatcac cagtctccaa gcttgcgggg atcgtttcgc atgattgaac aagatggatt    11340
gcacgcaggt tctccggccg cttggtggga gaggctattc ggctatgact gggcacaaca    11400
gacaatcggc tgctctgatg ccgccgtgtt ccggctgtca gcgcagggc gcccggttct    11460 ttttgtcaag accgacctgt ccggtgccct gaatgaactg caggacgagg cagcgcggct    11520
atcgtggctg gccacgacgg cgttccttg cgcagctgtg ctcgacgttg tcactgaagc    11580
gggaagggac tggctgctat tgggcgaagt gccggggcag atctcctgt catctcacct    11640 tgctcctgcc gagaaagtat ccatcatggc tgatgcaatg cggcggctgc atacgcttga    11700
tccggctacc tgcccattcg accaccaagc gaaacatcgc atcgagcgag cacgtactcg    11760
gatggaagcc ggtcttgtcg atcaggatga tctggacgaa gagcatcagg gctcgcgcc    11820 agccgaactg ttcgccaggc tcaaggcgcg catgcccgac ggcgaggatc tcgtcgtgac    11880
ccatggcgat gcctgcttgc cgaatatcat ggtggaaaat ggccgctttt ctggattcat    11940
cgactgtggc cggctgggtg tggcggaccg ctatcaggac atagcgttgg ctacccgtga    12000
tattgctgaa gagcttggcg gcgaatgggc tgaccgcttc ctcgtgcttt acggtatcgc    12060
cgctcccgat tcgcagcgca tcgccttcta tcgccttctt gacgagttct tctgagcggg    12120
actctggggt tcgaaatgac cgaccaagcg acgcccaacc tgccatcacg agatttcgat    12180
tccaccgccg ccttctatga aaggttgggc ttcggaatcg ttttccggga cgccggctgg    12240
atgatcctcc agcgcgggga tctcatgctg gagttcttcg cccaccccgg atcgatccaa    12300
cacttacgtt tgcaacgtcc aagagcaaat agaccacgaa cgccggaagg ttgccgcagc    12360
gtgtggattg cgtctcaatt ctctcttgca ggaatgcaat gatgaatatg atactgacta    12420
tgaaactttg agggaatact gcctagcacc gtcacctcat aacgtgcatc atgcatgccc    12480
tgacaacatg gaacatcgct atttttctga agaattatgc tcgttggagg atgtcgcggc    12540
aattgcagct attgccaaca tcgaactacc cctcacgcat gcattcatca atattattca    12600
tgcggggaaa ggcaagatta tccaactgg caaatcatcc agcgtgattg gtaacttcag    12660
ttccagcgac ttgattcgtt ttggtgctac ccacgttttc aataaggacg agatggtgga    12720
gtaaagaagg agtgcgtcga agcagatcgt tcaaacattt ggcaataaag tttcttaaga    12780
ttgaatcctg ttgccggtct tgcgatgatt atcatataat ttctgttgaa ttacgttaag    12840
catgtaataa ttaacatgta atgcatgacg ttatttatga gatgggtttt tatgattaga    12900
gtcccgcaat tatacattta atacgcgata gaaaacaaaa tatagcgcgc aaactaggat    12960
aaattatcgc gcgcggtgtc atctatgtta ctagatcgat caaacttcgg tactgtgtaa    13020
tgacgatgag caatcgagag gctgactaac aaaaggtaca tcgcgatgga tcgatccatt    13080
cgccattcag gctgcgcaac tgttgggaag ggcgatcggt gcgggcctct tcgctattac    13140
```

```
gccagctggc gaaaggggga tgtgctgcaa ggcgattaag ttgggtaacg ccagggtttt   13200
cccagtcacg acgttgtaaa acgacggcca gtgaattcct gcagcccggg ggatccgccc   13260
actcgaggcg cgccgtcgac ggatataatg agccgtaaac aaagatgatt aagtagtaat   13320
taatacgtac tagtaaaagt ggcaaaagat aacgagaaag aaccaatttc tttgcattcg   13380
gccttagcgg aaggcatata taagctttga ttattttatt tagtgtaatg atttcgtaca   13440
accaaagcat ttatttagta ctctcacact tgtgtcgcgg ccggccgcta caggaacagg   13500
tggtggcggc cctcggcgcg ctcgtactgc tccacgatgg tgtagtcctc gttgtgggag   13560
gtgatgtcca gcttggagtc cacgtagtag tagccgggca gctgcacggg cttcttggcc   13620
atgtagatgg acttgaactc caccaggtag tggccgccgt ccttcagctt cagggccttg   13680
tggatctcgc ccttcagcac gccgtcgcgg gggtacaggc gctcggtgga ggcctcccag   13740
cccatagtct tcttctgcat tacggggccg tcggagggga agttcacgcc gatgaacttc   13800
accttgtaga tgaaggagcc gtcctgcagg gaggagtcct gggtcacggt caccacgccg   13860
ccgtcctcga agttcatcac gcgctcccac ttgaagccct cggggaagga cagcttcttg   13920
tagtcgggga tgtcggcggg gtgcttcacg tacaccttgg agccgtactg gaactggggg   13980
gacaggatgt cccaggcgaa gggcagggtg ccgcccttgg tcaccttcag cttggcggtc   14040
tgggtgccct cgtaggggcg gccctcgccc tcgccctcga tctcgaactc gtggccgttc   14100
acggagccct ccatgcgcac cttgaagcgc atgaactcct tgatgacgtc ctcggaggag   14160
gccatgggcc gcttgggggg ctatggaaga ctttcttagt tagttgtgtg aataagcaat   14220
gttgggagaa tcgggactac ttataggata ggaataaaac agaaagtat taagtgctaa   14280 tgaaatattt agactgataa ttaaaatctt cacgtatgtc cacttgatat aaaaacgtca   14340
ggaataaagg aagtacagta gaatttaaag gtactctttt tatatatacc cgtgttctct   14400
ttttggctag ctagttgcat aaaaaataat ctatatttt atcattattt taaatatctt   14460
atgagatggt aaatatttat cataattttt tttactatta tttattattt gtgtgtgtaa   14520
tacatataga agttaattac aaattttatt tactttttca ttattttgat atgattcacc   14580 attaattag tgttattatt tataatagtt cattttaatc tttttgtata tattatgcgt   14640
gcagtacttt tttcctacat ataactacta ttacatttta tttatataat attttttatta  14700 atgaattttc gtgataatat gtaatattgt tcattattat ttcagatttt ttaaaaatat   14760
ttgtgttatt atttatgaaa tatgtaattt ttttagtatt tgattttatg atgataaagt   14820
gttctaaatt caaagaagg gggaaagcgt aaacattaaa aaacgtcatc aaacaaaaac    14880
aaaatcttgt taataaagat aaaactgttt gttttgatca ctgttatttc gtaatataaa   14940
aacattattt atatttatat tgttgacaac caaatttgcc tatcaaatct aaccaatata   15000
atgcatgcgt ggcaggtaat gtactaccat gaacttaagt catgacataa taaaccgtga   15060
atctgaccaa tgcatgtacc tanctaaatt gtatttgtga cacgaagcaa atgattcaat   15120
tcacaatgga gatgggaaac aaataatgaa gaacccagaa ctaagaaagc ttttctgaaa   15180
aataaaataa aggcaatgtc aaaagtatac tgcatcatca gtccagaaag cacatgatat   15240 tttttttatca gtatcaatgc agctagtttt attttacaat atcgatatag ctagtttaaa   15300
tatattgcag ctagatttat aaatatttgt gttattattt atcatttgtg taatcctgtt   15360
tttagtattt tagtttatat atgatgataa tgtattccaa atttaaaaga agggaaataa   15420
atttaaacaa gaaaaaaagt catcaaacaa aaaacaaatg aaagggtgga aagatgttac   15480
catgtaatgt gaatgttaca gtatttcttt tattatagag ttaacaaatt aactaatatg   15540
```

```
attttgttaa taatgataaa atattttttt tattattatt tcataatata aaaatagttt   15600
acttaatata aaaaaaattc tatcgttcac aacaaagttg gccacctaat ttaaccatgc   15660
atgtacccat ggaccatatt aggtaaccat caaacctgat gaagagataa agagatgaag   15720
acttaagtca taacacaaaa ccataaaaaa caaaaataca atcaaccgtc aatctgacca   15780
atgcatgaaa aagctgcaat agtgagtggc gacacaaagc acatgatttt cttacaacgg   15840
agataaaacc aaaaaaatat ttcatgaaca acctagaaca aataaagctt ttatataata   15900
aatatataaa taaataaagg ctatggaata atatacttca atatatttgg attaaataaa   15960
ttgttggcgg ggttgatata tttatacaca cctaaagtca cttcaatctc attttcactt   16020 aactttatt ttttttttct tttattttat cataaagaga atattgataa tatacttttt   16080
aacatatttt tatgacattt tttattggtg aaaacttatt aaaaatcata aattttgtaa   16140
gttagattta tttaaagagt tcctcttctt attttaaatt ttttaataaa ttttaaata   16200 actaaaattt gtgttaaaaa tgttaaaaaa gtgtgttatt aacccttctc ttcgaggatc   16260
cgtaccgagc tcggatccac tagtaacggc cgccagtgtg ctggaattca ggtcctgcag   16320
gtctactctt tacatgttct ttactccgtc tcaaaatttc ctttttttgt tggctctctc   16380
cgaacgagtt ggagaaatcg ttaaccctaa tcgaagatct agattcctct acatacgttt   16440
gatctctctc tcagtatgga ttacaaagcg ccaaggagat actactcaca cggagttgtt   16500
gcgagacagc aagatttcgc aacagatata gttacgagaa gaagacctta tgtcccttac   16560
gaccgtccaa ataagttttc aaggagtctg gtttggacgt caaagagta caaatcaccc   16620 gagggcaata atatgccaag gaccaatgat gtgtcaccga aaccaccagt tttaggtttg   16680
gcgaggaaga atgctgcttg tgggccaatg agatcttcta gtctcagaaa atgggtatgt   16740
aagtattgga aagatggaaa gtgcaagagg ggtgagcagt gccagttctt acactcttgg   16800
tcttgtttcc ctggattggc catggtagct tctcttgaag ggcacaataa ggaactaaag   16860
gggatcgctc tccctgaggg ttcagataaa ctcttttcag tcagtattga tggtacattg   16920
cgagtttggg actgcaattc tggtcagtgt gtacattcca tcaaccttga cgcagaagca   16980
gggtctctaa tcagtgaagg cccttgggtt ttccttggct tgccaaacgc tataaaggct   17040
tttaacgttc aaaccagtca agatttgcat cttcaagcag caggggtggt tggtcaggtg   17100
aatgcaatga ctattgcaaa cggaatgctt tttgctggaa caagttctgg tagtatctta   17160
gtctggaaag ctactacaga ctctgagtct gatccattca aatacttgac atctcttgag   17220
ggacatagtg gtgaagtcac ttgttttgct gttggaggtc aaatgctata ctctggttct   17280
gtcgataaaa caatcaagat gtgggatctc aacaccctgc aatgtataat gaccctgaag   17340
caacataccg gcactgtcac ttcactctta tgttgggata atgtttgat atcgtcttcc   17400 ttggatggga ccataaaagt ttgggcttat tctgaaaacg gaatcttgaa agttgttcaa   17460
actcgcagac aagaacagag tagtgttcat gctctttctg gtatgcatga tgcagaagcc   17520
aaaccgataa tattctgctc ttaccaaaac ggaaccgttg gcattttcga cctaccatct   17580
tttcaagaaa gaggaaggat gttctctacg cacacgatcg ccacactcac aattggtcct   17640
caaggattgt tattcagtgg agacgagagt ggtaacttgc gtgtatggac cttagctgct   17700
ggcaacaaag tttagtcttt tcgactaaag aattctgatt taattttgtg gtttatatgt   17760
tgagttaact gttaagagag ttttattttg taataggtgt atcagtcaat aaacaatctt   17820
tgtatcaacc aaatgtaatt tttctcgtta attcgatttc agagttttta ctttaagata   17880
aacaaactct ttcacacatc atttaatgaa agtggagaag cttaaaaaac aaacaaagaa   17940
```

-continued

```
actgatccat ttttggcggg tcttcttcta ctcttattca tatgtgttaa cgaactatag    18000
cgtaaaattc agagcaagcg atctccgatt tgaacgtggc tatcaccgga ggcccaccac    18060
tacgggcgat acgctctaag tgaggattaa agtgctctgg tggtgacgtt gaagaaactc    18120
gcccatggtt tttgttatct ctgcagccaa gtgtcgttct ttcttcgcca cttctcatca    18180
agctacagtg aatttaaaaa tggcgtcttt ctttgatctc gtatacataa gctggattgg    18240
tttcttaaac aaattcctct cctttgggt cttctgggtt tgccttgtaa gtgtttgtgt    18300
ttttgcctct gagaaaaaat cgcggccgca tggagagatc tcaacggcag tctcctccgc    18360
caccgtcgcc gtcctcctcc tcgtcctccg tctccgcgga caccgtcctc gtccctcccg    18420
gaaagaggcg gagggcggcg acggccaagg ccggcgccga gcctaataag aggatccgca    18480 aggacccgc cgccgccgcc gcggggaaga ggagctccgt ctacagggga gtcaccaggc    18540
acaggtggac gggcaggttc gaggcgcatc tctgggacaa gcactgcctc gccgcgctcc    18600
acaacaagaa gaaaggcagg caagtctacc tgggggcgta tgacagcgag gaggcagctg    18660
ctcgtgccta tgacctcgca gctctcaagt actgggtcc tgagactctg ctcaacttcc    18720
ctgtggagga ttactccagc gagatgccgg agatggaggc cgtgtcccgg gaggagtacc    18780
tggcctccct ccgccgcagg agcagcggct tctccagggg cgtctccaag tacagaggcg    18840
tcgccaggca tcaccacaac gggaggtggg aggcacggat tgggcgagtc tttgggaaca    18900
agtacctcta cttgggaaca tttgacactc aagaagaggc agccaaggcc tatgaccttg    18960
cggccattga ataccgtggc gtcaatgctg taaccaactt cgacatcagc tgctacctgg    19020 accaccgct gttcctggca cagctccaac aggagccaca ggtggtgccg gcactcaacc    19080
aagaacctca acctgatcag agcgaaaccg gaactacaga gcaagagccg gagtcaagcg    19140
aagccaagac accggatggc agtgcagaac ccgatgagaa cgcggtgcct gacgacaccg    19200
cggagcccct caccacagtc gacgacagca tcgaagaggg cttgtggagc ccttgcatgg    19260
attacgagct agacaccatg tcgagaccaa actttggcag ctcaatcaat ctgagcgagt    19320
ggttcgctga cgcagacttc gactgcaaca tcggatgcct gttcgatggg tgttctgcgg    19380
ctgacgaagg aagcaaggat ggtgtaggtc tggcagattt cagtctgttt gaggcaggtg    19440
atgtccagct gaaggatgtt ctttcggata tggaagaggg gatacaacct ccagcgatga    19500
tcagtgtgtg caacgcggcc gcaagtatga actaaaatgc atgtaggtgt aagagctcat    19560
ggagagcatg gaatattgta tccgaccatg taacagtata ataactgagc tccatctcac    19620
ttcttctatg aataaacaaa ggatgttatg atatattaac actctatcta tgcaccttat    19680
tgttctatga taaatttcct cttattatta taaatcatct gaatcgtgac ggcttatgga    19740
atgcttcaaa tagtacaaaa acaaatgtgt actataagac tttctaaaca attctaacct    19800
tagcattgtg aacgagacat aagtgttaag aagacataac aattataatg gaagaagttt    19860
gtctccattt atatattata tattacccac ttatgtatta tattaggatg ttaaggagac    19920
ataacaatta taagagaga agtttgtatc catttatata ttatatacta cccatttata    19980
tattatactt atccacttat ttaatgtctt tataaggttt gatccatgat atttctaata    20040
ttttagttga tatgtatatg aaagggtact atttgaactc tcttactctg tataaaggtt    20100
ggatcatcct taaagtgggt ctatttaatt ttattgcttc ttacagataa aaaaaaaatt    20160
atgagttggt tgataaaat attgaaggat ttaaaataat aataaataac atataatata    20220
tgtatataaa tttattataa tataacattt atctataaaa aagtaaatat tgtcataaat    20280
ctatacaatc gtttagcctt gctggacgaa tctcaattat ttaaacgaga gtaaacatat    20340
```

-continued

| | |
|---|---|
| ttgactttt ggttatttaa caaattatta tttaacacta tatgaaattt ttttttttat | 20400 |
| cagcaaagaa taaaattaaa ttaagaagga caatggtgtc ccaatcctta taaccaac | 20460 |
| ttccacaaga aagtcaagtc agagacaaca aaaaaacaag caaggaaat tttttaattt | 20520 |
| gagttgtctt gtttgctgca taatttatgc agtaaaacac tacacataac cctttagca | 20580 |
| gtagagcaat ggttgaccgt gtgcttagct tcttttattt tatttttta tcagcaaaga | 20640 |
| ataaataaaa taaaatgaga cacttcaggg atgtttcaac aagctctaga gggcccaatt | 20700 |
| cgccctatag tgagtcgtat tacaattcac tggccgtcgt tttacaacgt cgtgactggg | 20760 |
| aaaaccctgg cgttacccaa cttaatcgcc ttgcagcaca tccccctttc gccagctggc | 20820 |
| gtaatagcga gaggcccgc accgatcgcc cttcccaaca gttgcgcagc ctatacgtac | 20880 |
| gagatccggc cggccagatc ctgcaggaga tccaagcttg g | 20921 |

<210> SEQ ID NO 29
<211> LENGTH: 4906
<212> TYPE: DNA
<213> ORGANISM: Artificial Sequence
<220> FEATURE:
<223> OTHER INFORMATION: vector pKR268

<400> SEQUENCE: 29

| | |
|---|---|
| ggccgcatga gccgtaaagg ttcaatacaa cgagtgcttg ttttcttagg gacaagcatt | 60 |
| gtacttatgt atgattctgt gtaaccatga gtcttccacg ttgtactaat gtgaagggca | 120 |
| aaaataaaac acagaacaag ttcgtttttc tcaaataatg tgaaggtaga aaatggaacc | 180 |
| atgcctcctc tcttgcatgt gatttaaaat attagcagat ggtaccgtac gtgggcggat | 240 |
| cccccgggct gcaggaattc actggccgtc gttttacaac gtcgtgactg ggaaaaccct | 300 |
| ggcgttaccc aacttaatcg ccttgcagca catccccctt cgccagctg gcgtaatagc | 360 |
| gaagaggccc gcaccgatcg cccttcccaa cagttgcgca gcctgaatgg cgaatggcgc | 420 |
| ctgatgcggt attttctcct tacgcatctg tgcggtattt cacaccgcat atggtgcact | 480 |
| ctcagtacaa tctgctctga tgccgcatag ttaagccagc cccgacaccc gccaacaccc | 540 |
| gctgacgcgc cctgacgggc ttgtctgctc ccggcatccg cttacagaca agctgtgacc | 600 |
| gtctccggga gctgcatgtg tcagaggttt tcaccgtcat caccgaaacg cgcgagacga | 660 |
| aagggcctcg tgatacgcct atttttatag gttaatgtca tgataataat ggtttcttag | 720 |
| acgtcaggtg gcacttttcg gggaaatgtg cgcggaaccc ctatttgttt atttttctaa | 780 |
| atacattcaa atatgtatcc gctcatgaga caataaccct gataaatgct tcaataatat | 840 |
| tgaaaaagga agagtatgag tattcaacat ttccgtgtcg cccttattcc cttttttgcg | 900 |
| gcattttgcc ttcctgtttt tgctcaccca gaaacgctgg tgaaagtaaa agatgctgaa | 960 |
| gatcagttgg gtgcacgagt gggttacatc gaactggatc tcaacagcgg taagatcctt | 1020 |
| gagagtttc gccccgaaga cgttttccaa atgatgagca cttttaaagt tctgctatgt | 1080 |
| ggcgcggtat tatcccgtat tgacgccggg caagagcaac tcggtcgccg catacactat | 1140 |
| tctcagaatg acttggttga gtactcacca gtcacagaaa agcatcttac ggatggcatg | 1200 |
| acagtaagag aattatgcag tgctgccata accatgagtg ataacactgc ggccaactta | 1260 |
| cttctgacaa cgatcggagg accgaaggag ctaaccgctt ttttgcacaa catggggat | 1320 |
| catgtaactc gccttgatcg ttgggaaccg gagctgaatg aagccatacc aaacgacgag | 1380 |
| cgtgacacca cgatgcctgt agcaatggca acaacgttgc gcaaactatt aactggcgaa | 1440 |
| ctacttactc tagcttcccg gcaacaatta atagactgga tggaggcgga taaagttgca | 1500 |

```
ggaccacttc tgcgctcggc ccttccggct ggctggttta ttgctgataa atctggagcc   1560
ggtgagcgtg ggtctcgcgg tatcattgca gcactggggc cagatggtaa gccctcccgt   1620
atcgtagtta tctacacgac ggggagtcag gcaactatgg atgaacgaaa tagacagatc   1680
gctgagatag gtgcctcact gattaagcat tggtaactgt cagaccaagt ttactcatat   1740
atactttaga ttgatttaaa acttcatttt taatttaaaa ggatctaggt gaagatcctt   1800
tttgataatc tcatgaccaa aatcccttaa cgtgagtttt cgttccactg agcgtcagac   1860
cccgtagaaa agatcaaagg atcttcttga gatcctttt ttctgcgcgt aatctgctgc   1920
ttgcaaacaa aaaaccacc gctaccagcg gtggtttgtt tgccggatca agagctacca   1980
actctttttc cgaaggtaac tggcttcagc agagcgcaga taccaaatac tgtccttcta   2040
gtgtagccgt agttaggcca ccacttcaag aactctgtag caccgcctac atacctcgct   2100
ctgctaatcc tgttaccagt ggctgctgcc agtggcgata agtcgtgtct taccgggttg   2160
gactcaagac gatagttacc ggataaggcg cagcggtcgg gctgaacggg gggttcgtgc   2220
acacagccca gcttggagcg aacgacctac accgaactga gatacctaca gcgtgagcta   2280
tgagaaagcg ccacgcttcc cgaagggaga aaggcggaca ggtatccggt aagcggcagg   2340
gtcggaacag gagagcgcac gagggagctt ccaggggaa acgcctggta tctttatagt   2400
cctgtcgggt ttcgccacct ctgacttgag cgtcgatttt tgtgatgctc gtcaggggg   2460 cggagcctat ggaaaaacgc cagcaacgcg gccttttac ggttcctggc cttttgctgg   2520 cctttgctc acatgttctt tcctgcgtta tcccctgatt ctgtggataa ccgtattacc   2580
gcctttgagt gagctgatac cgctcgccgc agccgaacga ccgagcgcag cgagtcagtg   2640
agcgaggaag cggaagagcg cccaatacgc aaaccgcctc tccccgcgcg ttggccgatt   2700
cattaatgca gctggcacga caggtttccc gactggaaag cgggcagtga gcgcaacgca   2760
attaatgtga gttagctcac tcattaggca ccccaggctt tacactttat gcttccggct   2820
cgtatgttgt gtggaattgt gagcggataa caatttcaca caggaaacag ctatgaccat   2880
gattacgcca agcttgcatg cctgcaggtc gactcgacgt acgatcccac atgcaagttt   2940
ttatttcaat ccctttcct ttgaataact gaccaagaac aacaagaaaa aaaaaaaaa   3000 agaaaaggat cattttgaaa ggatattttt cgctcctatt caaatactgt attttaccca   3060
aaaaaactgt attttcctca cactctcaag ctttgttttt cgcttcgact ctcatgattt   3120
ccttcatatg ccaatcactc tatttataaa tggcataagg tagtgtgaac aattgcaaag   3180
cttgtcatca aaagcttgca atgtacaaat taatgttttt catgcctttc aaaattatct   3240 gcaccccta gctattaatc taacatctaa gtaaggctag tgaatttttt cgaatagtca   3300
tgcagtgcat taatttcccc gtgactattt tggctttgac tccaacactg gccccgtaca   3360
tccgtccctc attacatgaa aagaaatatt gtttatattc ttaattaaaa atattgtccc   3420
ttctaaattt tcatatagtt aattattata ttactttttt ctctattcta ttagttctat   3480
tttcaaatta ttatttatgc atatgtaaag tacattatat ttttgctata tacttaaata   3540
tttctaaatt attaaaaaaa gactgatatg aaaaatttat tcttttttaaa gctatatcat   3600 tttatatata cttttctttt tcttttcttt cattttctat tcaatttaat aagaaataaa   3660
ttttgtaaat tttatttat caattataaa aatattttta cttatatgt tttttcacat   3720 ttttgttaaa caaatcatat cattatgatt gaaagagagg aaattgacag tgagtaataa   3780
gtgatgagaa aaaatgtgt tatttcctaa aaaaaaccta aacaaacatg tatctactct   3840
ctatttcatc tatctctcat ttcatttttc tctttatctc tttctttatt tttttatcat   3900
```

```
atcatttcac attaattatt tttactctct ttattttttc tctctatccc tctcttattt    3960
ccactcatat atacactcca aaattggggc atgcctttat cactactcta tctcctccac    4020
taaatcattt aaatgaaact gaaaagcatt ggcaagtctc ctcccctcct caagtgattt    4080
ccaactcagc attggcatct aattgattca gtatatctat tgcatgtgta aaagtctttc    4140
cacaatacat aactattaat taatcttaaa taaataaagg ataaaatatt tttttttctt    4200
cataaaatta aaatatgtta ttttttgttt agatgtatat tcgaataaat ctaaatatat    4260
gataatgatt ttttatattg attaaacata taatcaatat taaatatgat atttttttat    4320
ataggttgta cacataattt tataaggata aaaaatatga taaaaataaa ttttaaatat    4380
ttttatattt acgagaaaaa aaaatatttt agccataaat aaatgaccag catattttac    4440
aaccttagta attcataaat tcctatatgt atatttgaaa ttaaaaacag ataatcgtta    4500
agggaaggaa tcctacgtca tctcttgcca tttgttttc atgcaaacag aaagggacga    4560
aaaaccacct caccatgaat cactcttcac accattttta ctagcaaaca agtctcaaca    4620
actgaagcca gctctctttc cgtttctttt tacaacactt tctttgaaat agtagtattt    4680
tttttttcaca tgatttatta acgtgccaaa agatgcttat tgaatagagt gcacatttgt    4740
aatgtactac taattagaac atgaaaaagc attgttctaa cacgataatc ctgtgaaggc    4800
gttaactcca aagatccaat ttcactatat aaattgtgac gaaagcaaaa tgaattcaca    4860
tagctgagag agaaaggaaa ggttaactaa gaagcaatac ttcagc                   4906
```

<210> SEQ ID NO 30  
<211> LENGTH: 10528  
<212> TYPE: DNA  
<213> ORGANISM: Artificial Sequence  
<220> FEATURE:  
<223> OTHER INFORMATION: vector pKR1143  
<220> FEATURE:  
<221> NAME/KEY: misc_feature  
<222> LOCATION: (7136)..(7136)  
<223> OTHER INFORMATION: n is a, c, g, or t

<400> SEQUENCE: 30

```
gtacgagatc cggccggcca gatcctgcag gagatccaag cttggcgcgc cgttctatag     60
tgtcacctaa atcgtatgtg tatgatacat aaggttatgt attaattgta gccgcgttct    120
aacgacaata tgtccatatg gtgcactctc agtacaatct gctctgatgc cgcatagtta    180
agccagcccc gacacccgcc aacacccgct gacgcgccct gacgggcttg tctgctcccg    240
gcatccgctt acagacaagc tgtgaccgtc tccgggagct gcatgtgtca gaggttttca    300
ccgtcatcac cgaaacgcgc gagacgaaag ggcctcgtga tacgcctatt tttataggtt    360
aatgtcatga ccaaaatccc ttaacgtgag ttttcgttcc actgagcgtc agaccccgta    420
gaaaagatca aaggatcttc ttgagatcct ttttttctgc gcgtaatctg ctgcttgcaa    480
acaaaaaaac caccgctacc agcggtggtt tgtttgccgg atcaagagct accaactctt    540
tttccgaagg taactggctt cagcagagcg cagataccaa atactgtcct tctagtgtag    600
ccgtagttag gccaccactt caagaactct gtagcaccgc ctacatacct cgctctgcta    660
atcctgttac cagtggctgc tgccagtggc gataagtcgt gtcttaccgg gttggactca    720
agacgatagt taccggataa ggcgcagcgg tcgggctgaa cggggggttc gtgcacacag    780
cccagcttgg agcgaacgac ctacaccgaa ctgagatacc tacagcgtga gcattgagaa    840
agcgccacgc ttcccgaagg gagaaaggcg gacaggtatc cggtaagcgg cagggtcgga    900
acaggagagc gcacgaggga gcttccaggg ggaaacgcct ggtatcttta tagtcctgtc    960
```

-continued

```
gggtttcgcc acctctgact tgagcgtcga ttttttgtgat gctcgtcagg ggggcggagc    1020
ctatggaaaa acgccagcaa cgcggccttt ttacggttcc tggccttttg ctggccttttt   1080
gctcacatgt tctttcctgc gttatcccct gattctgtgg ataaccgtat taccgccttt   1140
gagtgagctg ataccgctcg ccgcagccga acgaccgagc gcagcgagtc agtgagcgag   1200
gaagcggaag agcgcccaat acgcaaaccg cctctcccg cgcgttggcc gattcattaa    1260
tgcaggttga tcgattcgac atcgatctag taacatagat gacaccgcgc gcgataattt   1320
atcctagttt gcgcgctata ttttgttttc tatcgcgtat taaatgtata attgcgggac   1380
tctaatcata aaaacccatc tcataaataa cgtcatgcat tacatgttaa ttattacatg   1440
cttaacgtaa ttcaacagaa attatatgat aatcatcgca agaccggcaa caggattcaa   1500
tcttaagaaa ctttattgcc aaatgtttga acgatctgct tcgacgcact ccttctttag   1560
gtacctcact attcctttgc cctcggacga gtgctggggc gtcggtttcc actatcggcg   1620
agtacttcta cacagccatc ggtccagacg gccgcgcttc tgcgggcgat ttgtgtacgc   1680
ccgacagtcc cggctccgga tcggacgatt gcgtcgcatc gaccctgcgc ccaagctgca   1740
tcatcgaaat tgccgtcaac caagctctga tagagttggt caagaccaat gcggagcata   1800
tacgcccgga gccgcggcga tcctgcaagc tccggatgcc tccgctcgaa gtagcgcgtc   1860
tgctgctcca tacaagccaa ccacggcctc agaagaaga tgttggcgac ctcgtattgg    1920
gaatccccga acatcgcctc gctccagtca atgaccgctg ttatgcggcc attgtccgtc   1980
aggacattgt tggagccgaa atccgcgtgc acgaggtgcc ggacttcggg gcagtcctcg   2040
gcccaaagca tcagctcatc gagagcctgc gcgacggacg cactgacggt gtcgtccatc   2100
acagtttgcc agtgatacac atggggatca gcaatcgcgc atatgaaatc acgccatgta   2160
gtgtattgac cgattccttg cggtccgaat gggccgaacc cgctcgtctg gctaagatcg   2220
gccgcagcga tcgcatccat ggcctccgcg accggctgca gaacagcggg cagttcggtt   2280
tcaggcaggt cttgcaacgt gacaccctgt gcacggcggg agatgcaata ggtcaggctc   2340
tcgctgaatt ccccaatgtc aagcacttcc ggaatcggga gcgcggccga tgcaaagtgc   2400
cgataaacat aacgatcttt gtagaaacca tcggcgcagc tatttacccg caggacatat   2460
ccacgccctc ctacatcgaa gctgaaagca cgagattctt cgccctccga gagctgcatc   2520
aggtcggaga cgctgtcgaa cttttcgatc agaaacttct cgacagacgt cgcggtgagt   2580
tcaggctttt tcatggttta ataagaagag aaaagagttc ttttgttatg gctgaagtaa   2640
tagagaaatg agctcgagcg tgtcctctcc aaatgaaatg aacttcctta tatagaggaa   2700
gggtcttgcg aaggatagtg ggattgtgcg tcatccctta cgtcagtgga gatgtcacat   2760
caatccactt gctttgaaga cgtggttgga acgtcttctt ttttccacgat gctcctcgtg   2820
ggtgggggtc catctttggg accactgtcg gcagaggcat cttgaatgat agcctttcct   2880
ttatcgcaat gatggcattt gtaggagcca ccttcctttt ctactgtcct ttcgatgaag   2940
tgacagatag ctgggcaatg gaatccgagg aggtttcccg aaattatcct ttgttgaaaa   3000
gtctcaatag ccctttggtc ttctgagact gtatctttga catttttgga gtagaccaga   3060
gtgtcgtgct ccaccatgtt gacgaagatt ttcttcttgt cattgagtcg taaaagactc   3120
tgtatgaact gttcgccagt cttcacgcg agttctgtta gatcctcgat ttgaatctta    3180
gactccatgc atggccttag attcagtagg aactacctttt ttagagactc caatctctat   3240
tacttgccctt ggtttatgaa gcaagccttg aatcgtccat actggaatag tacttctgat   3300
cttgagaaat atgtctttct ctgtgttctt gatgcaatta gtcctgaatc ttttgactgc   3360
```

```
atctttaacc ttcttgggaa ggtatttgat ctcctggaga ttgttactcg ggtagatcgt   3420
cttgatgaga cctgctgcgt aggcctctct aaccatctgt gggtcagcat tctttctgaa   3480
attgaagagg ctaaccttct cattatcagt ggtgaacata gtgtcgtcac cttcaccttc   3540
gaacttcctt cctagatcgt aaagatagag gaaatcgtcc attgtaatct ccggggcaaa   3600
ggagatctct ttggggctg gatcactgct gggccttttg gttcctagcg tgagccagtg   3660 ggcttttgc tttggtgggc ttgttagggc cttagcaaag ctcttgggct tgagttgagc   3720
ttctcctttg gggatgaagt tcaacctgtc tgtttgctga cttgttgtgt acgcgtcagc   3780
tgctgctctt gcctctgtaa tagtggcaaa tttcttgtgt gcaactccgg gaacgccgtt   3840
tgttgccgcc tttgtacaac cccagtcatc gtatataccg gcatgtggac cgttatacac   3900
aacgtagtag ttgatatgag ggtgttgaat acccgattct gctctgagag gagcaactgt   3960
gctgttaagc tcagattttt gtgggattgg aattggatcg atctcgatcc cgcgaaatta   4020
atacgactca ctatagggag accacaacgg tttccctcta gaaataattt tgtttaactt   4080
taagaaggag atatacccat ggaaaagcct gaactcaccg cgacgtctgt cgagaagttt   4140
ctgatcgaaa agttcgacag cgtctccgac ctgatgcagc tctcggaggg cgaagaatct   4200
cgtgctttca gcttcgatgt aggagggcgt ggatatgtcc tgcgggtaaa tagctgcgcc   4260
gatggtttct acaaagatcg ttatgtttat cggcactttg catcggccgc gctcccgatt   4320
ccggaagtgc ttgacattgg ggaattcagc gagagcctga cctattgcat ctcccgccgt   4380
gcacagggtg tcacgttgca agacctgcct gaaaccgaac tgcccgctgt tctgcagccg   4440
gtcgcggagg ctatggatgc gatcgctgcg gccgatctta gccagacgag cgggttcggc   4500
ccattcggac cgcaaggaat cggtcaatac actacatggc gtgatttcat atgcgcgatt   4560
gctgatcccc atgtgtatca ctggcaaact gtgatggacg acaccgtcag tgcgtccgtc   4620
gcgcaggctc tcgatgagct gatgctttgg gccgaggact gccccgaagt ccggcacctc   4680
gtgcacgcgg atttcggctc caacaatgtc ctgacggaca atggccgcat aacagcggtc   4740
attgactgga gcgaggcgat gttcggggat tcccaatacg aggtcgccaa catcttcttc   4800
tggaggccgt ggttggcttg tatggagcag cagacgcgct acttcgagcg gaggcatccg   4860
gagcttgcag atcgccgcg gctccggcg tatatgctcc gcattggtct tgaccaactc   4920
tatcagagct tggttgacgg caatttcgat gatgcagctt gggcgcaggg tcgatgcgac   4980
gcaatcgtcc gatccggagc cgggactgtc gggcgtacac aaatcgcccg cagaagcgcg   5040
gccgtctgga ccgatggctg tgtagaagta ctcgccgata gtggaaaccg acgccccagc   5100
actcgtccga gggcaaagga atagtgaggt acagcttgga tcgatccggc tgctaacaaa   5160
gcccgaaagg aagctgagtt ggctgctgcc accgctgagc aataactagc ataacccctt   5220
ggggcctcta aacgggtctt gaggggtttt ttgctgaaag gaggaactat atccggatga   5280
tcgggcgcgc cgtcgacgga tccactagtt ctagagcggc ccgcgccgtc gacggatata   5340
atgagccgta aacaaagatg attaagtagt aattaatacg tactagtaaa agtggcaaaa   5400
gataacgaga aagaaccaat ttcctttgcat tcggccttag cggaaggcat atataagctt   5460
tgattatttt atttagtgta atgatttcgt acaaccaaag catttattta gtactctcac   5520
acttgtgtcg cggccggccg ctacaggaac aggtggtggc ggccctcggc gcgctcgtac   5580
tgctccacga tggtgtagtc ctcgttgtgg gaggtgatgt ccagcttgga gtccacgtag   5640
tagtagccgg gcagctgcac gggcttcttg gccatgtaga tggacttgaa ctccaccagg   5700
tagtggccgc cgtccttcag cttcagggcc ttgtggatct cgcccttcag cacgccgtcg   5760
```

```
cgggggtaca ggcgctcggt ggaggcctcc cagcccatag tcttcttctg cattacgggg   5820
ccgtcggagg ggaagttcac gccgatgaac ttcaccttgt agatgaagga gccgtcctgc   5880
agggaggagt cctgggtcac ggtcaccacg ccgccgtcct cgaagttcat cacgcgctcc   5940
cacttgaagc cctcggggaa ggacagcttc ttgtagtcgg ggatgtcggc ggggtgcttc   6000
acgtacacct tggagccgta ctggaactgg ggggacagga tgtcccaggc gaagggcagg   6060
gggccgccct tggtcacctt cagcttggcg gtctgggtgc cctcgtaggg gcggccctcg   6120
ccctcgccct cgatctcgaa ctcgtggccg ttcacggagc cctccatgcg caccttgaag   6180
cgcatgaact ccttgatgac gtcctcggag gaggccatgg gccgcttggg gggctatgga   6240
agactttctt agttagttgt gtgaataagc aatgttggga gaatcgggac tacttatagg   6300
ataggaataa aacagaaaag tattaagtgc taatgaaata tttagactga taattaaaat   6360
cttcacgtat gtccacttga tataaaacg tcaggaataa aggaagtaca gtagaattta   6420
aaggtactct ttttatatat acccgtgttc tcttttggc tagctagttg cataaaaaat   6480
aatctatatt tttatcatta ttttaaatat cttatgagat ggtaaatatt tatcataatt   6540 tttttacta ttatttatta tttgtgtgtg taatacatat agaagttaat tacaaatttt   6600
atttactttt tcattatttt gatatgattc accattaatt tagtgttatt atttataata   6660
gttcatttta atcttttttgt atatatattatg cgtgcagtac ttttttccta catataacta   6720
ctattacatt ttatttatat aatattttta ttaatgaatt ttcgtgataa tatgtaatat   6780
tgttcattat tatttcagat ttttttaaaaa tatttgtgtt attatttatg aaatatgtaa   6840 ttttttttagt atttgatttt atgatgataa agtgttctaa attcaaaaga aggggggaaag   6900 cgtaaacatt aaaaaacgtc atcaaacaaa aacaaaatct tgttaataaa gataaaactg   6960
tttgttttga tcactgttat ttcgtaatat aaaaacatta tttatattta tattgttgac   7020
aaccaaattt gcctatcaaa tctaaccaat ataatgcatg cgtggcaggt aatgtactac   7080
catgaactta agtcatgaca taataaaccg tgaatctgac caatgcatgt acctanctaa   7140
attgtatttg tgacacgaag caaatgattc aattcacaat ggagatggga aacaaataat   7200
gaagaaccca gaactaagaa agcttttctg aaaaataaaa taaaggcaat gtcaaaagta   7260
tactgcatca tcagtccaga aagcacatga tattttttta tcagtatcaa tgcagctagt   7320
tttattttac aatatcgata tagctagttt aaatatattg cagctagatt tataaatatt   7380
tgtgttatta tttatcattt gtgtaatcct gttttagta ttttagttta tatatgatga   7440
taatgtattc caaatttaaa agaagggaaa taaatttaaa caagaaaaaa agtcatcaaa   7500
caaaaaacaa atgaaagggt ggaaagatgt taccatgtaa tgtgaatgtt acagtatttc   7560
ttttattata gagttaacaa attaactaat atgattttgt taataatgat aaaatatttt   7620
ttttattatt atttcataat ataaaaatag tttacttaat ataaaaaaaa ttctatcgtt   7680
cacaacaaag ttggccacct aatttaacca tgcatgtacc catggaccat attaggtaac   7740
catcaaacct gatgaagaga taaagagatg aagacttaag tcataacaca aaaccataaa   7800
aaacaaaaat acaatcaacc gtcaatctga ccaatgcatg aaaaagctgc aatagtgagt   7860
ggcgacacaa agcacatgat tttcttacaa cggagataaa accaaaaaaa tatttcatga   7920
acaacctaga acaaataaag cttttatata ataaatatat aaataaataa aggctatgga   7980
ataatatact tcaatatatt tggattaaat aaattgttgg cggggttgat atatttatac   8040
acacctaaag tcacttcaat ctcatttttca cttaactttt attttttttt tcttttttatt   8100 tatcataaag agaatattga taatatactt tttaacatat tttatgaca tttttttattg   8160
```

```
gtgaaaactt attaaaaatc ataaattttg taagttagat ttatttaaag agttcctctt    8220
cttattttaa attttttaat aaattttttaa ataactaaaa tttgtgttaa aaatgttaaa    8280
aaagtgtgtt attaaccctt ctcttcgagg atccgtacga tcccacatgc aagtttttat    8340
ttcaatccct tttcctttga ataactgacc aagaacaaca agaaaaaaaa aaaaaaagaa    8400
aaggatcatt tgaaaggat attttcgct cctattcaaa tactgtattt ttaccaaaaa      8460
aactgtattt ttcctacact ctcaagcttt gttttcgct tcgactctca tgatttcctt     8520
catatgccaa tcactctatt tataaatggc ataaggtagt gtgaacaatt gcaaagcttg    8580
tcatcaaaag cttgcaatgt acaaattaat gtttttcatg cctttcaaaa ttatctgcac    8640
cccctagcta ttaatctaac atctaagtaa ggctagtgaa ttttttcgaa tagtcatgca    8700
gtgcattaat ttccccgtga ctattttggc tttgactcca acactggccc cgtacatccg    8760
tccctcatta catgaaaaga atattgttt atattcttaa ttaaaaatat tgtcccttct     8820
aaattttcat atagttaatt attatattac ttttttctct attctattag ttctattttc    8880
aaattattat ttatgcatat gtaaagtaca ttatatttt gctatatact taaatatttc     8940
taaattatta aaaaaagact gatatgaaaa atttattctt tttaaagcta tatcatttta    9000
tatatacttt ttcttttctt ttctttcatt ttctattcaa tttaataaga aataaatttt    9060
gtaaattttt atttatcaat ttataaaaat attttacttt atatgttttt tcacattttt    9120
gttaaacaaa tcatatcatt atgattgaaa gagaggaaat tgacagtgag taataagtga    9180
tgagaaaaaa atgtgttatt tcctaaaaaa aacctaaaca aacatgtatc tactctctat    9240
ttcatctatc tctcatttca tttttctctt tatctctttc tttattttt tatcatatca     9300 tttcacatta attattttta ctctctttat tttttctctc tatccctctc ttatttccac    9360
tcatatatac actccaaaat tggggcatgc ctttatcact actctatctc ctccactaaa    9420
tcatttaaat gaaactgaaa agcattggca agtctcctcc cctcctcaag tgatttccaa    9480
ctcagcattg gcatctaatt gattcagtat atctattgca tgtgtaaaag tctttccaca    9540
atacataact attaattaat cttaaataaa taaaggataa aatattttt tttcttcata     9600 aaattaaaat atgttatttt ttgtttagat gtatattcga ataaatctaa atatatgata    9660 atgattttt atattgatta aacatataat caatattaaa tatgatattt ttttatatag     9720
gttgtacaca taatttata aggataaaa atatgataaa aataaatttt aaatattttt      9780
atatttacga gaaaaaaaa tattttagcc ataaataaat gaccagcata ttttacaacc     9840
ttagtaattc ataaattcct atatgtatat ttgaaattaa aaacagataa tcgttaaggg    9900
aaggaatcct acgtcatctc ttgccatttg ttttcatgc aaacagaaag ggacgaaaaa     9960
ccacctcacc atgaatcact cttcacacca tttttactag caaacaagtc tcaacaactg   10020
aagccagctc tctttccgtt tcttttaca acactttctt tgaaatagta gtattttttt    10080
ttcacatgat ttattaacgt gccaaaagat gcttattgaa tagagtgcac atttgtaatg   10140
tactactaat tagaacatga aaaagcattg ttctaacacg ataatcctgt gaaggcgtta   10200
actccaaaga tccaatttca ctatataaat tgtgacgaaa gcaaatgaa ttcacatagc    10260 tgagagagaa aggaaaggtt aactaagaag caatacttca gcggccgcat gagccgtaaa   10320
ggttcaatac aacgagtgct tgttttctta gggacaagca ttgtacttat gtatgattct   10380
gtgtaaccat gagtcttcca cgttgtacta atgtgaaggg caaaaataaa acacagaaca   10440
agttcgtttt tctcaaataa tgtgaaggta gaaaatggaa ccatgcctcc tctcttgcat   10500
gtgatttaaa atattagcag atggtacc                                      10528
```

<210> SEQ ID NO 31
<211> LENGTH: 11721
<212> TYPE: DNA
<213> ORGANISM: Artificial Sequence
<220> FEATURE:
<223> OTHER INFORMATION: vector pKR1147
<220> FEATURE:
<221> NAME/KEY: misc_feature
<222> LOCATION: (7362)..(7362)
<223> OTHER INFORMATION: n is a, c, g, or t

<400> SEQUENCE: 31

```
ggccgcatga gccgtaaagg ttcaatacaa cgagtgcttg ttttcttagg gacaagcatt      60
gtacttatgt atgattctgt gtaaccatga gtcttccacg ttgtactaat gtgaagggca     120
aaaataaaac acagaacaag ttcgtttttc tcaaataatg tgaaggtaga aaatggaacc     180
atgcctcctc tcttgcatgt gatttaaaat attagcagat ggtaccgtac gagatccggc     240
cggccagatc ctgcaggaga tccaagcttg gcgcgccgtt ctatagtgtc acctaaatcg     300
tatgtgtatg atacataagg ttatgtatta attgtagccg cgttctaacg acaatatgtc     360
catatggtgc actctcagta caatctgctc tgatgccgca tagttaagcc agccccgaca     420
cccgccaaca cccgctgacg cgccctgacg ggcttgtctg ctcccggcat ccgcttacag     480
acaagctgtg accgtctccg ggagctgcat gtgtcagagg ttttcaccgt catcaccgaa     540
acgcgcgaga cgaaagggcc tcgtgatacg cctattttta taggttaatg tcatgaccaa     600
aatcccttaa cgtgagtttt cgttccactg agcgtcagac cccgtagaaa agatcaaagg     660
atcttcttga tccttttttt tctgcgcgt  aatctgctgc ttgcaaacaa aaaaaccacc     720
gctaccagcg gtggtttgtt tgccggatca agagctacca actcttttt  cgaaggtaac     780
tggcttcagc agagcgcaga taccaaatac tgtccttcta gtgtagccgt agttaggcca     840
ccacttcaag aactctgtag caccgcctac atacctcgct ctgctaatcc tgttaccagt     900
ggctgctgcc agtggcgata agtcgtgtct taccgggttg gactcaagac gatagttacc     960
ggataaggcg cagcggtcgg gctgaacggg gggttcgtgc acacagccca gcttggagcg    1020
aacgacctac accgaactga gatacctaca gcgtgagcat tgagaaagcg ccacgcttcc    1080
cgaagggaga aaggcggaca ggtatccggt aagcggcagg gtcggaacag gagagcgcac    1140
gagggagctt ccagggggaa acgcctggta tctttatagt cctgtcgggt ttcgccacct    1200
ctgacttgag cgtcgatttt tgtgatgctc gtcagggggg cggagcctat ggaaaaacgc    1260
cagcaacgcg gcctttttac ggttcctggc cttttgctgg ccttttgctc acatgttctt    1320
tcctgcgtta tcccctgatt ctgtggataa ccgtattacc gcctttgagt gagctgatac    1380
cgctcgccgc agccgaacga ccgagcgcag cgagtcagtg agcgaggaag cggaagagcg    1440
cccaatacgc aaaccgcctc tccccgcgcg ttggccgatt cattaatgca ggttgatcga    1500
ttcgacatcg atctagtaac atagatgaca ccgcgcgcga taatttatcc tagttttgcgc   1560
gctatatttt gttttctatc gcgtattaaa tgtataattg cgggactcta atcataaaaa    1620
cccatctcat aaataaacgtc atgcattaca tgttaattat tacatgctta acgtaattca    1680
acagaaatta tatgataatc atcgcaagac cggcaacagg attcaatctt aagaaacttt    1740
attgccaaat gtttgaacga tctgcttcga cgcactcctt ctttaggtac ctcactattc    1800
ctttgccctc ggacgagtgc tggggcgtcg gtttccacta tcggcgagta cttctacaca    1860
gccatcggtc cagacggccg cgcttctgcg ggcgatttgt gtacgcccga cagtcccggc    1920
tccggatcgg acgattgcgt cgcatcgacc ctgcgcccaa gctgcatcat cgaaattgcc    1980
```

```
gtcaaccaag ctctgataga gttggtcaag accaatgcgg agcatatacg cccggagccg   2040
cggcgatcct gcaagctccg gatgcctccg ctcgaagtag cgcgtctgct gctccataca   2100
agccaaccac ggcctccaga agaagatgtt ggcgacctcg tattgggaat ccccgaacat   2160
cgcctcgctc cagtcaatga ccgctgttat gcggccattg tccgtcagga cattgttgga   2220
gccgaaatcc gcgtgcacga ggtgccggac ttcggggcag tcctcggccc aaagcatcag   2280
ctcatcgaga gcctgcgcga cggacgcact gacggtgtcg tccatcacag tttgccagtg   2340
atacacatgg ggatcagcaa tcgcgcatat gaaatcacgc catgtagtgt attgaccgat   2400
tccttgcggt ccgaatgggc cgaacccgct cgtctggcta agatcggccg cagcgatcgc   2460
atccatggcc tccgcgaccg gctgcagaac agcgggcagt tcggtttcag gcaggtcttg   2520
caacgtgaca ccctgtgcac ggcgggagat gcaataggtc aggctctcgc tgaattcccc   2580
aatgtcaagc acttccggaa tcgggagcgc ggccgatgca aagtgccgat aaacataacg   2640
atctttgtag aaaccatcgg cgcagctatt tacccgcagg acatatccac gccctcctac   2700
atcgaagctg aaagcacgag attcttcgcc ctccgagagc tgcatcaggt cggagacgct   2760
gtcgaacttt tcgatcagaa acttctcgac agacgtcgcg gtgagttcag gcttttcat    2820 ggtttaataa gaagagaaaa gagttctttt gttatggctg aagtaataga gaatgagct    2880 cgagcgtgtc ctctccaaat gaaatgaact tccttatata gaggaagggg cttgcgaagg   2940
atagtgggat tgtgcgtcat cccttacgtc agtggagatg tcacatcaat ccacttgctt   3000
tgaagacgtg gttggaacgt cttctttttc cacgatgctc ctcgtgggtg ggggtccatc   3060
tttgggacca ctgtcggcag aggcatcttg aatgatagcc tttcctttat cgcaatgatg   3120
gcatttgtag gagccacctt ccttttctac tgtccttttcg atgaagtgac agatagctgg   3180
gcaatggaat ccgaggaggt ttcccgaaat tatcctttgt tgaaaagtct caatagccct   3240
ttggtcttct gagactgtat cttcgacatt tttggagtag accagagtgt cgtgctccac   3300
catgttgacg aagattttct tcttgtcatt gagtcgtaaa agactctgta tgaactgttc   3360
gccagtcttc acggcgagtt ctgttagatc ctcgatttga atcttagact ccatgcatgg   3420
ccttagattc agtaggaact acctttttag agactccaat ctctattact tgccttggtt   3480
tatgaagcaa gccttgaatc gtccatactg gaatagtact tctgatcttg agaaatatgt   3540 cttttctctgt gttcttgatg caattagtcc tgaatctttt gactgcatct ttaaccttct   3600
tgggaaggta tttgatctcc tggagattgt tactcgggta gatcgtcttg atgagacctg   3660
ctgcgtaggc ctctctaacc atctgtgggt cagcattctt tctgaaattg aagaggctaa   3720
ccttctcatt atcagtggtg aacatagtgt cgtcaccttc accttcgaac ttccttccta   3780
gatcgtaaag atagaggaaa tcgtccattg taatctccgg ggcaaaggag atctcttttg   3840
gggctggatc actgctgggc cttttggttc ctagcgtgag ccagtgggct ttttgctttg   3900
gtgggcttgt tagggcctta gcaaagctct tgggcttgag ttgagcttct cctttgggga   3960
tgaagttcaa cctgtctgtt tgctgacttg ttgtgtacgc gtcagctgct gctcttgcct   4020
ctgtaatagt ggcaaatttc ttgtgtgcaa ctccgggaac gccgtttgtt gccgcctttg   4080
tacaacccca gtcatcgtat ataccggcat gtggaccgtt atacacaacg tagtagttga   4140
tatgagggtg ttgaataccc gattctgctc tgagaggagc aactgtgctg ttaagctcag   4200 attttgtgg gattggaatt ggatcgatct cgatcccgcg aaattaatac gactcactat   4260
agggagacca caacggtttc cctctagaaa taattttgtt taactttaag aaggagatat   4320
acccatggaa aagcctgaac tcaccgcgac gtctgtcgag aagtttctga tcgaaaagtt   4380
```

```
cgacagcgtc tccgacctga tgcagctctc ggagggcgaa gaatctcgtg ctttcagctt   4440
cgatgtagga gggcgtggat atgtcctgcg ggtaaatagc tgcgccgatg gtttctacaa   4500
agatcgttat gtttatcggc actttgcatc ggccgcgctc ccgattccgg aagtgcttga   4560
cattggggaa ttcagcgaga gcctgaccta ttgcatctcc cgccgtgcac agggtgtcac   4620
gttgcaagac ctgcctgaaa ccgaactgcc cgctgttctg cagccggtcg cggaggctat   4680
ggatgcgatc gctgcggccg atcttagcca gacgagcggg ttcggcccat tcggaccgca   4740
aggaatcggt caatacacta catggcgtga tttcatatgc gcgattgctg atccccatgt   4800
gtatcactgg caaactgtga tggacgacac cgtcagtgcg tccgtcgcgc aggctctcga   4860
tgagctgatg ctttgggccg aggactgccc cgaagtccgg cacctcgtgc acgcggattt   4920
cggctccaac aatgtcctga cggacaatgg ccgcataaca gcggtcattg actgagcga   4980 ggcgatgttc ggggattccc aatacgaggt cgccaacatc ttcttctgga ggccgtggtt   5040
ggcttgtatg gagcagcaga cgcgctactt cgagcggagg catccggagc ttgcaggatc   5100
gccgcggctc cgggcgtata tgctccgcat tggtcttgac caactctatc agagcttggt   5160
tgacggcaat ttcgatgatg cagcttgggc gcagggtcga tgcgacgcaa tcgtccgatc   5220
cggagccggg actgtcgggc gtacacaaat cgcccgcaga agcgcggccg tctggaccga   5280
tggctgtgta gaagtactcg ccgatagtgg aaaccgacgc cccagcactc gtccgagggc   5340
aaaggaatag tgaggtacag cttggatcga tccggctgct aacaaagccc gaaaggaagc   5400
tgagttggct gctgccaccg ctgagcaata actagcataa ccccttgggg cctctaaacg   5460
ggtcttgagg ggtttttgc tgaaaggagg aactatatcc ggatgatcgg gcgcgccgtc   5520
gacggatcca ctagttctag agcggcccgc gccgtcgacg gatataatga gccgtaaaca   5580
aagatgatta agtagtaatt aatacgtact agtaaaagtg gcaaaagata acgagaaaga   5640
accaatttct ttgcattcgg ccttagcgga aggcatatat aagctttgat tattttattt   5700
agtgtaatga tttcgtacaa ccaaagcatt tatttagtac tctcacactt gtgtcgcggc   5760
cggccgctac aggaacaggt ggtggcggcc ctcggcgcgc tcgtactgct ccacgatggt   5820
gtagtcctcg ttgtgggagg tgatgtccag cttggagtcc acgtagtagt agccgggcag   5880
ctgcacgggc ttcttggcca tgtagatgga cttgaactcc accaggtagt ggccgccgtc   5940
cttcagcttc agggccttgt ggatctcgcc cttcagcacg ccgtcgcggg ggtacaggcg   6000
ctcggtggag gcctcccagc ccatagtctt cttctgcatt acggggccgt cggaggggaa   6060
gttcacgccg atgaacttca ccttgtagat gaaggagccg tcctgcaggg aggagtcctg   6120
ggtcacggtc accacgccgc cgtcctcgaa gttcatcacg cgctcccact gaagccctc   6180 ggggaaggac agcttcttgt agtcgggat gtcgcgggg tgcttcacgt acaccttgga   6240
gccgtactgg aactgggggg acaggatgtc ccaggcgaag ggcaggggc cgcccttggt   6300 caccttcagc ttggcggtct gggtgccctc gtaggggcgg ccctcgccct cgccctcgat   6360
ctcgaactcg tggccgttca cggagccctc catgcgcacc ttgaagcgca tgaactcctt   6420
gatgacgtcc tcggaggagg ccatgggccg cttgggggc tatggaagac tttcttagtt   6480
agttgtgtga ataagcaatg ttgggagaat cgggactact tataggatag gaataaaaca   6540
gaaaagtatt aagtgctaat gaaatattta gactgataat taaaatcttc acgtatgtcc   6600
acttgatata aaaacgtcag gaataaagga agtacagtag aatttaaagg tactcttttt   6660
atatatcccc gtgttctctt tttggctagc tagttgcata aaaaataatc tatatttta   6720 tcattatttt aaatatctta tgagatggta aatatttatc ataatttttt ttactattat   6780
```

```
ttattatttg tgtgtgtaat acatatagaa gttaattaca aatttatttt acttttcat    6840
tattttgata tgattcacca ttaatttagt gttattattt ataatagttc attttaatct   6900
ttttgtatat attatgcgtg cagtactttt ttcctacata taactactat tacatttat    6960
ttatataata tttttattaa tgaattttcg tgataatatg taatattgtt cattattatt   7020
tcagatttt taaaaatatt tgtgttatta tttatgaaat atgtaatttt tttagtattt    7080
gattttatga tgataaagtg ttctaaattc aaaagaaggg ggaaagcgta aacattaaaa   7140
aacgtcatca aacaaaaaca aaatcttgtt aataaagata aaactgtttg ttttgatcac   7200
tgttatttcg taatataaaa acattattta tatttatatt gttgacaacc aaatttgcct   7260
atcaaatcta accaatataa tgcatgcgtg gcaggtaatg tactaccatg aacttaagtc   7320
atgacataat aaaccgtgaa tctgaccaat gcatgtacct anctaaattg tatttgtgac   7380
acgaagcaaa tgattcaatt cacaatggag atgggaaaca aataatgaag aacccagaac   7440
taagaaagct tttctgaaaa ataaaataaa ggcaatgtca aagtatact gcatcatcag    7500
tccagaaagc acatgatatt tttttatcag tatcaatgca gctagtttta ttttacaata   7560
tcgatatagc tagtttaaat atattgcagc tagatttata aatatttgtg ttattattta   7620
tcatttgtgt aatcctgttt ttagtatttt agtttatata tgatgataat gtattccaaa   7680
tttaaaagaa gggaaataaa tttaaacaag aaaaaagtc atcaaacaaa aacaaatga    7740
aagggtggaa agatgttacc atgtaatgtg aatgttacag tatttctttt attatagagt   7800
taacaaatta actaatatga ttttgttaat aatgataaaa tatttttttt attattattt   7860
cataatataa aaatagttta cttaatataa aaaaaattct atcgttcaca acaaagttgg   7920
ccacctaatt taaccatgca tgtacccatg gaccatatta ggtaaccatc aaacctgatg   7980
aagagataaa gagatgaaga cttaagtcat aacacaaaac cataaaaaac aaaaatacaa   8040
tcaaccgtca atctgaccaa tgcatgaaaa agctgcaata gtgagtggcg acacaaagca   8100
catgatttc ttacaacgga gataaaacca aaaaatatt tcatgaacaa cctagaacaa    8160
ataaagcttt tatataataa atatataaat aaataaaggc tatggaataa tatacttcaa   8220
tatatttgga ttaaataaat tgttggcggg gttgatatat ttatacacac ctaaagtcac   8280
ttcaatctca ttttcactta acttttattt tttttttctt tttatttatc ataaagagaa   8340
tattgataat atactttta acatatttt atgacatttt ttattggtga aaacttatta    8400
aaaatcataa attttgtaag ttagatttat ttaaagagtt cctcttctta ttttaaattt   8460
tttaataaat ttttaaataa ctaaaatttg tgttaaaaat gttaaaaaag tgtgttatta   8520
acccttctct tcgaggatcc gtacgatccc acatgcaagt ttttatttca atccctttc    8580
ctttgaataa ctgaccaaga acaacaagaa aaaaaaaaa aagaaaagg atcattttga    8640
aaggatattt ttcgctccta ttcaaatact gtattttac caaaaaaact gtattttcc    8700
tacactctca agctttgttt ttcgcttcga ctctcatgat ttccttcata tgccaatcac   8760
tctatttata aatggcataa ggtagtgtga acaattgcaa agcttgtcat caaaagcttg   8820
caatgtacaa attaatgttt ttcatgcctt tcaaaattat ctgcaccccc tagctattaa   8880
tctaacatct aagtaaggct agtgaatttt ttcgaatagt catgcagtgc attaatttcc   8940
ccgtgactat tttggctttg actccaacac tggccccgta catccgtccc tcattacatg   9000
aaaagaaata ttgtttatat tcttaattaa aaatattgtc ccttctaaat tttcatatag   9060
ttaattatta tattactttt ttctctattc tattagttct attttcaaat tattatttat   9120
gcatatgtaa agtacattat attttttgcta tatacttaaa tatttctaaa ttattaaaaa   9180
```

```
aagactgata tgaaaaattt attcttttta aagctatatc attttatata tactttttct   9240
tttcttttct ttcattttct attcaattta ataagaaata aattttgtaa attttttattt  9300 atcaatttat aaaaatattt tactttatat gttttttcac attttgtta aacaaatcat    9360 atcattatga ttgaaagaga ggaaattgac agtgagtaat aagtgatgag aaaaaaatgt   9420
gttatttcct aaaaaaaacc taaacaaaca tgtatctact ctctatttca tctatctctc   9480
atttcatttt tctctttatc tctttcttta ttttttttatc atatcatttc acattaatta  9540
tttttactct ctttattttt tctctctatc cctctcttat ttccactcat atatacactc   9600
caaaattggg gcatgccttt atcactactc tatctcctcc actaaatcat ttaaatgaaa   9660
ctgaaaagca ttggcaagtc tcctcccctc ctcaagtgat ttccaactca gcattggcat   9720
ctaattgatt cagtatatct attgcatgtg taaaagtctt tccacaatac ataactatta   9780
attaatctta aataaataaa ggataaaata ttttttttttc ttcataaaat taaaatatgt   9840 tatttttgt ttagatgtat attcgaataa atctaaaatat atgataatga ttttttatat   9900
tgattaaaca tataatcaat attaaatatg atattttttt atataggttg tacacataat   9960
tttataagga taaaaaatat gataaaaata aattttaaat attttttatat ttacgagaaa  10020 aaaaaatatt ttagccataa ataaatgacc agcatatttt acaaccttag taattcataa   10080
attcctatat gtatatttga aattaaaaac agataatcgt taagggaagg aatcctacgt   10140
catctcttgc catttgtttt tcatgcaaac agaaagggac gaaaaaccac ctcaccatga   10200
atcactcttc acaccatttt tactagcaaa caagtctcaa caactgaagc cagctctctt   10260
tccgtttctt tttacaacac tttctttgaa atagtagtat ttttttttca catgatttat   10320
taacgtgcca aaagatgctt attgaataga gtgcacattt gtaatgtact actaattaga   10380
acatgaaaaa gcattgttct aacacgataa tcctgtgaag gcgttaactc caaagatcca   10440
atttcactat ataaattgtg acgaaagcaa aatgaattca catagctgag agagaaagga   10500
aaggttaact aagaagcaat acttcagcgg ccgcatggag agatctcaac ggcagtctcc   10560
tccgccaccg tcgccgtcct cctcctcgtc ctccgtctcc gcggacaccg tcctcgtccc   10620
tcccggaaag aggcggaggg cggcgacggc caaggccggc gccgagccta ataagaggat   10680
ccgcaaggac cccgccgccg ccgccgcggg gaagaggagc tccgtctaca ggggagtcac   10740
caggcacagg tggacgggca ggttcgaggc gcatctctgg gacaagcact gcctcgccgc   10800
gctccacaac aagaagaaag gcaggcaagt ctacctgggg gcgtatgaca gcgaggaggc   10860
agctgctcgt gcctatgacc tcgcagctct caagtactgg ggtcctgaga ctctgctcaa   10920
cttccctgtg gaggattact ccagcgagat gccggagatg gaggccgtgt cccgggagga   10980
gtacctggcc tccctccgcc gcaggagcag cggcttctcc aggggcgtct ccaagtacag   11040
aggcgtcgcc aggcatcacc acaacggag gtgggaggca cggattgggc gagtctttgg   11100
gaacaagtac ctctacttgg gaacatttga cactcaagaa gaggcagcca aggcctatga   11160
ccttgcggcc attgaatacc gtggcgtcaa tgctgtaacc aacttcgaca tcagctgcta   11220
cctggaccac ccgctgttcc tggcacagct ccaacaggag ccacaggtgg tgccggcact   11280
caaccaagaa cctcaacctg atcagagcga aaccggaact acagagcaag agccggagtc   11340
aagcgaagcc aagacaccgg atggcagtgc agaacccgat gagaacgcgg tgcctgacga   11400
caccgcggag cccctcacca cagtcgacga cagcatcgaa gagggcttgt ggagcccttg   11460
catggattac gagctagaca ccatgtcgag accaaacttt ggcagctcaa tcaatctgag   11520
cgagtggttc gctgacgcag acttcgactg caacatcgga tgcctgttcg atgggtgttc   11580
```

-continued

| | |
|---|---|
| tgcggctgac gaaggaagca aggatggtgt aggtctggca gatttcagtc tgtttgaggc | 11640 |
| aggtgatgtc cagctgaagg atgttctttc ggatatggaa gagggatac aacctccagc | 11700 |
| gatgatcagt gtgtgcaacg c | 11721 |

<210> SEQ ID NO 32
<211> LENGTH: 19713
<212> TYPE: DNA
<213> ORGANISM: Artificial Sequence
<220> FEATURE:
<223> OTHER INFORMATION: vector pKR1220
<220> FEATURE:
<221> NAME/KEY: misc_feature
<222> LOCATION: (15083)..(15083)
<223> OTHER INFORMATION: n is a, c, g, or t

<400> SEQUENCE: 32

| | |
|---|---|
| cgcgccagat cctctagagt cgacctgcag gcatgcaagc ttggcgtaat catggtcata | 60 |
| gctgtttcct gtgtgaaatt gttatccgct cacaattcca cacaacatac gagccggaag | 120 |
| cataaagtgt aaagcctggg gtgcctaatg agtgagctaa ctcacattaa ttgcgttgcg | 180 |
| ctcactgccc gctttccagt cgggaaacct gtcgtgccag ctgcattaat gaatcggcca | 240 |
| acgcgcgggg agaggcggtt tgcgtattgg atcgatccct gaaagcgacg ttggatgtta | 300 |
| acatctacaa attgcctttt cttatcgacc atgtacgtaa gcgcttacgt ttttggtgga | 360 |
| cccttgagga aactggtagc tgttgtgggc ctgtggtctc aagatggatc attaatttcc | 420 |
| accttcacct acgatggggg gcatcgcacc ggtgagtaat attgtacggc taagagcgaa | 480 |
| tttggcctgt agacctcaat tgcgagcttt ctaatttcaa actattcggg cctaactttt | 540 |
| ggtgtgatga tgctgactgg caggatatat accgttgtaa tttgagctcg tgtgaataag | 600 |
| tcgctgtgta tgtttgtttg attgtttctg ttggagtgca gcccatttca ccggacaagt | 660 |
| cggctagatt gatttagccc tgatgaactg ccgaggggaa gccatcttga gcgcggaatg | 720 |
| ggaatggatt tcgttgtaca acgagacgac agaacaccca cgggaccgag cttcgcgagc | 780 |
| ttttgtatcc gtggcatcct tggtccgggc gatttgttca cgtccatgag gcgctctcca | 840 |
| aaggaacgca tattttccgg tgcaaccttt ccggttcttc ctctactcga cctcttgaag | 900 |
| tcccagcatg aatgttcgac cgctccgcaa gcggatcttt ggcgcaacca gccggtttcg | 960 |
| cacgtcgatt ctcgcgagcc tgcatacttt ggcaagattg ctgaatgacg ctgatgcttc | 1020 |
| atcgcaatct gcgataatgg ggtaagtatc cggtgaaggc cgcaggtcag gccgcctgag | 1080 |
| cactcagtgt cttggatgtc cagttccacg gcagctgttg ctcaagcctg ctgatcggag | 1140 |
| cgtccgcaag gtcggcgcgg acgtcggcaa gccaggcctg cggatcgatg ttattgagct | 1200 |
| tggcgctcat gatcagtgtc gccatgaacg ccgcacgttc agcacaacga tccgatccgg | 1260 |
| caaacagcca tgacttcctg ccgagtacat agcctctgag cgttcgttcg gcagcattgt | 1320 |
| tcgtcaggca aatcgggccg tcatcgagga atgacgtaat gccatccat cgcttgagca | 1380 |
| tgtaatttat cgcctcggcg acgggagaac tgcgcgacaa tttccccgc tcggtttcga | 1440 |
| gccaatcatg cagctcttcg gcgagtgacc ttgatcaggc caccgccacg accgcggaag | 1500 |
| acgaacagat gcctgcgcat cggatcgcgc ttcagcgtct cttgcaccat cagcgacaaa | 1560 |
| ccgggaaagc ctttgcgcat gtccgtactt atgtcgccac ttgggagggc ttcgtctacg | 1620 |
| tggccttcgt gatcgacgtc ttcgcccgtc gcattgtcgg atggcgggcg agccggacag | 1680 |
| cacatgcagg ctttgtcctc gatgccctcg aggaggctca tcatgatcgg cgtcccgctc | 1740 |
| atggcggcct agtgcatcac tcggatcgcg gtgttcaata cgtgtccttt cgctattccg | 1800 |

```
agcggttggc agaagcaggt atcgagccat ctatcggaag cgtcggcgac agcacgacaa    1860
cgccctcgca gaagcgatca acggtctttta caaggccgag gtcattcatc ggcgtggacc    1920
atggaggagc ttcgaagcgg tcgagttcgc taccttggaa tggatagact ggttcaacca    1980
cggcggcttt tgaagcccat cggcaatata ccgccagccg aagacgagga tcagtattac    2040
gccatgctgg acgaagcagc catgctgcg cattttaacg aaatggcctc cggcaaaccc    2100
ggtgcggttc acttgttgcg tgggaaagtt cacgggactc cgcgcacgag ccttcttcgt    2160
aatagccata tcgaccgaat tgacctgcag gggggggggg gaaagccacg ttgtgtctca    2220
aaatctctga tgttacattg cacaagataa aaatatatca tcatgaacaa taaaactgtc    2280
tgcttacata aacagtaata caaggggtgt tatgagccat attcaacggg aaacgtcttg    2340
ctcgaggccg cgattaaatt ccaacatgga tgctgattta tatgggtata aatgggctcg    2400
cgataatgtc gggcaatcag gtgcgacaat ctatcgattg tatgggaagc ccgatgcgcc    2460
agagttgttt ctgaaacatg gcaaaggtag cgttgccaat gatgttacag atgagatggt    2520
cagactaaac tggctgacgg aatttatgcc tcttccgacc atcaagcatt ttatccgtac    2580
tcctgatgat gcatggttac tcaccactgc gatccccggg aaaacagcat ccaggtatt    2640 agaagaatat cctgattcag gtgaaaatat tgttgatgcg ctggcagtgt tcctgcgccg    2700
gttgcattcg attcctgttt gtaattgtcc ttttaacagc gatcgcgtat ttcgtctcgc    2760
tcaggcgcaa tcacgaatga ataacggttt ggttgatgcg agtgattttg atgacgagcg    2820
taatggctgg cctgttgaac aagtctggaa agaaatgcat aagcttttgc cattctcacc    2880
ggattcagtc gtcactcatg gtgatttctc acttgataac cttattttg acgagggaa    2940 attaataggt tgtattgatg ttggacgagt cggaatcgca gaccgatacc aggatcttgc    3000
catcctatgg aactgcctcg gtgagttttc tccttcatta cagaaacggc tttttcaaaa    3060
atatggtatt gataatcctg atatgaataa attgcagttt catttgatgc tcgatgagtt    3120
tttctaatca gaattggtta attggttgta acactggcag agcattacgc tgacttgacg    3180
ggacggcggc tttgttgaat aaatcgaact tttgctgagt tgaaggatca gatcacgcat    3240
cttcccgaca acgcagaccg ttccgtggca aagcaaaagt tcaaaatcac caactggtcc    3300
acctacaaca aagctctcat caaccgtggc tccctcactt tctggctgga tgatggggcg    3360
attcaggcct ggtatgagtc agcaacacct tcttcacgag gcagacctca gcgccccccc    3420 cccccctgcag gtcttttcca atgatgagca cttttaaagt tctgctatgt ggcgcggtat    3480
tatcccgtgt tgacgccggg caagagcaac tcggtcgccg catacactat tctcagaatg    3540
acttggttga gtactcacca gtcacagaaa agcatcttac ggatggcatg acagtaagag    3600
aattatgcag tgctgccata accatgagtg ataacactgc ggccaactta cttctgacaa    3660
cgatcggagg accgaaggag ctaaccgctt ttttgcacaa catgggggat catgtaactc    3720
gccttgatcg ttgggaaccg gagctgaatg aagccatacc aaacgacgag cgtgacacca    3780
cgatgcctgt agcaatggca acaacgttgc gcaaactatt aactggcgaa ctacttactc    3840
tagcttcccg gcaacaatta atagactgga tgaggcgga taaagttgca ggaccacttc    3900
tgcgctcggc ccttccggct ggctggttta ttgctgataa atctggagcc ggtgagcgtg    3960
ggtctcgcgg tatcattgca gcactggggc cagatggtaa gccctcccgt atcgtagtta    4020
tctacacgac ggggagtcag gcaactatgg atgaacgaaa tagacagatc gctgagatag    4080
gtgcctcact gattaagcat tggtaactgt cagaccaagt ttactcatat atactttaga    4140
ttgatttaaa acttcatttt taatttaaaa ggatctaggt gaagatcctt tttgataatc    4200
```

```
tcatgaccaa atcccttaa cgtgagtttt cgttccactg agcgtcagac cccgtagaaa    4260
agatcaaagg atcttcttga gatcctttt ttctgcgcgt aatctgctgc ttgcaaacaa    4320
aaaaaccacc gctaccagcg gtggtttgtt tgccggatca agagctacca actcttttc    4380 cgaaggtaac tggcttcagc agagcgcaga taccaaatac tgtccttcta gtgtagccgt    4440
agttaggcca ccacttcaag aactctgtag caccgcctac atacctcgct ctgctaatcc    4500
tgttaccagt ggctgctgcc agtggcgata agtcgtgtct taccgggttg gactcaagac    4560
gatagttacc ggataaggcg cagcggtcgg gctgaacggg gggttcgtgc acacagccca    4620
gcttggagcg aacgacctac accgaactga gatacctaca gcgtgagcta tgagaaagcg    4680
ccacgcttcc cgaagggaga aaggcggaca ggtatccggt aagcggcagg gtcggaacag    4740
gagagcgcac gagggagctt ccaggggaaa acgcctggta tctttatagt cctgtcgggt    4800
ttcgccacct ctgacttgag cgtcgatttt tgtgatgctc gtcaggggg cggagcctat    4860 ggaaaaacgc cagcaacgcg gcctttttac ggttcctggc cttttgctgg ccttttgctc    4920
acatgttctt cctgcgttta tcccctgatt ctgtggataa ccgtattacc gcctttgagt    4980
gagctgatac cgctcgccgc agccgaacga ccgagcgcag cgagtcagtg agcgaggaag    5040
cggaagagcg cctgatgcgg tattttctcc ttacgcatct gtgcggtatt tcacaccgca    5100
tatggtgcac tctcagtaca atctgctctg atgccgcata gttaagccag tatacactcc    5160
gctatcgcta cgtgactggg tcatggctgc gccccgacac ccgccaacac ccgctgacgc    5220
gccctgacgg gcttgtctgc tcccggcatc cgcttacaga caagctgtga ccgtctccgg    5280
gagctgcatg tgtcagaggt tttcaccgtc atcaccgaaa cgcgcgaggc agggtgcctt    5340
gatgtgggcg ccggcggtcg agtggcgacg gcgcggcttg tccgcgccct ggtagattgc    5400
ctggccgtag gccagccatt tttgagcggc cagcggccgc gataggccga cgcgaagcgg    5460
cggggcgtag ggagcgcagc gaccgaaggg taggcgcttt ttgcagctct cggctgtgc     5520 gctggccaga cagttatgca caggccaggc gggttttaag agttttaata agttttaaag    5580
agttttaggc ggaaaaatcg cctttttct ctttatatc agtcacttac atgtgtgacc      5640
ggttcccaat gtacggcttt gggttcccaa tgtacgggtt ccggttccca atgtacggct    5700
ttgggttccc aatgtacgtg ctatccacag gaaagagacc ttttcgacct ttttccctg     5760 ctagggcaat ttgccctagc atctgctccg tacattagga accggcggat gcttcgccct    5820
cgatcaggtt gcggtagcgc atgactagga tcgggccagc ctgccccgcc tcctccttca    5880
aatcgtactc cggcaggtca tttgacccga tcagcttgcg cacggtgaaa cagaacttct    5940
tgaactctcc ggcgctgcca ctgcgttcgt agatcgtctt gaacaaccat ctggcttctg    6000
ccttgcctgc ggcgcggcgt gccaggcggt agagaaaacg gccgatgccg ggatcgatca    6060
aaaagtaatc ggggtgaacc gtcagcacgt ccgggttctt gccttctgtg atctcgcggt    6120
acatccaatc agctagctcg atctcgatgt actccggccg cccggtttcg ctctttacga    6180
tcttgtagcg gctaatcaag gcttcaccct cggataccgt caccaggcgg ccgttcttgg    6240
ccttcttcgt acgctgcatg gcaacgtgcg tggtgtttaa ccgaatgcag gtttctacca    6300
ggtcgtcttt ctgctttccg ccatcggctc gccggcagaa cttgagtacg tccgcaacgt    6360
gtggacggaa cacgcggccg ggcttgtctc ccttcccttc ccgtatcgg ttcatggatt     6420 cggttagatg ggaaaccgcc atcagtacca ggtcgtaatc ccacacactg gccatgccgg    6480
ccggccctgc ggaaacctct acgtgcccgt ctggaagctc gtagcggatc acctcgccag    6540
ctcgtcggtc acgcttcgac agacggaaaa cggccacgtc catgatgctg cgactatcgc    6600
```

```
gggtgcccac gtcatagagc atcggaacga aaaaatctgg ttgctcgtcg cccttgggcg    6660
gcttcctaat cgacggcgca ccggctgccg gcggttgccg ggattctttg cggattcgat    6720
cagcggccgc ttgccacgat tcaccggggc gtgcttctgc ctcgatgcgt tgccgctggg    6780
cggcctgcgc ggccttcaac ttctccacca ggtcatcacc cagcgccgcg ccgatttgta    6840
ccgggccgga tggtttgcga ccgctcacgc cgattcctcg ggcttggggg ttccagtgcc    6900
attgcagggc cggcagacaa cccagccgct tacgcctggc caaccgcccg ttcctccaca    6960 catgggcat tccacggcgt cggtgcctgg ttgttcttga ttttccatgc cgcctccttt     7020
agccgctaaa attcatctac tcatttattc atttgctcat ttactctggt agctgcgcga    7080
tgtattcaga tagcagctcg gtaatggtct tgccttggcg taccgcgtac atcttcagct    7140
tggtgtgatc ctccgccggc aactgaaagt tgacccgctt catggctggc gtgtctgcca    7200
ggctggccaa cgttgcagcc ttgctgctgc gtgcgctcgg acggccggca cttagcgtgt    7260
ttgtgctttt gctcattttc tctttacctc attaactcaa atgagttttg atttaatttc    7320
agcggccagc gcctggacct cgcgggcagc gtcgccctcg ggttctgatt caagaacggt    7380
tgtgccggcg gcggcagtgc ctgggtagct cacgcgctgc gtgatacggg actcaagaat    7440
gggcagctcg tacccggcca gcgcctcggc aacctcaccg ccgatgcgcg tgcctttgat    7500
cgcccgcgac acgacaaagg ccgcttgtag ccttccatcc gtgacctcaa tgcgctgctt    7560
aaccagctcc accaggtcgg cggtggccca tatgtcgtaa gggcttggct gcaccggaat    7620
cagcacgaag tcgctgcct tgatcgcgga cacagccaag tccgccgcct ggggcgctcc     7680
gtcgatcact acgaagtcgc gccggccgat ggccttcacg tcgcggtcaa tcgtcgggcg    7740
gtcgatgccg acaacggtta gcggttgatc ttcccgcacg gccgcccaat cgcgggcact    7800
gccctgggga tcggaatcga ctaacagaac atcggcccg gcgagttgca gggcgcgggc      7860
tagatgggtt gcgatggtcg tcttgcctga cccgcctttc tggttaagta cagcgataac    7920
ttcatgcgtt cccttgcgta tttgtttatt tactcatcgc atcatatacg cagcgaccgc    7980
atgacgcaag ctgttttact caaatacaca tcaccttttt agacggcggc gctcggtttc    8040
ttcagcggcc aagctggccg gccaggccgc cagcttggca tcagacaaac cggccaggat    8100
ttcatgcagc cgcacggttg agacgtgcgc gggcggctcg aacacgtacc cggccgcgat    8160
catctccgcc tcgatctctt cggtaatgaa aaacggttcg tcctggccgt cctggtgcgg    8220
tttcatgctt gttcctcttg gcgttcattc tcggcggccg ccaggcgtc ggcctcggtc      8280 aatgcgtcct cacggaaggc accgcgccgc ctggcctcgg tgggcgtcac ttcctcgctg    8340
cgctcaagtg cgcggtacag ggtcgagcga tgcacgccaa gcagtgcagc cgcctctttc    8400
acggtgcggc cttcctggtc gatcagctcg cgggcgtgcg cgatctgtgc cggggtgagg    8460
gtagggcggg ggccaaactt cacgcctcgg gccttggcgg cctcgcgccc gctccgggtg    8520
cggtcgatga ttagggaacg ctcgaactcg gcaatgccgg cgaacacggt caacaccatg    8580
cggccggccg gcgtggtggt gtcggcccac ggctctgcca ggctacgcag gcccgcgccg    8640
gcctcctgga tgcgctcggc aatgtccagt aggtcgcggg tgctgcgggc caggcggtct    8700
agcctggtca ctgtcacaac gtcgccaggg cgtaggtggt caagcatcct ggccagctcc    8760
gggcggtcgc gcctggtgcc ggtgatcttc tcggaaaaca gcttggtgca gccggccgcg    8820
tgcagttcgg cccgttggtt ggtcaagtcc tggtcgtcgg tgctgacgcg ggcatagccc    8880
agcaggccag cggcggcgct cttgttcatg gcgtaatgtc tccggttcta gtcgcaagta    8940
ttctacttta tgcgactaaa acacgcgaca agaaaacgcc aggaaaaggg cagggcggca    9000
```

```
gcctgtcgcg taacttagga cttgtgcgac atgtcgtttt cagaagacgg ctgcactgaa   9060
cgtcagaagc cgactgcact atagcagcgg aggggttgga ccacaggacg ggtgtggtcg   9120
ccatgatcgc gtagtcgata gtggctccaa gtagcgaagc gagcaggact gggcggcggc   9180
caaagcggtc ggacagtgct ccgagaacgg gtgcgcatag aaattgcatc aacgcatata   9240
gcgctagcag cacgccatag tgactggcga tgctgtcgga atggacgata tcccgcaaga   9300
ggcccggcag taccggcata accaagccta tgcctacagc atccagggtg acggtgccga   9360
ggatgacgat gagcgcattg ttagatttca tacacggtgc ctgactgcgt tagcaattta   9420
actgtgataa actaccgcat taaagctagc ttgcttggtc gttccgcgtg aacgtcggct   9480
cgattgtacc tgcgttcaaa tactttgcga tcgtgttgcg cgcctgcccg gtgcgtcggc   9540
tgatctcacg gatcgactgc ttctctcgca acgccatccg acggatgatg tttaaaagtc   9600
ccatgtggat cactccgttg ccccgtcgct caccgtgttg gggggaaggt gcacatggct   9660
cagttctcaa tggaaattat ctgcctaacc ggctcagttc tgcgtagaaa ccaacatgca   9720
agctccaccg ggtgcaaagc ggcagcggcg gcaggatata ttcaattgta aatggcttca   9780
tgtccgggaa atctacatgg atcagcaatg agtatgatgg tcaatatgga gaaaagaaa    9840
gagtaattac caatttttt tcaattcaaa aatgtagatg tccgcagcgt tattataaaa    9900
tgaaagtaca ttttgataaa acgacaaatt acgatccgtc gtatttatag gcgaaagcaa   9960
taaacaaatt attctaattc ggaaatcttt atttcgacgt gtctacattc acgtccaaat  10020
gggggcttag atgagaaact tcacgatcga tgccttgatt tgccattcc cagatacccca  10080
tttcatcttc agattggtct gagattatgc gaaaatatac actcatatac ataaatactg  10140
acagtttgag ctaccaattc agtgtagccc attacctcac ataattcact caaatgctag  10200
gcagtctgtc aactcggcgt caatttgtcg gccactatac gatagttgcg caaattttca  10260
aagtcctggc ctaacatcac acctctgtcg gcggcgggtc ccatttgtga taatccacc   10320
atatcgaatt aattcagact cctttgcccc agagatcaca atggacgact tcctctatct  10380
ctacgatcta gtcaggaagt tcgacggaga aggtgacgat accatgttca ccactgataa  10440
tgagaagatt agccttttca atttcagaaa gaatgctaac ccacagatgg ttagagaggc  10500
ttacgcagca ggtctcatca agacgatcta cccgagcaat aatctccagg agatcaaata  10560
ccttcccaag aaggttaaag atgcagtcaa aagattcagg actaactgca tcaagaacac  10620
agagaaagat atatttctca agatcagaag tactattcca gtatggacga ttcaaggctt  10680
gcttcacaaa ccaaggcaag taatagagat tggagtctct aaaaaggtag ttcccactga  10740
atcaaaggcc atggagtcaa agattcaaat agaggaccta acagaactcg ccgtaaagac  10800
tggcgaacag ttcatacaga gtctcttacg actcaatgac aagaagaaaa tcttcgtcaa  10860
catggtggag cacgacacgc ttgtctactc caaaaatatc aaagatacag tctcagaaga  10920
ccaaagggca attgagactt tcaacaaag ggtaatatcc ggaaacctcc tcggattcca   10980
ttgcccagct atctgtcact ttattgtgaa gatagtggaa aaggaaggtg gctcctacaa  11040
atgccatcat tgcgataaag gaaaggccat cgttgaagat gcctctgccg acagtggtcc  11100
caaagatgga ccccacccca cgaggagcat cgtggaaaaa gaagacgttc caaccacgtc  11160
ttcaaagcaa gtggattgat gtgatatctc cactgacgta agggatgacg cacaatccca  11220
ctatccttcg caagacccct cctctatata aggaagttca tttcatttgg agaggacacg  11280
ctgaaatcac cagtctccaa gcttgcgggg atcgtttcgc atgattgaac aagatggatt  11340
gcacgcaggt tctccggccg cttgggtgga gaggctattc ggctatgact gggcacaaca  11400
```

```
gacaatcggc tgctctgatg ccgccgtgtt ccggctgtca gcgcagggc gcccggttct   11460 tttgtcaag  accgacctgt ccggtgccct gaatgaactg caggacgagg cagcgcggct   11520
atcgtggctg gccacgacgg gcgttccttg cgcagctgtg ctcgacgttg tcactgaagc   11580
gggaagggac tggctgctat tgggcgaagt gccggggcag gatctcctgt catctcacct   11640
tgctcctgcc gagaaagtat ccatcatggc tgatgcaatg cggcggctgc atacgcttga   11700
tccggctacc tgcccattcg accaccaagc gaaacatcgc atcgagcgag cacgtactcg   11760
gatggaagcc ggtcttgtcg atcaggatga tctggacgaa gagcatcagg gctcgcgcc    11820 agccgaactg ttcgccaggc tcaaggcgcg catgcccgac ggcgaggatc tcgtcgtgac   11880
ccatggcgat gcctgcttgc cgaatatcat ggtggaaaat ggccgctttt ctggattcat   11940
cgactgtggc cggctgggtg tggcggaccg ctatcaggac atagcgttgg ctacccgtga   12000
tattgctgaa gagcttggcg gcgaatgggc tgaccgcttc ctcgtgcttt acggtatcgc   12060
cgctcccgat tcgcagcgca tcgccttcta tcgccttctt gacgagttct tctgagcggg   12120
actctggggt tcgaaatgac cgaccaagcg acgcccaacc tgccatcacg agatttcgat   12180
tccaccgccg ccttctatga aaggttgggc ttcggaatcg ttttccggga cgccggctgg   12240
atgatcctcc agcgcgggga tctcatgctg gagttcttcg cccaccccgg atcgatccaa   12300
cacttacgtt tgcaacgtcc aagagcaaat agaccacgaa cgccggaagg ttgccgcagc   12360
gtgtggattg cgtctcaatt ctctcttgca ggaatgcaat gatgaatatg atactgacta   12420
tgaaactttg agggaatact gcctagcacc gtcacctcat aacgtgcatc atgcatgccc   12480
tgacaacatg gaacatcgct attttttctga agaattatgc tcgttggagg atgtcgcggc   12540
aattgcagct attgccaaca tcgaactacc cctcacgcat gcattcatca atattattca   12600
tgcggggaaa ggcaagatta atccaactgg caaatcatcc agcgtgattg gtaacttcag   12660
ttccagcgac ttgattcgtt ttggtgctac ccacgttttc aataaggacg agatggtgga   12720
gtaaagaagg agtgcgtcga agcagatcgt tcaaacattt ggcaataaag tttcttaaga   12780
ttgaatcctg ttgccggtct tgcgatgatt atcatataat ttctgttgaa ttacgttaag   12840
catgtaataa ttaacatgta atgcatgacg ttatttatga gatgggtttt tatgattaga   12900
gtcccgcaat tatacattta atacgcgata gaaaacaaaa tatagcgcgc aaactaggat   12960
aaattatcgc gcgcggtgtc atctatgtta ctagatcgat caaacttcgg tactgtgtaa   13020
tgacgatgag caatcgagag gctgactaac aaaaggtaca tcgcgatgga tcgatccatt   13080
cgccattcag gctgcgcaac tgttgggaag ggcgatcggt gcgggcctct tcgctattac   13140
gccagctggc gaaaggggga tgtgctgcaa ggcgattaag ttgggtaacg ccagggtttt   13200
cccagtcacg acgttgtaaa acgacggcca gtgaattcct gcagcccggg ggatccgccc   13260
actcgaggcg cgccgtcgac ggatataatg agccgtaaac aaagatgatt aagtagtaat   13320
taatacgtac tagtaaaagt ggcaaaagat aacgagaaag aaccaatttc tttgcattcg   13380
gccttagcgg aaggcatata taagctttga ttattttatt tagtgtaatg atttcgtaca   13440
accaaagcat ttatttagta ctctcacact tgtgtcgcgg ccggccgcta caggaacagg   13500
tggtggcggc cctcggcgcg ctcgtactgc tccacgatgg tgtagtcctc gttgtgggag   13560
gtgatgtcca gcttggagtc cacgtagtag tagccgggca gctgcacggg cttcttggcc   13620
atgtagatgg acttgaactc caccaggtag tggccgccgt ccttcagctt cagggccttg   13680
tggatctcgc ccttcagcac gccgtcgcgg gggtacaggc gctcggtgga ggcctccag    13740 cccatagtct tcttctgcat tacggggccg tcggagggga agttcacgcc gatgaacttc   13800
```

-continued

```
accttgtaga tgaaggagcc gtcctgcagg gaggagtcct gggtcacggt caccacgccg  13860
ccgtcctcga agttcatcac gcgctcccac ttgaagcccc cggggaagga cagcttcttg  13920
tagtcgggga tgtcggcggg gtgcttcacg tacaccttgg agccgtactg gaactggggg  13980
gacaggatgt cccaggcgaa gggcaggggg ccgcccttgg tcaccttcag cttggcggtc  14040
tgggtgccct cgtaggggcg gccctcgccc tcgccctcga tctcgaactc gtggccgttc  14100
acggagccct ccatgcgcac cttgaagcgc atgaactcct tgatgacgtc ctcggaggag  14160
gccatgggcc gcttgggggg ctatggaaga cttctcttagt tagttgtgtg aataagcaat  14220
gttgggagaa tcgggactac ttataggata ggaataaaac agaaagtat taagtgctaa  14280 tgaaatattt agactgataa ttaaaatctt cacgtatgtc cacttgatat aaaaacgtca  14340
ggaataaagg aagtacagta gaatttaaag gtactctttt tatatatacc cgtgttctct  14400
ttttggctag ctagttgcat aaaaaataat ctatatttttt atcattattt taaatatctt  14460
atgagatggt aaatatttat cataatttttt tttactatta tttattattt gtgtgtgtaa  14520
tacatataga agttaattac aaattttatt tactttttca ttattttgat atgattcacc  14580
attaatttag tgttattatt tataatagtt catttttaatc ttttttgtata tattatgcgt  14640 gcagtacttt tttcctacat ataactacta ttacatttta tttatataat attttttatta  14700 atgaatttttc gtgataatat gtaatattgt tcattattat ttcagatttt ttaaaaatat  14760
ttgtgttatt atttatgaaa tatgtaattt ttttagtatt tgatttttatg atgataaagt  14820 gttctaaatt caaagaagg gggaaagcgt aaacattaaa aaacgtcatc aaacaaaaac  14880
aaaatcttgt taataaagat aaaactgttt gttttgatca ctgttatttc gtaatataaa  14940
aacattattt atatttatat tgttgacaac caaatttgcc tatcaaatct aaccaatata  15000
atgcatgcgt ggcaggtaat gtactaccat gaacttaagt catgacataa taaaccgtga  15060
atctgaccaa tgcatgtacc tanctaaatt gtatttgtga cacgaagcaa atgattcaat  15120
tcacaatgga gatgggaaac aaataatgaa gaacccagaa ctaagaaagc ttttctgaaa  15180
aataaaataa aggcaatgtc aaagtatac tgcatcatca gtccagaaag cacatgatat  15240 tttttttatca gtatcaatgc agctagttttt attttacaat atcgatatag ctagtttaaa  15300
tatattgcag ctagatttat aaatatttgt gttattatttt atcatttgtg taatcctgtt  15360 tttagtatttt tagtttatat atgatgataa tgtattccaa atttaaaaga agggaaataa  15420
atttaaacaa gaaaaaaagt catcaaacaa aaaacaaatg aaagggtgga agatgttac  15480 catgtaatgt gaatgttaca gtatttcttt tattatagag ttaacaaatt aactaatatg  15540
attttgttaa taatgataaa atatttttt tattattatt tcataatata aaaatagttt  15600
acttaatata aaaaaaattc tatcgttcac aacaaagttg gccacctaat ttaaccatgc  15660
atgtacccat ggaccatatt aggtaaccat caaacctgat gaagagataa agagatgaag  15720
acttaagtca taacacaaaa ccataaaaaa caaaaataca atcaaccgtc aatctgacca  15780
atgcatgaaa aagctgcaat agtgagtggc gacacaaagc acatgatttt cttacaacgg  15840
agataaaacc aaaaaaatat ttcatgaaca acctagaaca aataaagctt ttatataata  15900
aatatataaa taaataaagg ctatggaata atatacttca atatatttgg attaaataaa  15960
ttgttggcgg ggttgatata tttatacaca cctaaagtca cttcaatctc attttcactt  16020
aactttattt tttttttttct ttttatttat cataaagaga atattgataa tatactttt  16080 aacatatttt tatgacattt tttattggtg aaaacttatt aaaaatcata aatttttgtaa  16140 gttagatttta tttaaagagt tcctcttctt attttaaatt ttttaataaa tttttaaata  16200
```

```
actaaaattt gtgttaaaaa tgttaaaaaa gtgtgttatt aacccttctc ttcgaggatc    16260
cgtacgatcc cacatgcaag tttttatttc aatccctttt cctttgaata actgaccaag    16320
aacaacaaga aaaaaaaaaa aaaagaaaag gatcattttg aaaggatatt tttcgctcct    16380
attcaaatac tgtatttta ccaaaaaaac tgtatttttc ctacactctc aagctttgtt    16440
tttcgcttcg actctcatga tttccttcat atgccaatca ctctatttat aaatggcata    16500
aggtagtgtg aacaattgca aagcttgtca tcaaaagctt gcaatgtaca aattaatgtt    16560
tttcatgcct ttcaaaatta tctgcacccc ctagctatta atctaacatc taagtaaggc    16620
tagtgaattt tttcgaatag tcatgcagtg cattaatttc cccgtgacta ttttggcttt    16680
gactccaaca ctggccccgt acatccgtcc ctcattacat gaaaagaaat attgtttata    16740
ttcttaatta aaaatattgt cccttctaaa ttttcatata gttaattatt atattacttt    16800
tttctctatt ctattagttc tatttcaaa ttattattta tgcatatgta aagtacatta    16860 tattttgct atacttaa atattctaa attattaaaa aaagactgat atgaaaaatt    16920 tattctttt aaagctatat cattttatat atacttttc ttttctttc tttcatttc    16980 tattcaattt aataagaaat aaattttgta aattttatt tatcaattta taaaaatatt    17040
ttactttata tgttttttca cattttgtt aaacaaatca tatcattatg attgaaagag    17100
aggaaattga cagtgagtaa taagtgatga gaaaaaatg tgttatttcc taaaaaaac    17160 ctaaacaaac atgtatctac tctctatttc atctatctct catttcattt ttctctttat    17220 ctcttctt atttttat catatcattt cacattaatt attttactc tctttatttt    17280 ttctctctat ccctctctta tttccactca tatatacact ccaaaattgg ggcatgcctt    17340
tatcactact ctatctcctc cactaaatca tttaaatgaa actgaaaagc attggcaagt    17400
ctcctcccct cctcaagtga tttccaactc agcattggca tctaattgat tcagtatatc    17460
tattgcatgt gtaaaagtct ttccacaata cataactatt aattaatctt aaataaataa    17520
aggataaaat attttttttt cttcataaaa ttaaaatatg ttatttttg tttagatgta    17580 tattcgaata aatctaaata tatgataatg atttttata ttgattaaac atataatcaa    17640
tattaaatat gatatttttt tataaggtt gtacacataa ttttataagg ataaaaaata    17700
tgataaaaat aaattttaaa tattttata tttacgagaa aaaaaaatat tttagccata    17760
aataaatgac cagcatattt tacaaccta gtaattcata aattcctata tgtatatttg    17820
aaattaaaaa cagataatcg ttaagggaag gaatcctacg tcatctcttg ccatttgttt    17880
ttcatgcaaa cagaaaggga cgaaaaacca cctcaccatg aatcactctt cacaccattt    17940
ttactagcaa acaagtctca acaactgaag ccagctctct ttccgtttct ttttacaaca    18000
ctttctttga aatagtagta tttttttttc acatgattta ttaacgtgcc aaaagatgct    18060
tattgaatag agtgcacatt tgtaatgtac tactaattag aacatgaaaa agcattgttc    18120
taacacgata atcctgtgaa ggcgttaact ccaaagatcc aatttcacta tataaattgt    18180
gacgaaagca aaatgaattc acatagctga gagagaaagg aaaggttaac taagaagcaa    18240
tacttcagcg gccgcatgga gagatctcaa cggcagtctc ctccgccacc gtcgccgtcc    18300
tcctcctcgt cctccgtctc cgcggacacc gtcctcgtcc ctcccggaaa gaggcggagg    18360
gcggcgacgg ccaaggccgg cgccgagcct aataagagga tccgcaagga ccccgccgcc    18420
gccgccgcgg ggaagaggag ctccgtctac aggggagtca ccaggcacag gtggacgggc    18480
aggttcgagg cgcatctctg ggacaagcac tgcctcgccg cgctccacaa caagaagaaa    18540
ggcaggcaag tctacctggg ggcgtatgac agcgaggagg cagctgctcg tgcctatgac    18600
```

```
ctcgcagctc tcaagtactg gggtcctgag actctgctca acttccctgt ggaggattac    18660
tccagcgaga tgccggagat ggaggccgtg tcccgggagg agtacctggc ctccctccgc    18720
cgcaggagca gcggcttctc caggggcgtc tccaagtaca gaggcgtcgc caggcatcac    18780
cacaacggga ggtgggaggc acggattggg cgagtctttg gaacaagta cctctacttg     18840 ggaacatttg acactcaaga agaggcagcc aaggcctatg accttgcggc cattgaatac    18900
cgtggcgtca atgctgtaac caacttcgac atcagctgct acctggacca cccgctgttc    18960
ctggcacagc tccaacagga gccacaggtg gtgccggcac tcaaccaaga acctcaacct    19020
gatcagagcg aaaccggaac tacagagcaa gagccggagt caagcgaagc caagacaccg    19080
gatggcagtg cagaacccga tgagaacgcg gtgcctgacg acaccgcgga gccctcacc     19140 acagtcgacg acagcatcga gagggcttg tggagccctt gcatggatta cgagctagac     19200
accatgtcga gaccaaactt tggcagctca atcaatctga gcgagtggtt cgctgacgca    19260
gacttcgact gcaacatcgg atgcctgttc gatgggtgtt ctgcggctga cgaaggaagc    19320
aaggatggtg taggtctggc agatttcagt ctgtttgagg caggtgatgt ccagctgaag    19380
gatgttcttt cggatatgga agaggggata caacctccag cgatgatcag tgtgtgcaac    19440
gcggccgcat gagccgtaaa ggttcaatac aacgagtgct tgttttctta gggacaagca    19500
ttgtacttat gtatgattct gtgtaaccat gagtcttcca cgttgtacta atgtgaaggg    19560
caaaaataaa acacagaaca agttcgtttt tctcaaataa tgtgaaggta gaaatggaa     19620 ccatgcctcc tctcttgcat gtgatttaaa atattagcag atggtaccgt acgagatccg    19680
gccggccaga tcctgcagga gatccaagct tgg                                 19713

<210> SEQ ID NO 33
<211> LENGTH: 10287
<212> TYPE: DNA
<213> ORGANISM: Artificial Sequence
<220> FEATURE:
<223> OTHER INFORMATION: vector pKR1144
<220> FEATURE:
<221> NAME/KEY: misc_feature
<222> LOCATION: (7136)..(7136)
<223> OTHER INFORMATION: n is a, c, g, or t

<400> SEQUENCE: 33
gtacgagatc cggccggcca gatcctgcag gagatccaag cttggcgcgc cgttctatag      60
tgtcacctaa atcgtatgtg tatgatacat aaggttatgt attaattgta gccgcgttct     120
aacgacaata tgtccatatg gtgcactctc agtacaatct gctctgatgc cgcatagtta     180
agccagcccc gacacccgcc aacaccgct gacgcgccct gacgggcttg tctgctcccg      240
gcatccgctt acagacaagc tgtgaccgtc tccgggagct gcatgtgtca gaggttttca    300
ccgtcatcac cgaaacgcgc gagacgaaag ggcctcgtga tacgcctatt tttataggtt    360
aatgtcatga ccaaaatccc ttaacgtgag ttttcgttcc actgagcgtc agaccccgta    420
gaaaagatca aaggatcttc ttgagatcct ttttttctgc gcgtaatctg ctgcttgcaa    480
acaaaaaaac caccgctacc agcggtggtt tgtttgccgg atcaagagct accaactctt    540
tttccgaagg taactggctt cagcagagcg cagataccaa atactgtcct tctagtgtag    600
ccgtagttag gccaccactt caagaactct gtagcaccgc ctacatacct cgctctgcta    660
atcctgttac cagtggctgc tgccagtggc gataagtcgt gtcttaccgg gttggactca    720
agacgatagt taccggataa ggcgcagcgg tcgggctgaa cggggggttc gtgcacacag    780
cccagcttgg agcgaacgac ctacaccgaa ctgagatacc tacagcgtga gcattgagaa    840
```

```
agcgccacgc ttcccgaagg gagaaaggcg gacaggtatc cggtaagcgg cagggtcgga    900
acaggagagc gcacgaggga gcttccaggg ggaaacgcct ggtatcttta tagtcctgtc    960
gggtttcgcc acctctgact tgagcgtcga ttttgtgat gctcgtcagg ggggcggagc   1020
ctatggaaaa acgccagcaa cgcggccttt ttacggttcc tggccttttg ctggcttttt   1080
gctcacatgt tctttcctgc gttatcccct gattctgtgg ataaccgtat taccgccttt   1140
gagtgagctg ataccgctcg ccgcagccga acgaccgagc gcagcgagtc agtgagcgag   1200
gaagcggaag agcgcccaat acgcaaaccg cctctcccg cgcgttggcc gattcattaa    1260
tgcaggttga tcgattcgac atcgatctag taacatagat gacaccgcgc gcgataattt   1320
atcctagttt gcgcgctata ttttgtttc tatcgcgtat taaatgtata attgcgggac    1380
tctaatcata aaaacccatc tcataaataa cgtcatgcat tacatgttaa ttattacatg   1440
cttaacgtaa ttcaacagaa attatatgat aatcatcgca agaccggcaa caggattcaa   1500
tcttaagaaa ctttattgcc aaatgtttga acgatctgct tcgacgcact ccttctttag   1560
gtacctcact attcctttgc cctcggacga gtgctggggc gtcggtttcc actatcggcg   1620
agtacttcta cacagccatc ggtccagacg gccgcgcttc tgcgggcgat ttgtgtacgc   1680
ccgacagtcc cggctccgga tcggacgatt gcgtcgcatc gaccctgcgc caagctgca    1740
tcatcgaaat tgccgtcaac caagctctga tagagttggt caagaccaat gcggagcata   1800
tacgcccgga gccgcggcga tcctgcaagc tccggatgcc tccgctcgaa gtagcgcgtc   1860
tgctgctcca tacaagccaa ccacggcctc cagaagaaga tgttggcgac ctcgtattgg   1920
gaatccccga acatcgcctc gctccagtca atgaccgctg ttatgcggcc attgtccgtc   1980
aggacattgt tggagccgaa atccgcgtgc acgaggtgcc ggacttcggg gcagtcctcg   2040
gcccaaagca tcagctcatc gagagcctgc gcgacggacg cactgacggt gtcgtccatc   2100
acagtttgcc agtgatacac atggggatca gcaatcgcgc atatgaaatc acgccatgta   2160
gtgtattgac cgattccttg cggtccgaat gggccgaacc cgctcgtctg gctaagatcg   2220
gccgcagcga tcgcatccat ggcctccgcg accggctgca gaacagcggg cagttcggtt   2280
tcaggcaggt cttgcaacgt gacaccctgt gcacggcggg agatgcaata ggtcaggctc   2340
tcgctgaatt ccccaatgtc aagcacttcc ggaatcggga gcgcggccga tgcaaagtgc   2400
cgataaacat aacgatcttt gtagaaacca tcggcgcagc tatttacccg caggacatat   2460
ccacgccctc ctacatcgaa gctgaaagca cgagattctt cgccctccga gagctgcatc   2520
aggtcggaga cgctgtcgaa cttttcgatc agaaacttct cgacagacgt cgcggtgagt   2580
tcaggctttt tcatggttta ataagaagag aaaagagttc ttttgttatg gctgaagtaa   2640
tagagaaatg agctcgagcg tgtcctctcc aaatgaaatg aacttcctta tatagaggaa   2700
gggtcttgcg aaggatagtg ggattgtgcg tcatccctta cgtcagtgga gatgtcacat   2760
caatccactt gctttgaaga cgtggttgga acgtcttctt tttccacgat gctcctcgtg   2820
ggtggggtc catctttggg accactgtcg gcagaggcat cttgaatgat agcctttcct    2880
ttatcgcaat gatggcattt gtaggagcca ccttcctttt ctactgtcct ttcgatgaag   2940
tgacagatag ctgggcaatg gaatccgagg aggtttcccg aaattatcct tgttgaaaa    3000
gtctcaatag ccctttggtc ttctgagact gtatctttga cattttgga gtagaccaga    3060
gtgtcgtgct ccaccatgtt gacgaagatt ttcttcttgt cattgagtcg taaaagactc   3120
tgtatgaact gttcgccagt cttcacgcg agttctgtta gatcctcgat ttgaatctta    3180
gactccatgc atggccttag attcagtagg aactaccttt ttagagactc caatctctat   3240
```

-continued

```
tacttgcctt ggtttatgaa gcaagccttg aatcgtccat actggaatag tacttctgat    3300
cttgagaaat atgtctttct ctgtgttctt gatgcaatta gtcctgaatc ttttgactgc    3360
atctttaacc ttcttgggaa ggtatttgat ctcctggaga ttgttactcg ggtagatcgt    3420
cttgatgaga cctgctgcgt aggcctctct aaccatctgt gggtcagcat tctttctgaa    3480
attgaagagg ctaaccttct cattatcagt ggtgaacata gtgtcgtcac cttcaccttc    3540
gaacttcctt cctagatcgt aaagatagag gaaatcgtcc attgtaatct ccggggcaaa    3600
ggagatctct tttggggctg atcactgct  gggcctttg  gttcctagcg tgagccagtg    3660 ggcttttgc  tttggtgggc ttgttagggc cttagcaaag ctcttgggct tgagttgagc    3720
ttctcctttg gggatgaagt tcaacctgtc tgtttgctga cttgttgtgt acgcgtcagc    3780
tgctgctctt gcctctgtaa tagtggcaaa tttcttgtgt gcaactccgg gaacgccgtt    3840
tgttgccgcc tttgtacaac cccagtcatc gtatataccg gcatgtggac cgttatacac    3900
aacgtagtag ttgatatgag ggtgttgaat acccgattct gctctgagag gagcaactgt    3960
gctgttaagc tcagattttt gtgggattgg aattggatcg atctcgatcc cgcgaaatta    4020
atacgactca ctatagggag accacaacgg tttccctcta gaaataattt tgtttaactt    4080
taagaaggag atatacccat ggaaaagcct gaactcaccg cgacgtctgt cgagaagttt    4140
ctgatcgaaa agttcgacag cgtctccgac ctgatgcagc tctcggaggg cgaagaatct    4200
cgtgctttca gcttcgatgt aggagggcgt ggatatgtcc tgcgggtaaa tagctgcgcc    4260
gatggtttct acaaagatcg ttatgtttat cggcactttg catcggccgc gctcccgatt    4320
ccggaagtgc ttgacattgg ggaattcagc gagagcctga cctattgcat ctcccgccgt    4380
gcacagggtg tcacgttgca agacctgcct gaaaccgaac tgcccgctgt tctgcagccg    4440
gtcgcggagg ctatggatgc gatcgctgcg gccgatctta gccagacgag cgggttcggc    4500
ccattcggac cgcaaggaat cggtcaatac actacatggc gtgatttcat atgcgcgatt    4560
gctgatcccc atgtgtatca ctggcaaact gtgatggacg acaccgtcag tgcgtccgtc    4620
gcgcaggctc tcgatgagct gatgctttgg gccgaggact gccccgaagt ccggcacctc    4680
gtgcacgcgg atttcggctc caacaatgtc ctgacggaca atggccgcat aacagcggtc    4740
attgactgga gcgaggcgat gttcggggat tcccaatacg aggtcgccaa catcttcttc    4800
tggaggccgt ggttggcttg tatggagcag cagacgcgct acttcgagcg gaggcatccg    4860
gagcttgcag atcgccgcg  gctccgggcg tatatgctcc gcattggtct tgaccaactc    4920
tatcagagct tggttgacgg caatttcgat gatgcagctt gggcgcaggg tcgatgcgac    4980
gcaatcgtcc gatccggagc cgggactgtc gggcgtacac aaatcgcccg cagaagcgcg    5040
gccgtctgga ccgatggctg tgtagaagta ctcgccgata gtggaaaccg acgccccagc    5100
actcgtccga gggcaaagga atagtgaggt acagcttgga tcgatccggc tgctaacaaa    5160
gcccgaaagg aagctgagtt ggctgctgcc accgctgagc aataactagc ataacccctt    5220
ggggcctcta aacgggtctt gaggggtttt ttgctgaaag gaggaactat atccggatga    5280
tcgggcgcgc cgtcgacgga tccactagtt ctagagcggc cgcgccgtc  gacggatata    5340 atgagccgta aacaaagatg attaagtagt aattaatacg tactagtaaa agtggcaaaa    5400
gataacgaga aagaaccaat ttcttttgcat tcggccttag cggaaggcat atataagctt    5460
tgattatttt atttagtgta atgatttcgt acaaccaaag catttattta gtactctcac    5520
acttgtgtcg cggccggccg ctacaggaac aggtggtggc ggccctcggc gcgctcgtac    5580
tgctccacga tggtgtagtc ctcgttgtgg gaggtgatgt ccagcttgga gtccacgtag    5640
```

```
tagtagccgg gcagctgcac gggcttcttg gccatgtaga tggacttgaa ctccaccagg    5700
tagtggccgc cgtccttcag cttcagggcc ttgtggatct cgcccttcag cacgccgtcg    5760
cgggggtaca ggcgctcggt ggaggcctcc cagcccatag tcttcttctg cattacgggg    5820
ccgtcggagg ggaagttcac gccgatgaac ttcaccttgt agatgaagga gccgtcctgc    5880
agggaggagt cctgggtcac ggtcaccacg ccgccgtcct cgaagttcat cacgcgctcc    5940
cacttgaagc cctcggggaa ggacagcttc ttgtagtcgg ggatgtcggc ggggtgcttc    6000
acgtacacct tggagccgta ctggaactgg ggggacagga tgtcccaggc gaagggcagg    6060
gggccgccct tggtcacctt cagcttggcg gtctgggtgc cctcgtaggg gcggccctcg    6120
ccctcgccct cgatctcgaa ctcgtggccg ttcacggagc cctccatgcg caccttgaag    6180
cgcatgaact ccttgatgac gtcctcggag gaggccatgg gccgcttggg gggctatgga    6240
agactttctt agttagttgt gtgaataagc aatgttggga gaatcgggac tacttatagg    6300
ataggaataa aacagaaaag tattaagtgc taatgaaata tttagactga taattaaaat    6360
cttcacgtat gtccacttga tataaaacg tcaggaataa aggaagtaca gtagaattta    6420
aaggtactct ttttatatat acccgtgttc tcttttttggc tagctagttg cataaaaaat    6480
aatctatatt tttatcatta ttttaaatat cttatgagat ggtaaatatt tatcataatt    6540 tttttacta ttatttatta tttgtgtgtg taatacatat agaagttaat tacaaatttt    6600 atttacttt tcattatttt gatatgattc accattaatt tagtgttatt atttataata    6660
gttcatttta atctttttgt atatattatg cgtgcagtac tttttccta catataacta    6720 ctattacatt ttatttatat aatattttta ttaatgaatt ttcgtgataa tatgtaatat    6780
tgttcattat tatttcagat ttttttaaaaa tatttgtgtt attatttatg aaatatgtaa    6840
tttttttagt atttgatttt atgatgataa agtgttctaa attcaaaaga aggggaaag    6900 cgtaaacatt aaaaaacgtc atcaaacaaa aacaaaatct tgttaataaa gataaaactg    6960
tttgttttga tcactgttat ttcgtaatat aaaaacatta tttatattta tattgttgac    7020
aaccaaattt gcctatcaaa tctaaccaat ataatgcatg cgtggcaggt aatgtactac    7080
catgaactta agtcatgaca taataaaccg tgaatctgac caatgcatgt acctanctaa    7140
attgtatttg tgacacgaag caaatgattc aattcacaat ggagatggga aacaaataat    7200
gaagaaccca gaactaagaa agcttttctg aaaaataaaa taaaggcaat gtcaaaagta    7260
tactgcatca tcagtccaga aagcacatga tattttttta tcagtatcaa tgcagctagt    7320 tttatttttac aatatcgata tagctagttt aaatatattg cagctagatt tataaatatt    7380
tgtgttatta tttatcattt gtgtaatcct gttttagta ttttagttta tatatgatga    7440
taatgtattc caaatttaaa agaagggaaa taaatttaaa caagaaaaaa agtcatcaaa    7500
caaaaaacaa atgaaagggt ggaaagatgt taccatgtaa tgtgaatgtt acagtatttc    7560
ttttattata gagttaacaa attaactaat atgattttgt taataatgat aaaatatttt    7620
ttttattatt atttcataat ataaaaatag tttacttaat ataaaaaaaa ttctatcgtt    7680
cacaacaaag ttggccacct aatttaacca tgcatgtacc catggaccat attaggtaac    7740
catcaaacct gatgaagaga taaagagatg aagacttaag tcataacaca aaaccataaa    7800
aaacaaaaat acaatcaacc gtcaatctga ccaatgcatg aaaaagctgc aatagtgagt    7860
ggcgacacaa agcacatgat tttcttacaa cggagataaa accaaaaaaa tatttcatga    7920
acaacctaga acaaataaag cttttatata ataaatatat aaataataa aggctatgga    7980 ataatatact tcaatatatt tggattaaat aaattgttgg cggggttgat atatttatac    8040
```

```
acacctaaag tcacttcaat ctcattttca cttaactttt attttttttt tcttttatt    8100
tatcataaag agaatattga taatatactt tttaacatat ttttatgaca tttttattg    8160
gtgaaaactt attaaaaatc ataaattttg taagttagat ttatttaaag agttcctctt    8220
cttattttaa atttttaat aaatttttaa ataactaaaa tttgtgttaa aaatgttaaa    8280
aaagtgtgtt attaacccct ctcttcgagg atccgtaccg agctcggatc ctctagaaat    8340
ccgtcaacat ggtggagcac gacactctcg tctactccaa gaatatcaaa gatacagtct    8400
cagaagacca aagggctatt gagacttttc aacaaagggt aatatcggga aacctcctcg    8460
gattccattg cccagctatc tgtcacttca tcaaaggac agtagaaaag gaaggtggca    8520
cctacaaatg ccatcattgc gataaaggaa aggctatcgt tcaagatgcc tctgccgaca    8580
gtggtcccaa agatggaccc ccacccacga ggagcatcgt ggaaaaagaa gacgttccaa    8640
ccacgtcttc aaagcaagtg gattgatgtg atgatcctat gcgtatggta tgacgtgtgt    8700
tcaagatgat gacttcaaac ctaccatga cgtatggtat gaacgtgtgt cgactgatga    8760
cttagatcca ctcgagcggc tataaatacg tacctacgca ccctgcgcta ccatccctag    8820
agctgcagct tattttaca acaattacca acaacaacaa acaacaaaca acattacaat    8880
tactatttac aattacagtc gacccgggat cgtacctcta gggtggcggc cgcaagtatg    8940
aactaaaatg catgtaggtg taagagctca tggagagcat ggaatattgt atccgaccat    9000
gtaacagtat aataactgag ctccatctca cttcttctat gaataaacaa aggatgttat    9060
gatatattaa cactctatct atgcacctta ttgttctatg ataaatttcc tcttattatt    9120
ataaatcatc tgaatcgtga cggcttatgg aatgcttcaa atagtacaaa aacaaatgtg    9180
tactataaga cttctaaac aattctaacc ttagcattgt gaacgagaca taagtgttaa    9240
gaagacataa caattataat ggaagaagtt tgtctccatt tatatattat atattaccca    9300
cttatgtatt atattaggat gttaaggaga cataacaatt ataaagagag aagtttgtat    9360
ccattatat attatatact acccatttat atattatact tatccactta tttaatgtct    9420
ttataaggtt tgatccatga tatttctaat attttagttg atatgtatat gaaagggtac    9480
tatttgaact ctcttactct gtataaaggt tggatcatcc ttaaagtggg tctatttaat    9540
tttattgctt cttacagata aaaaaaaaat tatgagttgg tttgataaaa tattgaagga    9600
tttaaaataa taataaataa catataatat atgtatataa atttattata atataacatt    9660
tatctataaa aaagtaaata ttgtcataaa tctatacaat cgtttagcct tgctggacga    9720
atctcaatta tttaaacgag agtaaacata tttgacttt tggttattta acaaattatt    9780
atttaacact atatgaaatt ttttttttta tcagcaaaga ataaaattaa attaagaagg    9840
acaatggtgt cccaatcctt atacaaccaa cttccacaag aaagtcaagt cagagacaac    9900
aaaaaaacaa gcaaaggaaa ttttttaatt tgagttgtct tgtttgctgc ataatttatg    9960
cagtaaaaca ctacacataa ccccttttagc agtagagcaa tggttgaccg tgtgcttagc   10020
ttcttttatt ttatttttt atcagcaaag aataaataaa ataaaatgag acacttcagg   10080
gatgtttcaa caagctctag agggcccaat tcgccctata gtgagtcgta ttacaattca   10140
ctggccgtcg ttttacaacg tcgtgactgg gaaaaccctg gcgttaccca acttaatcgc   10200
cttgcagcac atcccccttt cgccagctgg cgtaatagcg aagaggcccg caccgatcgc   10260
ccttcccaac agttgcgcag cctatac                                      10287
```

<210> SEQ ID NO 34
<211> LENGTH: 11480

```
<212> TYPE: DNA
<213> ORGANISM: Artificial Sequence
<220> FEATURE:
<223> OTHER INFORMATION: vector pKR1149
<220> FEATURE:
<221> NAME/KEY: misc_feature
<222> LOCATION: (8496)..(8496)
<223> OTHER INFORMATION: n is a, c, g, or t

<400> SEQUENCE: 34
ggccgcaagt atgaactaaa atgcatgtag gtgtaagagc tcatggagag catggaatat      60
tgtatccgac catgtaacag tataataact gagctccatc tcacttcttc tatgaataaa     120
caaaggatgt tatgatatat taacactcta tctatgcacc ttattgttct atgataaatt     180
tcctcttatt attataaatc atctgaatcg tgacggctta tggaatgctt caaatagtac     240
aaaaacaaat gtgtactata agactttcta aacaattcta accttagcat gtgaacgag      300
acataagtgt taagaagaca taacaattat aatggaagaa gtttgtctcc atttatatat     360
tatatattac ccacttatgt attatattag gatgttaagg agacataaca attataaga      420
gagaagtttg tatccattta tatattatat actacccatt tatatattat acttatccac     480
ttatttaatg tctttataag gtttgatcca tgatatttct aatattttag ttgatatgta     540
tatgaaaggg tactatttga actctcttac tctgtataaa ggttggatca tccttaaagt     600
gggtctattt aattttattg cttccttacag ataaaaaaaa aattatgagt tggtttgata    660
aaatattgaa ggatttaaaa taataataaa taacatataa tatatgtata taaatttatt    720
ataatataac atttatctat aaaaaagtaa atattgtcat aaatctatac aatcgtttag     780
ccttgctgga cgaatctcaa ttatttaaac gagagtaaac atatttgact ttttggttat     840
ttaacaaatt attatttaac actatatgaa atttttttt ttatcagcaa agaataaaat      900
taaattaaga aggacaatgg tgtcccaatc cttatacaac caacttccac aagaaagtca     960
agtcagagac aacaaaaaaa caagcaaagg aaatttttta atttgagttg tcttgtttgc    1020
tgcataattt atgcagtaaa acactacaca taacccttttt agcagtagag caatggttga    1080
ccgtgtgctt agcttctttt attttatttt tttatcagca aagaataaat aaaataaat     1140
gagacacttc agggatgttt caacaagctc tagagggccc aattcgccct atagtgagtc    1200
gtattacaat tcactggccg tcgttttaca acgtcgtgac tgggaaaacc ctggcgttac    1260
ccaacttaat cgccttgcag cacatcccc tttcgccagc tggcgtaata gcgaagaggc     1320
ccgcaccgat cgcccttccc aacagttgcg cagcctatac gtacgagatc cggccggcca    1380
gatcctgcag gagatccaag cttggcgcgc cgttctatag tgtcacctaa atcgtatgtg    1440
tatgatacat aaggttatgt attaattgta gccgcgttct aacgacaata tgtccatatg    1500
gtgcactctc agtacaatct gctctgatgc cgcatagtta agccagcccc gacacccgcc    1560
aacacccgct gacgcgccct gacgggcttg tctgctcccg gcatccgctt acagacaagc    1620
tgtgaccgtc tccgggagct gcatgtgtca gaggttttca ccgtcatcac cgaaacgcgc    1680
gagacgaaag ggcctcgtga tacgcctatt tttataggtt aatgtcatga ccaaaatccc    1740
ttaacgtgag ttttcgttcc actgagcgtc agaccccgta gaaaagatca aaggatcttc    1800
ttgagatcct ttttttctgc gcgtaatctg ctgcttgcaa acaaaaaaac caccgctacc    1860
agcggtggtt tgtttgccgg atcaagagct accaactctt tttccgaagg taactggctt    1920
cagcagagcg cagataccaa atactgtcct tctagtgtag ccgtagttag gccaccactt    1980
caagaactct gtagcaccgc ctacatacct cgctctgcta atcctgttac cagtggctgc    2040
tgccagtggc gataagtcgt gtcttaccgg gttggactca agacgatagt taccggataa    2100
```

```
ggcgcagcgg tcgggctgaa cgggggttc gtgcacacag cccagcttgg agcgaacgac    2160
ctacaccgaa ctgagatacc tacagcgtga gcattgagaa agcgccacgc ttcccgaagg    2220
gagaaaggcg gacaggtatc cggtaagcgg cagggtcgga acaggagagc gcacgaggga    2280
gcttccaggg ggaaacgcct ggtatcttta gtcctgtc ggggtttcgcc acctctgact     2340 tgagcgtcga ttttttgtgat gctcgtcagg ggggcggagc ctatggaaaa acgccagcaa   2400
cgcggccttt ttacggttcc tggccttttg ctggccttt gctcacatgt tctttcctgc     2460
gttatcccct gattctgtgg ataaccgtat taccgccttt gagtgagctg ataccgctcg    2520
ccgcagccga acgaccgagc gcagcgagtc agtgagcgag gaagcggaag agcgcccaat    2580
acgcaaaccg cctctccccg cgcgttggcc gattcattaa tgcaggttga tcgattcgac    2640
atcgatctag taacatagat gacaccgcgc gcgataattt atcctagttt gcgcgctata    2700
ttttgttttc tatcgcgtat taaatgtata attgcgggac tctaatcata aaaacccatc    2760
tcataaataa cgtcatgcat tacatgttaa ttattacatg cttaacgtaa ttcaacagaa    2820
attatatgat aatcatcgca agaccggcaa caggattcaa tcttaagaaa ctttattgcc    2880 aaaatgtttga acgatctgct tcgacgcact ccttctttag gtacctcact attcctttgc   2940
cctcggacga gtgctggggc gtcggtttcc actatcggcg agtacttcta cacagccatc    3000
ggtccagacg gccgcgcttc tgcgggcgat ttgtgtacgc ccgacagtcc cggctccgga    3060
tcggacgatt gcgtcgcatc gaccctgcgc ccaagctgca tcatcgaaat gccgtcaac     3120 caagctctga tagagttggt caagaccaat gcggagcata tacgcccgga gccgcggcga    3180
tcctgcaagc tccggatgcc tccgctcgaa gtagcgcgtc tgctgctcca tacaagccaa    3240
ccacggcctc cagaagaaga tgttggcgac ctcgtattgg gaatcccga acatcgcctc     3300 gctccagtca atgaccgctg ttatgcggcc attgtccgtc aggacattgt tggagccgaa    3360
atccgcgtgc acgaggtgcc ggacttcggg gcagtcctcg gcccaaagca tcagctcatc    3420
gagagcctgc gcgacggacg cactgacggt gtcgtccatc acagtttgcc agtgatacac    3480
atggggatca gcaatcgcgc atatgaaatc acgccatgta gtgtattgac cgattccttg    3540
cggtccgaat gggccgaacc cgctcgtctg gctaagatcg gccgcagcga tcgcatccat    3600
ggcctccgcg accggctgca gaacagcggg cagttcggtt tcaggcaggt cttgcaacgt    3660
gacaccctgt gcacggcggg agatgcaata ggtcaggctc tcgctgaatt ccccaatgtc    3720
aagcacttcc ggaatcggga gcgcggccga tgcaaagtgc cgataaacat aacgatcttt    3780
gtagaaacca tcggcgcagc tatttacccg caggacatat ccacgccctc ctacatcgaa    3840
gctgaaagca cgagattctt cgccctccga gagctgcatc aggtcggaga cgctgtcgaa    3900
cttttcgatc agaaacttct cgacagacgt cgcggtgagt tcaggctttt tcatggttta    3960
ataagaagag aaaagagttc ttttgttatg gctgaagtaa tagagaaatg agctcgagcg    4020
tgtcctctcc aaatgaaatg aacttcctta tatagaggaa gggtcttgcg aaggatagtg    4080
ggattgtgcg tcatccctta cgtcagtgga gatgtcacat caatccactt gctttgaaga    4140
cgtggttgga acgtcttctt tttccacgat gctcctcgtg ggtgggggtc catctttggg    4200
accactgtcg gcagaggcat cttgaatgat agcctttcct ttatcgcaat gatggcattt    4260
gtaggagcca ccttcctttt ctactgtcct ttcgatgaag tgacagatag ctgggcaatg    4320
gaatccgagg aggtttcccg aaattatcct ttgttgaaaa gtctcaatag ccctttggtc    4380
ttctgagact gtatctttga cattttttgga gtagaccaga gtgtcgtgct ccaccatgtt   4440
gacgaagatt ttcttcttgt cattgagtcg taaaagactc tgtatgaact gttcgccagt    4500
```

```
cttcacggcg agttctgtta gatcctcgat ttgaatctta gactccatgc atggccttag    4560
attcagtagg aactaccttt ttagagactc caatctctat tacttgcctt ggtttatgaa    4620
gcaagccttg aatcgtccat actggaatag tacttctgat cttgagaaat atgtctttct    4680
ctgtgttctt gatgcaatta gtcctgaatc ttttgactgc atctttaacc ttcttgggaa    4740
ggtatttgat ctcctggaga ttgttactcg ggtagatcgt cttgatgaga cctgctgcgt    4800
aggcctctct aaccatctgt gggtcagcat tctttctgaa attgaagagg ctaaccttct    4860
cattatcagt ggtgaacata gtgtcgtcac cttcaccttc gaacttcctt cctagatcgt    4920
aaagatagag gaaatcgtcc attgtaatct ccggggcaaa ggagatctct tttggggctg    4980
gatcactgct gggccttttg gttcctagcg tgagccagtg ggcttttttgc tttggtgggc    5040 ttgttagggc cttagcaaag ctcttgggct tgagttgagc ttctcctttg gggatgaagt    5100
tcaacctgtc tgtttgctga cttgttgtgt acgcgtcagc tgctgctctt gcctctgtaa    5160
tagtggcaaa tttcttgtgt gcaactccgg gaacgccgtt tgttgccgcc tttgtacaac    5220
cccagtcatc gtatataccg gcatgtggac cgttatacac aacgtagtag ttgatatgag    5280
ggtgttgaat acccgattct gctctgagag gagcaactgt gctgttaagc tcagattttt    5340
gtgggattgg aattggatcg atctcgatcc cgcgaaatta atacgactca ctatagggag    5400
accacaacgg tttccctcta gaaataattt tgtttaactt taagaaggag atatacccat    5460
ggaaaagcct gaactcaccg cgacgtctgt cgagaagttt ctgatcgaaa agttcgacag    5520
cgtctccgac ctgatgcagc tctcggaggg cgaagaatct cgtgctttca gcttcgatgt    5580
aggagggcgt ggatatgtcc tgcgggtaaa tagctgcgcc gatggtttct acaaagatcg    5640
ttatgtttat cggcactttg catcggccgc gctcccgatt ccggaagtgc ttgacattgg    5700
ggaattcagc gagagcctga cctattgcat ctcccgccgt gcacagggtg tcacgttgca    5760
agacctgcct gaaaccgaac tgcccgctgt tctgcagccg gtcgcggagg ctatggatgc    5820
gatcgctgcg gccgatctta gccagacgag cgggttcggc ccattcggac cgcaaggaat    5880
cggtcaatac actacatggc gtgatttcat atgcgcgatt gctgatcccc atgtgtatca    5940
ctggcaaact gtgatggacg acaccgtcag tgcgtccgtc gcgcaggctc tcgatgagct    6000
gatgctttgg gccgaggact gccccgaagt ccggcacctc gtgcacgcgg atttcggctc    6060
caacaatgtc ctgacggaca atggccgcat aacagcggtc attgactgga gcgaggcgat    6120
gttcggggat tcccaatacg aggtcgccaa catcttcttc tggaggccgt ggttggcttg    6180 tatgagcag cagacgcgct acttcgagcg gaggcatccg gagcttgcag gatcgccgcg    6240
gctccgggcg tatatgctcc gcattggtct tgaccaactc tatcagagct tggttgacgg    6300
caatttcgat gatgcagctt gggcgcaggg tcgatgcgac gcaatcgtcc gatccggagc    6360
cgggactgtc gggcgtacac aaatcgcccg cagaagcgcg gccgtctgga ccgatgctg    6420 tgtagaagta ctcgccgata gtggaaaccg acgccccagc actcgtccga gggcaaagga    6480
atagtgaggt acagcttgga tcgatccggc tgctaacaaa gcccgaaagg aagctgagtt    6540
ggctgctgcc accgctgagc aataactagc ataacccctt ggggcctcta aacgggtctt    6600
gaggggtttt ttgctgaaag gaggaactat atccggatga tcgggcgcgc cgtcgacgga    6660
tccactagtt ctagagcggc ccgcgccgtc gacggatata atgagccgta acaaagatg    6720 attaagtagt aattaatacg tactagtaaa agtggcaaaa gataacgaga aagaaccaat    6780
ttctttgcat tcggccttag cggaaggcat atataagctt tgattatttt atttagtgta    6840
atgatttcgt acaaccaaag catttattta gtactctcac acttgtgtcg cggccggccg    6900
```

```
ctacaggaac aggtggtggc ggccctcggc gcgctcgtac tgctccacga tggtgtagtc   6960
ctcgttgtgg gaggtgatgt ccagcttgga gtccacgtag tagtagccgg gcagctgcac   7020
gggcttcttg gccatgtaga tggacttgaa ctccaccagg tagtggccgc cgtccttcag   7080
cttcagggcc ttgtggatct cgcccttcag cacgccgtcg cggggtaca ggcgctcggt   7140
ggaggcctcc cagcccatag tcttcttctg cattacgggg ccgtcggagg ggaagttcac   7200
gccgatgaac ttcaccttgt agatgaagga gccgtcctgc agggaggagt cctgggtcac   7260
ggtcaccacg ccgccgtcct cgaagttcat cacgcgctcc cacttgaagc cctcggggaa   7320
ggacagcttc ttgtagtcgg ggatgtcggc ggggtgcttc acgtacacct tggagccgta   7380
ctggaactgg ggggacagga tgtcccaggc gaagggcagg gggccgcct  tggtcacctt   7440
cagcttggcg gtctgggtgc cctcgtaggg gcggccctcg ccctcgccct cgatctcgaa   7500
ctcgtggccg ttcacggagc cctccatgcg caccttgaag cgcatgaact ccttgatgac   7560
gtcctcggag gaggccatgg gccgcttggg gggctatgga agactttctt agttagttgt   7620
gtgaataagc aatgttggga gaatcgggac tacttatagg ataggaataa aacagaaaag   7680
tattaagtgc taatgaaata tttagactga taattaaaat cttcacgtat gtccacttga   7740
tataaaaacg tcaggaataa aggaagtaca gtagaattta aaggtactct ttttatatat   7800
acccgtgttc tcttttttggc tagctagttg cataaaaaat aatctatatt tttatcatta   7860
ttttaaatat cttatgagat ggtaaatatt tatcataatt ttttttacta ttatttatta   7920
tttgtgtgtg taatacatat agaagttaat tacaaatttt atttactttt tcattatttt   7980
gatatgattc accattaatt tagtgttatt atttataata gttcatttta atcttttttgt   8040
atatattatg cgtgcagtac ttttttccta catataacta ctattacatt ttatttatat   8100
aatatttttta ttaatgaatt ttcgtgataa tatgtaatat tgttcattat tatttcagat   8160
ttttttaaaaa tatttgtgtt attatttatg aaatatgtaa tttttttagt atttgatttt   8220
atgatgataa agtgttctaa attcaaaaga agggggaaag cgtaaacatt aaaaaacgtc   8280
atcaaacaaa aacaaaatct tgttaataaa gataaaactg tttgttttga tcactgttat   8340
ttcgtaatat aaaaacatta tttatattta tattgttgac aaccaaattt gcctatcaaa   8400
tctaaccaat ataatgcatg cgtggcaggt aatgtactac catgaactta agtcatgaca   8460
taataaaccg tgaatctgac caatgcatgt acctanctaa attgtatttg tgacacgaag   8520
caaatgattc aattcacaat ggagatggga aacaaataat gaagaaccca gaactaagaa   8580
agcttttctg aaaaataaaa taaaggcaat gtcaaaagta tactgcatca tcagtccaga   8640
aagcacatga tattttttta tcagtatcaa tgcagctagt tttatttac aatatcgata   8700
tagctagttt aaatatattg cagctagatt tataaatatt tgtgttatta tttatcatttt   8760
gtgtaatcct gtttttagta ttttagttta tatatgatga taatgtattc caaatttaaa   8820
agaagggaaa taaatttaaa caagaaaaaa agtcatcaaa caaaaaacaa atgaaagggt   8880
ggaaagatgt taccatgtaa tgtgaatgtt acagtatttc ttttattata gagttaacaa   8940
attaactaat atgattttgt taataatgat aaaatatttt ttttattatt atttcataat   9000
ataaaaatag tttacttaat ataaaaaaaa ttctatcgtt cacaacaaag ttggccacct   9060
aatttaaacca tgcatgtacc catggaccat attaggtaac catcaaacct gatgaagaga   9120
taaagagatg aagacttaag tcataacaca aaaccataaa aaacaaaaat acaatcaacc   9180
gtcaatctga ccaatgcatg aaaaagctgc aatagtgagt ggcgacacaa agcacatgat   9240
tttcttacaa cggagataaa accaaaaaaa tatttcatga acaacctaga acaaataaag   9300
```

```
cttttatata ataaatatat aaataaataa aggctatgga ataatatact tcaatatatt    9360
tggattaaat aaattgttgg cggggttgat atatttatac acacctaaag tcacttcaat    9420
ctcattttca cttaactttt attttttttt tcttttat  tatcataaag agaatattga    9480
taatatactt tttaacatat ttttatgaca ttttttattg gtgaaaactt attaaaaatc   9540
ataaattttg taagttagat ttatttaaag agttcctctt cttatttta atttttaat     9600
aaattttaa ataactaaaa tttgtgttaa aaatgttaaa aaagtgtgtt attacccctt    9660
ctcttcgagg atccgtaccg agctcggatc ctctagaaat ccgtcaacat ggtggagcac   9720
gacactctcg tctactccaa gaatatcaaa gatacagtct cagaagacca aagggctatt   9780
gagacttttc aacaaaggt aatatcggga aacctcctcg gattccattg cccagctatc    9840
tgtcacttca tcaaaaggac agtagaaaag gaaggtggca cctacaaatg ccatcattgc   9900
gataaaggaa aggctatcgt tcaagatgcc tctgccgaca gtggtcccaa agatggaccc   9960
ccacccacga ggagcatcgt ggaaaagaa gacgttccaa ccacgtcttc aaagcaagtg   10020
gattgatgtg atgatcctat gcgtatggta tgacgtgtgt tcaagatgat gacttcaaac  10080
ctacctatga cgtatggtat gaacgtgtgt cgactgatga cttagatcca ctcgagcggg  10140
tataaatacg tacctacgca ccctgcgcta ccatccctag agctgcagct tattttaca   10200
acaattacca acaacaacaa acaacaaaca acattacaat tactatttac aattacagtc  10260
gacccgggat cgtacctcta gggtggcggc cgcatggaga gatctcaacg gcagtctcct  10320
ccgccaccgt cgccgtcctc ctcctcgtcc tccgtctccg cggacaccgt cctcgtccct  10380
cccggaaaga ggcggagggc ggcgacggcc aaggccggcg ccgagcctaa taagaggatc  10440
cgcaaggacc ccgccgccgc cgccgcgggg aagaggagct ccgtctacag gggagtcacc  10500
aggcacaggt ggacgggcag gttcgaggcg catctctggg acaagcactg cctcgccgcg  10560
ctccacaaca agaagaaagg caggcaagtc tacctggggg cgtatgacag cgaggaggca  10620
gctgctcgtg cctatgacct cgcagctctc aagtactggg gtcctgagac tctgctcaac  10680
ttccctgtgg aggattactc cagcgagatg ccggagatgg aggccgtgtc ccggaggag   10740
tacctggcct ccctccgccg caggagcagc ggcttctcca ggggcgtctc caagtacaga  10800
ggcgtcgcca ggcatcacca caacgggagg tgggaggcac ggattgggcg agtctttggg  10860
aacaagtacc tctacttggg aacatttgac actcaagaag aggcagccaa ggcctatgac  10920
cttgcggcca ttgaataccg tggcgtcaat gctgtaacca acttcgacat cagctgctac  10980
ctggaccacc cgctgttcct ggcacagctc caacaggagc cacaggtggt gccggcactc  11040
aaccaagaac ctcaacctga tcagagcgaa accggaacta cagagcaaga gccggagtca  11100
agcgaagcca agacaccgga tggcagtgca gaacccgatg agaacgcggt gcctgacgac  11160
accgcggagc ccctcaccac agtcgacgac agcatcgaag agggcttgtg gagcccttgc  11220
atggattacg agctagacac catgtcgaga ccaaactttg gcagctcaat caatctgagc  11280
gagtggttcg ctgacgcaga cttcgactgc aacatcggat gcctgttcga tgggtgttct  11340
gcggctgacg aaggaagcaa ggatggtgta ggtctggcag atttcagtct gtttgaggca  11400
ggtgatgtcc agctgaagga tgttctttcg gatatggaag aggggataca acctccagcg  11460
atgatcagtg tgtgcaacgc                                              11480

<210> SEQ ID NO 35
<211> LENGTH: 19472
<212> TYPE: DNA
<213> ORGANISM: Artificial Sequence
```

<220> FEATURE:
<223> OTHER INFORMATION: vector pKR1221
<220> FEATURE:
<221> NAME/KEY: misc_feature
<222> LOCATION: (15083)..(15083)
<223> OTHER INFORMATION: n is a, c, g, or t

<400> SEQUENCE: 35

| | | | | | |
|---|---|---|---|---|---|
| cgcgccagat | cctctagagt | cgacctgcag | gcatgcaagc | ttggcgtaat | catggtcata | 60 |
| gctgtttcct | gtgtgaaatt | gttatccgct | cacaattcca | cacaacatac | gagccggaag | 120 |
| cataaagtgt | aaagcctggg | gtgcctaatg | agtgagctaa | ctcacattaa | ttgcgttgcg | 180 |
| ctcactgccc | gctttccagt | cgggaaacct | gtcgtgccag | ctgcattaat | gaatcggcca | 240 |
| acgcgcgggg | agaggcggtt | tgcgtattgg | gcgatccct | gaaagcgacg | ttggatgtta | 300 |
| acatctacaa | attgccttt | cttatcgacc | atgtacgtaa | gcgcttacgt | ttttggtgga | 360 |
| cccttgagga | aactggtagc | tgttgtgggc | ctgtggtctc | aagatggatc | attaatttcc | 420 |
| accttcacct | acgatggggg | gcatcgcacc | ggtgagtaat | attgtacggc | taagagcgaa | 480 |
| tttggcctgt | agacctcaat | tgcgagcttt | ctaatttcaa | actattcggg | cctaactttt | 540 |
| ggtgtgatga | tgctgactgg | caggatatat | accgttgtaa | tttgagctcg | tgtgaataag | 600 |
| tcgctgtgta | tgtttgtttg | attgtttctg | ttggagtgca | gcccatttca | ccggacaagt | 660 |
| cggctagatt | gatttagccc | tgatgaactg | ccgaggggaa | gccatcttga | gcgcggaatg | 720 |
| ggaatggatt | tcgttgtaca | acgagacgac | agaacaccca | cgggaccgag | cttcgcgagc | 780 |
| ttttgtatcc | gtggcatcct | tggtccggc | gatttgttca | cgtccatgag | gcgctctcca | 840 |
| aaggaacgca | tattttccgg | tgcaaccttt | ccggttcttc | ctctactcga | cctcttgaag | 900 |
| tcccagcatg | aatgttcgac | cgctccgcaa | gcggatcttt | ggcgcaacca | gccggtttcg | 960 |
| cacgtcgatt | ctcgcgagcc | tgcatacttt | ggcaagattg | ctgaatgacg | ctgatgcttc | 1020 |
| atcgcaatct | gcgataatgg | ggtaagtatc | cggtgaaggc | cgcaggtcag | gccgcctgag | 1080 |
| cactcagtgt | cttggatgtc | cagttccacg | gcagctgttg | ctcaagcctg | ctgatcggag | 1140 |
| cgtccgcaag | gtcggcgcgg | acgtcggcaa | gccaggcctg | cggatcgatg | ttattgagct | 1200 |
| tggcgctcat | gatcagtgtc | gccatgaacg | ccgcacgttc | agcacaacga | tccgatccgg | 1260 |
| caaacagcca | tgacttcctg | ccgagtacat | agcctctgag | cgttcgttcg | gcagcattgt | 1320 |
| tcgtcaggca | aatcgggccg | tcatcgagga | atgacgtaat | gccatcccat | cgcttgagca | 1380 |
| tgtaatttat | cgcctcggcg | acgggagaac | tgcgcgacaa | tttcccccgc | tcggtttcga | 1440 |
| gccaatcatg | cagctcttcg | gcgagtgacc | ttgatcaggc | caccgccacg | accgcggaag | 1500 |
| acgaacagat | gcctgcgcat | cggatcgcgc | ttcagcgtct | cttgcaccat | cagcgacaaa | 1560 |
| ccgggaaagc | ctttgcgcat | gtccgtactt | atgtcgccac | ttgggagggc | ttcgtctacg | 1620 |
| tggccttcgt | gatcgacgtc | ttcgcccgtc | gcattgtcgg | atggcgggcg | agccggacag | 1680 |
| cacatgcagg | ctttgtcctc | gatgccctcg | aggaggctca | tcatgatcgg | cgtcccgctc | 1740 |
| atggcggcct | agtgcatcac | tcggatcgcg | gtgttcaata | cgtgtccttt | cgctattccg | 1800 |
| agcggttggc | agaagcaggt | atcgagccat | ctatcggaag | cgtcggcgac | agcacgacaa | 1860 |
| cgccctcgca | gaagcgatca | acggtcttta | caaggccgag | gtcattcatc | ggcgtggacc | 1920 |
| atggaggagc | ttcgaagcgg | tcgagttcgc | taccttggaa | tggatagact | ggttcaacca | 1980 |
| cggcggcttt | tgaagcccat | cggcaatata | ccgccagccg | aagacgagga | tcagtattac | 2040 |
| gccatgctgg | acgaagcagc | catgctgcg | cattttaacg | aaatggcctc | cggcaaaccc | 2100 |
| ggtgcggttc | acttgttgcg | tgggaaagtt | cacgggactc | cgcgcacgag | ccttcttcgt | 2160 |

```
aatagccata tcgaccgaat tgacctgcag ggggggggg gaaagccacg ttgtgtctca   2220
aaatctctga tgttacattg cacaagataa aaatatatca tcatgaacaa taaaactgtc   2280
tgcttacata aacagtaata caagggggtgt tatgagccat attcaacggg aaacgtcttg   2340
ctcgaggccg cgattaaatt ccaacatgga tgctgattta tatgggtata aatgggctcg   2400
cgataatgtc gggcaatcag gtgcgacaat ctatcgattg tatgggaagc ccgatgcgcc   2460
agagttgttt ctgaaacatg gcaaaggtag cgttgccaat gatgttacag atgagatggt   2520
cagactaaac tggctgacgg aatttatgcc tcttccgacc atcaagcatt ttatccgtac   2580
tcctgatgat gcatggttac tcaccactgc gatccccggg aaaacagcat tccaggtatt   2640
agaagaatat cctgattcag gtgaaaatat tgttgatgcg ctggcagtgt tcctgcgccg   2700
gttgcattcg attcctgttt gtaattgtcc ttttaacagc gatcgcgtat ttcgtctcgc   2760
tcaggcgcaa tcacgaatga ataacggttt ggttgatgcg agtgattttg atgacgagcg   2820
taatggctgg cctgttgaac aagtctggaa agaaatgcat aagcttttgc cattctcacc   2880
ggattcagtc gtcactcatg gtgatttctc acttgataac cttattttg acgaggggaa   2940 attaataggt tgtattgatg ttggacgagt cggaatcgca gaccgatacc aggatcttgc   3000
catcctatgg aactgcctcg gtgagttttc tccttcatta cagaaacggc ttttttcaaaa   3060 atatggtatt gataatcctg atatgaataa attgcagttt catttgatgc tcgatgagtt   3120
tttctaatca gaattggtta attggttgta acactggcag agcattacgc tgacttgacg   3180
ggacggcggc tttgttgaat aaatcgaact tttgctgagt tgaaggatca gatcacgcat   3240
cttcccgaca acgcagaccg ttccgtggca aagcaaaagt tcaaaatcac caactggtcc   3300
acctacaaca aagctctcat caaccgtggc tccctcactt tctggctgga tgatggggcg   3360
attcaggcct ggtatgagtc agcaacacct tcttcacgag gcagacctca gcgcccccc   3420 cccctgcag gtcttttcca atgatgagca cttttaaagt tctgctatgt ggcgcggtat   3480
tatcccgtgt tgacgccggg caagagcaac tcggtcgccg catacactat tctcagaatg   3540
acttggttga gtactcacca gtcacagaaa agcatcttac ggatggcatg acagtaagag   3600
aattatgcag tgctgccata accatgagtg ataacactgc ggccaactta cttctgacaa   3660
cgatcggagg accgaaggag ctaaccgctt ttttgcacaa catgggggat catgtaactc   3720
gccttgatcg ttgggaaccg gagctgaatg aagccatacc aaacgacgag cgtgacacca   3780
cgatgcctgt agcaatggca acaacgttgc gcaaactatt aactggcgaa ctacttactc   3840
tagcttcccg gcaacaatta atagactgga tgaggcgga taaagttgca ggaccacttc   3900
tgcgctcggc ccttccggct ggctggttta ttgctgataa atctggagcc ggtgagcgtg   3960
ggtctcgcgg tatcattgca gcactggggc cagatggtaa gccctcccgt atcgtagtta   4020
tctacacgac ggggagtcag gcaactatgg atgaacgaaa tagacagatc gctgagatag   4080
gtgcctcact gattaagcat tggtaactgt cagaccaagt ttactcatat atactttaga   4140
ttgatttaaa acttcatttt taatttaaaa ggatctaggt gaagatcctt tttgataatc   4200
tcatgaccaa aatcccttaa cgtgagtttt cgttccactg agcgtcagac cccgtagaaa   4260
agatcaaagg atcttcttga gatcctttt ttctgcgcgt aatctgctgc ttgcaaacaa   4320
aaaaaccacc gctaccagcg gtggtttgtt tgccggatca gagctacca actcttttc    4380 cgaaggtaac tggcttcagc agagcgcaga taccaaatac tgtccttcta gtgtagccgt   4440
agttaggcca ccacttcaag aactctgtag caccgcctac atacctcgct ctgctaatcc   4500
tgttaccagt ggctgctgcc agtggcgata agtcgtgtct taccgggttg gactcaagac   4560
```

```
gatagttacc ggataaggcg cagcggtcgg gctgaacggg gggttcgtgc acacagccca   4620
gcttggagcg aacgacctac accgaactga gataacctaca gcgtgagcta tgagaaagcg  4680
ccacgcttcc cgaagggaga aaggcggaca ggtatccggt aagcggcagg gtcggaacag   4740
gagagcgcac gagggagctt ccaggggggaa acgcctggta tctttatagt cctgtcgggt  4800
ttcgccacct ctgacttgag cgtcgatttt tgtgatgctc gtcagggggg cggagcctat   4860
ggaaaaacgc cagcaacgcg gccttttttac ggttcctggc cttttgctgg ccttttgctc  4920
acatgttctt tcctgcgtta tcccctgatt ctgtggataa ccgtattacc gcctttgagt   4980
gagctgatac cgctcgccgc agccgaacga ccgagcgcag cgagtcagtg agcgaggaag   5040
cggaagagcg cctgatgcgg tattttctcc ttacgcatct gtgcggtatt tcacaccgca   5100
tatggtgcac tctcagtaca atctgctctg atgccgcata gttaagccag tatacactcc   5160
gctatcgcta cgtgactggg tcatggctgc gccccgacac ccgccaacac ccgctgacgc   5220
gccctgacgg gcttgtctgc tcccggcatc cgcttacaga caagctgtga ccgtctccgg   5280
gagctgcatg tgtcagaggt tttcaccgtc atcaccgaaa cgcgcgaggc agggtgcctt   5340
gatgtgggcg ccggcggtcg agtggcgacg gcgcggcttg tccgcgccct ggtagattgc   5400
ctggccgtag gccagccatt tttgagcggc cagcggccgc gataggccga cgcgaagcgg   5460
cggggcgtag ggagcgcagc gaccgaaggg taggcgcttt ttgcagctct tcggctgtgc   5520
gctggccaga cagttatgca caggccaggc gggttttaag agttttaata agttttaaag   5580
agttttaggc ggaaaaatcg cctttttttct cttttatatc agtcacttac atgtgtgacc   5640
ggttcccaat gtacggcttt gggttcccaa tgtacgggtt ccggttccca atgtacggct   5700
ttgggttccc aatgtacgtg ctatccacag gaaagagacc ttttcgacct ttttcccctg   5760
ctagggcaat ttgccctagc atctgctccg tacattagga accggcggat gcttcgccct   5820
cgatcaggtt gcggtagcgc atgactagga tcgggccagc ctgccccgcc tcctccttca   5880
aatcgtactc cggcaggtca tttgacccga tcagcttgcg cacggtgaaa cagaacttct   5940
tgaactctcc ggcgctgcca ctgcgttcgt agatcgtctt gaacaaccat ctggcttctg   6000
ccttgcctgc ggcgcggcgt gccaggcggt agagaaaacg gccgatgccg ggatcgatca   6060
aaaagtaatc ggggtgaacc gtcagcacgt ccgggttctt gccttctgtg atctcgcggt   6120
acatccaatc agctagctcg atctcgatgt actccggccg cccggtttcg ctcttttacga  6180 tcttgtagcg gctaatcaag gcttcacccct cggataccgt caccaggcgg ccgttcttgg   6240
ccttcttcgt acgctgcatg gcaacgtgcg tggtgtttaa ccgaatgcag gtttctacca   6300
ggtcgtcttt ctgctttccg ccatcggctc gccggcagaa cttgagtacg tccgcaacgt   6360
gtggacggaa cacgcggccg ggcttgtctc ccttcccttc ccggtatcgg ttcatggatt   6420
cggttagatg ggaaaccgcc atcagtacca ggtcgtaatc ccacacactg gccatgccgg   6480
ccggccctgc ggaaacctct acgtgcccgt ctggaagctc gtagcggatc acctcgccag   6540
ctcgtcggtc acgcttcgac agacggaaaa cggccacgtc catgatgctg cgactatcgc   6600
gggtgcccac gtcatagagc atcggaacga aaaaatctgg ttgctcgtcg cccttgggcg   6660
gcttcctaat cgacgcgcca ccggctgccg gcggttgccg ggattctttg cggattcgat   6720
cagcggccgc ttgccacgat tcaccggggc gtgcttctgc ctcgatgcgt tgccgctggg   6780
cggcctgcgc ggccttcaac ttctccacca ggtcatcacc cagcgccgcg ccgatttgta   6840
ccgggccgga tggtttgcga ccgctcacgc cgattcctcg ggcttggggg ttccagtgcc   6900
attgcagggc cggcagacaa cccagccgct tacgcctggc caaccgcccg ttcctccaca   6960
```

```
catgggcat  tccacggcgt  cggtgcctgg  ttgttcttga  ttttccatgc  cgcctccttt   7020
agccgctaaa  attcatctac  tcatttattc  atttgctcat  ttactctggt  agctgcgcga   7080
tgtattcaga  tagcagctcg  gtaatggtct  tgccttggcg  taccgcgtac  atcttcagct   7140
tggtgtgatc  ctccgccggc  aactgaaagt  tgacccgctt  catggctggc  gtgtctgcca   7200
ggctggccaa  cgttgcagcc  ttgctgctgc  gtgcgctcgg  acggccggca  cttagcgtgt   7260
ttgtgctttt  gctcattttc  tctttacctc  attaactcaa  atgagttttg  atttaatttc   7320
agcggccagc  gcctggacct  cgcgggcagc  gtcgccctcg  ggttctgatt  caagaacggt   7380
tgtgccggcg  gcggcagtgc  ctgggtagct  cacgcgctgc  gtgatacggg  actcaagaat   7440
gggcagctcg  tacccggcca  gcgcctcggc  aacctcaccg  ccgatgcgcg  tgcctttgat   7500
cgcccgcgac  acgacaaagg  ccgcttgtag  ccttccatcc  gtgacctcaa  tgcgctgctt   7560
aaccagctcc  accaggtcgg  cggtggccca  tatgtcgtaa  gggcttggct  gcaccggaat   7620
cagcacgaag  tcggctgcct  tgatcgcgga  cacagccaag  tccgccgcct  ggggcgctcc   7680
gtcgatcact  acgaagtcgc  gccggccgat  ggccttcacg  tcgcggtcaa  tcgtcgggcg   7740
gtcgatgccg  acaacggtta  gcggttgatc  ttcccgcacg  gccgcccaat  cgcgggcact   7800
gccctgggga  tcggaatcga  ctaacagaac  atcggccccg  gcgagttgca  gggcgcgggc   7860
tagatgggtt  gcgatggtcg  tcttgcctga  cccgcctttc  tggttaagta  cagcgataac   7920
ttcatgcgtt  cccttgcgta  tttgtttatt  tactcatcgc  atcatatacg  cagcgaccgc   7980
atgacgcaag  ctgttttact  caaatacaca  tcaccttttt  agacggcggc  gctcggtttc   8040
ttcagcggcc  aagctggccg  gccaggccgc  cagcttggca  tcagacaaac  cggccaggat   8100
ttcatgcagc  cgcacggttg  agacgtgcgc  gggcggctcg  aacacgtacc  cggccgcgat   8160
catctccgcc  tcgatctctt  cggtaatgaa  aaacggttcg  tcctggccgt  cctggtgcgg   8220
tttcatgctt  gttcctcttg  gcgttcattc  tcggcggccg  ccaggcgtc  ggcctcggtc   8280 aatgcgtcct  cacggaaggc  accgcgccgc  ctggcctcgg  tgggcgtcac  ttcctcgctg   8340
cgctcaagtg  cgcggtacag  ggtcgagcga  tgcacgccaa  gcagtgcagc  cgcctctttc   8400
acggtgcggc  cttcctggtc  gatcagctcg  cgggcgtgcg  cgatctgtgc  cggggtgagg   8460
gtagggcggg  ggccaaactt  cacgcctcgg  gccttggcgg  cctcgcgccc  gctccgggtg   8520
cggtcgatga  ttagggaacg  ctcgaactcg  gcaatgccgg  cgaacacggt  caacaccatg   8580
cggccggccg  gcgtggtggt  gtcggcccac  ggctctgcca  ggctacgcag  gcccgcgccg   8640
gcctcctgga  tgcgctcggc  aatgtccagt  aggtcgcggg  tgctgcgggc  caggcggtct   8700
agcctggtca  ctgtcacaac  gtcgccaggg  cgtaggtggt  caagcatcct  ggccagctcc   8760
gggcggtcgc  gcctggtgcc  ggtgatcttc  tcggaaaaca  gcttggtgca  gccggccgcg   8820
tgcagttcgg  cccgttggtt  ggtcaagtcc  tggtcgtcgg  tgctgacgcg  gcatagccc    8880 agcaggccag  cggcggcgct  cttgttcatg  gcgtaatgtc  tccggttcta  gtcgcaagta   8940
ttctacttta  tgcgactaaa  acacgcgaca  agaaaacgcc  aggaaaaggg  cagggcggca   9000
gcctgtcgcg  taacttagga  cttgtgcgac  atgtcgtttt  cagaagacgg  ctgcactgaa   9060
cgtcagaagc  cgactgcact  atagcagcgg  aggggttgga  ccacaggacg  ggtgtggtcg   9120
ccatgatcgc  gtagtcgata  gtggctccaa  gtagcgaagc  gagcaggact  gggcggcggc   9180
caaagcggtc  ggacagtgct  ccgagaacgg  gtgcgcatag  aaattgcatc  aacgcatata   9240
gcgctagcag  cacgccatag  tgactggcga  tgctgtcgga  atggacgata  tcccgcaaga   9300
ggcccggcag  taccggcata  accaagccta  tgcctacagc  atccagggtg  acggtgccga   9360
```

```
ggatgacgat gagcgcattg ttagatttca tacacggtgc ctgactgcgt tagcaattta   9420
actgtgataa actaccgcat taaagctagc ttgcttggtc gttccgcgtg aacgtcggct   9480
cgattgtacc tgcgttcaaa tactttgcga tcgtgttgcg cgcctgcccg gtgcgtcggc   9540
tgatctcacg gatcgactgc ttctctcgca acgccatccg acggatgatg tttaaaagtc   9600
ccatgtggat cactccgttg ccccgtcgct caccgtgttg gggggaaggt gcacatggct   9660
cagttctcaa tggaaattat ctgcctaacc ggctcagttc tgcgtagaaa ccaacatgca   9720
agctccaccg ggtgcaaagc ggcagcggcg gcaggatata ttcaattgta aatggcttca   9780
tgtccgggaa atctacatgg atcagcaatg agtatgatgg tcaatatgga gaaaagaaa   9840 gagtaattac cattttttt tcaattcaaa aatgtagatg tccgcagcgt tattataaaa   9900
tgaaagtaca ttttgataaa acgacaaatt acgatccgtc gtatttatag gcgaaagcaa   9960
taaacaaatt attctaattc ggaaatcttt atttcgacgt gtctacattc acgtccaaat  10020
gggggcttag atgagaaact tcacgatcga tgccttgatt tcgccattcc cagatacccca 10080 tttcatcttc agattggtct gagattatgc gaaaatatac actcatatac ataaatactg  10140
acagtttgag ctaccaattc agtgtagccc attacctcac ataattcact caaatgctag  10200
gcagtctgtc aactcggcgt caatttgtcg gccactatac gatagttgcg caaattttca  10260
aagtcctggc ctaacatcac acctctgtcg gcggcgggtc ccatttgtga taaatccacc  10320
atatcgaatt aattcagact cctttgcccc agagatcaca atggacgact tcctctatct  10380
ctacgatcta gtcaggaagt tcgacggaga aggtgacgat accatgttca ccactgataa  10440
tgagaagatt agccttttca atttcagaaa gaatgctaac ccacagatgg ttagagaggc  10500
ttacgcagca ggtctcatca agacgatcta cccgagcaat aatctccagg agatcaaata  10560
ccttcccaag aaggttaaag atgcagtcaa aagattcagg actaactgca tcaagaacac  10620
agagaaagat atatttctca agatcagaag tactattcca gtatggacga ttcaaggctt  10680
gcttcacaaa ccaaggcaag taatagagat tggagtctct aaaaaggtag ttcccactga  10740
atcaaaggcc atggagtcaa agattcaaat agaggaccta acagaactcg ccgtaaagac  10800
tggcgaacag ttcatacaga gtctcttacg actcaatgac aagaagaaaa tcttcgtcaa  10860
catggtggag cacgacacgc ttgtctactc caaaaatatc aaagatacag tctcagaaga  10920
ccaaagggca attgagactt tcaacaaag ggtaatatcc ggaaacctcc tcggattcca  10980
ttgcccagct atctgtcact ttattgtgaa gatagtggaa aaggaaggtg gctcctacaa  11040
atgccatcat tgcgataaag gaaaggccat cgttgaagat gcctctgccg acagtggtcc  11100
caaagatgga cccccaccca cgaggagcat cgtggaaaaa gaagacgttc caaccacgtc  11160
ttcaaagcaa gtggattgat gtgatatctc cactgacgta agggatgacg cacaatccca  11220
ctatccttcg caagacccctt cctctatata aggaagttca tttcatttgg agaggacacg  11280
ctgaaatcac cagtctccaa gcttgcgggg atcgtttcgc atgattgaac aagatggatt  11340
gcacgcaggt tctccggccg cttggtgga gaggctattc ggctatgact gggcacaaca  11400
gacaatcggc tgctctgatg ccgccgtgtt ccggctgtca gcgcagggc gcccggttct  11460 ttttgtcaag accgacctgt ccggtgccct gaatgaactg caggacgagg cagcgcggct  11520
atcgtggctg gccacgacgg gcgttccttg cgcagctgtg ctcgacgttg tcactgaagc  11580
gggaagggac tggctgctat tgggcgaagt gccggggcag gatctcctgt catctcacct  11640
tgctcctgcc gagaaagtat ccatcatggc tgatgcaatg cggcggctgc atacgcttga  11700
tccggctacc tgcccattcg accaccaagc gaaacatcgc atcgagcgag cacgtactcg  11760
```

```
gatggaagcc ggtcttgtcg atcaggatga tctggacgaa gagcatcagg ggctcgcgcc   11820
agccgaactg ttcgccaggc tcaaggcgcg catgcccgac ggcgaggatc tcgtcgtgac   11880
ccatggcgat gcctgcttgc cgaatatcat ggtggaaaat ggccgctttt ctggattcat   11940
cgactgtggc cggctgggtg tggcggaccg ctatcaggac atagcgttgg ctacccgtga   12000
tattgctgaa gagcttggcg gcgaatgggc tgaccgcttc ctcgtgcttt acggtatcgc   12060
cgctcccgat tcgcagcgca tcgccttcta tcgccttctt gacgagttct tctgagcggg   12120
actctggggt tcgaaatgac cgaccaagcg acgcccaacc tgccatcacg agatttcgat   12180
tccaccgccg ccttctatga aaggttgggc ttcggaatcg ttttccggga cgccggctgg   12240
atgatcctcc agcgcgggga tctcatgctg gagttcttcg cccacccgg atcgatccaa    12300 cacttacgtt tgcaacgtcc aagagcaaat agaccacgaa cgccgaagg ttgccgcagc    12360 gtgtggattg cgtctcaatt ctctcttgca ggaatgcaat gatgaatatg atactgacta   12420
tgaaactttg agggaatact gcctagcacc gtcacctcat aacgtgcatc atgcatgccc   12480
tgacaacatg gaacatcgct atttttctga agaattatgc tcgttggagg atgtcgcggc   12540
aattgcagct attgccaaca tcgaactacc cctcacgcat gcattcatca atattattca   12600
tgcggggaaa ggcaagatta atccaactgg caaatcatcc agcgtgattg gtaacttcag   12660
ttccagcgac ttgattcgtt ttggtgctac ccacgttttc aataaggacg agatggtgga   12720
gtaaagaagg agtgcgtcga agcagatcgt tcaaacattt ggcaataaag tttcttaaga   12780
ttgaatcctg ttgccggtct tgcgatgatt atcatataat ttctgttgaa ttacgttaag   12840
catgtaataa ttaacatgta atgcatgacg ttatttatga gatgggtttt tatgattaga   12900
gtcccgcaat tatacattta atacgcgata gaaaacaaaa tatagcgcgc aaactaggat   12960
aaattatcgc gcgcggtgtc atctatgtta ctagatcgat caaacttcgg tactgtgtaa   13020
tgacgatgag caatcgagag gctgactaac aaaaggtaca tcgcgatgga tcgatccatt   13080
cgccattcag gctgcgcaac tgttgggaag ggcgatcggt gcgggcctct tcgctattac   13140
gccagctggc gaaaggggga tgtgctgcaa ggcgattaag ttgggtaacg ccagggtttt   13200
cccagtcacg acgttgtaaa acgacggcca gtgaattcct gcagcccggg ggatccgccc   13260
actcgaggcg cgccgtcgac ggatataatg agccgtaaac aaagatgatt aagtagtaat   13320
taatacgtac tagtaaaagt ggcaaaagat aacgagaaag aaccaatttc tttgcattcg   13380
gccttagcgg aaggcatata taagctttga ttatttatt tagtgtaatg atttcgtaca    13440
accaaagcat ttatttagta ctctcacact tgtgtcgcgg ccggccgcta caggaacagg   13500
tggtggcggc cctcggcgcg ctcgtactgc tccacgatgg tgtagtcctc gttgtgggag   13560
gtgatgtcca gcttggagtc cacgtagtag tagccgggca gctgcacggg cttcttggcc   13620
atgtagatgg acttgaactc caccaggtag tggccgccgt ccttcagctt cagggccttg   13680
tggatctcgc ccttcagcac gccgtcgcgg gggtacaggc gctcggtgga ggcctcccag   13740
cccatagtct tcttctgcat tacggggccg tcgaggggga agttcacgcc gatgaacttc   13800
accttgtaga tgaaggagcc gtcctgcagg gaggagtcct gggtcacggt caccacgccg   13860
ccgtcctcga agttcatcac gcgctcccac ttgaagccct cggggaagga cagcttcttg   13920
tagtcgggga tgtcggcggg gtgcttcacg tacaccttgg agccgtactg gaactggggg   13980
gacaggatgt cccaggcgaa gggcaggggg ccgcccttgg tcaccttcag cttggcggtc   14040
tgggtgccct cgtaggggcg gccctcgccc tcgcccctcga tctcgaactc gtggccgttc   14100
acggagccct ccatgcgcac cttgaagcgc atgaactcct tgatgacgtc ctcggaggag   14160
```

```
gccatgggcc gcttgggggg ctatggaaga ctttcttagt tagttgtgtg aataagcaat    14220
gttgggagaa tcgggactac ttataggata ggaataaaac agaaaagtat taagtgctaa    14280
tgaaatattt agactgataa ttaaaatctt cacgtatgtc cacttgatat aaaaacgtca    14340
ggaataaagg aagtacagta gaatttaaag gtactctttt tatatatacc cgtgttctct    14400
ttttggctag ctagttgcat aaaaaataat ctatatttt atcattatt taaatatctt     14460 atgagatggt aaatatttat cataattttt tttactatta tttattattt gtgtgtgtaa    14520
tacatataga agttaattac aaattttatt tactttttca ttattttgat atgattcacc    14580
attaatttag tgttattatt tataatagtt cattttaatc tttttgtata tattatgcgt    14640
gcagtacttt tttcctacat ataactacta ttacatttta tttatataat atttttatta    14700
atgaattttc gtgataatat gtaatattgt tcattattat ttcagatttt ttaaaaatat    14760
ttgtgttatt atttatgaaa tatgtaattt ttttagtatt tgattttatg atgataaagt    14820
gttctaaatt caaagaagg gggaaagcgt aaacattaaa aaacgtcatc aaacaaaaac     14880
aaaatcttgt taataaagat aaaactgttt gttttgatca ctgttatttc gtaatataaa    14940
aacattattt atatttatat tgttgacaac caaatttgcc tatcaaatct aaccaatata    15000
atgcatgcgt ggcaggtaat gtactaccat gaacttaagt catgacataa taaaccgtga    15060
atctgaccaa tgcatgtacc tanctaaatt gtatttgtga cacgaagcaa atgattcaat    15120
tcacaatgga gatgggaaac aaataatgaa gaacccagaa ctaagaaagc ttttctgaaa    15180
aataaaataa aggcaatgtc aaagtatac tgcatcatca gtccagaaag cacatgatat      15240 tttttatca gtatcaatgc agctagtttt attttacaat atcgatatag ctagtttaaa     15300
tatattgcag ctagatttat aaatatttgt gttattatt tcatttgtg taatcctgtt      15360 tttagtattt tagtttatat atgatgataa tgtattccaa atttaaaaga agggaaataa    15420
atttaaacaa gaaaaaaagt catcaaacaa aaaacaaatg aaagggtgga agatgttac     15480 catgtaatgt gaatgttaca gtatttcttt tattatagag ttaacaaatt aactaatatg    15540
attttgttaa taatgataaa atattttttt tattattatt tcataatata aaaatagttt    15600
acttaatata aaaaaaattc tatcgttcac aacaaagttg gccacctaat ttaaccatgc    15660
atgtacccat ggaccatatt aggtaaccat caaacctgat gaagagataa agagatgaag    15720
acttaagtca taacacaaaa ccataaaaaa caaaaataca atcaaccgtc aatctgacca    15780
atgcatgaaa aagctgcaat agtgagtggc gacacaaagc acatgatttt cttacaacgg    15840
agataaaacc aaaaaaatat ttcatgaaca acctagaaca aataaagctt ttatataata    15900
aatatataaa taaataaagg ctatggaata atatacttca atatatttgg attaaataaa    15960
ttgttggcgg ggttgatata tttatacaca cctaaagtca cttcaatctc attttcactt    16020 aactttatt ttttttttct ttttatttat cataaagaga atattgataa tatactttt      16080 aacatatttt tatgacattt tttattggtg aaaacttatt aaaaatcata aattttgtaa    16140
gttagattta tttaaagagt tcctcttctt attttaaatt ttttaataaa ttttaaata     16200 actaaaattt gtgttaaaaa tgttaaaaaa gtgtgttatt aacccttctc ttcgaggatc    16260
cgtaccgagc tcggatcctc tagaaatccg tcaacatggt ggagcacgac actctcgtct    16320
actccaagaa tatcaaagat acagtctcag aagaccaaag ggctattgag acttttcaac    16380
aaagggtaat atcgggaaac ctcctcggat tccattgccc agctatctgt cacttcatca    16440
aaaggacagt agaaaggaa ggtggcacct acaaatgcca tcattgcgat aaaggaaagg     16500
ctatcgttca agatgcctct gccgacagtg gtcccaaaga tggacccca cccacgagga     16560
```

```
gcatcgtgga aaaagaagac gttccaacca cgtcttcaaa gcaagtggat tgatgtgatg   16620
atcctatgcg tatggtatga cgtgtgttca agatgatgac ttcaaaccta cctatgacgt   16680
atggtatgaa cgtgtgtcga ctgatgactt agatccactc gagcggctat aaatacgtac   16740
ctacgcaccc tgcgctacca tccctagagc tgcagcttat ttttacaaca attaccaaca   16800
acaacaaaca acaacaaca ttacaattac tatttacaat tacagtcgac ccgggatcgt   16860
acctctaggg tggcggccgc atggagagat ctcaacggca gtctcctccg ccaccgtcgc   16920
cgtcctcctc ctcgtcctcc gtctccgcgg acaccgtcct cgtccctccc ggaaagaggc   16980
ggagggcggc gacggccaag gccggcgccg agcctaataa gaggatccgc aaggaccccg   17040
ccgccgccgc cgcggggaag aggagctccg tctacagggg agtcaccagg cacaggtgga   17100
cgggcaggtt cgaggcgcat ctctgggaca agcactgcct cgccgcgctc cacaacaaga   17160
agaaaggcag gcaagtctac ctgggggcgt atgacagcga ggaggcagct gctcgtgcct   17220
atgacctcgc agctctcaag tactgggtc ctgagactct gctcaacttc cctgtggagg   17280
attactccag cgagatgccg gagatggagg ccgtgtcccg ggaggagtac ctggcctccc   17340
tccgccgcag gagcagcggc ttctccaggg gcgtctccaa gtacagaggc gtcgccaggc   17400
atcaccacaa cgggaggtgg gaggcacgga ttgggcgagt ctttgggaac aagtacctct   17460
acttgggaac atttgacact caagaagagg cagccaaggc ctatgacctt gcggccattg   17520
aataccgtgg cgtcaatgct gtaaccaact tcgacatcag ctgctacctg gaccacccgc   17580
tgttcctggc acagctccaa caggagccac aggtggtgcc ggcactcaac caagaacctc   17640
aacctgatca gagcgaaacc ggaactacag agcaagagcc ggagtcaagc gaagccaaga   17700
caccggatgg cagtgcagaa cccgatgaga acgcggtgcc tgacgacacc gcggagcccc   17760
tcaccacagt cgacgacagc atcgaagagg gcttgtggag cccttgcatg gattacgagc   17820
tagacaccat gtcgagacca aactttggca gctcaatcaa tctgagcgag tggttcgctg   17880
acgcagactt cgactgcaac atcggatgcc tgttcgatgg gtgttctgcg gctgacgaag   17940
gaagcaagga tggtgtaggt ctggcagatt tcagtctgtt tgaggcaggt gatgtccagc   18000
tgaaggatgt tctttcggat atggaagagg ggatacaacc tccagcgatg atcagtgtgt   18060
gcaacgcggc cgcaagtatg aactaaaatg catgtaggtg taagagctca tggagagcat   18120
ggaatattgt atccgaccat gtaacagtat aataactgag ctccatctca cttcttctat   18180
gaataaacaa aggatgttat gatatattaa cactctatct atgcacctta ttgttctatg   18240
ataaatttcc tcttattatt ataaatcatc tgaatcgtga cggcttatgg aatgcttcaa   18300
atagtacaaa aacaaatgtg tactataaga ctttctaaac aattctaacc ttagcattgt   18360
gaacgagaca taagtgttaa gaagacataa caattataat ggaagaagtt tgtctccatt   18420
tatatattat atattaccca cttatgtatt atattaggat gttaaggaga cataacaatt   18480
ataaagagag aagtttgtat ccatttatat attatatact acccatttat atattatact   18540
tatccactta tttaatgtct ttataaggtt tgatccatga tatttctaat atttagttg   18600 atatgtatat gaaagggtac tatttgaact ctcttactct gtataaaggt tggatcatcc   18660
ttaaagtggg tctatttaat tttattgctt cttacagata aaaaaaaaat tatgagttgg   18720
tttgataaaa tattgaagga tttaaaataa taataaataa catataatat atgtatataa   18780
atttattata atataacatt tatctataaa aaagtaaata ttgtcataaa tctatacaat   18840
cgtttagcct tgctggacga atctcaatta tttaaacgag agtaaacata tttgactttt   18900 tggttatttta acaaattatt atttaacact atatgaaatt tttttttta tcagcaaaga   18960
```

```
ataaaattaa attaagaagg acaatggtgt cccaatccctt atacaaccaa cttccacaag    19020
aaagtcaagt cagagacaac aaaaaaacaa gcaaaggaaa ttttttaatt tgagttgtct    19080
tgtttgctgc ataatttatg cagtaaaaca ctacacataa ccctttttagc agtagagcaa    19140 tggttgaccg tgtgcttagc ttcttttatt ttatttttttt atcagcaaag aataaataaa    19200
ataaaatgag acacttcagg gatgtttcaa caagctctag agggcccaat tcgccctata    19260
gtgagtcgta ttacaattca ctggccgtcg ttttacaacg tcgtgactgg gaaaaccctg    19320
gcgttaccca acttaatcgc cttgcagcac atccccctttt cgccagctgg cgtaatagcg    19380
aagaggcccg caccgatcgc ccttcccaac agttgcgcag cctatacgta cgagatccgg    19440
ccggccagat cctgcaggag atccaagctt gg                                   19472
```

<210> SEQ ID NO 36
<211> LENGTH: 1188
<212> TYPE: DNA
<213> ORGANISM: Zea mays

<400> SEQUENCE: 36

```
atggagagat ctcaacggca gtctcctccg ccaccgtcgc cgtcctcctc ctcgtcctcc     60
gtctccgcgg acaccgtcct cgtccctccc ggaaagaggc ggagggcggc gacggccaag    120
gccggcgccg agcctaataa gaggatccgc aaggaccccg ccgccgccgc cgcggggaag    180
aggagctccg tctacagggg agtcaccagg cacaggtgga cgggcaggtt cgaggcgcat    240
ctctgggaca gcactgcct cgccgcgctc cacaacaaga agaaaggcag gcaagtctac    300
ctgggggcgt atgacagcga ggaggcagct gctcgtgcct atgacctcgc agctctcaag    360 tactgggtc ctgagactct gctcaacttc cctgtggagg attactccag cgagatgccg    420
gagatggagg ccgtgtcccg ggaggagtac ctggcctccc tccgccgcag gagcagcggc    480
ttctccaggg gcgtctccaa gtacagaggc gtcgccaggc atcaccacaa cgggaggtgg    540
gaggcacgga ttgggcgagt ctttgggaac aagtacctct acttgggaac atttgacact    600
caagaagagg cagccaaggc ctatgacctt gcggccattg aataccgtgg cgtcaatgct    660
gtaaccaact tcgacatcag ctgctacctg gaccaccgc tgttcctggc acagctccaa    720
caggagccac aggtggtgcc ggcactcaac caagaacctc aacctgatca gagcgaaacc    780
ggaactacag agcaagagcc ggagtcaagc gaagccaaga caccggatgg cagtgcagaa    840
cccgatgaga acgcggtgcc tgacgacacc gcggagcccc tcaccacagt cgacgacagc    900
atcgaagagg gcttgtggag cccttgcatg gattacgagc tagacaccat gtcgagacca    960
aactttggca gctcaatcaa tctgagcgag tggttcgctg acgcagactt cgactgcaac   1020
atcggatgcc tgttcgatgg gtgttctgcg gctgacgaag gaagcaagga tggtgtaggt   1080
ctggcagatt tcagtctgtt tgaggcaggt gatgtccagc tgaaggatgt tcttttcggat   1140 atggaagagg ggatacaacc tccagcgatg atcagtgtgt gcaactaa                 1188
```

<210> SEQ ID NO 37
<211> LENGTH: 395
<212> TYPE: PRT
<213> ORGANISM: Zea mays

<400> SEQUENCE: 37

```
Met Glu Arg Ser Gln Arg Gln Ser Pro Pro Pro Ser Pro Ser Ser
1               5                   10                  15

Ser Ser Ser Ser Val Ser Ala Asp Thr Val Leu Val Pro Pro Gly Lys
            20                  25                  30
```

| | | | | | | | | | | | | |
|---|---|---|---|---|---|---|---|---|---|---|---|---|
|Arg|Arg|Arg|Ala|Ala|Thr|Ala|Lys|Ala|Gly|Ala|Glu|Pro|Asn|Lys|Arg|
| |35| | | |40| | | |45| | | |

Arg Arg Arg Ala Ala Thr Ala Lys Ala Gly Ala Glu Pro Asn Lys Arg
          35                  40                  45

Ile Arg Lys Asp Pro Ala Ala Ala Ala Gly Lys Arg Ser Ser Val
 50                  55                  60

Tyr Arg Gly Val Thr Arg His Arg Trp Thr Gly Arg Phe Glu Ala His
 65                  70                  75                  80

Leu Trp Asp Lys His Cys Leu Ala Ala Leu His Asn Lys Lys Lys Gly
                 85                  90                  95

Arg Gln Val Tyr Leu Gly Ala Tyr Asp Ser Glu Glu Ala Ala Ala Arg
                100                 105                 110

Ala Tyr Asp Leu Ala Ala Leu Lys Tyr Trp Gly Pro Glu Thr Leu Leu
                115                 120                 125

Asn Phe Pro Val Glu Asp Tyr Ser Ser Glu Met Pro Glu Met Glu Ala
                130                 135                 140

Val Ser Arg Glu Glu Tyr Leu Ala Ser Leu Arg Arg Arg Ser Ser Gly
145                 150                 155                 160

Phe Ser Arg Gly Val Ser Lys Tyr Arg Gly Val Ala Arg His His His
                165                 170                 175

Asn Gly Arg Trp Glu Ala Arg Ile Gly Arg Val Phe Gly Asn Lys Tyr
                180                 185                 190

Leu Tyr Leu Gly Thr Phe Asp Thr Gln Glu Glu Ala Ala Lys Ala Tyr
                195                 200                 205

Asp Leu Ala Ala Ile Glu Tyr Arg Gly Val Asn Ala Val Thr Asn Phe
                210                 215                 220

Asp Ile Ser Cys Tyr Leu Asp His Pro Leu Phe Leu Ala Gln Leu Gln
225                 230                 235                 240

Gln Glu Pro Gln Val Val Pro Ala Leu Asn Gln Glu Pro Gln Pro Asp
                245                 250                 255

Gln Ser Glu Thr Gly Thr Thr Glu Gln Glu Pro Glu Ser Ser Glu Ala
                260                 265                 270

Lys Thr Pro Asp Gly Ser Ala Glu Pro Asp Glu Asn Ala Val Pro Asp
                275                 280                 285

Asp Thr Ala Glu Pro Leu Thr Thr Val Asp Asp Ser Ile Glu Glu Gly
                290                 295                 300

Leu Trp Ser Pro Cys Met Asp Tyr Glu Leu Asp Thr Met Ser Arg Pro
305                 310                 315                 320

Asn Phe Gly Ser Ser Ile Asn Leu Ser Glu Trp Phe Ala Asp Ala Asp
                325                 330                 335

Phe Asp Cys Asn Ile Gly Cys Leu Phe Asp Gly Cys Ser Ala Ala Asp
                340                 345                 350

Glu Gly Ser Lys Asp Gly Val Gly Leu Ala Asp Phe Ser Leu Phe Glu
                355                 360                 365

Ala Gly Asp Val Gln Leu Lys Asp Val Leu Ser Asp Met Glu Glu Gly
                370                 375                 380

Ile Gln Pro Pro Ala Met Ile Ser Val Cys Asn
385                 390                 395

<210> SEQ ID NO 38
<211> LENGTH: 1239
<212> TYPE: DNA
<213> ORGANISM: Glycine max

<400> SEQUENCE: 38
atgaagaggt ctccagcatc ttcttgttca tcatctactt cctctgttgg gtttgaagct    60

-continued

```
cccattgaaa aaagaaggcc taagcatcca aggaggaata atttgaagtc acaaaaatgc      120
aagcagaacc aaaccaccac tggtggcaga agaagctcta tctatagagg agttacaagg      180
cataggtgga cagggaggtt tgaagctcac ctatgggata agagctcttg gaacaacatt      240
cagagcaaga agggtcgaca agtttatttg gggggcatatg atactgaaga atctgcagcc     300
cgtacctatg accttgcagc ccttaaatac tggggaaaag atgcaaccct gaatttcccg      360
atagaaactt ataccaagga gctcgaggaa atggacaagg tttcaagaga agaatatttg      420
gcttctttgc ggcgccaaag cagtggcttt tctagaggcc tgtctaagta ccgtgggggtt     480 gctaggcatc atcataatgg tcgctgggaa gcacgaattg gaagagtatg cggaaacaag      540
tacctctact tggggacata taaaactcaa gaggaggcag cagtggcata tgacatggca      600
gcaatagagt accgtggagt caatgcagtg accaattttg acataagcaa ctacatggac      660
aaaataaaga agaaaaatga ccaaacccaa caacaacaaa cagaagcaca aacggaaaca      720
gttcctaact cctctgactc tgaagaagta gaagtagaac aacagacaac aacaataacc      780
acaccacccc catctgaaaa tctgcacatg ccaccacagc agcaccaagt tcaatacacc      840
ccccatgtct ctccaaggga agaagaatca tcatcactga tcacaattat ggaccatgtg      900
cttgagcagg atctgccatg gagcttcatg tacactggct tgtctcagtt tcaagatcca      960
aacttggctt tctgcaaagg tgatgatgac ttggtgggca tgtttgatag tgcagggttt     1020
gaggaagaca ttgattttct gttcagcact caacctggtg atgagactga gagtgatgtc     1080
aacaatatga gcgcagtttt ggatagtgtt gagtgtggag acacaaatgg ggctggtgga     1140
agcatgatgc atgtggataa caagcagaag atagtatcat ttgcttcttc accatcatct     1200
acaactacag tttcttgtga ctatgctcta gatctatga                            1239
```

<210> SEQ ID NO 39
<211> LENGTH: 412
<212> TYPE: PRT
<213> ORGANISM: Glycine max

<400> SEQUENCE: 39

```
Met Lys Arg Ser Pro Ala Ser Ser Cys Ser Ser Ser Thr Ser Ser Val
1               5                   10                  15

Gly Phe Glu Ala Pro Ile Glu Lys Arg Arg Pro Lys His Pro Arg Arg
            20                  25                  30

Asn Asn Leu Lys Ser Gln Lys Cys Lys Gln Asn Gln Thr Thr Thr Gly
        35                  40                  45

Gly Arg Arg Ser Ser Ile Tyr Arg Gly Val Thr Arg His Arg Trp Thr
    50                  55                  60

Gly Arg Phe Glu Ala His Leu Trp Asp Lys Ser Ser Trp Asn Asn Ile
65                  70                  75                  80

Gln Ser Lys Lys Gly Arg Gln Val Tyr Leu Gly Ala Tyr Asp Thr Glu
                85                  90                  95

Glu Ser Ala Ala Arg Thr Tyr Asp Leu Ala Ala Leu Lys Tyr Trp Gly
            100                 105                 110

Lys Asp Ala Thr Leu Asn Phe Pro Ile Glu Thr Tyr Thr Lys Glu Leu
        115                 120                 125

Glu Glu Met Asp Lys Val Ser Arg Glu Glu Tyr Leu Ala Ser Leu Arg
    130                 135                 140

Arg Gln Ser Ser Gly Phe Ser Arg Gly Leu Ser Lys Tyr Arg Gly Val
145                 150                 155                 160

Ala Arg His His His Asn Gly Arg Trp Glu Ala Arg Ile Gly Arg Val
                165                 170                 175
```

```
Cys Gly Asn Lys Tyr Leu Tyr Leu Gly Thr Tyr Lys Thr Gln Glu Glu
            180                 185                 190

Ala Ala Val Ala Tyr Asp Met Ala Ala Ile Glu Tyr Arg Gly Val Asn
        195                 200                 205

Ala Val Thr Asn Phe Asp Ile Ser Asn Tyr Met Asp Lys Ile Lys Lys
    210                 215                 220

Lys Asn Asp Gln Thr Gln Gln Gln Thr Glu Ala Gln Thr Glu Thr
225                 230                 235                 240

Val Pro Asn Ser Ser Asp Ser Glu Glu Val Glu Val Glu Gln Thr
                245                 250                 255

Thr Thr Ile Thr Thr Pro Pro Ser Glu Asn Leu His Met Pro Pro
            260                 265                 270

Gln Gln His Gln Val Gln Tyr Thr Pro His Val Ser Pro Arg Glu Glu
            275                 280                 285

Glu Ser Ser Ser Leu Ile Thr Ile Met Asp His Val Leu Glu Gln Asp
            290                 295                 300

Leu Pro Trp Ser Phe Met Tyr Thr Gly Leu Ser Gln Phe Gln Asp Pro
305                 310                 315                 320

Asn Leu Ala Phe Cys Lys Gly Asp Asp Leu Val Gly Met Phe Asp
                325                 330                 335

Ser Ala Gly Phe Glu Glu Asp Ile Asp Phe Leu Phe Ser Thr Gln Pro
            340                 345                 350

Gly Asp Glu Thr Glu Ser Asp Val Asn Asn Met Ser Ala Val Leu Asp
            355                 360                 365

Ser Val Glu Cys Gly Asp Thr Asn Gly Ala Gly Gly Ser Met Met His
        370                 375                 380

Val Asp Asn Lys Gln Lys Ile Val Ser Phe Ala Ser Ser Pro Ser Ser
385                 390                 395                 400

Thr Thr Thr Val Ser Cys Asp Tyr Ala Leu Asp Leu
            405                 410

<210> SEQ ID NO 40
<211> LENGTH: 1230
<212> TYPE: DNA
<213> ORGANISM: Momordica charantia

<400> SEQUENCE: 40
atgagaaggt ctccctctgt ttctacttcc tcctcctcct cctcctcctg cgtcggcggc      60
ggcggcttcg acagcaataa tctcaatctc gccgccccte cgcgccggcc gcaatcggag     120
aagaccggag cgaaacgccg gaagcggaat caggacgacg ccaaatgcga gattgagaat     180
cgtaacggta ataacaacaa cagcagcaac aacaatgcct cttccggccg ccggagctcc     240
atttacagag gagtcactag gcaccgatgg accggccggt cgaagcgca tctctgggac      300 aagagttcgt ggaatagcat tcagaacaaa aaaggaaggc aagtttattt ggagcatac      360 gataacgagg aagctgccgc ccgaacttat gacctcgctg ccctcaagta ctgggtcccc     420
ggaaccaccc tcaatttccc ggtagagtcg tacaggaatg aaatagaaga atgcgcgaaa     480
gttacgaagg aggagtattt ggcgtcgtta cggcggcgga gcagcggatt ttcgagaggc     540
gtatcgaagt accgcggcgt ggcccgccac caccacaacg gccggtggga ggcgcggatc     600
ggccgtgttt tcggaagcaa atatctttac ctgggaactt acaacacaca agaggaagca     660
gcagcagcat atgacatggc tgcaattgag tacagagggg tcaatgcagt gaccaatttc     720
gacatcagca attacattgg gcggctggag aataaatcat cagtttttcc agcagcagag     780
```

```
cagcccctac agcccaactg ctcccctgct tcctcttctg aggaaggcga agtagtacag    840
cagcaacagc aacagacgac gatggcgttc tcaggctcgc ccctccagtt cccgtcgatg    900
gagaacagcc cgacgacaat ggaggaggat catgatctgc attggtcatt cctagacacg    960
gggttcgtgc aggtccccga cctcccctc gagaagtctg gcgaattgcc tgacctgttc    1020
tttgatgaga tcgggttcga ggacgacatc gggttgatat tcgaggcgag cttggaagac    1080
gagaggtgcg gggaggggg tgagaagtta aagatgtgg ggaaaatgga gatgatgaag     1140
agtgatcatg aggagagggg gttgttctcg actacttcgc catcttcgtc gtcgataacc    1200
acctcggttt cgtgtgaatt tagggtttga                                    1230
```

<210> SEQ ID NO 41
<211> LENGTH: 409
<212> TYPE: PRT
<213> ORGANISM: Momordica charantia

<400> SEQUENCE: 41

```
Met Arg Arg Ser Pro Ser Val Ser Thr Ser Ser Ser Ser Ser Ser Ser
1               5                   10                  15

Cys Val Gly Gly Gly Phe Asp Ser Asn Asn Leu Asn Leu Ala Ala
            20                  25                  30

Pro Pro Arg Arg Pro Gln Ser Glu Lys Thr Gly Ala Lys Arg Arg Lys
        35                  40                  45

Arg Asn Gln Asp Asp Ala Lys Cys Glu Ile Glu Asn Arg Asn Gly Asn
    50                  55                  60

Asn Asn Asn Ser Ser Asn Asn Asn Ala Ser Ser Gly Arg Arg Ser Ser
65                  70                  75                  80

Ile Tyr Arg Gly Val Thr Arg His Arg Trp Thr Gly Arg Phe Glu Ala
                85                  90                  95

His Leu Trp Asp Lys Ser Ser Trp Asn Ser Ile Gln Asn Lys Lys Gly
            100                 105                 110

Arg Gln Val Tyr Leu Gly Ala Tyr Asp Asn Glu Glu Ala Ala Ala Arg
        115                 120                 125

Thr Tyr Asp Leu Ala Ala Leu Lys Tyr Trp Gly Pro Gly Thr Thr Leu
    130                 135                 140

Asn Phe Pro Val Glu Ser Tyr Arg Asn Glu Ile Glu Glu Met Arg Lys
145                 150                 155                 160

Val Thr Lys Glu Glu Tyr Leu Ala Ser Leu Arg Arg Arg Ser Ser Gly
                165                 170                 175

Phe Ser Arg Gly Val Ser Lys Tyr Arg Gly Val Ala Arg His His His
            180                 185                 190

Asn Gly Arg Trp Glu Ala Arg Ile Gly Arg Val Phe Gly Ser Lys Tyr
        195                 200                 205

Leu Tyr Leu Gly Thr Tyr Asn Thr Gln Glu Glu Ala Ala Ala Tyr
    210                 215                 220

Asp Met Ala Ala Ile Glu Tyr Arg Gly Val Asn Ala Val Thr Asn Phe
225                 230                 235                 240

Asp Ile Ser Asn Tyr Ile Gly Arg Leu Glu Asn Lys Ser Ser Val Phe
                245                 250                 255

Pro Ala Ala Glu Gln Pro Leu Gln Pro Asn Cys Ser Pro Ala Ser Ser
            260                 265                 270

Ser Glu Glu Gly Glu Val Val Gln Gln Gln Gln Thr Thr Met
        275                 280                 285

Ala Phe Ser Gly Ser Pro Leu Gln Phe Pro Ser Met Glu Asn Ser Pro
    290                 295                 300
```

-continued

Thr Thr Met Glu Glu Asp His Asp Leu His Trp Ser Phe Leu Asp Thr
305                 310                 315                 320

Gly Phe Val Gln Val Pro Asp Leu Pro Leu Glu Lys Ser Gly Glu Leu
            325                 330                 335

Pro Asp Leu Phe Phe Asp Glu Ile Gly Phe Glu Asp Ile Gly Leu
            340                 345                 350

Ile Phe Glu Ala Ser Leu Glu Asp Glu Arg Cys Gly Glu Gly Gly Glu
        355                 360                 365

Lys Leu Glu Asp Val Gly Lys Met Glu Met Met Lys Ser Asp His Glu
        370                 375                 380

Glu Arg Gly Leu Phe Ser Thr Thr Ser Pro Ser Ser Ser Ser Ile Thr
385                 390                 395                 400

Thr Ser Val Ser Cys Glu Phe Arg Val
                405

<210> SEQ ID NO 42
<211> LENGTH: 430
<212> TYPE: PRT
<213> ORGANISM: Arabidopsis thaliana

<400> SEQUENCE: 42

Met Lys Lys Arg Leu Thr Thr Ser Thr Cys Ser Ser Ser Pro Ser Ser
1               5                   10                  15

Ser Val Ser Ser Ser Thr Thr Thr Ser Ser Pro Ile Gln Ser Glu Ala
            20                  25                  30

Pro Arg Pro Lys Arg Ala Lys Arg Ala Lys Lys Ser Ser Pro Ser Gly
        35                  40                  45

Asp Lys Ser His Asn Pro Thr Ser Pro Ala Ser Thr Arg Arg Ser Ser
50                  55                  60

Ile Tyr Arg Gly Val Thr Arg His Arg Trp Thr Gly Arg Phe Glu Ala
65                  70                  75                  80

His Leu Trp Asp Lys Ser Ser Trp Asn Ser Ile Gln Asn Lys Lys Gly
                85                  90                  95

Lys Gln Val Tyr Leu Gly Ala Tyr Asp Ser Glu Glu Ala Ala Ala His
            100                 105                 110

Thr Tyr Asp Leu Ala Ala Leu Lys Tyr Trp Gly Pro Asp Thr Ile Leu
        115                 120                 125

Asn Phe Pro Ala Glu Thr Tyr Thr Lys Glu Leu Glu Glu Met Gln Arg
130                 135                 140

Val Thr Lys Glu Glu Tyr Leu Ala Ser Leu Arg Arg Gln Ser Ser Gly
145                 150                 155                 160

Phe Ser Arg Gly Val Ser Lys Tyr Arg Gly Val Ala Arg His His His
                165                 170                 175

Asn Gly Arg Trp Glu Ala Arg Ile Gly Arg Val Phe Gly Asn Lys Tyr
            180                 185                 190

Leu Tyr Leu Gly Thr Tyr Asn Thr Gln Glu Glu Ala Ala Ala Ala Tyr
        195                 200                 205

Asp Met Ala Ala Ile Glu Tyr Arg Gly Ala Asn Ala Val Thr Asn Phe
210                 215                 220

Asp Ile Ser Asn Tyr Ile Asp Arg Leu Lys Lys Lys Gly Val Phe Pro
225                 230                 235                 240

Phe Pro Val Asn Gln Ala Asn His Gln Glu Gly Ile Leu Val Glu Ala
                245                 250                 255

Lys Gln Glu Val Glu Thr Arg Glu Ala Lys Glu Glu Pro Arg Glu Glu
            260                 265                 270

```
Val Lys Gln Gln Tyr Val Glu Glu Pro Pro Gln Glu Glu Glu Lys
        275                 280                 285
Glu Glu Glu Lys Ala Glu Gln Gln Ala Glu Ile Val Gly Tyr Ser
        290                 295                 300
Glu Glu Ala Ala Val Val Asn Cys Cys Ile Asp Ser Ser Thr Ile Met
305                 310                 315                 320
Glu Met Asp Arg Cys Gly Asp Asn Asn Glu Leu Ala Trp Asn Phe Cys
                325                 330                 335
Met Met Asp Thr Gly Phe Ser Pro Phe Leu Thr Asp Gln Asn Leu Ala
                340                 345                 350
Asn Glu Asn Pro Ile Glu Tyr Pro Glu Leu Phe Asn Glu Leu Ala Phe
        355                 360                 365
Glu Asp Asn Ile Asp Phe Met Phe Asp Asp Gly Lys His Glu Cys Leu
        370                 375                 380
Asn Leu Glu Asn Leu Asp Cys Cys Val Val Gly Arg Glu Ser Pro Pro
385                 390                 395                 400
Ser Ser Ser Ser Pro Leu Ser Cys Leu Ser Thr Asp Ser Ala Ser Ser
                405                 410                 415
Thr Thr Thr Thr Thr Thr Ser Val Ser Cys Asn Tyr Leu Val
                420                 425                 430

<210> SEQ ID NO 43
<211> LENGTH: 2004
<212> TYPE: DNA
<213> ORGANISM: Arabidopsis thaliana

<400> SEQUENCE: 43
ggtctactct ttacatgttc tttactccgt ctcaaaattt cctttttttg ttggctctct      60
ccgaacgagt tggagaaatc gttaacccta atcgaagatc tagattcctc tacatacgtt     120
tgatctctct ctcagtatgg attacaaagc gccaaggaga tactactcac acggagttgt     180
tgcgagacag caagatttcg caacagatat agttacgaga agaagacctt atgtccctta     240
cgaccgtcca aataagtttt caaggagtct ggtttggacg tcaaaagagt acaaatcacc     300
cgagggcaat aatatgccaa ggaccaatga tgtgtcaccg aaaccaccag ttttaggttt     360
ggcgaggaag aatgctgctt gtgggccaat gagatcttct agtctcagaa atgggtatg     420
taagtattgg aaagatggaa agtgcaagag gggtgagcag tgccagttct acactcttg     480
gtcttgtttc cctggattgg ccatggtagc ttctcttgaa gggcacaata aggaactaaa     540
ggggatcgct ctccctgagg ttcagataaa actcttttca gtcagtattg atggtacatt     600
gcgagtttgg gactgcaatt ctggtcagtg tgtacattcc atcaaccttg acgcagaagc     660
agggtctcta atcagtgaag gcccttgggt tttccttggc ttgccaaacg ctataaaggc     720
ttttaacgtt caaccagtc aagatttgca tcttcaagca gcaggggtgg ttggtcaggt     780
gaatgcaatg actattgcaa acggaatgct ttttgctgga acaagttctg gtagtatctt     840
agtctggaaa gctactacag actctgagtc tgatccattc aaatacttga catctcttga     900
gggacatagt ggtgaagtca cttgttttgc tgttggaggt caaatgctat actctggttc     960
tgtcgataaa acaatcaaga tgtgggatct caacaccctg caatgtataa tgaccctgaa    1020
gcaacatacc ggcactgtca cttcactctt atgtttggat aaatgtttga tatcgtcttc    1080
cttggatggg accataaaag tttgggctta ttctgaaaac ggaatcttga agttgttca    1140
aactcgcaga caagaacaga gtagtgttca tgctcttttct ggtatgcatg atgcagaagc    1200
caaaccgata atattctgct cttaccaaaa cggaaccgtt ggcattttcg acctaccatc    1260
```

```
ttttcaagaa agaggaagga tgttctctac gcacacgatc gccacactca caattggtcc   1320
tcaaggattg ttattcagtg gagacgagag tggtaacttg cgtgtatgga ccttagctgc   1380
tggcaacaaa gtttagtctt ttcgactaaa gaattctgat ttaattttgt ggtttatatg   1440
ttgagttaac tgttaagaga gttttatttt gtaataggtg tatcagtcaa taaacaatct   1500
ttgtatcaac caaatgtaat ttttctcgtt aattcgattt cagagttttt actttaagat   1560
aaacaaactc tttcacacat catttaatga aagtggagaa gcttaaaaaa caaacaaaga   1620
aactgatcca tttttggcgg gtcttcttct actcttattc atatgtgtta acgaactata   1680
gcgtaaaatt cagagcaagc gatctccgat ttgaacgtgg ctatcaccgg aggcccacca   1740
ctacgggcga tacgctctaa gtgaggatta aagtgctctg gtggtgacgt tgaagaaact   1800
cgcccatggt ttttgttatc tctgcagcca agtgtcgttc tttcttcgcc acttctcatc   1860
aagctacagt gaatttaaaa atggcgtctt tctttgatct cgtatacata agctggattg   1920
gtttcttaaa caaattcctc tccttttggg tcttctgggt ttgccttgta agtgtttgtg   1980
tttttgcctc tgagaaaaaa tcgc                                          2004

<210> SEQ ID NO 44
<211> LENGTH: 2790
<212> TYPE: DNA
<213> ORGANISM: Brassica napus
<220> FEATURE:
<221> NAME/KEY: misc_feature
<222> LOCATION: (2776)..(2776)
<223> OTHER INFORMATION: n is a, c, g, or t

<400> SEQUENCE: 44
ggccacttct catcatgtta cagggaccat aaaaatggcg tatttcttca gccccgggta     60
taaatacaca catgatcctg tggtggttts ttccacaagt tacatctcct tctggttttt    120
gtattgcaag tgtttgtgtt ttttgcctcc gagagaaaat catgccgacc ggtaggttcg    180
agacgatgcg tgaatgggtc cacgacgcca tctctgctca acgcaatgag ctcctctctc    240 tttttttccag atacgtagct caggggaaag ggatactgya gtcccaccag ctgattgacg    300
agttcctcaa gactgtgaaa gtggatggaa ctacagaaga tcttaagaat cgtcccttca    360
tgaaagttct gcagtctgca gaggaagcca tagttttgcc tcccttttgtt gcsctggcga    420 ttcgtcccag acctggtgtt agagaatatg tccgtgtgaa tgtctacgag ctgagcgtag    480
accatttaac tgtttctgag tatcttcggt tcaaggaaga gctcgttaat ggccatgcca    540
atgggaatta tcttctcgag cttgattttg aaccgttcaa cgcaacgttt cctcgtccaa    600
ctcggtcatc atctattggg aatggggttc agttcctcaa ccgtcacctc tcgtcaatca    660
tgttccgtaa caaagacagc ttggagcctt gcttgagtt tctccgcact cacaaacatg      720
acggccgtgc catgatgctg aatgatcgaa tacagaacat ccgcacactt caggaagctt    780
tggcgagggc agaggagttc ctctctaaac ttcctttggc tacaccatac tctgaattcg    840
aatttgract acaagggatg ggatttgaga ggggatgggg tgacacgkca cagaaggttt    900
cagaaatggt gcatctmctt ctggacatac tccaggcacc tgatccttct gtcttggaga    960
cgtttcttgg aaggattcct atggtgttca atgtygtkat tttgtctccg catggctact   1020
ttggccaagc caatgtcttg ggtcttcctg atactggtgg acaggttgtc tacattcttg   1080
atcaagtacg tgcttttggaa agcgagatgc tcctyaggat acagaagcaa ggactggatg   1140
ttactccaaa gattctcatt gtaacaaggt tgataccaga agcagaagga acaacatgca   1200
accagaggtt agaaaargtw agcggtacag aacacrcaca tattctrcga ataccrtttm   1260
```

-continued

```
ggactgaaaa gggcattctt cgcaagtgga tctcgaggtt tgatgtctgg ccatacctgg    1320
agactttcgc agaggatgca tcaaatgaaa ttgctgcgga gttgcaaggt gtgccaaatc    1380
tcatcattgg caactacagt gatgggaatc tcgtggcttc tttgttagct tgtaagctag    1440
gcgtgataca gtgcaatatt gctcatgctt tggagaaaac caagtatcca gagtctgaca    1500
tttactggag aaaccatgaa gataagtatc attttgcaag tcagttcact gcggacctaa    1560
ttgccatgaa taatgctgat ttcatcatca ccagcacata ccaagagatc gctggaagca    1620
aaaacaaagt tgggcaatac garagccaca cagctttcac ccttcctggt ctttacagag    1680
ttgtkcatgg aatcaatgtc tttgatccca agtttaatat agtctctcca ggagctgata    1740
tgaccatata cttyccwtat tctgacaagg aaagaagact aactgcccct catgagtcwa    1800
ttgaagaact yctgtttagc agygaacaga atgttgagca tgttggtttt ctkagcgacc    1860
agwygaagcc aatcattttc tccatggcca gacttgacag agtgaaaaac ttgactgggc    1920
tagttgagtg ctatgccaas aacrgcaasc tgagagaggt tgcgaaccty sttgtastwg    1980
gtggctacgt ggacgtgaat cagtccaggg acagagagga aatggctgag atacaaaaga    2040
tgcacagcct ratcaagcag tatggtttac acggtgagtt caggtggata gctgctcaaa    2100
tgaaccgtgc tmggaacggt gagctttacc gttatatcgc agacacwaaa ggtgtttttg    2160
ttcagcctgc tttctatgaa gcktttgggc tcacagttgt ggaatcaatg acttgtgggc    2220
tcccaacgtt tgctacatgt catggtggac ctgcggagat catcgagaat ggagtttctg    2280
gcttccacat cgacccwtat catccagaac agsttcaac tactttggtc agcttcttyg    2340
agacctgcaa cgctgatcca agtcactggg agaaaatctc tgatggaggg cttaagcgaa    2400
tctatgaaag gtacacatgg aagaagtact cagagaggct gcttacgctg gctggtgtct    2460
attcattctg gaaacatgtg tctaagcttg aaaggagaga acacgacgt tacctagaga    2520 tgtttttactc tctcaagtat cgtgatctgg ccaattcaat cccactggca actgatgagc    2580
attgagcaag ctatggttgg attctaatac ttgctgcact ccctgttgtg tgtttctgtt    2640
atctttgaat aaataagcta ttgtcggctt ttgtttccat gactagtttg gttttcagac    2700
ttttcctgtt gttttcttga tatgaataac aagtatcgtt gagttctaag ctcggcatta    2760
aataacttgt cgtgtnggaa agcttactga                                       2790
```

<210> SEQ ID NO 45
<211> LENGTH: 807
<212> TYPE: PRT
<213> ORGANISM: Brassica napus
<220> FEATURE:
<221> NAME/KEY: misc_feature
<222> LOCATION: (40)..(40)
<223> OTHER INFORMATION: Xaa can be any naturally occurring amino acid
<220> FEATURE:
<221> NAME/KEY: misc_feature
<222> LOCATION: (229)..(229)
<223> OTHER INFORMATION: Xaa can be any naturally occurring amino acid
<220> FEATURE:
<221> NAME/KEY: misc_feature
<222> LOCATION: (243)..(243)
<223> OTHER INFORMATION: Xaa can be any naturally occurring amino acid
<220> FEATURE:
<221> NAME/KEY: misc_feature
<222> LOCATION: (359)..(359)
<223> OTHER INFORMATION: Xaa can be any naturally occurring amino acid
<220> FEATURE:
<221> NAME/KEY: misc_feature
<222> LOCATION: (568)..(568)
<223> OTHER INFORMATION: Xaa can be any naturally occurring amino acid
<220> FEATURE:
<221> NAME/KEY: misc_feature

```
<222> LOCATION: (593)..(593)
<223> OTHER INFORMATION: Xaa can be any naturally occurring amino acid
<220> FEATURE:
<221> NAME/KEY: misc_feature
<222> LOCATION: (595)..(596)
<223> OTHER INFORMATION: Xaa can be any naturally occurring amino acid
<220> FEATURE:
<221> NAME/KEY: misc_feature
<222> LOCATION: (604)..(604)
<223> OTHER INFORMATION: Xaa can be any naturally occurring amino acid
<220> FEATURE:
<221> NAME/KEY: misc_feature
<222> LOCATION: (606)..(606)
<223> OTHER INFORMATION: Xaa can be any naturally occurring amino acid
<220> FEATURE:
<221> NAME/KEY: misc_feature
<222> LOCATION: (718)..(718)
<223> OTHER INFORMATION: Xaa can be any naturally occurring amino acid

<400> SEQUENCE: 45

Met Pro Thr Gly Arg Phe Glu Thr Met Arg Glu Trp Val His Asp Ala
1               5                   10                  15

Ile Ser Ala Gln Arg Asn Glu Leu Leu Ser Leu Phe Ser Arg Tyr Val
            20                  25                  30

Ala Gln Gly Lys Gly Ile Leu Xaa Ser His Gln Leu Ile Asp Glu Phe
        35                  40                  45

Leu Lys Thr Val Lys Val Asp Gly Thr Thr Glu Asp Leu Lys Asn Arg
50                  55                  60

Pro Phe Met Lys Val Leu Gln Ser Ala Glu Glu Ala Ile Val Leu Pro
65                  70                  75                  80

Pro Phe Val Ala Leu Ala Ile Arg Pro Arg Pro Gly Val Arg Glu Tyr
                85                  90                  95

Val Arg Val Asn Val Tyr Glu Leu Ser Val Asp His Leu Thr Val Ser
            100                 105                 110

Glu Tyr Leu Arg Phe Lys Glu Glu Leu Val Asn Gly His Ala Asn Gly
        115                 120                 125

Asn Tyr Leu Leu Glu Leu Asp Phe Glu Pro Phe Asn Ala Thr Phe Pro
    130                 135                 140

Arg Pro Thr Arg Ser Ser Ser Ile Gly Asn Gly Val Gln Phe Leu Asn
145                 150                 155                 160

Arg His Leu Ser Ser Ile Met Phe Arg Asn Lys Asp Ser Leu Glu Pro
                165                 170                 175

Leu Leu Glu Phe Leu Arg Thr His Lys His Asp Gly Arg Ala Met Met
            180                 185                 190

Leu Asn Asp Arg Ile Gln Asn Ile Arg Thr Leu Gln Glu Ala Leu Ala
        195                 200                 205

Arg Ala Glu Glu Phe Leu Ser Lys Leu Pro Leu Ala Thr Pro Tyr Ser
    210                 215                 220

Glu Phe Glu Phe Xaa Leu Gln Gly Met Gly Phe Glu Arg Gly Trp Gly
225                 230                 235                 240

Asp Thr Xaa Gln Lys Val Ser Glu Met Val His Leu Leu Leu Asp Ile
                245                 250                 255

Leu Gln Ala Pro Asp Pro Ser Val Leu Glu Thr Phe Leu Gly Arg Ile
            260                 265                 270

Pro Met Val Phe Asn Val Ile Leu Ser Pro His Gly Tyr Phe Gly
        275                 280                 285

Gln Ala Asn Val Leu Gly Leu Pro Asp Thr Gly Gly Gln Val Val Tyr
    290                 295                 300

Ile Leu Asp Gln Val Arg Ala Leu Glu Ser Glu Met Leu Leu Arg Ile
305                 310                 315                 320
```

-continued

```
Gln Lys Gln Gly Leu Asp Val Thr Pro Lys Ile Leu Ile Val Thr Arg
                325                 330                 335

Leu Ile Pro Glu Ala Glu Gly Thr Thr Cys Asn Gln Arg Leu Glu Lys
            340                 345                 350

Val Ser Gly Thr Glu His Xaa His Ile Leu Arg Ile Pro Phe Arg Thr
        355                 360                 365

Glu Lys Gly Ile Leu Arg Lys Trp Ile Ser Arg Phe Asp Val Trp Pro
    370                 375                 380

Tyr Leu Glu Thr Phe Ala Glu Asp Ala Ser Asn Glu Ile Ala Ala Glu
385                 390                 395                 400

Leu Gln Gly Val Pro Asn Leu Ile Ile Gly Asn Tyr Ser Asp Gly Asn
                405                 410                 415

Leu Val Ala Ser Leu Leu Ala Cys Lys Leu Gly Val Ile Gln Cys Asn
            420                 425                 430

Ile Ala His Ala Leu Glu Lys Thr Lys Tyr Pro Glu Ser Asp Ile Tyr
        435                 440                 445

Trp Arg Asn His Glu Asp Lys Tyr His Phe Ala Ser Gln Phe Thr Ala
    450                 455                 460

Asp Leu Ile Ala Met Asn Asn Ala Asp Phe Ile Ile Thr Ser Thr Tyr
465                 470                 475                 480

Gln Glu Ile Ala Gly Ser Lys Asn Lys Val Gly Gln Tyr Glu Ser His
                485                 490                 495

Thr Ala Phe Thr Leu Pro Gly Leu Tyr Arg Val Val His Gly Ile Asn
            500                 505                 510

Val Phe Asp Pro Lys Phe Asn Ile Val Ser Pro Gly Ala Asp Met Thr
        515                 520                 525

Ile Tyr Phe Pro Tyr Ser Asp Lys Glu Arg Arg Leu Thr Ala Leu His
    530                 535                 540

Glu Ser Ile Glu Glu Leu Leu Phe Ser Ser Glu Gln Asn Val Glu His
545                 550                 555                 560

Val Gly Phe Leu Ser Asp Gln Xaa Lys Pro Ile Ile Phe Ser Met Ala
                565                 570                 575

Arg Leu Asp Arg Val Lys Asn Leu Thr Gly Leu Val Glu Cys Tyr Ala
            580                 585                 590

Xaa Asn Xaa Xaa Leu Arg Glu Val Ala Asn Leu Xaa Val Xaa Gly Gly
        595                 600                 605

Tyr Val Asp Val Asn Gln Ser Arg Asp Arg Glu Glu Met Ala Glu Ile
    610                 615                 620

Gln Lys Met His Ser Leu Ile Lys Gln Tyr Gly Leu His Gly Glu Phe
625                 630                 635                 640

Arg Trp Ile Ala Ala Gln Met Asn Arg Ala Arg Asn Gly Glu Leu Tyr
                645                 650                 655

Arg Tyr Ile Ala Asp Thr Lys Gly Val Phe Val Gln Pro Ala Phe Tyr
            660                 665                 670

Glu Ala Phe Gly Leu Thr Val Val Glu Ser Met Thr Cys Gly Leu Pro
        675                 680                 685

Thr Phe Ala Thr Cys His Gly Gly Pro Ala Glu Ile Ile Glu Asn Gly
    690                 695                 700

Val Ser Gly Phe His Ile Asp Pro Tyr His Pro Glu Gln Xaa Ala Thr
705                 710                 715                 720

Thr Leu Val Ser Phe Phe Glu Thr Cys Asn Ala Asp Pro Ser His Trp
                725                 730                 735

Glu Lys Ile Ser Asp Gly Gly Leu Lys Arg Ile Tyr Glu Arg Tyr Thr
```

```
                    740                 745                 750
Trp Lys Lys Tyr Ser Glu Arg Leu Leu Thr Leu Ala Gly Val Tyr Ser
            755                 760                 765

Phe Trp Lys His Val Ser Lys Leu Glu Arg Arg Glu Thr Arg Arg Tyr
        770                 775                 780

Leu Glu Met Phe Tyr Ser Leu Lys Tyr Arg Asp Leu Ala Asn Ser Ile
785                 790                 795                 800

Pro Leu Ala Thr Asp Glu His
                805

<210> SEQ ID NO 46
<211> LENGTH: 26
<212> TYPE: DNA
<213> ORGANISM: Artificial sequence
<220> FEATURE:
<223> OTHER INFORMATION: Primer a

<400> SEQUENCE: 46
ccttgcaaaa cttaagatca aaagtc                                        26

<210> SEQ ID NO 47
<211> LENGTH: 26
<212> TYPE: DNA
<213> ORGANISM: Artificial sequence
<220> FEATURE:
<223> OTHER INFORMATION: Primer b

<400> SEQUENCE: 47
ctatagatgg gatgaagctg ctctcg                                        26

<210> SEQ ID NO 48
<211> LENGTH: 24
<212> TYPE: DNA
<213> ORGANISM: Artificial sequence
<220> FEATURE:
<223> OTHER INFORMATION: Primer c

<400> SEQUENCE: 48
agagaggagc tcattgcgtt gagc                                          24

<210> SEQ ID NO 49
<211> LENGTH: 24
<212> TYPE: DNA
<213> ORGANISM: Artificial sequence
<220> FEATURE:
<223> OTHER INFORMATION: Primer d

<400> SEQUENCE: 49
cccattcacg catcgtctcg aacc                                          24

<210> SEQ ID NO 50
<211> LENGTH: 2234
<212> TYPE: DNA
<213> ORGANISM: Brassica napus
<220> FEATURE:
<221> NAME/KEY: misc_feature
<222> LOCATION: (859)..(859)
<223> OTHER INFORMATION: n is a, c, g, or t

<400> SEQUENCE: 50
ctatagatgg gatgaagctg ctctcgacaa atctgataaa actaaagaag gttagtaatc    60 aattttaca aaatcataga ttatttttt cattgaatta tttttatgct ataccaagaa    120
ttgtatttta gtatttgttt taactacata taatagaatt aactacatat aaattaacta   180
```

```
aacttaaaat aaaaatagat ttgtttcctg aaattatttt aagaatatat atgtatatat    240
ctaaaatctt agacttagat agattttct atctatctat tttggttact taaaataaat    300
aaatttgtat aaataattgt atagttatca aaaattaaaa ctaattttt taaagttgtt    360
gatatataaa atactaaaga tttaacgatt aagtattat ttaagtatag aattttgttt    420
ttttttaag tttagttatg aagttgttaa ttatattaaa acaaacaat atttcgaaat    480
tttattatca tattcgaata tatttttt agtgatgatg tatgaattat tatcataatt    540
tgaaagttta ctaaaaata tatcaacatg aattgtaata tatgagttat taccttaacc    600
aaaattataa attaacatta aatataatta tatatgtcat atttagccat acaatgtgtc    660
atcaatatta atagtcatgt caatattaca taatgccaat attatgctac ttaaaccccca    720
aatccccctaa ctcccgttaa gtagccaaat tcataaatat acttattcga caaaataaaa    780
aactttaaaa tatttactaa tccgaccatg cacaagcatc cattccctat tccattgcca    840
cgggataaca atgcaaccna ctcctcaaaa aagaaaaat tcaagctctt ttgcaaaaaa    900
aaataaaata attttaacac ctaaaatttt ttgtttccaa acttctacag ggaacacaca    960
taaaagaaaa agaggacgtc cactcggatc acgcaacaaa ccaaaaggtg tgtcatgact   1020
cctaagatat aatatttcct tattcaaaat cataccattt taaattatga atgtatttcg   1080
tagtccacca gatatgtaat ccaccagcgt tcaaaccaaa gtttttatgat tgtaagttta   1140
agtgaattat aataatatat tcttcacggt atcttttcat aactaattga gttatcaaac   1200
ttgatcgcac atgtggcttt gataggtgtg acttttatgg tatacaattc tttcaaccta   1260
aaaacattat tgttcctcaa tatcttacat tatgcttgac tgcaacaaaa tattttctca   1320
tctgttttct tccttaaac caatttatta tcatctattt cctgacattt taatccatcc   1380
acctatgtca aaaacttata gaaaatgtca acttccaaac aaaacataat tgaacttcgc   1440
aaataaattc ttaataatat taaaaaatgt tacttaatta tttcttcaac cccatttttcc   1500
gcgcgtagcg cggacaaaga ctctagttaa atatagaagt ttccgattct catcgtataa   1560
aacggtgact ttggcgggct ttcatgtgta acaaattggt ttaacaaacc actgcctagt   1620
cgtttagtgt agaatcagcg catggaactc cgattggagc gtgactttca cgtgccggag   1680
gcccaccacc acagcgggcg ttacgctcta agaatctcgc ccacggtttt cttcatctgc   1740
cccccgccaa gtgtcttcct cgttcgccac ttctcaccaa gttacaggaa ccctaaaaat   1800
ggcctttctt cagccccggc tataatacac acatgatcct atagtgggtt cttccacaag   1860
ttacatctcc ttctggattg tacatttcaa gtgtttgtgt ttttctgcc tctgagagaa   1920
aatcatgccg acgggtaggt tcgagacgat gcgtgaatgg gttcacgacg ccatctctgc   1980
tcaacgcaat gagctcctct ctctcttttc caggtatctc tctctctctt actgaatatg   2040
cgttacatat ataagttcag tacatgcatt gtcactttgt caactttcaa cagttgagag   2100
tagagcatgt taaaaaaaa agttagttcg ttttacttgc atgtgtgttg tggttagtct   2160
caggaggagt aatgctttgg tttgctatgt ttagatacgt agctcagggg aaagggatac   2220
tgcagtccca ccag                                                    2234
```

<210> SEQ ID NO 51
<211> LENGTH: 632
<212> TYPE: DNA
<213> ORGANISM: Brassica napus

<400> SEQUENCE: 51

```
ccaatttatt atcatctatt tcctgacatt ttaatccatc cacctatgtc aaaaacttat    60
```

```
agaaaatgtc aacttccaaa caaaacataa ttgaacttcg caaataaatt cttaataata      120 ttaaaaatg ttacttaatt atttcttcaa ccccatttttc cgcgcgtagc gcggacaaag       180
actctagtta aatatagaag tttccgattc tcatcgtata aaacggtgac tttggcgggc      240
tttcatgtgt aacaaattgg tttaacaaac cactgcctag tcgtttagtg tagaatcagc     300
gcatggaact ccgattggag cgtgactttc acgtrccgga ggcccaccac cwcagcgggc     360
gttacgctct aagaatctcg cccacggttt tcttcatctc cccccccgcca agtgtctccc    420 tcgttcgcca cttctcatca tgttacaggg accataaaaa tggcgtattt cttcagcccc     480
gggtataaat acacacatga tcctgtggtg ggttcttcca caagttacat ctccttctgg     540
tttttgtatt gcaagtgttt gtatttttttg cctccgagag aaaatcatgc cgaccggtag    600
gttcgagacg atgcgtgaat gggcctgaat tc                                    632

<210> SEQ ID NO 52
<211> LENGTH: 35
<212> TYPE: DNA
<213> ORGANISM: Artificial sequence
<220> FEATURE:
<223> OTHER INFORMATION: Primer SA188

<400> SEQUENCE: 52
ggcgcgcccc aatttattat catctatttc ctgac                                 35

<210> SEQ ID NO 53
<211> LENGTH: 34
<212> TYPE: DNA
<213> ORGANISM: Artificial sequence
<220> FEATURE:
<223> OTHER INFORMATION: Primer SA189

<400> SEQUENCE: 53
gcggccgcga ttttctctcg gaggcaaaaa atac                                  34

<210> SEQ ID NO 54
<211> LENGTH: 36
<212> TYPE: DNA
<213> ORGANISM: Artificial sequence
<220> FEATURE:
<223> OTHER INFORMATION: Primer SA190

<400> SEQUENCE: 54
ggcgcgccct atagatggga tgaagctgct ctcgac                                36

<210> SEQ ID NO 55
<211> LENGTH: 36
<212> TYPE: DNA
<213> ORGANISM: Artificial sequence
<220> FEATURE:
<223> OTHER INFORMATION: Primer SA191

<400> SEQUENCE: 55
gcggccgcga ttttctctca gaggcagaaa aaacac                                36

<210> SEQ ID NO 56
<211> LENGTH: 4114
<212> TYPE: DNA
<213> ORGANISM: Artificial sequence
<220> FEATURE:
<223> OTHER INFORMATION: Plasmid BN SUS2 prom1/PCR blunt

<400> SEQUENCE: 56
cctgaattct gcagatatcc atcacactgg cggccgctcg agcatgcatc tagagggccc      60
```

```
aattcgccct atagtgagtc gtattacaat tcactggccg tcgttttaca acgtcgtgac    120
tgggaaaacc ctggcgttac ccaacttaat cgccttgcag cacatccccc tttcgccagc    180
tggcgtaata gcgaagaggc ccgcaccgat cgcccttccc aacagttgcg cagcctatac    240
gtacggcagt ttaaggttta cacctataaa agagagagcc gttatcgtct gtttgtggat    300
gtacagagtg atattattga cacgccgggg cgacggatgg tgatccccct ggccagtgca    360
cgtctgctgt cagataaagt ctcccgtgaa ctttacccgg tggtgcatat cggggatgaa    420
agctggcgca tgatgaccac cgatatggcc agtgtgccgg tctccgttat cggggaagaa    480
gtggctgatc tcagccaccg cgaaaatgac atcaaaaacg ccattaacct gatgttctgg    540
ggaatataaa tgtcaggcat gagattatca aaaaggatct tcacctagat ccttttcacg    600
tagaaagcca gtccgcagaa acggtgctga ccccggatga atgtcagcta ctgggctatc    660
tggacaaggg aaaacgcaag cgcaaagaga agcaggtag cttgcagtgg gcttacatgg    720
cgatagctag actgggcggt tttatggaca gcaagcgaac cggaattgcc agctggggcg    780
ccctctggta aggttgggaa gccctgcaaa gtaaactgga tggctttctt gccgccaagg    840
atctgatggc gcaggggatc aagctctgat caagagacag gatgaggatc gtttcgcatg    900
attgaacaag atggattgca cgcaggttct ccggccgctt gggtggagag gctattcggc    960
tatgactggg cacaacagac aatcggctgc tctgatgccg ccgtgttccg gctgtcagcg   1020
caggggcgcc cggttctttt tgtcaagacc gacctgtccg gtgccctgaa tgaactgcaa   1080
gacgaggcag cgcggctatc gtggctggcc acgacgggcg ttccttgcgc agctgtgctc   1140
gacgttgtca ctgaagcggg aagggactgg ctgctattgg gcgaagtgcc ggggcaggat   1200
ctcctgtcat ctcaccttgc tcctgccgag aaagtatcca tcatggctga tgcaatgcgg   1260
cggctgcata cgcttgatcc ggctacctgc ccattcgacc accaagcgaa acatcgcatc   1320
gagcgagcac gtactcggat ggaagccggt cttgtcgatc aggatgatct ggacgaagag   1380
catcaggggc tcgcgccagc cgaactgttc gccaggctca aggcgagcat gcccgacggc   1440
gaggatctcg tcgtgaccca tggcgatgcc tgcttgccga atatcatggt ggaaaatggc   1500
cgcttttctg gattcatcga ctgtggccgg ctgggtgtgg cggaccgcta tcaggacata   1560
gcgttggcta cccgtgatat tgctgaagag cttggcggcg aatgggctga ccgcttcctc   1620
gtgctttacg gtatcgccgc tcccgattcg cagcgcatcg ccttctatcg ccttcttgac   1680
gagttcttct gaattattaa cgcttacaat ttcctgatgc ggtattttct ccttacgcat   1740
ctgtgcggta tttcacaccg catcaggtgg cacttttcgg ggaaatgtgc gcggaacccc   1800
tatttgttta ttttttctaaa tacattcaaa tatgtatccg ctcatgagac aataaccctg   1860
ataaatgctt caataatagc acgtgaggag gccaccatg ccaagttga ccagtgccgt    1920 tccggtgctc accgcgcgcg acgtcgccgg agcggtcgag ttctggaccg accggctcgg   1980
gttctcccgg gacttcgtgg aggacgactt cgccggtgtg tccgggacg acgtgacct    2040 gttcatcagc gcggtccagg accaggtggt gccggacaac accctggcct gggtgtgggt   2100
gcgcggcctg gacgagctgt acgccgagtg gtcggaggtc gtgtccacga acttccggga   2160
cgcctccggg ccggccatga ccgagatcgg cgagcagccg tgggggcggg agttcgccct   2220
gcgcgacccg gccggcaact gcgtgcactt cgtggccgag gagcaggact gacacgtgct   2280
aaaacttcat ttttaattta aaaggatcta ggtgaagatc cttttttgata atctcatgac   2340 caaaatccct taacgtgagt tttcgttcca ctgagcgtca gaccccgtag aaaagatcaa   2400
aggatcttct tgagatcctt ttttttctgcg cgtaatctgc tgcttgcaaa caaaaaaacc   2460
```

```
accgctacca gcggtggttt gtttgccgga tcaagagcta ccaactcttt ttccgaaggt    2520
aactggcttc agcagagcgc agataccaaa tactgttctt ctagtgtagc cgtagttagg    2580 ccaccactic aagaactctg tagcaccgcc tacatacctc gctctgctaa tcctgttacc    2640
agtggctgct gccagtggcg ataagtcgtg tcttaccggg ttggactcaa gacgatagtt    2700
accggataag gcgcagcggt cgggctgaac gggggggttcg tgcacacagc ccagcttgga    2760
gcgaacgacc tacaccgaac tgagatacct acagcgtgag ctatgagaaa gcgccacgct    2820
tcccgaaggg agaaaggcgg acaggtatcc ggtaagcggc agggtcggaa caggagagcg    2880
cacgagggag cttccagggg gaaacgcctg gtatctttat agtcctgtcg ggtttcgcca    2940
cctctgactt gagcgtcgat ttttgtgatg ctcgtcaggg gggcggagcc tatggaaaaa    3000
cgccagcaac gcggccttt tacgttcct ggccttttgc tggccttttg ctcacatgtt    3060
ctttcctgcg ttatcccctg attctgtgga taaccgtatt accgcctttg agtgagctga    3120
taccgctcgc cgcagccgaa cgaccgagcg cagcgagtca gtgagcgagg aagcggaaga    3180
gcgcccaata cgcaaaccgc ctctccccgc gcgttggccg attcattaat gcagctggca    3240
cgacaggttt cccgactgga aagcgggcag tgagcgcaac gcaattaatg tgagttagct    3300
cactcattag gcaccccagg ctttacactt tatgcttccg gctcgtatgt tgtgtggaat    3360
tgtgagcgga taacaatttc acacaggaaa cagctatgac catgattacg ccaagctatt    3420
taggtgacgc gttagaatac tcaagctatg catcaagctt ggtaccgagc tcggatccac    3480
tagtaacggc cgccagtgtg ctggaattca ggggcgcgcc caatttatt atcatctatt    3540 tcctgacatt ttaatccatc cacctatgtc aaaaacttat agaaaatgtc aacttccaaa    3600
caaaacataa ttgaacttcg caaataaatt cttaataata ttaaaaaatg ttacttaatt    3660
atttcttcaa ccccattttc cgcgcgtagc gcggacaaag actctagtta aatatagaag    3720
tttccgattc tcatcgtata aaacggtgac tttggcgggc tttcatgtgt aacaaattgg    3780
tttaacaaac cactgcctag tcgtttagtg tagaatcagc gcatgaact ccgattggag    3840 cgtgactttc acgtgccgga ggccaccac cacagcgggc gttacgctct aagaatctcg    3900
cccacggttt tcttcatctc cccccgcca agtgtctccc tcgttcgcca cttctcatca    3960
tgttacaggg accataaaaa tggcgtattt cttcagcccc gggtataaat acacacatga    4020
tcctgtggtg ggttcttcca caagttacat ctccttctgg ttttttgtatt gcaagtgttt    4080 gtatttttg cctccgagag aaaatcgcgg ccgc                                 4114
```

<210> SEQ ID NO 57
<211> LENGTH: 5452
<212> TYPE: DNA
<213> ORGANISM: Artificial sequence
<220> FEATURE:
<223> OTHER INFORMATION: Plasmid BN SUS2 prom2/PCR blunt
<220> FEATURE:
<221> NAME/KEY: misc_feature
<222> LOCATION: (4379)..(4379)
<223> OTHER INFORMATION: n is a, c, g, or t

<400> SEQUENCE: 57

```
cctgaattct gcagatatcc atcacactgg cggccgctcg agcatgcatc tagagggccc      60
aattcgccct atagtgagtc gtattacaat tcactggccg tcgttttaca acgtcgtgac     120
tgggaaaacc ctggcgttac ccaacttaat cgccttgcag cacatccccc tttcgccagc     180
tggcgtaata gcgaagaggc ccgcaccgat cgcccttccc aacagttgcg cagcctatac     240
gtacggcagt ttaaggttta cacctataaa agagagagcc gttatcgtct gtttgtggat     300
```

```
gtacagagtg atattattga cacgccgggg cgacggatgg tgatccccct ggccagtgca    360
cgtctgctgt cagataaagt ctcccgtgaa ctttacccgg tggtgcatat cggggatgaa    420
agctggcgca tgatgaccac cgatatggcc agtgtgccgg tctccgttat cggggaagaa    480
gtggctgatc tcagccaccg cgaaaatgac atcaaaaacg ccattaacct gatgttctgg    540
ggaatataaa tgtcaggcat gagattatca aaaaggatct tcacctagat ccttttcacg    600
tagaaagcca gtccgcagaa acggtgctga ccccggatga atgtcagcta ctgggctatc    660
tggacaaggg aaaacgcaag cgcaaagaga aagcaggtag cttgcagtgg cttacatgg     720 cgatagctag actgggcggt tttatggaca gcaagcgaac cggaattgcc agctggggcg    780
ccctctggta aggttgggaa gccctgcaaa gtaaactgga tggctttctt gccgccaagg    840
atctgatggc gcaggggatc aagctctgat caagagacag gatgaggatc gtttcgcatg    900
attgaacaag atggattgca cgcaggttct ccggccgctt gggtggagag gctattcggc    960
tatgactggg cacaacagac aatcggctgc tctgatgccg ccgtgttccg gctgtcagcg   1020
caggggcgcc cggttctttt tgtcaagacc gacctgtccg gtgccctgaa tgaactgcaa   1080
gacgaggcag cgcggctatc gtggctggcc acgacgggcg ttccttgcgc agctgtgctc   1140
gacgttgtca ctgaagcggg aagggactgg ctgctattgg gcgaagtgcc ggggcaggat   1200
ctcctgtcat ctcaccttgc tcctgccgag aaagtatcca tcatggctga tgcaatgcgg   1260
cggctgcata cgcttgatcc ggctacctgc ccattcgacc accaagcgaa acatcgcatc   1320
gagcgagcac gtactcggat ggaagccggt cttgtcgatc aggatgatct ggacgaagag   1380
catcaggggc tcgcgccagc cgaactgttc gccaggctca aggcgagcat gcccgacggc   1440
gaggatctcg tcgtgaccca tggcgatgcc tgcttgccga atatcatggt ggaaaatggc   1500
cgcttttctg gattcatcga ctgtggccgg ctgggtgtgg cggaccgcta tcaggacata   1560
gcgttggcta cccgtgatat tgctgaagag cttggcggcg aatgggctga ccgcttcctc   1620
gtgctttacg gtatcgccgc tcccgattcg cagcgcatcg ccttctatcg ccttcttgac   1680
gagttcttct gaattattaa cgcttacaat ttcctgatgc ggtattttct ccttacgcat   1740
ctgtgcggta tttcacaccg catcaggtgg cacttttcgg ggaaatgtgc gcggaacccc   1800
tatttgttta ttttctaaa tacattcaaa tatgtatccg ctcatgagac aataaccctg    1860
ataaatgctt caataatagc acgtgaggag ggccaccatg gccaagttga ccagtgccgt   1920
tccggtgctc accgcgcgcg acgtcgccgg agcggtcgag ttctggaccg accggctcgg   1980
gttctcccgg gacttcgtgg aggacgactt cgccggtgtg gtccgggacg acgtgaccct   2040
gttcatcagc gcggtccagg accaggtggt gccggacaac accctggcct gggtgtgggt   2100
gcgcggcctg gacgagctgt acgccgagtg gtcggaggtc gtgtccacga acttccggga   2160
cgcctccggg ccggccatga ccgagatcgg cgagcagccg tgggggcggg agttcgccct   2220
gcgcgacccg gccggcaact gcgtgcactt cgtggccgag gagcaggact gacacgtgct   2280
aaaacttcat ttttaattta aaaggatcta ggtgaagatc ctttttgata atctcatgac   2340
caaaatccct taacgtgagt tttcgttcca ctgagcgtca gaccccgtag aaaagatcaa   2400
aggatcttct tgagatcctt ttttctgcg cgtaatctgc tgcttgcaaa caaaaaaacc    2460
accgctacca gcggtggttt gtttgccgga tcaagagcta ccaactcttt ttccgaaggt   2520
aactggcttc agcagagcgc agataccaaa tactgttctt ctagtgtagc cgtagttagg   2580
ccaccacttc aagaactctg tagcaccgcc tacatacctc gctctgctaa tcctgttacc   2640
agtggctgct gccagtggcg ataagtcgtg tcttaccggg ttggactcaa gacgatagtt   2700
```

```
accggataag gcgcagcggt cgggctgaac ggggggttcg tgcacacagc ccagcttgga    2760
gcgaacgacc tacaccgaac tgagatacct acagcgtgag ctatgagaaa gcgccacgct    2820
tcccgaaggg agaaaggcgg acaggtatcc ggtaagcggc agggtcggaa caggagagcg    2880
cacgagggag cttccagggg gaaacgcctg gtatctttat agtcctgtcg ggtttcgcca    2940
cctctgactt gagcgtcgat ttttgtgatg ctcgtcaggg gggcggagcc tatggaaaaa    3000
cgccagcaac gcggccttt tacgttcct ggccttttgc tggccttttg ctcacatgtt    3060
ctttcctgcg ttatcccctg attctgtgga taaccgtatt accgcctttg agtgagctga    3120
taccgctcgc cgcagccgaa cgaccgagcg cagcgagtca gtgagcgagg aagcggaaga    3180
gcgcccaata cgcaaaccgc ctctccccgc gcgttggccg attcattaat gcagctggca    3240
cgacaggttt cccgactgga aagcgggcag tgagcgcaac gcaattaatg tgagttagct    3300
cactcattag gcaccccagg ctttacactt tatgcttccg gctcgtatgt tgtgtggaat    3360
tgtgagcgga taacaatttc acacaggaaa cagctatgac catgattacg ccaagctatt    3420
taggtgacgc gttagaatac tcaagctatg catcaagctt ggtaccgagc tcggatccac    3480
tagtaacggc cgccagtgtg ctggaattca ggggcgcgcc ctatagatgg gatgaagctg    3540
ctctcgacaa atctgataaa actaaagaag gttagtaatc aattttaca aaatcataga    3600 ttattttttt cattgaatta ttttatgct ataccaagaa ttgtattta gtatttgttt    3660 taactacata taatagaatt aactacatat aaattaacta aacttaaaat aaaaatagat    3720
ttgtttcctg aaattatttt aagaatatat atgtatatat ctaaaatctt agacttagat    3780
agatttttct atctatctat tttggttact taaaataaat aaatttgtat aaataattgt    3840
atagttatca aaaattaaaa ctaatttttt taaagttgtt gatatataaa atactaaaga    3900
tttaacgatt aagtatttat ttaagtatag aattttgttt tttttttaag tttagttatg    3960
aagttgttaa ttatattaaa acaaaacaat atttcgaaat tttattatca tattcgaata    4020
tatttttttt agtgatgatg tatgaattat tatcataatt tgaaagttta ctaaaaaata    4080
tatcaacatg aattgtaata tatgagttat taccttaacc aaaattataa attaacatta    4140
aatataatta tatatgtcat atttagccat acaatgtgtc atcaatatta atagtcatgt    4200
caatattaca taatgccaat attatgctac ttaaacccca aatcccctaa ctcccgttaa    4260
gtagccaaat tcataaatat acttattcga caaaataaaa aacttaaaaa tatttactaa    4320
tccgaccatg cacaagcatc cattccctat tccattgcca cgggataaca atgcaaccna    4380
ctcctcaaaa aaagaaaaat tcaagctctt ttgcaaaaaa aaataaaata atttttaacac    4440 ctaaaatttt ttgtttccaa acttctacag ggaacacaca taaaagaaaa agaggacgtc    4500
cactcggatc acgcaacaaa ccaaaaggtg tgtcatgact cctaagatat aatatttcct    4560
tattcaaaat cataccattt taaattatga atgtatttcg tagtccacca gatatgtaat    4620
ccaccagcgt tcaaaccaaa gttttatgat tgtaagttta agtgaattat aataatatat    4680
tcttcacggt atcttttcat aactaattga gttatcaaac ttgatcgcac atgtggcttt    4740
gataggtgtg acttttatgg tatacaattc tttcaaccta aaacattat tgttcctcaa    4800 tatcttacat tatgcttgac tgcaacaaaa tattttctca tctgttttct tcctttaaac    4860
caatttatta tcatctattt cctgacattt taatccatcc acctatgtca aaacttata    4920 gaaaatgtca acttccaaac aaaacataat tgaacttcgc aaataaattc ttaataatat    4980
taaaaaatgt tacttaatta tttcttcaac cccattttcc cgcgcgtagcg cggacaaaga    5040 ctctagttaa atatagaagt ttccgattct catcgtataa aacggtgact ttggcgggct    5100
```

-continued

```
ttcatgtgta acaaattggt ttaacaaacc actgcctagt cgtttagtgt agaatcagcg    5160 catgaactc cgattggagc gtgactttca cgtgccggag gcccaccacc acagcgggcg    5220
ttacgctcta agaatctcgc ccacggtttt cttcatctgc ccccgccaa gtgtcttcct    5280 cgttcgccac ttctcaccaa gttacaggaa ccctaaaaat ggccttcctt cagccccggc    5340
tataatacac acatgatcct atagtgggtt cttccacaag ttacatctcc ttctggattg    5400
tacatttcaa gtgtttgtgt tttttctgcc tctgagagaa aatcgcggcc gc            5452
```

<210> SEQ ID NO 58
<211> LENGTH: 8227
<212> TYPE: DNA
<213> ORGANISM: Artificial sequence
<220> FEATURE:
<223> OTHER INFORMATION: Vector KS427
<220> FEATURE:
<221> NAME/KEY: misc_feature
<222> LOCATION: (6408)..(6408)
<223> OTHER INFORMATION: n is a, c, g, or t

<400> SEQUENCE: 58

```
ctagagggcc caattcgccc tatagtgagt cgtattacaa ttcactggcc gtcgttttac      60
aacgtcgtga ctgggaaaac cctggcgtta cccaacttaa tcgccttgca gcacatcccc     120
ctttcgccag ctggcgtaat agcgaagagg cccgcaccga tcgcccttcc caacagttgc     180
gcagcctata cgtacggcag tttaaggttt acacctataa aagagagagc cgttatcgtc     240
tgtttgtgga tgtacagagt gatattattg acacgccggg cgacggatg gtgatccccc     300 tggccagtgc acgtctgctg tcagataaag tctcccgtga actttacccg gtggtgcata     360
tcggggatga agctggcgc atgatgacca ccgatatggc cagtgtgccg gtctccgtta     420
tcggggaaga agtggctgat ctcagccacc gcgaaaatga catcaaaaac gccattaacc     480
tgatgttctg gggaatataa atgtcaggca tgagattatc aaaaaggatc ttcacctaga     540
tccttttcac gtagaaagcc agtccgcaga aacggtgctg accccggatg aatgtcagct     600
actgggctat ctggacaagg gaaaacgcaa gcgcaaagag aaagcaggta gcttgcagtg     660
ggcttacatg gcgatagcta gactgggcgg ttttatggac agcaagcgaa ccggaattgc     720
cagctggggc gccctctggt aaggttggga agccctgcaa agtaaactgg atggctttct     780
tgccgccaag gatctgatgg cgcaggggat caagctctga tcaagagaca ggatgaggat     840
cgtttcgcat gattgaacaa gatggattgc acgcaggttc tccggccgct gggtggaga     900 ggctattcgg ctatgactgg gcacaacaga caatcggctg ctctgatgcc gccgtgttcc     960
ggctgtcagc gcaggggcgc ccggttcttt ttgtcaagac cgacctgtcc ggtgccctga    1020
atgaactgca agacgaggca gcgcggctat cgtggctggc cacgacgggc gttccttgcg    1080
cagctgtgct cgacgttgtc actgaagcgg gaagggactg gctgctattg ggcgaagtgc    1140
cggggcagga tctcctgtca tctcaccttg ctcctgccga aaagtatcc atcatggctg    1200 atgcaatgcg gcggctgcat acgcttgatc cggctacctg cccattcgac caccaagcga    1260
aacatcgcat cgagcgagca cgtactcgga tggaagccgg tcttgtcgat caggatgatc    1320
tggacgaaga gcatcagggg ctcgcgccag ccgaactgtt cgccaggctc aaggcgagca    1380
tgcccgacgg cgaggatctc gtcgtgaccc atggcgatgc ctgcttgccg aatatcatgg    1440
tggaaaatgg ccgcttttct ggattcatcg actgtggccg ctgggtgtg gcggaccgct    1500 atcaggacat agcgttggct acccgtgata ttgctgaaga gcttggcggc gaatgggctg    1560
accgcttcct cgtgctttac ggtatcgccg ctcccgattc gcagcgcatc gccttctatc    1620
```

```
gccttcttga cgagttcttc tgaattatta acgcttacaa tttcctgatg cggtattttc   1680
tccttacgca tctgtgcggt atttcacacc gcatcaggtg gcacttttcg gggaaatgtg   1740
cgcggaaccc ctatttgttt attttttctaa atacattcaa atatgtatcc gctcatgaga   1800
caataaccct gataaatgct tcaataatag cacgtgagga gggccaccat ggccaagttg   1860
accagtgccg ttccggtgct caccgcgcgc gacgtcgccg gagcggtcga gttctggacc   1920
gaccggctcg ggttctcccg ggacttcgtg gaggacgact cgccggtgt ggtccgggac    1980
gacgtgaccc tgttcatcag cgcggtccag gaccaggtgg tgccggacaa caccctggcc   2040
tgggtgtggg tgcgcggcct ggacgagctg tacgccgagt ggtcggaggt cgtgtccacg   2100
aacttccggg acgcctccgg gccggccatg accgagatcg gcgagcagcc gtggggggcgg  2160
gagttcgccc tgcgcgaccc ggccggcaac tgcgtgcact cgtggccga ggagcaggac    2220
tgacacgtgc taaaacttca ttttttaattt aaaaggatct aggtgaagat ccttttttgat 2280
aatctcatga ccaaaatccc ttaacgtgag ttttcgttcc actgagcgtc agaccccgta   2340
gaaaagatca aggatcttc ttgagatcct ttttttctgc gcgtaatctg ctgcttgcaa    2400
acaaaaaaac caccgctacc agcggtggtt tgtttgccgg atcaagagct accaactctt   2460
tttccgaagg taactggctt cagcagagcg cagataccaa atactgttct tctagtgtag   2520
ccgtagttag gccaccactt caagaactct gtagcaccgc ctacatacct cgctctgcta   2580
atcctgttac cagtggctgc tgccagtggc gataagtcgt gtcttaccgg gttggactca   2640
agacgatagt taccggataa ggcgcagcgg tcgggctgaa cggggggttc gtgcacacag   2700
cccagcttgg agcgaacgac ctacaccgaa ctgagatacc tacagcgtga gctatgagaa   2760
agcgccacgc ttcccgaagg gagaaaggcg gacaggtatc cggtaagcgg cagggtcgga   2820
acaggagagc gcacgaggga gcttccaggg ggaaacgcct ggtatcttta tagtcctgtc   2880
gggtttcgcc acctctgact tgagcgtcga ttttttgtgat gctcgtcagg ggggcggagc   2940
ctatggaaaa acgccagcaa cgcggccttt ttacggttcc tggccttttg ctggcctttt   3000
gctcacatgt tctttcctgc gttatcccct gattctgtgg ataaccgtat taccgccttt   3060
gagtgagctg ataccgctcg ccgcagccga acgaccgagc gcagcgagtc agtgagcgag   3120
gaagcggaag agcgcccaat acgcaaaccg cctctccccg cgcgttggcc gattcattaa   3180
tgcagctggc acgacaggtt tcccgactgg aaagcgggca gtgagcgcaa cgcaattaat   3240
gtgagttagc tcactcatta ggcaccccag gctttacact ttatgcttcc ggctcgtatg   3300
ttgtgtggaa ttgtgagcgg ataacaattt cacacaggaa acagctatga ccatgattac   3360
gccaagctat ttaggtgacg cgttagaata ctcaagctat gcatcaagct tggtaccgag   3420
ctcggatcca ctagtaacgg ccgccagtgt gctggaattc aggggcgcgc ccaatttat    3480
tatcatctat ttcctgacat tttaatccat ccacctatgt caaaaactta tagaaaatgt   3540
caacttccaa acaaaacata attgaacttc gcaaataaat tcttaataat attaaaaaat   3600
gttacttaat tatttcttca accccatttt ccgcgcgtag cgcggacaaa gactctagtt   3660
aaatatagaa gttccgatt ctcatcgtat aaaacggtga ctttggcggg ctttcatgtg    3720
taacaaattg gtttaacaaa ccactgccta gtcgtttagt gtagaatcag cgcatggaac   3780
tccgattgga gcgtgacttt cacgtgccgg aggcccacca ccacagcggg cgttacgctc   3840
taagaatctc gcccacggtt ttcttcatct cccccccgcc aagtgtctcc ctcgttcgcc   3900
acttctcatc atgttacagg gaccataaaa atggcgtatt tcttcagccc cgggtataaa   3960
tacacacatg atcctgtggt gggttcttcc acaagttaca tctccttctg gttttgtat    4020
```

```
tgcaagtgtt tgtatttttt gcctccgaga gaaaatcgcg gccgcaagta tgaactaaaa    4080
tgcatgtagg tgtaagagct catggagagc atggaatatt gtatccgacc atgtaacagt    4140
ataataactg agctccatct cacttcttct atgaataaac aaaggatgtt atgatatatt    4200
aacactctat ctatgcacct tattgttcta tgataaattt cctcttatta ttataaatca    4260
tctgaatcgt gacggcttat ggaatgcttc aaatagtaca aaacaaatg tgtactataa     4320 gactttctaa acaattctaa ccttagcatt gtgaacgaga cataagtgtt aagaagacat    4380
aacaattata atggaagaag tttgtctcca tttatatatt atatattacc cacttatgta    4440
ttatattagg atgttaagga gacataacaa ttataaagag agaagtttgt atccatttat    4500
atattatata ctacccattt atatattata cttatccact tatttaatgt ctttataagg    4560
tttgatccat gatatttcta atattttagt tgatatgtat atgaaagggt actatttgaa    4620
ctctcttact ctgtataaag gttggatcat ccttaaagtg ggtctattta attttattgc    4680
ttcttacaga taaaaaaaaa attatgagtt ggtttgataa atattgaag gatttaaaat     4740 aataataaat aacatataat atatgtatat aaatttatta taatataaca tttatctata    4800
aaaaagtaaa tattgtcata aatctataca atcgtttagc cttgctggac gaatctcaat    4860
tatttaaacg agagtaaaca tatttgactt tttggttatt taacaaatta ttatttaaca    4920
ctatatgaaa ttttttttt tatcagcaaa gaataaaatt aaattaagaa ggacaatggt     4980
gtcccaatcc ttatacaacc aacttccaca agaaagtcaa gtcagagaca acaaaaaaac    5040
aagcaaagga aatttttaa tttgagttgt cttgtttgct gcataattta tgcagtaaaa     5100
cactacacat aaccctttta gcagtagagc aatggttgac cgtgtgctta gcttctttta    5160 ttttatttt ttatcagcaa agaataaata aaataaaatg agacacttca gggatgtttc     5220
aacaagcttg gatcctcgaa gagaaagggtt aataacacac ttttttaaca ttttttaacac    5280 aaatttagt tatttaaaaa tttattaaaa aatttaaaat aagaagagga actctttaaa     5340
taaatctaac ttacaaaatt tatgattttt aataagtttt caccaataaa aaatgtcata    5400
aaaatatgtt aaaagtata ttatcaatat tctctttatg ataaataaaa agaaaaaaaa     5460
aataaaagtt aagtgaaaat gagattgaag tgacttagg tgtgtataaa tatatcaacc     5520
ccgccaacaa tttatttaat ccaaatatat tgaagtatat tattccatag cctttattta    5580
tttatatatt tattatataa aagctttatt tgttctaggt tgttcatgaa atattttttt    5640
ggttttatct ccgttgtaag aaaatcatgt gctttgtgtc gccactcact attgcagctt    5700
tttcatgcat tggtcagatt gacggttgat tgtattttg ttttttatgg ttttgtgtta     5760
tgacttaagt cttcatctct ttatctcttc atcaggtttg atggttacct aatatggtcc    5820
atgggtacgc gcatggttaa attaggtggc caactttgtt gtgaacgata gaattttttt    5880
tatattaagt aaactatttt tatattatga ataataata aaaaaaatat tttatcatta     5940
ttaacaaaat catattagtt aatttgttaa ctctataata aaagaaatac tgtaacattc    6000
acattacatg gtaacatctt tccaccctttt catttgtttt ttgtttgatg actttttttc   6060
ttgtttaaat ttatttccct tcttttaaat ttggaataca ttatcatcat atataaacta    6120
aaatactaaa aacaggatta cacaaatgat aaataataac acaaatattt ataaatctag    6180
ctgcaatata tttaaactag ctatatcgat attgtaaaat aaaactagct gcattgatac    6240
tgataaaaaa atatcatgtg ctttctggac tgatgatgca gtatacttt gacattgcct     6300 ttatttatt tttcagaaaa gctttcttag ttctgggttc ttcattattt gtttcccatc     6360
tccattgtga attgaatcat ttgcttcgtg tcacaaatac aatttagnta ggtacatgca    6420
```

```
ttggtcagat tcacggttta ttatgtcatg acttaagttc atggtagtac attacctgcc   6480
acgcatgcat tatattggtt agatttgata ggcaaatttg gttgtcaaca atataaatat   6540
aaataatgtt tttatattac gaaataacag tgatcaaaac aaacagtttt atctttatta   6600
acaagatttt gttttgttt gatgacgttt tttaatgttt acgctttccc ccttcttttg    6660
aatttagaac actttatcat cataaaatca aatactaaaa aaattacata tttcataaat   6720
aataacacaa atattttaa aaaatctgaa ataataatga acaatattac atattatcac    6780
gaaaattcat taataaaaat attatataaa taaaatgtaa tagtagttat atgtaggaaa   6840
aaagtactgc acgcataata tatacaaaaa gattaaaatg aactattata aataataaca   6900
ctaaattaat ggtgaatcat atcaaaataa tgaaaaagta aataaaattt gtaattaact   6960
tctatatgta ttacacacac aaataataaa taatagtaaa aaaaattatg ataaatattt   7020
accatctcat aagatattta aaataatgat aaaaatatag attatttttt atgcaactag   7080
ctagccaaaa agagaacacg ggtatatata aaaagagtac ctttaaattc tactgtactt   7140
cctttattcc tgacgttttt atatcaagtg gacatacgtg aagattttaa ttatcagtct   7200
aaatatttca ttagcactta atactttct gttttattcc tatcctataa gtagtcccga    7260
ttctcccaac attgcttatt cacacaacta actaagaaag tcttccatag cccccccaagc  7320 ggcccatggc ctcctccgag gacgtcatca aggagttcat gcgcttcaag gtgcgcatgg   7380
agggctccgt gaacggccac gagttcgaga tcgagggcga gggcgagggc cgcccctacg   7440
agggcaccca gaccgccaag ctgaaggtga ccaaggggcgg cccctgccc ttcgcctggg   7500 acatcctgtc cccccagttc cagtacggct ccaaggtgta cgtgaagcac cccgccgaca   7560
tccccgacta caagaagctg tccttccccg agggcttcaa gtgggagcgc gtgatgaact   7620
tcgaggacgg cggcgtggtg accgtgaccc aggactcctc cctgcaggac ggctccttca   7680
tctacaaggt gaagttcatc ggcgtgaact tccctccga cggccccgta atgcagaaga    7740
agactatggg ctgggaggcc tccaccgagc gcctgtaccc ccgcgacggc gtgctgaagg   7800
gcgagatcca caaggccctg aagctgaagg acggcggcca ctacctggtg gagttcaagt   7860
ccatctacat ggccaagaag cccgtgcagc tgcccggcta ctactacgtg gactccaagc   7920
tggacatcac ctcccacaac gaggactaca ccatcgtgga gcagtacgag cgcgccgagg   7980
gccgccacca cctgttcctg tagcggccgg ccgcgcacaca agtgtgagag tactaaaataa  8040 atgctttggt tgtacgaaat cattacacta aataaaataa tcaaagctta tatatgcctt   8100
ccgctaaggc cgaatgcaaa gaattggtt ctttctcgtt atcttttgcc acttttacta    8160
gtacgtatta attactactt aatcatcttt gtttacggct cattatatcc gtcgacggcg   8220
cgccgct                                                             8227
```

<210> SEQ ID NO 59
<211> LENGTH: 5704
<212> TYPE: DNA
<213> ORGANISM: Artificial sequence
<220> FEATURE:
<223> OTHER INFORMATION: Vector KS130

<400> SEQUENCE: 59

```
ggccgcaagt atgaactaaa atgcatgtag gtgtaagagc tcatggagag catggaatat    60
tgtatccgac catgtaacag tataataact gagctccatc tcacttcttc tatgaataaa   120
caaaggatgt tatgatatat taacactcta tctatgcacc ttattgttct atgataaatt   180
tcctcttatt attataaatc atctgaatcg tgacggctta tggaatgctt caaatagtac   240
```

| | | | | | |
|---|---|---|---|---|---|
| aaaaacaaat | gtgtactata | agactttcta | aacaattcta | accttagcat | tgtgaacgag | 300 |
| acataagtgt | taagaagaca | taacaattat | aatggaagaa | gtttgtctcc | atttatatat | 360 |
| tatatattac | ccacttatgt | attatattag | gatgttaagg | agacataaca | attataaaga | 420 |
| gagaagtttg | tatccattta | tatattatat | actacccatt | tatatattat | acttatccac | 480 |
| ttatttaatg | tctttataag | gtttgatcca | tgatatttct | aatattttag | ttgatatgta | 540 |
| tatgaaaggg | tactatttga | actctcttac | tctgtataaa | ggttggatca | tccttaaagt | 600 |
| gggtctattt | aattttattg | cttcttacag | ataaaaaaaa | aattatgagt | tggtttgata | 660 |
| aaatattgaa | ggatttaaaa | taataataaa | taacatataa | tatatgtata | taaatttatt | 720 |
| ataatataac | atttatctat | aaaaaagtaa | atattgtcat | aaatctatac | aatcgtttag | 780 |
| ccttgctgga | cgaatctcaa | ttatttaaac | gagagtaaac | atatttgact | ttttggttat | 840 |
| ttaacaaatt | attatttaac | actatatgaa | atttttttt | ttatcagcaa | agaataaaat | 900 |
| taaattaaga | aggacaatgg | tgtcccaatc | cttatacaac | caacttccac | aagaaagtca | 960 |
| agtcagagac | aacaaaaaaa | caagcaaagg | aaattttta | atttgagttg | tcttgtttgc | 1020 |
| tgcataattt | atgcagtaaa | acactacaca | taaccctttt | agcagtagag | caatggttga | 1080 |
| ccgtgtgctt | agcttctttt | attttatttt | tttatcagca | aagaataaat | aaaataaaat | 1140 |
| gagacacttc | agggatgttt | caacaagctt | ggatccgtcg | acggcgcgcc | cgatcatccg | 1200 |
| gatatagttc | ctcctttcag | caaaaaaccc | ctcaagaccc | gtttagaggc | cccaaggggt | 1260 |
| tatgctagtt | attgctcagc | ggtggcagca | gccaactcag | cttcctttcg | ggctttgtta | 1320 |
| gcagccggat | cgatccaagc | tgtacctcac | tattcctttg | ccctcggacg | agtgctgggg | 1380 |
| cgtcggtttc | cactatcggc | gagtacttct | acacagccat | cggtccagac | ggccgcgctt | 1440 |
| ctgcgggcga | tttgtgtacg | cccgacagtc | ccggctccgg | atcggacgat | tgcgtcgcat | 1500 |
| cgaccctgcg | cccaagctgc | atcatcgaaa | ttgccgtcaa | ccaagctctg | atagagttgg | 1560 |
| tcaagaccaa | tgcggagcat | atacgcccgg | agccgcggcg | atcctgcaag | ctccggatgc | 1620 |
| ctccgctcga | agtagcgcgt | ctgctgctcc | atacaagcca | accacggcct | ccagaagaag | 1680 |
| atgttggcga | cctcgtattg | ggaatccccg | aacatcgcct | cgctccagtc | aatgaccgct | 1740 |
| gttatgcggc | cattgtccgt | caggacattg | ttggagccga | aatccgcgtg | cacgaggtgc | 1800 |
| cggacttcgg | ggcagtcctc | ggcccaaagc | atcagctcat | cgagagcctg | cgcgacggac | 1860 |
| gcactgacgg | tgtcgtccat | cacagtttgc | cagtgataca | catgggatc | agcaatcgcg | 1920 |
| catatgaaat | cacgccatgt | agtgtattga | ccgattcctt | gcggtccgaa | tgggccgaac | 1980 |
| ccgctcgtct | ggctaagatc | ggccgcagcg | atcgcatcca | tagcctccgc | gaccggctgc | 2040 |
| agaacagcgg | gcagttcggt | ttcaggcagg | tcttgcaacg | tgacaccctg | tgcacggcgg | 2100 |
| gagatgcaat | aggtcaggct | ctcgctgaat | tccccaatgt | caagcacttc | cggaatcggg | 2160 |
| agcgcggccg | atgcaaagtg | ccgataaaca | taacgatctt | tgtagaaacc | atcggcgcag | 2220 |
| ctatttaccc | gcaggacata | tccacgccct | cctacatcga | agctgaaagc | acgagattct | 2280 |
| tcgccctccg | agagctgcat | caggtcggag | acgctgtcga | actttcgat | cagaaacttc | 2340 |
| tcgacagacg | tcgcggtgag | ttcaggcttt | tccatgggta | tatctccttc | ttaaagttaa | 2400 |
| acaaaattat | ttctagaggg | aaaccgttgt | ggtctcccta | tagtgagtcg | tattaatttc | 2460 |
| gcgggatcga | gatctgatca | acctgcatta | atgaatcggc | caacgcgcgg | ggagaggcgg | 2520 |
| tttgcgtatt | gggcgctctt | ccgcttcctc | gctcactgac | tcgctgcgct | cggtcgttcg | 2580 |
| gctgcggcga | gcggtatcag | ctcactcaaa | ggcggtaata | cggttatcca | cagaatcagg | 2640 |

```
ggataacgca ggaaagaaca tgtgagcaaa aggccagcaa aaggccagga accgtaaaaa      2700
ggccgcgttg ctggcgtttt tccataggct ccgcccccct gacgagcatc acaaaaatcg      2760
acgctcaagt cagaggtggc gaaacccgac aggactataa agataccagg cgtttccccc      2820
tggaagctcc ctcgtgcgct ctcctgttcc gaccctgccg cttaccggat acctgtccgc      2880
ctttctccct tcgggaagcg tggcgctttc tcaatgctca cgctgtaggt atctcagttc      2940
ggtgtaggtc gttcgctcca agctgggctg tgtgcacgaa ccccccgttc agcccgaccg      3000
ctgcgcctta tccggtaact atcgtcttga gtccaacccg gtaagacacg acttatcgcc      3060
actggcagca gccactggta acaggattag cagagcgagg tatgtaggcg gtgctacaga      3120
gttcttgaag tggtggccta actacggcta cactagaagg acagtatttg gtatctgcgc      3180
tctgctgaag ccagttacct tcggaaaaag agttggtagc tcttgatccg gcaaacaaac      3240
caccgctggt agcggtggtt tttttgtttg caagcagcag attacgcgca gaaaaaaagg      3300
atctcaagaa gatcctttga tcttttctac ggggtctgac gctcagtgga acgaaaactc      3360
acgttaaggg attttggtca tgacattaac ctataaaaat aggcgtatca cgaggccctt      3420
tcgtctcgcg cgtttcggtg atgacggtga aacctctga cacatgcagc tcccggagac      3480
ggtcacagct tgtctgtaag cggatgccgg gagcagacaa gcccgtcagg gcgcgtcagc      3540
gggtgttggc gggtgtcggg gctggcttaa ctatgcggca tcagagcaga ttgtactgag      3600
agtgcaccat atggacatat tgtcgttaga acgcggctac aattaataca taaccttatg      3660
tatcatacac atacgattta ggtgacacta tagaacggcg cgccaagctt ttgatccatg      3720
cccttcattt gccgcttatt aattaatttg gtaacagtcc gtactaatca gttacttatc      3780
cttcccccat cataattaat cttggtagtc tcgaatgcca caacactgac tagtctcttg      3840
gatcataaga aaagccaag gaacaaaaga agacaaaaca caatgagagt atcctttgca      3900
tagcaatgtc taagttcata aaattcaaac aaaaacgcaa tcacacacag tggacatcac      3960
ttatccacta gctgatcagg atcgccgcgt caagaaaaaa aaactggacc ccaaaagcca      4020
tgcacaacaa cacgtactca caaaggtgtc aatcgagcag cccaaaacat tcaccaactc      4080
aacccatcat gagccctcac atttgttgtt tctaacccaa cctcaaactc gtattctctt      4140
ccgccacctc attttgtttt atttcaacac ccgtcaaact gcatgccacc ccgtggccaa      4200
atgtccatgc atgttaacaa gacctatgac tataaatagc tgcaatctcg gcccaggttt      4260
tcatcatcaa gaaccagttc aatatcctag tacaccgtat taagaatttt aagatatact      4320
gcggccgcat ggctgctgct cccagtgtga ggacgtttac tcgggccgag gttttgaatg      4380
ccgaggctct gaatgagggc aagaaggatg ccgaggcacc cttcttgatg atcatcgaca      4440
acaaggtgta cgatgtccgc gagttcgtcc ctgatcatcc cggtggaagt gtgattctca      4500
cgcacgttgg caaggacggc actgacgtct ttgacacttt tcaccccgag gctgcttggg      4560
agactcttgc caacttttac gttggtgata ttgacgagag cgaccgcgat atcaagaatg      4620
atgactttgc ggccgaggtc cgcaagctgc gtaccttgtt ccagtctctt ggttactacg      4680
attcttccaa ggcatactac gccttcaagg tctcgttcaa cctctgcatc tggggtttgt      4740
cgacggtcat tgtggccaag tggggccaga cctcgaccct cgccaacgtg ctctcggctg      4800
cgcttttggg tctgttctgg cagcagtgcg gatggttggc tcacgacttt ttgcatcacc      4860
aggtcttcca ggaccgtttc tggggtgatc ttttcggcgc cttcttggga ggtgtctgcc      4920
agggcttctc gtcctcgtgg tggaaggaca agcacaacac tcaccacgcc gcccccaacg      4980
tccacggcga ggatcccgac attgacaccc accctctgtt gacctggagt gagcatgcgt      5040
```

-continued

```
tggagatgtt ctcggatgtc ccagatgagg agctgacccg catgtggtcg cgtttcatgg    5100
tcctgaacca gacctggttt tacttcccca ttctctcgtt tgcccgtctc tcctggtgcc    5160
tccagtccat tctctttgtg ctgcctaacg gtcaggccca caagccctcg ggcgcgcgtg    5220
tgcccatctc gttggtcgag cagctgtcgc ttgcgatgca ctggacctgg tacctcgcca    5280
ccatgttcct gttcatcaag gatcccgtca acatgctggt gtacttttg tgtcgcagg     5340 cggtgtgcgg aaacttgttg gcgatcgtgt tctcgctcaa ccacaacggt atgcctgtga    5400
tctcgaagga ggaggcggtc gatatggatt tcttcacgaa gcagatcatc acgggtcgtg    5460
atgtccaccc gggtctattt gccaactggt tcacgggtgg attgaactat cagatcgagc    5520
accacttgtt cccttcgatg cctcgccaca acttttcaaa gatccagcct gctgtcgaga    5580
ccctgtgcaa aaagtacaat gtccgatacc acaccaccgg tatgatcgag ggaactgcag    5640
aggtctttag ccgtctgaac gaggtctcca aggctgcctc caagatgggt aaggcgcagt    5700
aagc                                                                 5704
```

<210> SEQ ID NO 60
<211> LENGTH: 9609
<212> TYPE: DNA
<213> ORGANISM: Artificial sequence
<220> FEATURE:
<223> OTHER INFORMATION: Vector KS432
<220> FEATURE:
<221> NAME/KEY: misc_feature
<222> LOCATION: (2349)..(2349)
<223> OTHER INFORMATION: n is a, c, g, or t

<400> SEQUENCE: 60

```
ggccgcaagt atgaactaaa atgcatgtag gtgtaagagc tcatggagag catggaatat      60
tgtatccgac catgtaacag tataataact gagctccatc tcacttcttc tatgaataaa     120
caaaggatgt tatgatatat taacactcta tctatgcacc ttattgttct atgataaatt     180
tcctcttatt attataaatc atctgaatcg tgacggctta tggaatgctt caaatagtac     240
aaaaacaaat gtgtactata agactttcta acaattcta accttagcat tgtgaacgag      300
acataagtgt taagaagaca taacaattat aatggaagaa gtttgtctcc atttatatat     360
tatatattac ccacttatgt attatattag gatgttaagg agacataaca attataaaga     420
gagaagtttg tatccatta tatattatat actacccatt tatatattat acttatccac      480
ttatttaatg tctttataag gtttgatcca tgatatttct aatatttag ttgatatgta      540 tatgaaaggg tactatttga actctcttac tctgtataaa ggttggatca tccttaaagt     600
gggtctattt aatttattg cttcttacag ataaaaaaaa aattatgagt tggtttgata     660
aaatattgaa ggatttaaaa taataataaa taacatataa tatatgtata taaatttatt     720
ataatataac atttatctat aaaaaagtaa atattgtcat aaatctatac aatcgtttag     780
ccttgctgga cgaatctcaa ttatttaaac gagagtaaac atatttgact ttttggttat     840
ttaacaaatt attatttaac actatatgaa atttttttt ttatcagcaa agaataaaat      900
taaattaaga aggacaatgg tgtcccaatc cttatacaac caacttccac aagaaagtca     960
agtcagagac aacaaaaaaa caagcaaagg aaatttttta atttgagttg tcttgtttgc    1020
tgcataattt atgcagtaaa acactacaca taacccttttt agcagtagag caatggttga    1080
ccgtgtgctt agcttctttt attttatttt tttatcagca aagaataaat aaaataaaat     1140
gagacacttc agggatgttt caacaagctt ggatcctcga agagaagggt taataacaca    1200
cttttttaac atttttaaca caaatttag ttatttaaaa atttattaaa aaatttaaaa     1260
```

```
taagaagagg aactctttaa ataaatctaa cttacaaaat ttatgatttt taataagttt    1320
tcaccaataa aaaatgtcat aaaaatatgt taaaaagtat attatcaata ttctctttat    1380
gataaataaa aagaaaaaaa aaataaaagt taagtgaaaa tgagattgaa gtgactttag    1440
gtgtgtataa atatatcaac cccgccaaca atttatttaa tccaaatata ttgaagtata    1500
ttattccata gcctttattt atttatatat ttattatata aaagctttat ttgttctagg    1560
ttgttcatga aatattttt tggttttatc tccgttgtaa gaaaatcatg tgctttgtgt    1620
cgccactcac tattgcagct ttttcatgca ttggtcagat tgacggttga ttgtattttt    1680
gttttttatg gttttgtgtt atgacttaag tcttcatctc tttatctctt catcaggttt    1740
gatggttacc taatatggtc catgggtaca tgcatggtta aattaggtgg ccaactttgt    1800
tgtgaacgat agaatttttt ttatattaag taaactattt ttatattatg aaataataat    1860
aaaaaaaata ttttatcatt attaacaaaa tcatattagt taatttgtta actctataat    1920
aaaagaaata ctgtaacatt cacattacat ggtaacatct ttccacccct tcatttgttt    1980
tttgtttgat gactttttt cttgtttaaa tttatttccc ttcttttaaa tttggaatac    2040
attatcatca tatataaact aaaatactaa aaacaggatt acacaaatga taaataataa    2100
cacaaatatt tataaatcta gctgcaatat atttaaacta gctatatcga tattgtaaaa    2160
taaaactagc tgcattgata ctgataaaaa aatatcatgt gctttctgga ctgatgatgc    2220
agtatacttt tgacattgcc tttattttat ttttcagaaa agctttctta gttctgggtt    2280
cttcattatt tgtttcccat ctccattgtg aattgaatca tttgcttcgt gtcacaaata    2340
caatttagnt aggtacatgc attggtcaga ttcacggttt attatgtcat gacttaagtt    2400
catggtagta cattacctgc cacgcatgca ttatattggt tagatttgat aggcaaattt    2460
ggttgtcaac aatataaata taaataatgt ttttatatta cgaaataaca gtgatcaaaa    2520
caaacagttt tatctttatt aacaagattt tgttttttgtt tgatgacgtt ttttaatgtt    2580
tacgctttcc cccttctttt gaatttagaa cactttatca tcataaaatc aaatactaaa    2640
aaaattacat atttcataaa taataacaca aatatttta aaaaatctga aataataatg    2700
aacaatatta catattatca cgaaaattca ttaataaaaa tattatataa ataaaatgta    2760
atagtagtta tatgtaggaa aaaagtactg cacgcataat atatacaaaa agattaaaat    2820
gaactattat aaataataac actaaattaa tggtgaatca tatcaaaata atgaaaaagt    2880
aaataaaatt tgtaattaac ttctatatgt attacacaca caaataataa ataatagtaa    2940
aaaaaattat gataaatatt taccatctca taagatattt aaaataatga taaaaatata    3000 gattatttt tatgcaacta gctagccaaa aagagaacac gggtatatat aaaaagagta    3060
cctttaaatt ctactgtact tcctttattc ctgacgtttt tatatcaagt ggacatacgt    3120
gaagatttta attatcagtc taaatatttc attagcactt aatactttc tgttttattc    3180 ctatcctata agtagtcccg attctcccaa cattgcttat tcacacaact aactaagaaa    3240
gtcttccata gcccccaag cggcccatgg cctcctccga ggacgtcatc aaggagttca    3300
tgcgcttcaa ggtgcgcatg gagggctccg tgaacggcca cgagttcgag atcgagggcg    3360
agggcgaggg ccgcccctac gagggcaccc agaccgccaa gctgaaggtg accaagggcg    3420
gccccctgcc cttcgcctgg gacatcctgt cccccccagtt ccagtacggc tccaaggtgt    3480
acgtgaagca ccccgccgac atccccgact acaagaagct gtccttcccc gagggcttca    3540
agtgggagcg cgtgatgaac ttcgaggacg gcggcgtggt gaccgtgacc caggactcct    3600
ccctgcagga cggctccttc atctacaagg tgaagttcat cggcgtgaac ttcccctccg    3660
```

```
acggccccgt aatgcagaag aagactatgg gctgggaggc ctccaccgag cgcctgtacc    3720
cccgcgacgg cgtgctgaag ggcgagatcc acaaggccct gaagctgaag gacggcggcc    3780
actacctggt ggagttcaag tccatctaca tggccaagaa gcccgtgcag ctgcccggct    3840
actactacgt ggactccaag ctggacatca cctcccacaa cgaggactac accatcgtgg    3900
agcagtacga gcgcgccgag ggccgccacc acctgttcct gtagcggccg gccgcgacac    3960
aagtgtgaga gtactaaata aatgctttgg ttgtacgaaa tcattacact aaataaaata    4020
atcaaagctt atatatgcct tccgctaagg ccgaatgcaa agaaattggt tctttctcgt    4080
tatcttttgc cacttttact agtacgtatt aattactact taatcatctt tgtttacggc    4140
tcattatatc cgtcgacggc gcgccgctct agagggccca attcgcccta tagtgagtcg    4200
tattacaatt cactggccgt cgttttacaa cgtcgtgact gggaaaaccc tggcgttacc    4260
caacttaatc gccttgcagc acatccccct ttcgccagct ggcgtaatag cgaagaggcc    4320
cgcaccgatc gcccttccca acagttgcgc agcctatacg tacggcagtt aaggtttac    4380 acctataaaa gagagagccg ttatcgtctg tttgtggatg tacagagtga tattattgac    4440
acgccggggc gacggatggt gatcccctg gccagtgcac gtctgctgtc agataaagtc    4500
tcccgtgaac tttacccggt ggtgcatatc ggggatgaaa gctggcgcat gatgaccacc    4560
gatatggcca gtgtgccggt ctccgttatc ggggaagaag tggctgatct cagccaccgc    4620
gaaaatgaca tcaaaaacgc cattaacctg atgttctggg aatataaat gtcaggcatg    4680 agattatcaa aaaggatctt cacctagatc ttttcacgt agaaagccag tccgcagaaa    4740
cggtgctgac cccggatgaa tgtcagctac tgggctatct ggacaaggga aaacgcaagc    4800
gcaaagagaa agcaggtagc ttgcagtggg cttacatggc gatagctaga ctgggcggtt    4860
ttatggacag caagcgaacc ggaattgcca gctgggcgc cctctggtaa ggttgggaag    4920
ccctgcaaag taaactggat ggcttttcttg ccgccaagga tctgatgcg caggggatca    4980 agctctgatc aagagacagg atgaggatcg tttcgcatga ttgaacaaga tggattgcac    5040
gcaggttctc cggccgcttg ggtggagagg ctattcggct atgactgggc acaacagaca    5100
atcggctgct ctgatgccgc cgtgttccgg ctgtcagcgc aggggcgccc ggttctttt    5160 gtcaagaccg acctgtccgg tgccctgaat gaactgcaag acgaggcagc gcggctatcg    5220
tggctggcca cgacgggcgt tccttgcgca gctgtgctcg acgttgtcac tgaagcggga    5280
agggactggc tgctattggg cgaagtgccg gggcaggatc tcctgtcatc tcaccttgct    5340
cctgccgaga aagtatccat catggctgat gcaatgcggc ggctgcatac gcttgatccg    5400
gctacctgcc cattcgacca ccaagcgaaa catcgcatcg agcgagcacg tactcggatg    5460
gaagccggtc ttgtcgatca ggatgatctg gacgaagagc atcaggggct cgcgccagcc    5520
gaactgttcg ccaggctcaa ggcgagcatg cccgacggcg aggatctcgt cgtgacccat    5580
ggcgatgcct gcttgccgaa tatcatggtg gaaaatggcc gcttttctgg attcatcgac    5640
tgtggccggc tgggtgtggc ggaccgctat caggacatag cgttggctac ccgtgatatt    5700
gctgaagagc ttggcggcga atgggctgac cgcttcctcg tgctttacgg tatcgccgct    5760
cccgattcgc agcgcatcgc cttctatcgc cttcttgacg agttcttctg aattattaac    5820
gcttacaatt tcctgatgcg gtattttctc cttacgcatc tgtgcggtat ttcacaccgc    5880
atcaggtggc acttttcggg gaaatgtgcg cggaaccct atttgtttat ttttctaaat    5940
acattcaaat atgtatccgc tcatgagaca ataaccctga taaatgcttc aataatagca    6000
cgtgaggagg gccaccatgg ccaagttgac cagtgccgtt ccggtgctca ccgcgcgcga    6060
```

```
cgtcgccgga gcggtcgagt tctggaccga ccggctcggg ttctcccggg acttcgtgga   6120
ggacgacttc gccggtgtgg tccgggacga cgtgaccctg ttcatcagcg cggtccagga   6180
ccaggtggtg ccggacaaca ccctggcctg ggtgtgggtg cgcggcctgg acgagctgta   6240
cgccgagtgg tcggaggtcg tgtccacgaa cttcccggac gcctccgggc cggccatgac   6300
cgagatcggc gagcagccgt gggggcggga gttcgccctg cgcgacccgg ccggcaactg   6360
cgtgcacttc gtggccgagg agcaggactg acacgtgcta aaacttcatt tttaatttaa   6420
aaggatctag gtgaagatcc ttttttgataa tctcatgacc aaaatccctt aacgtgagtt   6480
ttcgttccac tgagcgtcag accccgtaga aaagatcaaa ggatcttctt gagatccttt   6540
ttttctgcgc gtaatctgct gcttgcaaac aaaaaaacca ccgctaccag cggtggtttg   6600
tttgccggat caagagctac caactctttt tccgaaggta actggcttca gcagagcgca   6660
gataccaaat actgttcttc tagtgtagcc gtagttaggc caccacttca agaactctgt   6720
agcaccgcct acatacctcg ctctgctaat cctgttacca gtggctgctg ccagtggcga   6780
taagtcgtgt cttaccgggt tggactcaag acgatagtta ccggataagg cgcagcggtc   6840
gggctgaacg gggggttcgt gcacacagcc cagcttggag cgaacgacct acaccgaact   6900
gagataccta cagcgtgagc tatgagaaag cgccacgctt cccgaaggga gaaaggcgga   6960
caggtatccg gtaagcggca gggtcggaac aggagagcgc acgagggagc ttccaggggg   7020
aaacgcctgg tatctttata gtcctgtcgg gtttcgccac ctctgacttg agcgtcgatt   7080
tttgtgatgc tcgtcagggg ggcggagcct atggaaaaac gccagcaacg cggccttttt   7140
acggttcctg gccttttgct ggccttttgc tcacatgttc tttcctgcgt tatcccctga   7200
ttctgtggat aaccgtatta ccgcctttga gtgagctgat accgctcgcc gcagccgaac   7260
gaccgagcgc agcgagtcag tgagcgagga agcggaagag cgcccaatac gcaaaccgcc   7320
tctccccgcg cgttggccga ttcattaatg cagctggcac gacaggtttc ccgactggaa   7380
agcgggcagt gagcgcaacg caattaatgt gagttagctc actcattagg cacccccaggc   7440 tttacacttt atgcttccgg ctcgtatgtt gtgtggaatt gtgagcggat aacaatttca   7500
cacaggaaac agctatgacc atgattacgc caagctattt aggtgacgcg ttagaatact   7560
caagctatgc atcaagcttg gtaccgagct cggatccact agtaacggcc gccagtgtgc   7620
tggaattcag gggcgcgccc caatttatta tcatctattt cctgacattt taatccatcc   7680
acctatgtca aaaacttata gaaaatgtca acttccaaac aaaacataat tgaacttcgc   7740
aaataaattc ttaataatat taaaaaatgt tacttaatta ttcttcaac cccattttcc   7800 gcgcgtagcg cggacaaaga ctctagttaa atatagaagt ttccgattct catcgtataa   7860
aacggtgact ttggcgggct ttcatgtgta acaaattggt ttaacaaacc actgcctagt   7920
cgtttagtgt agaatcagcg catggaactc cgattggagc gtgactttca cgtgccggag   7980
gcccaccacc acagcgggcg ttacgctcta agaatctcgc ccacggtttt cttcatctcc   8040 ccccccgccaa gtgtctccct cgttcgccac ttctcatcat gttacaggga ccataaaaat   8100
ggcgtatttc ttcagccccg ggtataaata cacacatgat cctgtggtgg gttcttccac   8160
aagttacatc tccttctggt ttttgtattg caagtgtttg tatttttgc ctccgagaga   8220 aaatcgcggc cgcatggctg ctgctcccag tgtgaggacg tttactcggg ccgaggtttt   8280
gaatgccgag gctctgaatg agggcaagaa ggatgccgag gcacccttct tgatgatcat   8340
cgacaacaag gtgtacgatg tccgcgagtt cgtccctgat catcccggtg aagtgtgat   8400 tctcacgcac gttggcaagg acggcactga cgtctttgac acttttcacc ccgaggctgc   8460
```

```
ttgggagact cttgccaact tttacgttgg tgatattgac gagagcgacc gcgatatcaa    8520
gaatgatgac tttgcggccg aggtccgcaa gctgcgtacc ttgttccagt ctcttggtta    8580
ctacgattct tccaaggcat actacgcctt caaggtctcg ttcaacctct gcatctgggg    8640
tttgtcgacg gtcattgtgg ccaagtgggg ccagacctcg accctcgcca acgtgctctc    8700
ggctgcgctt tgggtctgt  tctggcagca gtgcggatgg ttggctcacg acttttttgca   8760
```

```
ggctgcgctt tgggtctgt tctggcagca gtgcggatgg ttggctcacg actttttgca     8760
tcaccaggtc ttccaggacc gtttctgggg tgatcttttc ggcgccttct tgggaggtgt    8820
ctgccagggc ttctcgtcct cgtggtggaa ggacaagcac aacactcacc acgccgcccc    8880
caacgtccac ggcgaggatc ccgacattga cacccaccct ctgttgacct ggagtgagca    8940
tgcgttggag atgttctcgg atgtcccaga tgaggagctg acccgcatgt ggtcgcgttt    9000
catggtcctg aaccagacct ggttttactt ccccattctc tcgtttgccc gtctctcctg    9060
gtgcctccag tccattctct ttgtgctgcc taacggtcag gcccacaagc cctcgggcgc    9120
gcgtgtgccc atctcgttgg tcgagcagct gtcgcttgcg atgcactgga cctggtacct    9180
cgccaccatg ttcctgttca tcaaggatcc cgtcaacatg ctggtgtact ttttggtgtc    9240
gcaggcggtg tgcggaaact tgttggcgat cgtgttctcg ctcaaccaca acggtatgcc    9300
tgtgatctcg aaggaggagg cggtcgatat ggatttcttc acgaagcaga tcatcacggg    9360
tcgtgatgtc cacccgggtc tatttgccaa ctggttcacg ggtggattga actatcagat    9420
cgagcaccac ttgttcccctt cgatgcctcg ccacaacttt tcaaagatcc agcctgctgt    9480
cgagaccctg tgcaaaaagt acaatgtccg ataccacacc accggtatga tcgagggaac    9540
tgcagaggtc tttagccgtc tgaacgaggt ctccaaggct gcctccaaga tgggtaaggc    9600
gcagtaagc                                                            9609
```

<210> SEQ ID NO 61
<211> LENGTH: 19404
<212> TYPE: DNA
<213> ORGANISM: Artificial sequence
<220> FEATURE:
<223> OTHER INFORMATION: Vector ARALO80
<220> FEATURE:
<221> NAME/KEY: misc_feature
<222> LOCATION: (17594)..(17594)
<223> OTHER INFORMATION: n is a, c, g, or t

<400> SEQUENCE: 61

```
cgcgcctcga gtgggcggat cccccgggct gcaggaattc actggccgtc gttttacaac     60
gtcgtgactg ggaaaaccct ggcgttaccc aacttaatcg ccttgcagca catcccctt     120 tcgccagctg gcgtaatagc gaagaggccc gcaccgatcg cccttcccaa cagttgcgca    180
gcctgaatgg cgaatggatc gatccatcgc gatgtacctt tgttagtca gcctctcgat     240 tgctcatcgt cattacacag taccgaagtt tgatcgatct agtaacatag atgacaccgc    300
gcgcgataat ttatcctagt ttgcgcgcta tattttgttt tctatcgcgt attaaatgta    360
taattgcggg actctaatca taaaaaccca tctcataaat aacgtcatgc attacatgtt    420
aattattaca tgcttaacgt aattcaacag aaattatatg ataatcatcg caagaccggc    480
aacaggattc aatcttaaga aactttattg ccaaatgttt gaacgatctg cttcgacgca    540
ctccttcttt actccaccat ctcgtcctta ttgaaaacgt gggtagcacc aaaacgaatc    600
aagtcgctgg aactgaagtt accaatcacg ctggatgatt tgccagttgg attaatcttg    660
cctttccccg catgaataat attgatgaat gcatgcgtga ggggtagttc gatgttggca    720
atagctgcaa ttgccgcgac atcctccaac gagcataatt cttcagaaaa atagcgatgt    780
```

```
tccatgttgt cagggcatgc atgatgcacg ttatgaggtg acggtgctag gcagtattcc    840
ctcaaagttt catagtcagt atcatattca tcattgcatt cctgcaagag agaattgaga    900
cgcaatccac acgctgcggc aaccttccgg cgttcgtggt ctatttgctc ttggacgttg    960
caaacgtaag tgttggatcg atccggggtg ggcgaagaac tccagcatga gatccccgcg   1020
ctggaggatc atccagccgg cgtcccggaa aacgattccg aagcccaacc tttcatagaa   1080
ggcggcggtg gaatcgaaat ctcgtgatgg caggttgggc gtcgcttggt cggtcatttc   1140
gaacccagga gtcccgctca agaactcg tcaagaaggc gatagaaggc gatgcgctgc   1200
gaatcgggag cggcgatacc gtaaagcacg aggaagcggt cagcccattc gccgccaagc   1260
tcttcagcaa tatcacgggt agccaacgct atgtcctgat agcggtccgc cacacccagc   1320
cggccacagt cgatgaatcc agaaaagcgg ccatttttcca ccatgatatt cggcaagcag   1380
gcatcgccat gggtcacgac gagatcctcg ccgtcgggca tgcgcgcctt gagcctggcg   1440
aacagttcgg ctggcgcgag cccctgatgc tcttcgtcca gatcatcctg atcgacaaga   1500
ccggcttcca tccgagtacg tgctcgctcg atgcgatgtt tcgcttggtg gtcgaatggg   1560
caggtagccg gatcaagcgt atgcagccgc cgcattgcat cagccatgat ggatactttc   1620
tcggcaggag caaggtgaga tgacaggaga tcctgccccg gcacttcgcc caatagcagc   1680
cagtcccttc ccgcttcagt gacaacgtcg agcacagctg cgcaaggaac gcccgtcgtg   1740
gccagccacg atagccgcgc tgcctcgtcc tgcagttcat cagggcacc ggacaggtcg   1800
gtcttgacaa aaagaaccgg gcgccctgc gctgacagcc ggaacacggc ggcatcagag   1860
cagccgattg tctgttgtgc ccagtcatag ccgaatagcc tctccaccca gcggccgga   1920
gaacctgcgt gcaatccatc ttgttcaatc atgcgaaacg atccccgcaa gcttggagac   1980
tggtgatttc agcgtgtcct ctccaaatga aatgaacttc cttatataga ggaagggtct   2040
tgcgaaggat agtgggattg tgcgtcatcc cttacgtcag tggagatatc acatcaatcc   2100
acttgctttg aagacgtggt tggaacgtct tcttttttcca cgatgctcct cgtgggtggg   2160
ggtccatctt tgggaccact gtcggcagag gcatcttcaa cgatggcctt tcctttatcg   2220
caatgatggc atttgtagga gccaccttcc ttttccacta tcttcacaat aaagtgacag   2280
atagctgggc aatggaatcc gaggaggttt ccggatatta ccctttgttg aaaagtctca   2340
attgcccttt ggtcttctga gactgtatct ttgatatttt tggagtagac aagcgtgtcg   2400
tgctccacca tgttgacgaa gattttcttc ttgtcattga gtcgtaagag actctgtatg   2460
aactgttcgc cagtctttac ggcgagttct gttaggtcct ctatttgaat ctttgactcc   2520
atggcctttg attcagtggg aactaccttt ttagagactc caatctctat tacttgcctt   2580
ggtttgtgaa gcaagccttg aatcgtccat actggaatag tacttctgat cttgagaaat   2640
atatctttct ctgtgttctt gatgcagtta gtcctgaatc ttttgactgc atctttaacc   2700
ttcttgggaa ggtatttgat ctcctggaga ttattgctcg ggtagatcgt cttgatgaga   2760
cctgctgcgt aagcctctct aaccatctgt gggttagcat tctttctgaa attgaaaagg   2820
ctaatcttct cattatcagt ggtgaacatg gtatcgtcac cttctccgtc gaacttcctg   2880
actagatcgt agagatagag gaagtcgtcc attgtgatct ctggggcaaa ggagatctga   2940
attaattcga tatggtggat ttatcacaaa tgggacccgc cgccgacaga ggtgtgatgt   3000
taggccagga ctttgaaaat ttgcgcaact atcgtatagt ggccgacaaa ttgacgccga   3060
gttgacagac tgcctagcat ttgagtgaat tatgtgaggt aatgggctac actgaattgg   3120
tagctcaaac tgtcagtatt tatgtatatg agtgtatatt ttcgcataat ctcagaccaa   3180
```

```
tctgaagatg aaatgggtat ctgggaatgg cgaaatcaag gcatcgatcg tgaagtttct    3240
catctaagcc cccatttgga cgtgaatgta gacacgtcga aataaagatt tccgaattag    3300
aataatttgt ttattgcttt cgcctataaa tacgacggat cgtaatttgt cgttttatca    3360
aaatgtactt tcattttata ataacgctgc ggacatctac attttttgaat tgaaaaaaaa    3420 ttggtaatta ctcttttcttt ttctccatat tgaccatcat actcattgct gatccatgta    3480
gatttcccgg acatgaagcc atttacaatt gaatatatcc tgccgccgct gccgctttgc    3540
acccggtgga gcttgcatgt tggtttctac gcagaactga gccggttagg cagataattt    3600
ccattgagaa ctgagccatg tgcaccttcc ccccaacacg gtgagcgacg gggcaacgga    3660
gtgatccaca tgggactttt aaacatcatc cgtcggatgg cgttgcgaga aagcagtcg    3720 atccgtgaga tcagccgacg caccgggcag gcgcgcaaca cgatcgcaaa gtatttgaac    3780
gcaggtacaa tcgagccgac gttcacgcgg aacgaccaag caagctagct ttaatgcggt    3840
agtttatcac agttaaattg ctaacgcagt caggcaccgt gtatgaaatc taacaatgcg    3900
ctcatcgtca tcctcggcac cgtcaccctg gatgctgtag gcataggctt ggttatgccg    3960
gtactgccgg gcctcttgcg ggatatcgtc cattccgaca gcatcgccag tcactatggc    4020
gtgctgctag cgctatatgc gttgatgcaa tttctatgcg cacccgttct cggagcactg    4080
tccgaccgct ttggccgccg cccagtcctg ctcgcttcgc tacttggagc cactatcgac    4140
tacgcgatca tggcgaccac accgtcctg tggtccaacc cctccgctgc tatagtgcag    4200
tcggcttctg acgttcagtg cagccgtctt ctgaaaacga catgtcgcac aagtcctaag    4260
ttacgcgaca ggctgccgcc ctgccctttt cctggcgttt tcttgtcgcg tgttttagtc    4320
gcataaagta gaatacttgc gactagaacc ggagacatta cgccatgaac aagagcgccg    4380
ccgctggcct gctgggctat gcccgcgtca gcaccgacga ccaggacttg accaaccaac    4440
gggccgaact gcacgcggcc ggctgcacca agctgttttc cgagaagatc accggcacca    4500
ggcgcgaccg cccggagctg ccaggatgc ttgaccacct acgccctggc gacgttgtga    4560
cagtgaccag gctagaccgc ctggcccgca gcacccgcga cctactggac attgccgagc    4620
gcatccagga ggcggcgcg ggcctgcgta gcctggcaga gccgtgggcc gacaccacca    4680
cgccggccgg ccgcatggtg ttgaccgtgt cgccggcat tgccgagttc gagcgttccc    4740
taatcatcga ccgcacccgg agcgggcgcg aggccgccaa ggcccgaggc gtgaagttg    4800 gccccgccc taccctcacc ccggcacaga tcgcgcacgc ccgcgagctg atcgaccagg    4860
aaggccgcac cgtgaaagag gcggctgcac tgcttggcgt gcatcgctcg accctgtacc    4920
gcgcacttga gcgcagcgag gaagtgacgc ccaccgaggc caggcggcgc ggtgccttcc    4980
gtgaggacgc attgaccgag gccgacgccc tggcggccgc cgagaatgaa cgccaagagg    5040
aacaagcatg aaaccgcacc aggacggcca ggacgaaccg ttttcatta ccgaagagat    5100 cgaggcggag atgatcgcgg ccgggtacgt gttcgagccg cccgcgcacg tctcaaccgt    5160
gcggctgcat gaaatcctgg ccggtttgtc tgatgccaag ctggcggcct ggccggccag    5220
cttggccgct gaagaaaccg agcgccgccg tctaaaaagg tgatgtgtat ttgagtaaaa    5280
cagcttgcgt catgcggtcg ctgcgtatat gatgcgatga gtaaataaac aaatacgcaa    5340
gggaacgcat gaagttatcg ctgtacttaa ccagaaaggc gggtcaggca agacgaccat    5400
cgcaacccat ctagcccgcg ccctgcaact cgccggggcc gatgttctgt tagtcgattc    5460
cgatccccag ggcagtgccc gcgattgggc ggccgtgcgg gaagatcaac cgctaaccgt    5520
tgtcggcatc gaccgcccga cgattgaccg cgacgtgaag gccatcggcc ggcgcgactt    5580
```

```
cgtagtgatc gacggagcgc cccaggcggc ggacttggct gtgtccgcga tcaaggcagc   5640
cgacttcgtg ctgattccgg tgcagccaag cccttacgac atatgggcca ccgccgacct   5700
ggtggagctg gttaagcagc gcattgaggt cacggatgga aggctacaag cggcctttgt   5760
cgtgtcgcgg gcgatcaaag gcacgcgcat cggcggtgag gttgccgagg cgctggccgg   5820
gtacgagctg cccattcttg agtcccgtat cacgcagcgc gtgagctacc caggcactgc   5880
cgccgccggc acaaccgttc ttgaatcaga cccgagggc gacgctgccc gcgaggtcca   5940
ggcgctggcc gctgaaatta aatcaaaact catttgagtt aatgaggtaa agagaaaatg   6000
agcaaaagca caaacacgct aagtgccggc cgtccgagcg cacgcagcag caaggctgca   6060
acgttggcca gcctggcaga cacgccagcc atgaagcggg tcaactttca gttgccggcg   6120
gaggatcaca ccaagctgaa gatgtacgcg gtacgccaag gcaagaccat taccgagctg   6180
ctatctgaat acatcgcgca gctaccagag taaatgagca aatgaataaa tgagtagatg   6240
aattttagcg gctaaaggag gcggcatgga aaatcaagaa caaccaggca ccgacgccgt   6300
ggaatgcccc atgtgtggag gaacgggcgg ttggccaggc gtaagcggct gggttgtctg   6360
ccggccctgc aatggcactg gaaccccccaa gcccgaggaa tcggcgtgag cggtcgcaaa   6420
ccatccggcc cggtacaaat cggcgcggcg ctgggtgatg acctggtgga aagttgaag   6480 gccgcgcagg ccgcccagcg gcaacgcatc gaggcagaag cacgcccccgg tgaatcgtgg   6540 caagcggccg ctgatcgaat ccgcaaagaa tcccggcaac cgccggcagc cggtgcgccg   6600
tcgattagga agccgcccaa gggcgacgag caaccagatt ttttcgttcc gatgctctat   6660
gacgtgggca cccgcgatag tcgcagcatc atggacgtgg ccgttttccg tctgtcgaag   6720
cgtgaccgac gagctggcga ggtgatccgc tacgagcttc cagacgggca cgtagaggtt   6780
tccgcagggc cggccggcat ggccagtgtg tgggattacg acctggtact gatggcggtt   6840
tcccatctaa ccgaatccat gaaccgatac cgggaaggga agggagacaa gcccggccgc   6900
gtgttccgtc cacacgttgc ggacgtactc aagttctgcc ggcgagccga tggcggaaag   6960
cagaaagacg acctggtaga aacctgcatt cggttaaaca ccacgcacgt tgccatgcag   7020
cgtacgaaga aggccaagaa cggccgcctg gtgacggtat ccgagggtga agccttgatt   7080
agccgctaca agatcgtaaa gagcgaaacc gggcggccgg agtacatcga gatcgagcta   7140
gctgattgga tgtaccgcga gatcacagaa ggcaagaacc cggacgtgct gacggttcac   7200
cccgattact ttttgatcga tcccggcatc ggccgttttc tctaccgcct ggcacgccgc   7260
gccgcaggca aggcagaagc cagatggttg ttcaagacga tctacgaacg cagtggcagc   7320
gccggagagt tcaagaagtt ctgtttcacc gtgcgcaagc tgatcgggtc aaatgacctg   7380
ccggagtacg atttgaagga ggaggcgggg caggctggcc cgatcctagt catgcgctac   7440
cgcaacctga tcgagggcga agcatccgcc ggttcctaat gtacggagca gatgctaggg   7500
caaattgccc tagcagggga aaaggtcga aaggtctct ttcctgtgga tagcacgtac   7560
attgggaacc caaagccgta cattgggaac cggaacccgt acattgggaa cccaaagccg   7620
tacattggga accggtcaca catgtaagtg actgatataa aagagaaaaa aggcgatttt   7680
tccgcctaaa actcttaaa acttattaaa actcttaaaa cccgcctggc ctgtgcataa   7740
ctgtctggcc agcgcacagc cgaagagctg caaaaagcgc ctacccttcg gtcgctgcgc   7800
tccctacgcc ccgccgcttc gcgtcggcct atcgcggccg ctggccgctc aaaaatggct   7860
ggcctacggc caggcaatct accagggcgc ggacaagccg cgccgtcgcc actgaccgc   7920 cggcgcccac atcaaggcac cctgcctcgc gcgtttcggt gatgacggtg aaaacctctg   7980
```

```
acacatgcag ctcccggaga cggtcacagc ttgtctgtaa gcggatgccg ggagcagaca   8040
agcccgtcag ggcgcgtcag cgggtgttgg cgggtgtcgg ggcgcagcca tgacccagtc   8100
acgtagcgat agcggagtgt atactggctt aactatgcgg catcagagca gattgtactg   8160
agagtgcacc atatgcggtg tgaaataccg cacagatgcg taaggagaaa ataccgcatc   8220
aggcgctctt ccgcttcctc gctcactgac tcgctgcgct cggtcgttcg gctgcggcga   8280
gcggtatcag ctcactcaaa ggcggtaata cggttatcca cagaatcagg gataacgca    8340
ggaaagaaca tgtgagcaaa aggccagcaa aaggccagga accgtaaaaa ggccgcgttg   8400
ctggcgtttt tccataggct ccgcccccct gacgagcatc acaaaaatcg acgctcaagt   8460
cagaggtggc gaaacccgac aggactataa agataccagg cgtttccccc tggaagctcc   8520
ctcgtgcgct ctcctgttcc gaccctgccg cttaccggat acctgtccgc ctttctccct   8580
tcgggaagcg tggcgctttc tcatagctca cgctgtaggt atctcagttc ggtgtaggtc   8640
gttcgctcca agctgggctg tgtgcacgaa ccccccgttc agcccgaccg ctgcgcctta   8700
tccggtaact atcgtcttga gtccaacccg gtaagacacg acttatcgcc actggcagca   8760
gccactggta acaggattag cagagcgagg tatgtaggcg gtgctacaga gttcttgaag   8820
tggtggccta actacggcta cactagaagg acagtatttg gtatctgcgc tctgctgaag   8880
ccagttacct tcggaaaaag agttggtagc tcttgatccg gcaaacaaac caccgctggt   8940
agcggtggtt tttttgtttg caagcagcag attacgcgca gaaaaaaagg atctcaagaa   9000
gatcctttga tcttttctac ggggtctgac gctcagtgga acgaaaactc acgttaaggg   9060
attttggtca tgagattatc aaaaaggatc ttcacctaga tccttttaaa ttaaaaatga   9120
agttttaaat caatctaaag tatatatgag taaacttggt ctgacagtta ccaatgctta   9180
atcagtgagg cacctatctc agcgatctgt ctatttcgtt catccatagt tgcctgactc   9240
cccgtcgtgt agataactac gatacgggag ggcttaccat ctggccccag tgctgcaatg   9300
ataccgcgag acccacgctc accggctcca gatttatcag caataaacca gccagccgga   9360
agggccgagc gcagaagtgg tcctgcaact ttatccgcct ccatccagtc tattaattgt   9420
tgccgggaag ctagagtaag tagttcgcca gttaatagtt tgcgcaacgt tgttgccatt   9480
gctacaggca tcgtggtgtc acgctcgtcg tttggtatgg cttcattcag ctccggttcc   9540
caacgatcaa ggcgagttac atgatccccc atgttgtgca aaaaagcggt tagctccttc   9600
ggtcctccga tcgttgtcag aagtaagttg gccgcagtgt tatcactcat ggttatggca   9660
gcactgcata attctcttac tgtcatgcca tccgtaagat gcttttctgt gactggtgag   9720
tactcaacca agtcattctg agaatagtgt atgcggcgac cgagttgctc ttgcccggcg   9780
tcaacacggg ataataccgc gccacatagc agaactttaa aagtgctcat cattggaaaa   9840
gacctgcagg ggggggggg cgctgaggtc tgcctcgtga agaaggtgtt gctgactcat   9900
accaggcctg aatcgcccca tcatccagcc agaaagtgag ggagccacgg ttgatgagag   9960
ctttgttgta ggtggaccag ttggtgattt tgaacttttg ctttgccacg gaacggtctg  10020
cgttgtcggg aagatgcgtg atctgatcct tcaactcagc aaaagttcga tttattcaac  10080
aaagccgccg tcccgtcaag tcagcgtaat gctctgccag tgttacaacc aattaaccaa  10140
ttctgattag aaaaactcat cgagcatcaa atgaaactgc aatttattca tatcaggatt  10200
atcaatacca tatttttgaa aaagccgttt ctgtaatgaa ggagaaaact caccgaggca  10260
gttccatagg atggcaagat cctggtatcg gtctgcgatt ccgactcgtc caacatcaat  10320
acaacctatt aatttcccct cgtcaaaaat aaggttatca agtgagaaat caccatgagt  10380
```

```
gacgactgaa tccggtgaga atggcaaaag cttatgcatt tctttccaga cttgttcaac    10440
aggccagcca ttacgctcgt catcaaaatc actcgcatca accaaaccgt tattcattcg    10500
tgattgcgcc tgagcgagac gaaatacgcg atcgctgtta aaaggacaat tacaaacagg    10560
aatcgaatgc aaccggcgca ggaacactgc cagcgcatca acaatatttt cacctgaatc    10620
aggatattct tctaataacct ggaatgctgt tttcccgggg atcgcagtgg tgagtaacca    10680
tgcatcatca ggagtacgga taaaatgctt gatggtcgga agaggcataa attccgtcag    10740
ccagtttagt ctgaccatct catctgtaac atcattggca acgctacctt tgccatgttt    10800
cagaaacaac tctggcgcat cgggcttccc atacaatcga tagattgtcg cacctgattg    10860
cccgacatta tcgcgagccc atttataccc atataaatca gcatccatgt tggaatttaa    10920
tcgcggcctc gagcaagacg tttcccgttg aatatggctc ataacacccc ttgtattact    10980
gtttatgtaa gcagacagtt ttattgttca tgatgatata tttttatctt gtgcaatgta    11040
acatcagaga ttttgagaca caacgtggct ttccccccccc cccctgcagg tcaattcggt    11100
cgatatggct attacgaaga aggctcgtgc gcggagtccc gtgaactttc ccacgcaaca    11160
agtgaaccgc accgggtttg ccggaggcca tttcgttaaa atgcgcagcc atggctgctt    11220
cgtccagcat ggcgtaatac tgatcctcgt cttcggctgg cggtatattg ccgatgggct    11280
tcaaaagccg ccgtggttga accagtctat ccattccaag gtagcgaact cgaccgcttc    11340
gaagctcctc catggtccac gccgatgaat gacctcggcc ttgtaaagac cgttgatcgc    11400
ttctgcgagg gcgttgtcgt gctgtcgccg acgcttccga tagatggctc gatacctgct    11460
tctgccaacc gctcggaata gcgaaaggac acgtattgaa caccgcgatc cgagtgatgc    11520
actaggccgc catgagcggg acgccgatca tgatgagcct cctcgagggc atcgaggaca    11580
aagcctgcat gtgctgtccg gctcgcccgc catccgacaa tgcgacgggc gaagacgtcg    11640
atcacgaagg ccacgtagac gaagccctcc caagtggcga cataagtacg gacatgcgca    11700 aaggcttttcc cggtttgtcg ctgatggtgc aagagacgct gaagcgcgat ccgatgcgca    11760
ggcatctgtt cgtcttccgc ggtcgtggcg gtggcctgat caaggtcact cgccgaagag    11820
ctgcatgatt ggctcgaaac cgagcggggg aaattgtcgc gcagttctcc cgtcgccgag    11880
gcgataaatt acatgctcaa gcgatgggat ggcattacgt cattcctcga tgacggcccg    11940
atttgcctga cgaacaatgc tgccgaacga acgtcagag gctatgtact cggcaggaag    12000
tcatggctgt ttgccggatc ggatcgttgt gctgaacgtg cggcgttcat ggcgacactg    12060
atcatgagcg ccaagctcaa taacatcgat ccgcaggcct ggcttgccga cgtccgcgcc    12120
gaccttgcgg acgctccgat cagcaggctt gagcaacagc tgccgtggaa ctggacatcc    12180
aagacactga gtgctcaggc ggcctgacct gcggccttca ccggatactt accccattat    12240
cgcagattgc gatgaagcat cagcgtcatt cagcaatctt gccaaagtat gcaggctcgc    12300
gagaatcgac gtgcgaaacc ggctggttgc gccaaagatc cgcttgcgga gcggtcgaac    12360
attcatgctg ggacttcaag aggtcgagta gaggaagaac cggaaaggtt gcaccggaaa    12420
atatgcgttc ctttggagag cgcctcatgg acgtgaacaa atcgcccgga ccaaggatgc    12480
cacggataca aaagctcgcg aagctcggtc ccgtgggtgt tctgtcgtct cgttgtacaa    12540
cgaaatccat tcccattccg cgctcaagat ggcttcccct cggcagttca tcagggctaa    12600
atcaatctag ccgacttgtc cggtgaaatg ggctgcactc aacagaaaac aatcaaacaa    12660
acatacacag cgacttattc acacgagctc aaattacaac ggtatatatc ctgccagtca    12720
gcatcatcac accaaaagtt aggcccgaat agtttgaaat tagaaagctc gcaattgagg    12780
```

```
tctacaggcc aaattcgctc ttagccgtac aatattactc accggtgcga tgcccccat    12840
cgtaggtgaa ggtggaaatt aatgatccat cttgagacca caggcccaca acagctacca   12900
gtttcctcaa gggtccacca aaaacgtaag cgcttacgta catggtcgat aagaaaaggc   12960
aatttgtaga tgttaacatc caacgtcgct ttcaggatc gatccaatac gcaaaccgcc    13020
tctccccgcg cgttggccga ttcattaatg cagctggcac gacaggtttc ccgactggaa   13080
agcgggcagt gagcgcaacg caattaatgt gagttagctc actcattagg caccccaggc   13140
tttacacttt atgcttccgg ctcgtatgtt gtgtggaatt gtgagcggat aacaatttca   13200
cacaggaaac agctatgacc atgattacgc caagcttgca tgcctgcagg tcgactctag   13260
aggatctggc gcgccccaat ttattatcat ctatttcctg acatttttaat ccatccacct  13320
atgtcaaaaa cttatagaaa atgtcaactt ccaaacaaaa cataattgaa cttcgcaaat   13380
aaattcttaa taatattaaa aaatgttact taattatttc ttcaaccccca ttttccgcgc  13440
gtagcgcgga caaagactct agttaaatat agaagtttcc gattctcatc gtataaaacg   13500
gtgactttgg cgggctttca tgtgtaacaa attggtttaa caaaccactg cctagtcgtt   13560
tagtgtagaa tcagcgcatg gaactccgat tggagcgtga cttcacgtg ccggaggccc    13620
accaccacag cgggcgttac gctctaagaa tctcgcccac ggttttcttc atctccccccc   13680
cgccaagtgt ctccctcgtt cgccacttct catcatgtta cagggaccat aaaaatggcg   13740
tatttcttca gccccgggta taaatacaca catgatcctg tggtgggttc ttccacaagt   13800
tacatctcct tctggttttt gtattgcaag tgtttgtatt ttttgcctcc gagagaaaat   13860
cgcggccgca tggctgctgc tcccagtgtg aggacgttta ctcgggccga ggttttgaat   13920
gccgaggctc tgaatgaggg caagaaggat gccgaggcac ccttcttgat gatcatcgac   13980
aacaaggtgt acgatgtccg cgagttcgtc cctgatcatc ccggtggaag tgtgattctc   14040
acgcacgttg gcaaggacgg cactgacgtc tttgacactt ttcacccccga ggctgcttgg  14100
gagactcttg ccaacttttta cgttggtgat attgacgaga gcgaccgcga tatcaagaat   14160
gatgactttg cggccgaggt ccgcaagctg cgtaccttgt tccagtctct tggttactac   14220
gattcttcca aggcatacta cgccttcaag gtctcgttca acctctgcat ctgggggtttg   14280
tcgacggtca ttgtggccaa gtggggccag acctcgaccc tcgccaacgt gctctcggct   14340
gcgcttttgg gtctgttctg gcagcagtgc ggatggttgg ctcacgactt tttgcatcac   14400
caggtcttcc aggaccgttt ctggggtgat cttttcggcg ccttcttggg aggtgtctgc   14460
cagggcttct cgtcctcgtg gtggaaggac aagcacaaca ctcaccacgc cgcccccaac   14520
gtccacggcg aggatcccga cattgacacc caccctctgt tgacctggag tgagcatgcg   14580
ttggagatgt tctcggatgt cccagatgag gagctgaccc gcatgtggtc gcgtttcatg   14640
gtcctgaacc agacctggtt ttacttcccc attctctcgt ttgcccgtct ctcctggtgc   14700
ctccagtcca ttctctttgt gctgcctaac ggtcaggccc acaagccctc gggcgcgcgt   14760
gtgcccatct cgttggtcga gcagctgtcg cttgcgatgc actggacctg gtacctcgcc   14820
accatgttcc tgttcatcaa ggatcccgtc aacatgctgg tgtacttttt ggtgtcgcag   14880
gcggtgtgcg gaaacttgtt ggcgatcgtg ttctcgctca accacaacgg tatgcctgtg   14940
atctcgaagg aggaggcggt cgatatggat ttcttcacga agcagatcat cacgggtcgt   15000
gatgtccacc cgggtctatt tgccaactgg ttcacgggtg gattgaacta tcagatcgag   15060
caccacttgt tcccttcgat gcctcgccac aacttttcaa agatccagcc tgctgtcgag   15120
accctgtgca aaaagtacaa tgtccgatac cacaccaccg gtatgatcga gggaactgca   15180
```

```
gaggtcttta gccgtctgaa cgaggtctcc aaggctgcct ccaagatggg taaggcgcag    15240
taagcggccg caagtatgaa ctaaaatgca tgtaggtgta agagctcatg gagagcatgg    15300
aatattgtat ccgaccatgt aacagtataa taactgagct ccatctcact tcttctatga    15360
ataaacaaag gatgttatga tatattaaca ctctatctat gcaccttatt gttctatgat    15420
aaatttcctc ttattattat aaatcatctg aatcgtgacg gcttatggaa tgcttcaaat    15480
agtacaaaaa caaatgtgta ctataagact ttctaaacaa ttctaacctt agcattgtga    15540
acgagacata agtgttaaga agacataaca attataatgg aagaagtttg tctccattta    15600
tatattatat attacccact tatgtattat attaggatgt taaggagaca taacaattat    15660
aaagagagaa gtttgtatcc atttatatat tatatactac ccatttatat attatactta    15720
tccacttatt taatgtcttt ataaggtttg atccatgata tttctaatat tttagttgat    15780
atgtatatga aagggtacta tttgaactct cttactctgt ataaaggttg gatcatcctt    15840
aaagtgggtc tatttaattt tattgcttct tacagataaa aaaaaaatta tgagttggtt    15900
tgataaaata ttgaaggatt taaaataata ataaataaca tataatatat gtatataaat    15960
ttattataat ataacattta tctataaaaa agtaaatatt gtcataaatc tatacaatcg    16020
tttagccttg ctggacgaat ctcaattatt taaacgagag taaacatatt tgactttttg    16080
gttatttaac aaattattat ttaacactat atgaaatttt ttttttttatc agcaaagaat    16140 aaaattaaat taagaaggac aatggtgtcc caatccttat acaaccaact tccacaagaa    16200
agtcaagtca gagacaacaa aaaaacaagc aaaggaaatt ttttaatttg agttgtcttg    16260
tttgctgcat aatttatgca gtaaaacact acacataacc cttttagcag tagagcaatg    16320
gttgaccgtg tgcttagctt cttttatttt attttttttat cagcaaagaa taaataaaat    16380
aaaatgagac acttcaggga tgtttcaaca agcttggatc ctcgaagaga agggttaata    16440
acacactttt ttaacatttt taacacaaat tttagttatt taaaaattta ttaaaaaatt    16500
taaaataaga agaggaactc tttaaataaa tctaacttac aaaatttatg attttttaata    16560 agttttcacc aataaaaaat gtcataaaaa tatgttaaaa agtatattat caatattctc    16620
tttatgataa ataaaaagaa aaaaaaaata aaagttaagt gaaaatgaga ttgaagtgac    16680
tttaggtgtg tataaatata tcaaccccgc caacaattta tttaatccaa atatattgaa    16740
gtatattatt ccatagcctt tatttattta tatatttatt atataaaagc tttatttgtt    16800
ctaggttgtt catgaaatat ttttttggtt ttatctccgt tgtaagaaaa tcatgtgctt    16860
tgtgtcgcca ctcactattg cagcttttc atgcattggt cagattgacg gttgattgta    16920
tttttgtttt ttatggtttt gtgttatgac ttaagtcttc atctctttat ctcttcatca    16980
ggtttgatgg ttacctaata tggtccatgg gtacatgcat ggttaaatta ggtggccaac    17040
tttgttgtga acgatagaat tttttttata ttaagtaaac tatttttata ttatgaaata    17100
ataataaaaa aaatattta tcattattaa caaaatcata ttagttaatt tgttaactct     17160
ataataaaag aaatactgta acattcacat tacatggtaa catctttcca cccttttcatt   17220 tgttttttgt ttgatgactt ttttttcttgt ttaaatttat ttcccttctt ttaaatttgg   17280
aatacattat catcatatat aaactaaaat actaaaaaca ggattacaca aatgataaat    17340
aataacacaa atatttataa atctagctgc aatatattta aactagctat atcgatattg    17400
taaaataaaa ctagctgcat tgatactgat aaaaaaatat catgtgcttt ctggactgat    17460
gatgcagtat acttttgaca ttgccttat tttatttttc agaaaagctt tcttagttct      17520
gggttcttca ttatttgttt cccatctcca ttgtgaattg aatcatttgc ttcgtgtcac     17580
```

```
aaatacaatt tagntaggta catgcattgg tcagattcac ggtttattat gtcatgactt    17640
aagttcatgg tagtacatta cctgccacgc atgcattata ttggttagat ttgataggca    17700
aatttggttg tcaacaatat aaatataaat aatgttttta tattacgaaa taacagtgat    17760
caaaacaaac agtttatctt ttattaacaa gattttgttt ttgtttgatg acgtttttta    17820
atgtttacgc tttccccctt cttttgaatt tagaacactt tatcatcata aaatcaaata    17880
ctaaaaaaat tacatatttc ataaataata acacaaatat ttttaaaaaa tctgaaataa    17940
taatgaacaa tattacatat tatcacgaaa attcattaat aaaaatatta tataaataaa    18000
atgtaatagt agttatatgt aggaaaaaag tactgcacgc ataatatata caaaagatt    18060 aaaatgaact attataaata ataacactaa attaatggtg aatcatatca aaataatgaa    18120
aaagtaaata aaatttgtaa ttaacttcta tatgtattac acacacaaat aataaataat    18180
agtaaaaaaa attatgataa atatttacca tctcataaga tatttaaaaat aatgataaaa    18240 atatagatta ttttttatgc aactagctag ccaaaaagag aacacgggta tatataaaaa    18300
gagtaccttt aaattctact gtacttcctt tattcctgac gtttttatat caagtggaca    18360
tacgtgaaga ttttaattat cagtctaaat atttcattag cacttaatac ttttctgttt    18420
tattcctatc ctataagtag tcccgattct cccaacattg cttattcaca caactaacta    18480
agaaagtctt ccatagcccc ccaagcggcc catggcctcc tccgaggacg tcatcaagga    18540
gttcatgcgc ttcaaggtgc gcatggaggg ctccgtgaac ggccacgagt tcgagatcga    18600
gggcgagggc gagggccgcc cctacgaggg cacccagacc gccaagctga aggtgaccaa    18660
gggcggcccc ctgcccttcg cctgggacat cctgtccccc cagttccagt acggctccaa    18720
ggtgtacgtg aagcaccccg ccgacatccc cgactacaag aagctgtcct tccccgaggg    18780
cttcaagtgg gagcgcgtga tgaacttcga ggacggcggc gtggtgaccg tgacccagga    18840
ctcctccctg caggacggct ccttcatcta caaggtgaag ttcatcggcg tgaacttccc    18900
ctccgacggc cccgtaatgc agaagaagac tatgggctgg gaggcctcca ccgagcgcct    18960 gtaccccgc gacggcgtgc tgaagggcga gatccacaag gccctgaagc tgaaggacgg    19020
cggccactac ctggtggagt tcaagtccat ctacatggcc aagaagcccg tgcagctgcc    19080
cggctactac tacgtggact ccaagctgga catcacctcc cacaacgagg actacaccat    19140
cgtggagcag tacgagcgcg ccgagggccg ccaccacctg ttcctgtagc ggccggccgc    19200
gacacaagtg tgagagtact aaataaatgc tttggttgta cgaaatcatt acactaaata    19260
aaataatcaa agcttatata tgccttccgc taaggccgaa tgcaaagaaa ttggttcttt    19320
ctcgttatct tttgccactt ttactagtac gtattaatta ctacttaatc atctttgttt    19380
acggctcatt atatccgtcg acgg                                           19404
```

<210> SEQ ID NO 62
<211> LENGTH: 30
<212> TYPE: DNA
<213> ORGANISM: Artificial sequence
<220> FEATURE:
<223> OTHER INFORMATION: Primer D6 fwd

<400> SEQUENCE: 62
gaattcgcgg ccgcatggct gctgctccca                                     30

<210> SEQ ID NO 63
<211> LENGTH: 30
<212> TYPE: DNA
<213> ORGANISM: Artificial sequence
<220> FEATURE:

<223> OTHER INFORMATION: Primer D6 rev

<400> SEQUENCE: 63
gaattcgcgg ccgcttactg cgccttaccc        30

<210> SEQ ID NO 64
<211> LENGTH: 4322
<212> TYPE: DNA
<213> ORGANISM: Artificial sequence
<220> FEATURE:
<223> OTHER INFORMATION: Vector KS119

<400> SEQUENCE: 64

```
agcttttgat ccatgccctt catttgccgc ttattaatta atttggtaac agtccgtact        60
aatcagttac ttatccttcc cccatcataa ttaatcttgg tagtctcgaa tgccacaaca       120
ctgactagtc tcttggatca taagaaaaag ccaaggaaca aaagaagaca aaacacaatg       180
agagtatcct ttgcatagca atgtctaagt tcataaaatt caaacaaaaa cgcaatcaca       240
cacagtggac atcacttatc cactagctga tcaggatcgc cgcgtcaaga aaaaaaaact       300
ggaccccaaa agccatgcac aacaacacgt actcacaaag gtgtcaatcg agcagcccaa       360
aacattcacc aactcaaccc atcatgagcc ctcacatttg ttgtttctaa cccaacctca       420
aactcgtatt ctcttccgcc acctcatttt tgtttatttc aacacccgtc aaactgcatg       480
ccaccccgtg gccaaatgtc catgcatgtt aacaagacct atgactataa atagctgcaa       540
tctcggccca ggttttcatc atcaagaacc agttcaatat cctagtacac cgtattaaag       600
aatttaagat atactgcggc cgcaagtatg aactaaaatg catgtaggtg taagagctca       660
tggagagcat ggaatattgt atccgaccat gtaacagtat aataactgag ctccatctca       720
cttcttctat gaataaacaa aggatgttat gatatattaa cactctatct atgcaccta       780
ttgttctatg ataaatttcc tcttattatt ataaatcatc tgaatcgtga cggcttatgg       840
aatgcttcaa atagtacaaa aacaaatgtg tactataaga ctttctaaac aattctaacc       900
ttagcattgt gaacgagaca taagtgttaa aagacataa caattataat ggaagaagtt       960
tgtctccatt tatatattat atattaccca cttatgtatt atattaggat gttaaggaga      1020
cataacaatt ataagagag aagtttgtat ccatttatat attatatact acccatttat      1080
atattatact tatccactta tttaatgtct ttataaggtt tgatccatga tatttctaat      1140
attttagttg atatgtatat gaaagggtac tatttgaact ctcttactct gtataaaggt      1200
tggatcatcc ttaaagtggg tctatttaat tttattgctt cttacagata aaaaaaaaat      1260
tatgagttgg tttgataaaa tattgaagga tttaaaataa taataaataa catataatat      1320
atgtatataa atttattata ataacatt tatctataaa aagtaaaata ttgtcataaa      1380
tctatacaat cgtttagcct tgctggacga atctcaatta tttaaacgag agtaaacata      1440
tttgactttt tggttatta acaaattatt atttaacact atatgaaatt tttttttta      1500
tcagcaaaga ataaaattaa attaagaagg acaatggtgt cccaatcctt atacaaccaa      1560
cttccacaag aaagtcaagt cagagacaac aaaaaaacaa gcaaaggaaa ttttttaatt      1620
tgagttgtct tgtttgctgc ataatttatg cagtaaaaca ctacacataa ccctttttagc      1680
agtagagcaa tggttgaccg tgtgcttagc ttcttttatt ttatttttt atcagcaaag      1740
aataaataaa ataaaatgag acacttcagg gatgtttcaa caagcttgga tccgtcgacg      1800
gcgcgcccga tcatccggat atagttcctc ctttcagcaa aaaacccctc aagaccccgtt      1860
tagaggcccc aaggggttat gctagttatt gctcagcggt ggcagcagcc aactcagctt      1920
```

```
cctttcgggc tttgttagca gccggatcga tccaagctgt acctcactat tcctttgccc    1980
tcggacgagt gctggggcgt cggtttccac tatcggcgag tacttctaca cagccatcgg    2040
tccagacggc cgcgcttctg cgggcgattt gtgtacgccc gacagtcccg gctccggatc    2100
ggacgattgc gtcgcatcga ccctgcgccc aagctgcatc atcgaaattg ccgtcaacca    2160
agctctgata gagttggtca agaccaatgc ggagcatata cgcccggagc gcggcgatc     2220
ctgcaagctc cggatgcctc cgctcgaagt agcgcgtctg ctgctccata caagccaacc    2280
acggcctcca gaagaagatg ttggcgacct cgtattggga atccccgaac atcgcctcgc    2340
tccagtcaat gaccgctgtt atgcggccat tgtccgtcag gacattgttg gagccgaaat    2400
ccgcgtgcac gaggtgccgg acttcggggc agtcctcggc ccaaagcatc agctcatcga    2460
gagcctgcgc gacggacgca ctgacggtgt cgtccatcac agtttgccag tgatacacat    2520
ggggatcagc aatcgcgcat atgaaatcac gccatgtagt gtattgaccg attccttgcg    2580
gtccgaatgg gccgaacccg ctcgtctggc taagatcggc cgcagcgatc gcatccatag    2640
cctccgcgac cggctgcaga acagcgggca gttcggtttc aggcaggtct tgcaacgtga    2700
caccctgtgc acggcgggag atgcaatagg tcaggctctc gctgaattcc ccaatgtcaa    2760
gcacttccgg aatcgggagc gcggccgatg caaagtgccg ataaacataa cgatctttgt    2820
agaaaccatc ggcgcagcta tttacccgca ggacatatcc acgccctcct acatcgaagc    2880
tgaaagcacg agattcttcg ccctccgaga gctgcatcag gtcggagacg ctgtcgaact    2940
tttcgatcag aaacttctcg acagacgtcg cggtgagttc aggcttttcc atgggtatat    3000
ctccttctta aagttaaaca aaattatttc tagagggaaa ccgttgtggt ctccctatag    3060
tgagtcgtat taatttcgcg ggatcgagat ctgatcaacc tgcattaatg aatcggccaa    3120
cgcgcgggga gaggcggttt gcgtattggg cgctcttccg cttcctcgct cactgactcg    3180
ctgcgctcgg tcgttcggct gcggcgagcg gtatcagctc actcaaaggc ggtaatacgg    3240
ttatccacag aatcagggga taacgcagga agaacatgt gagcaaaagg ccagcaaaag    3300
gccaggaacc gtaaaaaggc cgcgttgctg gcgttttttcc ataggctccg ccccccctgac    3360
gagcatcaca aaaatcgacg ctcaagtcag aggtggcgaa acccgacagg actataaaga    3420
taccaggcgt ttccccctgg aagctccctc gtgcgctctc ctgttccgac cctgccgctt    3480
accggatacc tgtccgcctt tctcccttcg ggaagcgtgg cgctttctca atgctcacgc    3540
tgtaggtatc tcagttcggt gtaggtcgtt cgctccaagc tgggctgtgt gcacgaaccc    3600
cccgttcagc ccgaccgctg cgccttatcc ggtaactatc gtcttgagtc aacccggta    3660
agacacgact tatcgccact ggcagcagcc actggtaaca ggattagcag agcgaggtat    3720
gtaggcggtg ctacagagtt cttgaagtgg tggcctaact acggctacac tagaaggaca    3780
gtatttggta tctgcgctct gctgaagcca gttaccttcg gaaaaagagt tggtagctct    3840
tgatccggca aacaaaccac cgctggtagc ggtggttttt ttgtttgcaa gcagcagatt    3900
acgcgcagaa aaaaggatc tcaagaagat cctttgatct tttctacggg gtctgacgct    3960
cagtggaacg aaaactcacg ttaagggatt ttggtcatga cattaaccta aaaaatagg    4020
cgtatcacga ggccctttcg tctcgcgcgt ttcggtgatg acggtgaaaa cctctgacac    4080
atgcagctcc cggagacggt cacagcttgt ctgtaagcgg atgccgggag cagacaagcc    4140
cgtcagggcg cgtcagcggg tgttggcggg tgtcggggct ggcttaacta tgcggcatca    4200
gagcagattg tactgagagt gcaccatatg gacatattgt cgttagaacg cggctacaat    4260
taatacataa ccttatgtat catacacata cgatttaggt gacactatag aacggcgcgc    4320
```

<210> SEQ ID NO 65
<211> LENGTH: 9420
<212> TYPE: DNA
<213> ORGANISM: Artificial sequence
<220> FEATURE:
<223> OTHER INFORMATION: Vector KS430
<220> FEATURE:
<221> NAME/KEY: misc_feature
<222> LOCATION: (2349)..(2349)
<223> OTHER INFORMATION: n is a, c, g, or t

<400> SEQUENCE: 65

```
ggccgcaagt atgaactaaa atgcatgtag gtgtaagagc tcatggagag catggaatat     60
tgtatccgac catgtaacag tataataact gagctccatc tcacttcttc tatgaataaa    120
caaggatgt tatgatatat taacactcta tctatgcacc ttattgttct atgataaatt    180
tcctcttatt attataaatc atctgaatcg tgacggctta tggaatgctt caaatagtac    240
aaaaacaaat gtgtactata agactttcta aacaattcta accttagcat tgtgaacgag    300
acataagtgt taagaagaca taacaattat aatggaagaa gtttgtctcc atttatatat    360
tatatattac ccactatgt attatattag gatgttaagg agacataaca attataaaga    420
gagaagtttg tatccattta tatattatat actacccatt tatatattat acttatccac    480
ttatttaatg tctttataag gtttgatcca tgatatttct aatattttag ttgatatgta    540
tatgaaaggg tactatttga actctcttac tctgtataaa ggttggatca tccttaaagt    600
gggtctattt aattttattg cttcttacag ataaaaaaaa aattatgagt tggtttgata    660
aaatattgaa ggatttaaaa taataataaa taacatataa tatatgtata taaatttatt    720
ataatataac atttatctat aaaaaagtaa atattgtcat aaatctatac aatcgtttag    780
ccttgctgga cgaatctcaa ttatttaaac gagagtaaac atatttgact ttttggttat    840
ttaacaaatt attatttaac actatatgaa attttttttt ttatcagcaa agaataaaat    900
taaattaaga aggacaatgg tgtcccaatc cttatacaac caacttccac aagaaagtca    960
agtcagagac aacaaaaaaa caagcaaagg aaatttttta atttgagttg tcttgtttgc   1020
tgcataattt atgcagtaaa acactacaca taaccctttt agcagtagag caatggttga   1080
ccgtgtgctt agcttctttt attttatttt tttatcagca aagaataaat aaaataaaat   1140
gagacacttc agggatgttt caacaagctt ggatcctcga agagaagggt taataacaca   1200
cttttttaac atttttaaca caaattttag ttatttaaaa atttattaaa aaatttaaaa   1260
taagaagagg aactctttaa ataaatctaa cttacaaaat ttatgatttt taataagttt   1320
tcaccaataa aaaatgtcat aaaatatgt taaaaagtat attatcaata ttctctttat   1380
gataaataaa aagaaaaaaa aaataaaagt taagtgaaaa tgagattgaa gtgactttag   1440
gtgtgtataa atatatcaac cccgccaaca atttatttaa tccaaatata ttgaagtata   1500
ttattccata gccttatttt atttatatat ttattatata aaagctttat tgttctagg   1560
ttgttcatga atattttttt tggttttatc tccgttgtaa gaaatcatg tgctttgtgt   1620
cgccactcac tattgcagct ttttcatgca ttggtcagat tgacggttga ttgtattttt   1680
gtttttatg gttttgtgtt atgacttaag tcttcatctc tttatctctt catcaggttt   1740
gatggttacc taatatggtc catgggtaca tgcatggtta aattaggtgg ccaactttgt   1800
tgtgaacgat agaatttttt ttatattaag taaactattt ttatattatg aaataataat   1860
aaaaaaaata ttttatcatt attaacaaaa tcatattagt taatttgtta actctataat   1920
```

```
aaaagaaata ctgtaacatt cacattacat ggtaacatct ttccacccct tcatttgttt    1980
tttgtttgat gacttttttt cttgtttaaa tttatttccc ttcttttaaa tttggaatac    2040
attatcatca tatataaact aaaatactaa aaacaggatt acacaaatga taaataataa    2100
cacaaatatt tataaatcta gctgcaatat atttaaacta gctatatcga tattgtaaaa    2160
taaaactagc tgcattgata ctgataaaaa aatatcatgt gctttctgga ctgatgatgc    2220
agtatacttt tgacattgcc tttattttat ttttcagaaa agcttcctta gttctgggtt    2280
cttcattatt tgtttcccat ctccattgtg aattgaatca tttgcttcgt gtcacaaata    2340
caatttagnt aggtacatgc attggtcaga ttcacggttt attatgtcat gacttaagtt    2400
catggtagta cattacctgc cacgcatgca ttatattggt tagatttgat aggcaaattt    2460
ggttgtcaac aatataaata taaataatgt ttttatatta cgaaataaca gtgatcaaaa    2520
caaacagttt tatctttatt aacaagattt tgttttttgtt tgatgacgtt ttttaatgtt    2580
tacgctttcc cccttctttt gaatttagaa cactttatca tcataaaatc aaatactaaa    2640
aaaattacat atttcataaa taataacaca aatatttta aaaaatctga aataataatg     2700
aacaatatta catattatca cgaaaattca ttaataaaaa tattatataa ataaaatgta    2760
atagtagtta tatgtaggaa aaaagtactg cacgcataat atatacaaaa agattaaaat    2820
gaactattat aaataataac actaaattaa tggtgaatca tatcaaaata atgaaaaagt    2880
aaataaaatt tgtaattaac ttctatatgt attacacaca caaataataa ataatagtaa   2940
aaaaaattat gataaatatt taccatctca taagatattt aaaataatga taaaaatata   3000
gattattttt tatgcaacta gctagccaaa aagagaacac gggtatatat aaaaagagta   3060
cctttaaatt ctactgtact tccttttattc ctgacgtttt tatatcaagt ggacatacgt   3120
gaagatttta attatcagtc taaatatttc attagcactt aatactttc tgttttattc    3180 ctatcctata agtagtcccg attctcccaa cattgcttat tcacacaact aactaagaaa   3240
gtcttccata gccccccaag cggcccatgg cctcctccga ggacgtcatc aaggagttca   3300
tgcgcttcaa ggtgcgcatg gagggctccg tgaacggcca cgagttcgag atcgagggcg   3360
agggcgaggg ccgcccctac gagggcaccc agaccgccaa gctgaaggtg accaagggcg   3420
gccccctgcc cttcgcctgg gacatcctgt cccccccagtt ccagtacggc tccaaggtgt   3480
acgtgaagca ccccgccgac atccccgact acaagaagct gtccttcccc gagggcttca   3540
agtgggagcg cgtgatgaac ttcgaggacg gcggcgtggt gaccgtgacc caggactcct   3600
ccctgcagga cggctccttc atctacaagg tgaagttcat cggcgtgaac ttcccctccg   3660
acggccccgt aatgcagaag aagactatgg gctgggaggc ctccaccgag cgcctgtacc   3720
cccgcgacgt cgtgctgaag ggcgagatcc acaaggccct gaagctgaag gacggcggcc   3780
actacctggt ggagttcaag tccatctaca tggccaagaa gcccgtgcag ctgcccggct   3840
actactacgt ggactccaag ctggacatca cctcccacaa cgaggactac accatcgtgg   3900
agcagtacga gcgcgccgag ggccgccacc acctgttcct gtagcggccg gccgcgacac   3960
aagtgtgaga gtactaaata aatgctttgg ttgtacgaaa tcattacact aaataaaata   4020
atcaaagctt atatatgcct tccgctaagg ccgaatgcaa agaaattggt tctttctcgt   4080
tatcttttgc cactttttact agtacgtatt aattactact taatcatctt tgtttacggc   4140
tcattatatc cgtcgacggc gcgccgctct agagggccca attcgcccta gtgtgagtcg   4200
tattacaatt cactggccgt cgttttacaa cgtcgtgact gggaaaaccc tggcgttacc   4260
caacttaatc gccttgcagc acatccccct ttcgccagct ggcgtaatag cgaagaggcc   4320
```

```
cgcaccgatc gcccttccca acagttgcgc agcctatacg tacggcagtt taaggtttac    4380
acctataaaa gagagagccg ttatcgtctg tttgtggatg tacagagtga tattattgac    4440
acgccggggc gacggatggt gatcccctg gccagtgcac gtctgctgtc agataaagtc    4500
tcccgtgaac tttacccggt ggtgcatatc ggggatgaaa gctggcgcat gatgaccacc    4560
gatatggcca gtgtgccggt ctccgttatc ggggaagaag tggctgatct cagccaccgc    4620
gaaaatgaca tcaaaaacgc cattaacctg atgttctggg aatataaat gtcaggcatg    4680 agattatcaa aaaggatctt cacctagatc cttttcacgt agaaagccag tccgcagaaa    4740
cggtgctgac cccggatgaa tgtcagctac tgggctatct ggacaaggga aaacgcaagc    4800
gcaaagagaa agcaggtagc ttgcagtggg cttacatggc gatagctaga ctggcggtt    4860 ttatggacag caagcgaacc ggaattgcca gctgggcgc cctctggtaa ggttgggaag    4920
ccctgcaaag taaactggat ggctttcttg ccgccaagga tctgatggcg cagggatca    4980 agctctgatc aagagacagg atgaggatcg tttcgcatga ttgaacaaga tggattgcac    5040
gcaggttctc cggccgcttg ggtggagagg ctattcggct atgactgggc acaacagaca    5100
atcggctgct ctgatgccgc cgtgttccgg ctgtcagcgc aggggcgccc ggttctttt    5160 gtcaagaccg acctgtccgg tgccctgaat gaactgcaag acgaggcagc gcggctatcg    5220
tggctggcca cgacgggcgt tccttgcgca gctgtgctcg acgttgtcac tgaagcggga    5280
agggactggc tgctattggg cgaagtgccg gggcaggatc tcctgtcatc tcaccttgct    5340
cctgccgaga agtatccat catggctgat gcaatgcggc ggctgcatac gcttgatccg    5400
gctacctgcc cattcgacca ccaagcgaaa catcgcatcg agcgagcacg tactcggatg    5460
gaagccggtc ttgtcgatca ggatgatctg gacgaagagc atcaggggct cgcgccagcc    5520
gaactgttcg ccaggctcaa ggcgagcatg cccgacggcg aggatctcgt cgtgacccat    5580
ggcgatgcct gcttgccgaa tatcatggtg gaaaatggcc gcttttctgg attcatcgac    5640
tgtggccggc tgggtgtggc ggaccgctat caggacatag cgttggctac ccgtgatatt    5700
gctgaagagc ttggcggcga atgggctgac cgcttcctcg tgctttacgg tatcgccgct    5760
cccgattcgc agcgcatcgc cttctatcgc cttcttgacg agttcttctg aattattaac    5820
gcttacaatt tcctgatgcg gtattttctc cttacgcatc tgtgcggtat ttcacaccgc    5880
atcaggtggc acttttcggg gaaatgtgcg cggaacccct atttgtttat ttttctaaat    5940
acattcaaat atgtatccgc tcatgagaca ataaccctga taaatgcttc aataatagca    6000
cgtgaggagg gccaccatgg ccaagttgac cagtgccgtt ccggtgctca ccgcgcgcga    6060
cgtcgccgga gcggtcgagt tctggaccga ccggctcggg ttctcccggg acttcgtgga    6120
ggacgacttc gccggtgtgg tccgggacga cgtgaccctg ttcatcagcg cggtccagga    6180
ccaggtggtg ccggacaaca ccctggcctg ggtgtgggtg cgcggcctgg acgagctgta    6240
cgccgagtgg tcggaggtcg tgtccacgaa cttccgggac gcctccggcc ggccatgac    6300 cgagatcggc gagcagccgt gggggcggga gttcgccctg cgcgaccggg ccggcaactg    6360
cgtgcacttc gtggccgagg agcaggactg acacgtgcta aaacttcatt tttaatttaa    6420
aaggatctag gtgaagatcc ttttgataa tctcatgacc aaaatccctt aacgtgagtt    6480
ttcgttccac tgagcgtcag accccgtaga aagatcaaa ggatcttctt gagatccttt    6540
ttttctgcgc gtaatctgct gcttgcaaac aaaaaaacca ccgctaccag cggtggtttg    6600
tttgccggat caagagctac caactctttt tccgaaggta actggcttca gcagagcgca    6660
gataccaaat actgttcttc tagtgtagcc gtagttaggc caccacttca agaactctgt    6720
```

```
agcaccgcct acatacctcg ctctgctaat cctgttacca gtggctgctg ccagtggcga    6780
taagtcgtgt cttaccgggt tggactcaag acgatagtta ccggataagg cgcagcggtc    6840
gggctgaacg gggggttcgt gcacacagcc cagcttggag cgaacgacct acaccgaact    6900
gagataccta cagcgtgagc tatgagaaag cgccacgctt cccgaaggga gaaaggcgga    6960
caggtatccg gtaagcggca gggtcggaac aggagagcgc acgagggagc ttccaggggg    7020
aaacgcctgg tatctttata gtcctgtcgg gtttcgccac ctctgacttg agcgtcgatt    7080
tttgtgatgc tcgtcagggg ggcggagcct atggaaaaac gccagcaacg cggccttttt    7140
acggttcctg gccttttgct ggcctttgc tcacatgttc tttcctgcgt tatccctga    7200 ttctgtggat aaccgtatta ccgcctttga gtgagctgat accgctcgcc gcagccgaac    7260
gaccgagcgc agcgagtcag tgagcgagga agcggaagag cgcccaatac gcaaaccgcc    7320
tctccccgcg cgttggccga ttcattaatg cagctggcac gacaggtttc ccgactggaa    7380
agcgggcagt gagcgcaacg caattaatgt gagttagctc actcattagg cacccccaggc    7440 tttacacttt atgcttccgg ctcgtatgtt gtgtggaatt gtgagcggat aacaatttca    7500
cacaggaaac agctatgacc atgattacgc caagctattt aggtgacgcg ttagaatact    7560
caagctatgc atcaagcttg gtaccgagct cggatccact agtaacggcc gccagtgtgc    7620
tggaattcag gggcgcgccc caatttatta tcatctattt cctgacattt taatccatcc    7680
acctatgtca aaaacttata gaaaatgtca acttccaaac aaaacataat tgaacttcgc    7740
aaataaattc ttaataatat taaaaaatgt tacttaatta tttcttcaac cccatttttcc    7800 gcgcgtagcg cggacaaaga ctctagttaa atatagaagt ttccgattct catcgtataa    7860
aacggtgact ttggcgggct ttcatgtgta acaaattggt ttaacaaacc actgcctagt    7920
cgtttagtgt agaatcagcg catggaactc cgattggagc gtgactttca cgtgccggag    7980
gcccaccacc acagcgggcg ttacgctcta agaatctcgc ccacggtttt cttcatctcc    8040 ccccccgccaa gtgtctccct cgttcgccac ttctcatcat gttacaggga ccataaaaat    8100
ggcgtatttc ttcagccccg ggtataaata cacacatgat cctgtggtgg gttcttccac    8160
aagttacatc tccttctggt ttttgtattg caagtgtttg tattttttgc ctccagaga    8220 aaatcgcggc cgcatggaga gatctcaacg gcagtctcct ccgccaccgt cgccgtcctc    8280
ctcctcgtcc tccgtctccg cggacaccgt cctcgtccct cccggaaaga ggcggagggc    8340
ggcgacggcc aaggccggcg ccgagcctaa taagaggatc cgcaaggacc ccgccgccgc    8400
cgccgcgggg aagaggagct ccgtctacag gggagtcacc aggcacaggt ggacgggcag    8460
gttcgaggcg catctctggg acaagcactg cctcgccgcg ctccacaaca agaagaaagg    8520
caggcaagtc tacctggggg cgtatgacag cgaggaggca gctgctcgtg cctatgacct    8580
cgcagctctc aagtactggg gtcctgagac tctgctcaac ttccctgtgg aggattactc    8640
cagcgagatg ccggagatgg aggccgtgtc ccggaggag tacctggcct ccctccgccg    8700
caggagcagc ggcttctcca ggggcgtctc caagtacaga ggcgtcgcca ggcatcacca    8760 caacggggagg tgggaggcac ggattgggcg agtctttggg aacaagtacc tctacttggg    8820
aacatttgac actcaagaag aggcagccaa ggcctatgac cttgcggcca ttgaataccg    8880
tggcgtcaat gctgtaacca acttcgacat cagctgctac ctggaccacc gctgttcct    8940 ggcacagctc caacaggagc acaggtggt gccggcactc aaccaagaac ctcaacctga    9000
tcagagcgaa accggaacta cagagcaaga gccggagtca agcgaagcca agacaccgga    9060
tggcagtgca gaacccgatg agaacgcggt gcctgacgac accgcggagc ccctcaccac    9120
```

```
agtcgacgac agcatcgaag agggcttgtg gagcccttgc atggattacg agctagacac    9180
catgtcgaga ccaaactttg gcagctcaat caatctgagc gagtggttcg ctgacgcaga    9240
cttcgactgc aacatcggat gcctgttcga tgggtgttct gcggctgacg aaggaagcaa    9300
ggatggtgta ggtctggcag atttcagtct gtttgaggca ggtgatgtcc agctgaagga    9360
tgttctttcg gatatggaag aggggataca acctccagcg atgatcagtg tgtgcaacgc    9420
```

<210> SEQ ID NO 66
<211> LENGTH: 19215
<212> TYPE: DNA
<213> ORGANISM: Artificial sequence
<220> FEATURE:
<223> OTHER INFORMATION: Vector ARALO78
<220> FEATURE:
<221> NAME/KEY: misc_feature
<222> LOCATION: (17405)..(17405)
<223> OTHER INFORMATION: n is a, c, g, or t

<400> SEQUENCE: 66

```
cgcgcctcga gtgggcggat ccccgggct gcaggaattc actggccgtc gttttacaac      60
gtcgtgactg ggaaaaccct ggcgttaccc aacttaatcg ccttgcagca catccccctt    120
tcgccagctg gcgtaatagc gaagaggccc gcaccgatcg cccttcccaa cagttgcgca    180
gcctgaatgg cgaatggatc gatccatcgc gatgtacctt tgttagtca gcctctcgat     240 tgctcatcgt cattacacag taccgaagtt tgatcgatct agtaacatag atgacaccgc    300
gcgcgataat ttatcctagt ttgcgcgcta tattttgttt tctatcgcgt attaaatgta    360
taattgcggg actctaatca taaaaaccca tctcataaat aacgtcatgc attacatgtt    420
aattattaca tgcttaacgt aattcaacag aaattatatg ataatcatcg caagaccggc    480
aacaggattc aatcttaaga aactttattg ccaaatgttt gaacgatctg cttcgacgca    540
ctccttcttt actccaccat ctcgtcctta ttgaaaacgt gggtagcacc aaaacgaatc    600
aagtcgctgg aactgaagtt accaatcacg ctggatgatt tgccagttgg attaatcttg    660
cctttccccg catgaataat attgatgaat gcatgcgtga ggggtagttc gatgttggca    720
atagctgcaa ttgccgcgac atcctccaac gagcataatt cttcagaaaa atagcgatgt    780
tccatgttgt cagggcatgc atgatgcacg ttatgaggtg acggtgctag gcagtattcc    840
ctcaaagttt catagtcagt atcatattca tcattgcatt cctgcaagag agaattgaga    900
cgcaatccac acgctgcggc aaccttccgg cgttcgtggt ctatttgctc ttggacgttg    960
caaacgtaag tgttggatcg atccggggtg ggcgaagaac tccagcatga atccccgcg    1020 ctggaggatc atccagccgg cgtcccggaa acgattccg aagcccaacc tttcatagaa    1080
ggcggcggtg gaatcgaaat ctcgtgatgg caggttgggc gtcgcttggt cggtcatttc    1140
gaaccccaga gtcccgctca aagaactcg tcaagaaggc gatagaaggc gatgcgctgc    1200
gaatcgggag cggcgatacc gtaaagcacg aggaagcgt cagcccattc gccgccaagc    1260
tcttcagcaa tatcacgggt agccaacgct atgtcctgat agcggtccgc cacacccagc    1320
cggccacagt cgatgaatcc agaaaagcgg ccatttccca ccatgatatt cggcaagcag    1380
gcatcgccat gggtcacgac gagatcctcg ccgtcgggca tgcgcgcctt gagcctggcg    1440
aacagttcgg ctggcgcgag cccctgatgc tcttcgtcca gatcatcctg atcgacaaga    1500
ccggcttcca tccgagtacg tgctcgctcg atgcgatgtt tcgcttggtg gtcgaatggg    1560
caggtagccg gatcaagcgt atgcagccgc cgcattgcat cagccatgat ggatactttc    1620
tcggcaggag caaggtgaga tgacaggaga tcctgccccg gcacttcgcc caatagcagc    1680
```

-continued

```
cagtcccttc ccgcttcagt gacaacgtcg agcacagctg cgcaaggaac gcccgtcgtg    1740
gccagccacg atagccgcgc tgcctcgtcc tgcagttcat tcagggcacc ggacaggtcg    1800
gtcttgacaa aaagaaccgg gcgcccctgc gctgacagcc ggaacacggc ggcatcagag    1860
cagccgattg tctgttgtgc ccagtcatag ccgaatagcc tctccaccca agcggccgga    1920
gaacctgcgt gcaatccatc ttgttcaatc atgcgaaacg atccccgcaa gcttggagac    1980
tggtgatttc agcgtgtcct ctccaaatga aatgaacttc cttatataga ggaagggtct    2040
tgcgaaggat agtgggattg tgcgtcatcc cttacgtcag tggagatatc acatcaatcc    2100
acttgctttg aagacgtggt tggaacgtct tcttttttcca cgatgctcct cgtgggtggg    2160
ggtccatctt tgggaccact gtcggcagag gcatcttcaa cgatggcctt tcctttatcg    2220
caatgatggc atttgtagga gccaccttcc ttttccacta tcttcacaat aaagtgacag    2280
atagctgggc aatggaatcc gaggaggttt ccggatatta cccttttgttg aaaagtctca    2340
attgcccttt ggtcttctga gactgtatct ttgatatttt tggagtagac aagcgtgtcg    2400
tgctccacca tgttgacgaa gattttcttc ttgtcattga gtcgtaagag actctgtatg    2460
aactgttcgc cagtctttac ggcgagttct gttaggtcct ctatttgaat ctttgactcc    2520
atggcctttg attcagtggg aactaccttt ttagagactc caatctctat tacttgcctt    2580
ggtttgtgaa gcaagccttg aatcgtccat actggaatag tacttctgat cttgagaaat    2640
atatctttct ctgtgttctt gatgcagtta gtcctgaatc ttttgactgc atctttaacc    2700
ttcttgggaa ggtatttgat ctcctggaga ttattgctcg ggtagatcgt cttgatgaga    2760
cctgctgcgt aagcctctct aaccatctgt gggttagcat tctttctgaa attgaaaagg    2820
ctaatcttct cattatcagt ggtgaacatg gtatcgtcac cttctccgtc gaacttcctg    2880
actagatcgt agagatagag gaagtcgtcc attgtgatct ctggggcaaa ggagatctga    2940
attaattcga tatggtggat ttatcacaaa tgggacccgc cgccgacaga ggtgtgatgt    3000
taggccagga ctttgaaaat ttgcgcaact atcgtatagt ggccgacaaa ttgacgccga    3060
gttgacagac tgcctagcat ttgagtgaat tatgtgaggt aatgggctac actgaattgg    3120
tagctcaaac tgtcagtatt tatgtatatg agtgtatatt ttcgcataat ctcagaccaa    3180
tctgaagatg aaatgggtat ctgggaatgg cgaaatcaag gcatcgatcg tgaagtttct    3240
catctaagcc cccatttgga cgtgaatgta gacacgtcga aataaagatt tccgaattag    3300
aataatttgt ttattgcttt cgcctataaa tacgacggat cgtaatttgt cgttttatca    3360
aaatgtactt tcattttata ataacgctgc ggacatctac attttttgaat tgaaaaaaaa    3420
ttggtaatta ctcttttcttt ttctccatat tgaccatcat actcattgct gatccatgta    3480
gatttcccgg acatgaagcc atttacaatt gaatatatcc tgccgccgct gccgctttgc    3540
acccggtgga gcttgcatgt tggtttctac gcagaactga gccggttagg cagataattt    3600
ccattgagaa ctgagccatg tgcaccttcc ccccaacacg tgagcgacg gggcaacgga    3660
gtgatccaca tgggactttt aaacatcatc cgtcggatgg cgttgcgaga gaagcagtcg    3720
atccgtgaga tcagccgacg caccgggcag gcgcgcaaca cgatcgcaaa gtatttgaac    3780
gcaggtacaa tcgagccgac gttcacgcgg aacgaccaag caagctagct ttaatgcggt    3840
agtttatcac agttaaattg ctaacgcagt caggcaccgt gtatgaaatc taacaatgcg    3900
ctcatcgtca tcctcggcac cgtcaccctg gatgctgtag gcataggctt ggttatgccg    3960
gtactgccgg gcctcttgcg ggatatcgtc cattccgaca gcatcgccag tcactatggc    4020
gtgctgctag cgctatatgc gttgatgcaa tttctatgcg cacccgttct cggagcactg    4080
```

```
tccgaccgct ttggccgccg cccagtcctg ctcgcttcgc tacttggagc cactatcgac    4140
tacgcgatca tggcgaccac acccgtcctg tggtccaacc cctccgctgc tatagtgcag    4200
tcggcttctg acgttcagtg cagccgtctt ctgaaaacga catgtcgcac aagtcctaag    4260
ttacgcgaca ggctgccgcc ctgccctttt cctggcgttt tcttgtcgcg tgttttagtc    4320
gcataaagta gaatacttgc gactagaacc ggagacatta cgccatgaac aagagcgccg    4380
ccgctggcct gctgggctat gcccgcgtca gcaccgacga ccaggacttg accaaccaac    4440
gggccgaact gcacgcggcc ggctgcacca agctgttttc cgagaagatc accggcacca    4500
ggcgcgaccg cccggagctg gccaggatgc ttgaccacct acgccctggc gacgttgtga    4560
cagtgaccag gctagaccgc ctggcccgca gcacccgcga cctactggac attgccgagc    4620
gcatccagga ggccggcgcg ggcctgcgta gcctggcaga gccgtgggcc gacaccacca    4680
cgccggccgg ccgcatggtg ttgaccgtgt tcgccggcat tgccgagttc gagcgttccc    4740
taatcatcga ccgcacccgg agcgggcgcg aggccgccaa ggcccgaggc gtgaagtttg    4800
gccccgccc taccctcacc ccggcacaga tcgcgcacgc ccgcgagctg atcgaccagg    4860
aaggccgcac cgtgaaagag gcggctgcac tgcttggcgt gcatcgctcg accctgtacc    4920
gcgcacttga gcgcagcgag gaagtgacgc ccaccgaggc caggcggcgc ggtgccttcc    4980
gtgaggacgc attgaccgag gccgacgccc tggcggccgc cgagaatgaa cgccaagagg    5040
aacaagcatg aaaccgcacc aggacggcca ggacgaaccg ttttcatta ccgaagagat    5100
cgaggcggag atgatcgcgg ccgggtacgt gttcgagccg cccgcgcacg tctcaaccgt    5160
gcggctgcat gaaatcctgg ccggtttgtc tgatgccaag ctggcggcct ggccggccag    5220
cttggccgct gaagaaaccg agcgccgccg tctaaaaagg tgatgtgtat ttgagtaaaa    5280
cagcttgcgt catgcggtcg ctgcgtatat gatgcgatga gtaaataaac aaatacgcaa    5340
gggaacgcat gaagttatcg ctgtacttaa ccagaaaggc gggtcaggca agacgaccat    5400
cgcaacccat ctagcccgcg ccctgcaact cgccggggcc gatgttctgt tagtcgattc    5460
cgatccccag ggcagtgccc gcgattgggc ggcgtgcgg aagatcaac cgctaaccgt    5520
tgtcggcatc gaccgcccga cgattgaccg cgacgtgaag gccatcggcc ggcgcgactt    5580
cgtagtgatc gacggagcgc cccaggcggc ggacttggct gtgtccgcga tcaaggcagc    5640
cgacttcgtg ctgattccgg tgcagccaag cccttacgac atatgggcca ccgccgacct    5700
ggtggagctg gttaagcagc gcattgaggt cacggatgga aggctacaag cggcctttgt    5760
cgtgtcgcgg gcgatcaaag gcacgcgcat cggcggtgag gttgccgagg cgctggccgg    5820
gtacgagctg cccattcttg agtcccgtat cacgcagcgc gtgagctacc aggcactgc    5880
cgccgccgg acaaccgttc ttgaatcaga acccgagggc gacgctgccc gcgaggtcca    5940
ggcgctggcc gctgaaatta aatcaaaact catttgagtt aatgaggtaa agagaaaatg    6000
agcaaaagca caaacacgct aagtgccggc cgtccgagcg cacgcagcag caaggctgca    6060
acgttggcca gcctggcaga cacgccagcc atgaagcggg tcaactttca gttgccggcg    6120
gaggatcaca ccaagctgaa gatgtacgcg gtacgccaag gcaagaccat taccgagctg    6180
ctatctgaat acatcgcgca gctaccagag taaatgagca aatgaataaa tgagtagatg    6240
aattttagcg gctaaaggag gcggcatgga aaatcaagaa caaccaggca ccgacgccgt    6300
ggaatgcccc atgtgtggag gaacgggcgg ttggccaggc gtaagcggct gggttgtctg    6360
ccggccctgc aatggcactg gaaccccaa gcccgaggaa tcggcgtgag cggtcgcaaa    6420
ccatccggcc cggtacaaat cggcgcggcg ctgggtgatg acctggtgga gaagttgaag    6480
```

-continued

| | |
|---|---|
| gccgcgcagg ccgcccagcg gcaacgcatc gaggcagaag cacgcccegg tgaatcgtgg | 6540 |
| caagcggccg ctgatcgaat ccgcaaagaa tcccggcaac cgccggcagc cggtgcgccg | 6600 |
| tcgattagga agccgcccaa gggcgacgag caaccagatt ttttcgttcc gatgctctat | 6660 |
| gacgtgggca cccgcgatag tcgcagcatc atggacgtgg ccgttttccg tctgtcgaag | 6720 |
| cgtgaccgac gagctggcga ggtgatccgc tacgagcttc cagacgggca cgtagaggtt | 6780 |
| tccgcagggc cggccggcat ggccagtgtg tgggattacg acctggtact gatggcggtt | 6840 |
| tcccatctaa ccgaatccat gaaccgatac cgggaaggga agggagacaa gcccggccgc | 6900 |
| gtgttccgtc cacacgttgc ggacgtactc aagttctgcc ggcgagccga tggcggaaag | 6960 |
| cagaaagacg acctggtaga aacctgcatt cggttaaaca ccacgcacgt tgccatgcag | 7020 |
| cgtacgaaga aggccaagaa cggccgcctg gtgacggtat ccgagggtga agccttgatt | 7080 |
| agccgctaca agatcgtaaa gagcgaaacc gggcggccgg agtacatcga gatcgagcta | 7140 |
| gctgattgga tgtaccgcga gatcacgaaa ggcaagaacc cggacgtgct gacggttcac | 7200 |
| cccgattact ttttgatcga tcccggcatc ggccgttttc tctaccgcct ggcacgccgc | 7260 |
| gccgcaggca aggcagaagc cagatggttg ttcaagacga tctacgaacg cagtggcagc | 7320 |
| gccggagagt tcaagaagtt ctgtttcacc gtgcgcaagc tgatcgggtc aaatgacctg | 7380 |
| ccggagtacg atttgaagga ggaggcgggg caggctggcc cgatcctagt catgcgctac | 7440 |
| cgcaacctga tcgagggcga agcatccgcc ggttcctaat gtacggagca gatgctaggg | 7500 |
| caaattgccc tagcagggga aaaggtcga aaggtctct ttcctgtgga tagcacgtac | 7560 |
| attgggaacc caaagccgta cattgggaac cggaacccgt acattgggaa cccaaagccg | 7620 |
| tacattggga accggtcaca catgtaagtg actgatataa aagagaaaaa aggcgatttt | 7680 |
| tccgcctaaa actctttaaa acttattaaa actcttaaaa cccgcctggc ctgtgcataa | 7740 |
| ctgtctggcc agcgcacagc cgaagagctg caaaaagcgc ctaccctteg gtcgctgcgc | 7800 |
| tccctacgcc ccgccgcttc gcgtcggcct atcgcggccg ctggccgctc aaaaatggct | 7860 |
| ggcctacggc caggcaatct accagggcgg ggacaagccg cgccgtcgcc actcgaccgc | 7920 |
| cggcgcccac atcaaggcac cctgcctcgc gcgtttcggt gatgacggtg aaaacctctg | 7980 |
| acacatgcag ctcccggaga cggtcacagc ttgtctgtaa gcggatgccg ggagcagaca | 8040 |
| agcccgtcag ggcgcgtcag cgggtgttgg cgggtgtcgg ggcgcagcca tgacccagtc | 8100 |
| acgtagcgat agcggagtgt atactggctt aactatgcgg catcagagca gattgtactg | 8160 |
| agagtgcacc atatgcggtg tgaaataccg cacagatgcg taaggagaaa ataccgcatc | 8220 |
| aggcgctctt ccgcttcctc gctcactgac tcgctgcgct cggtcgttcg gctgcggcga | 8280 |
| gcggtatcag ctcactcaaa ggcggtaata cggttatcca cagaatcagg ggataacgca | 8340 |
| ggaaagaaca tgtgagcaaa aggccagcaa aaggccagga accgtaaaaa ggccgcgttg | 8400 |
| ctggcgtttt tccataggct ccgcccccct gacgagcatc acaaaaatcg acgctcaagt | 8460 |
| cagaggtggc gaaacccgac aggactataa agataccagg cgtttccccc tggaagctcc | 8520 |
| ctcgtgcgct ctcctgttcc gaccctgccg cttaccggat acctgtccgc ctttctccct | 8580 |
| tcgggaagcg tggcgctttc tcatagctca cgctgtaggt atctcagttc ggtgtaggtc | 8640 |
| gttcgctcca agctgggctg tgtgcacgaa ccccccgttc agcccgaccg ctgcgcctta | 8700 |
| tccggtaact atcgtcttga gtccaacccg gtaagacacg acttatcgcc actggcagca | 8760 |
| gccactggta acaggattag cagagcgagg tatgtaggcg gtgctacaga gttcttgaag | 8820 |
| tggtggccta actacggcta cactagaagg acagtatttg gtatctgcgc tctgctgaag | 8880 |

-continued

```
ccagttacct tcggaaaaag agttggtagc tcttgatccg gcaaacaaac caccgctggt    8940
agcggtggtt ttttttgtttg caagcagcag attacgcgca gaaaaaaagg atctcaagaa    9000
gatcctttga tcttttctac ggggtctgac gctcagtgga acgaaaactc acgttaaggg    9060
attttggtca tgagattatc aaaaaggatc ttcacctaga tccttttaaa ttaaaaatga    9120
agttttaaat caatctaaag tatatatgag taaacttggt ctgacagtta ccaatgctta    9180
atcagtgagg cacctatctc agcgatctgt ctatttcgtt catccatagt tgcctgactc    9240
cccgtcgtgt agataactac gatacgggag ggcttaccat ctggccccag tgctgcaatg    9300
ataccgcgag acccacgctc accggctcca gatttatcag caataaacca gccagccgga    9360
agggccgagc gcagaagtgg tcctgcaact ttatccgcct ccatccagtc tattaattgt    9420
tgccgggaag ctagagtaag tagttcgcca gttaatagtt tgcgcaacgt tgttgccatt    9480
gctacaggca tcgtggtgtc acgctcgtcg tttggtatgg cttcattcag ctccggttcc    9540
caacgatcaa ggcgagttac atgatccccc atgttgtgca aaaaagcggt tagctccttc    9600
ggtcctccga tcgttgtcag aagtaagttg gccgcagtgt tatcactcat ggttatggca    9660
gcactgcata attctcttac tgtcatgcca tccgtaagat gcttttctgt gactggtgag    9720
tactcaacca agtcattctg agaatagtgt atgcggcgac cgagttgctc ttgcccggcg    9780
tcaacacggg ataataccgc gccacatagc agaactttaa aagtgctcat cattggaaaa    9840
gacctgcagg ggggggggg cgctgaggtc tgcctcgtga agaaggtgtt gctgactcat    9900
accaggcctg aatcgcccca tcatccagcc agaaagtgag ggagccacgg ttgatgagag    9960
ctttgttgta ggtggaccag ttggtgattt tgaacttttg ctttgccacg gaacggtctg   10020
cgttgtcggg aagatgcgtg atctgatcct tcaactcagc aaaagttcga tttattcaac   10080
aaagccgccg tcccgtcaag tcagcgtaat gctctgccag tgttacaacc aattaaccaa   10140
ttctgattag aaaaactcat cgagcatcaa atgaaactgc aatttattca tatcaggatt   10200
atcaatacca tatttttgaa aaagccgttt ctgtaatgaa ggagaaaact caccgaggca   10260
gttccatagg atggcaagat cctggtatcg gtctgcgatt ccgactcgtc caacatcaat   10320
acaacctatt aatttcccct cgtcaaaaat aaggttatca agtgagaaat caccatgagt   10380
gacgactgaa tccggtgaga atggcaaaag cttatgcatt tctttccaga cttgttcaac   10440
aggccagcca ttacgctcgt catcaaaatc actcgcatca accaaaccgt tattcattcg   10500
tgattgcgcc tgagcgagac gaaatacgcg atcgctgtta aaaggacaat acaaacagg    10560
aatcgaatgc aaccggcgca ggaacactgc cagcgcatca acaatatttt cacctgaatc   10620
aggatattct tctaatacct ggaatgctgt ttcccgggg atcgcagtgg tgagtaacca   10680
tgcatcatca ggagtacgga taaaatgctt gatggtcgga agaggcataa attccgtcag   10740
ccagtttagt ctgaccatct catctgtaac atcattggca acgctacctt tgccatgttt   10800
cagaaacaac tctggcgcat cgggcttccc atacaatcga tagattgtcg cacctgattg   10860
cccgacatta tcgcgagccc atttatacc atataaatca gcatccatgt tggaatttaa   10920
tcgcggcctc gagcaagacg tttcccgttg aatatggctc ataacacccc ttgtattact   10980
gtttatgtaa gcagacagtt ttattgttca tgatgatata ttttatctt gtgcaatgta   11040
acatcagaga ttttgagaca caacgtggct ttccccccccc ccctgcagg tcaattcggt   11100
cgatatggct attacgaaga aggctcgtgc gcggagtccc gtgaactttc ccacgcaaca   11160
agtgaaccgc accgggtttg ccggaggcca tttcgttaaa atgcgcagcc atggctgctt   11220
cgtccagcat ggcgtaatac tgatcctcgt cttcggctgg cggtatattg ccgatgggct   11280
```

```
tcaaaagccg ccgtggttga accagtctat ccattccaag gtagcgaact cgaccgcttc    11340
gaagctcctc catggtccac gccgatgaat gacctcggcc ttgtaaagac cgttgatcgc    11400
ttctgcgagg gcgttgtcgt gctgtcgccg acgcttccga tagatggctc gatacctgct    11460
tctgccaacc gctcggaata gcgaaaggac acgtattgaa caccgcgatc cgagtgatgc    11520
actaggccgc catgagcggg acgccgatca tgatgagcct cctcgagggc atcgaggaca    11580
aagcctgcat gtgctgtccg gctcgcccgc catccgacaa tgcgacgggc gaagacgtcg    11640
atcacgaagg ccacgtagac gaagccctcc caagtggcga cataagtacg gacatgcgca    11700 aaggcttttcc cggtttgtcg ctgatggtgc aagagacgct gaagcgcgat ccgatgcgca    11760
ggcatctgtt cgtcttccgc ggtcgtggcg gtggcctgat caaggtcact cgccgaagag    11820
ctgcatgatt ggctcgaaac cgagcggggg aaattgtcgc gcagttctcc cgtcgccgag    11880
gcgataaatt acatgctcaa gcgatgggat ggcattacgt cattcctcga tgacggcccg    11940
atttgcctga cgaacaatgc tgccgaacga acgctcagag gctatgtact cggcaggaag    12000
tcatggctgt ttgccggatc ggatcgttgt gctgaacgtg cggcgttcat ggcgacactg    12060
atcatgagcg ccaagctcaa taacatcgat ccgcaggcct ggcttgccga cgtccgcgcc    12120
gaccttgcgg acgctccgat cagcaggctt gagcaacagc tgccgtggaa ctggacatcc    12180
aagacactga gtgctcaggc ggcctgacct gcggccttca ccggatactt accccattat    12240
cgcagattgc gatgaagcat cagcgtcatt cagcaatctt gccaaagtat gcaggctcgc    12300
gagaatcgac gtgcgaaacc ggctggttgc gccaaagatc cgcttgcgga gcggtcgaac    12360
attcatgctg ggacttcaag aggtcgagta gaggaagaac cggaaaggtt gcaccggaaa    12420
atatgcgttc cttttggagag cgcctcatgg acgtgaacaa atcgcccgga ccaaggatgc    12480
cacggataca aaagctcgcg aagctcggtc ccgtgggtgt tctgtcgtct cgttgtacaa    12540
cgaaatccat tcccattccg cgctcaagat ggcttcccct cggcagttca tcagggctaa    12600
atcaatctag ccgacttgtc cggtgaaatg ggctgcactc caacagaaac aatcaaacaa    12660
acatacacag cgacttattc acacgagctc aaattacaac ggtatatatc ctgccagtca    12720
gcatcatcac accaaaagtt aggcccgaat agtttgaaat tagaaagctc gcaattgagg    12780
tctacaggcc aaattcgctc ttagccgtac aatattactc accggtgcga tgcccccccat    12840 cgtaggtgaa ggtggaaatt aatgatccat cttgagacca caggcccaca acagctacca    12900
gtttcctcaa gggtccacca aaaacgtaag cgcttacgta catggtcgat aagaaaaggc    12960
aatttgtaga tgttaacatc caacgtcgct ttcaggggatc gatccaatac gcaaaccgcc    13020
tctccccgcg cgttggccga ttcattaatg cagctggcac gacaggtttc ccgactggaa    13080
agcgggcagt gagcgcaacg caattaatgt gagttagctc actcattagg caccccaggc    13140
tttacacttt atgcttccgg ctcgtatgtt gtgtggaatt gtgagcggat aacaatttca    13200
cacaggaaac agctatgacc atgattacgc caagcttgca tgcctgcagg tcgactctag    13260
aggatctggc gcgccccaat ttattatcat ctatttcctg acattttaat ccatccacct    13320
atgtcaaaaa cttatagaaa atgtcaactt ccaaacaaaa cataattgaa cttcgcaaat    13380
aaattcttaa taatattaaa aaatgttact taattatttc ttcaaccccca ttttccgcgc    13440 gtagcgcgga caaagactct agttaaatat agaagtttcc gattctcatc gtataaaacg    13500
gtgactttgg cgggctttca tgtgtaacaa attggtttaa caaaccactg cctagtcgtt    13560
tagtgtagaa tcagcgcatg gaactccgat tggagcgtga cttttcacgtg ccggaggccc    13620 accaccacag cgggcgttac gctctaagaa tctcgcccac ggttttcttc atctcccccc    13680
```

```
cgccaagtgt ctccctcgtt cgccacttct catcatgtta cagggaccat aaaaatggcg   13740
tatttcttca gccccgggta taaatacaca catgatcctg tggtgggttc ttccacaagt   13800
tacatctcct tctggttttt gtattgcaag tgtttgtatt ttttgcctcc gagagaaaat   13860
cgcggccgca tggagagatc tcaacggcag tctcctccgc caccgtcgcc gtcctcctcc   13920
tcgtcctccg tctccgcgga caccgtcctc gtccctcccg gaaagaggcg gagggcggcg   13980
acggccaagg ccggcgccga gcctaataag aggatccgca aggaccccgc cgccgccgcc   14040
gcggggaaga ggagctccgt ctacagggga gtcaccaggc acaggtggac gggcaggttc   14100
gaggcgcatc tctgggacaa gcactgcctc gccgcgctcc acaacaagaa gaaaggcagg   14160
caagtctacc tgggggcgta tgacagcgag gaggcagctg ctcgtgccta tgacctcgca   14220
gctctcaagt actggggtcc tgagactctg ctcaacttcc ctgtggagga ttactccagc   14280
gagatgccgg agatggaggc cgtgtcccgg gaggagtacc tggcctccct ccgccgcagg   14340
agcagcggct tctccagggg cgtctccaag tacagaggcg tcgccaggca tcaccacaac   14400
gggaggtggg aggcacggat tgggcgagtc tttgggaaca agtacctcta cttgggaaca   14460
tttgacactc aagaagaggc agccaaggcc tatgaccttg cggccattga ataccgtggc   14520
gtcaatgctg taaccaactt cgacatcagc tgctacctgg accaccgct gttcctggca   14580 cagctccaac aggagccaca ggtggtgccg gcactcaacc aagaacctca acctgatcag   14640
agcgaaaccg gaactacaga gcaagagccg gagtcaagcg aagccaagac accggatggc   14700
agtgcagaac ccgatgagaa cgcggtgcct gacgacaccg cggagcccct caccacagtc   14760
gacgacagca tcgaagaggg cttgtggagc ccttgcatgg attacgagct agacaccatg   14820
tcgagaccaa actttggcag ctcaatcaat ctgagcgagt ggttcgctga cgcagacttc   14880
gactgcaaca tcggatgcct gttcgatggg tgttctgcgg ctgacgaagg aagcaaggat   14940
ggtgtaggtc tggcagattt cagtctgttt gaggcaggtg atgtccagct gaaggatgtt   15000
ctttcggata tggaagaggg gatacaacct ccagcgatga tcagtgtgtg caacgcggcc   15060
gcaagtatga actaaaatgc atgtaggtgt aagagctcat ggagagcatg gaatattgta   15120
tccgaccatg taacagtata ataactgagc tccatctcac ttcttctatg aataaacaaa   15180
ggatgttatg atatattaac actctatcta tgcaccttat tgttctatga taaatttcct   15240
cttattatta taaatcatct gaatcgtgac ggcttatgga atgcttcaaa tagtacaaaa   15300
acaaatgtgt actataagac tttctaaaca attctaacct tagcattgtg aacgagacat   15360
aagtgttaag aagacataac aattataatg gaagaagttt gtctccattt atatattata   15420
tattacccac ttatgtatta tattaggatg ttaaggagac ataacaatta taagagaga   15480 agtttgtatc catttatata ttatatacta cccatttata tattatactt atccacttat   15540
ttaatgtctt tataaggttt gatccatgat atttctaata ttttagttga tatgtatatg   15600
aaagggtact atttgaactc tcttactctg tataaaggtt ggatcatcct taaagtgggt   15660
ctatttaatt ttattgcttc ttacagataa aaaaaaaatt atgagttggt ttgataaaat   15720
attgaaggat ttaaaataat aataaataac atataatata tgtatataaa tttattataa   15780
tataacattt atctataaaa aagtaaatat tgtcataaat ctatacaatc gtttagcctt   15840
gctggacgaa tctcaattat ttaaacgaga gtaaacatat ttgactttt ggttatttaa   15900 caaattatta tttaacacta tatgaaattt ttttttttat cagcaaagaa taaaattaaa   15960
ttaagaagga caatggtgtc ccaatcctta tacaaccaac ttccacaaga aagtcaagtc   16020
agagacaaca aaaaaacaag caaaggaaat tttttaattt gagttgtctt gtttgctgca   16080
```

```
taatttatgc agtaaaacac tacacataac ccttttagca gtagagcaat ggttgaccgt  16140
gtgcttagct tctttttattt tatttttta tcagcaaaga ataaataaaa taaaatgaga  16200
cacttcaggg atgtttcaac aagcttggat cctcgaagag aagggttaat aacacacttt  16260
tttaacatttt ttaacacaaa ttttagttat ttaaaaattt attaaaaaat ttaaaataag  16320
aagaggaact ctttaaataa atctaactta caaaatttat gattttttaat aagttttcac  16380
caataaaaaa tgtcataaaa atatgttaaa aagtatatta tcaatattct ctttatgata  16440
aataaaaga aaaaaaaat aaaagttaag tgaaaatgag attgaagtga ctttaggtgt  16500
gtataaaatat atcaaccccg ccaacaattt atttaatcca aatatattga agtatattat  16560
tccatagcct ttatttattt atatattat tatataaaag ctttatttgt tctaggttgt  16620
tcatgaaata ttttttggt tttatctccg ttgtaagaaa atcatgtgct ttgtgtcgcc  16680
actcactatt gcagcttttt catgcattgg tcagattgac ggttgattgt attttgttt  16740
tttatggttt tgtgttatga cttaagtctt catctcttta tctcttcatc aggtttgatg  16800
gttacctaat atggtccatg ggtacatgca tggttaaatt aggtggccaa ctttgttgtg  16860
aacgatagaa ttttttttat attaagtaaa ctatttttat attatgaaat aataataaaa  16920
aaaatatttt atcattatta acaaaatcat attagttaat ttgttaactc tataataaaa  16980
gaaatactgt aacattcaca ttacatggta acatctttcc acctttcat ttgtttttg  17040
tttgatgact tttttttcttg tttaaattta tttcccttct tttaaatttg gaatacatta  17100
tcatcatata taaactaaaa tactaaaaac aggattacac aaatgataaa taataacaca  17160
aatatttata aatctagctg caatatattt aaactagcta tatcgatatt gtaaaatataaa  17220
actagctgca ttgatactga taaaaaaata tcatgtgctt tctggactga tgatgcagta  17280
tactttttgac attgcctttta ttttattttt cagaaaagct ttcttagttc tgggttcttc  17340
attatttgtt tcccatctcc attgtgaatt gaatcatttg cttcgtgtca caaatacaat  17400
ttagntaggt acatgcattg gtcagattca cggttttatta tgtcatgact taagttcatg  17460
gtagtacatt acctgccacg catgcattat attggttaga tttgataggc aaatttggtt  17520
gtcaacaata taaatataaa taatgttttt atattacgaa ataacagtga tcaaaacaaa  17580
cagttttatc tttattaaca agattttgtt tttgtttgat gacgtttttt aatgtttacg  17640
cttttccccct tcttttgaat ttagaacact ttatcatcat aaaatcaaat actaaaaaaa  17700
ttacatattt cataaataat aacacaaata ttttaaaaa atctgaaata ataatgaaca  17760
atattacata ttatcacgaa aattcattaa taaaaatatt atataaataa aatgtaatag  17820
tagttatatg taggaaaaaa gtactgcacg cataatatat acaaaaagat taaaatgaac  17880
tattataaat aataacacta aattaatggt gaatcatatc aaaataatga aaagtaaat  17940
aaaattgta attaacttct atatgtatta cacacacaaa taataaataa tagtaaaaaa  18000
aattatgata aatatttacc atctcataag atatttaaaa taatgataaa aatatagatt  18060
attttttatg caactagcta gccaaaaaga gaacacgggt atatataaaa agagtacctt  18120
taaattctac tgtacttcct ttattcctga cgttttttata tcaagtggac atacgtgaag  18180
attttaatta tcagtctaaa tatttcatta gcacttaata cttttctgtt ttattcctat  18240
cctataagta gtcccgattc tcccaacatt gcttattcac acaactaact aagaaagtct  18300
tccatagccc cccaagcggc ccatggcctc ctccgaggac gtcatcaagg agttcatgcg  18360
cttcaaggtg cgcatggagg gctccgtgaa cggccacgag ttcgagatcg agggcgaggg  18420
cgagggccgc ccctacgagg gcacccagac cgccaagctg aaggtgacca agggcggccc  18480
```

```
cctgcccttc gcctgggaca tcctgtcccc ccagttccag tacggctcca aggtgtacgt   18540
gaagcacccc gccgacatcc ccgactacaa gaagctgtcc ttccccgagg gcttcaagtg   18600
ggagcgcgtg atgaacttcg aggacggcgg cgtggtgacc gtgacccagg actcctccct   18660
gcaggacggc tccttcatct acaaggtgaa gttcatcggc gtgaacttcc cctccgacgg   18720
ccccgtaatg cagaagaaga ctatgggctg ggaggcctcc accgagcgcc tgtaccccg    18780 cgacggcgtg ctgaagggcg agatccacaa ggccctgaag ctgaaggacg gcggccacta   18840
cctggtggag ttcaagtcca tctacatggc caagaagccc gtgcagctgc ccggctacta   18900
ctacgtggac tccaagctgg acatcaccct ccacaacgag gactacacca tcgtggagca   18960
gtacgagcgc gccgagggcc gccaccacct gttcctgtag cggccggccg cgacacaagt   19020
gtgagagtac taaataaatg ctttggttgt acgaaatcat tacactaaat aaaataatca   19080
aagcttatat atgccttccg ctaaggccga atgcaaagaa attggttctt tctcgttatc   19140
ttttgccact tttactagta cgtattaatt actacttaat catctttgtt tacggctcat   19200
tatatccgtc gacgg                                                    19215

<210> SEQ ID NO 67
<211> LENGTH: 9565
<212> TYPE: DNA
<213> ORGANISM: Artificial sequence
<220> FEATURE:
<223> OTHER INFORMATION: Vector KS428
<220> FEATURE:
<221> NAME/KEY: misc_feature
<222> LOCATION: (4330)..(4330)
<223> OTHER INFORMATION: n is a, c, g, or t
<220> FEATURE:
<221> NAME/KEY: misc_feature
<222> LOCATION: (7746)..(7746)
<223> OTHER INFORMATION: n is a, c, g, or t

<400> SEQUENCE: 67
ctagagggcc caattcgccc tatagtgagt cgtattacaa ttcactggcc gtcgttttac     60
aacgtcgtga ctgggaaaac cctggcgtta cccaacttaa tcgccttgca gcacatcccc    120
ctttcgccag ctggcgtaat agcgaagagg cccgcaccga tcgcccttcc caacagttgc    180
gcagcctata cgtacggcag tttaaggttt acacctataa agagagagc cgttatcgtc     240 tgtttgtgga tgtacagagt gatattattg acacgccggg cgacggatg gtgatccccc     300 tggccagtgc acgtctgctg tcagataaag tctcccgtga actttacccg gtggtgcata    360
tcggggatga aagctggcgc atgatgacca ccgatatggc cagtgtgccg gtctccgtta    420
tcggggaaga agtggctgat ctcagccacc gcgaaaatga catcaaaaac gccattaacc    480
tgatgttctg gggaatataa atgtcaggca tgagattatc aaaaaggatc ttcacctaga    540
tccttttcac gtagaaagcc agtccgcaga aacggtgctg accccggatg aatgtcagct    600
actgggctat ctggacaagg gaaaacgcaa gcgcaaagag aaagcaggta gcttgcagtg    660
ggcttacatg gcgatagcta actgggcgg ttttatggac agcaagcgaa ccggaattgc    720
cagctggggc gccctctggt aaggttggga agccctgcaa agtaaactgg atggctttct    780
tgccgccaag gatctgatgg cgcaggggat caagctctga tcaagagaca ggatgaggat    840
cgtttcgcat gattgaacaa gatggattgc acgcaggttc tccggccgct tgggtggaga    900
ggctattcgg ctatgactgg gcacaacaga caatcggctg ctctgatgcc gccgtgttcc    960
ggctgtcagc gcaggggcgc ccggttcttt ttgtcaagac cgacctgtcc ggtgccctga   1020
atgaactgca agacgaggca gcgcggctat cgtggctggc cacgacgggc gttccttgcg   1080
```

```
cagctgtgct cgacgttgtc actgaagcgg aagggactg gctgctattg ggcgaagtgc      1140
cggggcagga tctcctgtca tctcaccttg ctcctgccga gaaagtatcc atcatggctg      1200
atgcaatgcg gcggctgcat acgcttgatc cggctacctg cccattcgac caccaagcga      1260
aacatcgcat cgagcgagca cgtactcgga tggaagccgg tcttgtcgat caggatgatc      1320
tggacgaaga gcatcagggg ctcgcgccag ccgaactgtt cgccaggctc aaggcgagca      1380
tgcccgacgc cgaggatctc gtcgtgaccc atggcgatgc ctgcttgccg aatatcatgg      1440
tggaaaatgg ccgcttttct ggattcatcg actgtggccg gctgggtgtg gcggaccgct      1500
atcaggacat agcgttggct acccgtgata ttgctgaaga gcttggcggc gaatgggctg      1560
accgcttcct cgtgctttac ggtatcgccg ctcccgattc gcagcgcatc gccttctatc      1620
gccttcttga cgagttcttc tgaattatta acgcttacaa tttcctgatg cggtattttc      1680
tccttacgca tctgtgcggt atttcacacc gcatcaggtg cacttttcg gggaaatgtg      1740
cgcggaaccc ctatttgttt attttctaa atacattcaa atatgtatcc gctcatgaga      1800
caataaccct gataaatgct tcaataatag cacgtgagga gggccaccat ggccaagttg      1860
accagtgccg ttccggtgct caccgcgcgc gacgtcgccg gagcggtcga gttctggacc      1920
gaccggctcg ggttctcccg ggacttcgtg gaggacgact cgccggtgt ggtccgggac      1980
gacgtgaccc tgttcatcag cgcggtccag gaccaggtgg tgccggacaa caccctggcc      2040
tgggtgtggg tgcgcggcct ggacgagctg tacgccgagt ggtcggaggt cgtgtccacg      2100
aacttccggg acgcctccgg gccggccatg accgagatcg gcgagcagcc gtgggggcgg      2160
gagttcgccc tgcgcgaccc ggccggcaac tgcgtgcact cgtggccga ggagcaggac      2220
tgacacgtgc taaaacttca ttttttaattt aaaaggatct aggtgaagat cctttttgat      2280
aatctcatga ccaaaatccc ttaacgtgag ttttcgttcc actgagcgtc agaccccgta      2340
gaaaagatca aaggatcttc ttgagatcct ttttttctgc gcgtaatctg ctgcttgcaa      2400
acaaaaaaac caccgctacc agcggtggtt tgtttgccgg atcaagagct accaactctt      2460
tttccgaagg taactggctt cagcagagcg cagataccaa atactgttct ctagtgtag      2520
ccgtagttag gccaccactt caagaactct gtagcaccgc ctacatacct cgctctgcta      2580
atcctgttac cagtggctgc tgccagtggc gataagtcgt gtcttaccgg gttggactca      2640
agacgatagt taccggataa ggcgcagcgg tcgggctgaa cggggggttc gtgcacacag      2700
cccagcttgg agcgaacgac ctacaccgaa ctgagatacc tacagcgtga gctatgagaa      2760
agcgccacgc ttcccgaagg gagaaaggcg gacaggtatc cggtaagcgg cagggtcgga      2820
acaggagagc gcacgaggga gcttccaggg ggaaacgcct ggtatcttta tagtcctgtc      2880
gggtttcgcc acctctgact tgagcgtcga ttttttgtgat gctcgtcagg ggggcggagc      2940
ctatggaaaa acgccagcaa cgcggccttt ttacggttcc tggccttttg ctggcctttt      3000
gctcacatgt tctttcctgc gttatcccct gattctgtgg ataaccgtat taccgccttt      3060
gagtgagctg ataccgctcg ccgcagccga acgaccgagc gcagcgagtc agtgagcgag      3120
gaagcggaag agcgcccaat acgcaaaccg cctctccccg cgcgttggcc gattcattaa      3180
tgcagctggc acgacaggtt tcccgactgg aaagcgggca gtgagcgcaa cgcaattaat      3240
gtgagttagc tcactcatta ggcaccccag gctttacact ttatgcttcc ggctcgtatg      3300
ttgtgtggaa ttgtgagcgg ataacaattt cacacaggaa acagctatga ccatgattac      3360
gccaagctat ttaggtgacg cgttagaata tcaagctat gcatcaagct tggtaccgag      3420
ctcggatcca ctagtaacgg ccgccagtgt gctggaattc agggcgcgc cctatagatg      3480
```

```
ggatgaagct gctctcgaca aatctgataa aactaaagaa ggttagtaat caattttttac    3540 aaaatcatag attattttt tcattgaatt atttttatgc tataccaaga attgtatttt     3600
agtatttgtt ttaactacat ataatagaat taactacata taaattaact aaacttaaaa    3660
taaaaataga tttgtttcct gaaattattt taagaatata tatgtatata tctaaaatct    3720
tagacttaga tagattttc tatctatcta ttttggttac ttaaaataaa taaatttgta     3780
taaataattg tatagttatc aaaaattaaa actaattttt ttaaagttgt tgatatataa    3840
aatactaaag atttaacgat taagtattta tttaagtata gaattttgtt ttttttttaa    3900
gtttagttat gaagttgtta attatattaa aacaaaacaa tatttcgaaa ttttattatc    3960
atattcgaat atatttttt tagtgatgat gtatgaatta ttatcataat ttgaaagttt     4020
actaaaaaat atatcaacat gaattgtaat atatgagtta ttaccttaac caaaattata    4080
aattaacatt aaatataatt atatatgtca tatttagcca tacaatgtgt catcaatatt    4140
aatagtcatg tcaatattac ataatgccaa tattatgcta cttaaacccc aaatccccta    4200
actcccgtta agtagccaaa ttcataaata tacttattcg acaaaataaa aaactttaaa    4260
atatttacta atccgaccat gcacaagcat ccattccta ttccattgcc acgggataac     4320
aatgcaaccn actcctcaaa aaagaaaaa ttcaagctct tttgcaaaaa aaaataaaat     4380
aattttaaca cctaaaattt tttgtttcca aacttctaca gggaacacac ataaaagaaa    4440
aagaggacgt ccactcggat cacgcaacaa accaaaaggt gtgtcatgac tcctaagata    4500
taatatttcc ttattcaaaa tcataccatt ttaaattatg aatgtatttc gtagtccacc    4560
agatatgtaa tccaccagcg ttcaaaccaa agttttatga ttgtaagttt aagtgaatta    4620
taataatata ttcttcacgg tatcttttca taactaattg agttatcaaa cttgatcgca    4680
catgtggctt tgataggtgt gacttttatg gtatacaatt ctttcaacct aaaaacatta    4740
ttgttcctca atatcttaca ttatgcttga ctgcaacaaa atattttctc atctgttttc    4800
ttcctttaaa ccaattatt atcatctatt tcctgacatt ttaatccatc cacctatgtc     4860
aaaaacttat agaaaatgtc aacttccaaa caaaacataa ttgaacttcg caaataaatt    4920
cttaataata ttaaaaaatg ttacttaatt atttcttcaa ccccattttc cgcgcgtagc    4980
gcggacaaag actctagtta aatatagaag tttccgattc tcatcgtata aaacggtgac    5040
tttggcgggc tttcatgtgt aacaaattgg tttaacaaac cactgcctag tcgtttagtg    5100
tagaatcagc gcatggaact ccgattggag cgtgactttc acgtgccgga ggcccaccac    5160
cacagcgggg gttacgctct aagaatctcg cccacggttt tcttcatctg ccccccgcca    5220
agtgtcttcc tcgttcgcca cttctcacca agttacagga accctaaaaa tggccttttct   5280 tcagccccgg ctataataca cacatgatcc tatagtgggt tcttccacaa gttacatctc    5340
cttctggatt gtacatttca agtgtttgtg ttttttctgc ctctgagaga aaatcgcggc    5400
cgcaagtatg aactaaaatg catgtaggtg taagagctca tggagagcat ggaatattgt    5460
atccgaccat gtaacagtat aataactgag ctccatctca cttcttctat gaataaacaa    5520
aggatgttat gatatattaa cactctatct atgcaccta ttgttctatg ataaatttcc     5580
tcttattatt ataaatcatc tgaatcgtga cggcttatgg aatgcttcaa atagtacaaa    5640
aacaaatgtg tactataaga ctttctaaac aattctaacc ttagcattgt gaacgagaca    5700
taagtgttaa gaagacataa caattataat ggaagaagtt tgtctccatt tatatattat    5760
atattaccca cttatgtatt atattaggat gttaaggaga cataacaatt ataaagagag    5820
aagtttgtat ccatttatat attatatact acccatttat atattatact tatccactta    5880
```

```
tttaatgtct ttataaggtt tgatccatga tatttctaat attttagttg atatgtatat    5940
gaaagggtac tatttgaact ctcttactct gtataaaggt tggatcatcc ttaaagtggg    6000
tctatttaat tttattgctt cttacagata aaaaaaaaat tatgagttgg tttgataaaa    6060
tattgaagga tttaaaataa taataaataa catataaatt atgtatataa atttattata    6120
atataacatt tatctataaa aaagtaaata ttgtcataaa tctatacaat cgtttagcct    6180
tgctggacga atctcaatta tttaaacgag agtaaacata tttgacttttt tggttatttta   6240 acaaattatt atttaacact atatgaaatt tttttttta tcagcaaaga ataaaattaa    6300
attaagaagg acaatggtgt cccaatcctt atacaaccaa cttccacaag aaagtcaagt    6360
cagagacaac aaaaaaacaa gcaaaggaaa tttttttaatt tgagttgtct tgtttgctgc    6420
ataatttatg cagtaaaaca ctacacataa ccctttttagc agtagagcaa tggttgaccg    6480
tgtgcttagc ttcttttatt ttattttttt atcagcaaag aataaataaa ataaaatgag    6540
acacttcagg gatgtttcaa caagcttgga tcctcgaaga aagggttaa taacacactt    6600 ttttaacatt tttaacacaa attttagtta tttaaaaatt tattaaaaaa tttaaaataa    6660
gaagaggaac tctttaaata aatctaactt acaaaatta tgatttttaa taagttttca    6720
ccaataaaaa atgtcataaa aatatgttaa aaagtatatt atcaatattc tctttatgat    6780
aaataaaaag aaaaaaaaaa taaaagttaa gtgaaaatga gattgaagtg actttaggtg    6840
tgtataaata tatcaacccc gccaacaatt tatttaatcc aaatatattg aagtatatta    6900
ttccatagcc tttatttatt tatatattta ttatataaaa gctttatttg ttctaggttg    6960
ttcatgaaat attttttttgg tttaatctcc gttgtaagaa aatcatgtgc tttgtgtcgc    7020
cactcactat tgcagctttt tcatgcattg gtcagattga cggttgattg tattttttgtt    7080 ttttatggtt ttgtgttatg acttaagtct tcatctcttt atctcttcat caggtttgat    7140
ggttacctaa tatggtccat gggtacatgc atggttaaat taggtggcca actttgttgt    7200
gaacgataga atttttttta tattaagtaa actatttta tattatgaaa taataataaa    7260
aaaaatattt tatcattatt aacaaaatca tattagttaa tttgttaact ctataataaa    7320
agaaatactg taacattcac attacatggt aacatctttc caccctttca tttgttttttt    7380 gtttgatgac tttttttctt gtttaaattt atttcccttc ttttaaattt ggaatacatt    7440
atcatcatat ataaactaaa atactaaaaa caggattaca caaatgataa ataataacac    7500
aaatatttat aaatctagct gcaatatatt taaactagct atatcgatat tgtaaaataa    7560
aactagctgc attgatactg ataaaaaaat atcatgtgct ttctggactg atgatgcagt    7620
atacttttga cattgccttt atttttatttt tcagaaaagc tttcttagtt ctgggttctt    7680
cattatttgt ttcccatctc cattgtgaat tgaatcattt gcttcgtgtc acaaatacaa    7740
tttagntagg tacatgcatt ggtcagattc acggtttatt atgtcatgac ttaagttcat    7800
ggtagtacat tacctgccac gcatgcatta tattggttag atttgatagg caaatttggt    7860
tgtcaacaat ataatataa ataatgtttt tatattacga aataacagtg atcaaaacaa    7920 acagtttttat cttattaac aagatttttgt ttttgtttga tgacgttttt taatgtttac    7980
gctttccccc ttcttttgaa tttagaacac tttatcatca taaaatcaaa tactaaaaaa    8040
attacatatt tcataaataa taacacaaat atttttaaaa aatctgaaat aataatgaac    8100
aatattacat attatcacga aaattcatta ataaaaatat tatataaata aaatgtaata    8160
gtagttatat gtaggaaaaa agtactgcac gcataatata tacaaaaaga ttaaaatgaa    8220
ctattataaa taataacact aaattaatgg tgaatcatat caaaataatg aaaaagtaaa    8280
```

-continued

| | |
|---|---|
| taaaatttgt aattaacttc tatatgtatt acacacacaa ataataaata atagtaaaaa | 8340 |
| aaattatgat aaatatttac catctcataa gatatttaaa ataatgataa aaatatagat | 8400 |
| tattttttat gcaactagct agccaaaaag agaacacggg tatatataaa agagtacct | 8460 |
| ttaaattcta ctgtacttcc tttattcctg acgttttat atcaagtgga catacgtgaa | 8520 |
| gattttaatt atcagtctaa atatttcatt agcacttaat acttttctgt tttattccta | 8580 |
| tcctataagt agtcccgatt ctcccaacat tgcttattca cacaactaac taagaaagtc | 8640 |
| ttccatagcc ccccaagcgg cccatggcct cctccgagga cgtcatcaag gagttcatgc | 8700 |
| gcttcaaggt gcgcatggag ggctccgtga acggccacga gttcgagatc gagggcgagg | 8760 |
| gcgagggccg cccctacgag ggcacccaga ccgccaagct gaaggtgacc aagggcggcc | 8820 |
| ccctgccctt cgcctgggac atcctgtccc ccagttcca gtacggctcc aaggtgtacg | 8880 |
| tgaagcaccc cgccgacatc cccgactaca agaagctgtc cttccccgag ggcttcaagt | 8940 |
| gggagcgcgt gatgaacttc gaggacggcg gcgtggtgac cgtgacccag gactcctccc | 9000 |
| tgcaggacgg ctccttcatc tacaaggtga agttcatcgg cgtgaacttc ccctccgacg | 9060 |
| gccccgtaat gcagaagaag actatgggct gggaggcctc caccgagcgc ctgtacccc | 9120 |
| gcgacggcgt gctgaagggc gagatccaca aggcccctgaa gctgaaggac ggcggccact | 9180 |
| acctggtgga gttcaagtcc atctacatgg ccaagaagcc cgtgcagctg cccggctact | 9240 |
| actacgtgga ctccaagctg gacatcacct cccacaacga ggactacacc atcgtggagc | 9300 |
| agtacgagcg cgccgagggc cgccaccacc tgttcctgta cggccggcc gcgacacaag | 9360 |
| tgtgagagta ctaaataaat gctttggttg tacgaaatca ttcactaaa taaaataatc | 9420 |
| aaagcttata tatgccttcc gctaaggccg aatgcaaaga aattggttct ttctcgttat | 9480 |
| cttttgccac ttttactagt acgtattaat tactacttaa tcatctttgt ttacggctca | 9540 |
| ttatatccgt cgacggcgcg ccgct | 9565 |

<210> SEQ ID NO 68  
<211> LENGTH: 10947  
<212> TYPE: DNA  
<213> ORGANISM: Artificial sequence  
<220> FEATURE:  
<223> OTHER INFORMATION: Vector KS429  
<220> FEATURE:  
<221> NAME/KEY: misc_feature  
<222> LOCATION: (2349)..(2349)  
<223> OTHER INFORMATION: n is a, c, g, or t  
<220> FEATURE:  
<221> NAME/KEY: misc_feature  
<222> LOCATION: (8498)..(8498)  
<223> OTHER INFORMATION: n is a, c, g, or t

<400> SEQUENCE: 68

| | |
|---|---|
| ggccgcaagt atgaactaaa atgcatgtag gtgtaagagc tcatggagag catggaatat | 60 |
| tgtatccgac catgtaacag tataataact gagctccatc tcacttcttc tatgaataaa | 120 |
| caaaggatgt tatgatatat taacactcta tctatgcacc ttattgttct atgataaatt | 180 |
| tcctcttatt attataaatc atctgaatcg tgacggctta tggaatgctt caaatagtac | 240 |
| aaaaacaaat gtgtactata agactttcta aacaattcta accttagcat tgtgaacgag | 300 |
| acataagtgt taagaagaca taacaattat aatggaagaa gtttgtctcc atttatatat | 360 |
| tatatattac ccacttatgt attatattag gatgttaagg agacataaca attataaaga | 420 |
| gagaagtttg tatccatta tatattatat actaccattt tatatattat acttatccac | 480 |
| ttatttaatg tctttataag gtttgatcca tgatatttct aatatttag ttgatatgta | 540 |

```
tatgaaaggg tactatttga actctcttac tctgtataaa ggttggatca tccttaaagt      600
gggtctattt aattttattg cttcttacag ataaaaaaaa aattatgagt tggtttgata      660
aaatattgaa ggatttaaaa taataataaa taacatataa tatatgtata taaatttatt      720 ataaatataac atttatctat aaaaaagtaa atattgtcat aaatctatac aatcgtttag     780
ccttgctgga cgaatctcaa ttatttaaac gagagtaaac atatttgact ttttggttat      840
ttaacaaatt attatttaac actatatgaa attttttttt ttatcagcaa agaataaaat      900
taaattaaga aggacaatgg tgtcccaatc cttatacaac caacttccac aagaaagtca      960
agtcagagac aacaaaaaaa caagcaaagg aaatttttta atttgagttg tcttgtttgc     1020
tgcataattt atgcagtaaa acactacaca taacccttttt agcagtagag caatggttga    1080
ccgtgtgctt agcttctttt attttatttt tttatcagca agaataaaat aaaataaaat     1140
gagacacttc agggatgttt caacaagctt ggatcctcga agagaagggt taataacaca    1200 ctttttttaac attttttaaca caaattttag ttatttaaaa atttattaaa aaatttaaaa   1260
taagaagagg aactctttaa ataaatctaa cttacaaaat ttatgatttt taataagttt     1320
tcaccaataa aaaatgtcat aaaaatatgt taaaaagtat attatcaata ttctctttat     1380
gataaataaa aagaaaaaaa aaataaaagt taagtgaaaa tgagattgaa gtgactttag     1440
gtgtgtataa atatatcaac cccgccaaca atttatttaa tccaaatata ttgaagtata     1500
ttattccata gcctttattt atttatatat ttattatata aaagctttat ttgttctagg     1560
ttgttcatga atattttttt tggttttatc tccgttgtaa gaaatcatg tgctttgtgt      1620 cgccactcac tattgcagct ttttcatgca ttggtcagat tgacggttga ttgtatttttt    1680 gttttttatg gttttgtgtt atgacttaag tcttcatctc tttatctctt catcaggttt     1740
gatggttacc taatatggtc catgggtaca tgcatggtta aattaggtgg ccaactttgt     1800
tgtgaacgat agaattttttt ttatattaag taaactattt ttatattatg aaataataat    1860
aaaaaaaata ttttatcatt attaacaaaa tcatattagt taatttgtta actctataat     1920
aaaagaaata ctgtaacatt cacattacat ggtaacatct ttccacccctt tcatttgttt    1980 tttgtttgat gactttttttt cttgtttaaa tttatttccc ttcttttaaa tttggaatac    2040
attatcatca tatataaact aaaatactaa aaacaggatt acacaaatga taaataataa     2100
cacaaatatt tataaatcta gctgcaatat atttaaacta gctatatcga tattgtaaaa     2160
taaaactagc tgcattgata ctgataaaaaa aatatcatgt gctttctgga ctgatgatgc    2220
agtatacttt tgacattgcc tttattttat ttttcagaaa agcttttctta gttctgggtt   2280 cttcattatt tgtttcccat ctccattgtg aattgaatca tttgcttcgt gtcacaaata    2340
caatttagnt aggtacatgc attggtcaga ttcacggttt attatgtcat gacttaagtt    2400
catggtagta cattacctgc cacgcatgca ttatattggt tagatttgat aggcaaattt    2460
ggttgtcaac aatataaata taaataatgt ttttatatta cgaaataaca gtgatcaaaa    2520
caaacagttt tatctttatt aacaagattt tgttttttgtt tgatgacgtt ttttaatgtt    2580
tacgctttcc cccttcttttt gaatttagaa cactttatca tcataaaatc aaatactaaa    2640
aaaattacat atttcataaa taataacaca atatttttta aaaaatctga ataataatg     2700 aacaatatta catattatca cgaaaattca ttaataaaaa tattatataa ataaaatgta    2760
atagtagtta tatgtaggaa aaaagtactg cacgcataat atatacaaaa agattaaaat    2820
gaactattat aaataataac actaaattaa tggtgaatca tatcaaaata atgaaaaagt    2880
aaataaaatt tgtaattaac ttctatatgt attacacaca caaataataa ataatagtaa    2940
```

```
aaaaaattat gataaatatt taccatctca taagatattt aaaataatga taaaaatata    3000
gattattttt tatgcaacta gctagccaaa aagagaacac gggtatatat aaaaagagta    3060
cctttaaatt ctactgtact tcctttattc ctgacgtttt tatatcaagt ggacatacgt    3120
gaagatttta attatcagtc taaatatttc attagcactt aatactttc tgttttattc     3180 ctatcctata agtagtcccg attctcccaa cattgcttat tcacacaact aactaagaaa    3240
gtcttccata gccccccaag cggcccatgg cctcctccga ggacgtcatc aaggagttca    3300
tgcgcttcaa ggtgcgcatg gagggctccg tgaacggcca cgagttcgag atcgagggcg    3360
agggcgaggg ccgcccctac gagggcaccc agaccgccaa gctgaaggtg accaagggcg    3420
gccccctgcc cttcgcctgg gacatcctgt cccccagtt ccagtacggc tccaaggtgt     3480
acgtgaagca ccccgccgac atccccgact acaagaagct gtccttcccc gagggcttca    3540
agtgggagcg cgtgatgaac ttcgaggacg gcggcgtggt gaccgtgacc caggactcct    3600
ccctgcagga cggctccttc atctacaagg tgaagttcat cggcgtgaac ttcccctccg    3660
acggccccgt aatgcagaag aagactatgg gctgggaggc ctccaccgag cgcctgtacc    3720
cccgcgacgg cgtgctgaag ggcgagatcc acaaggccct gaagctgaag gacggcggcc    3780
actacctggt ggagttcaag tccatctaca tggccaagaa gcccgtgcag ctgcccggct    3840
actactacgt ggactccaag ctggacatca cctcccacaa cgaggactac accatcgtgg    3900
agcagtacga gcgcgccgag ggccgccacc acctgttcct gtagcggccg gccgcgacac    3960
aagtgtgaga gtactaaata aatgctttgg ttgtacgaaa tcattacact aaataaaata    4020
atcaaagctt atatatgcct tccgctaagg ccgaatgcaa agaaattggt tctttctcgt    4080
tatcttttgc cacttttact agtacgtatt aattactact taatcatctt tgtttacggc    4140
tcattatatc cgtcgacggc gcgccgctct agagggccca attcgcccta tagtgagtcg    4200
tattacaatt cactggccgt cgttttacaa cgtcgtgact gggaaaaccc tggcgttacc    4260
caacttaatc gccttgcagc acatcccct ttcgccagct ggcgtaatag cgaagaggcc     4320
cgcaccgatc gcccttccca acagttgcgc agcctatacg tacggcagtt taaggtttac    4380
acctataaaa gagagagccg ttatcgtctg tttgtggatg tacagagtga tattattgac    4440
acgccggggc gacggatggt gatcccccctg gccagtgcac gtctgctgtc agataaagtc   4500
tcccgtgaac tttacccggt ggtgcatatc ggggatgaaa gctggcgcat gatgaccacc    4560
gatatggcca gtgtgccggt ctccgttatc ggggaagaag tggctgatct cagccaccgc    4620
gaaaatgaca tcaaaaacgc cattaacctg atgttctggg aatataaat gtcaggcatg     4680 agattatcaa aaaggatctt cacctagatc cttttcacgt agaaagccag tccgcagaaa    4740
cggtgctgac cccggatgaa tgtcagctac tgggctatct ggacaaggga aaacgcaagc    4800
gcaaagagaa agcaggtagc ttgcagtggg cttacatggc gatagctaga ctgggcggtt    4860
ttatggacag caagcgaacc ggaattgcca gctgggcgc cctctggtaa ggttgggaag     4920
ccctgcaaag taaactggat ggctttcttg ccgccaagga tctgatggcg cagggatca     4980 agctctgatc aagagacagg atgaggatcg tttcgcatga ttgaacaaga tggattgcac    5040
gcaggttctc cggccgcttg ggtggagagg ctattcggct atgactgggc acaacagaca    5100
atcggctgct ctgatgccgc cgtgttccgg ctgtcagcgc aggggcgccc ggttcttttt    5160
gtcaagaccg acctgtccgg tgccctgaat gaactgcaag acgaggcagc gcggctatcg    5220
tggctggcca cgacgggcgt tccttgcgca gctgtgctcg acgttgtcac tgaagcggga    5280
agggactggc tgctattggg cgaagtgccg gggcaggatc tcctgtcatc tcaccttgct    5340
```

```
cctgccgaga aagtatccat catggctgat gcaatgcggc ggctgcatac gcttgatccg   5400
gctacctgcc cattcgacca ccaagcgaaa catcgcatcg agcgagcacg tactcggatg   5460
gaagccggtc ttgtcgatca ggatgatctg gacgaagagc atcaggggct cgcgccagcc   5520
gaactgttcg ccaggctcaa ggcgagcatg cccgacggcg aggatctcgt cgtgacccat   5580
ggcgatgcct gcttgccgaa tatcatggtg gaaaatggcc gcttttctgg attcatcgac   5640
tgtggccggc tgggtgtggc ggaccgctat caggacatag cgttggctac ccgtgatatt   5700
gctgaagagc ttggcggcga atgggctgac cgcttcctcg tgctttacgg tatcgccgct   5760
cccgattcgc agcgcatcgc cttctatcgc cttcttgacg agttcttctg aattattaac   5820
gcttacaatt tcctgatgcg gtattttctc cttacgcatc tgtgcggtat tcacaccgc    5880 atcaggtggc acttttcggg gaaatgtgcg cggaacccct atttgtttat ttttctaaat   5940
acattcaaat atgtatccgc tcatgagaca ataaccctga taaatgcttc aataatagca   6000
cgtgaggagg gccaccatgg ccaagttgac cagtgccgtt ccggtgctca ccgcgcgcga   6060
cgtcgccgga gcggtcgagt ctggaccga ccggctcggg ttctcccggg acttcgtgga   6120
ggacgacttc gccggtgtgg tccgggacga cgtgaccctg ttcatcagcg cggtccagga   6180
ccaggtggtg ccggacaaca ccctggcctg ggtgtgggtg cgcggcctgg acgagctgta   6240
cgccgagtgg tcggaggtcg tgtccacgaa cttccgggac gcctccgggc cggccatgac   6300
cgagatcggc gagcagccgt ggggcggga gttcgccctg cgcgacccgg ccggcaactg   6360
cgtgcacttc gtggccgagg agcaggactg acacgtgcta aaacttcatt tttaatttaa   6420
aaggatctag gtgaagatcc ttttgataa tctcatgacc aaaatccctt aacgtgagtt   6480
ttcgttccac tgagcgtcag accccgtaga aagatcaaa ggatcttctt gagatccttt   6540
ttttctgcgc gtaatctgct gcttgcaaac aaaaaaacca ccgctaccag cggtggtttg   6600
tttgccggat caagagctac caactctttt tccgaaggta actggcttca gcagagcgca   6660
gataccaaat actgttcttc tagtgtagcc gtagttaggc caccacttca agaactctgt   6720
agcaccgcct acatacctcg ctctgctaat cctgttacca gtggctgctg ccagtggcga   6780
taagtcgtgt cttaccgggt tggactcaag acgatagtta ccggataagg cgcagcggtc   6840
gggctgaacg gggggttcgt gcacacagcc cagcttggag cgaacgacct acaccgaact   6900
gagataccta cagcgtgagc tatgagaaag cgccacgctt cccgaaggga aaaggcgga   6960 caggtatccg gtaagcggca gggtcggaac aggagagcgc acgagggagc ttccagggg   7020 aaacgcctgg tatctttata gtcctgtcgg gtttcgccac ctctgacttg agcgtcgatt   7080
tttgtgatgc tcgtcagggg ggcggagcct atggaaaaac gccagcaacg cggccttttt   7140
acggttcctg gccttttgct ggccttttgc tcacatgttc tttcctgcgt tatcccctga   7200
ttctgtggat aaccgtatta ccgcctttga gtgagctgat accgctcgcc gcagccgaac   7260
gaccgagcgc agcgagtcag tgagcgagga agcggaagag cgcccaatac gcaaaccgcc   7320
tctccccgcg cgttggccga ttcattaatg cagctggcac gacaggtttc ccgactggaa   7380
agcgggcagt gagcgcaacg caattaatgt gagttagctc actcattagg caccccaggc   7440
tttacacttt atgcttccgg ctcgtatgtt gtgtggaatt gtgagcggat aacaatttca   7500
cacaggaaac agctatgacc atgattacgc caagctattt aggtgacgcg ttagaatact   7560
caagctatgc atcaagcttg gtaccgagct cggatccact agtaacggcc gccagtgtgc   7620
tggaattcag gggcgcgccc tatagatggg atgaagctgc tctcgacaaa tctgataaaa   7680
ctaaagaagg ttagtaatca attttcacaa aatcatagat tatttttttc attgaattat   7740
```

```
ttttatgcta taccaagaat tgtattttag tatttgtttt aactacatat aatagaatta    7800
actacatata aattaactaa acttaaaata aaaatagatt tgtttcctga aattatttta    7860
agaatatata tgtatatatc taaaatctta gacttagata gattttttcta tctatctatt    7920 ttggttactt aaaataaata aatttgtata ataattgta tagttatcaa aaattaaaac    7980
taattttttt aaagttgttg atatataaaa tactaaagat ttaacgatta agtatttatt    8040
taagtataga attttgtttt tttttttaagt ttagttatga agttgttaat tatattaaaa    8100
caaaacaata tttcgaaatt ttattatcat attcgaatat attttttta gtgatgatgt    8160 atgaattatt atcataattt gaaagtttac taaaaaatat atcaacatga attgtaatat    8220
atgagttatt accttaacca aaattataaa ttaacattaa ataatttat atatgtcata    8280 tttagccata caatgtgtca tcaatattaa tagtcatgtc aatattacat aatgccaata    8340
ttatgctact taaaccccaa atcccctaac tcccgttaag tagccaaatt cataaatata    8400
cttattcgac aaaataaaaa actttaaaat atttactaat ccgaccatgc acaagcatcc    8460
attccctatt ccattgccac gggataacaa tgcaaccnac tcctcaaaaa aagaaaaatt    8520
caagctcttt tgcaaaaaaa aataaaataa ttttaacacc taaaattttt tgttccaaa    8580 cttctacagg gaacacacat aaaagaaaaa gaggacgtcc actcggatca cgcaacaaac    8640
caaaaggtgt gtcatgactc ctaagatata atatttcctt attcaaaatc ataccatttt    8700
aaattatgaa tgtatttcgt agtccaccag atatgtaatc caccagcgtt caaaccaaag    8760
ttttatgatt gtaagtttaa gtgaattata ataatatatt cttcacggta tcttttcata    8820
actaattgag ttatcaaact tgatcgcaca tgtggctttg ataggtgtga cttttatggt    8880
atacaattct ttcaacctaa aaacattatt gttcctcaat atcttacatt atgcttgact    8940
gcaacaaaat atttttctcat ctgtttttctt cctttaaacc aatttattat catctatttc    9000
ctgacatttt aatccatcca cctatgtcaa aaacttatag aaaatgtcaa cttccaaaca    9060
aaacataatt gaacttcgca aataaattct taataatatt aaaaaatgtt acttaattat    9120
ttcttcaacc ccattttccg cgcgtagcgc ggacaaagac tctagttaaa tatagaagtt    9180
tccgattctc atcgtataaa acggtgactt tggcgggctt tcatgtgtaa caaattggtt    9240
taacaaacca ctgcctagtc gtttagtgta gaatcagcgc atggaactcc gattggagcg    9300
tgactttcac gtgccggagg cccaccacca cagcgggcgt tacgctctaa gaatctcgcc    9360
cacggttttc ttcatctgcc ccccgccaag tgtcttcctc gttcgccact tctcaccaag    9420
ttacaggaac cctaaaaatg gcctttcttc agccccggct ataatacaca catgatccta    9480
tagtgggttc ttccacaagt tacatctcct tctggattgt acatttcaag tgtttgtgtt    9540
ttttctgcct ctgagagaaa atcgcggccg catggctgct gctcccagtg tgaggacgtt    9600
tactcgggcc gaggttttga atgccgaggc tctgaatgag ggcaagaagg atgccgaggc    9660 accccttcttg atgatcatcg acaacaaggt gtacgatgtc cgcgagttcg tccctgatca    9720
tcccggtgga agtgtgattc tcacgcacgt tggcaaggac ggcactgacg tctttgacac    9780 ttttcaccccc gaggctgctt gggagactct tgccaacttt tacgttggtg atattgcgaa    9840
gagcgaccgc gatatcaaga atgatgactt tgcggccgag gtccgcaagc tgcgtacctt    9900
gttccagtct cttggttact acgattcttc caaggcatac tacgccttca aggtctcgtt    9960
caacctctgc atctggggtt tgtcgacggt cattgtggcc aagtggggcc agacctcgac   10020
cctcgccaac gtgctctcgg ctgcgctttt gggtctgttc tggcagcagt gcggatggtt   10080
ggctcacgac ttttttgcatc accaggtctt ccaggaccgt ttctggggtg atcttttcgg   10140
```

```
cgccttcttg ggaggtgtct gccagggctt ctcgtcctcg tggtggaagg acaagcacaa    10200
cactcaccac gccgccccca acgtccacgg cgaggatccc gacattgaca cccaccctct    10260
gttgacctgg agtgagcatg cgttggagat gttctcggat gtcccagatg aggagctgac    10320
ccgcatgtgt tcgcgtttca tggtcctgaa ccagacctgg ttttacttcc ccattctctc    10380
gtttgcccgt ctctcctggt gcctccagtc cattctcttt gtgctgccta acggtcaggc    10440
ccacaagccc tcgggcgcgc gtgtgcccat ctcgttggtc gagcagctgt cgcttgcgat    10500
gcactggacc tggtacctcg ccaccatgtt cctgttcatc aaggatcccg tcaacatgct    10560
ggtgtacttt ttggtgtcgc aggcggtgtg cggaaacttg ttggcgatcg tgttctcgct    10620
caaccacaac ggtatgcctg tgatctcgaa ggaggaggcg tcgatatgg atttcttcac     10680 gaagcagatc atcacgggtc gtgatgtcca cccgggtcta tttgccaact ggttcacggg    10740
tggattgaac tatcagatcg agcaccactt gttcccttcg atgcctcgcc acaacttttc    10800
aaagatccag cctgctgtcg agaccctgtg caaaaagtac aatgtccgat accacaccac    10860
cggtatgatc gagggaactg cagaggtctt tagccgtctg aacgaggtct ccaaggctgc    10920
ctccaagatg ggtaaggcgc agtaagc                                         10947

<210> SEQ ID NO 69
<211> LENGTH: 20742
<212> TYPE: DNA
<213> ORGANISM: Artificial sequence
<220> FEATURE:
<223> OTHER INFORMATION: Vector ARAL077
<220> FEATURE:
<221> NAME/KEY: misc_feature
<222> LOCATION: (14134)..(14134)
<223> OTHER INFORMATION: n is a, c, g, or t
<220> FEATURE:
<221> NAME/KEY: misc_feature
<222> LOCATION: (18932)..(18932)
<223> OTHER INFORMATION: n is a, c, g, or t

<400> SEQUENCE: 69
cgcgcctcga gtgggcggat cccccgggct gcaggaattc actggccgtc gttttacaac      60
gtcgtgactg ggaaaaccct ggcgttaccc aacttaatcg ccttgcagca catccccctt     120
tcgccagctg gcgtaatagc gaagaggccc gcaccgatcg cccttcccaa cagttgcgca     180
gcctgaatgg cgaatggatc gatccatcgc gatgtacctt tgttagtca gcctctcgat      240 tgctcatcgt cattacacag taccgaagtt tgatcgatct agtaacatag atgacaccgc     300
gcgcgataat ttatcctagt ttgcgcgcta tattttgttt tctatcgcgt attaaatgta     360
taattgcggg actctaatca taaaaaccca tctcataaat aacgtcatgc attacatgtt     420
aattattaca tgcttaacgt aattcaacag aaattatatg ataatcatcg caagaccggc     480
aacaggattc aatcttaaga aactttattg ccaaatgttt gaacgatctg cttcgacgca     540
ctccttcttt actccaccat ctcgtcctta ttgaaaacgt gggtagcacc aaaacgaatc     600
aagtcgctgg aactgaagtt accaatcacg ctggatgatt tgccagttgg attaatcttg     660
cctttccccg catgaataat attgatgaat gcatgcgtga gggtagttc gatgttggca     720 atagctgcaa ttgccgcgac atcctccaac gagcataatt cttcagaaaa atagcgatgt     780
tccatgttgt cagggcatgc atgatgcacg ttatgaggtg acggtgctag gcagtattcc     840
ctcaaagttt catagtcagt atcatattca tcattgcatt cctgcaagag agaattgaga     900
cgcaatccac acgctgcggc aaccttccgg cgttcgtggt ctatttgctc ttggacgttg     960
caaacgtaag tgttggatcg atccggggtg ggcgaagaac tccagcatga gatccccgcg    1020
```

```
ctggaggatc atccagccgg cgtcccggaa aacgattccg aagcccaacc tttcatagaa    1080
ggcggcggtg gaatcgaaat ctcgtgatgg caggttgggc gtcgcttggt cggtcatttc    1140 gaacccccaga gtcccgctca aagaactccg tcaagaaggc gatagaaggc gatgcgctgc   1200
gaatcgggag cggcgatacc gtaaagcacg aggaagcggt cagcccattc gccgccaagc    1260
tcttcagcaa tatcacgggt agccaacgct atgtcctgat agcggtccgc cacacccagc    1320
cggccacagt cgatgaatcc agaaaagcgg ccatttttcca ccatgatatt cggcaagcag   1380
gcatcgccat gggtcacgac gagatcctcg ccgtcgggca tgcgcgcctt gagcctggcg    1440
aacagttcgg ctggcgcgag cccctgatgc tcttcgtcca gatcatcctg atcgacaaga    1500
ccggcttcca tccgagtacg tgctcgctcg atgcgatgtt tcgcttggtg gtcgaatggg    1560
caggtagccg gatcaagcgt atgcagccgc cgcattgcat cagccatgat ggatactttc    1620
tcggcaggag caaggtgaga tgacaggaga tcctgccccg gcacttcgcc caatagcagc    1680
cagtcccttc ccgcttcagt gacaacgtcg agcacagctg cgcaaggaac gcccgtcgtg    1740
gccagccacg atagccgcgc tgcctcgtcc tgcagttcat tcagggcacc ggacaggtcg    1800
gtcttgacaa aaagaaccgg gcgccccctgc gctgacagcc ggaacacggc ggcatcagag    1860
cagccgattg tctgttgtgc ccagtcatag ccgaatagcc tctccaccca gcggccgga    1920 gaacctgcgt gcaatccatc ttgttcaatc atgcgaaacg atccccgcaa gcttggagac    1980
tggtgatttc agcgtgtcct ctccaaatga aatgaacttc cttatataga ggaagggtct    2040
tgcgaaggat agtgggattg tgcgtcatcc cttacgtcag tggagatatc acatcaatcc    2100
acttgctttg aagacgtggt tggaacgtct tcttttttcca cgatgctcct cgtgggtggg    2160
ggtccatctt tgggaccact gtcggcagag gcatcttcaa cgatggcctt tcctttatcg    2220
caatgatggc atttgtagga gccaccttcc tttttccacta tcttcacaat aaagtgacag    2280
atagctgggc aatggaatcc gaggaggttt ccggatatta cccttttgttg aaaagtctca    2340 attgcccttt ggtcttctga gactgtatct ttgatatttt tggagtagac aagcgtgtcg    2400
tgctccacca tgttgacgaa gatttttcttc ttgtcattga gtcgtaagag actctgtatg    2460
aactgttcgc cagtctttac ggcgagttct gttaggtcct ctatttgaat cttttgactcc    2520 atggcctttg attcagtggg aactaccttt ttagagactc caatctctat tacttgcctt    2580
ggtttgtgaa gcaagccttg aatcgtccat actggaatag tacttctgat cttgagaaat    2640
atatctttct ctgtgttctt gatgcagtta gtcctgaatc ttttgactgc atctttaacc    2700
ttcttgggaa ggtatttgat ctcctggaga ttattgctcg ggtagatcgt cttgatgaga    2760
cctgctgcgt aagcctctct aaccatctgt gggttagcat tctttctgaa attgaaaagg    2820
ctaatcttct cattatcagt ggtgaacatg gtatcgtcac cttctccgtc gaacttcctg    2880
actagatcgt agagatagag gaagtcgtcc attgtgatct ctggggcaaa ggagatctga    2940
attaattcga tatggtggat ttatcacaaa tgggacccgc cgccgacaga ggtgtgatgt    3000
taggccagga ctttgaaaat ttgcgcaact atcgtatagt ggccgacaaa ttgacgccga    3060
gttgacagac tgcctagcat ttgagtgaat tatgtgaggt aatgggctac actgaattgg    3120
tagctcaaac tgtcagtatt tatgtatatg agtgtatatt ttcgcataat ctcagaccaa    3180
tctgaagatg aaatgggtat ctgggaatgg cgaaatcaag gcatcgatcg tgaagtttct    3240
catctaagcc cccatttgga cgtgaatgta gacacgtcga aataaagatt tccgaattag    3300
aataatttgt ttattgcttt cgcctataaa tacgacggat cgtaatttgt cgttttatca    3360
aaatgtactt tcatttttata ataacgctgc ggacatctac atttttgaat tgaaaaaaaa    3420
```

```
ttggtaatta ctctttcttt ttctccatat tgaccatcat actcattgct gatccatgta   3480
gatttcccgg acatgaagcc atttacaatt gaatatatcc tgccgccgct gccgctttgc   3540
acccggtgga gcttgcatgt tggtttctac gcagaactga gccggttagg cagataattt   3600
ccattgagaa ctgagccatg tgcaccttcc ccccaacacg gtgagcgacg gggcaacgga   3660
gtgatccaca tgggactttt aaacatcatc cgtcggatgg cgttgcgaga gaagcagtcg   3720
atccgtgaga tcagccgacg caccgggcag gcgcgcaaca cgatcgcaaa gtatttgaac   3780
gcaggtacaa tcgagccgac gttcacgcgg aacgaccaag caagctagct ttaatgcggt   3840
agtttatcac agttaaattg ctaacgcagt caggcaccgt gtatgaaatc taacaatgcg   3900
ctcatcgtca tcctcggcac cgtcaccctg gatgctgtag gcataggctt ggttatgccg   3960
gtactgccgg gcctcttgcg ggatatcgtc cattccgaca gcatcgccag tcactatggc   4020
gtgctgctag cgctatatgc gttgatgcaa tttctatgcg cacccgttct cggagcactg   4080
tccgaccgct ttggccgccg cccagtcctg ctcgcttcgc tacttggagc cactatcgac   4140
tacgcgatca tggcgaccac accgtcctg tggtccaacc cctccgctgc tatagtgcag   4200
tcggcttctg acgttcagtg cagccgtctt ctgaaaacga catgtcgcac aagtcctaag   4260
ttacgcgaca ggctgccgcc ctgcccttt cctggcgttt tcttgtcgcg tgttttagtc   4320
gcataaagta gaatacttgc gactagaacc ggagacatta cgccatgaac aagagcgccg   4380
ccgctggcct gctgggctat gcccgcgtca gcaccgacga ccaggacttg accaaccaac   4440
gggccgaact gcacgcggcc ggctgcacca agctgttttc cgagaagatc accggcacca   4500
ggcgcgaccg cccggagctg gccaggatgc ttgaccacct acgccctggc gacgttgtga   4560
cagtgaccag gctagaccgc ctggcccgca gcacccgcga cctactggac attgccgagc   4620
gcatccagga ggcggcgcg ggcctgcgta gcctggcaga gccgtgggcc gacaccacca   4680
cgccggccgg ccgcatggtg ttgaccgtgt cgccggcat tgccgagttc gagcgttccc   4740
taatcatcga ccgcacccgg agcgggcgcg aggccgccaa ggcccgaggc gtgaagtttg   4800
gcccccgccc taccctcacc ccggcacaga tcgcgcacgc ccgcgagctg atcgaccagg   4860
aaggccgcac cgtgaaagag gcggctgcac tgcttggcgt gcatcgctcg accctgtacc   4920
gcgcacttga gcgcagcgag gaagtgacgc ccaccgaggc caggcggcgc ggtgccttcc   4980
gtgaggacgc attgaccgag gccgacgccc tggcggccgc cgagaatgaa cgccaagagg   5040
aacaagcatg aaaccgcacc aggacggcca ggacgaaccg ttttcatta ccgaagagat   5100
cgaggcggag atgatcgcgg ccgggtacgt gttcgagccg cccgcgcacg tctcaaccgt   5160
gcggctgcat gaaatcctgg ccggtttgtc tgatgccaag ctggcggcct ggccggccag   5220
cttggccgct gaagaaaccg agcgccgccg tctaaaaagg tgatgtgtat ttgagtaaaa   5280
cagcttgcgt catgcggtcg ctgcgtatat gatgcgatga gtaaataaac aaatacgcaa   5340
gggaacgcat gaagttatcg ctgtacttaa ccagaaaggc gggtcaggca agacgaccat   5400
cgcaacccat ctagcccgcg ccctgcaact cgccggggcc gatgttctgt tagtcgattc   5460
cgatccccag ggcagtgccc gcgattgggc ggccgtgcgg gaagatcaac cgctaaccgt   5520
tgtcggcatc gaccgcccga cgattgaccg cgacgtgaag gccatcggcc ggcgcgactt   5580
cgtagtgatc gacggagcgc ccaggcggc ggacttggct gtgtccgcga tcaaggcagc   5640
cgacttcgtg ctgattccgg tgcagccaag cccttacgac atatgggcca ccgccgacct   5700
ggtggagctg gttaagcagc gcattgaggt cacggatgga aggctacaag cggcctttgt   5760
cgtgtcgcgg gcgatcaaag gcacgcgcat cggcggtgag gttgccgagg cgctggccgg   5820
```

```
gtacgagctg cccattcttg agtcccgtat cacgcagcgc gtgagctacc caggcactgc    5880
cgccgccggc acaaccgttc ttgaatcaga acccgagggc gacgctgccc gcgaggtcca    5940
ggcgctggcc gctgaaatta aatcaaaact catttgagtt aatgaggtaa agagaaaatg    6000
agcaaaagca caaacacgct aagtgccggc cgtccgagcg cacgcagcag caaggctgca    6060
acgttggcca gcctggcaga cacgccagcc atgaagcggg tcaactttca gttgccggcg    6120
gaggatcaca ccaagctgaa gatgtacgcg gtacgccaag gcaagaccat taccgagctg    6180
ctatctgaat acatcgcgca gctaccagag taaatgagca aatgaataaa tgagtagatg    6240
aattttagcg gctaaaggag gcggcatgga aaatcaagaa caaccaggca ccgacgccgt    6300
ggaatgcccc atgtgtggag gaacgggcgg ttggccaggc gtaagcggct gggttgtctg    6360
ccggccctgc aatggcactg gaaccccaa gcccgaggaa tcggcgtgag cggtcgcaaa     6420
ccatccggcc cggtacaaat cggcgcggcg ctgggtgatg acctggtgga aagttgaag    6480 gccgcgcagg ccgcccagcg gcaacgcatc gaggcagaag cacgcccgg tgaatcgtgg     6540 caagcggccg ctgatcgaat ccgcaaagaa tcccggcaac cgccggcagc cggtgcgccg    6600
tcgattagga agccgcccaa gggcgacgag caaccagatt ttttcgttcc gatgctctat    6660
gacgtgggca cccgcgatag tcgcagcatc atggacgtgg ccgttttccg tctgtcgaag    6720
cgtgaccgac gagctggcga ggtgatccgc tacgagcttc cagacgggca cgtagaggtt    6780
tccgcagggc cggccggcat ggccagtgtg tgggattacg acctggtact gatggcggtt    6840
tcccatctaa ccgaatccat gaaccgatac cgggaaggga agggagacaa gcccggccgc    6900
gtgttccgtc cacacgttgc ggacgtactc aagttctgcc ggcgagccga tggcggaaag    6960
cagaaagacg acctggtaga aacctgcatt cggttaaaca ccacgcacgt tgccatgcag    7020
cgtacgaaga aggccaagaa cggccgcctg gtgacggtat ccgagggtga agccttgatt    7080
agccgctaca agatcgtaaa gagcgaaacc gggcggccgg agtacatcga gatcgagcta    7140
gctgattgga tgtaccgcga gatcacagaa ggcaagaacc cggacgtgct gacggttcac    7200
cccgattact ttttgatcga tcccggcatc ggccgttttc tctaccgcct ggcacgccgc    7260
gccgcaggca aggcagaagc cagatggttg ttcaagacga tctacgaacg cagtggcagc    7320
gccggagagt tcaagaagtt ctgtttcacc gtgcgcaagc tgatcgggtc aaatgacctg    7380
ccggagtacg atttgaagga ggaggcgggg caggctggcc cgatcctagt catgcgctac    7440
cgcaacctga tcgagggcga agcatccgcc ggttcctaat gtacggagca gatgctaggg    7500
caaattgccc tagcagggga aaaaggtcga aaggtctct ttcctgtgga tagcacgtac     7560
attgggaacc caaagccgta cattgggaac cggaacccgt acattgggaa cccaaagccg    7620
tacattggga accggtcaca catgtaagtg actgatataa aagagaaaaa aggcgatttt    7680
tccgcctaaa actctttaaa acttattaaa actcttaaaa cccgcctggc ctgtgcataa    7740
ctgtctggcc agcgcacagc cgaagagctg caaaaagcgc ctacccttcg gtcgctgcgc    7800
tccctacgcc ccgccgcttc gcgtcggcct atcgcggccg ctggccgctc aaaaatggct    7860
ggcctacggc caggcaatct accagggcgc ggacaagccg cgccgtcgcc actcgaccgc    7920
cggcgcccac atcaaggcac cctgcctcgc gcgtttcggt gatgacggtg aaaacctctg    7980
acacatgcag ctcccggaga cggtcacagc ttgtctgtaa gcggatgccg ggagcagaca    8040
agcccgtcag ggcgcgtcag cgggtgttgg cgggtgtcgg ggcgcagcca tgacccagtc    8100
acgtagcgat agcggagtgt atactggctt aactatgcgg catcagagca gattgtactg    8160
agagtgcacc atatgcggtg tgaaataccg cacagatgcg taaggagaaa ataccgcatc    8220
```

```
aggcgctctt ccgcttcctc gctcactgac tcgctgcgct cggtcgttcg gctgcggcga   8280
gcggtatcag ctcactcaaa ggcggtaata cggttatcca cagaatcagg ggataacgca   8340
ggaaagaaca tgtgagcaaa aggccagcaa aaggccagga accgtaaaaa ggccgcgttg   8400
ctggcgtttt tccataggct ccgcccccct gacgagcatc acaaaaatcg acgctcaagt   8460
cagaggtggc gaaacccgac aggactataa agataccagg cgtttccccc tggaagctcc   8520
ctcgtgcgct ctcctgttcc gaccctgccg cttaccggat acctgtccgc ctttctccct   8580
tcgggaagcg tggcgctttc tcatagctca cgctgtaggt atctcagttc ggtgtaggtc   8640
gttcgctcca agctgggctg tgtgcacgaa ccccccgttc agcccgaccg ctgcgcctta   8700
tccggtaact atcgtcttga gtccaacccg gtaagacacg acttatcgcc actggcagca   8760
gccactggta acaggattag cagagcgagg tatgtaggcg gtgctacaga gttcttgaag   8820
tggtggccta actacggcta cactagaagg acagtatttg gtatctgcgc tctgctgaag   8880
ccagttacct tcggaaaaag agttggtagc tcttgatccg gcaaacaaac caccgctggt   8940
agcggtggtt tttttgtttg caagcagcag attacgcgca gaaaaaaagg atctcaagaa   9000
gatcctttga tcttttctac ggggtctgac gctcagtgga acgaaaactc acgttaaggg   9060
attttggtca tgagattatc aaaaaggatc ttcacctaga tccttttaaa ttaaaaatga   9120
agttttaaat caatctaaag tatatatgag taaacttggt ctgacagtta ccaatgctta   9180
atcagtgagg cacctatctc agcgatctgt ctatttcgtt catccatagt tgcctgactc   9240
cccgtcgtgt agataactac gatacgggag ggcttaccat ctggccccag tgctgcaatg   9300
ataccgcgag acccacgctc accggctcca gatttatcag caataaacca gccagccgga   9360
agggccgagc gcagaagtgg tcctgcaact ttatccgcct ccatccagtc tattaattgt   9420
tgccgggaag ctagagtaag tagttcgcca gttaatagtt tgcgcaacgt tgttgccatt   9480
gctacaggca tcgtggtgtc acgctcgtcg tttggtatgg cttcattcag ctccggttcc   9540
caacgatcaa ggcgagttac atgatccccc atgttgtgca aaaaagcggt tagctccttc   9600
ggtcctccga tcgttgtcag aagtaagttg gccgcagtgt tatcactcat ggttatggca   9660
gcactgcata attctcttac tgtcatgcca tccgtaagat gcttttctgt gactggtgag   9720
tactcaacca agtcattctg agaatagtgt atgcggcgac cgagttgctc ttgcccggcg   9780
tcaacacggg ataataccgc gccacatagc agaactttaa aagtgctcat cattggaaaa   9840
gacctgcagg ggggggggg cgctgaggtc tgcctcgtga agaaggtgtt gctgactcat   9900
accaggcctg aatcgcccca tcatccagcc agaaagtgag ggagccacgg ttgatgagag   9960
ctttgttgta ggtggaccag ttggtgattt tgaacttttg ctttgccacg gaacggtctg  10020
cgttgtcggg aagatgcgtg atctgatcct tcaactcagc aaaagttcga tttattcaac  10080
aaagccgccg tcccgtcaag tcagcgtaat gctctgccag tgttacaacc aattaaccaa  10140
ttctgattag aaaaactcat cgagcatcaa atgaaactgc aatttattca tcaggatt   10200
atcaatacca tatttttgaa aaagccgttt ctgtaatgaa ggagaaaact caccgaggca  10260
gttccatagg atggcaagat cctggtatcg gtctgcgatt ccgactcgtc aacatcaat   10320
acaacctatt aatttcccct cgtcaaaaat aaggttatca agtgagaaat caccatgagt  10380
gacgactgaa tccggtgaga atggcaaaag cttatgcatt tctttccaga cttgttcaac  10440
aggccagcca ttacgctcgt catcaaaatc actcgcatca accaaaccgt tattcattcg  10500
tgattgcgcc tgagcgagac gaaatacgcg atcgctgtta aaaggacaat acaaacagg   10560
aatcgaatgc aaccggcgca ggaacactgc cagcgcatca acaatatttt cacctgaatc  10620
```

```
aggatattct tctaataacct ggaatgctgt tttcccgggg atcgcagtgg tgagtaacca   10680
tgcatcatca ggagtacgga taaaatgctt gatggtcgga agaggcataa attccgtcag   10740
ccagtttagt ctgaccatct catctgtaac atcattggca acgctacctt tgccatgttt   10800
cagaaacaac tctggcgcat cgggcttccc atacaatcga tagattgtcg cacctgattg   10860
cccgacatta tcgcgagccc atttataccc atataaatca gcatccatgt tggaatttaa   10920
tcgcggcctc gagcaagacg tttcccgttg aatatggctc ataacacccc ttgtattact   10980
gtttatgtaa gcagacagtt ttattgttca tgatgatata tttttatctt gtgcaatgta   11040
acatcagaga ttttgagaca caacgtggct ttccccccccc cccctgcagg tcaattcggt   11100
cgatatggct attacgaaga aggctcgtgc gcggagtccc gtgaactttc ccacgcaaca   11160
agtgaaccgc accgggtttg ccggaggcca tttcgttaaa atgcgcagcc atggctgctt   11220
cgtccagcat ggcgtaatac tgatcctcgt cttcggctgg cggtatattg ccgatgggct   11280
tcaaaagccg ccgtggttga accagtctat ccattccaag gtagcgaact cgaccgcttc   11340
gaagctcctc catggtccac gccgatgaat gacctcggcc ttgtaaagac cgttgatcgc   11400
ttctgcgagg gcgttgtcgt gctgtcgccg acgcttccga tagatggctc gatacctgct   11460
tctgccaacc gctcggaata gcgaaaggac acgtattgaa caccgcgatc cgagtgatgc   11520
actaggccgc catgagcggg acgccgatca tgatgagcct cctcgagggc atcgaggaca   11580
aagcctgcat gtgctgtccg gctcgcccgc catccgacaa tgcgacgggc gaagacgtcg   11640
atcacgaagg ccacgtagac gaagccctcc aagtggcga cataagtacg gacatgcgca   11700
aaggctttcc cggtttgtcg ctgatggtgc aagagacgct gaagcgcgat ccgatgcgca   11760
ggcatctgtt cgtcttccgc ggtcgtggcg gtggcctgat caaggtcact cgccgaagag   11820
ctgcatgatt ggctcgaaac cgagcggggg aaattgtcgc gcagttctcc cgtcgccgag   11880
gcgataaatt acatgctcaa gcgatgggat ggcattacgt cattcctcga tgacggcccg   11940
atttgcctga cgaacaatgc tgccgaacga acgctcagag gctatgtact cggcaggaag   12000
tcatggctgt ttgccggatc ggatcgttgt gctgaacgtg cggcgttcat ggcgacactg   12060
atcatgagcg ccaagctcaa taacatcgat ccgcaggcct ggcttgccga cgtccgcgcc   12120
gaccttgcgg acgctccgat cagcaggctt gagcaacagc tgccgtggaa ctggacatcc   12180
aagacactga gtgctcaggc ggcctgacct gcggccttca ccggatactt acccccattat   12240 cgcagattgc gatgaagcat cagcgtcatt cagcaatctt gccaaagtat gcaggctcgc   12300
gagaatcgac gtgcgaaacc ggctggttgc gccaaagatc cgcttgcgga gcggtcgaac   12360
attcatgctg ggacttcaag aggtcgagta gaggaagaac cggaaaggtt gcaccggaaa   12420
atatgcgttc ctttggagag cgcctcatgg acgtgaacaa atcgcccgga ccaaggatgc   12480
cacggataca aaagctcgcg aagctcggtc ccgtgggtgt tctgtcgtct cgttgtacaa   12540
cgaaatccat tcccattccg cgctcaagat ggcttcccct cggcagttca tcagggctaa   12600
atcaatctag ccgacttgtc cggtgaaatg gctgcactc caacagaaac aatcaaacaa   12660
acatacacag cgacttattc acacgagctc aaattacaac ggtatatatc ctgccagtca   12720
gcatcatcac accaaaagtt aggcccgaat agtttgaaat tagaaagctc gcaattgagg   12780
tctacaggcc aaattcgctc ttagccgtac aatattactc accggtgcga tgcccccat    12840 cgtaggtgaa ggtggaaatt aatgatccat cttgagacca caggcccaca acagctacca   12900
gtttcctcaa gggtccacca aaaacgtaag cgcttacgta catggtcgat aagaaaaggc   12960
aatttgtaga tgttaacatc caacgtcgct ttcagggatc gatccaatac gcaaaccgcc   13020
```

```
tctccccgcg cgttggccga ttcattaatg cagctggcac gacaggtttc ccgactggaa   13080
agcgggcagt gagcgcaacg caattaatgt gagttagctc actcattagg cacccaggc    13140 tttacacttt atgcttccgg ctcgtatgtt gtgtggaatt gtgagcggat aacaatttca   13200
cacaggaaac agctatgacc atgattacgc caagcttgca tgcctgcagg tcgactctag   13260
aggatctggc gcgccctata gatgggatga gctgctctc gacaaatctg ataaaactaa    13320
agaaggttag taatcaattt ttacaaaatc atagattatt tttttcattg aattattttt   13380
atgctatacc aagaattgta ttttagtatt tgttttaact acatataata gaattaacta   13440
catataaatt aactaaactt aaaataaaaa tagatttgtt tcctgaaatt attttaagaa   13500
tatatatgta tatatctaaa atcttagact tagatagatt tttctatcta tctattttgg   13560
ttacttaaaa taaataaatt tgtataaata attgtatagt tatcaaaaat taaaactaat   13620 tttttttaaag ttgttgatat ataaaatact aaagatttaa cgattaagta tttatttaag  13680
tatagaattt tgttttttttt ttaagtttag ttatgaagtt gttaattata ttaaaacaaa  13740
acaatatttc gaaattttat tatcatattc gaatatattt tttttagtga tgatgtatga   13800
attattatca taatttgaaa gtttactaaa aaatatatca acatgaattg taatatatga   13860
gttattacct taaccaaaat tataaattaa cattaaatat aattatatat gtcatattta   13920
gccatacaat gtgtcatcaa tattaatagt catgtcaata ttacataatg ccaatattat   13980
gctacttaaa ccccaaatcc cctaactccc gttaagtagc caaattcata aatatactta   14040
ttcgacaaaa taaaaaactt taaaatattt actaatccga ccatgcacaa gcatccattc   14100
cctattccat tgccacggga taacaatgca accnactcct caaaaaaaga aaaattcaag   14160
ctcttttgca aaaaaaaata aaataatttt aacacctaaa attttttgtt tccaaacttc   14220
tacagggaac acacataaaa gaaaagagg acgtccactc ggatcacgca acaaaccaaa    14280
aggtgtgtca tgactcctaa gatataatat ttccttattc aaaatcatac cattttaaat   14340
tatgaatgta tttcgtagtc caccagatat gtaatccacc agcgttcaaa ccaaagtttt   14400
atgattgtaa gtttaagtga attataataa tatattcttc acggtatctt ttcataacta   14460
attgagttat caaacttgat cgcacatgtg gctttgatag gtgtgacttt tatggtatac   14520
aattctttca acctaaaaac attattgttc ctcaatatct tacattatgc ttgactgcaa   14580
caaaatattt tctcatctgt tttcttcctt taaaccaatt tattatcatc tatttcctga   14640
cattttaatc catccaccta tgtcaaaaac ttatagaaaa tgtcaacttc caaacaaaac   14700
ataattgaac ttcgcaaata aattcttaat aatattaaaa aatgttactt aattatttct   14760
tcaaccccat tttccgcgcg tagcgcggac aaagactcta gttaaatata aagtttccg    14820 attctcatcg tataaaacgg tgactttggc gggctttcat gtgtaacaaa ttggtttaac   14880
aaaccactgc ctagtcgttt agtgtagaat cagcgcatgg aactccgatt ggagcgtgac   14940
tttcacgtgc cggaggccca ccaccacagc gggcgttacg ctctaagaat ctcgcccacg   15000
gttttcttca tctgccccc gccaagtgtc ttcctcgttc gccacttctc accaagttac    15060 aggaaccta aaaatggcct tcttcagcc ccggctataa tacacacatg atcctatagt     15120
gggttcttcc acaagttaca tctccttctg gattgtacat ttcaagtgtt tgtgtttttt   15180
ctgcctctga gagaaaatcg cggccgcatg gctgctgctc ccagtgtgag gacgtttact   15240
cgggccgagg ttttgaatgc cgaggctctg aatgagggca agaaggatgc cgaggcaccc   15300
ttcttgatga tcatcgacaa caaggtgtac gatgtccgcg agttcgtccc tgatcatccc   15360
ggtggaagtg tgattctcac gcacgttggc aaggacggca ctgacgtctt tgacactttt   15420
```

```
caccccgagg ctgcttggga gactcttgcc aacttttacg ttggtgatat tgacgagagc    15480
gaccgcgata tcaagaatga tgactttgcg gccgaggtcc gcaagctgcg taccttgttc    15540
cagtctcttg gttactacga ttcttccaag gcatactacg ccttcaaggt ctcgttcaac    15600
ctctgcatct ggggtttgtc gacggtcatt gtggccaagt ggggccagac ctcgaccctc    15660
gccaacgtgc tctcggctgc gcttttgggt ctgttctggc agcagtgcgg atggttggct    15720
cacgactttt tgcatcacca ggtcttccag gaccgtttct ggggtgatct tttcggcgcc    15780
ttcttgggag gtgtctgcca gggcttctcg tcctcgtggt ggaaggacaa gcacaacact    15840
caccacgccg cccccaacgt ccacggcgag gatcccgaca ttgacaccca ccctctgttg    15900
acctggagtg agcatgcgtt ggagatgttc tcggatgtcc cagatgagga gctgacccgc    15960
atgtggtcgc gtttcatggt cctgaaccag acctggtttt acttccccat tctctcgttt    16020
gcccgtctct cctggtgcct ccagtccatt ctctttgtgc tgcctaacgg tcaggcccac    16080 aagcctcgg gcgcgcgtgt gcccatctcg ttggtcgagc agctgtcgct tgcgatgcac    16140
tggacctggt acctcgccac catgttcctg ttcatcaagg atcccgtcaa catgctggtg    16200 tacttttttgg tgtcgcaggc ggtgtgcgga aacttgttgg cgatcgtgtt ctcgctcaac    16260
cacaacggta tgcctgtgat ctcgaaggag gaggcggtcg atatggattt cttcacgaag    16320
cagatcatca cgggtcgtga tgtccacccg ggtctatttg ccaactggtt cacgggtgga    16380
ttgaactatc agatcgagca ccacttgttc ccttcgatgc ctcgccacaa cttttcaaag    16440
atccagcctg ctgtcgagac cctgtgcaaa aagtacaatg tccgatacca caccaccggt    16500
atgatcgagg gaactgcaga ggtctttagc cgtctgaacg aggtctccaa ggctgcctcc    16560
aagatgggta aggcgcagta agcggccgca agtatgaact aaaatgcatg taggtgtaag    16620
agctcatgga gagcatggaa tattgtatcc gaccatgtaa cagtataata actgagctcc    16680
atctcacttc ttctatgaat aaacaaagga tgttatgata tattaacact ctatctatgc    16740
accttattgt tctatgataa atttcctctt attattataa atcatctgaa tcgtgacggc    16800
ttatggaatg cttcaaatag tacaaaaaca aatgtgtact ataagacttt ctaaacaatt    16860
ctaaccttag cattgtgaac gagacataag tgttaagaag acataacaat tataatggaa    16920
gaagtttgtc tccatttata tattatatat tacccactta tgtattatat taggatgtta    16980
aggagacata acaattataa agagagaagt ttgtatccat ttatatatta tatactaccc    17040
atttatatat tatacttatc cacttattta atgtctttat aaggtttgat ccatgatatt    17100
tctaatattt tagttgatat gtatatgaaa gggtactatt tgaactctct tactctgtat    17160
aaaggttgga tcatccttaa agtgggtcta tttaattttta ttgcttctta cagataaaaa    17220
aaaaattatg agttggtttg ataaaatatt gaaggattta aataataat aaataacata    17280 taatatatgt atataaattt attataatat aacatttatc tataaaaag taaatattgt    17340 cataaatcta tacaatcgtt tagccttgct ggacgaatct caattattta aacgagagta    17400
aacatatttg acttttggt tatttaacaa attattattt aacactatat gaaattttt    17460 tttttatcag caaagaataa aattaaatta agaaggacaa tggtgtccca atccttatac    17520
aaccaacttc cacaagaaag tcaagtcaga gacaacaaaa aacaagcaa aggaaattt    17580 ttaatttgag ttgtcttgtt tgctgcataa tttatgcagt aaaacactac acataaccct    17640
tttagcagta gagcaatggt tgaccgtgtg cttagcttct tttattttat ttttttatca    17700
gcaaagaata aataaaataa aatgagacac ttcagggatg tttcaacaag cttggatcct    17760
cgaagagaag ggttaataac acactttttt aacattttta acacaaattt tagttattta    17820
```

```
aaaatttatt aaaaaattta aaataagaag aggaactctt taaataaatc taacttacaa    17880
aatttatgat ttttaataag ttttcaccaa taaaaaatgt cataaaaata tgttaaaaag    17940
tatattatca atattctctt tatgataaat aaaagaaaa  aaaaaataaa agttaagtga    18000
aaatgagatt gaagtgactt taggtgtgta taaatatatc aaccccgcca acaatttatt    18060
taatccaaat atattgaagt atattattcc atagccttta tttatttata tatttattat    18120
ataaaagctt tatttgttct aggttgttca tgaaatattt ttttggtttt atctccgttg    18180
taagaaaatc atgtgctttg tgtcgccact cactattgca gcttttcat  gcattggtca    18240 gattgacggt tgattgtatt tttgttttt  atggttttgt gttatgactt aagtcttcat    18300
ctctttatct cttcatcagg tttgatggtt acctaatatg gtccatgggt acatgcatgg    18360
ttaaattagg tggccaactt tgttgtgaac gatagaattt tttttatatt aagtaaaacta   18420 tttttatatt atgaaataat aataaaaaaa atattttatc attattaaca aaatcatatt    18480
agttaatttg ttaactctat aataaaagaa atactgtaac attcacatta catggtaaca    18540
tctttccacc ctttcatttg ttttttgttt gatgacttt  ttcttgttt aaatttattt    18600 cccttctttt aaatttggaa tacattatca tcatatataa actaaaatac taaaaacagg    18660
attacacaaa tgataaataa taacacaaat atttataaat ctagctgcaa tatatttaaa    18720
ctagctatat cgatattgta aaataaaact agctgcattg atactgataa aaaaatatca    18780
tgtgctttct ggactgatga tgcagtatac ttttgacatt gcctttattt tattttttcag   18840 aaaagctttc ttagttctgg gttcttcatt atttgtttcc catctccatt gtgaattgaa    18900
tcatttgctt cgtgtcacaa atacaattta gntaggtaca tgcattggtc agattcacgg    18960
tttattatgt catgacttaa gttcatggta gtacattacc tgccacgcat gcattatatt    19020
ggttagattt gataggcaaa tttggttgtc aacaatataa atataaataa tgttttata    19080 ttacgaaata acagtgatca aaacaaacag ttttatcttt attaacaaga ttttgttttt    19140
gtttgatgac gttttttaat gtttacgctt tccccttct  tttgaattta gaacactta    19200 tcatcataaa atcaaatact aaaaaaatta catatttcat aaataataac acaaatattt    19260
ttaaaaaatc tgaaataata atgaacaata ttacatatta tcacgaaaat tcattaataa    19320
aaatattata taaataaat  gtaatagtag ttatatgtag gaaaaaagta ctgcacgcat    19380
aatatataca aaaagattaa aatgaactat tataaataat aacactaaat taatggtgaa    19440
tcatatcaaa ataatgaaaa agtaaataaa atttgtaatt aacttctata tgtattacac    19500
acacaaataa taaataatag taaaaaaaat tatgataaat atttaccatc tcataagata    19560
tttaaaataa tgataaaaat atagattatt ttttatgcaa ctagctagcc aaaaagagaa    19620
cacgggtata tataaaaaga gtacctttaa attctactgt acttcctta  ttcctgacgt    19680 ttttatatca agtggacata cgtgaagatt ttaattatca gtctaaatat ttcattagca    19740
cttaatactt ttctgtttta ttcctatcct ataagtagtc ccgattctcc caacattgct    19800
tattcacaca actaactaag aaagtcttcc atagccccc  aagcggccca tggcctcctc    19860
cgaggacgtc atcaaggagt tcatgcgctt caaggtgcgc atggagggct ccgtgaacgg    19920
ccacgagttc gagatcgagg gcgagggcga gggccgcccc tacgagggca cccagaccgc    19980
caagctgaag gtgaccaagg gcggcccct  gcccttcgcc tgggacatcc tgtcccccca    20040
gttccagtac ggctccaagg tgtacgtgaa gcaccccgcc gacatccccg actacaagaa    20100
gctgtccttc cccgagggct tcaagtggga gcgcgtgatg aacttcgagg acggcggcgt    20160
ggtgaccgtg acccaggact cctccctgca ggacggctcc ttcatctaca aggtgaagtt    20220
```

```
catcggcgtg aacttcccct ccgacggccc cgtaatgcag aagaagacta tgggctggga    20280
ggcctccacc gagcgcctgt accccgcgca cggcgtgctg aagggcgaga tccacaaggc    20340
cctgaagctg aaggacggcg gccactacct ggtggagttc aagtccatct acatggccaa    20400
gaagcccgtg cagctgcccg gctactacta cgtggactcc aagctggaca tcacctccca    20460
caacgaggac tacaccatcg tggagcagta cgagcgcgcc gagggccgcc accacctgtt    20520
cctgtagcgg ccgccgcgca cacaagtgtg agagtactaa ataaatgctt tggttgtacg    20580
aaatcattac actaaataaa ataatcaaag cttatatatg ccttccgcta aggccgaatg    20640
caaagaaatt ggttctttct cgttatcttt tgccacttt actagtacgt attaattact    20700
acttaatcat ctttgtttac ggctcattat atccgtcgac gg                      20742

<210> SEQ ID NO 70
<211> LENGTH: 10758
<212> TYPE: DNA
<213> ORGANISM: Artificial sequence
<220> FEATURE:
<223> OTHER INFORMATION: Vector KS431
<220> FEATURE:
<221> NAME/KEY: misc_feature
<222> LOCATION: (2349)..(2349)
<223> OTHER INFORMATION: n is a, c, g, or t
<220> FEATURE:
<221> NAME/KEY: misc_feature
<222> LOCATION: (8498)..(8498)
<223> OTHER INFORMATION: n is a, c, g, or t

<400> SEQUENCE: 70
ggccgcaagt atgaactaaa atgcatgtag gtgtaagagc tcatggagag catggaatat      60
tgtatccgac catgtaacag tataataact gagctccatc tcacttcttc tatgaataaa     120
caaaggatgt tatgatatat taacactcta tctatgcacc ttattgttct atgataaatt     180
tcctcttatt attataaatc atctgaatcg tgacggctta tggaatgctt caaatagtac     240
aaaaacaaat gtgtactata agactttcta aacaattcta accttagcat tgtgaacgag     300
acataagtgt taagaagaca taacaattat aatggaagaa gtttgtctcc atttatatat     360
tatatattac ccactatgt attatattag gatgttaagg agacataaca attataaaga     420
gagaagtttg tatccattta tatattatat actacccatt tatatattat acttatccac     480
ttatttaatg tctttataag gtttgatcca tgatatttct aatatttag ttgatatgta     540 tatgaaaggg tactatttga actctcttac tctgtataaa ggttggatca tccttaaagt     600
gggtctattt aattttattg cttccttacag ataaaaaaaa aattatgagt tggtttgata     660
aaatattgaa ggatttaaaa taataataaa taacatataa tatatgtata taaatttatt     720
ataatataac atttatctat aaaaaagtaa atattgtcat aaatctatac aatcgtttag     780
ccttgctgga cgaatctcaa ttatttaaac gagagtaaac atatttgact ttttggttat     840
ttaacaaatt attatttaac actatatgaa attttttttt ttatcagcaa agaataaaat     900
taaattaaga aggacaatgg tgtcccaatc cttatacaac caacttccac aagaaagtca     960
agtcagagac aacaaaaaaa caagcaaagg aaatttttta atttgagttg tcttgtttgc    1020
tgcataattt atgcagtaaa acactacaca taacccttt agcagtagag caatggttga    1080
ccgtgtgctt agcttctttt attttatttt tttatcagca aagaataaat aaaataaaat    1140
gagacacttc agggatgttt caacaagctt ggatcctcga agagaagggt taataacaca    1200
cttttttaac atttttaaca caaattttag ttatttaaaa atttattaaa aaattttaaaa    1260 taagaagagg aactctttaa ataaatctaa cttacaaaat ttatgatttt taataagttt    1320
```

```
tcaccaataa aaaatgtcat aaaaatatgt taaaaagtat attatcaata ttctctttat    1380
gataaataaa aagaaaaaaa aaataaaagt taagtgaaaa tgagattgaa gtgactttag    1440
gtgtgtataa atatatcaac cccgccaaca atttatttaa tccaaatata ttgaagtata    1500
ttattccata gcctttafft atttatatat ttattatata aaagctttat ttgttctagg    1560
ttgttcatga aatattttff tggttttatc tccgttgtaa gaaatcatg tgctttgtgt     1620 cgccactcac tattgcagct ttttcatgca ttggtcagat tgacggttga ttgtattttt    1680
gttttttatg gttttgtgtt atgacttaag tcttcatctc tttatctctt catcaggttt    1740
gatggttacc taatatggtc catgggtaca tgcatggtta aattaggtgg ccaactttgt    1800
tgtgaacgat agaattfttt ttatattaag taaactattt ttatattatg aaataataat    1860
aaaaaaaata ttttatcatt attaacaaaa tcatattagt taatttgtta actctataat    1920
aaaagaaata ctgtaacatt cacattacat ggtaacatct ttccaccctt tcatttgttt    1980
tttgtttgat gacttttttt cttgtttaaa tttattfccc ttcttttaaa tttggaatac    2040
attatcatca tatataaact aaaatactaa aaacaggatt acacaaatga taaataataa    2100
cacaaatatt tataaatcta gctgcaatat atttaaacta gctatatcga tattgtaaaa    2160
taaaactagc tgcattgata ctgataaaaa aatatcatgt gctttctgga ctgatgatgc    2220
agtatacttt tgacattgcc tttattttat ttttcagaaa agctttctta gttctgggtt    2280
cttcattatt tgtttcccat ctccattgtg aattgaatca tttgcttcgt gtcacaaata    2340
caatttagnt aggtacatgc attggtcaga ttcacggttt attatgtcat gacttaagtt    2400
catggtagta cattacctgc cacgcatgca ttatattggt tagatttgat aggcaaattt    2460
ggttgtcaac aatataaata taaataatgt ttttatatta cgaaataaca gtgatcaaaa    2520
caaacagttt tatcttfatt aacaagattt tgttffltgtt tgatgacgtt ttttaatgtt    2580
tacgctttcc cccttctttt gaatttagaa cactttatca tcataaaatc aaatactaaa    2640
aaaattacat atttcataaa taataacaca aatatttfta aaaaatctga ataataatg     2700 aacaatatta catattatca cgaaaattca ttaataaaaa tattatataa ataaaatgta    2760
atagtagtta tatgtaggaa aaaagtactg cacgcataat atatacaaaa agattaaaat    2820
gaactattat aaataataac actaaattaa tggtgaatca tatcaaaata atgaaaaagt    2880
aaataaaatt tgtaattaac ttctatatgt attacacaca caaataataa ataatagtaa    2940
aaaaaattat gataaatatt taccatctca taagatattt aaaataatga taaaaatata    3000
gattattttt tatgcaacta gctagccaaa aagagaacac gggtatatat aaaaagagta    3060
cctttaaatt ctactgtact tcctttattc ctgacgtttt tatatcaagt ggacatacgt    3120
gaagatttta attatcagtc taaatatttc attagcactt aatactttc tgttttattc     3180 ctatcctata agtagtcccg attctcccaa cattgcttat tcacacaact aactaagaaa    3240
gtcttccata gcccccaag cggcccatgg cctcctccga ggacgtcatc aaggagttca    3300
tgcgcttcaa ggtgcgcatg gagggctccg tgaacggcca cgagttcgag atcgagggcg    3360
agggcgaggg ccgcccctac gagggcaccc agaccgccaa gctgaaggtg accaagggcg    3420
gccccctgcc cttcgcctgg gacatcctgt cccccagtt ccagtacggc tccaaggtgt     3480
acgtgaagca ccccgccgac atccccgact acaagaagct gtccttcccc gagggcttca    3540
agtgggagcg cgtgatgaac ttcgaggacg gcggcgtggt gaccgtgacc caggactcct    3600
ccctgcagga cggctccttc atctacaagg tgaagttcat cggcgtgaac ttcccctccg    3660
acggccccgt aatgcagaag aagactatgg gctgggaggc ctccaccgag cgcctgtacc    3720
```

```
cccgcgacgg cgtgctgaag ggcgagatcc acaaggccct gaagctgaag gacggcggcc   3780
actacctggt ggagttcaag tccatctaca tggccaagaa gcccgtgcag ctgcccggct   3840
actactacgt ggactccaag ctggacatca cctcccacaa cgaggactac accatcgtgg   3900
agcagtacga gcgcgccgag ggccgccacc acctgttcct gtagcggccg ccgcgacac    3960 aagtgtgaga gtactaaata aatgctttgg ttgtacgaaa tcattacact aaataaaata   4020
atcaaagctt atatatgcct tccgctaagg ccgaatgcaa agaaattggt tctttctcgt   4080
tatcttttgc cacttttact agtacgtatt aattactact taatcatctt tgtttacggc   4140
tcattatatc cgtcgacggc gcgccgctct agagggccca attcgcccta tagtgagtcg   4200
tattacaatt cactggccgt cgttttacaa cgtcgtgact gggaaaaccc tggcgttacc   4260
caacttaatc gccttgcagc acatccccct ttcgccagct ggcgtaatag cgaagaggcc   4320
cgcaccgatc gcccttccca acagttgcgc agcctatacg tacggcagtt taaggtttac   4380
acctataaaa gagagagccg ttatcgtctg tttgtggatg tacagagtga tattattgac   4440
acgccggggc gacggatggt gatcccctg ccagtgcac gtctgctgtc agataaagtc    4500
tcccgtgaac tttacccggt ggtgcatatc ggggatgaaa gctggcgcat gatgaccacc   4560
gatatggcca gtgtgccggt ctccgttatc ggggaagaag tggctgatct cagccaccgc   4620
gaaaatgaca tcaaaaacgc cattaacctg atgttctggg aatataaat gtcaggcatg   4680 agattatcaa aaaggatctt cacctagatc cttttcacgt agaaagccag tccgcagaaa   4740
cggtgctgac cccggatgaa tgtcagctac tgggctatct ggacaaggga aaacgcaagc   4800
gcaaagagaa agcaggtagc ttgcagtggg cttacatggc gatagctaga ctgggcggtt   4860
ttatggacag caagcgaacc ggaattgcca gctgggcgc cctctggtaa ggttgggaag    4920
ccctgcaaag taaactggat ggctttcttg ccgccaagga tctgatggcg cagggatca    4980 agctctgatc aagagacagg atgaggatcg tttcgcatga ttgaacaaga tggattgcac   5040
gcaggttctc cggccgcttg ggtggagagg ctattcggct atgactgggc acaacagaca   5100
atcggctgct ctgatgccgc cgtgttccgg ctgtcagcgc aggggcgccc ggttcttttt   5160
gtcaagaccg acctgtccgg tgccctgaat gaactgcaag acgaggcagc gcggctatcg   5220
tggctggcca cgacgggcgt tccttgcgca gctgtgctcg acgttgtcac tgaagcggga   5280
agggactggc tgctattggg cgaagtgccg gggcaggatc tcctgtcatc tcaccttgct   5340
cctgccgaga agtatccat catggctgat gcaatgcggc ggctgcatac gcttgatccg    5400
gctacctgcc cattcgacca ccaagcgaaa catcgcatcg agcgagcacg tactcggatg   5460
gaagccggtc ttgtcgatca ggatgatctg gacgaagagc atcagggct cgcgccagcc    5520 gaactgttcg ccaggctcaa ggcgagcatg cccgacggcg aggatctcgt cgtgacccat   5580
ggcgatgcct gcttgccgaa tatcatggtg aaaatggcc gcttttctgg attcatcgac    5640
tgtggccggc tgggtgtggc ggaccgctat caggacatag cgttggctac ccgtgatatt   5700
gctgaagagc ttggcggcga atgggctgac cgcttcctcg tgctttacgg tatcgccgct   5760
cccgattcgc agcgcatcgc cttctatcgc cttcttgacg agttcttctg aattattaac   5820
gcttacaatt tcctgatgcg gtattttctc cttacgcatc tgtgcggtat tcacaccgc    5880 atcaggtggc acttttcggg gaaatgtgcg cggaacccct atttgtttat ttttctaaat   5940
acattcaaat atgtatccgc tcatgagaca ataaccctga taaatgcttc aataatagca   6000
cgtgaggagg gccaccatgg ccaagttgac cagtgccgtt ccggtgctca ccgcgcgcga   6060
cgtcgccgga gcggtcgagt tctggaccga ccggctcggg ttctccgggg acttcgtgga   6120
```

-continued

| | |
|---|---|
| ggacgacttc gccggtgtgg tccgggacga cgtgaccctg ttcatcagcg cggtccagga | 6180 |
| ccaggtggtg ccggacaaca ccctggcctg ggtgtgggtg cgcggcctgg acgagctgta | 6240 |
| cgccgagtgg tcggaggtcg tgtccacgaa cttccgggac gcctccgggc cggccatgac | 6300 |
| cgagatcggc gagcagccgt gggggcggga gttcgccctg cgcgaccggg ccggcaactg | 6360 |
| cgtgcacttc gtggccgagg agcaggactg acacgtgcta aaacttcatt tttaatttaa | 6420 |
| aaggatctag gtgaagatcc ttttgataa tctcatgacc aaaatccctt aacgtgagtt | 6480 |
| ttcgttccac tgagcgtcag accccgtaga aagatcaaa ggatcttctt gagatccttt | 6540 |
| ttttctgcgc gtaatctgct gcttgcaaac aaaaaaacca ccgctaccag cggtggtttg | 6600 |
| tttgccggat caagagctac caactctttt tccgaaggta actggcttca gcagagcgca | 6660 |
| gataccaaat actgttcttc tagtgtagcc gtagttaggc caccacttca agaactctgt | 6720 |
| agcaccgcct acatacctcg ctctgctaat cctgttacca gtggctgctg ccagtggcga | 6780 |
| taagtcgtgt cttaccgggt tggactcaag acgatagtta ccggataagg cgcagcggtc | 6840 |
| gggctgaacg gggggttcgt gcacacagcc cagcttggag cgaacgacct acaccgaact | 6900 |
| gagataccta gcgtgagc tatgagaaag cgccacgctt cccgaaggga gaaggcgga | 6960 |
| caggtatccg gtaagcggca gggtcggaac aggagagcgc acgagggagc ttccaggggg | 7020 |
| aaacgcctgg tatctttata gtcctgtcgg gtttcgccac ctctgacttg agcgtcgatt | 7080 |
| tttgtgatgc tcgtcagggg ggcggagcct atggaaaaac gccagcaacg cggcctttttt | 7140 |
| acggttcctg gccttttgct ggcctttttgc tcacatgttc tttcctgcgt tatcccctga | 7200 |
| ttctgtggat aaccgtatta ccgcctttga gtgagctgat accgctcgcc gcagccgaac | 7260 |
| gaccgagcgc agcgagtcag tgagcgagga agcggaagag cgcccaatac gcaaaccgcc | 7320 |
| tctccccgcg cgttggccga ttcattaatg cagctggcac gacaggtttc ccgactggaa | 7380 |
| agcgggcagt gagcgcaacg caattaatgt gagttagctc actcattagg cacccccaggc | 7440 |
| tttacacttt atgcttccgg ctcgtatgtt gtgtggaatt gtgagcggat aacaatttca | 7500 |
| cacaggaaac agctatgacc atgattacgc caagctattt aggtgacgcg ttagaatact | 7560 |
| caagctatgc atcaagcttg gtaccgagct cggatccact agtaacggcc gccagtgtgc | 7620 |
| tggaattcag gggcgcgccc tatagatggg atgaagctgc tctcgacaaa tctgataaaa | 7680 |
| ctaaagaagg ttagtaatca ttttttacaa aatcatagat tatttttttc attgaattat | 7740 |
| ttttatgcta taccaagaat tgtatttag tatttgtttt aactacatat aatagaatta | 7800 |
| actacatata aattaactaa acttaaaata aaaatagatt tgtttcctga aattatttta | 7860 |
| agaatatata tgtatatatc taaaatctta gacttagata gattttttcta tctatctatt | 7920 |
| ttggttactt aaaataaata aatttgtata ataattgta tagttatcaa aaattaaaac | 7980 |
| taattttttt aaagttgttg atatatatatataaaa tactaaagat ttaacgatta agtatttatt | 8040 |
| taagtataga atttgtttt tttttaagt ttagttatga agttgttaat tatattaaaa | 8100 |
| caaaacaata tttcgaaatt ttattatcat attcgaatat attttttta gtgatgatgt | 8160 |
| atgaattatt atcataatttt gaagtttac taaaaaatat atcaacatga attgtaatat | 8220 |
| atgagttatt accttaacca aaattataaa ttaacattaa atataattat atatgtcata | 8280 |
| tttagccata caatgtgtca tcaatattaa tagtcatgtc aatattacat aatgccaata | 8340 |
| ttatgctact taaaccccaa atcccctaac tcccgttaag tagccaaatt cataaatata | 8400 |
| cttattcgac aaaataaaaa actttaaaat atttactaat ccgaccatgc acaagcatcc | 8460 |
| attccctatt ccattgccac gggataacaa tgcaaccnac tcctcaaaaa aagaaaaatt | 8520 |

```
caagctctttt tgcaaaaaaa aataaaataa ttttaacacc taaaatttttt tgtttccaaa    8580
cttctacagg gaacacacat aaaagaaaaa gaggacgtcc actcggatca cgcaacaaac    8640
caaaaggtgt gtcatgactc ctaagatata atatttcctt attcaaaatc ataccatttt    8700
aaattatgaa tgtatttcgt agtccaccag atatgtaatc caccagcgtt caaaccaaag    8760
ttttatgatt gtaagtttaa gtgaattata ataatatatt cttcacggta tcttttcata    8820
actaattgag ttatcaaact tgatcgcaca tgtggctttg ataggtgtga cttttatggt    8880
atacaattct ttcaacctaa aaacattatt gttcctcaat atcttacatt atgcttgact    8940
gcaacaaaat attttctcat ctgttttctt cctttaaacc aatttattat catctatttc    9000
ctgacatttt aatccatcca cctatgtcaa aaacttatag aaaatgtcaa cttccaaaca    9060
aaacataatt gaacttcgca aataaattct taataatatt aaaaaatgtt acttaattat    9120
ttcttcaacc ccatttttccg cgcgtagcgc ggacaaagac tctagttaaa tatagaagtt    9180
tccgattctc atcgtataaa acggtgactt tggcgggctt tcatgtgtaa caaattggtt    9240
taacaaacca ctgcctagtc gtttagtgta gaatcagcgc atggaactcc gattggagcg    9300
tgactttcac gtgccggagg cccaccacca cagcgggcgt tacgctctaa gaatctcgcc    9360
cacggttttc ttcatctgcc ccccgccaag tgtcttcctc gttcgccact tctcaccaag    9420
ttacaggaac cctaaaaatg gccttttcttc agccccggct ataatacaca catgatccta    9480
tagtgggttc ttccacaagt tacatctcct tctggattgt acatttcaag tgtttgtgtt    9540
ttttctgcct ctgagagaaa atcgcggccg catggagaga tctcaacggc agtctcctcc    9600
gccaccgtcg ccgtcctcct cctcgtcctc cgtctccgcg gacaccgtcc tcgtccctcc    9660
cggaaagagg cggagggcgg cgacggccaa ggccggcgcc gagcctaata agaggatccg    9720
caaggacccc gccgccgccg ccgcggggaa gaggagctcc gtctacaggg gagtcaccag    9780
gcacaggtgg acgggcaggt tcgaggcgca tctctgggac aagcactgcc tcgccgcgct    9840
ccacaacaag aagaaaggca ggcaagtcta cctggggggcg tatgacagcg aggaggcagc    9900
tgctcgtgcc tatgacctcg cagctctcaa gtactgggt cctgagactc tgctcaactt    9960
ccctgtggag gattactcca gcgagatgcc ggagatggag gccgtgtccc gggaggagta   10020
cctggcctcc ctccgccgca ggagcagcgg cttctccagg ggcgtctcca agtacagagg   10080
cgtcgccagg catcaccaca acgggaggtg ggaggcacgg attgggcgag tctttgggaa   10140
caagtacctc tacttgggaa catttgacac tcaagaagag gcagccaagg cctatgacct   10200
tgcggccatt gaataccgtg gcgtcaatgc tgtaaccaac ttcgacatca gctgctacct   10260
ggaccacccg ctgttcctgg cacagctcca acaggagcca caggtggtgc cggcactcaa   10320
ccaagaacct caacctgatc agagcgaaac cggaactaca gagcaagagc cggagtcaag   10380
cgaagccaag acaccggatg gcagtgcaga acccgatgag aacgcggtgc ctgacgacac   10440
cgcggagccc ctcaccacag tcgacgacag catcgaagag ggcttgtgga gcccttgcat   10500
ggattacgag ctagacacca tgtcgagacc aaactttggc agctcaatca atctgagcga   10560
gtggttcgct gacgcagact tcgactgcaa catcggatgc ctgttcgatg ggtgttctgc   10620
ggctgacgaa ggaagcaagg atggtgtagg tctggcagat tcagtctgt ttgaggcagg   10680
tgatgtccag ctgaaggatg ttccttcgga tatggaagag gggatacaac ctccagcgat   10740
gatcagtgtg tgcaacgc                                                10758

<210> SEQ ID NO 71
<211> LENGTH: 20553
<212> TYPE: DNA
```

```
<213> ORGANISM: Artificial sequence
<220> FEATURE:
<223> OTHER INFORMATION: Vector ARAL079
<220> FEATURE:
<221> NAME/KEY: misc_feature
<222> LOCATION: (14134)..(14134)
<223> OTHER INFORMATION: n is a, c, g, or t
<220> FEATURE:
<221> NAME/KEY: misc_feature
<222> LOCATION: (18743)..(18743)
<223> OTHER INFORMATION: n is a, c, g, or t

<400> SEQUENCE: 71
cgcgcctcga gtgggcggat cccccgggct gcaggaattc actggccgtc gttttacaac      60
gtcgtgactg ggaaaaccct ggcgttaccc aacttaatcg ccttgcagca catccccctt     120
tcgccagctg gcgtaatagc gaagaggccc gcaccgatcg cccttcccaa cagttgcgca     180
gcctgaatgg cgaatggatc gatccatcgc gatgtacctt tgttagtca gcctctcgat      240
tgctcatcgt cattacacag taccgaagtt tgatcgatct agtaacatag atgacaccgc     300
gcgcgataat ttatcctagt ttgcgcgcta tattttgttt tctatcgcgt attaaatgta     360
taattgcggg actctaatca taaaaaccca tctcataaat aacgtcatgc attacatgtt     420
aattattaca tgcttaacgt aattcaacag aaattatatg ataatcatcg caagaccggc     480
aacaggattc aatcttaaga aactttattg ccaaatgttt gaacgatctg cttcgacgca     540
ctccttcttt actccaccat ctcgtcctta ttgaaaacgt gggtagcacc aaaacgaatc     600
aagtcgctgg aactgaagtt accaatcacg ctggatgatt tgccagttgg attaatcttg     660
cctttccccg catgaataat attgatgaat gcatgcgtga ggggtagttc gatgttggca     720
atagctgcaa ttgccgcgac atcctccaac gagcataatt cttcagaaaa atagcgatgt     780
tccatgttgt cagggcatgc atgatgcacg ttatgaggtg acggtgctag gcagtattcc     840
ctcaaagttt catagtcagt atcatattca tcattgcatt cctgcaagag agaattgaga     900
cgcaatccac acgctgcggc aaccttccgg cgttcgtggt ctatttgctc ttggacgttg     960
caaacgtaag tgttggatcg atccggggtg ggcgaagaac tccagcatga gatccccgcg    1020
ctggaggatc atccagccgg cgtcccggaa aacgattccg aagcccaacc tttcatagaa    1080
ggcggcggtg gaatcgaaat ctcgtgatgg caggttgggc gtcgcttggt cggtcatttc    1140
gaaccccaga gtcccgctca gaagaactcg tcaagaaggc gatagaaggc gatgcgctgc    1200
gaatcgggag cggcgatacc gtaaagcacg aggaagcggt cagcccattc gccgccaagc    1260
tcttcagcaa tatcacgggt agccaacgct atgtcctgat agcggtccgc cacacccagc    1320
cggccacagt cgatgaatcc agaaaagcgg ccattttcca ccatgatatt cggcaagcag    1380
gcatcgccat gggtcacgac gagatcctcg ccgtcgggca tgcgcgcctt gagcctggcg    1440
aacagttcgg ctggcgcgag cccctgatgc tcttcgtcca gatcatcctg atcgacaaga    1500
ccggcttcca tccgagtacg tgctcgctcg atgcgatgtt tcgcttggtg gtcgaatggg    1560
caggtagccg gatcaagcgt atgcagccgc cgcattgcat cagccatgat ggatactttc    1620
tcggcaggag caaggtgaga tgacaggaga tcctgccccg gcacttcgcc caatagcagc    1680
cagtcccttc ccgcttcagt gacaacgtcg agcacagctg cgcaaggaac gcccgtcgtg    1740
gccagccacg atagccgcgc tgcctcgtcc tgcagttcat tcagggcacc ggacaggtcg    1800
gtcttgacaa aaagaaccgg gcgcccctgc gctgacagcc ggaacacggc ggcatcagag    1860
cagccgattg tctgttgtgc ccagtcatag ccgaatagcc tctccaccca agcggccgga    1920
gaacctgcgt gcaatccatc ttgttcaatc atgcgaaacg atccccgcaa gcttggagac    1980
```

```
tggtgatttc agcgtgtcct ctccaaatga aatgaacttc cttatataga ggaagggtct    2040
tgcgaaggat agtgggattg tgcgtcatcc cttacgtcag tggagatatc acatcaatcc    2100
acttgctttg aagacgtggt tggaacgtct tcttttcca cgatgctcct cgtgggtggg    2160
ggtccatctt tgggaccact gtcggcagag gcatcttcaa cgatggcctt tcctttatcg    2220
caatgatggc atttgtagga gccaccttcc ttttccacta tcttcacaat aaagtgacag    2280
atagctgggc aatggaatcc gaggaggttt ccggatatta cccttttgttg aaaagtctca   2340 attgcccttt ggtcttctga gactgtatct ttgatatttt tggagtagac aagcgtgtcg    2400
tgctccacca tgttgacgaa gattttcttc ttgtcattga gtcgtaagag actctgtatg    2460
aactgttcgc cagtctttac ggcgagttct gttaggtcct ctatttgaat ctttgactcc    2520
atggcctttg attcagtggg aactaccttt ttagagactc caatctctat tacttgcctt    2580
ggtttgtgaa gcaagccttg aatcgtccat actggaatag tacttctgat cttgagaaat    2640
atatctttct ctgtgttctt gatgcagtta gtcctgaatc ttttgactgc atctttaacc    2700
ttcttgggaa ggtatttgat ctcctggaga ttattgctcg ggtagatcgt cttgatgaga    2760
cctgctgcgt aagcctctct aaccatctgt gggttagcat tctttctgaa attgaaaagg    2820
ctaatcttct cattatcagt ggtgaacatg gtatcgtcac cttctccgtc gaacttcctg    2880
actagatcgt agagatagag gaagtcgtcc attgtgatct ctgggcaaa ggagatctga    2940 attaattcga tatggtggat ttatcacaaa tgggacccgc cgccgacaga ggtgtgatgt    3000
taggccagga ctttgaaaat ttgcgcaact atcgtatagt ggccgacaaa ttgacgccga    3060
gttgacagac tgcctagcat ttgagtgaat tatgtgaggt aatgggctac actgaattgg    3120
tagctcaaac tgtcagtatt tatgtatatg agtgtatatt ttcgcataat ctcagaccaa    3180
tctgaagatg aaatgggtat ctgggaatgg cgaaatcaag gcatcgatcg tgaagtttct    3240
catctaagcc cccatttgga cgtgaatgta gacacgtcga aataaagatt tccgaattag    3300
aataatttgt ttattgcttt cgcctataaa tacgacggat cgtaatttgt cgttttatca    3360
aaatgtactt tcattttata ataacgctgc ggacatctac attttgaat tgaaaaaaa     3420 ttggtaatta ctcttctt ttctccatat tgaccatcat actcattgct gatccatgta     3480
gatttcccgg acatgaagcc atttacaatt gaatatatcc tgccgccgct gccgctttgc    3540
acccggtgga gcttgcatgt tggtttctac gcagaactga gccggttagg cagataattt    3600
ccattgagaa ctgagccatg tgcaccttcc ccccaacacg gtgagcgacg gggcaacgga    3660
gtgatccaca tgggactttt aaacatcatc cgtcggatgg cgttgcgaga gaagcagtcg    3720
atccgtgaga tcagccgacg caccgggcag gcgcgcaaca cgatcgcaaa gtatttgaac    3780
gcaggtacaa tcgagccgac gttcacgcgg aacgaccaag caagctagct ttaatgcggt    3840
agtttatcac agttaaattg ctaacgcagt caggcaccgt gtatgaaatc taacaatgcg    3900
ctcatcgtca tcctcggcac cgtcacccctg atgctgtag gcataggctt ggttatgccg    3960
gtactgccgg gcctcttgcg ggatatcgtc cattccgaca gcatcgccag tcactatggc    4020
gtgctgctag cgctatatgc gttgatgcaa tttctatgcg cacccgttct cggagcactg    4080
tccgaccgct ttggccgccg cccagtcctg ctcgcttcgc tacttggagc cactatcgac    4140
tacgcgatca tggcgaccac acccgtcctg tggtccaacc cctccgctgc tatagtgcag    4200
tcggcttctg acgttcagtg cagccgtctt ctgaaaacga catgtcgcac aagtcctaag    4260
ttacgcgaca ggctgccgcc ctgccctttt cctggcgttt tcttgtcgcg tgttttagtc    4320
gcataaagta gaatacttgc gactagaacc ggagacatta cgccatgaac aagagcgccg    4380
```

-continued

```
ccgctggcct gctgggctat gcccgcgtca gcaccgacga ccaggacttg accaaccaac    4440
gggccgaact gcacgcggcc ggctgcacca agctgttttc cgagaagatc accggcacca    4500
ggcgcgaccg cccggagctg gccaggatgc ttgaccacct acgccctggc gacgttgtga    4560
cagtgaccag gctagaccgc ctggcccgca gcacccgcga cctactggac attgccgagc    4620
gcatccagga ggccggcgcg ggcctgcgta gcctggcaga gccgtgggcc gacaccacca    4680
cgccggccgc ccgcatggtg ttgaccgtgt tcgccggcat tgccgagttc gagcgttccc    4740
taatcatcga ccgcacccgg agcgggcgcg aggccgccaa ggcccgaggc gtgaagtttg    4800
gcccccgccc taccctcacc ccggcacaga tcgcgcacgc ccgcgagctg atcgaccagg    4860
aaggccgcac cgtgaaagag gcggctgcac tgcttggcgt gcatcgctcg accctgtacc    4920
gcgcacttga gcgcagcgag gaagtgacgc ccaccgagcc caggcggcgc ggtgccttcc    4980
gtgaggacgc attgaccgag gccgacgccc tggcggccgc cgagaatgaa cgccaagagg    5040
aacaagcatg aaaccgcacc aggacggcca ggacgaaccg ttttttcatta ccgaagagat    5100 cgaggcggag atgatcgcgg ccgggtacgt gttcgagccg cccgcgcacg tctcaaccgt    5160
gcggctgcat gaaatcctgg ccggtttgtc tgatgccaag ctggcggcct ggccggccag    5220
cttggccgct gaagaaaccg agcgccgccg tctaaaaagg tgatgtgtat ttgagtaaaa    5280
cagcttgcgt catgcggtcg ctgcgtatat gatgcgatga gtaaataaac aaatacgcaa    5340
gggaacgcat gaagttatcg ctgtacttaa ccagaaaggc gggtcaggca agacgaccat    5400
cgcaacccat ctagcccgcg ccctgcaact cgccggggcc gatgttctgt tagtcgattc    5460
cgatccccag ggcagtgccc gcgattgggc ggccgtgcgg gaagatcaac cgctaaccgt    5520
tgtcggcatc gaccgcccga cgattgaccg cgacgtgaag gccatcggcc ggcgcgactt    5580
cgtagtgatc gacggagcgc cccaggcggc ggacttggct gtgtccgcga tcaaggcagc    5640
cgacttcgtg ctgattccgg tgcagccaag cccttacgac atatgggcca ccgccgacct    5700
ggtggagctg gttaagcagc gcattgaggt cacggatgga aggctacaag cggcctttgt    5760
cgtgtcgcgg gcgatcaaag gcacgcgcat cggcggtgag gttgccgagg cgctggccgg    5820
gtacgagctg cccattcttg agtcccgtat cacgcagcgc gtgagctacc caggcactgc    5880
cgccgccggc acaaccgttc ttgaatcaga acccgagggc gacgctgccc gcgaggtcca    5940
ggcgctggcc gctgaaatta aatcaaaact catttgagtt aatgaggtaa agagaaaatg    6000
agcaaaagca caaacacgct aagtgccggc cgtccgagcg cacgcagcag caaggctgca    6060
acgttggcca gcctggcaga cacgccagcc atgaagcggg tcaactttca gttgccggcg    6120
gaggatcaca ccaagctgaa gatgtacgcg gtacgccaag gcaagaccat taccgagctg    6180
ctatctgaat acatcgcgca gctaccagag taaatgagca aatgaataaa tgagtagatg    6240
aattttagcg gctaaaggag gcggcatgga aaatcaagaa caaccaggca ccgacgccgt    6300
ggaatgcccc atgtgtggag gaacgggcgg ttggccaggc gtaagcggct gggttgtctg    6360
ccggccctgc aatggcactg gaacccccaa gcccgaggaa tcggcgtgag cggtcgcaaa    6420
ccatccggcc cggtacaaat cggcgcggcg ctgggtgatg acctggtgga aagttgaag    6480 gccgcgcagg ccgcccagcg gcaacgcatc gaggcagaag cacgcccggg tgaatcgtgg    6540
caagcggccg ctgatcgaat ccgcaaagaa tcccggcaac cgccgcagc cggtgcgccg    6600 tcgattagga agccgcccaa gggcgacgag caaccagatt ttttcgttcc gatgctctat    6660
gacgtgggca cccgcgatag tcgcagcatc atggacgtgg ccgttttccg tctgtcgaag    6720
cgtgaccgac gagctggcga ggtgatccgc tacgagcttc cagacgggca cgtagaggtt    6780
```

```
-continued tccgcagggc cggccggcat ggccagtgtg tgggattacg acctggtact gatggcggtt    6840
tcccatctaa ccgaatccat gaaccgatac cgggaaggga agggagacaa gcccggccgc    6900
gtgttccgtc cacacgttgc ggacgtactc aagttctgcc ggcgagccga tggcggaaag    6960
cagaaagacg acctggtaga aacctgcatt cggttaaaca ccacgcacgt tgccatgcag    7020
cgtacgaaga aggccaagaa cggccgcctg gtgacggtat ccgagggtga agccttgatt    7080
agccgctaca agatcgtaaa gagcgaaacc gggcggccgg agtacatcga gatcgagcta    7140
gctgattgga tgtaccgcga gatcacagaa ggcaagaacc cggacgtgct gacggttcac    7200
cccgattact ttttgatcga tcccggcatc ggccgttttc tctaccgcct ggcacgccgc    7260
gccgcaggca aggcagaagc cagatggttg ttcaagacga tctacgaacg cagtggcagc    7320
gccgagagt tcaagaagtt ctgtttcacc gtgcgcaagc tgatcgggtc aaatgacctg    7380
ccggagtacg atttgaagga ggaggcgggg caggctggcc cgatcctagt catgcgctac    7440
cgcaacctga tcgagggcga agcatccgcc ggttcctaat gtacgagca gatgctaggg    7500
caaattgccc tagcagggga aaaggtcga aaaggtctct ttcctgtgga tagcacgtac    7560
attgggaacc caaagccgta cattgggaac cggaacccgt acattgggaa cccaaagccg    7620
tacattggga accggtcaca catgtaagtg actgatataa aagagaaaaa aggcgatttt    7680
tccgcctaaa actcttttaaa acttattaaa actcttaaaa cccgcctggc ctgtgcataa    7740
ctgtctggcc agcgcacagc cgaagagctg caaaaagcgc ctaccttcg tcgctgcgc    7800
tccctacgcc ccgccgcttc gcgtcggcct atcgcggccg ctggccgctc aaaaatggct    7860
ggcctacggc caggcaatct accagggcgc ggacaagccg cgccgtcgcc actcgaccgc    7920
cggcgcccac atcaaggcac cctgcctcgc gcgtttcggt gatgacggtg aaaacctctg    7980
acacatgcag ctcccggaga cggtcacagc ttgtctgtaa gcggatgccg ggagcagaca    8040
agcccgtcag ggcgcgtcag cgggtgttgg cgggtgtcgg ggcgcagcca tgacccagtc    8100
acgtagcgat agcggagtgt atactggctt aactatgcgg catcagagca gattgtactg    8160
agagtgcacc atatgcggtg tgaaataccg cacagatgcg taaggagaaa ataccgcatc    8220
aggcgctctt ccgcttcctc gctcactgac tcgctgcgct cggtcgttcg gctgcggcga    8280
gcggtatcag ctcactcaaa ggcggtaata cggttatcca cagaatcagg ggataacgca    8340
ggaaagaaca tgtgagcaaa aggccagcaa aaggccagga accgtaaaaa ggccgcgttg    8400
ctggcgtttt tccataggct ccgcccccct gacgagcatc acaaaaatcg acgctcaagt    8460
cagaggtggc gaaacccgac aggactataa agataccagg cgtttccccc tggaagctcc    8520
ctcgtgcgct ctcctgttcc gaccctgccg cttaccggat acctgtccgc ctttctccct    8580
tcgggaagcg tggcgctttc tcatagctca cgctgtaggt atctcagttc ggtgtaggtc    8640
gttcgctcca agctgggctg tgtgcacgaa ccccccgttc agcccgaccg ctgcgcctta    8700
tccggtaact atcgtcttga gtccaacccg gtaagacacg acttatcgcc actggcagca    8760
gccactggta acaggattag cagagcgagg tatgtaggcg gtgctacaga gttcttgaag    8820
tggtggccta actacggcta cactagaagg acagtatttg gtatctgcgc tctgctgaag    8880
ccagttacct tcggaaaaag agttggtagc tcttgatccg gcaaacaaac caccgctggt    8940
agcggtggtt tttttgtttg caagcagcag attacgcgca gaaaaaaagg atctcaagaa    9000
gatcctttga tcttttctac ggggtctgac gctcagtgga acgaaaactc acgttaaggg    9060
attttggtca tgagattatc aaaaaggatc ttcacctaga tccttttaaa ttaaaaatga    9120
agttttaaat caatctaaag tatatatgag taaacttggt ctgacagtta ccaatgctta    9180
```

```
atcagtgagg cacctatctc agcgatctgt ctatttcgtt catccatagt tgcctgactc   9240
cccgtcgtgt agataactac gatacgggag ggcttaccat ctggcccag tgctgcaatg    9300
ataccgcgag acccacgctc accggctcca gatttatcag caataaacca gccagccgga   9360
agggccgagc gcagaagtgg tcctgcaact ttatccgcct ccatccagtc tattaattgt   9420
tgccgggaag ctagagtaag tagttcgcca gttaatagtt tgcgcaacgt tgttgccatt   9480
gctacaggca tcgtggtgtc acgctcgtcg tttggtatgg cttcattcag ctccggttcc   9540
caacgatcaa ggcgagttac atgatccccc atgttgtgca aaaagcggt tagctccttc    9600
ggtcctccga tcgttgtcag aagtaagttg gccgcagtgt tatcactcat ggttatggca   9660
gcactgcata attctcttac tgtcatgcca tccgtaagat gcttttctgt gactggtgag   9720
tactcaacca agtcattctg agaatagtgt atgcggcgac cgagttgctc ttgcccggcg   9780
tcaacacggg ataataccgc gccacatagc agaactttaa aagtgctcat cattggaaaa   9840
gacctgcagg ggggggggg cgctgaggtc tgcctcgtga agaaggtgtt gctgactcat    9900
accaggcctg aatcgcccca tcatccagcc agaaagtgag ggagccacgg ttgatgagag   9960
ctttgttgta ggtggaccag ttggtgattt tgaacttttg ctttgccacg gaacggtctg  10020
cgttgtcggg aagatgcgtg atctgatcct tcaactcagc aaaagttcga tttattcaac  10080
aaagccgccg tcccgtcaag tcagcgtaat gctctgccag tgttacaacc aattaaccaa  10140
ttctgattag aaaaactcat cgagcatcaa atgaaactgc aatttattca tatcaggatt  10200
atcaatacca tatttttgaa aaagccgttt ctgtaatgaa ggagaaaact caccgaggca  10260
gttccatagg atggcaagat cctggtatcg gtctgcgatt ccgactcgtc caacatcaat  10320
acaacctatt aatttcccct cgtcaaaaat aaggttatca agtgagaaat caccatgagt  10380
gacgactgaa tccggtgaga atggcaaaag cttatgcatt tctttccaga cttgttcaac  10440
aggccagcca ttacgctcgt catcaaaatc actcgcatca accaaaccgt tattcattcg  10500
tgattgcgcc tgagcgagac gaaatacgcg atcgctgtta aaaggacaat acaaacagg   10560
aatcgaatgc aaccggcgca ggaacactgc cagcgcatca acaatatttt cacctgaatc  10620
aggatattct tctaatacct ggaatgctgt tttcccgggg atcgcagtgg tgagtaacca  10680
tgcatcatca ggagtacgga taaaatgctt gatggtcgga agaggcataa attccgtcag  10740
ccagtttagt ctgaccatct catctgtaac atcattggca acgctacctt tgccatgttt  10800
cagaaacaac tctggcgcat cgggcttccc atacaatcga tagattgtcg cacctgattg  10860
cccgacatta tcgcgagccc atttataccc atataaatca gcatccatgt tggaatttaa  10920
tcgcggcctc gagcaagacg tttcccgttg aatatggctc ataacacccc ttgtattact  10980
gtttatgtaa gcagacagtt ttattgttca tgatgatata ttttatctt gtgcaatgta   11040
acatcagaga ttttgagaca caacgtggct ttcccccccc ccctgcagg tcaattcggt   11100
cgatatggct attacgaaga aggctcgtgc gcggagtccc gtgaactttc ccacgcaaca  11160
agtgaaccgc accgggtttg ccggaggcca tttcgttaaa atgcgcagcc atggctgctt  11220
cgtccagcat ggcgtaatac tgatcctcgt cttcggctgg cggtatattg ccgatggct   11280
tcaaaagccg ccgtggttga accagtctat ccattccaag gtagcgaact cgaccgcttc  11340
gaagctcctc catggtccac gccgatgaat gacctcggcc ttgtaaagac cgttgatcgc  11400
ttctgcgagg gcgttgtcgt gctgtcgccg acgcttccga tagatggctc gatacctgct  11460
tctgccaacc gctcggaata gcgaaaggac acgtattgaa caccgcgatc cgagtgatgc  11520
actaggccgc catgagcggg acgccgatca tgatgagcct cctcgagggc atcgaggaca  11580
```

```
aagcctgcat gtgctgtccg gctcgcccgc catccgacaa tgcgacgggc gaagacgtcg    11640
atcacgaagg ccacgtagac gaagccctcc caagtggcga cataagtacg gacatgcgca    11700
aaggctttcc cggtttgtcg ctgatggtgc aagagacgct gaagcgcgat ccgatgcgca    11760
ggcatctgtt cgtcttccgc ggtcgtggcg gtggcctgat caaggtcact cgccgaagag    11820
ctgcatgatt ggctcgaaac cgagcggggg aaattgtcgc gcagttctcc cgtcgccgag    11880
gcgataaatt acatgctcaa gcgatgggat ggcattacgg cattcctcga tgacggcccg    11940
atttgcctga cgaacaatgc tgccgaacga acgctcagag gctatgtact cggcaggaag    12000
tcatggctgt ttgccggatc ggatcgttgt gctgaacgtg cggcgttcat ggcgacactg    12060
atcatgagcg ccaagctcaa taacatcgat ccgcaggcct ggcttgccga cgtccgcgcc    12120
gaccttgcgg acgctccgat cagcaggctt gagcaacagc tgccgtggaa ctggacatcc    12180
aagacactga gtgctcaggc ggcctgacct gcggccttca ccggatactt accccattat    12240
cgcagattgc gatgaagcat cagcgtcatt cagcaatctt gccaaagtat gcaggctcgc    12300
gagaatcgac gtgcgaaacc ggctggttgc gccaaagatc cgcttgcgga gcggtcgaac    12360
attcatgctg ggacttcaag aggtcgagta gaggaagaac cggaaaggtt gcaccggaaa    12420
atatgcgttc ctttggagag cgcctcatgg acgtgaacaa atcgcccgga ccaaggatgc    12480
cacggataca aaagctcgcg aagctcggtc ccgtgggtgt tctgtcgtct cgttgtacaa    12540
cgaaatccat tcccattccg cgctcaagat ggcttcccct cggcagttca tcagggctaa    12600
atcaatctag ccgacttgtc cggtgaaatg ggctgcactc caacagaaac aatcaaacaa    12660
acatacacag cgacttattc acacgagctc aaattacaac ggtatatatc ctgccagtca    12720
gcatcatcac accaaaagtt aggcccgaat agtttgaaat tagaaagctc gcaattgagg    12780
tctacaggcc aaattcgctc ttagccgtac aatattactc accggtgcga tgcccccat    12840 cgtaggtgaa ggtggaaatt aatgatccat cttgagacca caggcccaca acagctacca    12900
gtttcctcaa gggtccacca aaaacgtaag cgcttacgta catggtcgat aagaaaaggc    12960
aatttgtaga tgttaacatc caacgtcgct ttcagggatc gatccaatac gcaaaccgcc    13020
tctccccgcg cgttggccga ttcattaatg cagctggcac gacaggtttc ccgactggaa    13080
agcgggcagt gagcgcaacg caattaatgt gagttagctc actcattagg caccccaggc    13140
tttacacttt atgcttccgg ctcgtatgtt gtgtggaatt gtgagcggat aacaatttca    13200
cacaggaaac agctatgacc atgattacgc caagcttgca tgcctgcagg tcgactctag    13260
aggatctggc gcgccctata gatgggatga agctgctctc gacaaatctg ataaaactaa    13320
agaaggttag taatcaattt ttacaaaatc atagattatt ttttccattg aattattttt    13380
atgctatacc aagaattgta ttttagtatt tgttttaact acatataata gaattaacta    13440
catataaatt aactaaactt aaaataaaaa tagatttgtt tcctgaaatt attttaagaa    13500
tatatatgta tatatctaaa atcttagact tagatagatt tttctatcta tctatttgg    13560 ttacttaaaa taaataaatt tgtataaata attgtatagt tatcaaaaat taaaactaat    13620 tttttttaaag ttgttgatat ataaaatact aaagatttaa cgattaagta tttatttaag    13680
tatagaattt tgttttttt ttaagtttag ttatgaagtt gttaattata ttaaaacaaa    13740
acaatatttc gaaattttat tatcatattc gaatatattt tttttagtga tgatgtatga    13800
attattatca taatttgaaa gtttactaaa aaatatatca acatgaattg taatatatga    13860
gttattacct taaccaaaat tataaattaa cattaaatat aattatatat gtcatattta    13920
gccatacaat gtgtcatcaa tattaatagt catgtcaata ttacataatg ccaatattat    13980
```

```
gctacttaaa ccccaaatcc cctaactccc gttaagtagc caaattcata aatatactta   14040
ttcgacaaaa taaaaaactt taaaatattt actaatccga ccatgcacaa gcatccattc   14100
cctattccat tgccacggga taacaatgca accnactcct caaaaaaaga aaaattcaag   14160
ctcttttgca aaaaaaaata aaataatttt aacacctaaa attttttgtt tccaaacttc   14220
tacagggaac acacataaaa gaaaagagg acgtccactc ggatcacgca acaaaccaaa    14280
aggtgtgtca tgactcctaa gatataatat ttccttattc aaaatcatac cattttaaat   14340
tatgaatgta tttcgtagtc caccagatat gtaatccacc agcgttcaaa ccaaagtttt   14400
atgattgtaa gtttaagtga attataataa tatattcttc acggtatctt ttcataacta   14460
attgagttat caaacttgat cgcacatgtg gctttgatag gtgtgacttt tatggtatac   14520
aattctttca acctaaaaac attattgttc ctcaatatct tacattatgc ttgactgcaa   14580
caaaatattt tctcatctgt tttcttcctt taaaccaatt tattatcatc tatttcctga   14640
cattttaatc catccaccta tgtcaaaaac ttatagaaaa tgtcaacttc caaacaaaac   14700
ataattgaac ttcgcaaata aattcttaat aatattaaaa aatgttactt aattatttct   14760
tcaaccccat tttccgcgcg tagcgcggac aaagactcta gttaaatata gaagtttccg   14820
attctcatcg tataaaacgg tgactttggc gggctttcat gtgtaacaaa ttggtttaac   14880
aaaccactgc ctagtcgttt agtgtagaat cagcgcatgg aactccgatt ggagcgtgac   14940
tttcacgtgc cggaggccca ccaccacagc gggcgttacg ctctaagaat ctcgcccacg   15000
gttttcttca tctgccccc gccaagtgtc ttcctcgttc gccacttctc accaagttac    15060 aggaaccta aaaatggcct ttcttcagcc ccggctataa tacacacatg atcctatagt    15120
gggttcttcc acaagttaca tctccttctg gattgtacat ttcaagtgtt tgtgtttttt   15180
ctgcctctga gagaaaatcg cggccgcatg gagagatctc aacggcagtc tcctccgcca   15240
ccgtcgccgt cctcctcctc gtcctccgtc tccgcggaca ccgtcctcgt ccctcccgga   15300
aagaggcgga gggcggcgac ggccaaggcc ggcgccgagc ctaataagag gatccgcaag   15360
gaccccgccg ccgccgccgc ggggaagagg agctccgtct acaggggagt caccaggcac   15420
aggtggacgg gcaggttcga ggcgcatctc tgggacaagc actgcctcgc cgcgctccac   15480
aacaagaaga aaggcaggca agtctacctg ggggcgtatg acagcgagga ggcagctgct   15540
cgtgcctatg acctcgcagc tctcaagtac tggggtcctg agactctgct caacttccct   15600
gtggaggatt actccagcga gatgccggag atggaggccg tgtcccggga ggagtacctg   15660
gcctccctcc gccgcaggag cagcggcttc tccaggggcg tctccaagta cagaggcgtc   15720
gccaggcatc accacaacgg gaggtgggag gcacggattg ggcgagtctt tgggaacaag   15780
tacctctact tgggaacatt tgacactcaa gaagaggcag ccaaggccta tgaccttgcg   15840
gccattgaat accgtggcgt caatgctgta accaacttcg acatcagctg ctacctggac   15900
cacccgctgt tcctggcaca gctccaacag gagccacagg tggtgccggc actcaaccaa   15960
gaacctcaac ctgatcagag cgaaaccgga actacagagc aagagccgga gtcaagcgaa   16020
gccaagacac cggatggcag tgcagaaccc gatgagaacg cggtgcctga cgacaccgcg   16080
gagcccctca ccacagtcga cgacagcatc gaagagggct tgtggagccc ttgcatggat   16140
tacgagctag acaccatgtc gagaccaaac tttggcagct caatcaatct gagcgagtgg   16200
ttcgctgacg cagacttcga ctgcaacatc ggatgcctgt tcgatgggtg ttctgcggct   16260
gacgaaggaa gcaaggatgg tgtaggtctg gcagatttca gtctgtttga ggcaggtgat   16320
gtccagctga aggatgttct ttcggatatg gaagaggga tacaacctcc agcgatgatc    16380
```

```
agtgtgtgca acgcggccgc aagtatgaac taaaatgcat gtaggtgtaa gagctcatgg   16440
agagcatgga atattgtatc cgaccatgta acagtataat aactgagctc catctcactt   16500
cttctatgaa taaacaaagg atgttatgat atattaacac tctatctatg caccttattg   16560
ttctatgata aatttcctct tattattata aatcatctga atcgtgacgg cttatggaat   16620
gcttcaaata gtacaaaaac aaatgtgtac tataagactt tctaaacaat tctaaccttta  16680 gcattgtgaa cgagacataa gtgttaagaa gacataacaa ttataatgga agaagtttgt   16740
ctccatttat atattatata ttacccactt atgtattata ttaggatgtt aaggagacat   16800
aacaattata agagagaag tttgtatcca tttatatatt atatactacc catttatata   16860
ttatacttat ccacttattt aatgtcttta taaggtttga tccatgatat ttctaatatt   16920
ttagttgata tgtatatgaa agggtactat ttgaactctc ttactctgta taaaggttgg   16980
atcatcctta aagtgggtct attttaattttt attgcttctt acagataaaa aaaaaattat  17040
gagttggttt gataaaatat tgaaggattt aaaataataa taaataacat ataatatatg   17100
tatataaatt tattataata taacatttat ctataaaaaa gtaaatattg tcataaatct   17160
atacaatcgt ttagccttgc tggacgaatc tcaattattt aaacgagagt aaacatattt   17220 gacttttttgg ttatttaaca aattattatt taacactata tgaaattttt tttttttatca  17280 gcaaagaata aaattaaatt aagaaggaca atggtgtccc aatccttata caaccaactt   17340
ccacaagaaa gtcaagtcag agacaacaaa aaaacaagca aaggaaattt tttaatttga   17400
gttgtcttgt ttgctgcata atttatgcag taaaacacta cacataaccc ttttagcagt   17460
agagcaatgg ttgaccgtgt gcttagcttc ttttatttta ttttttttatc agcaaagaat  17520 aaataaaata aaatgagaca cttcagggat gtttcaacaa gcttggatcc tcgaagagaa   17580
gggttaataa cacactttt taacattttt aacacaaatt ttagttatttt aaaaattat    17640 taaaaaattt aaaataagaa gaggaactct ttaaataaat ctaacttaca aaatttatga   17700
tttttaataa gttttcacca ataaaaaatg tcataaaaat atgttaaaaa gtatattatc   17760
aatattctct ttatgataaa taaaaagaaa aaaaaaataa aagttaagtg aaaatgagat   17820
tgaagtgact ttaggtgtgt ataaatatat caaccccgcc aacaatttat ttaatccaaa   17880
tatattgaag tatattattc catagccttt atttatttat atatttatta tataaaagct   17940
ttatttgttc taggttgttc atgaaatatt ttttggttt tatctccgtt gtaagaaaat    18000
catgtgcttt gtgtcgccac tcactattgc agcttttttca tgcattggtc agattgacgg   18060
ttgattgtat ttttgttttt tatggttttg tgttatgact taagtcttca tctctttatc   18120
tcttcatcag gtttgatggt tacctaatat ggtccatggg tacatgcatg gttaaattag   18180
gtggccaact ttgttgtgaa cgatagaatt ttttttatat taagtaaact attttttatat  18240 tatgaaataa taataaaaaa aatattttat cattattaac aaaatcatat tagttaattt   18300
gttaactcta taataaaaga aatactgtaa cattcacatt acatggtaac atcttttccac  18360 cctttcattt gttttttgtt tgatgacttt ttttcttgtt taaatttatt tcccttctttt   18420 taaatttgga atacattatc atcatatata aactaaaata ctaaaaacag gattacacaa   18480
atgataaata ataacacaaa tatttataaa tctagctgca atatatttaa actagctata   18540
tcgatattgt aaaataaaac tagctgcatt gatactgata aaaaaatatc atgtgctttc   18600
tggactgatg atgcagtata cttttgacat tgcctttatt ttattttttca gaaaagcttt   18660 cttagttctg ggttcttcat tatttgtttc ccatctccat tgtgaattga atcatttgct   18720
tcgtgtcaca aatacaattt agntaggtac atgcattggt cagattcacg gtttattatg   18780
```

```
tcatgactta agttcatggt agtacattac ctgccacgca tgcattatat tggttagatt      18840
tgataggcaa atttggttgt caacaatata aatataaata atgtttttat attacgaaat      18900
aacagtgatc aaaacaaaca gttttatctt tattaacaag attttgtttt tgtttgatga      18960
cgttttttaa tgtttacgct ttccccctct ttttgaattt agaacacttt atcatcataa      19020
aatcaaatac taaaaaaatt acatatttca taaataataa cacaaatatt tttaaaaaat      19080
ctgaaataat aatgaacaat attacatatt atcacgaaaa ttcattaata aaaatattat      19140
ataaataaaa tgtaatagta gttatatgta ggaaaaaagt actgcacgca taatatatac      19200
aaaaagatta aaatgaacta ttataaataa taacactaaa ttaatggtga atcatatcaa      19260
aataatgaaa aagtaaataa aatttgtaat taacttctat atgtattaca cacacaaata      19320
ataaataata gtaaaaaaaa ttatgataaa tatttaccat ctcataagat atttaaaata      19380
atgataaaaa tatagattat tttttatgca actagctagc caaaaagaga acacgggtat      19440
atataaaaag agtacccttta aattctactg tacttccttt attcctgacg tttttatatc      19500
aagtggacat acgtgaagat tttaattatc agtctaaata tttcattagc acttaatact      19560
tttctgtttt attcctatcc tataagtagt cccgattctc ccaacattgc ttattcacac      19620
aactaactaa gaaagtcttc catagccccc caagcggccc atggcctcct ccgaggacgt      19680
catcaaggag ttcatgcgct tcaaggtgcg catggagggc tccgtgaacg gccacgagtt      19740
cgagatcgag ggcgagggcg agggccgccc ctacgagggc acccagaccg ccaagctgaa      19800
ggtgaccaag gcggcccccc tgcccttcgc ctgggacatc ctgtcccccc agttccagta      19860
cggctccaag gtgtacgtga agcaccccgc cgacatcccc gactacaaga gctgtcctt       19920 ccccgagggc ttcaagtggg agcgcgtgat gaacttcgag gacggcggcg tggtgaccgt      19980
gacccaggac tcctccctgc aggacggctc cttcatctac aaggtgaagt tcatcggcgt      20040
gaacttcccc tccgacggcc ccgtaatgca gaagaagact atgggctggg aggcctccac      20100
cgagcgcctg taccccgcg acggcgtgct gaagggcgag atccacaagg ccctgaagct      20160
gaaggacggc ggccactacc tggtggagtt caagtccatc tacatggcca agaagcccgt      20220
gcagctgccc ggctactact acgtggactc caagctggac atcacctccc acaacgagga      20280
ctacaccatc gtggagcagt acgagcgcgc cgagggccgc caccacctgt cctgtagcg       20340 gccggccgcg acacaagtgt gagagtacta aataaatgct ttggttgtac gaatcatta       20400 cactaaataa aataatcaaa gcttatatat gccttccgct aaggccgaat gcaaagaaat      20460
tggttctttc tcgttatctt ttgccacttt tactagtacg tattaattac tacttaatca      20520
tctttgttta cggctcatta tatccgtcga cgg                                   20553
```

<210> SEQ ID NO 72
<211> LENGTH: 586
<212> TYPE: DNA
<213> ORGANISM: Brassica napus

<400> SEQUENCE: 72

```
ccaatttatt atcatctatt tcctgacatt ttaatccatc cacctatgtc aaaaacttat          60
agaaaatgtc aacttccaaa caaaacataa ttgaacttcg caaataaatt cttaataata         120
ttaaaaaatg ttacttaatt atttcttcaa ccccatttcc cgcgcgtagc gcggacaaag         180
actctagtta aatatagaag tttccgattc tcatcgtata aaacggtgac tttggcgggc         240
tttcatgtgt aacaaattgg tttaacaaac cactgcctag tcgtttagtg tagaatcagc         300
gcatggaact ccgattggag cgtgactttc acgtrccgga ggcccaccac cwcagcgggc         360
```

```
gttacgctct aagaatctcg cccacggttt tcttcatctc cccccgcca agtgtctccc    420 tcgttcgcca cttctcatca tgttacaggg accataaaaa tggcgtattt cttcagcccc    480
gggtataaat acacacatga tcctgtggtg ggttcttcca caagttacat ctccttctgg    540
tttttgtatt gcaagtgttt gtattttttg cctccgagag aaaatc                  586
```

<210> SEQ ID NO 73
<211> LENGTH: 1924
<212> TYPE: DNA
<213> ORGANISM: Brassica napus
<220> FEATURE:
<221> NAME/KEY: misc_feature
<222> LOCATION: (859)..(859)
<223> OTHER INFORMATION: n is a, c, g, or t

<400> SEQUENCE: 73

```
ctatagatgg gatgaagctg ctctcgacaa atctgataaa actaaagaag gttagtaatc     60 aattttttaca aaatcataga ttattttttt cattgaatta ttttatgct ataccaagaa    120 ttgtatttta gtatttgttt taactacata taatagaatt aactacatat aaattaacta    180
aacttaaaat aaaatagat ttgtttcctg aaattatttt aagaatatat atgtatatat    240
ctaaaatctt agacttagat agattttct atctatctat tttggttact taaaataaat    300
aaatttgtat aaataattgt atagttatca aaaattaaaa ctaattttttt taaagttgtt    360 gatatataaa atactaaaga tttaacgatt aagtatttat ttaagtatag aattttgttt    420
tttttttaag tttagttatg aagttgttaa ttatattaaa acaaaacaat atttcgaaat    480
tttattatca tattcgaata tatttttttt agtgatgatg tatgaattat tatcataatt    540
tgaaagttta ctaaaaaata tatcaacatg aattgtaata tatgagttat taccttaacc    600
aaaattataa attaacatta aatataatta tatatgtcat atttagccat acaatgtgtc    660
atcaatatta atagtcatgt caatattaca taatgccaat attatgctac ttaaaccccca    720 aatcccctaa ctcccgttaa gtagccaaat tcataaatat acttattcga caaaataaaa    780
aactttaaaa tatttactaa tccgaccatg cacaagcatc cattccctat tccattgcca    840
cgggataaca atgcaaccna ctcctcaaaa aagaaaaat tcaagctctt ttgcaaaaaa    900
aaataaaata attttaacac ctaaaatttt ttgtttccaa acttctacag ggaacacaca    960 taaagaaaa agaggacgtc cactcggatc acgcaacaaa ccaaaaggtg tgtcatgact   1020
cctaagatat aatatttcct tattcaaaat cataccattt taaattatga atgtatttcg   1080
tagtccacca gatatgtaat ccaccagcgt tcaaaccaaa gttttatgat tgtaagttta   1140
agtgaattat aataatatat tcttcacggt atcttttcat aactaattga gttatcaaac   1200
ttgatcgcac atgtggcttt gataggtgtg acttttatgg tatacaattc tttcaaccta   1260
aaaacattat tgttcctcaa tatcttacat tatgcttgac tgcaacaaaa tattttctca   1320
tctgttttct tcctttaaac caatttatta tcatctattt cctgacattt taatccatcc   1380
acctatgtca aaaacttata gaaaatgtca acttccaaac aaaacataat tgaacttcgc   1440
aaataaattc ttaataatat taaaaaatgt tacttaatta tttcttcaac cccatttttcc   1500 gcgcgtagcg cggacaaaga ctctagttaa atatagaagt ttccgattct catcgtataa   1560
aacggtgact ttggcgggct ttcatgtgta acaaattggt ttaacaaacc actgcctagt   1620
cgtttagtgt agaatcagcg catggaactc cgattggagc gtgactttca cgtgccggag   1680
gcccaccacc acagcgggcg ttacgctcta agaatctcgc ccacggtttt cttcatctgc   1740
cccccgccaa gtgtcttcct cgttcgccac ttctcaccaa gttacaggaa ccctaaaaat   1800
```

-continued

```
ggcctttctt cagccccggc tataatacac acatgatcct atagtgggtt cttccacaag    1860
ttacatctcc ttctggattg tacatttcaa gtgtttgtgt tttttctgcc tctgagagaa    1920
aatc                                                                 1924
```

<210> SEQ ID NO 74
<211> LENGTH: 444
<212> TYPE: PRT
<213> ORGANISM: Artificial Sequence
<220> FEATURE:
<223> OTHER INFORMATION: ODP1 consensus sequence
<220> FEATURE:
<221> NAME/KEY: misc_feature
<222> LOCATION: 2, 3, 4, 5, 6, 7, 9, 10, 11, 12, 13, 14, 16, 17, 18, 19,
  20, 21, 22, 23, 24, 25, 26, 27, 28, 29, 30, 31, 32, 33,
  34, 35, 37, 38, 39, 40, 41, 42, 43, 44, 45, 46, 47, 48,
  50, 51, 52, 53, 54, 55, 56, 57, 58, 59, 60, 61, 62, 63,
  64, 65
<223> OTHER INFORMATION: n = A,T,C or G
<220> FEATURE:
<221> NAME/KEY: misc_feature
<222> LOCATION: 66, 67, 68, 69, 70, 71, 72, 73, 74, 75, 76, 77, 78, 82,
  103, 104, 105, 106, 107, 108, 109, 110, 113, 115, 124, 127, 130,
  131, 142, 143, 144, 145, 150, 152, 154, 155, 157, 158, 161,
  162, 164, 165, 175, 183, 206, 208, 216, 217, 224
<223> OTHER INFORMATION: n = A,T,C or G
<220> FEATURE:
<221> NAME/KEY: misc_feature
<222> LOCATION: 228, 236, 246, 248, 249, 250, 251, 252, 253, 254, 255,
  256, 257, 258, 259, 260, 261, 262, 263, 264, 265, 266, 267, 268,
  269, 270, 271, 272, 273, 274, 275, 276, 277, 278, 279, 280,
  281, 282, 283, 284, 285, 287, 288, 289, 290, 291, 292
<223> OTHER INFORMATION: n = A,T,C or G
<220> FEATURE:
<221> NAME/KEY: misc_feature
<222> LOCATION: 293, 294, 295, 296, 297, 298, 299, 300, 302, 303, 304,
  305, 306, 307, 308, 309, 310, 311, 312, 313, 314, 315, 316, 317,
  318, 319, 320, 321, 322, 323, 324, 325, 326, 327, 328, 329,
  331, 333, 334, 335, 336, 337, 338, 339, 340, 341, 342
<223> OTHER INFORMATION: n = A,T,C or G
<220> FEATURE:
<221> NAME/KEY: misc_feature
<222> LOCATION: 343, 344, 345, 346, 347, 348, 349, 350, 351, 352, 353,
  354, 355, 356, 357, 358, 359, 360, 361, 362, 363, 364, 365, 366,
  367, 368, 370, 371, 372, 374, 375, 376, 378, 379, 380, 381,
  382, 383, 384, 385, 386, 387, 388, 389, 390, 391, 392
<223> OTHER INFORMATION: n = A,T,C or G
<220> FEATURE:
<221> NAME/KEY: misc_feature
<222> LOCATION: 393, 394, 395, 396, 397, 398, 399, 400, 385, 386, 387,
  388, 389, 390, 391, 392, 393, 394, 395, 396, 397, 398, 399, 400,
  401, 402, 403, 404, 405, 406, 407, 408, 409, 410, 411, 412, 413,
  414, 415, 416, 417, 418, 419, 420, 421, 422, 423, 424, 425, 426,
  427
<223> OTHER INFORMATION: n = A,T,C or G
<220> FEATURE:
<221> NAME/KEY: misc_feature
<222> LOCATION: 428, 429, 430, 431, 432, 433, 434, 435, 436, 437, 439,
  440, 441, 442, 443, 444
<223> OTHER INFORMATION: n = A,T,C or G

<400> SEQUENCE: 74

```
Met Xaa Xaa Xaa Xaa Xaa Xaa Ser Xaa Xaa Xaa Xaa Xaa Xaa Ser Xaa
1               5                   10                  15

Xaa Xaa Xaa Xaa Xaa Xaa Xaa Xaa Xaa Xaa Xaa Xaa Xaa Xaa
            20                  25                  30

Xaa Xaa Xaa Arg Xaa Xaa Xaa Xaa Xaa Xaa Xaa Xaa Xaa Xaa
        35                  40                  45

Arg Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Arg Ser
65                  70                  75                  80
```

-continued

```
Ser Xaa Tyr Arg Gly Val Thr Arg His Arg Trp Thr Gly Arg Phe Glu
            85                  90                  95

Ala His Leu Trp Asp Lys Xaa Xaa Xaa Xaa Xaa Xaa Xaa Xaa Lys Lys
            100                 105                 110

Xaa Gly Xaa Gln Val Tyr Leu Gly Ala Tyr Asp Xaa Glu Glu Xaa Ala
            115                 120                 125

Ala Xaa Xaa Tyr Asp Leu Ala Ala Leu Lys Tyr Trp Gly Xaa Xaa
    130                 135                 140

Xaa Leu Asn Phe Pro Xaa Glu Xaa Tyr Xaa Xaa Glu Xaa Xaa Glu Met
145                 150                 155                 160

Xaa Xaa Val Xaa Xaa Glu Glu Tyr Leu Ala Ser Leu Arg Arg Xaa Ser
            165                 170                 175

Ser Gly Phe Ser Arg Gly Xaa Ser Lys Tyr Arg Gly Val Ala Arg His
            180                 185                 190

His His Asn Gly Arg Trp Glu Ala Arg Ile Gly Arg Val Xaa Gly Xaa
            195                 200                 205

Lys Tyr Leu Tyr Leu Gly Thr Xaa Xaa Thr Gln Glu Glu Ala Ala Xaa
    210                 215                 220

Ala Tyr Asp Xaa Ala Ala Ile Glu Tyr Arg Gly Xaa Asn Ala Val Thr
225                 230                 235                 240

Asn Phe Asp Ile Ser Xaa Tyr Xaa Xaa Xaa Xaa Xaa Xaa Xaa Xaa Xaa
            245                 250                 255

Xaa Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Glu Xaa Xaa
    275                 280                 285

Xaa Xaa Xaa Xaa Xaa Xaa Xaa Xaa Xaa Xaa Pro Xaa Xaa Xaa
290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Leu Xaa Trp Xaa Xaa Xaa
            325                 330                 335

Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa
            355                 360                 365

Phe Xaa Xaa Xaa Ile Xaa Xaa Xaa Phe Xaa Xaa Xaa Xaa Xaa Xaa
    370                 375                 380

Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa Xaa Xaa Xaa Xaa Xaa Xaa
            405                 410                 415

Xaa Xaa Xaa Xaa Xaa Xaa Xaa Xaa Xaa Xaa Xaa Xaa Xaa Xaa Xaa
            420                 425                 430

Xaa Xaa Xaa Xaa Xaa Cys Xaa Xaa Xaa Xaa Xaa
            435                 440
```